United States Patent
Bouché et al.

(10) Patent No.: US 12,357,603 B2
(45) Date of Patent: Jul. 15, 2025

(54) ACYL SULFONAMIDES FOR TREATING CANCER

(71) Applicants: Bayer Aktiengesellschaft, Leverkusen (DE); The Broad Institute, Inc., Cambridge, MA (US)

(72) Inventors: Léa Aurelie Bouché, Berlin (DE); Daniel Korr, Berlin (DE); Antonius ter Laak, Berlin (DE); Ernesto Amaury Fernandez-Montalvan, Le Pecq (FR); Naomi Barak, Berlin (DE); Roman Hillig, Berlin (DE); Roland Neuhaus, Berlin (DE); Matyas Gorjanacz, Berlin (DE); Vera Pütter, Berlin (DE); Stefan Niklaus Gradl, Berlin (DE); Simon Anthony Herbert, Berlin (DE); Steven James Ferrara, Cambridge, MA (US); Craig Strathdee, Watertown, MA (US); Jacob Jaffe, Cambridge, MA (US)

(73) Assignees: Bayer Aktiengesellschaft, Leverkusen (DE); The Broad Institute, Inc., Cambridge, MA (US)

( * ) Notice: Subject to any disclaimer, the term of this patent is extended or adjusted under 35 U.S.C. 154(b) by 887 days.

(21) Appl. No.: 17/605,818

(22) PCT Filed: Apr. 20, 2020

(86) PCT No.: PCT/EP2020/060962
§ 371 (c)(1),
(2) Date: Oct. 22, 2021

(87) PCT Pub. No.: WO2020/216701
PCT Pub. Date: Oct. 29, 2020

(65) Prior Publication Data
US 2022/0226279 A1    Jul. 21, 2022

Related U.S. Application Data

(60) Provisional application No. 62/838,477, filed on Apr. 25, 2019.

(51) Int. Cl.
*A61K 31/343*    (2006.01)
*A61K 31/351*    (2006.01)
(Continued)

(52) U.S. Cl.
CPC .......... *A61K 31/343* (2013.01); *A61K 31/351* (2013.01); *A61K 31/357* (2013.01);
(Continued)

(58) Field of Classification Search
CPC ................ A61K 31/343; A61K 31/351; A61K 31/357; A61K 31/381; A61K 31/4025;
(Continued)

(56) References Cited

U.S. PATENT DOCUMENTS

| 2022/0226279 A1 | 7/2022 | Bouche et al. |
| 2024/0279207 A1 | 8/2024 | Bouche et al. |
| 2024/0287048 A1 | 8/2024 | Bouche et al. |

FOREIGN PATENT DOCUMENTS

| CN | 107098846 A | 8/2017 |
| WO | WO-2009/064250 A1 | 5/2009 |

(Continued)

OTHER PUBLICATIONS

Baell et al. "Inhibitors of histone acetyltransferases KAT6A/B induce senescence and arrest tumour growth." Nature 560, No. 7717 (2018): 253-257 (Year: 2018).*
International Search Report and Written Opinion for International Application No. PCT/US2021/054921 dated Jan. 27, 2022.
International Search Report and Written Opinion for International Application No. PCT/US2021/054979 dated Jan. 26, 2022.
International Preliminary Report on Patentability for International Application No. PCT/EP2020/060962 dated Sep. 28, 2021.
International Search Report and Written Opinion for International Application No. PCT/EP2020/060962 dated Jun. 22, 2020.
(Continued)

*Primary Examiner* — James H Alstrum-Acevedo
*Assistant Examiner* — Carolyn L. Ladd
(74) *Attorney, Agent, or Firm* — Foley Hoag LLP; David P. Halstead; David S. Surry

(57) ABSTRACT

The present invention provides acyl sulfonamide compounds of general formula (I):

in which X, $R^1$, $R^2$, $R^3$, $R^4$, $R^5$, $R^{6'}$ $R^a$ and $R^b$ are as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients as well as methods of treating and/or prophylaxing diseases, particularly cancer, more particularly cancer in which KAT6A and/or KAT6B is focally amplified, said method comprising administering an effective amount of at least one compound of formula (I) to a subject in need thereof.

17 Claims, No Drawings

(51) Int. Cl.
| | |
|---|---|
| A61K 31/357 | (2006.01) |
| A61K 31/381 | (2006.01) |
| A61K 31/4025 | (2006.01) |
| A61K 31/4035 | (2006.01) |
| A61K 31/4155 | (2006.01) |
| A61K 31/4245 | (2006.01) |
| A61K 31/443 | (2006.01) |
| A61K 31/4525 | (2006.01) |
| A61K 31/4709 | (2006.01) |
| A61K 31/5025 | (2006.01) |
| A61P 35/00 | (2006.01) |
| C07D 307/85 | (2006.01) |
| C07D 333/70 | (2006.01) |
| C07D 405/04 | (2006.01) |
| C07D 405/12 | (2006.01) |
| C07D 407/12 | (2006.01) |
| C07D 413/12 | (2006.01) |
| C07D 487/04 | (2006.01) |

(52) U.S. Cl.
CPC ........ *A61K 31/381* (2013.01); *A61K 31/4025* (2013.01); *A61K 31/4035* (2013.01); *A61K 31/4155* (2013.01); *A61K 31/4245* (2013.01); *A61K 31/443* (2013.01); *A61K 31/4525* (2013.01); *A61K 31/4709* (2013.01); *A61K 31/5025* (2013.01); *A61P 35/00* (2018.01); *C07D 307/85* (2013.01); *C07D 333/70* (2013.01); *C07D 405/04* (2013.01); *C07D 405/12* (2013.01); *C07D 407/12* (2013.01); *C07D 413/12* (2013.01); *C07D 487/04* (2013.01)

(58) Field of Classification Search
CPC ............ A61K 31/4035; A61K 31/4155; A61K 31/4245; A61K 31/443; A61K 31/4525; A61K 31/4709; A61K 31/5025; A61P 35/00; C07D 307/85; C07D 333/70; C07D 405/04; C07D 405/12; C07D 407/12; C07D 413/12; C07D 487/04
See application file for complete search history.

(56) References Cited

FOREIGN PATENT DOCUMENTS

| | | | |
|---|---|---|---|
| WO | WO-2012170209 A2 * | 12/2012 | ........... A61K 31/496 |
| WO | WO-2016/198507 A1 | 12/2016 | |
| WO | WO-2018/102419 A1 | 6/2018 | |
| WO | WO-2019/108824 A1 | 6/2019 | |
| WO | WO-2020/216701 A1 | 10/2020 | |
| WO | WO-2022/013369 A1 | 1/2022 | |
| WO | WO-2022/081807 A1 | 4/2022 | |
| WO | WO-2022/081842 A1 | 4/2022 | |

OTHER PUBLICATIONS

Jansen et al., "Variations of acidic functions at position 2 and substituents at positions 4, 5 and 6 of the indole moiety and their effect on NMDA-glycine site affinity," European Journal of Medicinal Chemistry, 38(10): 855-865 (2003).
Extended European Search Report for EP Application No. 21881060.4 dated Oct. 22, 2024.
Extended European Search Report for EP Application No. 21881085.1 dated Sep. 18, 2024.
U.S. Appl. No. 18/032,067, Published.
U.S. Appl. No. 18/032,096, Published.

* cited by examiner

ACYL SULFONAMIDES FOR TREATING CANCER

This application is a U.S. National Stage Application of International Application PCT/EP2020/060962, filed Apr. 20, 2020, which claims the benefit of U.S. Provisional Application 62/838,477 filed Apr. 25, 2019, the contents of which are incorporated herein by reference in their entirety.

BACKGROUND

The present invention provides acyl sulfonamide compounds of general formula (I) which inhibit the activity of lysine acetyl transferase 6A (KAT6A) and lysine acetyl transferase 6B (KAT6B). In particular, the present invention provides compositions and methods for the treatment of lysine acetyl transferase 6A (KAT6A) activated cancers and lysine acetyl transferase 6B (KAT6B) activated cancers. More particularly, the present disclosure provides inhibitors of KAT6A and KAT6B for the treatment of breast cancer, lung cancer, ovarian cancer, endometrial cancer, esophageal cancer, bladder cancer, and acute myeloid leukemia. Even more particularly, the present disclosure provides inhibitors of KAT6A and KAT6B for the treatment of lung cancer, breast cancer, bladder cancer, uterine cancer, endometrial cancer, prostate cancer and leukemia.

Epigenetic regulation of gene expression is a complex process which confers stable, long term and in some cases heritable alterations in cellular gene expression. Rather than involving changes to the actual DNA sequence of the gene, epigenetic regulation is mediated through modifications to either the DNA backbone or to its associated chromatin proteins. These modifications facilitate interaction with the epigenetic gene regulation machinery, with the end result being stable gene activation/expression or stable gene silencing/repression. Alterations to the epigenetic gene regulation machinery underlie many different and diverse disease pathologies, and this is now recognized as a major driver in the oncogenic process for most cancers.

Histone proteins are the key chromatin proteins that facilitate the effector functions of the epigenetic gene regulation machinery. These are a family of five closely related proteins, denoted as histones H1, H2A, H2B, H3, and H4, that package and order the DNA into structural units called nucleosomes. Histones H3 and H4 both feature long amino-terminal polypeptide tails that protrude from the nucleosome, and that are rich in lysine and arginine amino acid residues which confer a net positive charge that enables the histone tails to interact with and bind to the negatively charged phosphate groups of the DNA backbone. Post-translational modification (PTM) of the lysine and arginine residues alters the nucleosome structure by altering the ability of the histones to bind DNA, and also by providing specific binding sites for the epigenetic gene regulation machinery. Such PTMs include methylation, acetylation, phosphorylation, ubiquitylation, and sumoylation.

Histone acetyltransferases (HATs) comprise a discrete family of enzymes which catalyze the transfer of an acetyl group from acetyl coenzyme A to a lysine residue in histones as well as other protein substrates. Lysine acetyl transferase 6A (KAT6A) and lysine acetyl transferase 6B (KAT6B) are the two HATs which are the focus of this disclosure. Both proteins have been implicated in cancer. KAT6A is the target of recurrent chromosomal translocations in acute myeloid leukemia, and it is focally amplified in lung, breast, ovarian, endometrial, bladder, and esophageal cancers. Similarly, KAT6B chromosomal translocations have been identified in a diverse range of cancers, and it is focally amplified in breast, ovarian, uterine, stomach, bladder, and lung cancer. Expression of KAT6A and KAT6B correlates well with gene copy number in tumors that have these focal amplifications, suggesting that there has been selective pressure to maintaining their activity during the oncogenic process. Moreover, cancer cell lines derived from tumors which bear these focal amplifications have high levels of KAT6A or KAT6B expression and are genetically dependent on this activity in long term proliferation experiments.

The biological pathways impacted by KAT6A and KAT6B activity are poorly defined, although there is some data which supports a gene activation function, notably the control of ESR1 expression in breast cancer cell lines. Similarly, the histone substrates of KAT6A and KAT6B are also poorly defined, and are thought to include lysine 9 of histone H3 (H3K9), lysine 14 of histone 3 (H3K14) and lysine 23 of histone H3 (H3K23). Acetylation at these positions is associated with such diverse functions as gene activation and DNA damage recognition, and it remains unclear which of these PTMs are the critical effectors in tumor cells that are dependent on KAT6A or KAT6B.

From WO2016198507 some aryl sulfonhydrazide derivatives are known as MOZ (KAT6A) inhibitors. However, there are currently no FDA-approved targeted therapeutics for KAT6A or KAT6B. Accordingly, there is an urgent need for compounds, compositions and methods for treating KAT6A- or KAT6B-activated cancers.

SUMMARY

The present invention provides acyl sulfonamide compounds of general formula (I):

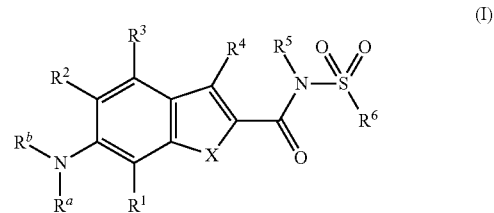

in which X, $R^1$, $R^2$, $R^3$, $R^4$, $R^5$, $R^{6'}$ $R^a$ and $R^b$ are as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative disorders, as a sole agent or in combination with other active ingredients.

DESCRIPTION OF THE INVENTION

It has now been found that the compounds of the present invention effectively inhibit the activity of lysine acetyl transferase 6A (KAT6A) and/or lysine acetyl transferase 6B (KAT6B) for which data are given in the biological experimental section and may therefore be used for the treatment or prophylaxis of hyperproliferative disorders, such as cancer disorders.

In accordance with a first aspect, the present invention provides compounds of general formula (I):

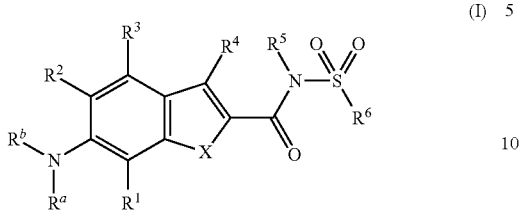

wherein

X is selected from an oxygen atom, a sulfur atom and a $NR^0$ group;

$R^0$ is selected from a hydrogen atom and a $C_1$-$C_6$-alkyl group;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a $C_1$-$C_6$-thioalkyl group, a heterocycloalkyl group, a (heterocycloalkyl)-O— group, a $R^7R^8N$— group, a ($R^7R^8N$)—(S(=O)$_2$)— group, a ($C_1$-$C_2$-alkyl)-(S(=O)$_2$)— group, a $CH_3$—C(=O)—$CH_2$— group, a ($R^7R^8N$)—($C_1$-$C_6$-alkyl)-(C=O)—NH— group, a ($R^7R^8N$)—($C_1$-$C_6$-alkyl)- group, a ($R^7R^8N$)—($C_1$-$C_6$-alkyl)-O— group, a $R^9$OOC— group, a phenyl group, a naphthyl group, a (phenyl)-($C_1$-$C_2$-alkyl)-O— group, a (phenyl)-O— group, a heteroaryl group and a heteroaryl-($C_1$-$C_2$-alkyl)- group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group,
  wherein said heterocycloalkyl group is connected to the rest of the molecule via a carbon atom of said heterocycloalkyl group;
$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_2$-alkyl)-$(C(=O))$— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a $R^9OOC$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, and a $R^9OOC$— group,
  wherein said heterocycloalkyl group is connected to the rest of the molecule via a carbon atom of said heterocycloalkyl group;
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group and a $R^9OOC$— group,
  wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group, a $(H_2N)$—$(C=O)$— group and oxo;
or a tautomer, or an N-oxide, or a salt thereof, or a salt of a tautomer, or a salt of an N-oxide, or a mixture of same.

DETAILED DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3, more particularly 1 or 2, and even more particularly 1.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two or three identical or different substituents, particularly with one, two or three substituents, more particularly with one substituent.

The terms "oxo", "an oxo group" or "an oxo substituent" mean a doubly bonded oxygen atom =O. Oxo may be attached to atoms of suitable valency, for example to a saturated carbon atom or to a sulfur atom. For example, but without limitation, one oxo group can be attached to a carbon atom, resulting in the formation of a carbonyl group C(=O), or two oxo groups can be attached to one sulfur atom, resulting in the formation of a sulfonyl group —S(=O)$_2$.

The term "ring substituent" means a substituent attached to an aromatic or nonaromatic ring which replaces an available hydrogen atom on the ring.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

If within the present text any item is referred to as "supra" within the description it indicates any of the respective disclosures made within the specification in any of the preceding pages, or above on the same page.

If within the present text any item is referred to as "infra" within the description it indicates any of the respective disclosures made within the specification in any of the subsequent pages, or below on the same page.

The terms as mentioned in the present text have the following meanings:

The term "halogen atom" means a fluorine, chlorine, bromine or iodine atom, particularly a fluorine, chlorine or bromine atom, more particularly a fluorine atom.

The term "$C_1$-$C_6$-alkyl" means a linear or branched, saturated, monovalent hydrocarbon group having 1, 2, 3, 4, 5 or 6 carbon atoms, e.g. a methyl-, ethyl-, propyl-, isopropyl-, butyl-, sec-butyl-, isobutyl-, tert-butyl-, pentyl-, isopentyl-, 2-methylbutyl-, 1-methylbutyl-, 1-ethylpropyl-, 1,2-dimethylpropyl-, neo-pentyl-, 1,1-dimethylpropyl-, hexyl-, 1-methylpentyl-, 2-methylpentyl-, 3-methylpentyl-, 4-methylpentyl-, 1-ethylbutyl-, 2-ethylbutyl-, 1,1-dimethylbutyl-, 2,2-dimethylbutyl-, 3,3-dimethylbutyl-, 2,3-dimethylbutyl-, 1,2-dimethylbutyl- or a 1,3-dimethylbutyl- group, or an isomer thereof. Particularly, said group has 1, 2, 3 or 4 carbon atoms ("$C_1$-$C_4$-alkyl"), e.g. a methyl-, ethyl-, propyl-, isopropyl-, butyl-, sec-butyl-, isobutyl- or a tert-butyl group, more particularly 1, 2 or 3 carbon atoms ("$C_1$-$C_3$-alkyl"), e.g. a methyl-, ethyl-, n-propyl- or an isopropyl group.

The term "$C_1$-$C_6$-hydroxyalkyl" means a linear or branched, saturated, monovalent hydrocarbon group in which the term "$C_1$-$C_6$-alkyl" is defined supra, and in which one or more hydrogen atoms are replaced with a hydroxy group, e.g. a hydroxymethyl-, 1-hydroxyethyl-, 2-hydroxyethyl-, 1,2-dihydroxyethyl-, 3-hydroxypropyl-, 2-hydroxypropyl-, 1-hydroxypropyl-, 1-hydroxypropan-2-yl-, 2-hydroxypropan-2-yl-, 2,3-dihydroxypropyl-, 1,3-dihydroxypropan-2-yl-, 3-hydroxy-2-methyl-propyl-, 2-hydroxy-2-methyl-propyl- or a 1-hydroxy-2-methyl-propyl- group.

The term "$C_1$-$C_6$-alkylsulfanyl" means a linear or branched, saturated, monovalent group of formula ($C_1$-$C_6$-alkyl)-S—, in which the term "$C_1$-$C_6$-alkyl" is as defined supra, e.g. a methylsulfanyl-, ethylsulfanyl-, propylsulfanyl-, isopropylsulfanyl-, butylsulfanyl-, sec-butylsulfanyl-, isobutylsulfanyl-, tert-butylsulfanyl-, pentylsulfanyl-, isopentylsulfanyl- or a hexylsulfanyl- group.

The term "$C_1$-$C_6$-haloalkyl" means a linear or branched, saturated, monovalent hydrocarbon group in which the term "$C_1$-$C_6$-alkyl" is as defined supra and in which one or more of the hydrogen atoms are replaced, identically or differently, with a halogen atom. Preferably, said halogen atom is a fluorine atom. Said $C_1$-$C_6$-haloalkyl, particularly a $C_1$-$C_3$-haloalkyl group is, for example, fluoromethyl-, difluoromethyl-, trifluoromethyl-, 2-fluoroethyl-, 2,2-difluoroethyl-, 2,2,2-trifluoroethyl-, pentafluoroethyl-, 3,3,3-trifluoropropyl- or a 1,3-difluoropropan-2-yl group.

The term "$C_1$-$C_6$-alkoxy" means a linear or branched, saturated, monovalent group of formula ($C_1$-$C_6$-alkyl)-O—, in which the term "$C_1$-$C_6$-alkyl" group is as defined supra, e.g. methoxy-, ethoxy-, n-propoxy-, isopropoxy-, n-butoxy-, sec-butoxy-, isobutoxy-, tert-butoxy-, pentyloxy-, isopentyloxy- or a n-hexyloxy group, or an isomer thereof.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Preferably, said halogen atom in "$C_1$-$C_6$-haloalkoxy-" is fluorine, resulting in a group referred herein as "$C_1$-$C_6$-fluoroalkoxy-". Representative $C_1$-$C_6$-fluoroalkoxy- groups include, for example, —$OCF_3$, —$OCHF_2$, —$OCH_2F$, —$OCF_2CF_3$ and —$OCH_2CF_3$.

The term "$C_2$-$C_6$-alkenyl-" means a linear or branched, monovalent hydrocarbon group, which contains one or more double bonds and which has 2, 3, 4, 5 or 6 carbon atoms, preferably 2, 3 or 4 carbon atoms ("$C_2$-$C_4$-alkenyl-") or 2 or 3 carbon atoms ("$C_2$-$C_3$-alkenyl-"), it being understood that in the case in which said alkenyl- group contains more than one double bond, then said double bonds may be isolated from, or conjugated with, each other. Representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (2)-but-1-enyl-, 2-methylprop-2-enyl-, 1-methylprop-2-enyl-, 2-methylprop-1-enyl-, (E)-1-methylprop-1-enyl-, (2)-1-methylprop-1-enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (2)-pent-1-enyl-, 3-methylbut-3- enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and a 1-(1,1-dimethylethyl-)ethenyl group. Particularly, said group is an ethenyl- or a prop-2-enyl group.

The same definitions can be applied should the alkenyl group be placed within a chain as a bivalent "$C_2$-$C_6$-alkenylene" moiety. All names as mentioned above then will bear a "ene" added to their end, thus e.g., a "pentenyl" becomes a bivalent "pentenylene" group.

The term "$C_2$-$C_6$-haloalkenyl-" means a linear or branched hydrocarbon group in which one or more of the hydrogen atoms of a "$C_2$-$C_6$-alkenyl-" as defined supra are each replaced, identically or differently, by a halogen atom. Preferably, said halogen atom is fluorine, resulting in a group referred herein as "$C_2$-$C_6$-fluoroalkenyl-". Representative $C_2$-$C_6$-fluoroalkenyl- groups include, for example, —CH=CF$_2$, —CF=CH$_2$, —CF=CF$_2$, —C(CH$_3$)=CF$_2$, —CH=C(F)—CH$_3$, —CH$_2$—CF=CF$_2$ and —CF$_2$—CH=CH$_2$.

The term "$C_2$-$C_6$-alkynyl-" means a linear or branched, monovalent hydrocarbon group which contains one or more triple bonds, and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl- groups include, for example, an ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and a 3,3-dimethylbut-1-ynyl- group. Particularly, said alkynyl- group is an ethynyl-, a prop-1-ynyl- or a prop-2-ynyl group.

The term "$C_3$-$C_8$-cycloalkyl" means a saturated, monovalent, mono- or bicyclic hydrocarbon ring which contains 3, 4, 5, 6, 7 or 8 carbon atoms ("$C_3$-$C_8$-cycloalkyl"). Said $C_3$-$C_8$-cycloalkyl group is for example, a monocyclic hydrocarbon ring, e.g. a cyclopropyl-, cyclobutyl-, cyclopentyl-, cyclohexyl-, cycloheptyl- or cyclooctyl- group, or a bicyclic hydrocarbon ring, e.g. a bicyclo[4.2.0]octyl- or a octahydropentalenyl- group.

The term "$C_3$-$C_8$-halocycloalkyl" means a saturated, monovalent, mono- or bicyclic hydrocarbon ring which contains 3, 4, 5, 6, 7 or 8 carbon atoms ("$C_3$-$C_8$-cycloalkyl") which is substituted one, two or three times with a halogen atom selected from the group consisting of fluorine, chlorine, bromine and iodine. Preferably, the halogen atom is a chlorine or a fluorine atom. More preferably, the halogen atom is a fluorine atom. The $C_3$-$C_8$-cycloalkyl group—which is substituted one, two or three times with a halogen atom selected from the group consisting of fluorine, chlorine, bromine and iodine—is as defined above herein, i.e. said $C_3$-$C_8$-cycloalkyl group is for example, a monocyclic hydrocarbon ring, e.g. a cyclopropyl-, cyclobutyl-, cyclopentyl-, cyclohexyl-, cycloheptyl- or cyclooctyl- group, or a bicyclic hydrocarbon ring, e.g. a bicyclo[4.2.0]octyl- or a octahydropentalenyl- group.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g., a cyclobutenyl-, cyclopentenyl-, cyclohexenyl-, cycloheptenyl- or a cyclooctenyl group, or a bicyclic hydrocarbon ring, e.g., a bicyclo[2.2.1]hept-2-enyl- or a bicyclo[2.2.2]oct-2-enyl group.

The term "$C_3$-$C_8$-cycloalkoxy" means a saturated, monovalent, mono- or bicyclic group of formula ($C_3$-$C_8$-cycloalkyl)-O—, which contains 3, 4, 5, 6, 7 or 8 carbon atoms, in which the term "$C_3$-$C_8$-cycloalkyl" is defined supra, e.g. a cyclopropyloxy-, cyclobutyloxy-, cyclopentyloxy-, cyclohexyloxy-, cycloheptyloxy- or a cyclooctyloxy- group.

If the term "heterocycloalkyl" is used without specifying a number of atoms it is meant to be a "4- to 10-membered heterocycloalkyl-" group, more particularly a 5- to 6-membered heterocycloalkyl group. The terms "4- to 7-membered heterocycloalkyl", "4- to 6-membered heterocycloalkyl" and "5- to 7-membered heterocycloalkyl" mean a monocyclic, saturated heterocycle with "4, 5, 6 or 7" or, respectively, "4, 5 or 6" or "5, 6 or 7" ring atoms in total, which are saturated or partially unsaturated monocycles, bicycles or polycycles that contain one or two identical or different ring heteroatoms selected from nitrogen, oxygen and sulfur. It is possible for said heterocycloalkyl group to be attached to the rest of the molecule via any one of the carbon atoms or, if present, a nitrogen atom.

Exemplarily, without being limited thereto, said "4- to 7-membered heterocycloalkyl", can be a 4-membered ring, a "4-membered heterocycloalkyl-" group, such as an azetidinyl- or an oxetanyl group; or a 5-membered ring, a "5-membered heterocycloalkyl-" group, such as a tetrahydrofuranyl-, dioxolinyl-, pyrrolidinyl-, imidazolidinyl-, pyrazolidinyl- or a pyrrolinyl group; or a 6-membered ring, a "6-membered heterocycloalkyl-" group, such as a tetrahydropyranyl-, piperidinyl-, morpholinyl-, 3-oxomorpholin- 4-yl, dithianyl-, thiomorpholinyl- or a piperazinyl group; or a 7-membered ring, a "7-membered heterocycloalkyl-" group, such as an azepanyl-, diazepanyl- or an oxazepanyl group, for example. The heterocycloalkyl groups may be substituted one or more times independently with $C_1$-$C_3$-alkyl, $C_1$-$C_3$-alkoxy, hydroxy, halogen or a carbonyl group.

Particularly, "4- to 6-membered heterocycloalkyl" means a 4- to 6-membered heterocycloalkyl as defined supra containing one ring nitrogen atom and optionally one further ring heteroatom selected from nitrogen, oxygen and sulfur. Particularly, "5- to 7-membered heterocycloalkyl" means a 5- to 7-membered heterocycloalkyl as defined supra containing one ring nitrogen atom and optionally one further ring heteroatom selected from nitrogen, oxygen and sulfur. More particularly, "5- or 6-membered heterocycloalkyl" means a monocyclic, saturated heterocycle with 5 or 6 ring atoms in total, containing one ring nitrogen atom and optionally one further ring heteroatom selected from nitrogen and oxygen.

The term "heteroaryl-" means a monocyclic, bicyclic or tricyclic aromatic ring system having 5, 6, 7, 8, 9, 10, 11, 12, 13 or 14 ring atoms (a "5- to 14-membered heteroaryl-" group), preferably 5, 6, 9 or 10 ring atoms and which contains 1, 2, 3 or 4 heteroatoms which may be identical or different, said heteroatoms being selected from oxygen, nitrogen and sulfur. Said heteroaryl- group can be a 5-membered heteroaryl group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl- or a tetrazolyl group; or a 6-membered heteroaryl group, such as, for example, a pyridyl-, pyridazinyl-, pyrimidyl-, pyrazinyl- or a triazinyl group; or a benzo-fused 5-membered heteroaryl- group, such as, for example, a benzofuranyl-, benzothienyl-, benzoxazolyl-, benzisoxazolyl-, benzimidazolyl-, benzothiazolyl-, benzotriazolyl-, indazolyl-, indolyl- or a isoindolyl group; or a benzo-fused 6-membered heteroaryl group, such as, for example, a quinolinyl-, quinazolinyl-, isoquinolinyl-, cinnolinyl-, phthalazinyl- or quinoxalinyl-; or another bicyclic group, such as, for example, indolizinyl-, purinyl- or a pteridinyl group.

Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur, a ("5- to 6-membered monocyclic heteroaryl-") group, such as, for example, a thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-, pyridyl-, pyridazinyl-, pyrimidyl-, pyrazinyl- or a triazinyl group.

In general, and unless otherwise mentioned, said heteroaryl- groups include all the possible isomeric forms thereof, e.g., the positional isomers thereof. Thus, for some illustrative non-restricting example, the term pyridyl- includes pyridin-2-yl-, pyridin-3-yl- and pyridin-4-yl-; the term thienyl- includes thien-2-yl- and thien-3-yl-, and a heteroarylene group may be inserted into a chain also in the inverse way such as e.g. a 2,3-pyridinylene includes pyridine-2,3-yl as well as pyridine-3,2-yl. Furthermore, said heteroaryl- groups can be attached to the rest of the molecule via any one of the carbon atoms, or, if applicable, a nitrogen atom, e.g., a pyrrol-1-yl-, a pyrazol-1-yl- or an imidazol-1-yl- group.

Particularly, the heteroaryl group is a pyridyl- or pyrimidyl group or a imidazolyl group, including a hydroxy substitution of the pyridyl group leading, e.g., to a 2-hydroxy-pyridine which is the tautomeric form to a 2-oxo-2 (1H)-pyridine. In some embodiments, the heteroaryl group is an oxazolyl group.

Further, as used herein, the term "$C_3$-$C_8$", as used throughout this text, e.g., in the context of the definition of "$C_3$-$C_8$-cycloalkyl-", is to be understood as meaning e.g. a cycloalkyl- group having a whole number of carbon atoms of 3 to 8, i.e., 3, 4, 5, 6, 7 or 8 carbon atoms. It is to be understood further that said term "$C_3$-$C_8$" is to be interpreted as disclosing any sub-range comprised therein, e.g., $C_3$-$C_6$, $C_4$-$C_5$, $C_3$-$C_5$, $C_3$-$C_4$, $C_4$-$C_6$, $C_5$-$C_7$; preferably $C_3$-$C_6$.

Similarly, as used herein, the term "$C_2$-$C_6$", as used throughout this text, e.g., in the context of the definitions of "$C_2$-$C_6$-alkenyl-" and "$C_2$-$C_6$-alkynyl-", is to be understood as meaning an alkenyl- group or an alkynyl- group having a whole number of carbon atoms from 2 to 6, i.e., 2, 3, 4, 5 or 6 carbon atoms. It is to be understood further that said term "$C_2$-$C_6$" is to be interpreted as disclosing any sub-range comprised therein, e.g., $C_2$-$C_6$, $C_3$-$C_5$, $C_3$-$C_4$, $C_2$-$C_3$, $C_2$-$C_4$, $C_2$-$C_5$; preferably $C_2$-$C_3$.

The term "$C_1$-$C_6$", as used throughout this text, e.g., in the context of the definition of "$C_1$-$C_6$-alkyl-", "$C_1$-$C_6$-haloalkyl-", "$C_1$-$C_6$-alkoxy-" or "$C_1$-$C_6$-haloalkoxy-" is to be understood as meaning an alkyl group having a whole number of carbon atoms from 1 to 6, i.e., 1, 2, 3, 4, 5 or 6 carbon atoms. It is to be understood further that said term "$C_1$-$C_6$" is to be interpreted as disclosing any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$; in the case of "$C_1$-$C_6$-haloalkyl-" or "$C_1$-$C_6$-haloalkoxy-" even more preferably $C_1$-$C_2$.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" refers to an atom or a group of atoms that is displaced in a chemical reaction as stable species taking with it the bonding electrons, e.g., typically forming an anion. Preferably, a leaving group is selected from the group comprising: halo, in particular a chloro, bromo or iodo, (methylsulfonyl)oxy-, [(4-methylphenyl)sulfonyl]oxy-, [(trifluoromethyl)sulfonyl]oxy-, [(nonafluorobutyl)sulfonyl]oxy-, [(4-bromophenyl)sulfonyl]oxy-, [(4-nitrophenyl)sulfonyl]oxy-, [(2-nitro-phenyl)sulfonyl]oxy-, [(4-isopropylphenyl)sulfonyl]oxy-, [(2,4,6-triisopropylphenyl)sulfonyl]oxy-, [(2,4,6-trimethylphenyl)sulfonyl]oxy-, [(4-tert-butylphenyl)sulfonyl]oxy-, (phenylsulfonyl)oxy-, and a [(4-methoxyphenyl)sulfonyl]oxy group.

As used herein, the term "protective group" is a protective group attached to an oxygen or nitrogen atom in intermediates used for the preparation of compounds of the general formula (I). Such groups are introduced e.g., by chemical modification of the respective hydroxy or amino group in order to obtain chemoselectivity in a subsequent chemical reaction. Protective groups for hydroxy and amino groups are described for example in T. W. Greene and P. G. M. Wuts in *Protective Groups in Organic Synthesis*, 4$^{th}$ edition, Wiley 2006; more specifically, protective groups for amino groups can be selected from substituted sulfonyl groups, such as a mesyl-, tosyl- or a phenylsulfonyl group, acyl groups such as a benzoyl-, acetyl- or a tetrahydropyranoyl group, or carbamate based groups, such as a tert-butoxycarbonyl group (Boc). Protective groups for hydroxy groups can be selected from acyl groups such as a benzoyl-, acetyl-, pivaloyl- or a tetrahydropyranoyl group, or can include silicon, as in e.g., a tert-butyldimethylsilyl-, tert-butyldiphenylsilyl-, triethylsilyl- or a triisopropylsilyl group.

The term "substituent" refers to a group "substituted" on, e.g., an alkyl-, haloalkyl-, cycloalkyl-, heterocyclyl-, heterocycloalkenyl-, cycloalkenyl-, aryl-, or a heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

It is possible for the compounds of general formula (I) to exist as isotopic variants. The invention therefore includes one or more isotopic variant(s) of the compounds of general formula (I), particularly deuterium-containing compounds of general formula (I).

The invention also includes all suitable isotopic variations of a compound of the invention.

The term "isotopic variant" of a compound or a reagent is defined as a compound exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Accordingly, recitation of "hydrogen" or "H" should be understood to encompass $^1$H (protium), $^2$H (deuterium), and $^3$H (tritium) unless otherwise specified. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

With respect to the treatment and/or prophylaxis of the disorders specified herein, the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful, e.g., in drug and/or substrate tissue distribution studies. These isotopes are particularly preferred for the ease of their incorporation and detectability. Positron-emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it may be possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

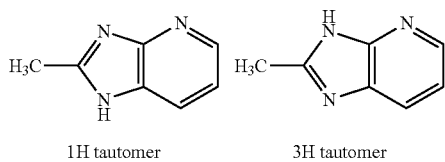

1H tautomer     3H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also provides useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic acid, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalenedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

A "pharmaceutically acceptable anion" refers to the deprotonated form of a conventional acid, such as, for example, a hydroxide, a carboxylate, a sulfate, a halide, a phosphate, or a nitrate.

Physiologically acceptable salts of the compounds according to the invention also comprise salts of conventional bases, such as, by way of example and by preference, alkali metal salts (for example lithium, sodium and potassium salts), alkaline earth metal salts (for example calcium, strontium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl) aminomethane, aminopropanediol, Sovak base, and 1-amino-2,3,4-butanetriol.

Additionally, the compounds according to the invention may form salts with a quaternary ammonium ion obtainable, e.g., by quaternisation of a basic nitrogen-containing group with agents such as lower alkylhalides such as methyl-, ethyl-, propyl-, and butylchlorides, -bromides and -iodides; dialkylsulfates such as dimethyl-, diethyl-, dibutyl- and diamylsulfates, long chain halides such as decyl-, lauryl-, myristyl- and stearylchlorides, -bromides and -iodides, aralkylhalides such as benzyl- and phenethylbromides and others. Examples of suitable quaternary ammonium ions are tetramethylammonium, tetraethylammonium, tetra(n-propyl)ammonium, tetra (n-butyl)ammonium, or N-benzyl-N, N,N-trimethylammonium.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Unless specified otherwise, suffixes to chemical names or structural formulae relating to salts, such as "hydrochloride", "trifluoroacetate", "sodium salt", or "x HCl", "x $CF_3COOH$", "x $Na^+$", for example, mean a salt form, the stoichiometry of which salt form not being specified.

Solvates and hydrates of disclosed intermediates or example compounds, or salts thereof, which have been obtained, by the preparation and/or purification processes described herein, may be formed in any ratio.

Furthermore, the present invention includes all possible crystalline forms, or polymorphs, of the compounds of the present invention, either as a single polymorph, or as a mixture of more than one polymorph, in any ratio.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. For example, a prodrug may be in the form of an in vivo hydrolysable ester of the specified compound. Derivatives of the compounds of formula (I) and the salts thereof which are converted into a compound of formula (I) or a salt thereof in a biological system (bioprecursors or pro-drugs) are covered by the invention. Said biological system may be, for example, a mammalian organism, particularly a human subject. The bioprecursor is, for example, converted into the compound of formula (I) or a salt thereof by metabolic processes.

DESCRIPTION

Further embodiments of the first aspect of the present invention

In accordance with further embodiments, the present invention provides compounds of general formula (I), supra, wherein X is selected from an oxygen atom, a sulfur atom and a $NR^0$ group;

$R^0$ is selected from a hydrogen atom and a $C_1$-$C_6$-alkyl group;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group, wherein said heterocycloalkyl group is connected to the rest of the molecule via a carbon atom of said heterocycloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group, wherein said heterocycloalkyl group is connected to the rest of the molecule via a carbon atom of said heterocycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group, wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group,
    wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, and a $R^9OOC$— group,
    wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group and a $R^9OOC$— group,
    wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom $R^1$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N—$ group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^2$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N—$ group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^3$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N—$ group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalky)-($C_1$-$C_2$-alkyl)-O— group, a $C_1$-$C_6$-thioalkyl group, a heterocycloalkyl group, a (heterocycloalkyl)-O— group, a $R^7R^8N—$ group, a $(R^7R^8N)—(S(=O)_2)—$ group, a ($C_1$-$C_2$-alkyl)-$(S(=O)_2)—$ group, a $CH_3—C(=O)—CH_2—$ group, a $(R^7R^8N)—(C_1$-$C_6$-alkyl)-(C=O)— NH— group, a $(R^7R^8N)—(C_1$-$C_6$-alkyl)- group, a $(R^7R^8N)—(C_1$-$C_6$-alkyl)-O— group, a $R^9OOC—$ group, a phenyl group, a naphthyl group, a (phenyl)-($C_1$-$C_2$-alkyl)-O— group, a (phenyl)-O— group, a heteroaryl group and a heteroaryl-($C_1$-$C_2$-alkyl)- group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N—$ group, a $(R^7R^8N)—(S=O)_2—$ group, a $(R^7R^8N)—(C_1$-$C_6$-alkyl)-(C=O)—NH—$ group, a $(R^7R^8N)—(C_1$-$C_6$-alkyl)- group, and a $R^9OOC—$ group,
      wherein said heterocycloalkyl group is connected to the rest of the molecule via a carbon atom of said heterocycloalkyl group;

R$^7$ and R$^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_2$-alkyl)-C(=O))— group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a (phenyl)-(S=O)$_2$— group, a $(C_1$-$C_6$-alkyl)-(S=O)$_2$— group, a $(C_1$-$C_6$-haloalkyl)-(S=O)$_2$— group, a R$^9$OOC— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, and a R$^9$OOC— group,
  wherein said heterocycloalkyl group is connected to the rest of the molecule via a carbon atom of said heterocycloalkyl group;
or R$^7$ and R$^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a R$^9$OOC— group,
  wherein said heterocycloalkyl group is connected to the rest of the molecule via a carbon atom of said heterocycloalkyl group;
R$^9$ is selected from a hydrogen atom, a $C_1$-$C_6$-alkyl group and a $C_3$-$C_8$-cycloalkyl group;
R$^a$ and R$^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a R$^7$R$^8$N— group, a (R$^7$R$^8$N)—(S=O)$_2$— group, a (R$^7$R$^8$N)—($C_1$-$C_6$-alkyl)-(C=O)—NH— group, a (R$^7$R$^8$N)—($C_1$-$C_6$-alkyl)- group and a R$^9$OOC— group,
  wherein said heterocycloalkyl group is connected to the rest of the molecule via a carbon atom of said heterocycloalkyl group;
or R$^a$ and R$^b$ together with the nitrogen atom to which they are attached form a 4- to 7-membered nitrogen-containing heterocycloalkyl group,
or R$^1$ and one of R$^a$ and R$^b$, together with the carbon and the nitrogen atom to which they are respectively attached form a 5- to 7-membered nitrogen-containing heterocycloalkyl group,
or R$^2$ and one of R$^a$ and R$^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group, a (H$_2$N)—(C=O)— group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
  X is selected from an oxygen atom and a sulfur atom;
  R$^1$ is selected from a hydrogen atom, a halogen atom, a cyano group, a nitro group, a R$^7$R$^8$N— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
    wherein said heterocycloalkyl group is connected to the rest of the molecule via a carbon atom of said heterocycloalkyl group,
    wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a R$^7$R$^8$N— group, a heterocycloalkyl group, a phenyl group, a naphthyl group and a heteroaryl group,
      wherein said heterocycloalkyl group is connected to the rest of the molecule via a carbon atom of said heterocycloalkyl group;
  R$^2$ is selected from a hydrogen atom, a halogen atom, a cyano group, a nitro group, a R$^7$R$^8$N— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a naphthyl group, a (phenyl)-O— group and a heteroaryl group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, and a $R^9OOC$— group,
      wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
    wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9$OOC— group wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8$N— group, a $(R^7R^8$N)—(S=O)$_2$— group, a $(R^7R^8$N)—$(C_1$-$C_6$-alkyl)-(C=O)—NH— group, a $(R^7R^8$N)—$(C_1$-$C_6$-alkyl)- group and a $R^9$OOC— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group, and a $C_1$-$C_6$-haloalkyl group;

$R^2$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group, and a $C_1$-$C_6$-haloalkyl group;

$R^3$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8$N— group, a heterocycloalkyl group, a phenyl group, a naphthyl group and a heteroaryl group, wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-$(C_1$-$C_6$-alkyl)- group, a (naphthyl)-$(C_1$-$C_6$-alkyl)- group, a (heteroaryl)-$(C_1$-$C_6$-alkyl)- group, a (heterocycloalkyl)-$(C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8$N— group, a $(R^7R^8$N)—(S=O)$_2$— group, a $(R^7R^8$N)—$(C_1$-$C_6$-alkyl)-(C=O)—NH— group, a $(R^7R^8$N)—$(C_1$-$C_6$-alkyl)- group, a $R^9$OOC— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S$=$O)_2$— group, a $(R^7R^8N)$—$(C_1$-$C_6$-alkyl)-$(C$=$O)$—NH— group, a $(R^7R^8N)$—$(C_1$-$C_6$-alkyl)- group, and a $R^9OOC$— group, wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S$=$O)_2$— group, a $(C_1$-$C_6$-alkyl)-$(S$=$O)_2$— group, a $(C_1$-$C_6$-haloalkyl)-$(S$=$O)_2$— group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S$=$O)_2$— group, a $(R^7R^8N)$—$(C_1$-$C_6$-alkyl)-$(C$=$O)$—NH— group, a $(R^7R^8N)$—$(C_1$-$C_6$-alkyl)- group and a $R^9OOC$— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a $R^7R^8N$— group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
  wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a naphthyl group, a (phenyl)-O— group and a heteroaryl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, and a $R^9OOC$— group,
  wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—

($C_1$-$C_6$-alkyl)-(C=O)—NH— group, a ($R^7R^8N$)—($C_1$-$C_6$-alkyl)- group and a $R^9$OOC— group,
  wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, a $R^9$OOC— group, a phenyl group, a naphthyl group, a (phenyl)-O— group and a heteroaryl group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, and a $R^9$OOC— group,
      wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
 wherein said heterocycloalkyl group is connected to the rest of the molecule via a carbon atom of said heterocycloalkyl group;
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
 wherein said heterocycloalkyl group is connected to the rest of the molecule via a carbon atom of said heterocycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)$C$(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
 wherein said heterocycloalkyl group is connected to the rest of the molecule via a carbon atom of said heterocycloalkyl group,
 wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group and a $R^9OOC$— group,
 wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
 wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;
$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a $C_1$-$C_6$-alkyl group, a phenyl group, a naphthyl group, a heteroaryl group, a (phenyl)-$(C_1$-$C_6$-alkyl)- group, a (naphthyl)-$(C_1$-$C_6$-alkyl)- group, a (heteroaryl)-$(C_1$-$C_6$-alkyl)- group, a (heterocycloalkyl)-$(C_1$-$C_6$-alkyl)- group and a heterocycloalkyl group,
 wherein said heterocycloalkyl group is connected to the rest of the molecule via a carbon atom of said heterocycloalkyl group,
 wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group,
 wherein said heterocycloalkyl group is connected to the rest of the molecule via a carbon atom of said heterocycloalkyl group,
 wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group, wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group and a $R^9OOC$— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)-group and a heterocycloalkyl group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group,
      wherein said heterocycloalkyl group is connected to the rest of the molecule via a carbon atom of said heterocycloalkyl group,
      wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group,
        wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
    wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
    wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group and a $R^9OOC$— group,
    wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
    wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with a further embodiment, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—($C_1$-$C_6$-alkyl)-(C=O)—NH— group, a $(R^7R^8N)$—($C_1$-$C_6$-alkyl)- group and a $R^9OOC$— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a naphthyl group, a (phenyl)-O— group and a heteroaryl group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group and a $R^9OOC$— group,
    wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (naphthyl)-($C_1$-$C_6$-alkyl)- group and a (heteroaryl)-($C_1$-$C_6$-alkyl)- group, wherein said phenyl, naphthyl or heteroaryl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9$OOC— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9$OOC— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a (phenyl)-O— group and a heteroaryl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group,
  wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
- wherein said heterocycloalkyl group is connected to the rest of the molecule via a carbon atom of said heterocycloalkyl group,
- wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
  - wherein said heterocycloalkyl group is connected to the rest of the molecule via a carbon atom of said heterocycloalkyl group,
  - wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
- wherein said heterocycloalkyl group is connected to the rest of the molecule via a carbon atom of said heterocycloalkyl group,
- wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
- wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
- wherein said heterocycloalkyl group is connected to the rest of the molecule via a carbon atom of said heterocycloalkyl group,
- wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
  - wherein said heterocycloalkyl group is connected to the rest of the molecule via a carbon atom of said heterocycloalkyl group,
  - wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group and a $(C_1$-$C_6$-alkoxy$)$-$(C_1$-$C_6$-alkyl$)$- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group, a $(C_1$-$C_6$-alkoxy$)$-$(C_1$-$C_6$-alkyl$)$- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a heteroaryl group, a (phenyl)-$(C_1$-$C_6$-alkyl)- group and a (heteroaryl)-$(C_1$-$C_6$-alkyl)- group, wherein said phenyl or heteroaryl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group and a $(C_1$-$C_6$-alkoxy$)$-$(C_1$-$C_6$-alkyl$)$- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group, a $(C_1$-$C_6$-alkoxy$)$-$(C_1$-$C_6$-alkyl$)$- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a heteroaryl group, a (phenyl)-($C_1$-$C_6$-alkyl)- group and a (heteroaryl)-($C_1$-$C_6$-alkyl)- group, wherein said phenyl or heteroaryl group is each optionally substituted with one or more substituents independently selected from a halogen atom, a cyano group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a $R^9OOC$— group, a phenyl group, a (phenyl)-O— group, a (phenyl)-($C_1$-$C_2$-alkyl)-O— group, a heteroaryl-($C_1$-$C_2$-alkyl)- group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;
$R^1$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group and a $C_1$-$C_6$-haloalkyl group;
$R^2$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group and a $C_1$-$C_6$-haloalkyl group;
$R^3$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group and a $C_1$-$C_6$-haloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a phenyl group, a heteroaryl group, a (phenyl)-($C_1$-$C_6$-alkyl)- group and a (heteroaryl)-($C_1$-$C_6$-alkyl)- group,
  wherein said phenyl or heteroaryl group is each optionally substituted with one or more substituents independently selected from a halogen atom, a cyano group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N—$ group, a $R^9OOC—$ group, a phenyl group, a (phenyl)-O— group, a (phenyl)-($C_1$-$C_2$-alkyl)-O— group, a heteroaryl-($C_1$-$C_2$-alkyl)- group and a heteroaryl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC—$ group;
$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a $C_1$-$C_6$-alkyl group and a $R^7R^8N—$ group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;
$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;
$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;
$R^3$ is selected from a hydrogen atom, a halogen atom, a cyano group, a nitro group, a $R^7R^8N—$ group, a $C_1$-$C_6$-alkyl group, a $C_3$-$C_8$-cycloalkyl group, a $C_1$-$C_6$-alkoxy group and a $C_1$-$C_6$-haloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group and a $(C_1$-$C_6$-alkoxy)-$(C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;

$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-$(C_1$-$C_6$-alkyl)- group, a (heteroaryl)-$(C_1$-$C_6$-alkyl)- group, a (heterocycloalkyl)-$(C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $(C_1$-$C_2$-alkyl)-O—$(C_1$-$C_2$-alkyl)-O— group, a $(C_3$-$C_8$-cycloalkyl)-$(C_1$-$C_2$-alkyl)-O— group, a $(C_3$-$C_8$-halocycloalkyl)-$(C_1$-$C_2$-alkyl)-O— group, a (heterocycloalkyl)-O— group, a heterocycloalkyl group, a $(R^7R^8N)$—$(C_1$-$C_6$-alkyl)-O— group, a $R^7R^8N$— group, a $R^9OOC$— group, a phenyl group, a (phenyl)-O— group, a (phenyl)-$(C_1$-$C_2$-alkyl)-O— group, a heteroaryl-$(C_1$-$C_2$-alkyl)- group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group and a $(C_1$-$C_6$-alkoxy)-$(C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1\text{-}C_6\text{-alkoxy})\text{-}(C_1\text{-}C_6\text{-alkyl})\text{-}$ group, a heterocycloalkyl group, a heteroaryl group and a phenyl group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1\text{-}C_2$-alkyl group, a $C_1\text{-}C_2$-haloalkyl group, a $C_1\text{-}C_2$-alkoxy group, a $C_3\text{-}C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1\text{-}C_6$-alkyl group, a $C_3\text{-}C_8$-cycloalkyl group, a $C_1\text{-}C_6$-alkoxy group and a $C_1\text{-}C_6$-haloalkyl group;

$R^2$ is selected from a hydrogen atom, a halogen atom, a cyano group, a nitro group, a $R^7R^8N$— group, a $C_1\text{-}C_6$-alkyl group, a $C_3\text{-}C_8$-cycloalkyl group, a $C_1\text{-}C_6$-alkoxy group and a $C_1\text{-}C_6$-haloalkyl group;

$R^3$ is selected from a hydrogen atom, a halogen atom, a cyano group, a nitro group, a $R^7R^8N$— group, a $C_1\text{-}C_6$-alkyl group, a $C_3\text{-}C_8$-cycloalkyl group, a $C_1\text{-}C_6$-alkoxy group and a $C_1\text{-}C_6$-haloalkyl group;

$R^4$ is selected from a hydrogen atom, a halogen atom, a $C_1\text{-}C_6$-alkyl group and a $C_3\text{-}C_8$-cycloalkyl group;

$R^5$ is selected from a hydrogen atom and a $C_1\text{-}C_6$-alkyl group;

$R^6$ is selected from a phenyl group, a heteroaryl group, a (phenyl)-$(C_1\text{-}C_6\text{-alkyl})$- group and a (heteroaryl)-$(C_1\text{-}C_6\text{-alkyl})$- group, wherein said phenyl or heteroaryl group is each optionally substituted with one or more substituents independently selected from a halogen atom, a cyano group, a $C_1\text{-}C_6$-alkyl group, a $C_1\text{-}C_6$-hydroxyalkyl group, a $C_1\text{-}C_6$-haloalkyl group, a $C_1\text{-}C_6$-alkoxy group, a $C_1\text{-}C_6$-haloalkoxy group, a $C_3\text{-}C_8$-cycloalkyl group, a $C_3\text{-}C_8$-cycloalkoxy group, a heterocycloalkyl group, a $R^7R^8N$— group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1\text{-}C_6$-alkyl group, a $C_1\text{-}C_6$-hydroxyalkyl group, a $C_1\text{-}C_6$-haloalkyl group, a $C_1\text{-}C_6$-alkoxy group, a $C_3\text{-}C_8$-cycloalkyl group, and a $R^9OOC$— group;

$R^7$ and $R^8$ are each independently selected from a $C_1\text{-}C_6$-alkyl group, a $C_3\text{-}C_8$-cycloalkyl group, a $C_1\text{-}C_6$-haloalkyl group, a $(C_1\text{-}C_6\text{-alkyl})C(=O)$— group, a $(C_1\text{-}C_6$-haloalkyl)$C(=O)$— group, a $(C_3\text{-}C_8$-cycloalkyl)-$(C_1\text{-}C_6\text{-alkyl})$- group, a $C_1\text{-}C_6$-hydroxyalkyl group and a $(C_1\text{-}C_6\text{-alkoxy})\text{-}(C_1\text{-}C_6\text{-alkyl})$- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1\text{-}C_6$-alkyl group, a $C_1\text{-}C_6$-hydroxyalkyl group, a $C_1\text{-}C_6$-haloalkyl group, a $C_1\text{-}C_6$-alkoxy group, a $C_1\text{-}C_6$-haloalkoxy group, and a $C_3\text{-}C_8$-cycloalkyl group;

$R^9$ is selected from a hydrogen atom, a $C_1\text{-}C_6$-alkyl group and a $C_3\text{-}C_8$-cycloalkyl group;

$R^a$ and $R^b$ are each independently selected from a hydrogen atom, a $C_1\text{-}C_6$-alkyl group, a $C_3\text{-}C_8$-cycloalkyl group, a $C_1\text{-}C_6$-haloalkyl group, a $(C_1\text{-}C_6\text{-alkyl})C(=O)$— group, a $(C_1\text{-}C_6$-haloalkyl)$C(=O)$— group, a $(C_3\text{-}C_8$-cycloalkyl)-$(C_1\text{-}C_6\text{-alkyl})$- group, a $C_1\text{-}C_6$-hydroxyalkyl group, a $(C_1\text{-}C_6\text{-alkoxy})\text{-}(C_1\text{-}C_6\text{-alkyl})\text{-}$ group, a heterocycloalkyl group, a heteroaryl group and a phenyl group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1\text{-}C_2$-alkyl group, a $C_1\text{-}C_2$-haloalkyl group, a $C_1\text{-}C_2$-alkoxy group, a $C_3\text{-}C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a nitro group, a $R^7R^8N$— group, a $C_1\text{-}C_6$- alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9$OOC— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;

$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8$N— group, a $R^9$OOC— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9$OOC— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or R² and one of Rᵃ and Rᵇ, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
  X is an oxygen atom;
  $R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;
  $R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;
  $R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
  $R^4$ is selected from a hydrogen atom, a halogen atom, a $C_1$-$C_6$-alkyl group and a $C_3$-$C_8$-cycloalkyl group;
  $R^5$ is selected from a hydrogen atom and a $C_1$-$C_6$-alkyl group;
  $R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a $R^9OOC$— group, a phenyl group, a (phenyl)-O— group, a (phenyl)-($C_1$-$C_2$-alkyl)-O— group, a heteroaryl-($C_1$-$C_2$-alkyl)- group and a heteroaryl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;
  $R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group,
  or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
  $R^9$ is selected from a hydrogen atom, a $C_1$-$C_6$-alkyl group and a $C_3$-$C_8$-cycloalkyl group;
  $R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;
  or $R^a$ and $R^b$ together with the nitrogen atom to which they are attached form a 4- to 7-membered nitrogen-containing heterocycloalkyl group,
  or $R^1$ and one of $R^a$ and $R^b$, together with the carbon and the nitrogen atom to which they are respectively attached form a 5- to 7-membered nitrogen-containing heterocycloalkyl group,
  or $R^2$ and one of $R^a$ and $R^b$, together with the carbon and the nitrogen atom to which they are respectively attached form a 5- to 7-membered nitrogen-containing heterocycloalkyl group,
    wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
  X is selected from an oxygen atom and a sulfur atom;
  $R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;
  $R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;
  $R^3$ is selected from a hydrogen atom, a halogen atom, a cyano group, a nitro group, a $R^7R^8N$— group, a $C_1$-$C_6$- alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group and a heteroaryl group, wherein said phenyl or heteroaryl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group and a $(C_1$-$C_6$-alkoxy)-$(C_1$-$C_6$-alkyl)- group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group and a $(C_1$-$C_6$-alkoxy)-$(C_1$-$C_6$-alkyl)- group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group;
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a $R^7R^8N$— group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-$(C_1$-$C_6$-alkyl)- group, a (naphthyl)-$(C_1$-$C_6$-alkyl)- group, a (heteroaryl)-$(C_1$-$C_6$-alkyl)- group, a (heterocycloalkyl)-$(C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a ($R^7R^8N$)—($C_1$-$C_6$-alkyl)-(C=O)—NH— group, a ($R^7R^8N$)—($C_1$-$C_6$-alkyl)- group, and a $R^9$OOC— group,
  wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9$OOC— group,
    wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9$OOC— group,
  wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group and a $R^9$OOC— group,
    wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;

$R^1$ is selected from a hydrogen atom, a halogen atom, a cyano group, a $R^7R^8N$— group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a hydroxy group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a $C_1$-$C_6$-thioalkyl group, a heterocycloalkyl group, a ($R^7R^8N$)—($C_1$-$C_6$-alkyl)-O— group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a naphthyl group, a (phenyl)-O— group, a (phenyl)-($C_1$-$C_2$-alkyl)-O— group, a heteroaryl-($C_1$-$C_2$-alkyl)- group and a heteroaryl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, and a $R^9OOC$— group,
wherein said heterocycloalkyl group is connected to the rest of the molecule via a carbon atom of said heterocycloalkyl group;
$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C (=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
wherein said heterocycloalkyl group is connected to the rest of the molecule via a carbon atom of said heterocycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C (=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group and a $R^9OOC$— group,
wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a $R^7R^8N$— group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a $(R^7R^8N)$—$(C_1$-$C_6$-alkyl)-(C$=$O)—NH— group, a $(R^7R^8N)$—$(C_1$-$C_6$-alkyl)- group, a $R^9OOC$— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC($=$O)— group, a $(C_1$-$C_6$-alkyl)C($=$O)— group, a $(C_1$-$C_6$-haloalkyl)C($=$O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a (phenyl)-(S$=$O)$_2$— group, a $(C_1$-$C_6$-alkyl)-(S$=$O)$_2$— group, a $(C_1$-$C_6$-haloalkyl)-(S$=$O)$_2$— group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC($=$O)— group, a $(C_1$-$C_6$-alkyl)C($=$O)— group, a $(C_1$-$C_6$-haloalkyl)C($=$O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—(S$=$O)$_2$— group, a $(R^7R^8N)$—$(C_1$-$C_6$-alkyl)-(C$=$O)—NH— group, a $(R^7R^8N)$—$(C_1$-$C_6$-alkyl)- group and a $R^9OOC$— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group,
wherein said heterocycloalkyl group is connected to the rest of the molecule via a carbon atom of said heterocycloalkyl group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a $(R^7R^8N)$—($C_1$-$C_6$-alkyl)-O— group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a R⁹OOC— group, a phenyl group, a (phenyl)-O— group, a (phenyl)-($C_1$-$C_2$-alkyl)-O— group, a heteroaryl-($C_1$-$C_2$-alkyl)- group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group,
  wherein said heterocycloalkyl group is connected to the rest of the molecule via a carbon atom of said heterocycloalkyl group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a $C_1$-$C_6$-alkyl group and a $R^7R^8N$— group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group and a heteroaryl group,
  wherein said phenyl or heteroaryl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a (phenyl)-O— group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group,
  wherein said heterocycloalkyl group is connected to the rest of the molecule via a carbon atom of said heterocycloalkyl group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group and a heteroaryl group, wherein said phenyl or heteroaryl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a (phenyl)-O— group, a (phenyl)-($C_1$-$C_2$-alkyl)-O— group, a heteroaryl-($C_1$-$C_2$-alkyl)- group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkyl group, and a $C_3$-$C_8$-cycloalkyl group;

$R^3$ is selected from a hydrogen atom, a halogen atom, a cyano group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;
$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group and a $(C_1$-$C_6$-alkoxy$)$-$(C_1$-$C_6$-alkyl$)$- group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group, a $(C_1$-$C_6$-alkoxy$)$-$(C_1$-$C_6$-alkyl$)$- group, a heterocycloalkyl group, a heteroaryl group and a phenyl group,
wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is selected from an oxygen atom and a sulfur atom;
$R^1$ is selected from a hydrogen atom, a halogen atom, a $C_1$-$C_6$-alkoxy group, a $C_1$-$C_6$-alkyl group, and a $C_3$-$C_8$-cycloalkyl group;
$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;
$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a phenyl group and a heteroaryl group,
wherein said phenyl or heteroaryl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;
$R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group and a $(C_1$-$C_6$-alkoxy$)$-$(C_1$-$C_6$-alkyl$)$- group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
  or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

X is an oxygen atom;
$R^1$ is selected from a hydrogen atom, a halogen atom, a $C_1$-$C_6$-alkoxy group, a $C_1$-$C_6$-alkyl group, and a $C_3$-$C_8$-cycloalkyl group;
$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;
$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a phenyl group and a heteroaryl group,
  wherein said phenyl or heteroaryl group is each optionally substituted with one or more substituents independently selected from a halogen atom, a cyano group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a $R^9OOC$— group, a phenyl group, a (phenyl)-O— group, a (phenyl)-($C_1$-$C_2$-alkyl)-O— group, a heteroaryl-($C_1$-$C_2$-alkyl)-group and a heteroaryl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;
$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is selected from a hydrogen atom and a halogen atom;
$R^2$ is a hydrogen atom;

R³ is selected from a hydrogen atom and a halogen atom;
R⁴ is a hydrogen atom;
R⁵ is selected from a hydrogen atom and a $C_1$-$C_6$-alkyl group;
R⁶ is selected from a phenyl group and a heteroaryl group,
  wherein said phenyl or heteroaryl group is each optionally substituted with one or more substituents independently selected from a halogen atom, a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group,
R$^a$ and R$^b$ are each independently selected from a hydrogen atom and a $C_1$-$C_6$-alkyl group,
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
R¹ is a hydrogen atom;
R² is a hydrogen atom;
R³ is selected from a hydrogen atom and a halogen atom;
R⁴ is a hydrogen atom;
R⁵ is a hydrogen atom;
R⁶ is selected from a phenyl group and a heteroaryl group,
  wherein said phenyl or heteroaryl group is each optionally substituted with one or more substituents independently selected from a halogen atom, a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group,
R$^a$ and R$^b$ are each independently selected from a hydrogen atom and a $C_1$-$C_6$-alkyl group,
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
R¹ is a hydrogen atom;
R² is a hydrogen atom;
R³ is selected from a hydrogen atom and a fluorine atom;
R⁴ is a hydrogen atom;
R⁵ is a hydrogen atom;
R⁶ is selected from a phenyl group and a heteroaryl group,
  wherein said phenyl or heteroaryl group is each optionally substituted with one or more substituents independently selected from a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkoxy group,
R$^a$ and R$^b$ are each independently selected from a hydrogen atom and a methyl group,
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
R¹ is a hydrogen atom;
R² is a hydrogen atom;
R³ is a fluorine atom;
R⁴ is a hydrogen atom;
R⁵ is a hydrogen atom;
R⁶ is selected from a phenyl group and a heteroaryl group,
  wherein said phenyl or heteroaryl group is each optionally substituted with one or more substituents independently selected from a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkoxy group,
R$^a$ and R$^b$ are each independently selected from a hydrogen atom and a methyl group,
or a tautomer, or an N-oxide, or a salt thereof, or a salt of a tautomer, or a salt of an N-oxide, or a mixture of same.

In accordance with a further embodiment, the present invention provides compounds of general formula (I), supra, wherein:
X is an oxygen atom;
R¹ is a hydrogen atom;
R² is a hydrogen atom;
R³ is selected from a hydrogen atom and a halogen atom;
R⁴ is a hydrogen atom;
R⁵ is a hydrogen atom;
R⁶ is selected from a phenyl group, a naphthyl group and a heteroaryl group,
  wherein said phenyl, naphthyl or heteroaryl group is each optionally substituted with one or more substituents independently selected from a halogen atom, a $C_1$-$C_6$-alkyl group, a $C_1$-$C_6$-alkoxy group and a phenyl group,
    wherein said phenyl group is optionally substituted with one or more substituents independently selected from a halogen atom, a $C_1$-$C_6$-alkyl group, a $C_1$-$C_6$-hydroxyalkyl group, a $C_1$-$C_6$-haloalkyl group, a $C_1$-$C_6$-alkoxy group and a $C_3$-$C_8$-cycloalkyl group;
R$^a$ and R$^b$ are each independently selected from a $C_1$-$C_6$-alkyl group, a $C_3$-$C_8$-cycloalkyl group, a $C_1$-$C_6$-haloalkyl group and a ($C_1$-$C_6$-alkoxy)-($C_1$-$C_6$-alkyl)- group,
or R$^a$ and R$^b$ together with the nitrogen atom to which they are attached form a 4- to 7-membered nitrogen-containing heterocycloalkyl group,
or R¹ and one of R$^a$ and R$^b$, together with the carbon and the nitrogen atom to which they are respectively attached form a 5- to 7-membered nitrogen-containing heterocycloalkyl group,
or R² and one of R$^a$ and R$^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
R¹ is a hydrogen atom;
R² is a hydrogen atom;

$R^3$ is selected from a hydrogen atom and a halogen atom;
$R^4$ is a hydrogen atom;
$R^5$ is a hydrogen atom;
$R^6$ is selected from a phenyl group, a naphthyl group and a heteroaryl group,
  wherein said phenyl, naphthyl or heteroaryl group is each optionally substituted with one or more substituents independently selected from a halogen atom, a $C_1$-$C_6$-alkyl group, a $C_1$-$C_6$-alkoxy group and a phenyl group,
    wherein said phenyl group is optionally substituted with one or more substituents independently selected from a halogen atom, a $C_1$-$C_6$-alkyl group, a $C_1$-$C_6$-hydroxyalkyl group, a $C_1$-$C_6$-haloalkyl group, a $C_1$-$C_6$-alkoxy group and a $C_3$-$C_8$-cycloalkyl group;
$R^a$ and $R^b$ are each independently selected from a $C_1$-$C_6$-alkyl group, a $C_3$-$C_8$-cycloalkyl group, a $C_1$-$C_6$-haloalkyl group and a ($C_1$-$C_6$-alkoxy)-($C_1$-$C_6$-alkyl)- group,
or $R^a$ and $R^b$ together with the nitrogen atom to which they are attached form a 4- to 7-membered nitrogen-containing heterocycloalkyl group,
  wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is a hydrogen atom;
$R^2$ is a hydrogen atom;
$R^3$ is selected from a hydrogen atom and a halogen atom;
$R^4$ is a hydrogen atom;
$R^5$ is a hydrogen atom;
$R^6$ is selected from a phenyl group, a naphthyl group and a heteroaryl group,
  wherein said phenyl, naphthyl or heteroaryl group is each optionally substituted with one or more substituents independently selected from a halogen atom, a $C_1$-$C_6$-alkyl group, a $C_1$-$C_6$-alkoxy group, a $C_3$-$C_8$-cycloalkoxy group and a phenyl group,
    wherein said phenyl group is optionally substituted with one or more substituents independently selected from a halogen atom, a $C_1$-$C_6$-alkyl group, a $C_1$-$C_6$-hydroxyalkyl group, a $C_1$-$C_6$-haloalkyl group, a $C_1$-$C_6$-alkoxy group and a $C_3$-$C_8$-cycloalkyl group;
$R^a$ and $R^b$ are each independently selected from a $C_1$-$C_6$-alkyl group, a $C_3$-$C_8$-cycloalkyl group, a $C_1$-$C_6$-haloalkyl group and a ($C_1$-$C_6$-alkoxy)-($C_1$-$C_6$-alkyl)- group,
or $R^a$ and $R^b$ together with the nitrogen atom to which they are attached form a 4- to 7-membered nitrogen-containing heterocycloalkyl group,
  wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is selected from a hydrogen atom, a $C_1$-$C_6$-alkyl group, and a $C_3$-$C_8$-cycloalkyl group;
$R^2$ is a hydrogen atom;
$R^3$ is selected from a hydrogen atom, a $C_1$-$C_6$-alkyl group, and a $C_3$-$C_8$-cycloalkyl group;
$R^4$ is a hydrogen atom;
$R^5$ is a hydrogen atom;
$R^6$ is selected from a phenyl group, a heteroaryl group, and a heterocycloalkyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-haloalkyl group, a $C_1$-$C_6$-alkoxy group, a $C_1$-$C_6$-haloalkoxy group, a $R^9$OOC— group and a phenyl group,
    wherein said phenyl group is optionally substituted with one or more substituents independently selected from a halogen atom, a $C_1$-$C_6$-alkyl group and a $C_1$-$C_6$-hydroxyalkyl group;
$R^9$ is selected from a hydrogen atom and a $C_1$-$C_6$-alkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_3$-$C_6$-cycloalkyl)-($C_1$-$C_3$-alkyl)- group and a phenyl group,
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is selected from a hydrogen atom, a $C_1$-$C_6$-alkyl group, and a $C_3$-$C_8$-cycloalkyl group;
$R^2$ is a hydrogen atom;

R³ is selected from a hydrogen atom, a C₁-C₆-alkyl group, and a C₃-C₈-cycloalkyl group;
R⁴ is a hydrogen atom;
R⁵ is a hydrogen atom;
R⁶ is selected from a phenyl group, a heteroaryl group, and a heterocycloalkyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a C₁-C₆-alkyl group, a C₁-C₆-haloalkyl group, a C₁-C₆-alkoxy group, a C₁-C₆-haloalkoxy group, a R⁹OOC— group and a phenyl group,
wherein said phenyl group is optionally substituted with one or more substituents independently selected from a halogen atom, a C₁-C₆-alkyl group and a C₁-C₆-hydroxyalkyl group;
R⁹ is selected from a hydrogen atom and a C₁-C₆-alkyl group;
Rᵃ and Rᵇ are each independently selected from a hydrogen atom, a C₁-C₆-alkyl group, a C₃-C₈-cycloalkyl group, a C₁-C₆-haloalkyl group, a (C₃-C₆-cycloalkyl)-(C₁-C₃-alkyl)- group and a phenyl group,
or Rᵃ and Rᵇ together with the nitrogen atom to which they are attached form a 4- to 7-membered nitrogen-containing heterocycloalkyl group,
wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a C₁-C₂-alkyl group, a C₁-C₂-haloalkyl group, a C₁-C₂-alkoxy group, a C₃-C₄-cycloalkyl group and oxo;
or a tautomer, or an N-oxide, or a salt thereof, or a salt of a tautomer, or a salt of an N-oxide, or a mixture of same.
In accordance with further embodiments, the present invention provides compounds of general formula (I), supra, wherein:
X is an oxygen atom;
R¹ is selected from a hydrogen atom, a cyano group, a C₁-C₆-alkyl group, and a C₃-C₈-cycloalkyl group;
R² is a hydrogen atom;
R³ is a hydrogen atom;
R⁴ is a hydrogen atom;
R⁵ is selected from a hydrogen atom, a C₁-C₆-alkyl group, and a C₃-C₈-cycloalkyl group;
R⁶ is selected from a C₁-C₆-alkyl group, a C₃-C₈-cycloalkyl group, a phenyl group, a heteroaryl group, and a heterocycloalkyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a C₁-C₆-alkyl group, a (R⁷R⁸N)—(C₁-C₆-alkyl)-(C=O)—NH— group and a phenyl group;
R⁷ and R⁸ are each independently selected from a hydrogen atom and a C₁-C₆-alkyl group;
Rᵃ and Rᵇ are each independently selected from a hydrogen atom, a C₁-C₆-alkyl group, a C₃-C₈-cycloalkyl group, a C₁-C₆-haloalkyl group and a phenyl group,
or Rᵃ and Rᵇ together with the nitrogen atom to which they are attached form a 4- to 7-membered nitrogen-containing heterocycloalkyl group,
or R¹ and one of Rᵃ and Rᵇ, together with the carbon and the nitrogen atom to which they are respectively attached form a 5- to 7-membered nitrogen-containing heterocycloalkyl group,
or R² and one of Rᵃ and Rᵇ, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a C₁-C₂-alkyl group, a C₁-C₂-haloalkyl group, a C₁-C₂-alkoxy group, a C₃-C₄-cycloalkyl group and oxo;
or a tautomer, or an N-oxide, or a salt thereof, or a salt of a tautomer, or a salt of an N-oxide, or a mixture of same.
In accordance with further embodiments, the present invention provides compounds of general formula (I), supra, wherein:
X is an oxygen atom;
R¹ is selected from a hydrogen atom, a cyano group, a C₁-C₆-alkyl group, and a C₃-C₈-cycloalkyl group;
R² is a hydrogen atom;
R³ is a hydrogen atom;
R⁴ is a hydrogen atom;
R⁵ is selected from a hydrogen atom, a C₁-C₆-alkyl group, and a C₃-C₈-cycloalkyl group;
R⁶ is selected from a C₁-C₆-alkyl group, a C₃-C₈-cycloalkyl group, a phenyl group, a heteroaryl group, and a heterocycloalkyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a C₁-C₆-alkyl group, a (R⁷R⁸N)—(C₁-C₆-alkyl)-(C=O)—NH— group and a phenyl group;
R⁷ and R⁸ are each independently selected from a hydrogen atom and a C₁-C₆-alkyl group;
Rᵃ and Rᵇ are each independently selected from a hydrogen atom, a C₁-C₆-alkyl group, a C₃-C₈-cycloalkyl group, a C₁-C₆-haloalkyl group and a phenyl group,
or Rᵃ and Rᵇ together with the nitrogen atom to which they are attached form a 4- to 7-membered nitrogen-containing heterocycloalkyl group,
wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a C₁-C₂-alkyl group, a C₁-C₂-haloalkyl group, a C₁-C₂-alkoxy group, a C₃-C₄-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is selected from a hydrogen atom and a $C_1$-$C_3$-alkyl group;
$R^2$ is a hydrogen atom;
$R^3$ is a hydrogen atom;
$R^4$ is a hydrogen atom;
$R^5$ is a hydrogen atom;
$R^6$ is selected from a phenyl group and a heteroaryl group, wherein said phenyl or heteroaryl group is each optionally substituted with one or more substituents independently selected from a $C_1$-$C_3$-alkyl group, a $C_1$-$C_6$-alkoxy group and a phenyl group;
$R^a$ and $R^b$ are each independently selected from a hydrogen atom and a $C_1$-$C_3$-alkyl group;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is a hydrogen atom;
$R^2$ is a hydrogen atom;
$R^3$ is a hydrogen atom;
$R^4$ is a hydrogen atom;
$R^5$ is a hydrogen atom;
$R^6$ is selected from a phenyl group and a heteroaryl group, wherein said phenyl or heteroaryl group is each optionally substituted with one or more substituents independently selected from a $C_1$-$C_3$-alkyl group, a $C_1$-$C_6$-alkoxy group and a phenyl group;
$R^a$ and $R^b$ are each independently selected from a hydrogen atom and a $C_1$-$C_3$-alkyl group;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is a hydrogen atom;
$R^2$ is a hydrogen atom;
$R^3$ is a hydrogen atom;
$R^4$ is a hydrogen atom;
$R^5$ is a hydrogen atom;
$R^6$ is selected from a phenyl group and a heteroaryl group, wherein said phenyl or heteroaryl group is each optionally substituted with one or more substituents independently selected from a methyl group, a $(CH_3CH_2)$—O— group and a phenyl group;
$R^a$ and $R^b$ are each independently selected from a hydrogen atom and methyl group;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is a hydrogen atom;
$R^2$ is a hydrogen atom;
$R^3$ is a hydrogen atom;
$R^4$ is a hydrogen atom;
$R^5$ is a hydrogen atom;
$R^6$ is selected from a phenyl group and a heteroaryl group, wherein said phenyl or heteroaryl group is each optionally substituted with one or more substituents independently selected from a methyl group, a $(CH_3CH_2)$—O— group and a phenyl group;
$R^a$ and $R^b$ are each a methyl group;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:
X is an oxygen atom;
$R^1$ is a hydrogen atom;
$R^2$ is a hydrogen atom;
$R^3$ is a hydrogen atom;
$R^4$ is a hydrogen atom;
$R^5$ is a hydrogen atom;
$R^6$ is selected from a phenyl group and a quinoline group, wherein said phenyl or quinoline group is each optionally substituted with one or more substituents independently selected from a methyl group, a $(CH_3CH_2)$—O— group and a phenyl group;
$R^a$ and $R^b$ are each a methyl group;
or a tautomer, or an N-oxide, or a salt thereof, or a salt of a tautomer, or a salt of an N-oxide, or a mixture of same.

In accordance with further embodiments, the present invention provides salts of the compounds of general formula (I), supra, wherein:
X is an oxygen atom;
$R^1$ is a hydrogen atom;
$R^2$ is a hydrogen atom;
$R^3$ is a hydrogen atom;
$R^4$ is a hydrogen atom;
$R^5$ is a hydrogen atom;
$R^6$ is selected from a phenyl group and a quinoline group, wherein said phenyl or quinoline group is each optionally substituted with one or more substituents independently selected from a methyl group, a $(CH_3CH_2)$—O— group and a phenyl group and wherein
$R^a$ and $R^b$ are each a methyl group;
or a tautomer, or an N-oxide, or a salt thereof, or a salt of a tautomer, or a salt of an N-oxide, or a mixture of same.

In accordance with further embodiments, the present invention provides sodium salts of the compounds of general formula (I), supra, wherein:
X is an oxygen atom;
$R^1$ is a hydrogen atom;
$R^2$ is a hydrogen atom;
$R^3$ is a hydrogen atom;
$R^4$ is a hydrogen atom;
$R^5$ is a hydrogen atom;
$R^6$ is selected from a phenyl group and a quinoline group, wherein said phenyl or quinoline group is each optionally substituted with one or more substituents independently selected from a methyl group, a $(CH_3CH_2)$—O— group and a phenyl group and wherein
$R^a$ and $R^b$ are each a methyl group;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein:

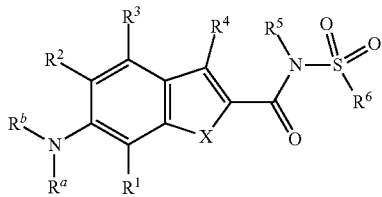

wherein
X is selected from an oxygen atom, a sulfur atom and a $NR^0$ group;
$R^0$ is selected from a hydrogen atom and a $C_1$-$C_6$-alkyl group;
$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8N$— group, and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a naphthyl group, a (phenyl)-O— group and a heteroaryl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—(S=O)$_2$— group, a $(R^7R^8N)$—($C_1$-$C_6$-alkyl)-(C=O)—NH— group, a $(R^7R^8N)$—($C_1$-$C_6$-alkyl)- group, and a $R^9OOC$— group,
  wherein said heterocycloalkyl group is connected to the rest of the molecule via a carbon atom of said heterocycloalkyl group;
$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, and a $R^9OOC$— group,
  wherein said heterocycloalkyl group is connected to the rest of the molecule via a carbon atom of said heterocycloalkyl group;
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, and a $R^9OOC$— group,
  wherein said heterocycloalkyl group is connected to the rest of the molecule via a carbon atom of said heterocycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—(S=O)$_2$— group, a $(R^7R^8N)$—($C_1$-$C_6$-alkyl)-(C=O)—NH— group, a $(R^7R^8N)$—($C_1$-$C_6$-alkyl)- group and a $R^9OOC$— group,
  wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein X is selected from an oxygen atom and a sulfur atom;
$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_1$-$C_8$-cycloalkenyl group, a $C_3$-$C_8$-cycloalkoxy group, a $R^7R^8N$— group, a heterocycloalkyl group, a phenyl group, a naphthyl group and a heteroaryl group, wherein said heterocycloalkyl group is connected to the rest of the molecule via a carbon atom of said heterocycloalkyl group;

$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group, wherein said heterocycloalkyl group is connected to the rest of the molecule via a carbon atom of said heterocycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group, wherein said heterocycloalkyl group is connected to the rest of the molecule via a carbon atom of said heterocycloalkyl group, wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group, wherein said heterocycloalkyl group is connected to the rest of the molecule via a carbon atom of said heterocycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8N$— group, and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group, wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9$OOC— group,
wherein said heterocycloalkyl group is connected to the rest of the molecule via a carbon atom of said heterocycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C (=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8$N— group, a $(R^7R^8N)$—(S=O)$_2$— group, a $(R^7R^8N)$—$(C_1$-$C_6$-alkyl)-(C=O)—NH— group, a $(R^7R^8N)$—$(C_1$-$C_6$-alkyl)- group and a $R^9$OOC— group,
wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein
X is selected from an oxygen atom and a sulfur atom;
$R^1$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group, and a $C_1$-$C_6$-haloalkyl group;
$R^2$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group, and a $C_1$-$C_6$-haloalkyl group;
$R^3$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8$N— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8$N— group, and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8$N— group, a $(R^7R^8N)$—(S=O)$_2$— group, a $(R^7R^8N)$—$(C_1$-$C_6$-alkyl)-(C=O)—NH— group, a $(R^7R^8N)$—$(C_1$-$C_6$-alkyl)- group, a $R^9$OOC— group, a phenyl group, a naphthyl group, a (phenyl)-O— group and a heteroaryl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group, wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group and a $R^9OOC$— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein X is selected from an oxygen atom and a sulfur atom;

$R^1$ is selected from a hydrogen atom, a halogen atom, a cyano group, a $R^7R^8N$— group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
  wherein said heterocycloalkyl group is connected to the rest of the molecule via a carbon atom of said heterocycloalkyl group,
  wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
    wherein said heterocycloalkyl group is connected to the rest of the molecule via a carbon atom of said heterocycloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8N$— group, and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group,
    wherein said heterocycloalkyl group is connected to the rest of the molecule via a carbon atom of said heterocycloalkyl group,
    wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-$(C=O)$—NH— group, a $(R^7R^8N)$—$(C_1$-$C_6$-alkyl)- group, and a $R^9OOC$— group,
      wherein said heterocycloalkyl group is connected to the rest of the molecule via a carbon atom of said heterocycloalkyl group;
$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
    wherein said heterocycloalkyl group is connected to the rest of the molecule via a carbon atom of said heterocycloalkyl group;
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $HC(=O)$— group, a $(C_1$-$C_6$-alkyl)$C(=O)$— group, a $(C_1$-$C_6$-haloalkyl)$C(=O)$— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-(C=O)—NH— group, a $(R^7R^8N)$—$(C_1$-$C_6$-alkyl)- group and a $R^9OOC$— group,
  wherein said heterocycloalkyl group is connected to the rest of the molecule via a carbon atom of said heterocycloalkyl group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In accordance with further embodiments, the present invention provides compounds of general formula (I), supra, wherein X is selected from an oxygen atom and a sulfur atom;
$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8N$— group, and a heterocycloalkyl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—$(C_1$-$C_6$-alkyl)-(C=O)—NH— group, a $(R^7R^8N)$—$(C_1$-$C_6$-alkyl)- group, a $R^9OOC$— group, a phenyl group, a naphthyl group, a (phenyl)-O— group and a heteroaryl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—$(C_1$-$C_6$-alkyl)-(C=O)—NH— group, a $(R^7R^8N)$—$(C_1$-$C_6$-alkyl)- group, and a $R^9OOC$— group,
  wherein said heterocycloalkyl group is connected to the rest of the molecule via a carbon atom of said heterocycloalkyl group;
$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a (phenyl)-$(S=O)_2$— group, a $(C_1$-$C_6$-alkyl)-$(S=O)_2$— group, a $(C_1$-$C_6$-haloalkyl)-$(S=O)_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9$OOC— group,
wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-($C_1$-$C_6$-alkyl)- group, a $C_1$-$C_6$-hydroxyalkyl group, a $(C_1$-$C_6$-alkoxy)-($C_1$-$C_6$-alkyl)- group, a heterocycloalkyl group, a heteroaryl group and a phenyl group,
wherein said heterocycloalkyl group is connected to the rest of the molecule via a carbon atom of said heterocycloalkyl group,
wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8$N— group, a $(R^7R^8$N)—(S=O)$_2$— group, a $(R^7R^8$N)—($C_1$-$C_6$-alkyl)-(C=O)—NH— group, a $(R^7R^8$N)—($C_1$-$C_6$-alkyl)- group and a $R^9$OOC— group,
wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein X is selected from an oxygen atom and a sulfur atom;

$R^1$ is selected from a hydrogen atom, a halogen atom, a cyano group, a $R^7R^8$N— group, a $C_1$-$C_6$-alkyl group, and a $C_3$-$C_8$-cycloalkyl group;

$R^2$ is selected from a hydrogen atom, a halogen atom, a cyano group, a $R^7R^8$N— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8$N— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8$N— group, and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8$N— group, a $(R^7R^8$N)—(S=O)$_2$— group, a $(R^7R^8$N)—($C_1$-$C_6$-alkyl)-(C=O)—NH— group, a $(R^7R^8$N)—($C_1$-$C_6$-alkyl)- group, a $R^9$OOC— group, a phenyl group, a naphthyl group, a (phenyl)-O— group and a heteroaryl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8$N— group, a $(R^7R^8$N)—(S=O)$_2$— group, a ($R^7R^8N$)—($C_1$-$C_6$-alkyl)-(C=O)—NH— group, a ($R^7R^8N$)—($C_1$-$C_6$-alkyl)- group, and a $R^9OOC$— group, wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a (phenyl)-(S=O)$_2$— group, a ($C_1$-$C_6$-alkyl)-(S=O)$_2$— group, a ($C_1$-$C_6$-haloalkyl)-(S=O)$_2$— group, a phenyl group, a heterocycloalkyl group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group, wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group and a $R^9OOC$— group, wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

In accordance with further embodiments, the present invention provides compounds of general formula (I), supra, wherein X is selected from an oxygen atom and a sulfur atom;

$R^1$ is selected from a hydrogen atom, a halogen atom, a cyano group, a $R^7R^8N$— group, a $C_1$-$C_6$-alkyl group, and a $C_3$-$C_8$-cycloalkyl group;

$R^2$ is selected from a hydrogen atom, a halogen atom, a cyano group, a $R^7R^8N$— group, a $C_1$-$C_6$-alkyl group, and a $C_3$-$C_8$-cycloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group, a $R^7R^8N$— group, and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a $C_1$-$C_6$-thioalkyl group, a heterocycloalkyl group, a $R^7R^8N$— group, a $(R^7R^8N)$—$(C_1$-$C_6$-alkyl)-$(C$=$O)$—NH— group, a $(R^7R^8N)$—$(C_1$-$C_6$-alkyl)- group, a $R^9OOC$— group, a phenyl group, a naphthyl group, a (phenyl)-O— group and a heteroaryl group,
  wherein said heterocycloalkyl group is connected to the rest of the molecule via a carbon atom of said heterocycloalkyl group,
  wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-$(S$=$O)_2$— group, a $(C_1$-$C_6$-alkyl)-$(S$=$O)_2$— group, a $(C_1$-$C_6$-haloalkyl)-$(S$=$O)_2$— group, a phenyl group, a heterocycloalkyl group and a heteroaryl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
  wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_6$-alkyl)C(=O)— group, a $(C_1$-$C_6$-haloalkyl)C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
  wherein said heterocycloalkyl group is connected to the rest of the molecule via a carbon atom of said heterocycloalkyl group,
  wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S$=$O)_2$— group, a $(R^7R^8N)$—$(C_1$-$C_6$-alkyl)-$(C$=$O)$—NH— group, a $(R^7R^8N)$—$(C_1$-$C_6$-alkyl)- group and a $R^9OOC$— group,
  wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
  wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

The present invention provides the compounds of general formula (I) which are disclosed in the Example Section of the Experimental Section of this text, infra.

In some embodiments, the present invention includes compounds of general formula (I) selected from:

N-([1,1'-biphenyl]-2-sulfonyl)-6-[ethyl(methyl)amino]-1-benzofuran-2-carboxamide, N-(benzenesulfonyl)-6-[ethyl(methyl)amino]-1-benzofuran-2-carboxamide,
N-(2,4-dichlorobenzene-1-sulfonyl)-6-[ethyl(methyl)amino]-1-benzofuran-2-carboxamide,
N-(2-chlorobenzene-1-sulfonyl)-6-[ethyl(methyl)amino]-1-benzofuran-2-carboxamide,
N-(2-ethoxybenzene-1-sulfonyl)-6-[ethyl(methyl)amino]-1-benzofuran-2-carboxamide,
N-(2-ethoxybenzene-1-sulfonyl)-6-[methyl(phenyl)amino]-1-benzofuran-2-carboxamide,
N-(benzenesulfonyl)-6-[methyl(phenyl)amino]-1-benzofuran-2-carboxamide,
N-(2-chlorobenzene-1-sulfonyl)-6-[methyl(phenyl)amino]-1-benzofuran-2-carboxamide,
N-(2,4-dichlorobenzene-1-sulfonyl)-6-[methyl(phenyl)amino]-1-benzofuran-2-carboxamide,
N-([1,1'-biphenyl]-2-sulfonyl)-6-[methyl(phenyl)amino]-1-benzofuran-2-carboxamide,
N-([1,1'-biphenyl]-2-sulfonyl)-6-(methylamino)-1-benzofuran-2-carboxamide,
7-(5-chloro-2-methoxyphenyl)-3-[2-oxo-2-(pyrrolidin-1-yl)ethyl][1,2,4]triazolo[1,5-a]pyrimidin-5(3H)-one,
6-(dimethylamino)-N-(2-ethoxybenzene-1-sulfonyl)-4-fluoro-1-benzofuran-2-carboxamide,
N-([1,1'-biphenyl]-2-sulfonyl)-6-(dimethylamino)-1-benzofuran-2-carboxamide,
N-([1,1'-biphenyl]-4-sulfonyl)-6-(dimethylamino)-1-benzofuran-2-carboxamide,
N-(3'-chloro[1,1'-biphenyl]-2-sulfonyl)-6-(dimethylamino)-1-benzofuran-2-carboxamide,
6-(dimethylamino)-N-(2'-methyl[1,1'-biphenyl]-2-sulfonyl)-1-benzofuran-2-carboxamide,
N-(2-bromobenzene-1-sulfonyl)-6-(dimethylamino)-1-benzofuran-2-carboxamide,
6-(dimethylamino)-N-(2-ethoxybenzene-1-sulfonyl)-1-benzofuran-2-carboxamide,
6-(dimethylamino)-N-(naphthalene-1-sulfonyl)-1-benzofuran-2-carboxamide,
6-(dimethylamino)-N-(2-methylquinoline-8-sulfonyl)-1-benzofuran-2-carboxamide,
N-(2-chlorobenzene-1-sulfonyl)-6-(dimethylamino)-1-benzofuran-2-carboxamide,
6-(dimethylamino)-N-(2-propoxybenzene-1-sulfonyl)-1-benzofuran-2-carboxamide,
6-(dimethylamino)-N-(5-methyl[1,1'-biphenyl]-2-sulfonyl)-1-benzofuran-2-carboxamide,
N-(3'-chloro-3-ethoxy[1,1'-biphenyl]-2-sulfonyl)-6-(dimethylamino)-1-benzofuran-2-carboxamide,
6-(dimethylamino)-N-(4-methylbenzene-1-sulfonyl)-1-benzofuran-2-carboxamide,
N-(2,4-dichlorobenzene-1-sulfonyl)-6-(dimethylamino)-1-benzofuran-2-carboxamide,
6-(dimethylamino)-N-(oxane-4-sulfonyl)-1-benzofuran-2-carboxamide,
N-(4-cyanopyridine-2-sulfonyl)-6-(dimethylamino)-1-benzofuran-2-carboxamide,
N-(2,3-dihydro-1-benzofuran-7-sulfonyl)-6-(dimethylamino)-1-benzofuran-2-carboxamide,
6-(dimethylamino)-N-[2-(trifluoromethoxy)benzene-1-sulfonyl]-1-benzofuran-2-carboxamide,
6-(dimethylamino)-N-(2-methylbenzene-1-sulfonyl)-1-benzofuran-2-carboxamide,
N-(2-cyanobenzene-1-sulfonyl)-6-(dimethylamino)-1-benzofuran-2-carboxamide,
6-(dimethylamino)-N-(2-fluorobenzene-1-sulfonyl)-1-benzofuran-2-carboxamide,
N-([1,1'-biphenyl]-2-sulfonyl)-6-(dimethylamino)-4-methyl-1-benzofuran-2-carboxamide,
2-{[6-(dimethylamino)-1-benzofuran-2-carbonyl]sulfamoyl}benzoic acid,
N-([1,1'-biphenyl]-2-sulfonyl)-6-[methyl(propyl)amino]-1-benzofuran-2-carboxamide,
N-([1,1'-biphenyl]-2-sulfonyl)-6-(diethylamino)-1-benzofuran-2-carboxamide,
N-([1,1'-biphenyl]-2-sulfonyl)-6-[(2-methoxyethyl)(methyl)amino]-1-benzofuran-2-carboxamide,
N-([1,1'-biphenyl]-2-sulfonyl)-6-[(cyclopropylmethyl)(methyl)amino]-1-benzofuran-2-carboxamide,
N-([1,1'-biphenyl]-2-sulfonyl)-6-(dibutylamino)-1-benzofuran-2-carboxamide,
6-amino-N-([1,1'-biphenyl]-2-sulfonyl)-1-benzofuran-2-carboxamide,
6-acetamido-N—([1,1'-biphenyl]-2-sulfonyl)-1-benzofuran-2-carboxamide,
N-([1,1'-biphenyl]-2-sulfonyl)-6-[(2S)-2-methylpyrrolidin-1-yl]-1-benzofuran-2-carboxamide,
N-([1,1'-biphenyl]-2-sulfonyl)-6-(pyrrolidin-1-yl)-1-benzofuran-2-carboxamide,
N-([1,1'-biphenyl]-2-sulfonyl)-6-[cyclopentyl(methyl)amino]-1-benzofuran-2-carboxamide,
N-([1,1'-biphenyl]-2-sulfonyl)-6-(piperidin-1-yl)-1-benzofuran-2-carboxamide,
N-([1,1'-biphenyl]-2-sulfonyl)-6-(dimethylamino)-1-benzothiophene-2-carboxamide,
N-(3'-chloro[1,1'-biphenyl]-2-sulfonyl)-6-(dimethylamino)-1-benzothiophene-2-carboxamide,
N-([1,1'-biphenyl]-2-sulfonyl)-7-cyclopropyl-6-(dimethylamino)-1-benzofuran-2-carboxamide,
6-(dimethylamino)-N-[4'-(hydroxymethyl)[1,1'-biphenyl]-2-sulfonyl]-1-benzofuran-2-carboxamide,
6-(dimethylamino)-N-(2-propylbenzene-1-sulfonyl)-1-benzofuran-2-carboxamide,
N-(4-cyano-2-methoxybenzene-1-sulfonyl)-6-(dimethylamino)-1-benzofuran-2-carboxamide,
6-(dimethylamino)-N-[2-(trifluoromethyl)benzene-1-sulfonyl]-1-benzofuran-2-carboxamide ammonia (1/1),
N-[1-(2,4-dichlorophenyl)ethanesulfonyl]-6-(dimethylamino)-1-benzofuran-2-carboxamide,
N-[1-(2,6-dichlorophenyl)ethanesulfonyl]-6-(dimethylamino)-1-benzofuran-2-carboxamide,
N-(5-bromo-2-ethoxybenzene-1-sulfonyl)-6-(dimethylamino)-1-benzofuran-2-carboxamide,
6-(dimethylamino)-N-(4-ethoxypyridine-3-sulfonyl)-1-benzofuran-2-carboxamide,
6-(dimethylamino)-N-(2-hydroxybenzene-1-sulfonyl)-1-benzofuran-2-carboxamide,
ethyl 4-{[6-(dimethylamino)-1-benzofuran-2-carbonyl]sulfamoyl}piperidine-1-carboxylate,
6-(dimethylamino)-N-(ethanesulfonyl)-1-benzofuran-2-carboxamide,
N-([1,1'-biphenyl]-2-sulfonyl)-6-(2-oxopyrrolidin-1-yl)-1-benzofuran-2-carboxamide,
6-(dimethylamino)-N-(methanesulfonyl)-1-benzofuran-2-carboxamide,
N-([1,1'-biphenyl]-2-sulfonyl)-7-cyano-6-(dimethylamino)-1-benzofuran-2-carboxamide,
N-[2-(cyclopropyloxy)benzene-1-sulfonyl]-6-(dimethylamino)-1-benzofuran-2-carboxamide,
6-(dimethylamino)-N-{2-[(propan-2-yl)oxy]benzene-1-sulfonyl}-1-benzofuran-2-carboxamide,
6-(dimethylamino)-N-(2-ethoxy-5-methylbenzene-1-sulfonyl)-1-benzofuran-2-carboxamide, N-(2-tert-butoxybenzene-1-sulfonyl)-6-(dimethylamino)-1-benzofuran-2-carboxamide,
N-[2-(benzyloxy)-6-(cyclobutyloxy)benzene-1-sulfonyl]-6-(dimethylamino)-1-benzofuran-2-carboxamide,
6-(dimethylamino)-N-(7-methoxyquinoline-8-sulfonyl)-1-benzofuran-2-carboxamide,
N-[2-(cyclopropylmethoxy)benzene-1-sulfonyl]-6-(dimethylamino)-1-benzofuran-2-carboxamide,
6-(dimethylamino)-N-[2-(2-fluoroethoxy)benzene-1-sulfonyl]-1-benzofuran-2-carboxamide,
6-(dimethylamino)-N-(quinoline-8-sulfonyl)-1-benzofuran-2-carboxamide,
6-(dimethylamino)-N-[2-(2,2,2-trifluoroethoxy)benzene-1-sulfonyl]-1-benzofuran-2-carboxamide,
N-[2-(2,2-difluoroethoxy)benzene-1-sulfonyl]-6-(dimethylamino)-1-benzofuran-2-carboxamide,
6-(dimethylamino)-N-[2-(2-methylpropoxy)benzene-1-sulfonyl]-1-benzofuran-2-carboxamide,
6-(dimethylamino)-N-[2-(propan-2-yl)benzene-1-sulfonyl]-1-benzofuran-2-carboxamide,
6-(dimethylamino)-N-(2-ethoxy-5-iodobenzene-1-sulfonyl)-1-benzofuran-2-carboxamide,
N-[2-(difluoromethoxy)benzene-1-sulfonyl]-6-(dimethylamino)-1-benzofuran-2-carboxamide,
6-(dimethylamino)-N-(3-ethoxy[1,1'-biphenyl]-2-sulfonyl)-1-benzofuran-2-carboxamide,
6-(dimethylamino)-N-(2-ethoxypyridine-3-sulfonyl)-1-benzofuran-2-carboxamide,
6-(dimethylamino)-N-{2-[(oxetan-3-yl)oxy]benzene-1-sulfonyl}-1-benzofuran-2-carboxamide,
N-(4-chloro-2-methylquinoline-8-sulfonyl)-6-(dimethylamino)-1-benzofuran-2-carboxamide,
N-[2-(cyclobutyloxy)-6-{[(2S)-1,1,1-trifluoropropan-2-yl]oxy}benzene-1-sulfonyl]-6-(dimethylamino)-1-benzofuran-2-carboxamide,
6-(dimethylamino)-N-(2-phenoxybenzene-1-sulfonyl)-1-benzofuran-2-carboxamide,
6-(dimethylamino)-N-{2-methoxy-5-[(1H-pyrazol-1-yl)methyl]benzene-1-sulfonyl}-1-benzofuran-2-carboxamide,
6-(dimethylamino)-N-(3-methylquinoline-8-sulfonyl)-1-benzofuran-2-carboxamide,
6-(dimethylamino)-N-(2-ethoxy-5-nitrobenzene-1-sulfonyl)-1-benzofuran-2-carboxamide ammonia (1/1),
N-{2-chloro-6-[(propan-2-yl)oxy]benzene-1-sulfonyl}-6-(dimethylamino)-1-benzofuran-2-carboxamide,
6-(dimethylamino)-N-[2-(pentyloxy)benzene-1-sulfonyl]-1-benzofuran-2-carboxamide,
6-(dimethylamino)-N-(4-methylquinoline-8-sulfonyl)-1-benzofuran-2-carboxamide,
6-(dimethylamino)-N-(5-nitroquinoline-8-sulfonyl)-1-benzofuran-2-carboxamide,
6-(dimethylamino)-N-[2-(2-methylpropyl)quinoline-8-sulfonyl]-1-benzofuran-2-carboxamide,
6-(dimethylamino)-N-(6-ethyl-2-methylimidazo[1,2-b]pyridazine-3-sulfonyl)-1-benzofuran-2-carboxamide ammonia (1/1),
6-(dimethylamino)-N-(2-methyl-3-oxo-2,3-dihydro-1H-isoindole-4-sulfonyl)-1-benzofuran-2-carboxamide,
6-(dimethylamino)-N-[2-(pentafluoroethoxy)benzene-1-sulfonyl]-1-benzofuran-2-carboxamide,
N-[2-chloro-6-(trifluoromethyl)benzene-1-sulfonyl]-6-(dimethylamino)-1-benzofuran-2-carboxamide,
N-(2,6-dichlorobenzene-1-sulfonyl)-6-(dimethylamino)-1-benzofuran-2-carboxamide,
N-(benzenesulfonyl)-6-(dimethylamino)-1-benzofuran-2-carboxamide,
6-(dimethylamino)-N-{2,3-dimethyl-5-[(1H-pyrazol-1-yl)methyl]benzene-1-sulfonyl}-1-benzofuran-2-carboxamide,
6-(dimethylamino)-N-(3-ethoxypyridine-2-sulfonyl)-1-benzofuran-2-carboxamide,
6-(dimethylamino)-N-{2-ethyl-5-[(1H-pyrazol-1-yl)methyl]benzene-1-sulfonyl}-1-benzofuran-2-carboxamide,
N-{3,4-dimethoxy-5-[(1H-pyrazol-1-yl)methyl]benzene-1-sulfonyl}-6-(dimethylamino)-1-benzofuran-2-carboxamide,
6-(dimethylamino)-N-(2-ethylbenzene-1-sulfonyl)-1-benzofuran-2-carboxamide,
6-(dimethylamino)-N-[(3-methylpyridin-2-yl)methanesulfonyl]-1-benzofuran-2-carboxamide,
6-(dimethylamino)-N-[(pyridin-2-yl)methanesulfonyl]-1-benzofuran-2-carboxamide ammonia (1/1),
6-(dimethylamino)-N-[2-ethoxy-5-(propan-2-yl)benzene-1-sulfonyl]-4-fluoro-1-benzofuran-2-carboxamide,
6-(dimethylamino)-4-fluoro-N-(2-methylquinoline-8-sulfonyl)-1-benzofuran-2-carboxamide,
6-(dimethylamino)-4-fluoro-N-{2-[(propan-2-yl)oxy]benzene-1-sulfonyl}-1-benzofuran-2-carboxamide,
N-[2-(cyclopropyloxy)benzene-1-sulfonyl]-6-(dimethylamino)-4-fluoro-1-benzofuran-2-carboxamide,
6-(dimethylamino)-4-fluoro-N-(2-propoxybenzene-1-sulfonyl)-1-benzofuran-2-carboxamide,
6-(dimethylamino)-4-fluoro-N-(2-methoxybenzene-1-sulfonyl)-1-benzofuran-2-carboxamide,
1-{6-[5-chloro-2-(2-chlorobenzamido)phenyl]pyridin-2-yl}-5-(trifluoromethyl)-1H-pyrazole-4-carboxylic acid,
6-(dimethylamino)-N-(2-methoxybenzene-1-sulfonyl)-1-benzofuran-2-carboxamide,
6-(dimethylamino)-N-(5-methyl-2-propoxybenzene-1-sulfonyl)-1-benzofuran-2-carboxamide,
6-(dimethylamino)-N-(2-ethoxy-6-methylbenzene-1-sulfonyl)-1-benzofuran-2-carboxamide,
tert-butyl [2-(2-{[6-(dimethylamino)-1-benzofuran-2-carbonyl]sulfamoyl}phenoxy)ethyl]carbamate,
N-[4-bromo-2-(trifluoromethoxy)benzene-1-sulfonyl]-6-(dimethylamino)-1-benzofuran-2-carboxamide,
6-(dimethylamino)-N-(2-ethyl-6-propoxybenzene-1-sulfonyl)-1-benzofuran-2-carboxamide,
6-(dimethylamino)-N-[2-ethoxy-4-(trifluoromethyl)pyridine-3-sulfonyl]-1-benzofuran-2-carboxamide,
N-(2-bromo-6-ethoxybenzene-1-sulfonyl)-6-(dimethylamino)-1-benzofuran-2-carboxamide,
N-(3-chloro-2-ethoxybenzene-1-sulfonyl)-6-(dimethylamino)-1-benzofuran-2-carboxamide,
6-(dimethylamino)-N-(2-ethoxy-6-fluorobenzene-1-sulfonyl)-1-benzofuran-2-carboxamide,
N-(6-chloroquinoline-8-sulfonyl)-6-(dimethylamino)-1-benzofuran-2-carboxamide,
6-(dimethylamino)-N-(4-hydroxypyridine-3-sulfonyl)-1-benzofuran-2-carboxamide,
2-[(S)-methanesulfinyl]ethyl 3-[(5-chlorothiophene-2-carbonyl)amino]-N-{3-[(3S)-3-hydroxypyrrolidin-1-yl]benzene-1-sulfonyl}-L-alaninate,
6-(dimethylamino)-N-(2-methoxy-4-methylbenzene-1-sulfonyl)-1-benzofuran-2-carboxamide,
N-(5-acetamido-2-ethoxybenzene-1-sulfonyl)-6-(dimethylamino)-1-benzofuran-2-carboxamide,
6-(dimethylamino)-N-[2-ethoxy-5-(propan-2-yl)benzene-1-sulfonyl]-1-benzofuran-2-carboxamide,
N-(2-amino-6-methylpyridine-3-sulfonyl)-6-(dimethylamino)-1-benzofuran-2-carboxamide, 6-(dimethylamino)-N-(4-ethyl-6-methoxypyrimidine-5-sulfonyl)-1-benzofuran-2-carboxamide,
6-(dimethylamino)-N-[2-methoxy-6-(trifluoromethyl)benzene-1-sulfonyl]-1-benzofuran-2-carboxamide,
6-(dimethylamino)-N-(2-methyl-6-propoxybenzene-1-sulfonyl)-1-benzofuran-2-carboxamide,
6-(dimethylamino)-N-(2,2,3,3-tetrafluoro-2,3-dihydro-1,4-benzodioxine-5-sulfonyl)-1-benzofuran-2-carboxamide,
6-(dimethylamino)-N-(2-{[(2R)-1,1,1-trifluoropropan-2-yl]oxy}benzene-1-sulfonyl)-1-benzofuran-2-carboxamide,
N-(5-bromo-2-chloropyridine-3-sulfonyl)-6-(dimethylamino)-1-benzofuran-2-carboxamide,
N-[4,5-dichloro-2-(trifluoromethoxy)benzene-1-sulfonyl]-6-(dimethylamino)-1-benzofuran-2-carboxamide,
N-(5-chloro-2-methoxy-4-methylbenzene-1-sulfonyl)-6-(dimethylamino)-1-benzofuran-2-carboxamide,
N-(2-chloro-5-methoxybenzene-1-sulfonyl)-6-(dimethylamino)-1-benzofuran-2-carboxamide,
6-(dimethylamino)-N-[2-(methanesulfonyl)-6-methoxybenzene-1-sulfonyl]-1-benzofuran-2-carboxamide,
6-(dimethylamino)-N-[2-(dimethylsulfamoyl)-6-methoxybenzene-1-sulfonyl]-1-benzofuran-2-carboxamide,
N-[2-(cyclobutyloxy)-6-fluorobenzene-1-sulfonyl]-6-(dimethylamino)-1-benzofuran-2-carboxamide,
6-(dimethylamino)-N-(2-ethoxy-5-ethylbenzene-1-sulfonyl)-1-benzofuran-2-carboxamide,
6-(dimethylamino)-N-[2-(2-methoxyethoxy)benzene-1-sulfonyl]-1-benzofuran-2-carboxamide,
N-{5-bromo-2-[(propan-2-yl)amino]pyridine-3-sulfonyl}-6-(dimethylamino)-1-benzofuran-2-carboxamide,
N-[5-bromo-2-(cyclopropylamino)pyridine-3-sulfonyl]-6-(dimethylamino)-1-benzofuran-2-carboxamide,
6-(dimethylamino)-N-(2-ethyl-6-methoxybenzene-1-sulfonyl)-1-benzofuran-2-carboxamide,
N-(5-bromo-2-methoxybenzene-1-sulfonyl)-6-(dimethylamino)-1-benzofuran-2-carboxamide,
N-(5-chloro-2-methoxybenzene-1-sulfonyl)-6-(dimethylamino)-1-benzofuran-2-carboxamide,
N-[5-bromo-2-(propylamino)pyridine-3-sulfonyl]-6-(dimethylamino)-1-benzofuran-2-carboxamide,
6-(dimethylamino)-N-[4-(3-methylanilino)pyridine-3-sulfonyl]-1-benzofuran-2-carboxamide,
6-(dimethylamino)-N-(6-methoxypyridine-3-sulfonyl)-1-benzofuran-2-carboxamide,
6-(dimethylamino)-N-(2,3,4-trifluorobenzene-1-sulfonyl)-1-benzofuran-2-carboxamide,
N-(2-chloro-5-methylpyridine-3-sulfonyl)-6-(dimethylamino)-1-benzofuran-2-carboxamide,
6-(dimethylamino)-N-{2-fluoro-6-[(propan-2-yl)amino]benzene-1-sulfonyl}-1-benzofuran-2-carboxamide,
N-(2-chloropyridine-3-sulfonyl)-6-(dimethylamino)-1-benzofuran-2-carboxamide,
N-(2-cyclopentyl-6-methylbenzene-1-sulfonyl)-6-(dimethylamino)-1-benzofuran-2-carboxamide,
N-(2-cyclobutyl-6-fluorobenzene-1-sulfonyl)-6-(dimethylamino)-1-benzofuran-2-carboxamide,
N-[2-(difluoromethoxy)-4-methylbenzene-1-sulfonyl]-6-(dimethylamino)-1-benzofuran-2-carboxamide,
N-[2-(cyclopropylmethoxy)-6-fluorobenzene-1-sulfonyl]-6-(dimethylamino)-1-benzofuran-2-carboxamide,
6-(dimethylamino)-N-[5-(hydroxymethyl)-2-(trifluoromethoxy)benzene-1-sulfonyl]-1-benzofuran-2-carboxamide,
6-(dimethylamino)-N-[2,5-di(propan-2-yl)benzene-1-sulfonyl]-1-benzofuran-2-carboxamide,
N-[2-chloro-5-(1-hydroxyethyl)benzene-1-sulfonyl]-6-(dimethylamino)-1-benzofuran-2-carboxamide,
N-[2-chloro-5-(2-methoxyethoxy)benzene-1-sulfonyl]-6-(dimethylamino)-1-benzofuran-2-carboxamide,
N-{2-[(2,2-difluoroethyl)amino]-5-(trifluoromethyl)benzene-1-sulfonyl}-6-(dimethylamino)-1-benzofuran-2-carboxamide,
N-(5-aminoquinoline-8-sulfonyl)-6-(dimethylamino)-1-benzofuran-2-carboxamide,
N-[2-(2-aminoethoxy)benzene-1-sulfonyl]-6-(dimethylamino)-1-benzofuran-2-carboxamide hydrogen chloride (1/1),
6-(dimethylamino)-N-(2-{2-[2-(2-{2-[(7-nitro-2,1,3-benzoxadiazol-4-yl)amino]ethoxy}ethoxy)ethoxy]ethoxy}benzene-1-sulfonyl)-1-benzofuran-2-carboxamide,
6-(dimethylamino)-N-(2-ethoxy-3-fluorobenzene-1-sulfonyl)-1-benzofuran-2-carboxamide,
N-{5-[(2S)-butan-2-yl]-2-ethoxybenzene-1-sulfonyl}-6-(dimethylamino)-1-benzofuran-2-carboxamide,
6-(dimethylamino)-N-(2-ethoxy-4-fluorobenzene-1-sulfonyl)-1-benzofuran-2-carboxamide,
6-(dimethylamino)-N-[2-ethoxy-5-(trifluoromethyl)benzene-1-sulfonyl]-1-benzofuran-2-carboxamide,
6-(dimethylamino)-N-(2-ethoxy-5-fluorobenzene-1-sulfonyl)-1-benzofuran-2-carboxamide,
6-(dimethylamino)-N-(2-ethoxy-5-phenoxybenzene-1-sulfonyl)-1-benzofuran-2-carboxamide,
6-(Dimethylamino)-N-[2-ethoxy-5-(trifluoromethoxy)phenyl]sulfonyl-benzofuran-2-carboxamide,
N-[2-(benzyloxy)-5-(propan-2-yl)benzene-1-sulfonyl]-6-(dimethylamino)-1-benzofuran-2-carboxamide,
N-[2-(cyclopropylmethoxy)-5-(propan-2-yl)benzene-1-sulfonyl]-6-(dimethylamino)-1-benzofuran-2-carboxamide,
6-(dimethylamino)-N-[5-(propan-2-yl)-2-(2,2,2-trifluoroethoxy)benzene-1-sulfonyl]-1-benzofuran-2-carboxamide,
N-[2-(benzyloxy)-5-tert-butylbenzene-1-sulfonyl]-6-(dimethylamino)-1-benzofuran-2-carboxamide,
N-[5-tert-butyl-2-(cyclopropylmethoxy)benzene-1-sulfonyl]-6-(dimethylamino)-1-benzofuran-2-carboxamide,
N-[5-tert-butyl-2-(2,2,2-trifluoroethoxy)benzene-1-sulfonyl]-6-(dimethylamino)-1-benzofuran-2-carboxamide,
N-[5-tert-butyl-2-(cyclobutyloxy)benzene-1-sulfonyl]-6-(dimethylamino)-1-benzofuran-2-carboxamide,
N-{5-tert-butyl-2-[(propan-2-yl)oxy]benzene-1-sulfonyl}-6-(dimethylamino)-1-benzofuran-2-carboxamide,
N-[2-(cyclobutyloxy)-5-(propan-2-yl)benzene-1-sulfonyl]-6-(dimethylamino)-1-benzofuran-2-carboxamide,
N-(5-tert-butyl-2-methoxybenzene-1-sulfonyl)-6-(dimethylamino)-1-benzofuran-2-carboxamide,
N-[2-{[(1R)-2,2-difluorocyclopropyl]methoxy}-5-(propan-2-yl)benzene-1-sulfonyl]-6-(dimethylamino)-1-benzofuran-2-carboxamide,
4-[(3Z)-3-{1-cyano-2-[(oxan-4-yl)methoxy]-2-oxoethylidene}-3,4-dihydropyrazin-2-yl]piperazin-1-ium formate,
4-[(3Z)-3-{1-cyano-2-[(oxan-4-yl)methoxy]-2-oxoethylidene}-3,4-dihydropyrazin-2-yl]piperazin-1-ium formate,
5-chloro-6-(dimethylamino)-N-(2-ethoxybenzene-1-sulfonyl)-1-benzofuran-2-carboxamide,
5-chloro-6-(dimethylamino)-1-benzofuran-2-carboxylic acid,
N-([1,1'-biphenyl]-2-sulfonyl)-5-(pyridin-3-yl)thiophene-2-carboxamide,
propan-2-yl (4R*)-4-(5-chloro-3-fluoropyridin-2-yl)-2-[5-(difluoromethoxy)pyridin-3-yl]-6-methyl-1,4-dihydropyrimidine-5-carboxylate, N-([1,1'-biphenyl]-2-sulfonyl)-6-(dimethylamino)-4-(trifluoromethyl)-1-benzofuran-2-carboxamide,
N-(benzenesulfonyl)-6-(dimethylamino)-4-(trifluoromethyl)-1-benzofuran-2-carboxamide,
6-(dimethylamino)-N-(2-ethoxybenzene-1-sulfonyl)-4-(trifluoromethyl)-1-benzofuran-2-carboxamide,
6-(Dimethylamino)-N-((2-methylquinolin-8-yl)sulfonyl)-4-(trifluoromethyl)benzofuran-2-carboxamide,
6-(Dimethylamino)-5-fluoro-N-((2-methylquinolin-8-yl)sulfonyl)benzofuran-2-carboxamide,
6-(Dimethylamino)-N-((2-ethoxyphenyl)sulfonyl)-5-fluorobenzofuran-2-carboxamide,
N-([1,1'-biphenyl]-2-ylsulfonyl)-6-(dimethylamino)-5-fluorobenzofuran-2-carboxamide,
(9R,12R,15S)-9-[(1H-indol-3-yl)methyl]-17-methyl-12,15-di(propan-2-yl)-6,7,8,9,11,12,14,15,18,19-decahydro[1,4,7,10,13]pentaazacycloheptadecino[16,17,1-hi]indazole-10,13,16(17H)-trione,
6-(dimethylamino)-N-(2-ethoxybenzene-1-sulfonyl)-5-(trifluoromethyl)-1-benzofuran-2-carboxamide,
(3R)-3-[4-(2-cyclopropylethyl)phenyl]-3-methyl-6-(trifluoromethyl)-1,3-dihydro-2H-indol-2-one,
N-([1,1'-biphenyl]-2-sulfonyl)-7-bromo-6-(dimethylamino)-1-benzofuran-2-carboxamide,
5-cyano-6-(dimethylamino)-N-(2-ethoxybenzene-1-sulfonyl)-1-benzofuran-2-carboxamide,
6-[(2-methoxyethyl)(methyl)amino]-N-(2-methylquinoline-8-sulfonyl)-1-benzofuran-2-carboxamide,
N-([1,1'-biphenyl]-2-sulfonyl)-5-bromo-6-(dimethylamino)-7-fluoro-1-benzofuran-2-carboxamide,
5-bromo-N-[2-(cyclopropyloxy)benzene-1-sulfonyl]-6-(dimethylamino)-1-benzofuran-2-carboxamide,
5-bromo-6-(dimethylamino)-N-{2-[(propan-2-yl)oxy]benzene-1-sulfonyl}-1-benzofuran-2-carboxamide,
2-[(3R)-4,4-difluoro-3-methyl[1,4'-bipiperidin]-1'-yl]-N-[(3,5-difluoropyridin-2-yl)methyl]-1,3-thiazole-5-carboxamide,
N-([1,1'-biphenyl]-2-sulfonyl)-6-(dimethylamino)-1-methyl-1H-indole-2-carboxamide,
N-([1,1'-biphenyl]-2-sulfonyl)-6-(ethylamino)-1-benzofuran-2-carboxamide,
N-(2-ethoxybenzene-1-sulfonyl)-6-(ethylamino)-1-benzofuran-2-carboxamide,
N-(5-bromo-2-ethoxybenzene-1-sulfonyl)-6-[(2-methoxyethyl)(methyl)amino]-1-benzofuran-2-carboxamide,
6-[(2-methoxyethyl)(methyl)amino]-N-(5-methyl[1,1'-biphenyl]-2-sulfonyl)-1-benzofuran-2-carboxamide,
N-(2-ethoxybenzene-1-sulfonyl)-6-[(2-methoxyethyl)(methyl)amino]-1-benzofuran-2-carboxamide,
5-bromo-6-(dimethylamino)-N-(2-methylquinoline-8-sulfonyl)-1-benzofuran-2-carboxamide,
N-([1,1'-biphenyl]-2-sulfonyl)-5-bromo-6-(dimethylamino)-1-benzofuran-2-carboxamide,
5-bromo-6-(dimethylamino)-N-(2-ethoxybenzene-1-sulfonyl)-1-benzofuran-2-carboxamide,
2-(4-chloro-3-fluorophenyl)-5-cyclopropyl-N-[(1R)-1-(4-fluorophenyl)-3-hydroxypropyl]-4-oxo-3,4-dihydropyrrolo[2,1-f][1,2,4]triazine-6-carboxamide,
6-(ethylamino)-N-(2-methylquinoline-8-sulfonyl)-1-benzofuran-2-carboxamide,
N-[2-(cyclobutyloxy)-6-{[(2R*)-1,1,1-trifluoropropan-2-yl]oxy}benzene-1-sulfonyl]-6-(dimethylamino)-1-benzofuran-2-carboxamide,
N-[2-(cyclobutyloxy)-6-{[(2R*)-1,1,1-trifluoropropan-2-yl]oxy}benzene-1-sulfonyl]-6-(dimethylamino)-1-benzofuran-2-carboxamide,
sodium [6-(dimethylamino)-1-benzofuran-2-carbonyl](2-ethoxybenzene-1-sulfonyl)azanide,
sodium [6-(dimethylamino)-1-benzofuran-2-carbonyl]{2-[(propan-2-yl)oxy]benzene-1-sulfonyl}azanide,
sodium [6-(dimethylamino)-1-benzofuran-2-carbonyl](2-methylquinoline-8-sulfonyl)azanide,
tert-butyl (4-amino-5-benzoyl-1,3-thiazol-2-yl)pyridin-3-ylcarbamate,
sodium [6-(dimethylamino)-4-fluoro-1-benzofuran-2-carbonyl](2-methylquinoline-8-sulfonyl)azanide,
6-(Dimethylamino)-N-((2-ethoxy-4,5-difluorophenyl)sulfonyl)benzofuran-2-carboxamide,
N-((5-cyclopropyl-2-ethoxyphenyl)sulfonyl)-6-(dimethylamino)benzofuran-2-carboxamide,
6-(Dimethylamino)-N-((2-methoxy-5-(2-oxopropyl)phenyl)sulfonyl)benzofuran-2-carboxamide and
N-((5-(tert-butyl)-2-cyclopropoxyphenyl)sulfonyl)-6-(dimethylamino)benzofuran-2-carboxamide In some embodiments, the present invention includes compounds of general formula (I) selected from:
N-[2-(cyclopropyloxy)benzene-1-sulfonyl]-6-(dimethylamino)-1-benzofuran-2-carboxamide,
6-(dimethylamino)-N-{2-[(propan-2-yl)oxy]benzene-1-sulfonyl}-1-benzofuran-2-carboxamide,
6-(dimethylamino)-N-(2-ethoxy-5-methylbenzene-1-sulfonyl)-1-benzofuran-2-carboxamide,
N-(2-tert-butoxybenzene-1-sulfonyl)-6-(dimethylamino)-1-benzofuran-2-carboxamide,
N-[2-(benzyloxy)-6-(cyclobutyloxy)benzene-1-sulfonyl]-6-(dimethylamino)-1-benzofuran-2-carboxamide,
6-(dimethylamino)-N-(7-methoxyquinoline-8-sulfonyl)-1-benzofuran-2-carboxamide,
N-[2-(cyclopropylmethoxy)benzene-1-sulfonyl]-6-(dimethylamino)-1-benzofuran-2-carboxamide,
6-(dimethylamino)-N-[2-(2-fluoroethoxy)benzene-1-sulfonyl]-1-benzofuran-2-carboxamide,
6-(dimethylamino)-N-(quinoline-8-sulfonyl)-1-benzofuran-2-carboxamide,
6-(dimethylamino)-N-[2-(2,2,2-trifluoroethoxy)benzene-1-sulfonyl]-1-benzofuran-2-carboxamide,
N-[2-(2,2-difluoroethoxy)benzene-1-sulfonyl]-6-(dimethylamino)-1-benzofuran-2-carboxamide,
6-(dimethylamino)-N-[2-(2-methylpropoxy)benzene-1-sulfonyl]-1-benzofuran-2-carboxamide,
6-(dimethylamino)-N-[2-(propan-2-yl)benzene-1-sulfonyl]-1-benzofuran-2-carboxamide,
6-(dimethylamino)-N-(2-ethoxy-5-iodobenzene-1-sulfonyl)-1-benzofuran-2-carboxamide,
N-[2-(difluoromethoxy)benzene-1-sulfonyl]-6-(dimethylamino)-1-benzofuran-2-carboxamide,
6-(dimethylamino)-N-(3-ethoxy[1,1'-biphenyl]-2-sulfonyl)-1-benzofuran-2-carboxamide,
6-(dimethylamino)-N-(2-ethoxypyridine-3-sulfonyl)-1-benzofuran-2-carboxamide,
6-(dimethylamino)-N-{2-[(oxetan-3-yl)oxy]benzene-1-sulfonyl}-1-benzofuran-2-carboxamide,
N-(4-chloro-2-methylquinoline-8-sulfonyl)-6-(dimethylamino)-1-benzofuran-2-carboxamide,
N-[2-(cyclobutyloxy)-6-{[(2S)-1,1,1-trifluoropropan-2-yl]oxy}benzene-1-sulfonyl]-6-(dimethylamino)-1-benzofuran-2-carboxamide,
6-(dimethylamino)-N-(2-phenoxybenzene-1-sulfonyl)-1-benzofuran-2-carboxamide,
6-(dimethylamino)-N-{2-methoxy-5-[(1H-pyrazol-1-yl)methyl]benzene-1-sulfonyl}-1-benzofuran-2-carboxamide, 6-(dimethylamino)-N-(3-methylquinoline-8-sulfonyl)-1-benzofuran-2-carboxamide,
6-(dimethylamino)-N-(2-ethoxy-5-nitrobenzene-1-sulfonyl)-1-benzofuran-2-carboxamide ammonia (1/1),
N-{2-chloro-6-[(propan-2-yl)oxy]benzene-1-sulfonyl}-6-(dimethylamino)-1-benzofuran-2-carboxamide,
6-(dimethylamino)-N-[2-(pentyloxy)benzene-1-sulfonyl]-1-benzofuran-2-carboxamide,
6-(dimethylamino)-N-(4-methylquinoline-8-sulfonyl)-1-benzofuran-2-carboxamide,
6-(dimethylamino)-N-(5-nitroquinoline-8-sulfonyl)-1-benzofuran-2-carboxamide,
6-(dimethylamino)-N-[2-(2-methylpropyl)quinoline-8-sulfonyl]-1-benzofuran-2-carboxamide,
6-(dimethylamino)-N-(6-ethyl-2-methylimidazo[1,2-b]pyridazine-3-sulfonyl)-1-benzofuran-2-carboxamide ammonia (1/1),
6-(dimethylamino)-N-(2-methyl-3-oxo-2,3-dihydro-1H-isoindole-4-sulfonyl)-1-benzofuran-2-carboxamide,
6-(dimethylamino)-N-[2-(pentafluoroethoxy)benzene-1-sulfonyl]-1-benzofuran-2-carboxamide,
N-[2-chloro-6-(trifluoromethyl)benzene-1-sulfonyl]-6-(dimethylamino)-1-benzofuran-2-carboxamide,
N-(2,6-dichlorobenzene-1-sulfonyl)-6-(dimethylamino)-1-benzofuran-2-carboxamide,
N-(benzenesulfonyl)-6-(dimethylamino)-1-benzofuran-2-carboxamide,
6-(dimethylamino)-N-{2,3-dimethyl-5-[(1H-pyrazol-1-yl)methyl]benzene-1-sulfonyl}-1-benzofuran-2-carboxamide,
6-(dimethylamino)-N-(3-ethoxypyridine-2-sulfonyl)-1-benzofuran-2-carboxamide,
6-(dimethylamino)-N-{2-ethyl-5-[(1H-pyrazol-1-yl)methyl]benzene-1-sulfonyl}-1-benzofuran-2-carboxamide,
N-{3,4-dimethoxy-5-[(1H-pyrazol-1-yl)methyl]benzene-1-sulfonyl}-6-(dimethylamino)-1-benzofuran-2-carboxamide,
6-(dimethylamino)-N-(2-ethylbenzene-1-sulfonyl)-1-benzofuran-2-carboxamide,
6-(dimethylamino)-N-[(3-methylpyridin-2-yl)methanesulfonyl]-1-benzofuran-2-carboxamide,
6-(dimethylamino)-N-[(pyridin-2-yl)methanesulfonyl]-1-benzofuran-2-carboxamide ammonia (1/1),
6-(dimethylamino)-N-[2-ethoxy-5-(propan-2-yl)benzene-1-sulfonyl]-4-fluoro-1-benzofuran-2-carboxamide,
6-(dimethylamino)-4-fluoro-N-(2-methylquinoline-8-sulfonyl)-1-benzofuran-2-carboxamide,
6-(dimethylamino)-4-fluoro-N-{2-[(propan-2-yl)oxy]benzene-1-sulfonyl}-1-benzofuran-2-carboxamide,
N-[2-(cyclopropyloxy)benzene-1-sulfonyl]-6-(dimethylamino)-4-fluoro-1-benzofuran-2-carboxamide,
6-(dimethylamino)-4-fluoro-N-(2-propoxybenzene-1-sulfonyl)-1-benzofuran-2-carboxamide,
6-(dimethylamino)-4-fluoro-N-(2-methoxybenzene-1-sulfonyl)-1-benzofuran-2-carboxamide,
1-{6-[5-chloro-2-(2-chlorobenzamido)phenyl]pyridin-2-yl}-5-(trifluoromethyl)-1H-pyrazole-4-carboxylic acid,
6-(dimethylamino)-N-(2-methoxybenzene-1-sulfonyl)-1-benzofuran-2-carboxamide,
6-(dimethylamino)-N-(5-methyl-2-propoxybenzene-1-sulfonyl)-1-benzofuran-2-carboxamide,
6-(dimethylamino)-N-(2-ethoxy-6-methylbenzene-1-sulfonyl)-1-benzofuran-2-carboxamide,
tert-butyl [2-(2-{[6-(dimethylamino)-1-benzofuran-2-carbonyl]sulfamoyl}phenoxy)ethyl]carbamate,
N-[4-bromo-2-(trifluoromethoxy)benzene-1-sulfonyl]-6-(dimethylamino)-1-benzofuran-2-carboxamide,
6-(dimethylamino)-N-(2-ethyl-6-propoxybenzene-1-sulfonyl)-1-benzofuran-2-carboxamide,
6-(dimethylamino)-N-[2-ethoxy-4-(trifluoromethyl)pyridine-3-sulfonyl]-1-benzofuran-2-carboxamide,
N-(2-bromo-6-ethoxybenzene-1-sulfonyl)-6-(dimethylamino)-1-benzofuran-2-carboxamide,
N-(3-chloro-2-ethoxybenzene-1-sulfonyl)-6-(dimethylamino)-1-benzofuran-2-carboxamide,
6-(dimethylamino)-N-(2-ethoxy-6-fluorobenzene-1-sulfonyl)-1-benzofuran-2-carboxamide,
N-(6-chloroquinoline-8-sulfonyl)-6-(dimethylamino)-1-benzofuran-2-carboxamide,
6-(dimethylamino)-N-(4-hydroxypyridine-3-sulfonyl)-1-benzofuran-2-carboxamide,
2-[(S)-methanesulfinyl]ethyl 3-[(5-chlorothiophene-2-carbonyl)amino]-N-{3-[(3S)-3-hydroxypyrrolidin-1-yl]benzene-1-sulfonyl}-L-alaninate,
6-(dimethylamino)-N-(2-methoxy-4-methylbenzene-1-sulfonyl)-1-benzofuran-2-carboxamide,
N-(5-acetamido-2-ethoxybenzene-1-sulfonyl)-6-(dimethylamino)-1-benzofuran-2-carboxamide,
6-(dimethylamino)-N-[2-ethoxy-5-(propan-2-yl)benzene-1-sulfonyl]-1-benzofuran-2-carboxamide,
N-(2-amino-6-methylpyridine-3-sulfonyl)-6-(dimethylamino)-1-benzofuran-2-carboxamide,
6-(dimethylamino)-N-(4-ethyl-6-methoxypyrimidine-5-sulfonyl)-1-benzofuran-2-carboxamide,
6-(dimethylamino)-N-[2-methoxy-6-(trifluoromethyl)benzene-1-sulfonyl]-1-benzofuran-2-carboxamide,
6-(dimethylamino)-N-(2-methyl-6-propoxybenzene-1-sulfonyl)-1-benzofuran-2-carboxamide,
6-(dimethylamino)-N-(2,2,3,3-tetrafluoro-2,3-dihydro-1,4-benzodioxine-5-sulfonyl)-1-benzofuran-2-carboxamide,
6-(dimethylamino)-N-(2-{[(2R)-1,1,1-trifluoropropan-2-yl]oxy}benzene-1-sulfonyl)-1-benzofuran-2-carboxamide,
N-(5-bromo-2-chloropyridine-3-sulfonyl)-6-(dimethylamino)-1-benzofuran-2-carboxamide,
N-[4,5-dichloro-2-(trifluoromethoxy)benzene-1-sulfonyl]-6-(dimethylamino)-1-benzofuran-2-carboxamide,
N-(5-chloro-2-methoxy-4-methylbenzene-1-sulfonyl)-6-(dimethylamino)-1-benzofuran-2-carboxamide,
N-(2-chloro-5-methoxybenzene-1-sulfonyl)-6-(dimethylamino)-1-benzofuran-2-carboxamide,
6-(dimethylamino)-N-[2-(methanesulfonyl)-6-methoxybenzene-1-sulfonyl]-1-benzofuran-2-carboxamide,
6-(dimethylamino)-N-[2-(dimethylsulfamoyl)-6-methoxybenzene-1-sulfonyl]-1-benzofuran-2-carboxamide,
N-[2-(cyclobutyloxy)-6-fluorobenzene-1-sulfonyl]-6-(dimethylamino)-1-benzofuran-2-carboxamide,
6-(dimethylamino)-N-(2-ethoxy-5-ethylbenzene-1-sulfonyl)-1-benzofuran-2-carboxamide,
6-(dimethylamino)-N-[2-(2-methoxyethoxy)benzene-1-sulfonyl]-1-benzofuran-2-carboxamide,
N-{5-bromo-2-[(propan-2-yl)amino]pyridine-3-sulfonyl}-6-(dimethylamino)-1-benzofuran-2-carboxamide,
N-[5-bromo-2-(cyclopropylamino)pyridine-3-sulfonyl]-6-(dimethylamino)-1-benzofuran-2-carboxamide,
6-(dimethylamino)-N-(2-ethyl-6-methoxybenzene-1-sulfonyl)-1-benzofuran-2-carboxamide,
N-(5-bromo-2-methoxybenzene-1-sulfonyl)-6-(dimethylamino)-1-benzofuran-2-carboxamide,
N-(5-chloro-2-methoxybenzene-1-sulfonyl)-6-(dimethylamino)-1-benzofuran-2-carboxamide,
N-[5-bromo-2-(propylamino)pyridine-3-sulfonyl]-6-(dimethylamino)-1-benzofuran-2-carboxamide, 6-(dimethylamino)-N-[4-(3-methylanilino)pyridine-3-sulfonyl]-1-benzofuran-2-carboxamide,
6-(dimethylamino)-N-(6-methoxypyridine-3-sulfonyl)-1-benzofuran-2-carboxamide,
6-(dimethylamino)-N-(2,3,4-trifluorobenzene-1-sulfonyl)-1-benzofuran-2-carboxamide,
N-(2-chloro-5-methylpyridine-3-sulfonyl)-6-(dimethylamino)-1-benzofuran-2-carboxamide,
6-(dimethylamino)-N-{2-fluoro-6-[(propan-2-yl)amino]benzene-1-sulfonyl}-1-benzofuran-2-carboxamide,
N-(2-chloropyridine-3-sulfonyl)-6-(dimethylamino)-1-benzofuran-2-carboxamide,
N-(2-cyclopentyl-6-methylbenzene-1-sulfonyl)-6-(dimethylamino)-1-benzofuran-2-carboxamide,
N-(2-cyclobutyl-6-fluorobenzene-1-sulfonyl)-6-(dimethylamino)-1-benzofuran-2-carboxamide,
N-[2-(difluoromethoxy)-4-methylbenzene-1-sulfonyl]-6-(dimethylamino)-1-benzofuran-2-carboxamide,
N-[2-(cyclopropylmethoxy)-6-fluorobenzene-1-sulfonyl]-6-(dimethylamino)-1-benzofuran-2-carboxamide,
6-(dimethylamino)-N-[5-(hydroxymethyl)-2-(trifluoromethoxy)benzene-1-sulfonyl]-1-benzofuran-2-carboxamide,
6-(dimethylamino)-N-[2,5-di(propan-2-yl)benzene-1-sulfonyl]-1-benzofuran-2-carboxamide,
N-[2-chloro-5-(1-hydroxyethyl)benzene-1-sulfonyl]-6-(dimethylamino)-1-benzofuran-2-carboxamide,
N-[2-chloro-5-(2-methoxyethoxy)benzene-1-sulfonyl]-6-(dimethylamino)-1-benzofuran-2-carboxamide,
N-{2-[(2,2-difluoroethyl)amino]-5-(trifluoromethyl)benzene-1-sulfonyl}-6-(dimethylamino)-1-benzofuran-2-carboxamide,
N-(5-aminoquinoline-8-sulfonyl)-6-(dimethylamino)-1-benzofuran-2-carboxamide,
N-[2-(2-aminoethoxy)benzene-1-sulfonyl]-6-(dimethylamino)-1-benzofuran-2-carboxamide hydrogen chloride (1/1),
6-(dimethylamino)-N-(2-{2-[2-(2-{2-[(7-nitro-2,1,3-benzoxadiazol-4-yl)amino]ethoxy}ethoxy)ethoxy]ethoxy}benzene-1-sulfonyl)-1-benzofuran-2-carboxamide,
6-(dimethylamino)-N-(2-ethoxy-3-fluorobenzene-1-sulfonyl)-1-benzofuran-2-carboxamide,
N-{5-[(2S)-butan-2-yl]-2-ethoxybenzene-1-sulfonyl}-6-(dimethylamino)-1-benzofuran-2-carboxamide,
6-(dimethylamino)-N-(2-ethoxy-4-fluorobenzene-1-sulfonyl)-1-benzofuran-2-carboxamide,
6-(dimethylamino)-N-[2-ethoxy-5-(trifluoromethyl)benzene-1-sulfonyl]-1-benzofuran-2-carboxamide,
6-(dimethylamino)-N-(2-ethoxy-5-fluorobenzene-1-sulfonyl)-1-benzofuran-2-carboxamide,
6-(dimethylamino)-N-(2-ethoxy-5-phenoxybenzene-1-sulfonyl)-1-benzofuran-2-carboxamide,
6-(Dimethylamino)-N-[2-ethoxy-5-(trifluoromethoxy)phenyl]sulfonyl-benzofuran-2-carboxamide,
N-[2-(benzyloxy)-5-(propan-2-yl)benzene-1-sulfonyl]-6-(dimethylamino)-1-benzofuran-2-carboxamide,
N-[2-(cyclopropylmethoxy)-5-(propan-2-yl)benzene-1-sulfonyl]-6-(dimethylamino)-1-benzofuran-2-carboxamide,
6-(dimethylamino)-N-[5-(propan-2-yl)-2-(2,2,2-trifluoroethoxy)benzene-1-sulfonyl]-1-benzofuran-2-carboxamide,
N-[2-(benzyloxy)-5-tert-butylbenzene-1-sulfonyl]-6-(dimethylamino)-1-benzofuran-2-carboxamide,
N-[5-tert-butyl-2-(cyclopropylmethoxy)benzene-1-sulfonyl]-6-(dimethylamino)-1-benzofuran-2-carboxamide,
N-[5-tert-butyl-2-(2,2,2-trifluoroethoxy)benzene-1-sulfonyl]-6-(dimethylamino)-1-benzofuran-2-carboxamide,
N-[5-tert-butyl-2-(cyclobutyloxy)benzene-1-sulfonyl]-6-(dimethylamino)-1-benzofuran-2-carboxamide,
N-{5-tert-butyl-2-[(propan-2-yl)oxy]benzene-1-sulfonyl}-6-(dimethylamino)-1-benzofuran-2-carboxamide,
N-[2-(cyclobutyloxy)-5-(propan-2-yl)benzene-1-sulfonyl]-6-(dimethylamino)-1-benzofuran-2-carboxamide,
N-(5-tert-butyl-2-methoxybenzene-1-sulfonyl)-6-(dimethylamino)-1-benzofuran-2-carboxamide,
N-[2-{[(1R)-2,2-difluorocyclopropyl]methoxy}-5-(propan-2-yl)benzene-1-sulfonyl]-6-(dimethylamino)-1-benzofuran-2-carboxamide,
4-[(3Z)-3-{1-cyano-2-[(oxan-4-yl)methoxy]-2-oxoethylidene}-3,4-dihydropyrazin-2-yl]piperazin-1-ium formate,
4-[(3Z)-3-{1-cyano-2-[(oxan-4-yl)methoxy]-2-oxoethylidene}-3,4-dihydropyrazin-2-yl]piperazin-1-ium formate,
5-chloro-6-(dimethylamino)-N-(2-ethoxybenzene-1-sulfonyl)-1-benzofuran-2-carboxamide,
5-chloro-6-(dimethylamino)-1-benzofuran-2-carboxylic acid,
N-([1,1'-biphenyl]-2-sulfonyl)-5-(pyridin-3-yl)thiophene-2-carboxamide,
propan-2-yl (4R*)-4-(5-chloro-3-fluoropyridin-2-yl)-2-[5-(difluoromethoxy)pyridin-3-yl]-6-methyl-1,4-dihydropyrimidine-5-carboxylate,
N-([1,1'-biphenyl]-2-sulfonyl)-6-(dimethylamino)-4-(trifluoromethyl)-1-benzofuran-2-carboxamide,
N-(benzenesulfonyl)-6-(dimethylamino)-4-(trifluoromethyl)-1-benzofuran-2-carboxamide,
6-(dimethylamino)-N-(2-ethoxybenzene-1-sulfonyl)-4-(trifluoromethyl)-1-benzofuran-2-carboxamide,
6-(Dimethylamino)-N-((2-methylquinolin-8-yl)sulfonyl)-4-(trifluoromethyl)benzofuran-2-carboxamide,
6-(Dimethylamino)-5-fluoro-N-((2-methylquinolin-8-yl)sulfonyl)benzofuran-2-carboxamide,
6-(Dimethylamino)-N-((2-ethoxyphenyl)sulfonyl)-5-fluorobenzofuran-2-carboxamide,
N-([1,1'-biphenyl]-2-ylsulfonyl)-6-(dimethylamino)-5-fluorobenzofuran-2-carboxamide,
(9R,12R,15S)-9-[(1H-indol-3-yl)methyl]-17-methyl-12,15-di(propan-2-yl)-6,7,8,9,11,12,14,15,18,19-decahydro[1,4,7,10,13]pentaazacycloheptadecino[16,17,1-hi]indazole-10,13,16(17H)-trione,
6-(dimethylamino)-N-(2-ethoxybenzene-1-sulfonyl)-5-(trifluoromethyl)-1-benzofuran-2-carboxamide,
(3R)-3-[4-(2-cyclopropylethyl)phenyl]-3-methyl-6-(trifluoromethyl)-1,3-dihydro-2H-indol-2-one,
N-([1,1'-biphenyl]-2-sulfonyl)-7-bromo-6-(dimethylamino)-1-benzofuran-2-carboxamide,
5-cyano-6-(dimethylamino)-N-(2-ethoxybenzene-1-sulfonyl)-1-benzofuran-2-carboxamide,
6-[(2-methoxyethyl)(methyl)amino]-N-(2-methylquinoline-8-sulfonyl)-1-benzofuran-2-carboxamide,
N-([1,1'-biphenyl]-2-sulfonyl)-5-bromo-6-(dimethylamino)-7-fluoro-1-benzofuran-2-carboxamide,
5-bromo-N-[2-(cyclopropyloxy)benzene-1-sulfonyl]-6-(dimethylamino)-1-benzofuran-2-carboxamide,
5-bromo-6-(dimethylamino)-N-{2-[(propan-2-yl)oxy]benzene-1-sulfonyl}-1-benzofuran-2-carboxamide,
2-[(3R)-4,4-difluoro-3-methyl[1,4'-bipiperidin]-1'-yl]-N-[(3,5-difluoropyridin-2-yl)methyl]-1,3-thiazole-5-carboxamide,
N-([1,1'-biphenyl]-2-sulfonyl)-6-(dimethylamino)-1-methyl-1H-indole-2-carboxamide,
N-([1,1'-biphenyl]-2-sulfonyl)-6-(ethylamino)-1-benzofuran-2-carboxamide, N-(2-ethoxybenzene-1-sulfonyl)-6-(ethylamino)-1-benzofuran-2-carboxamide,
N-(5-bromo-2-ethoxybenzene-1-sulfonyl)-6-[(2-methoxyethyl)(methyl)amino]-1-benzofuran-2-carboxamide,
6-[(2-methoxyethyl)(methyl)amino]-N-(5-methyl[1,1'-biphenyl]-2-sulfonyl)-1-benzofuran-2-carboxamide,
N-(2-ethoxybenzene-1-sulfonyl)-6-[(2-methoxyethyl)(methyl)amino]-1-benzofuran-2-carboxamide,
5-bromo-6-(dimethylamino)-N-(2-methylquinoline-8-sulfonyl)-1-benzofuran-2-carboxamide,
N-([1,1'-biphenyl]-2-sulfonyl)-5-bromo-6-(dimethylamino)-1-benzofuran-2-carboxamide,
5-bromo-6-(dimethylamino)-N-(2-ethoxybenzene-1-sulfonyl)-1-benzofuran-2-carboxamide,
2-(4-chloro-3-fluorophenyl)-5-cyclopropyl-N-[(1R)-1-(4-fluorophenyl)-3-hydroxypropyl]-4-oxo-3,4-dihydropyrrolo[2,1-f][1,2,4]triazine-6-carboxamide,
6-(ethylamino)-N-(2-methylquinoline-8-sulfonyl)-1-benzofuran-2-carboxamide,
N-[2-(cyclobutyloxy)-6-{[(2R*)-1,1,1-trifluoropropan-2-yl]oxy}benzene-1-sulfonyl]-6-(dimethylamino)-1-benzofuran-2-carboxamide,
N-[2-(cyclobutyloxy)-6-{[(2R*)-1,1,1-trifluoropropan-2-yl]oxy}benzene-1-sulfonyl]-6-(dimethylamino)-1-benzofuran-2-carboxamide,
sodium [6-(dimethylamino)-1-benzofuran-2-carbonyl](2-ethoxybenzene-1-sulfonyl)azanide,
sodium [6-(dimethylamino)-1-benzofuran-2-carbonyl]{2-[(propan-2-yl)oxy]benzene-1-sulfonyl}azanide,
sodium [6-(dimethylamino)-1-benzofuran-2-carbonyl](2-methylquinoline-8-sulfonyl)azanide,
tert-butyl (4-amino-5-benzoyl-1,3-thiazol-2-yl)pyridin-3-ylcarbamate,
sodium [6-(dimethylamino)-4-fluoro-1-benzofuran-2-carbonyl](2-methylquinoline-8-sulfonyl)azanide,
6-(Dimethylamino)-N-((2-ethoxy-4,5-difluorophenyl)sulfonyl)benzofuran-2-carboxamide,
N-((5-cyclopropyl-2-ethoxyphenyl)sulfonyl)-6-(dimethylamino)benzofuran-2-carboxamide,
6-(Dimethylamino)-N-((2-methoxy-5-(2-oxopropyl)phenyl)sulfonyl)benzofuran-2-carboxamide and
N-((5-(tert-butyl)-2-cyclopropoxyphenyl)sulfonyl)-6-(dimethylamino)benzofuran-2-carboxamide.

In some embodiments, the present invention includes compounds of general formula (I) selected from:
N-([1,1'-biphenyl]-2-sulfonyl)-6-[ethyl(methyl)amino]-1-benzofuran-2-carboxamide,
N-(benzenesulfonyl)-6-[ethyl(methyl)amino]-1-benzofuran-2-carboxamide,
N-(2,4-dichlorobenzene-1-sulfonyl)-6-[ethyl(methyl)amino]-1-benzofuran-2-carboxamide,
N-(2-chlorobenzene-1-sulfonyl)-6-[ethyl(methyl)amino]-1-benzofuran-2-carboxamide,
N-(2-ethoxybenzene-1-sulfonyl)-6-[ethyl(methyl)amino]-1-benzofuran-2-carboxamide,
N-(2-ethoxybenzene-1-sulfonyl)-6-[methyl(phenyl)amino]-1-benzofuran-2-carboxamide,
N-(benzenesulfonyl)-6-[methyl(phenyl)amino]-1-benzofuran-2-carboxamide,
N-(2-chlorobenzene-1-sulfonyl)-6-[methyl(phenyl)amino]-1-benzofuran-2-carboxamide,
N-(2,4-dichlorobenzene-1-sulfonyl)-6-[methyl(phenyl)amino]-1-benzofuran-2-carboxamide,
N-([1,1'-biphenyl]-2-sulfonyl)-6-[methyl(phenyl)amino]-1-benzofuran-2-carboxamide,
N-([1,1'-biphenyl]-2-sulfonyl)-6-(methylamino)-1-benzofuran-2-carboxamide,
N-([1,1'-biphenyl]-2-sulfonyl)-6-(dimethylamino)-4-fluoro-1-benzofuran-2-carboxamide,
6-(dimethylamino)-N-(2-ethoxybenzene-1-sulfonyl)-4-fluoro-1-benzofuran-2-carboxamide,
N-([1,1'-biphenyl]-2-sulfonyl)-6-(dimethylamino)-1-benzofuran-2-carboxamide,
N-([1,1'-biphenyl]-4-sulfonyl)-6-(dimethylamino)-1-benzofuran-2-carboxamide,
N-(3'-chloro[1,1'-biphenyl]-2-sulfonyl)-6-(dimethylamino)-1-benzofuran-2-carboxamide,
6-(dimethylamino)-N-(2'-methyl[1,1'-biphenyl]-2-sulfonyl)-1-benzofuran-2-carboxamide,
N-(2-bromobenzene-1-sulfonyl)-6-(dimethylamino)-1-benzofuran-2-carboxamide,
6-(dimethylamino)-N-(2-ethoxybenzene-1-sulfonyl)-1-benzofuran-2-carboxamide,
6-(dimethylamino)-N-(naphthalene-1-sulfonyl)-1-benzofuran-2-carboxamide,
6-(dimethylamino)-N-(2-methylquinoline-8-sulfonyl)-1-benzofuran-2-carboxamide,
N-(2-chlorobenzene-1-sulfonyl)-6-(dimethylamino)-1-benzofuran-2-carboxamide,
6-(dimethylamino)-N-(2-propoxybenzene-1-sulfonyl)-1-benzofuran-2-carboxamide,
6-(dimethylamino)-N-(5-methyl[1,1'-biphenyl]-2-sulfonyl)-1-benzofuran-2-carboxamide,
N-(3'-chloro-3-ethoxy[1,1'-biphenyl]-2-sulfonyl)-6-(dimethylamino)-1-benzofuran-2-carboxamide,
6-(dimethylamino)-N-(4-methylbenzene-1-sulfonyl)-1-benzofuran-2-carboxamide,
N-(2,4-dichlorobenzene-1-sulfonyl)-6-(dimethylamino)-1-benzofuran-2-carboxamide,
6-(dimethylamino)-N-(oxane-4-sulfonyl)-1-benzofuran-2-carboxamide,
N-(4-cyanopyridine-2-sulfonyl)-6-(dimethylamino)-1-benzofuran-2-carboxamide,
N-(2,3-dihydro-1-benzofuran-7-sulfonyl)-6-(dimethylamino)-1-benzofuran-2-carboxamide,
6-(dimethylamino)-N-[2-(trifluoromethoxy)benzene-1-sulfonyl]-1-benzofuran-2-carboxamide,
6-(dimethylamino)-N-(2-methylbenzene-1-sulfonyl)-1-benzofuran-2-carboxamide,
N-(2-cyanobenzene-1-sulfonyl)-6-(dimethylamino)-1-benzofuran-2-carboxamide,
6-(dimethylamino)-N-(2-fluorobenzene-1-sulfonyl)-1-benzofuran-2-carboxamide,
N-([1,1'-biphenyl]-2-sulfonyl)-6-(dimethylamino)-4-methyl-1-benzofuran-2-carboxamide,
2-{[6-(dimethylamino)-1-benzofuran-2-carbonyl]sulfamoyl}benzoic acid,
N-([1,1'-biphenyl]-2-sulfonyl)-6-[methyl(propyl)amino]-1-benzofuran-2-carboxamide,
N-([1,1'-biphenyl]-2-sulfonyl)-6-(diethylamino)-1-benzofuran-2-carboxamide,
N-([1,1'-biphenyl]-2-sulfonyl)-6-[(2-methoxyethyl)(methyl)amino]-1-benzofuran-2-carboxamide,
N-([1,1'-biphenyl]-2-sulfonyl)-6-[(cyclopropylmethyl)(methyl)amino]-1-benzofuran-2-carboxamide,
N-([1,1'-biphenyl]-2-sulfonyl)-6-(dibutylamino)-1-benzofuran-2-carboxamide,
6-amino-N-([1,1'-biphenyl]-2-sulfonyl)-1-benzofuran-2-carboxamide,
6-acetamido-N-([1,1'-biphenyl]-2-sulfonyl)-1-benzofuran-2-carboxamide,
N-([1,1'-biphenyl]-2-sulfonyl)-6-[(2S)-2-methylpyrrolidin-1-yl]-1-benzofuran-2-carboxamide, N-([1,1'-biphenyl]-2-sulfonyl)-6-(pyrrolidin-1-yl)-1-benzofuran-2-carboxamide,
N-([1,1'-biphenyl]-2-sulfonyl)-6-[cyclopentyl(methyl)amino]-1-benzofuran-2-carboxamide,
N-([1,1'-biphenyl]-2-sulfonyl)-6-(piperidin-1-yl)-1-benzofuran-2-carboxamide,
N-([1,1'-biphenyl]-2-sulfonyl)-6-(dimethylamino)-1-benzothiophene-2-carboxamide,
N-(3'-chloro[1,1'-biphenyl]-2-sulfonyl)-6-(dimethylamino)-1-benzothiophene-2-carboxamide,
N-([1,1'-biphenyl]-2-sulfonyl)-7-cyclopropyl-6-(dimethylamino)-1-benzofuran-2-carboxamide,
6-(dimethylamino)-N-[4'-(hydroxymethyl)[1,1'-biphenyl]-2-sulfonyl]-1-benzofuran-2-carboxamide,
6-(dimethylamino)-N-(2-propylbenzene-1-sulfonyl)-1-benzofuran-2-carboxamide,
N-(4-cyano-2-methoxybenzene-1-sulfonyl)-6-(dimethylamino)-1-benzofuran-2-carboxamide,
6-(dimethylamino)-N-[2-(trifluoromethyl)benzene-1-sulfonyl]-1-benzofuran-2-carboxamide:ammonia (1/1),
N-[1-(2,4-dichlorophenyl)ethanesulfonyl]-6-(dimethylamino)-1-benzofuran-2-carboxamide,
N-[1-(2,6-dichlorophenyl)ethanesulfonyl]-6-(dimethylamino)-1-benzofuran-2-carboxamide,
N-(5-bromo-2-ethoxybenzene-1-sulfonyl)-6-(dimethylamino)-1-benzofuran-2-carboxamide,
6-(dimethylamino)-N-(4-ethoxypyridine-3-sulfonyl)-1-benzofuran-2-carboxamide,
6-(dimethylamino)-N-(2-hydroxybenzene-1-sulfonyl)-1-benzofuran-2-carboxamide,
ethyl 4-{[6-(dimethylamino)-1-benzofuran-2-carbonyl]sulfamoyl}piperidine-1-carboxylate
6-(dimethylamino)-N-(ethanesulfonyl)-1-benzofuran-2-carboxamide,
N-([1,1'-biphenyl]-2-sulfonyl)-6-(2-oxopyrrolidin-1-yl)-1-benzofuran-2-carboxamide,
6-(dimethylamino)-N-(methanesulfonyl)-1-benzofuran-2-carboxamide and
N-([1,1'-biphenyl]-2-sulfonyl)-7-cyano-6-(dimethylamino)-1-benzofuran-2-carboxamide.

In some embodiments, the present invention includes compounds of general formula (I) selected from:
N-(2-ethoxybenzene-1-sulfonyl)-6-[ethyl(methyl)amino]-1-benzofuran-2-carboxamide,
N-([1,1'-biphenyl]-2-sulfonyl)-6-(dimethylamino)-4-fluoro-1-benzofuran-2-carboxamide,
6-(dimethylamino)-N-(2-ethoxybenzene-1-sulfonyl)-4-fluoro-1-benzofuran-2-carboxamide,
N-([1,1'-biphenyl]-2-sulfonyl)-6-(dimethylamino)-1-benzofuran-2-carboxamide,
N-(3'-chloro[1,1'-biphenyl]-2-sulfonyl)-6-(dimethylamino)-1-benzofuran-2-carboxamide,
6-(dimethylamino)-N-(2'-methyl[1,1'-biphenyl]-2-sulfonyl)-1-benzofuran-2-carboxamide,
6-(dimethylamino)-N-(2-ethoxybenzene-1-sulfonyl)-1-benzofuran-2-carboxamide,
6-(dimethylamino)-N-(naphthalene-1-sulfonyl)-1-benzofuran-2-carboxamide,
6-(dimethylamino)-N-(2-methylquinoline-8-sulfonyl)-1-benzofuran-2-carboxamide,
N-(2-chlorobenzene-1-sulfonyl)-6-(dimethylamino)-1-benzofuran-2-carboxamide,
6-(dimethylamino)-N-(2-propoxybenzene-1-sulfonyl)-1-benzofuran-2-carboxamide,
6-(dimethylamino)-N-(5-methyl[1,1'-biphenyl]-2-sulfonyl)-1-benzofuran-2-carboxamide,
N-(3'-chloro-3-ethoxy[1,1'-biphenyl]-2-sulfonyl)-6-(dimethylamino)-1-benzofuran-2-carboxamide,
6-(dimethylamino)-N-(4-methylbenzene-1-sulfonyl)-1-benzofuran-2-carboxamide,
N-([1,1'-biphenyl]-2-sulfonyl)-6-(dimethylamino)-1-benzothiophene-2-carboxamide,
6-(dimethylamino)-N-(2-propylbenzene-1-sulfonyl)-1-benzofuran-2-carboxamide,
N-(4-cyano-2-methoxybenzene-1-sulfonyl)-6-(dimethylamino)-1-benzofuran-2-carboxamide,
6-(dimethylamino)-N-[2-(trifluoromethyl)benzene-1-sulfonyl]-1-benzofuran-2-carboxamide:ammonia (1/1),
N-[1-(2,4-dichlorophenyl)ethanesulfonyl]-6-(dimethylamino)-1-benzofuran-2-carboxamide,
N-[1-(2,6-dichlorophenyl)ethanesulfonyl]-6-(dimethylamino)-1-benzofuran-2-carboxamide,
N-(5-bromo-2-ethoxybenzene-1-sulfonyl)-6-(dimethylamino)-1-benzofuran-2-carboxamide,
6-(dimethylamino)-N-(4-ethoxypyridine-3-sulfonyl)-1-benzofuran-2-carboxamide and
6-(dimethylamino)-N-(2-hydroxybenzene-1-sulfonyl)-1-benzofuran-2-carboxamide.

In some embodiments, the present invention includes compounds of general formula (I) selected from:
N-(2-ethoxybenzene-1-sulfonyl)-6-[ethyl(methyl)amino]-1-benzofuran-2-carboxamide,
N-([1,1'-biphenyl]-2-sulfonyl)-6-(dimethylamino)-4-fluoro-1-benzofuran-2-carboxamide,
6-(dimethylamino)-N-(2-ethoxybenzene-1-sulfonyl)-4-fluoro-1-benzofuran-2-carboxamide,
N-([1,1'-biphenyl]-2-sulfonyl)-6-(dimethylamino)-1-benzofuran-2-carboxamide,
N-(3'-chloro[1,1'-biphenyl]-2-sulfonyl)-6-(dimethylamino)-1-benzofuran-2-carboxamide,
6-(dimethylamino)-N-(2'-methyl[1,1'-biphenyl]-2-sulfonyl)-1-benzofuran-2-carboxamide,
6-(dimethylamino)-N-(2-ethoxybenzene-1-sulfonyl)-1-benzofuran-2-carboxamide,
6-(dimethylamino)-N-(naphthalene-1-sulfonyl)-1-benzofuran-2-carboxamide,
6-(dimethylamino)-N-(2-methylquinoline-8-sulfonyl)-1-benzofuran-2-carboxamide,
N-(2-chlorobenzene-1-sulfonyl)-6-(dimethylamino)-1-benzofuran-2-carboxamide,
6-(dimethylamino)-N-(2-propoxybenzene-1-sulfonyl)-1-benzofuran-2-carboxamide,
6-(dimethylamino)-N-(5-methyl[1,1'-biphenyl]-2-sulfonyl)-1-benzofuran-2-carboxamide,
N-(3'-chloro-3-ethoxy[1,1'-biphenyl]-2-sulfonyl)-6-(dimethylamino)-1-benzofuran-2-carboxamide,
6-(dimethylamino)-N-(4-methylbenzene-1-sulfonyl)-1-benzofuran-2-carboxamide,
N-([1,1'-biphenyl]-2-sulfonyl)-6-(dimethylamino)-1-benzothiophene-2-carboxamide,
6-(dimethylamino)-N-(2-propylbenzene-1-sulfonyl)-1-benzofuran-2-carboxamide,
N-(4-cyano-2-methoxybenzene-1-sulfonyl)-6-(dimethylamino)-1-benzofuran-2-carboxamide,
6-(dimethylamino)-N-[2-(trifluoromethyl)benzene-1-sulfonyl]-1-benzofuran-2-carboxamide:ammonia (1/1),
N-[1-(2,4-dichlorophenyl)ethanesulfonyl]-6-(dimethylamino)-1-benzofuran-2-carboxamide,
N-[1-(2,6-dichlorophenyl)ethanesulfonyl]-6-(dimethylamino)-1-benzofuran-2-carboxamide,
N-(5-bromo-2-ethoxybenzene-1-sulfonyl)-6-(dimethylamino)-1-benzofuran-2-carboxamide, 6-(dimethylamino)-N-(4-ethoxypyridine-3-sulfonyl)-1-benzofuran-2-carboxamide,
6-(dimethylamino)-N-(2-hydroxybenzene-1-sulfonyl)-1-benzofuran-2-carboxamide,
N-([1,1'-biphenyl]-2-sulfonyl)-6-[ethyl(methyl)amino]-1-benzofuran-2-carboxamide,
N-(benzenesulfonyl)-6-[ethyl(methyl)amino]-1-benzofuran-2-carboxamide,
N-(2,4-dichlorobenzene-1-sulfonyl)-6-[ethyl(methyl)amino]-1-benzofuran-2-carboxamide,
N-(2-chlorobenzene-1-sulfonyl)-6-[ethyl(methyl)amino]-1-benzofuran-2-carboxamide,
N-(2-ethoxybenzene-1-sulfonyl)-6-[methyl(phenyl)amino]-1-benzofuran-2-carboxamide,
N-(2-chlorobenzene-1-sulfonyl)-6-[methyl(phenyl)amino]-1-benzofuran-2-carboxamide,
N-(2,4-dichlorobenzene-1-sulfonyl)-6-[methyl(phenyl)amino]-1-benzofuran-2-carboxamide,
N-([1,1'-biphenyl]-2-sulfonyl)-6-[methyl(phenyl)amino]-1-benzofuran-2-carboxamide,
N-([1,1'-biphenyl]-2-sulfonyl)-6-(methylamino)-1-benzofuran-2-carboxamide,
N-([1,1'-biphenyl]-4-sulfonyl)-6-(dimethylamino)-1-benzofuran-2-carboxamide,
N-(2-bromobenzene-1-sulfonyl)-6-(dimethylamino)-1-benzofuran-2-carboxamide,
N-(2,4-dichlorobenzene-1-sulfonyl)-6-(dimethylamino)-1-benzofuran-2-carboxamide,
N-(2,3-dihydro-1-benzofuran-7-sulfonyl)-6-(dimethylamino)-1-benzofuran-2-carboxamide,
6-(dimethylamino)-N-[2-(trifluoromethoxy)benzene-1-sulfonyl]-1-benzofuran-2-carboxamide,
6-(dimethylamino)-N-(2-methylbenzene-1-sulfonyl)-1-benzofuran-2-carboxamide,
N-(2-cyanobenzene-1-sulfonyl)-6-(dimethylamino)-1-benzofuran-2-carboxamide,
6-(dimethylamino)-N-(2-fluorobenzene-1-sulfonyl)-1-benzofuran-2-carboxamide,
N-([1,1'-biphenyl]-2-sulfonyl)-6-(dimethylamino)-4-methyl-1-benzofuran-2-carboxamide,
2-{[6-(dimethylamino)-1-benzofuran-2-carbonyl]sulfamoyl}benzoic acid,
N-([1,1'-biphenyl]-2-sulfonyl)-6-[methyl(propyl)amino]-1-benzofuran-2-carboxamide,
N-([1,1'-biphenyl]-2-sulfonyl)-6-(diethylamino)-1-benzofuran-2-carboxamide,
N-([1,1'-biphenyl]-2-sulfonyl)-6-[(2-methoxyethyl)(methyl)amino]-1-benzofuran-2-carboxamide,
N-([1,1'-biphenyl]-2-sulfonyl)-6-[(cyclopropylmethyl)(methyl)amino]-1-benzofuran-2-carboxamide,
N-([1,1'-biphenyl]-2-sulfonyl)-6-(dibutylamino)-1-benzofuran-2-carboxamide,
6-amino-N-([1,1'-biphenyl]-2-sulfonyl)-1-benzofuran-2-carboxamide,
6-acetamido-N-([1,1'-biphenyl]-2-sulfonyl)-1-benzofuran-2-carboxamide,
N-([1,1'-biphenyl]-2-sulfonyl)-6-[(2S)-2-methylpyrrolidin-1-yl]-1-benzofuran-2-carboxamide,
N-([1,1'-biphenyl]-2-sulfonyl)-6-(pyrrolidin-1-yl)-1-benzofuran-2-carboxamide,
N-([1,1'-biphenyl]-2-sulfonyl)-6-[cyclopentyl(methyl)amino]-1-benzofuran-2-carboxamide,
N-(3'-chloro[1,1'-biphenyl]-2-sulfonyl)-6-(dimethylamino)-1-benzothiophene-2-carboxamide,
N-([1,1'-biphenyl]-2-sulfonyl)-7-cyclopropyl-6-(dimethylamino)-1-benzofuran-2-carboxamide,
6-(dimethylamino)-N-[4'-(hydroxymethyl)[1,1'-biphenyl]-2-sulfonyl]-1-benzofuran-2-carboxamide and
ethyl 4-{[6-(dimethylamino)-1-benzofuran-2-carbonyl]sulfamoyl}piperidine-1-carboxylate.

In some embodiments, the present invention includes compounds of general formula (I) selected from:
N-([1,1'-biphenyl]-2-sulfonyl)-6-[ethyl(methyl)amino]-1-benzofuran-2-carboxamide,
N-(benzenesulfonyl)-6-[ethyl(methyl)amino]-1-benzofuran-2-carboxamide,
N-(2,4-dichlorobenzene-1-sulfonyl)-6-[ethyl(methyl)amino]-1-benzofuran-2-carboxamide,
N-(2-chlorobenzene-1-sulfonyl)-6-[ethyl(methyl)amino]-1-benzofuran-2-carboxamide,
N-(2-ethoxybenzene-1-sulfonyl)-6-[methyl(phenyl)amino]-1-benzofuran-2-carboxamide,
N-(2-chlorobenzene-1-sulfonyl)-6-[methyl(phenyl)amino]-1-benzofuran-2-carboxamide,
N-(2,4-dichlorobenzene-1-sulfonyl)-6-[methyl(phenyl)amino]-1-benzofuran-2-carboxamide,
N-([1,1'-biphenyl]-2-sulfonyl)-6-[methyl(phenyl)amino]-1-benzofuran-2-carboxamide,
N-([1,1'-biphenyl]-2-sulfonyl)-6-(methylamino)-1-benzofuran-2-carboxamide,
N-([1,1'-biphenyl]-4-sulfonyl)-6-(dimethylamino)-1-benzofuran-2-carboxamide,
N-(2-bromobenzene-1-sulfonyl)-6-(dimethylamino)-1-benzofuran-2-carboxamide,
N-(2,4-dichlorobenzene-1-sulfonyl)-6-(dimethylamino)-1-benzofuran-2-carboxamide,
N-(2,3-dihydro-1-benzofuran-7-sulfonyl)-6-(dimethylamino)-1-benzofuran-2-carboxamide,
6-(dimethylamino)-N-[2-(trifluoromethoxy)benzene-1-sulfonyl]-1-benzofuran-2-carboxamide,
6-(dimethylamino)-N-(2-methylbenzene-1-sulfonyl)-1-benzofuran-2-carboxamide,
N-(2-cyanobenzene-1-sulfonyl)-6-(dimethylamino)-1-benzofuran-2-carboxamide,
6-(dimethylamino)-N-(2-fluorobenzene-1-sulfonyl)-1-benzofuran-2-carboxamide,
N-([1,1'-biphenyl]-2-sulfonyl)-6-(dimethylamino)-4-methyl-1-benzofuran-2-carboxamide,
2-{[6-(dimethylamino)-1-benzofuran-2-carbonyl]sulfamoyl}benzoic acid,
N-([1,1'-biphenyl]-2-sulfonyl)-6-[methyl(propyl)amino]-1-benzofuran-2-carboxamide,
N-([1,1'-biphenyl]-2-sulfonyl)-6-(diethylamino)-1-benzofuran-2-carboxamide,
N-([1,1'-biphenyl]-2-sulfonyl)-6-[(2-methoxyethyl)(methyl)amino]-1-benzofuran-2-carboxamide,
N-([1,1'-biphenyl]-2-sulfonyl)-6-[(cyclopropylmethyl)(methyl)amino]-1-benzofuran-2-carboxamide,
N-([1,1'-biphenyl]-2-sulfonyl)-6-(dibutylamino)-1-benzofuran-2-carboxamide,
6-amino-N-([1,1'-biphenyl]-2-sulfonyl)-1-benzofuran-2-carboxamide,
6-acetamido-N-([1,1'-biphenyl]-2-sulfonyl)-1-benzofuran-2-carboxamide,
N-([1,1'-biphenyl]-2-sulfonyl)-6-[(2S)-2-methylpyrrolidin-1-yl]-1-benzofuran-2-carboxamide,
N-([1,1'-biphenyl]-2-sulfonyl)-6-(pyrrolidin-1-yl)-1-benzofuran-2-carboxamide,
N-([1,1'-biphenyl]-2-sulfonyl)-6-[cyclopentyl(methyl)amino]-1-benzofuran-2-carboxamide,
N-(3'-chloro[1,1'-biphenyl]-2-sulfonyl)-6-(dimethylamino)-1-benzothiophene-2-carboxamide, N-([1,1'-biphenyl]-2-sulfonyl)-7-cyclopropyl-6-(dimethylamino)-1-benzofuran-2-carboxamide, 6-(dimethylamino)-N-[4'-(hydroxymethyl)[1,1'-biphenyl]-2-sulfonyl]-1-benzofuran-2-carboxamide and ethyl 4-{[6-(dimethylamino)-1-benzofuran-2-carbonyl]sulfamoyl}piperidine-1-carboxylate.

In some embodiments, the present invention includes compounds of general formula (I) selected from:

N-(benzenesulfonyl)-6-[methyl(phenyl)amino]-1-benzofuran-2-carboxamide, 6-(dimethylamino)-N-(oxane-4-sulfonyl)-1-benzofuran-2-carboxamide, N-(4-cyanopyridine-2-sulfonyl)-6-(dimethylamino)-1-benzofuran-2-carboxamide, N-([1,1'-biphenyl]-2-sulfonyl)-6-(piperidin-1-yl)-1-benzofuran-2-carboxamide, 6-(dimethylamino)-N-(ethanesulfonyl)-1-benzofuran-2-carboxamide, N-([1,1'-biphenyl]-2-sulfonyl)-6-(2-oxopyrrolidin-1-yl)-1-benzofuran-2-carboxamide, 6-(dimethylamino)-N-(methanesulfonyl)-1-benzofuran-2-carboxamide and N-([1,1'-biphenyl]-2-sulfonyl)-7-cyano-6-(dimethylamino)-1-benzofuran-2-carboxamide.

Further embodiments of the first aspect of the present invention:

In some embodiments, the present invention provides compounds of formula (I), supra, in which X is selected from an oxygen atom, a sulfur atom and a $NR^0$ group, wherein $R^0$ is selected from a hydrogen atom and a $C_1$-$C_6$-alkyl group or a tautomer, or an N-oxide, or a salt thereof, or a salt of a tautomer, or a salt of an N-oxide, or a mixture of same.

In some embodiments, the present invention provides compounds of formula (I), supra, in which X is selected from an oxygen atom, a sulfur atom and a $NR^0$ group, wherein $R^0$ is a hydrogen atom or a tautomer, or an N-oxide, or a salt thereof, or a salt of a tautomer, or a salt of an N-oxide, or a mixture of same.

In some embodiments, the present invention provides compounds of formula (I), supra, in which X is selected from an oxygen atom, a sulfur atom and a $NR^0$ group, wherein $R^0$ is a $C_1$-$C_3$-alkyl group or a tautomer, or an N-oxide, or a salt thereof, or a salt of a tautomer, or a salt of an N-oxide, or a mixture of same.

In some embodiments, the present invention provides compounds of formula (I), supra, in which X is an oxygen atom or a tautomer, or an N-oxide, or a salt thereof, or a salt of a tautomer, or a salt of an N-oxide, or a mixture of same.

In some embodiments, the present invention provides compounds of formula (I), supra, in which X is a sulfur atom or a tautomer, or an N-oxide, or a salt thereof, or a salt of a tautomer, or a salt of an N-oxide, or a mixture of same.

In some embodiments, the present invention provides compounds of formula (I), supra, in which $R^1$, $R^2$ and $R^3$ are each independently selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, and a $C_1$-$C_6$-haloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$, $R^2$ and $R^3$ are each independently selected from a hydrogen atom, a halogen atom, a cyano group, a $R^7R^8N$— group, a $C_1$-$C_6$-alkoxy group, a $C_1$-$C_6$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$, $R^2$ and $R^3$ are each independently selected from a hydrogen atom, a halogen atom, a cyano group, a $C_1$-$C_6$-alkoxy group, a $C_1$-$C_6$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$, $R^2$ and $R^3$ are each independently selected from a hydrogen atom, a halogen atom, a cyano group, a $C_1$-$C_3$-alkoxy group, a $C_1$-$C_3$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$, $R^2$ and $R^3$ are each independently selected from a hydrogen atom, a halogen atom, a cyano group, a $C_1$-$C_3$-alkoxy group and a $C_1$-$C_3$-alkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$ is selected from a hydrogen atom, a halogen atom, a $C_1$-$C_6$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$ is selected from a hydrogen atom, a halogen atom, a $C_1$-$C_3$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^1$ is selected from a hydrogen atom and a halogen atom or a tautomer, or an N-oxide, or a salt thereof, or a salt of a tautomer, or a salt of an N-oxide, or a mixture of same.

In some embodiments, the present invention provides compounds of formula (I), supra, in which $R^1$ is a hydrogen atom or a tautomer, or an N-oxide, or a salt thereof, or a salt of a tautomer, or a salt of an N-oxide, or a mixture of same.

In some embodiments, the present invention provides compounds of formula (I), supra, in which $R^2$ is selected from a hydrogen atom, a halogen atom, a cyano group, a $C_1$-$C_6$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^2$ is selected from a hydrogen atom, a halogen atom, a cyano group, a $C_1$-$C_3$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^2$ is selected from a hydrogen atom and a halogen atom or a tautomer, or an N-oxide, or a salt thereof, or a salt of a tautomer, or a salt of an N-oxide, or a mixture of same.

In some embodiments, the present invention provides compounds of formula (I), supra, in which $R^2$ is a hydrogen atom or a tautomer, or an N-oxide, or a salt thereof, or a salt of a tautomer, or a salt of an N-oxide, or a mixture of same.

In some embodiments, the present invention provides compounds of formula (I), supra, in which $R^3$ is selected from a hydrogen atom, a halogen atom, a cyano group, a $C_1$-$C_6$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^3$ is selected from a hydrogen atom, a halogen atom, a cyano group, a $C_1$-$C_3$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^3$ is selected from a hydrogen atom and a halogen atom, or a tautomer, or an N-oxide, or a salt thereof, or a salt of a tautomer, or a salt of an N-oxide, or a mixture of same.

In some embodiments, the present invention provides compounds of formula (I), supra, in which $R^3$ is a fluorine atom, or a tautomer, or an N-oxide, or a salt thereof, or a salt of a tautomer, or a salt of an N-oxide, or a mixture of same.

In some embodiments, the present invention provides compounds of formula (I), supra, in which $R^4$ is selected from a hydrogen atom, a halogen atom, a $C_1$-$C_6$-alkyl group and a $C_3$-$C_8$-cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^4$ is selected from a hydrogen atom, a halogen atom and a $C_1$-$C_3$-alkyl group or a tautomer, or an N-oxide, or a salt thereof, or a salt of a tautomer, or a salt of an N-oxide, or a mixture of same.

In some embodiments, the present invention provides compounds of formula (I), supra, in which $R^4$ is selected from a hydrogen atom and a halogen atom or a tautomer, or an N-oxide, or a salt thereof, or a salt of a tautomer, or a salt of an N-oxide, or a mixture of same.

In some embodiments, the present invention provides compounds of formula (I), supra, in which $R^4$ is a hydrogen atom or a tautomer, or an N-oxide, or a salt thereof, or a salt of a tautomer, or a salt of an N-oxide, or a mixture of same.

In some embodiments, the present invention provides compounds of formula (I), supra, in which $R^5$ is selected from a hydrogen atom and a $C_1$-$C_3$-alkyl group or a tautomer, or an N-oxide, or a salt thereof, or a salt of a tautomer, or a salt of an N-oxide, or a mixture of same.

In some embodiments, the present invention provides compounds of formula (I), supra, in which $R^5$ is a hydrogen atom or a tautomer, or an N-oxide, or a salt thereof, or a salt of a tautomer, or a salt of an N-oxide, or a mixture of same.

In some embodiments, the present invention provides compounds of formula (I), supra, in which $R^5$ is a $C_1$-$C_3$-alkyl group or a tautomer, or an N-oxide, or a salt thereof, or a salt of a tautomer, or a salt of an N-oxide, or a mixture of same.

In some embodiments, the present invention provides compounds of formula (I), supra, in which
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S=O)_2$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a naphthyl group, a (phenyl)-O— group and a heteroaryl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S=O)_2$— group, a $(R^7R^8N)$—($C_1$-$C_6$-alkyl)-(C=O)—NH— group, a $(R^7R^8N)$—($C_1$-$C_6$-alkyl)- group, and a $R^9OOC$— group
wherein said heterocycloalkyl group is connected to the rest of the molecule via a carbon atom of said heterocycloalkyl group;
or a tautomer, or an N-oxide, or a salt thereof, or a salt of a tautomer, or a salt of an N-oxide, or a mixture of same.

In some embodiments, the present invention provides compounds of formula (I), supra, in which
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $(R^7R^8N)$—($C_1$-$C_6$-alkyl)-(C=O)—NH— group, a $(R^7R^8N)$—($C_1$-$C_6$-alkyl)- group, a $R^9OOC$— group, a phenyl group, a (phenyl)-O— group and a heteroaryl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a $C_1$-$C_6$-thioalkyl group, a heterocycloalkyl group, a (heterocycloalkyl)-O— group, a $R^7R^8N$— group, a ($R^7R^8N$)—(S(=O)$_2$)— group, a ($C_1$-$C_2$-alkyl)-(S(=O)$_2$)— group, a $CH_3$—C(=O)—$CH_2$— group, a ($R^7R^8N$)—($C_1$-$C_6$-alkyl)-(C=O)—NH— group, a ($R^7R^8N$)—($C_1$-$C_6$-alkyl)- group, a ($R^7R^8N$)—($C_1$-$C_6$-alkyl)-O— group, a $R^9OOC$— group, a phenyl group, a naphthyl group, a (phenyl)-($C_1$-$C_2$-alkyl)-O— group, a (phenyl)-O— group, a heteroaryl group and a heteroaryl-($C_1$-$C_2$-alkyl)- group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a ($R^7R^8N$)—(S=O)$_2$— group, a ($R^7R^8N$)—($C_1$-$C_6$-alkyl)-(C=O)—NH— group, a ($R^7R^8N$)—($C_1$-$C_6$-alkyl)- group, and a $R^9OOC$— group, wherein said heterocycloalkyl group is connected to the rest of the molecule via a carbon atom of said heterocycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a (phenyl)-O— group, a (phenyl)-($C_1$-$C_2$-alkyl)-O— group, a heteroaryl-($C_1$-$C_2$-alkyl)- group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a phenyl group, a naphthyl group, a heteroaryl group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a phenyl group and a heteroaryl group, wherein said phenyl or heteroaryl group is each optionally substituted with one or more substituents independently selected from a halogen atom, a cyano group, a $C_1$-$C_6$-alkyl group, a $C_1$-$C_6$-haloalkyl group, a $C_1$-$C_6$-alkoxy group and a $C_3$-$C_8$-cycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a phenyl group and a heterocycloalkyl group, wherein said heterocycloalkyl group is connected to the rest of the molecule via a carbon atom of said heterocycloalkyl group, wherein said phenyl or heterocycloalkyl group is each optionally substituted with one or more substituents independently selected from a halogen atom, a cyano group, a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a phenyl group and a heteroaryl group, wherein said phenyl or heteroaryl group is each optionally substituted with one or more substituents independently selected from a halogen atom, a $C_1$-$C_3$-alkyl group, a $C_1$-$C_3$-haloalkyl group, a $C_1$-$C_3$-alkoxy group and a $C_3$-$C_8$-cycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a phenyl group and a heterocycloalkyl group, wherein said heterocycloalkyl group is connected to the rest of the molecule via a carbon atom of said heterocycloalkyl group, wherein said phenyl or heterocycloalkyl group is each optionally substituted with one or more substituents independently selected from a halogen atom, a cyano group, a hydroxy group, a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a phenyl group, a (phenyl)-O— group, a (phenyl)-($C_1$-$C_2$-alkyl)-O— group, a heteroaryl-($C_1$-$C_2$-alkyl)- group and a heteroaryl group, wherein said phenyl or heteroaryl group is each optionally substituted with one or more substituents independently selected from a halogen atom, a $C_1$-$C_3$-alkyl group, a $C_1$-$C_3$-haloalkyl group, a $C_1$-$C_3$-alkoxy group and a $C_3$-$C_8$-cycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a phenyl group and a heteroaryl group, wherein said phenyl or heteroaryl group is each optionally substituted with one or more substituents independently selected from a halogen atom, a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $C_3$-$C_8$-cycloalkoxy group;

or a tautomer, or an N-oxide, or a salt thereof, or a salt of a tautomer, or a salt of an N-oxide, or a mixture of same.

In some embodiments, the present invention provides compounds of formula (I), supra, in which $R^6$ is selected from a phenyl group and a heteroaryl group,
  wherein said phenyl or heteroaryl group is each optionally substituted with one or more substituents independently selected from a $C_1$-$C_6$-alkyl group, a $C_1$-$C_6$-haloalkyl group, a $C_1$-$C_6$-alkoxy group, a $C_1$-$C_6$-haloalkoxy group, and a $C_3$-$C_8$-cycloalkoxy group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group, a $(C_1$-$C_6$-alkoxy$)$-$(C_1$-$C_6$-alkyl$)$- group, a phenyl group, a heterocycloalkyl group and a heteroaryl group,
    wherein said heterocycloalkyl group is connected to the rest of the molecule via a carbon atom of said heterocycloalkyl group,
    wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group,
  or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group and a $C_3$-$C_8$-cycloalkyl group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group, a $(C_1$-$C_6$-alkoxy$)$-$(C_1$-$C_6$-alkyl$)$- group, a phenyl group, a heterocycloalkyl group and a heteroaryl group,
    wherein said heterocycloalkyl group is connected to the rest of the molecule via a carbon atom of said heterocycloalkyl group,
  or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group and a $(C_1$-$C_6$-alkoxy$)$-$(C_1$-$C_6$-alkyl$)$- group,
  or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a $C_1$-$C_6$-alkyl group, a $C_3$-$C_8$-cycloalkyl group, a $C_1$-$C_6$-haloalkyl group, a $(C_1$-$C_6$-alkyl$)C(=O)$— group, a $(C_1$-$C_6$-haloalkyl$)C(=O)$— group, a $(C_3$-$C_8$-cycloalkyl$)$-$(C_1$-$C_6$-alkyl$)$- group, a $C_1$-$C_6$-hydroxyalkyl group and a $(C_1$-$C_6$-alkoxy$)$-$(C_1$-$C_6$-alkyl$)$- group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a $C_1$-$C_3$-alkyl group, a $C_3$-$C_8$-cycloalkyl group, a $C_1$-$C_3$-haloalkyl group, a $C_1$-$C_3$-hydroxyalkyl group and a $(C_1$-$C_6$-alkoxy$)$-$(C_1$-$C_6$-alkyl$)$- group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a hydrogen atom, a $C_1$-$C_3$-alkyl group and a $C_3$-$C_8$-cycloalkyl group;
  or a tautomer, or an N-oxide, or a salt thereof, or a salt of a tautomer, or a salt of an N-oxide, or a mixture of same.

In some embodiments, the present invention provides compounds of formula (I), supra, in which
  $R^7$ and $R^8$ are each independently selected from a hydrogen atom and a $C_1$-$C_3$-alkyl group;
  or a tautomer, or an N-oxide, or a salt thereof, or a salt of a tautomer, or a salt of an N-oxide, or a mixture of same.

In some embodiments, the present invention provides compounds of formula (I), supra, in which $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a $C_1$-$C_6$-alkyl group, a $C_1$-$C_6$-haloalkyl group, a $C_1$-$C_6$-alkoxy group and a $C_3$-$C_8$-cycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a $C_1$-$C_3$-alkyl group and a $C_3$-$C_8$-cycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group and a $R^7R^8N$— group;

or a tautomer, or an N-oxide, or a salt thereof, or a salt of a tautomer, or a salt of an N-oxide, or a mixture of same.

In some embodiments, the present invention provides compounds of formula (I), supra, in which $R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or a tautomer, or an N-oxide, or a salt thereof, or a salt of a tautomer, or a salt of an N-oxide, or a mixture of same.

In some embodiments, the present invention provides compounds of formula (I), supra, in which $R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl)C(=O)— group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which $R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl)C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;

or a tautomer, or an N-oxide, or a salt thereof, or a salt of a tautomer, or a salt of an N-oxide, or a mixture of same.

In some embodiments, the present invention provides compounds of formula (I), supra, in which $R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a $C_1$-$C_6$-hydroxyalkyl group and a ($C_1$-$C_6$-alkoxy)-($C_1$-$C_6$-alkyl)- group;

or a tautomer, or an N-oxide, or a salt thereof, or a salt of a tautomer, or a salt of an N-oxide, or a mixture of same.

In some embodiments, the present invention provides compounds of formula (I), supra, in which $R^a$ and $R^b$ are each independently selected from a hydrogen atom, a $C_1$-$C_6$-alkyl group, a $C_3$-$C_8$-cycloalkyl group and a $C_1$-$C_6$-haloalkyl group;

or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ are each independently selected from a hydrogen atom, a $C_1$-$C_3$-alkyl group, and a $C_1$-$C_3$-haloalkyl group;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ are each independently selected from a hydrogen atom and a $C_1$-$C_3$-alkyl group;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ are each independently selected from a hydrogen atom and a methyl group;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ are each a methyl group;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ are each independently selected from a hydrogen atom and a $C_1$-$C_3$-haloalkyl group;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ together with the nitrogen atom to which they are attached form a 4- to 7-membered nitrogen-containing heterocycloalkyl group,
wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In some embodiments, the present invention provides compounds of formula (I), supra, in which
$R^a$ and $R^b$ together with the nitrogen atom to which they are attached form a 4- to 7-membered nitrogen-containing heterocycloalkyl group,
wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In some embodiments, the present invention provides compounds of formula (I), supra, in which
$R^1$ and one of $R^a$ and $R^b$, together with the carbon and the nitrogen atom to which they are respectively attached form a 5- to 7-membered nitrogen-containing heterocycloalkyl group,
wherein said 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In some embodiments, the present invention provides compounds of formula (I), supra, in which
$R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or an N-oxide, or a salt thereof, or a salt of a tautomer, or a salt of an N-oxide, or a mixture of same.

In some embodiments, the present invention provides compounds of formula (I), supra, in which $R^9$ is selected from a hydrogen atom, a $C_1$-$C_6$-alkyl group and a $C_3$-$C_8$- cycloalkyl group or a tautomer, or an N-oxide, or a salt thereof, or a salt of a tautomer, or a salt of an N-oxide, or a mixture of same.

In some embodiments, the present invention provides compounds of formula (I), supra, in which $R^9$ is selected from a hydrogen atom and a $C_1$-$C_3$-alkyl group or a tautomer, or an N-oxide, or a salt thereof, or a salt of a tautomer, or a salt of an N-oxide, or a mixture of same.

In some embodiments, the present invention provides compounds of formula (I), supra, in which $R^9$ is a $C_1$-$C_3$-alkyl group or a tautomer, or an N-oxide, or a salt thereof, or a salt of a tautomer, or a salt of an N-oxide, or a mixture of same.

In further embodiments, the present invention includes compounds of formula (I), or a tautomer, an N-oxide, or a salt thereof, or a salt of a tautomer or an N-oxide, or a mixture of same.

In further embodiments, the present invention includes compounds of formula (I), or a salt thereof.

In further embodiments, the present invention includes compounds of formula (I), or a tautomer, or a salt thereof, or a salt of a tautomer, or a mixture of same.

In further embodiments, the present invention includes compounds of formula (I), which are a salt.

In further embodiments, the present invention includes compounds of formula (I), which are a tautomer or a salt thereof, or a salt of a tautomer, or a mixture of same.

In further embodiments, the present invention includes compounds of formula (I), which are an N-oxide, or a salt thereof, or a salt of an N-oxide, or a mixture of same.

In further embodiments of the first aspect, the present invention provides combinations of two or more of the above mentioned embodiments under the heading "further embodiments of the first aspect of the present invention".

Furthermore it is understood that the invention includes any subcombination of the disclosed single embodiments herein for certain residues or subcombination of residues of formula (I).

The present invention includes any sub-combination within any embodiments or aspects of the present invention of compounds of general formula (I), supra.

The present invention includes any sub-combination within any embodiments or aspects of the present invention of compounds of general formula (I) or intermediate compounds. The present invention includes the compounds of general formula (I) which are disclosed in the Example Section of this text, infra.

General Synthesis of Compounds of General Formula (I) of the Present Invention

The compounds of general formula (I) according to the invention as well as relevant intermediate and/or precursor compounds can be prepared according to the following schemes 1, 2, 3, 4 and 5. The schemes and procedures described below illustrate synthetic routes to the compounds of general formula (I) of the invention as well as to relevant intermediate and/or precursor compounds and are not intended to be limiting. It is clear to the person skilled in the art that the order of transformations as exemplified in schemes 1, 2, 3, 4 and 5 can be modified in various ways. The order of transformations exemplified in these schemes is therefore not intended to be limiting. In addition, interconversion of any of the substituents, X, $R^1$, $R^2$, $R^3$, $R^4$, $R^5$, $R^6$, $R^a$ and $R^b$ can often be achieved before and/or after the exemplified transformations. These modifications can include the introduction of protecting groups, cleavage of protecting groups, reduction or oxidation of functional groups, halogenation, metallation, substitution or other suitable reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs and in the Experimental Section.

Scheme 1 describes one possible route for the preparation of compounds of general formula (I), in which X, $R^1$, $R^2$, $R^3$, $R^4$, $R^5$, $R^6$, $R^a$ and $R^b$ have the meaning as given for the compounds of general formula (I), supra.

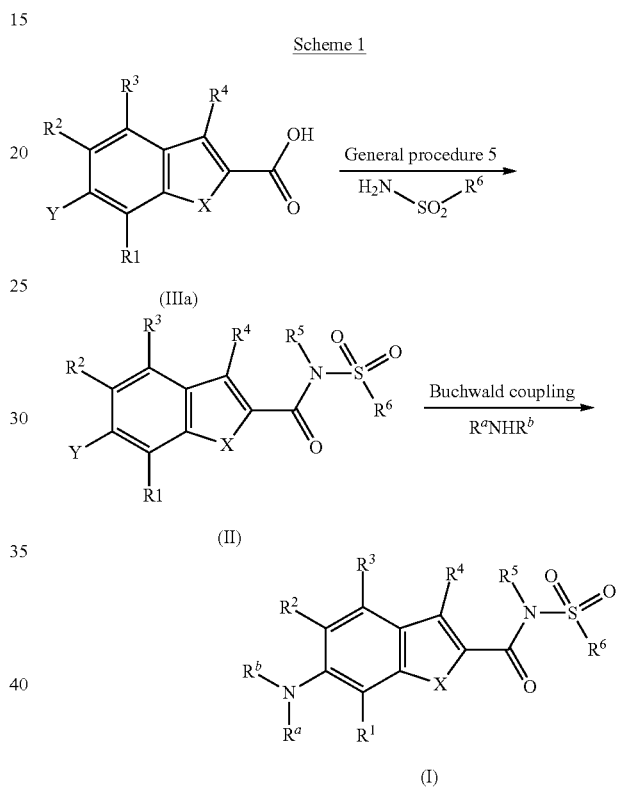

Scheme 1

As depicted in Scheme 1, compounds of general formula (I) can be synthesized via Buchwald-Hartwig amination of a derivative of formula (II) with a suitable amine $R^aNHR^b$, wherein X, $R^1$, $R^2$, $R^3$, $R^4$, $R^5$, $R^6$, $R^a$ and $R^b$ have the meaning as given for general formula (I), supra and Y is a halogen atom, such as e.g. fluorine, chlorine, bromine or iodine, preferably chlorine, bromine or iodine, more preferably chlorine or bromine. For the Buchwald-Hartwig amination reactions described in the context of the present invention, see, for example: *Chem Sci.* 2011, 2, 27-50; *RSC Adv.*, 2017, 7, 51972-51977. Specific examples are described in the Experimental Section. Said Buchwald-Hartwig amination reactions are carried out in the presence of a catalyst, preferably in the presence of a second- or third-generation Buchwald precatalyst (G2 or G3), which are widely known to the skilled person and/or commercially available. The reaction is preferably carried out in a solvent such as e.g. dimethyl formamide.

In turn, derivatives of formula (II) can be prepared via the coupling of an intermediate of formula (IIIa) with a primary sulfonamide of formula $H_2N—S(=O)_2—R^6$, wherein $R^6$ has the meaning as given for the compounds of general formula (I), supra. For the coupling of sulfonamides in the context of the present invention see, for example: *Org. Proc. Res. Dev.,* 2009, 13, 255-262; *Angew. Chem. Int. Ed.* 2018, 57, 3488-3492. Specific examples are described in the Experimental Section.

Depending inter alia on the nature of the substituents X, $R^1$, $R^2$, $R^3$, $R^4$, $R^5$, $R^6$, $R^a$ and $R^b$, compounds of general formula (I) can also be prepared via intermediates of formula (IIIb), in which the —$NR^aR^b$ moiety is introduced before the coupling with a primary sulfonamide of formula $H_2N$—$S(=O)_2$—$R^6$, wherein $R^6$ has the meaning as given for the compounds of general formula (I), supra (Scheme 2). Said compounds of formula (IIIb) can be prepared via Buchwald-Hartwig amination starting from compounds of formula (IIIa), wherein Y is a halogen atom, such as e.g. fluorine, chlorine, bromine or iodine, preferably chlorine, bromine or iodine, more preferably chlorine or bromine. Specific examples are described in the Experimental Section.

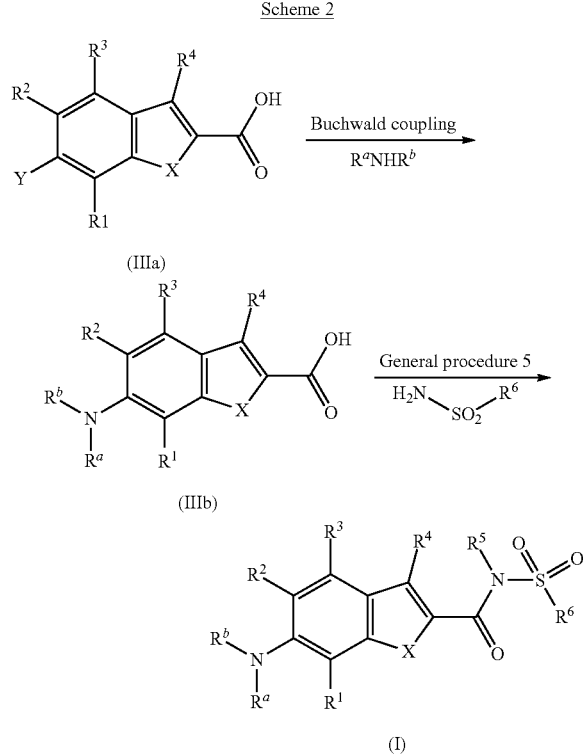

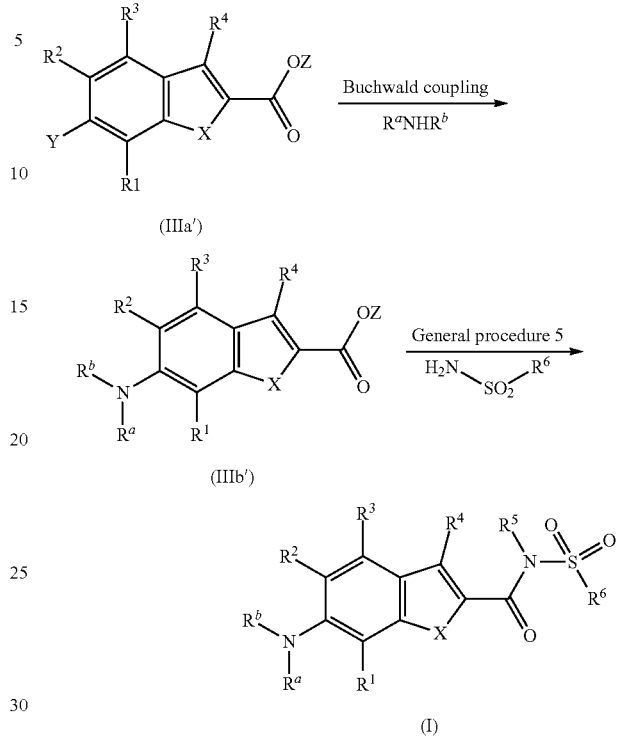

Depending inter alia on the nature of the substituents X, $R^1$, $R^2$, $R^3$, $R^4$, $R^5$, $R^6$, $R^a$ and $R^b$, compounds of formula (IIIb') can be prepared as described herein via Buchwald-Hartwig amination starting from compounds of formula (IIIa'), wherein Y is a halogen atom, such as e.g. fluorine, chlorine, bromine or iodine, preferably chlorine, bromine or iodine, more preferably chlorine or bromine and wherein Z is a $C_1$-$C_6$ alkyl group, preferably a $C_1$-$C_3$ alkyl group such as e.g. methyl or ethyl, more preferably wherein Z is a methyl group (Scheme 2'). The compounds of formula (IIIb') can then be coupled with a primary sulfonamide of formula $H_2N$—$S(=O)_2$—$R^6$, wherein $R^6$ has the meaning as given for the compounds of general formula (I), supra, to furnish the compounds of formula (I) as described herein for the compounds of formula (IIIb).

In general, the synthesis of the compounds of formula (I) of the present invention is preferably carried out following the sequence depicted in Scheme 2.

The compounds of formula (IIIa) and/or (IIIb) are either commercially available or can be prepared according to procedures available from the public domain, as understandable to the person skilled in the art. Specific examples are described in the Experimental Section.

For example, the benzofurane derivatives of formula (IIIa) in which X is an oxygen atom and wherein $R^1$, $R^2$, $R^3$ and $R^4$ have the meaning as given for the compounds of general formula (I), supra and Y is a halogen atom, such as e.g. fluorine, chlorine, bromine or iodine, preferably chlorine, bromine or iodine, more preferably chlorine or bromine, can be prepared via the reaction between a hydroxybenzaldehyde of formula (IVa) and for example ethyl chloro- or bromoacetate or any other suitable reagent of similar nature (Scheme 3). It can happen that mixtures of the free carboxylic acid and the corresponding ester are obtained. In this case, a saponification step might be necessary, which can be carried out using standard methods known in the art. Analogously, compounds of formula (IIIb) can be prepared starting from compounds of formula (IVb) wherein $R^1$, $R^2$, $R^3$, $R^4$, $R^a$ and $R^b$ have the meaning as given for the compounds of general formula (I), supra and Y is a halogen atom, such as e.g. fluorine, chlorine, bromine or iodine, preferably chlorine, bromine or iodine, more preferably chlorine or bromine (Scheme 4). For the cyclization reactions described herein, see, for example: *Chem. Biol. Drug. Des.,* 2018, 92, 1497-1503; *J. of enzyme inh. Med. Chem.* 2018, 33, 1, 1212-1224. Specific examples are described in the Experimental Section.

Scheme 3

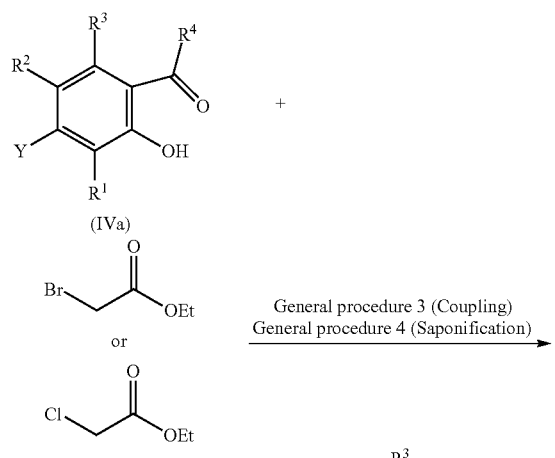

Scheme 4

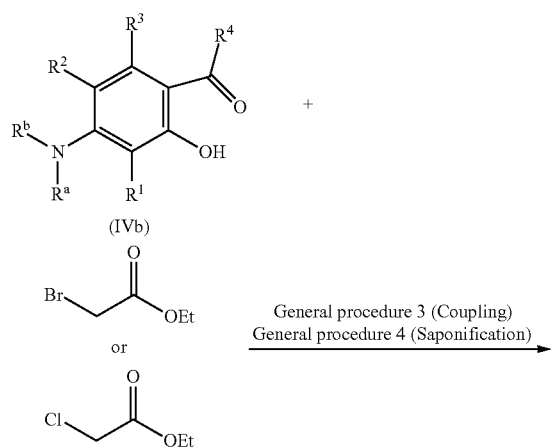

The sulfonamides of formula H$_2$N—S(=O)$_2$—R$^6$ are either commercially available or can be prepared according to procedures available from the public domain, as understandable to the person skilled in the art. Specific examples are described in the Experimental Section.

For example, suitable sulfonamides comprising a (phenyl)-(phenyl)-moiety can be prepared via the sequence depicted in Scheme 5, comprising the protection of an aryl sulfonamide with 1,1-dimethoxy-N,N-dimethylmethanamine, a coupling reaction with a suitable boronic acid derivative and optional deprotection, if necessary. The phenyl moieties can each be individually unsubstituted or substituted as defined for the compounds of general formula (I), supra. [B] indicates a boron-containing functionality suitable for the carbon-carbon coupling of the two phenyl moieties, e.g. a group —B(OR$^B$)$_2$ wherein OR$^B$ is a substituent that, when attached to the boron atom, can be used as coupling partner in a Suzuki reaction. For the reaction of aryl sulfonamides with 1,1-dimethoxy-N,N-dimethylmethanamine see, for example: *Organic Preparations and Procedures International* 2002, 34(5), 545-549; WO2005/26158; *Green Chemistry* 2013, 15(8), 2294-2301. Specific examples are described in the Experimental Section.

Scheme 5

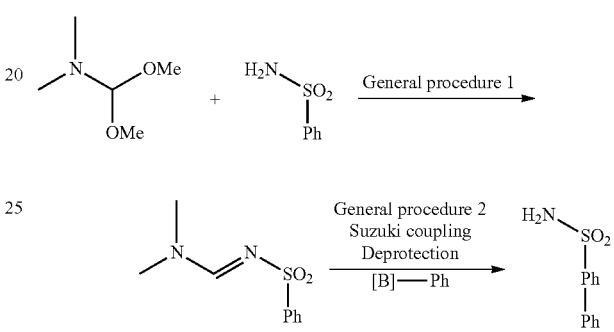

Further, for the compounds of formula (I) wherein R$^4$ is as defined for the compounds of general formula (I), supra but not a hydrogen atom, the corresponding substituent can be already be incorporated in one of the starting materials or if necessary it can be introduced at different stages during the reaction sequence leading to the compounds of formula (I). This can be achieved using methods, reagents and conditions well-known to the person skilled in the art. Specific examples are described in the Experimental Section.

In accordance with a second aspect, the present invention provides methods of preparing compounds of general formula (I) as defined supra, said method comprising the reaction of an intermediate compound of formula (II)

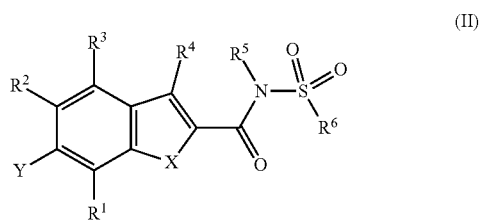

(II)

with an amine, wherein X, R$^1$, R$^2$, R$^3$, R$^4$, R$^5$ and R$^6$ are as defined for the compounds of general formula (I) supra, or a tautomer, or an N-oxide, or a salt thereof, or a salt of a tautomer, or a salt of an N-oxide, or a mixture of same and Y is a halogen atom selected from fluorine, chlorine, bromine or iodine, preferably chlorine, bromine or iodine, more preferably chlorine or bromine, thereby giving a compound of general formula (I)

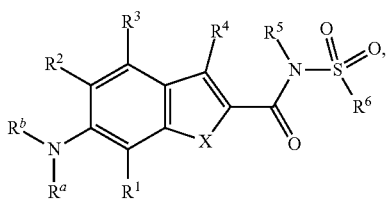

(I)

wherein X, $R^1$, $R^2$, $R^3$, $R^4$, $R^5$, $R^6$, $R^a$ and $R^b$ are as defined supra, or a tautomer, or an N-oxide, or a salt thereof, or a salt of a tautomer, or a salt of an N-oxide, or a mixture of same.

Further, the present invention provides intermediate compounds of general formula (II)

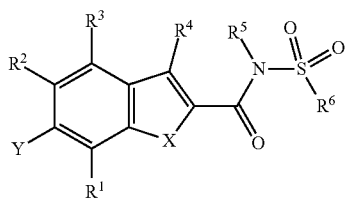

(II)

wherein X, $R^1$, $R^2$, $R^3$, $R^4$, $R^5$ and $R^6$ are as defined for the compounds of general formula (I) supra and Y is a halogen atom selected from chlorine and bromine or a tautomer, or an N-oxide, or a salt thereof, or a salt of a tautomer, or a salt of an N-oxide, or a mixture of same.

Particularly, the present invention provides the use of intermediate compounds of general formula (II):

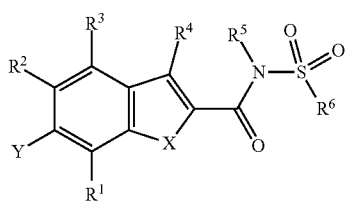

(II)

wherein X, $R^1$, $R^2$, $R^3$, $R^4$, $R^5$ and $R^6$ are as defined for the compounds of general formula (I) supra, or a tautomer, or an N-oxide, or a salt thereof, or a salt of a tautomer, or a salt of an N-oxide, or a mixture of same and Y is a halogen atom selected from fluorine, chlorine, bromine or iodine, preferably chlorine, bromine or iodine, more preferably chlorine or bromine, for the preparation of a compound of general formula (I) as defined supra.

The present invention includes the intermediate compounds which are disclosed in the Example Section of this text, infra.

The present invention includes any sub-combination within any embodiments or aspects of the present invention of intermediate compounds of general formula (II), of general formula (IIIa), of general formula (IIIb), of general formula (IVa), of general formula (IVa), supra.

The compounds of general formula (I) of the present invention can be converted to any salt, preferably pharmaceutically acceptable salts, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action which could not have been predicted. The compounds of the present invention effectively inhibit the activity of lysine acetyl transferase 6A (KAT6A) and/or lysine acetyl transferase 6B (KAT6B) for which data are given in the biological experimental section and may therefore be used for the treatment or prophylaxis of hyperproliferative disorders, such as cancer disorders in humans and animals.

Methods and Administration

Compounds of general formula (I) of the present invention demonstrate a valuable pharmacological spectrum of action and pharmacokinetic profile, both of which could not have been predicted. Compounds of the present invention have surprisingly been found to effectively inhibit the activity of lysine acetyl transferase 6A (KAT6A) and lysine acetyl transferase 6B (KAT6B), and it is possible therefore that said compounds can be used for the treatment or prophylaxis of diseases, preferably hyperproliferative disorders in humans and animals.

As used herein, "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

Compounds of the present invention can be utilized to inhibit, block, reduce, decrease, etc., cell proliferation and/or cell division, and/or produce apoptosis, which are all types of "treatment". This method comprises administering to a mammal in need thereof, including a human, an amount of a compound of general formula (I) of the present invention, or a pharmaceutically acceptable salt, isomer, polymorph, metabolite, hydrate, solvate or ester thereof, which is effective to treat the disorder.

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalamic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, basal cell carcinoma, squamous cell carcinoma, Kaposi's sarcoma, malignant melanoma, Merkel cell skin cancer and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, osteosarcoma, malignant fibrous histiocytoma, lymphosarcoma, and rhabdomyosarcoma.

Leukemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia (CLL), chronic myelogenous leukemia, chronic myeloid leukemia (CML), chronic myelomonocytic leukemia (CMML), large granular lymphocytic leukemia, plasma cell leukemia and also myelodysplastic syndrome (MDS), which can develop into an acute myeloid leukemia.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Ophthalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

These disorders have been well characterized in humans, but also exist with a similar etiology in other mammals, and can be treated by administering pharmaceutical compositions of the present invention.

The term "treating" or "treatment" as stated throughout this document is used conventionally, for example the management or care of a subject for the purpose of combating, alleviating, reducing, relieving and/or improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:

1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the cell or killing the cell.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In some embodiments, a compound of general formula (I) of the present invention is administered to a cell prior to the radiation or other induction of DNA damage in the cell. In some embodiments of the invention, a compound of general formula (I) of the present invention is administered to a cell concomitantly with the radiation or other induction of DNA damage in the cell. In yet some embodiments of the invention, a compound of general formula (I) of the present invention is administered to a cell after radiation or other induction of DNA damage in the cell has begun. In yet some embodiments of the invention, a compound of general formula (I) of the present invention is administered to a cell immediately after radiation or other induction of DNA damage in the cell has begun.

In some embodiments, the cell is in vitro. In another embodiment, the cell is in vivo.

Thus in some embodiments, the present invention includes a method of inhibiting proliferation of a cell and/or the induction of apoptosis in a cell, comprising contacting the cell with a compound of formula (I) according to any one of claims 1-13.

Another aspect of the invention is a method for treating, preventing or prophylaxing cancer (i.e. a method for the treatment, prevention or prophylaxis of cancer) in a subject (e.g., human, other mammal, such as rat, etc.) by administering an effective amount of at least one compound of general formula (I), or a pharmaceutically acceptable salt, polymorph, metabolite, hydrate, solvate or ester thereof to the subject.

In some embodiments, the subject may be administered a medicament, comprising at least one compound of general formula (I) and one or more pharmaceutically acceptable carriers, excipients and/or diluents.

Furthermore in some embodiments, the present invention includes a method of using a compound of general formula (I) for the treatment of diseases.

Particularly in some embodiments, the present invention includes a method of treating a hyperproliferative disease, more particularly cancer, comprising administering an effective amount of at least one compound of general formula (I) to a subject in need thereof according to any one of claim 1-13.

In some embodiments, the method of treatment and/or prophylaxis of a hyperproliferative disorder in a subject may comprise administering to the subject an effective amount of a compound of general formula (I). The hyperproliferative disorder may be, for example, cancer (e.g., lung cancer, acute myeloid leukemia, lymphoma, glioblastoma, prostate cancer, etc.).

Furthermore in some embodiments, the present invention includes a method of treating cancer, particularly lymphoma, non-Hodgkin-lymphoma type, diffuse large B-cell lymphoma subtype, acute leukemia, acute myeloid leukemia type, multiple myeloma, ovarian cancer, comprising administering an effective amount of at least one compound of formula (I) to a subject in need thereof according to any one of claim 1-13.

Furthermore in some embodiments, the present invention includes a method of treating cancer, particularly multiple myeloma, ovarian carcinoma, acute monocytic leukemia, melanoma and lung cancer, comprising administering an effective amount of at least one compound of formula (I) to a subject in need thereof according to any one of claim 1-13.

Furthermore in some embodiments, the present invention includes a method of treating cancer, particularly breast cancer; lung cancer; lymphoma including non-Hodgkin-lymphoma type, diffuse large B-cell lymphoma subtype including GC-DLBCL* and ABC-DLBCL subtypes, and mantle cell lymphoma; acute leukemia, acute myeloid leukemia type, acute monocytic leukemia; melanoma; multiple myeloma; ovarian cancer; and pancreas cancer, comprising administering an effective amount of at least one compound of formula (I) to a subject in need thereof according to any one of claim 1-13. GC-DLBCL means Germinal B-cell Diffuse Large B-Cell Lymphoma and ABC-DLBCL means Activated B-cell Diffuse Large B-Cell Lymphoma.

Furthermore in some embodiments, the present invention includes a method of treating cancer, particularly breast cancer, lung cancer, diffuse large B-cell lymphoma subtype including GC-DLBCL* and ABC-DLBCL subtypes, mantle cell lymphoma, acute monocytic leukemia, melanoma, ovarian cancer, and pancreas cancer comprising administering an effective amount of at least one compound of formula (I) to a subject in need thereof according to any one of claim 1-13**. Furthermore in some embodiments, the present invention provides a compound of formula (I) for use of treating diseases.

Furthermore in some embodiments, the present invention includes a method of treating cancer, particularly breast cancer; lymphoma, leukemia, multiple myeloma; and ovarian cancer, comprising administering an effective amount of at least one compound of formula (I) to a subject in need thereof according to any one of claim 1-13.

Furthermore in some embodiments, the present invention includes a method of treating cancer, particularly lymphoma, non-Hodgkin-lymphoma type, diffuse large B-cell lymphoma subtype, acute leukemia, acute myeloid leukemia type, multiple myeloma, and ovarian cancer, comprising administering an effective amount of at least one compound of formula (I) to a subject in need thereof according to any one of claim 1-13.

Furthermore in some embodiments, the present invention includes a method of treating cancer, particularly breast cancer, lymphoma (including non-Hodgkin-lymphoma type, diffuse large B-cell lymphoma subtype, mantle cell lymphoma), leukemia (including acute monocytic leukemia), liver cancer, multiple myeloma, melanoma, non-small cell lung cancer, small cell lung cancer, ovarian cancer, ovarian carcinoma, stomach cancer, and squamous cell carcinoma, comprising administering an effective amount of at least one compound of formula (I) to a subject in need thereof according to any one of claim 1-13.

Furthermore in some embodiments, the present invention includes a method of treating cancer, particularly breast cancer, diffuse large B-cell lymphoma subtype, mantle cell lymphoma, acute monocytic leukemia, liver cancer, multiple myeloma, melanoma, non-small cell lung cancer, small cell lung cancer, ovarian cancer, ovarian carcinoma, prostate cancer, stomach cancer, and squamous cell carcinoma, comprising administering an effective amount of at least one compound of formula (I) to a subject in need thereof according to any one of claim 1-13.

Furthermore in some embodiments, the present invention includes a method of treating cancer, particularly bladder cancer, bone cancer, brain cancer, breast cancer, colon cancer (colorectal cancer), endometrial (uterine) cancer, gastric cancer, head and neck cancer, kidney cancer, leukemia, liver cancer, lung cancer, lymphoma, lung cancer, myeloma, neuroblastoma, ovarian cancer, pancreatic cancer, rhabdoid tumor, sarcoma and skin cancer, comprising administering an effective amount of at least one compound of formula (I) to a subject in need thereof according to any one of claim 1-13.

Furthermore in some embodiments, the present invention includes a method of treating cancer, particularly lung cancer, breast cancer, bladder cancer, uterine cancer, endometrial cancer, prostate cancer and leukemia comprising administering an effective amount of at least one compound of formula (I) to a subject in need thereof according to any one of claim 1-13.

Furthermore in some embodiments, the present invention includes a method of treating cancer, particularly cancer in which KAT6A and/or KAT6B is focally amplified, said method comprising administering an effective amount of at least one compound of formula (I) to a subject in need thereof according to any one of claim 1-13.

Furthermore in some embodiments, the present invention includes a method of treating cancer, particularly cancer in which KAT6A is focally amplified, said method comprising administering an effective amount of at least one compound of formula (I) to a subject in need thereof according to any one of claim 1-13.

Furthermore in some embodiments, the present invention includes a method of treating cancer, particularly cancer in which KAT6B is focally amplified, said method comprising administering an effective amount of at least one compound of formula (I) to a subject in need thereof according to any one of claim 1-13.

Furthermore in some embodiments, the present invention includes a method of treating cancer, particularly breast cancer, lung cancer, endometrial cancer, ovarian cancer, bladder cancer, esophageal cancer, uterine cancer and epithelial cancer comprising administering an effective amount of at least one compound of formula (I) to a subject in need thereof according to any one of claim 1-13.

Furthermore in some embodiments, the present invention includes a method of treating cancer, particularly breast cancer, lung cancer, endometrial cancer, ovarian cancer, bladder cancer and esophageal cancer comprising administering an effective amount of at least one compound of formula (I) to a subject in need thereof according to any one of claim 1-13.

Furthermore in some embodiments, the present invention includes a method of treating cancer, particularly breast cancer, uterine cancer and epithelial cancer comprising administering an effective amount of at least one compound of formula (I) to a subject in need thereof according to any one of claim 1-13.

Furthermore in some embodiments, the present invention includes a method of treating cancer, particularly luminal A breast cancer, comprising administering an effective amount of at least one compound of formula (I) to a subject in need thereof according to any one of claim 1-13.

In accordance with some embodiments, the present invention provides compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular hyperproliferative disorders.

Furthermore in accordance with a further aspect, the present invention provides a compound of formula (I) for use of treating diseases.

In accordance with a further aspect, the present invention includes a compound of general formula (I) for use in a method of inhibiting proliferation of a cell and/or the induction of apoptosis in a cell, comprising contacting the cell with a compound of formula (I) according to any one of claim 1-13.

Particularly in some embodiments, the present invention includes compounds of general formula (I) for use in a method of treating a hyperproliferative disease, more particularly wherein the hyperproliferative disease is cancer, and yet even more particularly wherein the cancer disease is selected from lymphoma, non-Hodgkin-lymphoma type, diffuse large B-cell lymphoma subtype, ovarian cancer, multiple myeloma, acute leukemia, and acute myeloid leukemia.

More particularly in some embodiments, the present invention includes compounds of general formula (I) for use in a method of treating a hyperproliferative disease, more particularly wherein the hyperproliferative disease is cancer, and yet even more particularly wherein the cancer disease is selected from breast cancer; lymphoma, leukemia, multiple myeloma; and ovarian cancer.

Particularly in some embodiments, the present invention includes compounds of general formula (I) for use in a method of treating a hyperproliferative disease, more particularly wherein the hyperproliferative disease is cancer, and yet even more particularly wherein the cancer is selected from breast cancer; esophageal cancer; liver cancer; lung cancer; lymphoma including non-Hodgkin-lymphoma type, diffuse large B-cell lymphoma subtype including GC-DLBCL* and ABC-DLBCL** subtypes, and mantle cell lymphoma; acute leukemia, acute myeloid leukemia type, acute monocytic leukemia; melanoma; multiple myeloma; melanoma; ovarian cancer; or pancreas cancer.

More particularly in some embodiments, the present invention includes compounds of general formula (I) for use in a method of treating cancer wherein the cancer disease is selected from breast cancer; lymphoma, leukemia, multiple myeloma; and ovarian cancer.

More particularly in some embodiments, the present invention includes compounds of general formula (I) for use in a method of treating cancer wherein the cancer disease is selected from lung cancer, breast cancer, bladder cancer, uterine cancer, endometrial cancer, prostate cancer and leukemia.

More particularly in some embodiments, the present invention includes compounds of general formula (I) for use in a method of treating cancer in which KAT6A and/or KAT6B is focally amplified.

More particularly in some embodiments, the present invention includes compounds of general formula (I) for use in a method of treating cancer in which KAT6A is focally amplified.

More particularly in some embodiments, the present invention includes compounds of general formula (I) for use in a method of treating cancer in which KAT6B is focally amplified.

More particularly in some embodiments, the present invention includes compounds of general formula (I) for use in a method of treating cancer wherein the cancer disease is selected from breast cancer, lung cancer, endometrial cancer, ovarian cancer, bladder cancer, esophageal cancer, uterine cancer and epithelial cancer.

More particularly in some embodiments, the present invention includes compounds of general formula (I) for use in a method of treating cancer wherein the cancer disease is selected from breast cancer, lung cancer, endometrial cancer, ovarian cancer, bladder cancer and esophageal cancer.

More particularly in some embodiments, the present invention includes compounds of general formula (I) for use in a method of treating cancer wherein the cancer disease is selected from breast cancer, uterine cancer and epithelial cancer.

More particularly in some embodiments, the present invention includes compounds of general formula (I) for use in a method of treating cancer wherein the cancer disease is breast cancer, particularly luminal A breast cancer.

In some embodiments, the present invention includes the use of the compounds of general formula (I) for the manufacture of a medicament for the treatment and/or prophylaxis of a hyperproliferative disease.

In some embodiments, the present invention includes the use of the compounds of general formula (I) for the manufacture of a medicament for the treatment and/or prophylaxis of a hyperproliferative disease, wherein the hyperproliferative disease is cancer.

In some embodiments, the present invention includes the use of the compounds of general formula (I) for the manufacture of a medicament for the treatment of a hyperproliferative disease, particularly cancer and more particularly lymphoma, non-Hodgkin-lymphoma type, diffuse large B-cell lymphoma subtype, ovarian cancer, multiple myeloma, acute leukemia, and acute myeloid leukemia type.

In some embodiments, the present invention includes the use of the compounds of general formula (I) for the manufacture of a medicament for the treatment of a hyperproliferative disease, particularly cancer and more particularly lung cancer, breast cancer, bladder cancer, uterine cancer, endometrial cancer, prostate cancer and leukemia.

In some embodiments, the present invention includes the use of the compounds of general formula (I) for the manufacture of a medicament for the treatment of a hyperproliferative disease, particularly cancer and more particularly cancer in which KAT6A and/or KAT6B is focally amplified.

In some embodiments, the present invention includes the use of the compounds of general formula (I) for the manufacture of a medicament for the treatment of a hyperproliferative disease, particularly cancer and more particularly cancer in which KAT6A is focally amplified.

In some embodiments, the present invention includes the use of the compounds of general formula (I) for the manufacture of a medicament for the treatment of a hyperproliferative disease, particularly cancer and more particularly cancer in which KAT6B is focally amplified.

In some embodiments, the present invention includes the use of the compounds of general formula (I) for the manufacture of a medicament for the treatment of a hyperproliferative disease, particularly cancer and more particularly breast cancer, lung cancer, endometrial cancer, ovarian cancer, bladder cancer, esophageal cancer, uterine cancer and epithelial cancer.

In some embodiments, the present invention includes the use of the compounds of general formula (I) for the manufacture of a medicament for the treatment of a hyperproliferative disease, particularly cancer and more particularly breast cancer, lung cancer, endometrial cancer, ovarian cancer, bladder cancer and esophageal cancer.

In some embodiments, the present invention includes the use of the compounds of general formula (I) for the manufacture of a medicament for the treatment of a hyperproliferative disease, particularly cancer and more particularly breast cancer, uterine cancer and epithelial cancer.

In some embodiments, the present invention includes the use of the compounds of general formula (I) for the manufacture of a medicament for the treatment of a hyperproliferative disease, said hyperproliferative disease being cancer and more particularly luminal A breast cancer.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly lung cancer, breast cancer, bladder cancer, uterine cancer, endometrial cancer, prostate cancer and leukemia.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly cancer in which KAT6A and/or KAT6B is focally amplified.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly cancer in which KAT6A is focally amplified.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly cancer in which KAT6B is focally amplified.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly breast cancer, lung cancer, endometrial cancer, ovarian cancer, bladder cancer, esophageal cancer, uterine cancer and epithelial cancer.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly breast cancer, lung cancer, endometrial cancer, ovarian cancer, bladder cancer and esophageal cancer.

In some embodiments, the present invention provides use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular hyperproliferative disorders, particularly cancer, more particularly breast cancer, uterine cancer and epithelial cancer.

In some embodiments, the present invention provides a method of treatment or prophylaxis of diseases, in particular hyperproliferative disorders, particularly cancer, comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly lung cancer, breast cancer, bladder cancer, uterine cancer, endometrial cancer, prostate cancer and leukemia comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly cancer in which KAT6A and/or KAT6B is focally amplified comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly cancer in which KAT6A is focally amplified comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly cancer in which KAT6B is focally amplified comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly breast cancer, lung cancer, endometrial cancer, ovarian cancer, bladder cancer, esophageal cancer, uterine cancer and epithelial cancer comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly breast cancer, lung cancer, endometrial cancer, ovarian cancer, bladder cancer and esophageal cancer comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly breast cancer, uterine cancer and epithelial cancer comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides a method of treatment or prophylaxis of diseases, in particular hyperproliferative disorders, particularly cancer, more particularly luminal A breast cancer, comprising administering an effective amount of a compound of general formula (I), as described supra, or stereoisomers, tautomers, N-oxides, hydrates, solvates, and salts thereof, particularly pharmaceutically acceptable salts thereof, or mixtures of same to a subject in need thereof.

In some embodiments, the present invention provides pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore provides pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,
- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example gelatine, hydroxypropylmethylcellulose),
- synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide),
- flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In some embodiments, the present invention provides pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention provides a pharmaceutical combination, which comprises:
- one or more first active ingredients, in particular compounds of general formula (I) as defined supra, and
- one or more further active ingredients, in particular for the treatment and/or prophylaxis of a hyperproliferative disorder, particularly cancer.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also provides such pharmaceutical combinations. For example, the compounds of the present invention can be combined with known anti-cancer agents.

Examples of anti-cancer agents include:
131I-chTNT, abarelix, abemaciclib, abiraterone, acalabrutinib, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, apalutamide, aprepitant, arcitumomab, arglabin, arsenic trioxide, asparaginase, atezolizumab, avelumab, axicabtagene ciloleucel, axitinib, azacitidine, basiliximab, belotecan, bendamustine, besilesomab, belinostat, bevacizumab, bexarotene, bicalutamide, bisantrene, bleomycin, blinatumomab, bortezomib, bosutinib, buserelin, brentuximab vedotin, brigatinib, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, durvalumab, eculizumab, edrecolomab, elliptinium acetate, elotuzumab, eltrombopag, enasidenib, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, inotuzumab ozogamicin, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, lutetium Lu 177 dotatate, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, midostaurin, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, mvasi, nabilone, nabiximols, nafarelin, naloxone+pentazocine, naltrexone, nartograstim, necitumumab, nedaplatin, nelarabine, neratinib, neridronic acid, netupitant/palonosetron, nivolumab, pentetreotide, nilotinib, nilutamide, nimorazole, nimotuzumab, nimustine, nintedanib, niraparib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, ribociclib, risedronic acid, rhenium-186 etidronate, rituximab, rolapitant, romidepsin, romiplostim, romurtide, rucaparib, samarium (153Sm) lexidronam, sargramostim, sarilumab, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tisagenlecleucel, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid and zorubicin.

Based upon standard laboratory techniques known to evaluate compounds useful for the treatment of hyperproliferative disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

Experimental Part

General Remarks:

In the text, the chemical names and the numbers of the compounds are given in bold. The intermediates are defined by INT-.

Chemical names were generated using the ACD/Name software from ACD/Labs. In some cases generally accepted names of commercially available reagents were used in place of ACD/Name generated names.

If the purity of the obtained example product are not mentioned, the compounds are 90 to 100% pure.

The following table 1 lists the abbreviations used in this paragraph and in the Examples section as far as they are not explained within the text body. Other abbreviations have their meanings customary per se to the skilled person.

TABLE 1

Abbreviations

| Abbreviation | Meaning |
| --- | --- |
| aq. | aqueous |
| DCM | dichloromethane |
| DIPEA | N,N-diisopropylethylamine |
| DMF | N,N-dimethylformamide |
| DMSO | dimethylsulfoxide |
| eq. | equivalent |
| EtOH | ethanol |
| EtOAc | ethyl acetate |
| h | hour(s) |
| HT | High throughput |
| NMR | nuclear magnetic resonance spectroscopy: chemical |
| MeOH | methanol |
| MS | mass spectrometry |
| min | minute(s) |
| PyBOP | Benzotriazol-1-yl-oxytripyrrolidinophosphonium hexafluorophosphate |
| RT | room temperature |
| Rt | retention time (as measured either with HPLC or UPLC) |
| THF | tetrahydrofuran |
| TPP | Triphenylphospine | cat. catalytic
DAD diode array detector
ESI electrospray (ES) ionisation
HCI hydrochloric acid
HPLC high performance liquid chromatography
LC-MS liquid chromatography mass spectrometry
shifts (δ) are given in ppm. The chemical shifts were corrected by setting the DMSO signal to 2.50 ppm unless otherwise stated.
rac racemic
t triplet
UPLC ultra performance liquid chromatography
Other abbreviations have their meanings customary per se to the skilled person.

The following table lists the abbreviations used herein.
Solvents
The following solvents were purchased from commercial sources and used without further purification:
acetic acid (CAS: 64-19-7)
aqueous ammonia, 25% (CAS: 1336-21-6)
dichloromethane (CAS: 75-09-2)
dimethyl sulfoxide (CAS: 67-68-5)
Ethyl acetate (CAS: 141-78-6)
ethanol (CAS: 64-17-5)
formic acid (CAS: 64-18-6)
methanol (CAS: 67-56-1)
N,N-dimethylformamide (CAS: 68-12-2)
tetrahydrofuran (CAS: 109-99-9)
toluene (CAS: 108-88-3)

Reagents

All reagents, for which the synthesis is not described in the experimental part, are either commercially available or synthesized according to literature procedures.

The following reactants were purchased from commercial sources and were used without further purification:
- (2'-Aminobiphenyl-2-yl)(chloro)palladium-dicyclohexyl [2',4',6'-tri(propan-2-yl)biphenyl-3-yl]phosphane (1:1) (Palladium-Xphos G2) (CAS: 1310584-14-5)
- (Benzotriazol-1-yl-oxytripyrrolidinophosphonium hexafluorophosphate PyBOP (CAS: 128625-52-5)
- Bis(triphenylphosphine)palladium(II) dichloride (CAS: 13965-03-2)
- N,N-diisopropylethylamine (CAS: 7087-68-5)
- 1,1-dimethoxy-N,N-dimethylmethanamine (CAS: 4637-24-5)
- cesium carbonate (CAS: 534-17-8)
- Copper(I) iodide (CAS: 7681-65-4)
- lithium hydroxide (CAS: 1310-65-2)
- Palladium (II)acetate (CAS: 3375-31-3)
- sodium carbonate (CAS: 497-19-8)
- tetrakis(triphenylphosphin)palladium(0) (CAS: 14221-01-3)
- 1,1'-Bis(diphenylphosphino)ferrocene (CAS: 12150-46-8)

UPLC-MS Standard Procedures

Analytical UPLC-MS was performed as described below. The masses (m/z) are reported from the positive mode electrospray ionization unless the negative mode is indicated (ESI−).

Analytical UPLC Methods:

Method 1:
Instrument: Waters Acquity UPLCMS SingleQuad; Column: Acquity UPLC BEH $C_{18}$ 1.7 µm, 50×2.1 mm; eluent A: water+0.1 vol % formic acid (99%), eluent B: acetonitrile; gradient: 0-1.6 min 1-99% B, 1.6-2.0 min 99% B; flow 0.8 mL/min; temperature: 60° C.; DAD scan: 210-400 nm.

Method 2:
Instrument: Waters Acquity UPLCMS SingleQuad; Column: Acquity UPLC BEH $C_{18}$ 1.7 µm, 50×2.1 mm; eluent A: water+0.2 vol % aq. ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 3:
Instrument: Waters Acquity UPLCMS SingleQuad; Column: Acquity UPLC BEH $C_{18}$ 1.7 50×2.1 mm; eluent A: water+0.2 vol % aq. ammonia (32%), eluent B: acetonitrile; gradient: 0-1.6 min 1-99% B, 1.6-2.0 min 99% B; flow 0.8 mL/min; temperature: 60° C.; DAD scan: 210-400 nm.

Method 4:
Instrument: Waters Acquity UPLCMS SingleQuad; Column: Waters Acquity BEH $C_{18}$ 50 mm×2.1 mm×1.7 µm; eluent A: Water (MilliQ)+0.01 vol % formic acid, eluent B: acetonitrile+0.01 vol % formic acid; gradient: 0-0.3 min 3-4% B, 0.3-1.5 min 4-95% B, 1.5-1.9 min 95% B; 1.9-2.0 min 5% B; flow: 0.65 mL/min; temperature: 50° C.; DAD scan: 200-500 nm.

Method 5:
Instrument: Waters Autopurification MS SingleQuad; Column: Waters XBrigde $C_{18}$ 5 am 100×30 mm; eluent A: water+0.1 vol % formic acid (99%), Eluent B: Acetonitrile; Gradient: 0-5.5 min 5-100% B; flow 70 mL/min; temperature: 25° C.; DAD scan: 210-400 nm.

Method 6:
Instrument: Waters Acquity UPLCMS SingleQuad; Column: Acquity UPLC BEH $C_{18}$ 1.7 50×2. 1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method 7:
Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.5 min 5% B, 0.5-4.0 min 5-95% B, 4.0-4.5 min 95% B; 4.5-5.0 min 5% B; flow: 0.65 mL/min; temperature: 50° C.; DAD scan: 200-500 nm.

Method 8:
Instrument: Waters Acquity; Column: Waters Acquity BEH C18 50 mm×2.1 mm×1.7 µm; eluent A: Water (MilliQ)+0.01 vol % formic acid, eluent B: acetonitrile+0.01 vol % formic acid; gradient: 0-0.5 min 5% B, 0.5-9.0 min 5-95% B, 9.0-9.5 min 95% B; 9.5-10.0 min 5% B; flow: 0.65 mL/min; temperature: 50° C.; DAD scan: 200-500 nm.

Method 9:
Instrument: Waters Autopurification MS SingleQuad; column: Waters XBrigde C18 5 µm 100×30 mm; water+0.1 Vol-% formic acid (99%), Eluent B: Acetonitrile; Gradient: 0-5.5 min 5-100% B; flow 70 ml/min; temperature: 25° C.; DAD scan: 210-400 nm.

General Procedures (GP)

GP1: Protection of Sulfonamide

The commercially available 1,1-dimethoxy-N,N-dimethylmethanamine (2.0 eq.) and the sulfonamide (1.0 eq.) were dissolved in DMF (3-6 mL/mmol) under argon atmosphere and the solution was stirred for 3 h. After reaction completion, the solvent was removed under vacuum. The residue was dissolved in EtOAc, water was added and the layers were separated. The aqueous layer was extracted with EtOAc. The combined organic layers were washed with brine. After filtration over a coated filter, the solvent was removed under vacuum. The crude was used without any further purification into the next step.

GP2: One-Pot SUZUKI Coupling and Protecting Group Removal Under Basic Conditions The aforementioned protected sulfonamide (1.0 eq.), the commercially available boronic acid partner (2.0 eq.), the commercially available catalyst Bis(triphenylphosphine) palladium(II)dichloride (0.05 eq.) and TPP (0.05 eq.) were suspended in DMF (4 mL/mmol) under argon atmosphere. Then an aqueous sodium carbonate solution (320 µL, 2 M, 0.64 mmol) was added and the resulted mixture was stirred intensively for a short time at RT and then overnight at 120° C. Usually, additional 3.0 eq. of an aqueous sodium carbonate solution were added and the mixture was further heated at 100° C. for 2 h. The reaction mixture was filtered, washed with DCM and the solvent was removed under vacuum. The resulted residue was purified using either preparative HPLC or column chromatography (EtOAc/MeOH mixture) giving the desired free sulfonamide.

GP3: Synthesis of Benzofuran-2-Carboxylates

The commercially available hydroxybenzaldehydes (1.0 eq.), commercially available ethyl chloro- or bromo-acetate (1.0-1.5 eq.) and potassium carbonate (1.0-1.5 eq.) were suspended in DMF (0.61 mmol/mL) at 0° C. Following complete addition, the resulting reaction mixture was heated at 160° C. for 2 h to overnight to give a mixture of the desired product and ethyl ester. After cooling to RT, an aq. solution of sodium hydroxide (4.0 M, 200 mL) was added to the mixture and the resulting solution was in some cases further heated at 70° C. for 24 h. The reaction mixture was concentrated under reduced pressure and then neutralized with 2.0 M hydrochloric acid. The build precipitate was collected by filtration and dried in the vacuum oven at 40° C. to give the crude material which was directly used for the next step.

GP4: Saponification

The benzofuran methylester was dissolved in THF (4 mL/mmol) and an aq. solution of lithium hydroxide (5 eq., 18 mL/mmol) was slowly added to the solution. After reaction completion (2-5 h) the mixture was concentrated under reduced pressure and the residue was carefully acidified with an HCl (6 M) solution. The obtained crude product was usually used in the next step without any further purification step.

GP5: Coupling Between a Carboxylic Acid and a Sulfonamide

The intermediates and examples were synthesized using two different coupling methods:

A/ Using PyBOP as a Coupling Agent (GP5A)

The sulfonamide partner (1.2 eq.), the acid partner (1.0 eq) and the commercially available coupling agent PyBOP (1.2 eq.) were suspended in DCM (0.1 mL/mmol) under argon atmosphere. After degassing with argon for 5 min, DIPEA (4.0 eq.) was added and the mixture was stirred at RT for 16 h-3 d. After reaction completion, the mixture was diluted with DCM, water was added and the layers were separated. The aqueous layer was extracted with DCM. The combined organic layers were washed with brine and dried with sodium sulfate. After filtration, the solvent was removed under vacuum. The residue was purified by HPLC HT or column chromatography to give the desired sulfonamide.

B/ Using CDI (GP5B)

The acid partner (1.0 eq) was stirred at RT with CDI (1.18-1.2 eq.) in THF (4.1 mL/mmol) for 1 h at RT. Then were successively added the sulfonamide partner (1.1 eq.) and the commercially available base DBU (1.38 eq.) added and the resulting reaction mixture was stirred at RT for an additional hour. The reaction mixture was dissolved in DMF and purified by HPLC.

GP6: BUCHWALD Coupling

The aryl bromide partner (1.0 eq.), the commercially available amine (1.1-2.0 eq.), the commercially available palladium-Xphos G2 catalyst (0.1 eq.) and caesium carbonate (2.5 eq.) were suspended in dioxane (3.9 mL/mmol) under argon atmosphere. In the case were N-methylmethanamine also DMF was also used. The resulted mixture was heated to 85 to 100° C. for 4 h to overnight. The mixture was diluted with ethyl acetate, water was added and the layers were separated. The aqueous layer was extracted with ethyl acetate. The combined organic layers were washed with brine and dried with sodium sulfate. After filtration, the solvent was removed under vacuum. The resulted residue was purified using either preparative HPLC or column chromatography (EtOAc/MeOH mixture) giving the desired free sulfonamide.

INTERMEDIATES

The following intermediates INT-1 and INT-2 were prepared using respectively 2-bromo-6-ethoxybenzenesulfonamide (which can be prepared in analogy to a procedure described in BayerCropScience AG US2010/285964, 2010, A1), commercially available 2-bromobenzenesulfonamide (CAS: 92748-09-9) according to GP1.

TABLE 2 intermediates INT-1 and INT-2

| Intermediate | Structure, IUPAC-Name and analytics |
|---|---|
| INT-1 | 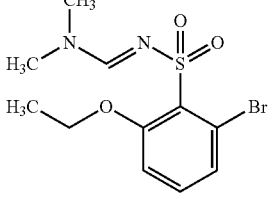<br>N'-(2-Bromo-6-ethoxybenzene-1-sulfonyl)-N,N-dimethylmethanimidamide<br>$^1$H-NMR (400 MHz, DMSO-d$_6$) δ [ppm]:<br>1.282 (4.30), 1.300 (9.28), 1.310 (0.87), 1.317 (4.42), 2.518 (1.35), 2.522 (0.84), 2.902 (1.45), 2.908 (14.37), 3.195 (16.00), 4.081 (1.30), 4.098 (4.03), 4.116 (4.01), 4.133 (1.16), 5.759 (0.52), 7.157 (1.38), 7.162 (1.38), 7.176 (1.62), 7.181 (1.69), 7.314 (1.03), 7.329 (4.11), 7.332 (4.87 ), 7.350 (2.65), 7.370 (0.79), 8.180 (3.73); LC-MS (method 1): R$_t$ = 88.00 min; MS (ESIpos): m/z = 337 [M + H]$^+$. |
| INT2 | 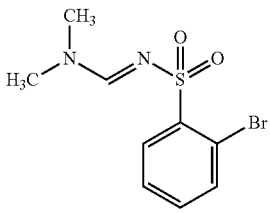<br>N'-(2-Bromobenzene-1-sulfonyl)-N,N-dimethylmethanimidamide<br>$^1$H-NMR (400 MHz, DMSO-d$_6$) δ [ppm]:<br>2.937 (14.71), 2.939 (14.83), 3.189 (16.00), 7.462 (0.87), 7.466 (0.97), 7.480 (1.80), 7.485 (1.65), 7.500 (1.74), 7.504 (1.68), 7.531 (1.40), 7.534 (1.74), 7.550 (1.84), 7.553 (1.94), 7.569 (1.03), 7.572 (0.99), 7.765 (2.06), 7.768 (2.23), 7.784 (1.73), 7.787 (1.82), 8.047 (1.97), 8.052 (1.92), 8.067 (2.07), 8.071 (1.86), 8.283 (3.33); LC-MS (method 1): R$_t$ = 0.84 min; MS (ESIpos): m/z = 293 [M + H]$^+$. |

Intermediate INT-3

N'-(3'-chloro[1,1'-biphenyl]-2-sulfonyl)-N,N-dimethylmethanimidamide

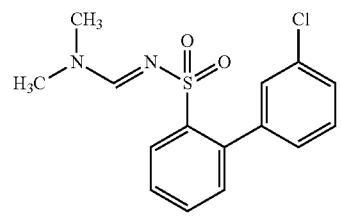 [SMILES: CN(C)/C=N/S(=O)(=O)c1ccccc1-c1cccc(Cl)c1]

The aforementioned protected sulfonamide INT-2 (70.0 mg, 240 µmol), the commercially available boronic acid partner 3-chlorophenylboronic acid (CAS: 63503-60-6, 41.4 mg, 264 µmol), the commercially available catalyst dichloro[bis(triphenyl-lambda5-phosphanyl)]palladium (CAS: 13965-03-2, 8.44 mg, 12.0 µmol) and commercially available TPP (CAS: 603-35-0, 3.15 mg, 12.0 µmol) were suspended in 1-propanol (2 mL) under argon atmosphere. Then an aqueous sodium carbonate solution (360 µL, 2.0 M, 720

μmol) was added and the resulted mixture was heated to 90° C. for 3 h. After reaction completion the solvent was removed under vacuum. The residue was dissolved in DCM and The solution was extracted with water and the aqueous layer was washed with DCM. The combinated organic layers were dried over a coated filter and concentrated under reduced pressure. The obtained crude product was purified using HPLC HT giving the desired free sulfonamide (42.7 mg, 78%). $^1$H-NMR (400 MHz, DMSO-d$_6$) δ [ppm]: 2.518 (3.06), 2.523 (2.19), 2.719 (13.72), 2.854 (15.30), 5.759 (16.00), 7.238 (3.60), 7.244 (1.27), 7.247 (1.52), 7.251 (1.10), 7.263 (1.30), 7.266 (1.85), 7.270 (1.35), 7.300 (1.55), 7.303 (1.44), 7.318 (1.92), 7.321 (1.77), 7.329 (1.86), 7.333 (2.93), 7.337 (1.63), 7.407 (1.27), 7.426 (2.81), 7.445 (1.85), 7.474 (1.63), 7.477 (1.82), 7.479 (1.55), 7.482 (1.58), 7.494 (0.90), 7.497 (0.81), 7.499 (0.92), 7.502 (0.76), 7.570 (0.74), 7.573 (0.85), 7.589 (2.00), 7.592 (1.75), 7.608 (1.75), 7.611 (1.38), 7.623 (1.44), 7.627 (1.80), 7.642 (2.08), 7.646 (1.94), 7.660 (0.78), 7.664 (0.67), 8.053 (1.72), 8.057 (2.00), 8.072 (1.49), 8.076 (1.55); LC-MS (method 1): R$_t$=1.15 min; MS (ESIpos): m/z=323 [M+H]$^+$.

Intermediate INT-4

3'-Chloro[1,1'-biphenyl]-2-sulfonamide (CAS: 1350725-94-8)

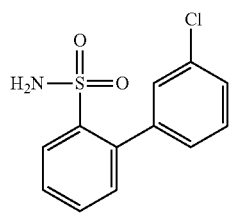 [SMILES: NS(=O)(=O)c1ccccc1-c1cccc(Cl)c1]

The aforementioned protected sulfonamide INT-3 (20 mg, 62 μmol) was dissolved in MeOH (5 mL) and an 25%-aq. solution of ammonia (10 mL) was slowly added to the solution at RT. The mixture was stirred at RT for 17 h. after reaction completion the mixture was concentrated under vacuum. The residue was purified by HPLC HT giving the desired sulfonamide as a light-brown resin (7.7 mg, 46%). $^1$H-NMR (400 MHz, METHANOL-d$_4$) δ [ppm]: 1.291 (1.71), 1.308 (0.54), 1.318 (0.41), 2.657 (0.59), 2.694 (0.54), 7.316 (7.40), 7.319 (6.93), 7.328 (3.02), 7.335 (10.56), 7.338 (11.21), 7.343 (5.44), 7.348 (7.07), 7.350 (8.64), 7.354 (8.48), 7.362 (5.23), 7.364 (4.56), 7.368 (1.51), 7.382 (12.66), 7.384 (12.91), 7.390 (9.71), 7.395 (12.77), 7.397 (16.00), 7.401 (12.52), 7.409 (1.10), 7.414 (2.72), 7.421 (1.74), 7.424 (7.37), 7.426 (8.37), 7.428 (9.84), 7.431 (11.62), 7.434 (4.15), 7.538 (4.13), 7.541 (3.85), 7.557 (8.46), 7.560 (7.95), 7.576 (7.17), 7.580 (6.71), 7.609 (6.62), 7.613 (7.83), 7.628 (10.87), 7.632 (10.50), 7.647 (4.15), 7.650 (3.76), 8.103 (7.98), 8.106 (8.59), 8.122 (7.07), 8.126 (7.51); LC-MS (method 1): R$_t$=1.05 min; MS (ESIneg): m/z=266 [M−H]$^−$.

Intermediate INT-5

3'-Chloro-3-ethoxy[1,1'-biphenyl]-2-sulfonamide

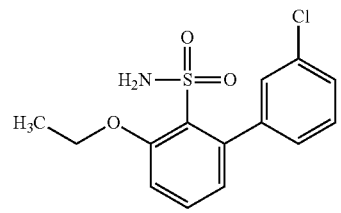 [SMILES: CCOc1cccc(-c2cccc(Cl)c2)c1S(N)(=O)=O]

According to GP2, the aforementioned protected sulfonamide INT-1 (193 mg, 0.576 mmol), the commercially available boronic acid partner 3-chlorophenylboronic acid (CAS: 63503-60-6, 180 mg, 11.51 mmol), the commercially available catalyst dichloro[bis(triphenyl-lambda5-phosphanyl)]palladium (CAS: 13965-03-2, 20.2 mg, 28.8 μmol) and commercially available TPP (CAS: 603-35-0, 7.6 mg, 28.8 μmol) and an aq. solution of potassium carbonate (238.7 mg, 17.3 mmol, 863.6 μL, 2 M) were suspended in DMF (2.4 mL) under argon atmosphere). The mixture was heated zo 120° C. overnight. After reaction completion, workup and purification the desired product was isolated as a colourless solid (57 mg, 32%). $^1$H-NMR (400 MHz, DMSO-d6) δ[ppm]: 1.391 (7.45), 1.408 (16.00), 1.425 (7.62), 2.074 (0.43), 2.331 (0.90), 2.518 (4.76), 2.523 (3.03), 2.673 (0.90), 2.888 (0.43), 4.268 (1.90), 4.285 (6.22), 4.303 (6.12), 4.320 (1.80), 6.792 (3.46), 6.795 (3.79), 6.811 (3.86), 6.814 (3.59), 6.880 (3.83), 7.171 (1.63), 7.175 (1.86), 7.178 (1.73), 7.181 (1.93), 7.186 (1.80), 7.191 (2.56), 7.193 (2.16), 7.197 (2.10), 7.251 (2.23), 7.253 (2.96), 7.255 (3.83), 7.258 (4.86), 7.262 (2.06), 7.279 (2.66), 7.282 (2.73), 7.300 (3.29), 7.303 (2.99), 7.332 (0.80), 7.353 (4.06), 7.360 (3.69), 7.364 (3.99), 7.367 (7.65), 7.370 (6.02), 7.379 (0.60), 7.384 (0.67), 7.505 (4.02), 7.524 (4.22), 7.526 (3.69), 7.545 (2.86), 7.737 (0.43), 8.259 (0.70); LC-MS (method 1): R$_t$=1.12 min; MS (ESIneg): m/z=310 [M−H]$^−$.

Intermediate INT-6

3-[Ethyl(methyl)amino]phenol

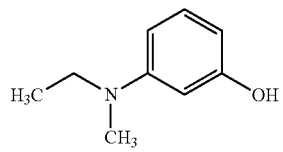

To an oven dried 250 mL flask under an argon atmosphere was added 3-bromophenol (4.00 g, 27.7 mmol, 1.00 eq.) and palladium(II)acetate (103 mg, 0.46 mmol, 2.00 mol %). To this mixture was then added argon degassed toluene (46.2 mL), ethyl(methyl)amine (2.36 mL, 27.7 mmol, 1.20 eq.), triisobutylphosphatrane (163 μL, 0.46 mmol, 2.00 mol %) and a 1.0 M solution of LiHMDS in toluene (53.1 mL, 53.1 mmol, 2.30 eq.). The resulting mixture was heated at 80° C. for 17 h and then cooled to RT. The reaction mixture was carefully acidified with saturated aqueous ammonium chloride (100 mL) and then extracted with EtOAc (3×100 mL). The combined organic extracts were washed with brine (100 mL), dried (magnesium sulfate) and concentrated under reduced pressure. The residue was purified by flash column chromatography (120 g HP silica, 0-100% ethyl acetate/hexanes gradient) to give the title compound as a red oil (1.65 g). $^1$H NMR (400 MHz, CDCl$_3$) δ [ppm]: 8.12 (s, 1H), 7.10 (t, 1H), 6.42-6.35 (m, 2H), 6.29-6.23 (m, 1H), 3.38 (q, 2H), 2.91 (s, 3H), 1.12 (t, 3H); LC-MS (Method 4): R$_t$=1.45 min, MS (ESIpos): m/z=152 [M+H]$^+$.

Intermediate INT-7

4-[Ethyl(methyl)amino]-2-hydroxy-benzaldehyde

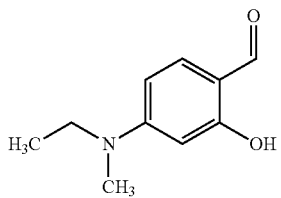

To a 0° C. stirred solution of INT-6 (1.97 g, 13.0 mmol, 1.00 eq.) in anhydrous DMF (13.0 mL, 1.00 M) was added phosphorous oxychloride (1.33 mL, 14.3 mmol, 1.10 eq.) dropwise. Following complete addition, the mixture was stirred at 0° C. for 30 min and then warmed to RT and stirred for 16 h. The mixture was carefully quenched with water (50 mL) and then extracted with ethyl acetate (3×50 mL). The combined organic extracts were washed with brine (50 mL), dried (magnesium sulfate) and concentrated under reduced pressure. The residue was purified by reverse phase flash column chromatography (275 g HP C$_{18}$, 20-100% acetonitrile/water with 0.1% formic acid gradient) to give the title compound as a red solid (624 mg). $^1$H NMR (400 MHz, DMSO-d$_6$) δ [ppm]: 11.24 (s, 1H), 9.63 (s, 1H), 7.43 (d, J=8.9 Hz, 1H), 6.38 (dd, J=8.9, 2.4 Hz, 1H), 6.06 (d, J=2.4 Hz, 1H), 3.45 (q, J=7.1 Hz, 2H), 2.97 (s, 3H), 1.08 (t, J=7.0 Hz, 3H); LC-MS (Method 4): R$_t$=1.35 min, MS (ESIpos): m/z=180 [M+H]$^+$.

Intermediate INT-8

6-[Ethyl(methyl)amino]benzofuran-2-carboxylic acid

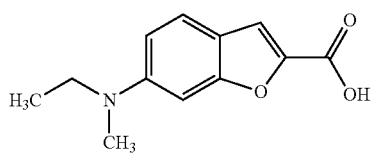 [SMILES: CCN(C)c1ccc2cc(C(=O)O)oc2c1]

To a 0° C. stirred suspension of aforementioned INT-7 (615 mg, 3.43 mmol, 1.00 eq.) and potassium carbonate (710 mg, 5.14 mmol, 1.50 eq.) in anhydrous DMF (17.1 mL, 0.20 M) was added ethyl bromoacetate (455 µL, 4.11 mmol, 1.20 eq.). Following complete addition, the mixture was heated at 160° C. for 16 h and then cooled to RT. The reaction mixture was diluted with water (20 mL), acidified with 1.0 M aqueous hydrochloric acid (10 mL) and then extracted with DCM (3×20 mL). The combined organic extracts were dried (magnesium sulfate), filtered and concentrated under reduced pressure. The residue was purified by reverse phase flash column chromatography (100 g HP C$_{18}$, 20-100% water/acetonitrile 0.1% formic acid gradient) to give the title compound as a yellow solid (276 mg). $^1$H NMR (400 MHz, CDCl$_3$) δ [ppm]: 7.54 (s, 1H), 7.48 (d, J=8.7 Hz, 1H), 6.80 (dd, J=8.7, 2.3 Hz, 1H), 6.78-6.75 (m, 1H), 3.48 (q, J=7.1 Hz, 2H), 3.00 (s, 3H), 1.17 (t, J=7.1 Hz, 3H); LC-MS (method 4): R$_t$=1.03 min, MS (ESIpos): m/z=220 [M+H]$^+$.

Intermediate INT-9

3-(N-Methylanilino)phenol

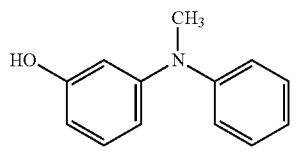

To an oven dried 250 mL flask under an argon atmosphere was added 3-bromophenol (5.00 g, 28.9 mmol, 1.00 eq.) and palladium(II)acetate (129 mg, 0.59 mmol, 2.00 mol %). To this mixture was then added argon degassed toluene (57.8 mL), N-methylaniline (3.74 mL, 34.6 mmol, 1.20 eq.), triisobutylphosphatrane (204 µL, 0.59 mmol, 2.00 mol %) and a 1.0 M solution of LiHMDS in toluene (53.1 mL, 53.1 mmol, 2.30 eq.). The resulting mixture was heated at 80° C. for 21 h and then cooled to RT. The reaction mixture was carefully acidified with saturated aqueous ammonium chloride (100 mL) and then extracted with ethyl acetate (3×100 mL). The combined organic extracts were washed with brine (100 mL), dried (magnesium sulfate) and concentrated under reduced pressure. The residue was purified by reverse phase flash column chromatography (275 g HP C$_{18}$, 20-100% acetonitrile/water with 0.1% formic acid gradient) to give the title compound as a red oil (3.09 g). $^1$H NMR (400 MHz, CDCl$_3$) δ [ppm]: 7.35-7.27 (m, 2H), 7.13-7.07 (m, 3H), 7.03 (tt, 1H), 6.53 (ddd, 1H), 6.42 (t, 1H), 6.37 (ddd, 1H), 4.65 (s, 1H), 3.29 (s, 3H); LC-MS (method 4): R$_t$=1.42 min, MS (ESIpos): m/z=200 [M+H]$^+$.

Intermediate INT-10

2-Hydroxy-4-(N-methylanilino)benzaldehyde

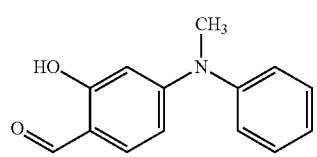 [SMILES: CN(c1ccccc1)c1ccc(C=O)c(O)c1]

To a 0° C. stirred solution of INT-9 (3.09 g, 15.5 mmol, 1.00 eq.) in anhydrous DMF (15.5 mL, 1.00 M) was added phosphorous oxychloride (1.58 mL, 17.0 mmol, 1.10 eq.) dropwise. Following complete addition, the mixture was stirred at 0° C. for 30 min and then warmed to RT and stirred for 18 h. The mixture was carefully quenched with 2.0 M aqueous sodium hydroxide (10 mL) and then extracted with EtOAc (3×50 mL). The combined organic extracts were washed with brine (50 mL), dried (magnesium sulfate) and concentrated under reduced pressure. The residue was purified by reverse phase flash column chromatography (275 g HP $C_{18}$, 20-100% acetonitrile/water with 0.1% formic acid gradient) to give the title compound as a beige solid (450 mg). $^1$H NMR (400 MHz, CDCl$_3$) δ [ppm]: 11.55 (s, 1H), 9.55 (s, 1H), 7.47-7.40 (m, 2H), 7.30 (tt, 1H), 7.24-7.18 (m, 3H), 6.25 (dd, 1H), 6.18 (d, 1H), 3.37 (s, 3H); LC-MS (method 4): R$_t$=1.52 min, MS (ESIpos): m/z=228 [M+H]$^+$.

Intermediate INT-11

6-(Dimethylamino)benzofuran-2-carboxylic acid

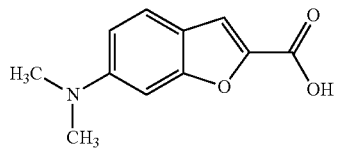

According to GP3: to a 0° C. stirred suspension of commercially available 4-(dimethylamino)-2-hydroxybenzaldehyde (CAS: 41602-56-6, 52.0 g, 314 mmol, 1.00 eq.) and potassium carbonate (64.9 g, 470 mmol, 1.50 eq.) in anhydrous N,N-dimethylformamide (628 mL, 0.50 M) was added ethyl bromoacetate (41.5 mL, 376 mmol, 1.20 eq.). Following complete addition, the mixture was heated at 160° C. for 16 h to give a mixture of the desired product and ethyl ester. After cooling to room temperature, a 4.0 M solution of sodium hydroxide in water (200 mL) was added to the mixture and the resulting solution was heated at 70° C. for 24 h. The reaction mixture was concentrated under reduced pressure and then neutralized with 2.0 M hydrochloric acid. The aqueous layer was extracted with 7:3 DCM/isopropanol (3×500 mL) and then concentrated under reduced pressure. The residue was recrystallized from hot dichloromethane to give the title compound as a beige solid (37.5 g). $^1$H NMR (400 MHz, DMSO-d$_6$) δ [ppm]: 13.00 (s, 1H), 7.66-7.37 (m, 2H), 7.02-6.62 (m, 2H), 2.98 (s, 6H); LC-MS (method 4): R$_t$=1.13 min; MS (ESIpos): m/z=206 [M+H]$^+$.

Intermediate INT-12

6-(N-Methylanilino)benzofuran-2-carboxylic acid

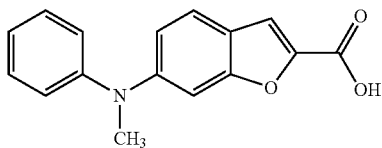

To a 0° C. stirred suspension aforementioned INT-10 (440 mg, 1.93 mmol, 1.00 eq.) and potassium carbonate (399 mg, 2.89 mmol, 1.50 eq.) in anhydrous DMF (9.65 mL, 0.20 M) was added ethyl bromoacetate (255 µL, 2.31 mmol, 1.20 eq.). Following complete addition, the mixture was heated at 160° C. for 16 h and then cooled to room temperature. The reaction mixture was diluted with water (20 mL), acidified with 1.0 M aqueous hydrochloric acid (10 mL) and then extracted with DCM (3×20 mL). The combined organic extracts were dried (magnesium sulfate), filtered and concentrated under reduced pressure. The residue was purified by reverse phase flash column chromatography (100 g $C_{18}$ HP, 20-100% water/acetonitrile 0.1% formic acid gradient) to give the title compound as a yellow solid (280 mg). $^1$H NMR (400 MHz, CDCl$_3$) δ [ppm]: 7.55 (s, 1H), 7.44 (dd, 1H), 7.37 (t, 2H), 7.20-7.12 (m, 3H), 7.02 (s, 1H), 6.91-6.86 (m, 1H), 3.38 (s, 3H), LC-MS (method 4): R$_t$=1.46 min, MS (ESIpos): m/z=268 [M+H]$^+$.

Intermediate INT-13

6-(Methylamino)benzofuran-2-carboxylic acid

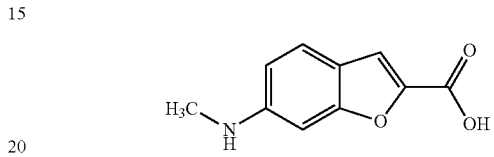

To an oven dried 1 dram vial under argon atmosphere was added 6-Bromo-1-benzofuran-2-carboxylic acid (300 mg, 1.24 mmol, 1.00 eq.) and copper powder (15.6 mg, 0.25 mmol, 0.20 eq.). To this mixture was then added a 40 wt. % solution of methylamine in water (535 µL, 6.19 mmol, 5.00 eq.). The resulting mixture was heated at 100° C. for 18 h and then cooled to RT and concentrated under reduced pressure. Water (10 mL) was added to the residue and extracted with 7:3 DCM/isopropanol (3×10 mL). The combined organic extracts were dried (magnesium sulfate), filtered and concentrated under reduced pressure. The residue was purified by preparative column chromatography (Waters XBridge Prep, $C_{18}$, 5 µM, 30×150 mm, 40-100% acetonitrile/water gradient buffered with 0.1% formic acid) to give the title compound as a white solid (26.3 mg). $^1$H NMR (400 MHz, CDCl$_3$) δ [ppm]: 7.52 (d, 1H), 7.42 (d, 1H), 6.68 (s, 1H), 6.63 (dd, 1H), 2.90 (s, 3H); LC-MS (method 4): R$_t$=0.80 min, MS (ESIpos): m/z=192 [M+H]$^+$.

Intermediate INT-14

6-Bromo-4-fluoro-1-benzofuran-2-carboxylic acid

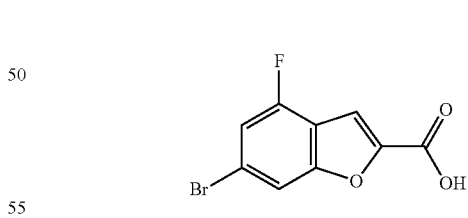

According to GP3, commercially available 4-bromo-2-fluoro-6-hydroxybenzaldehyde (CAS: 1427438-90-1, 500 mg, 2.28 mmol), ethyl chloroacetate (240 µL, 2.3 mmol), potassium carbonate (3.09 g, 22.4 mmol) were stirred in DMF (11 mL) for 2 h. After reaction completion and workup the desired residue was obtained as a brown solid (210 mg, 32%, containing traces of DMF) which was directly used in the next step without any further purification step. $^1$H-NMR (400 MHz, DMSO-d$_6$) δ [ppm]: 7.53 (dd, 1H), 7.77 (d, 1H), 7.99 (me, 1H), 13.92 (bs, 1H); LC-MS (method 1): R$_t$=0.95 min, MS (ESIpos): m/z=258 [M+H]$^+$.

Intermediate INT-15

Ethyl 6-(dibutylamino)-1-benzofuran-2-carboxylate

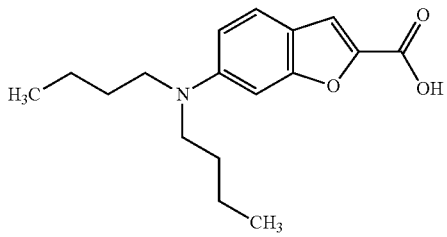 [SMILES: CCCCN(CCCC)c1ccc2cc(C(=O)O)oc2c1]

According to GP3, commercially available 4-(dibutylamino)-2-hydroxybenzaldehyde (CAS: 57771-09-2, 1.0 g, 4.01 mmol), ethyl chloroacetate (430 µL, 4.0 mmol), sodium carbonate (5.43 g, 39.3 mmol) were dissolved in DMF (19 mL) and the solution was heated at 160° C. for 2 h. After reaction completion and work up the isolated residue (containing DMF) was submitted to the saponification according to GP4 with lithium hydroxide (415 mg, 17.3 mmol in 15 mL water) in THF (29 mL). The resulting mixture was stirred for 18 h at RT. After reaction completion, the desired product was obtained as a brown oil (850 mg, containing ca. 20% intermediate as ethylester, 60% purity). $^1$H-NMR (400 MHz, DMSO-$d_6$) δ [ppm]: 0.772 (0.45), 0.790 (0.86), 0.807 (0.58), 0.895 (1.99), 0.913 (1.72), 0.931 (0.63), 1.152 (1.08), 1.163 (1.20), 1.169 (2.32), 1.187 (1.25), 1.266 (0.59), 1.291 (1.35), 1.309 (2.20), 1.326 (1.45), 1.350 (0.93), 1.501 (0.56), 1.519 (0.57), 1.906 (16.00), 1.985 (3.61), 2.518 (0.58), 3.357 (0.71), 4.014 (0.86), 4.032 (0.83), 8.137 (4.12); LC-MS (method 1): $R_t$=1.39 min; MS (ESIpos): m/z=291 [M+H]$^+$.

Intermediate INT-16

6-[2-Methylpyrrolidin-1-yl]-1-benzofuran-2-carboxylic acid (rac)

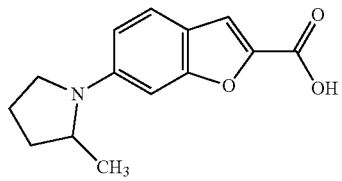 [SMILES: CC1CCCN1c1ccc2cc(C(=O)O)oc2c1]

According to GP6, commercially available methyl 6-bromo-1-benzofuran-2-carboxylate (CAS: 439107-94-5, 200 mg, 784 µmol), commercially available 2-methylpyrrolidine (CAS: 765-38-8, 80.1 mg, 941 µmol), caesium carbonate (639 mg, 1.96 mmol), commercially available catalyst palladium-Xphos G2 (CAS: 1310584-14-5, 61.7 mg, 78.4 µmol) were stirred in dioxane (2 mL) for 5 h. After reaction completion and workup the obtained residue (230 mg) was stirred according to GP4 with lithium hydroxide (106 mg, 4.43 mmol) in THF/water (8 mL/4 mL) were stirred at RT for 18 h. After reaction completion and work up a precipitate was collected giving the desired intermediate as a brown solid (180 mg, 83%, 20% purity) which was not further purified and directly submitted to the next step. $^1$H-NMR (400 MHz, DMSO-$d_6$) δ [ppm]: 0.881 (0.94), 0.897 (0.98), 1.009 (1.67), 1.026 (1.66), 1.122 (1.54), 1.137 (1.66), 1.154 (4.52), 1.166 (2.30), 1.172 (8.81), 1.190 (4.59), 1.228 (1.61), 1.231 (2.01), 1.245 (1.49), 1.249 (1.88), 1.907 (9.80), 1.987 (16.00), 2.518 (0.57), 3.999 (1.25), 4.017 (3.71), 4.034 (3.62), 4.052 (1.16), 6.659 (0.45), 6.925 (0.90), 7.048 (0.65), 7.315 (0.49), 7.442 (0.69), 7.445 (0.77), 7.450 (0.90), 7.456 (1.36), 7.466 (1.06), 7.468 (1.01), 7.488 (0.62), 7.509 (0.53), 7.827 (0.75), 7.829 (0.75), 8.052 (0.48), 8.073 (0.46), 8.081 (0.46), 8.262 (0.68), 8.281 (0.67); LC-MS (method 1): $R_t$=1.13 min; MS (ESIpos): m/z=246 [M+H]$^+$.

Intermediate INT-17

6-(Pyrrolidin-1-yl)-1-benzofuran-2-carboxylic acid

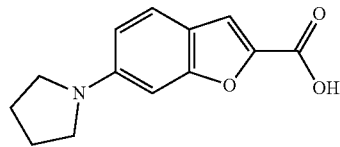 [SMILES: O=C(O)c1cc2ccc(N3CCCC3)cc2o1]

According to GP6, commercially available methyl 6-bromo-1-benzofuran-2-carboxylate (CAS: 425675-94-1, 100 mg, 392 µmol), commercially pyrrolidine (CAS: 123-75-1, 39 µL, 470 µmol;), caesium carbonate (319 mg, 980 µmol), commercially available catalyst palladium-Xphos G2 (CAS: 1310584-14-5, 30.8 mg, 39.2 µmol) were stirred in dioxane (1 mL) for 5 h. After reaction completion and workup the obtained residue (80 mg) was stirred according to GP4 with lithium hydroxide (23.4 mg, 978 µmol) in THF/water (4 mL/2 mL) were stirred at RT for 18 h. After reaction completion and work up a precipitate was collected giving the desired intermediate as a brown solid (40 mg, 71%, 80% purity) which was used without further purification. $^1$H-NMR (400 MHz, DMSO-$d_6$) δ [ppm]: 0.878 (0.69), 0.894 (0.67), 1.006 (0.50), 1.023 (0.51), 1.146 (0.76), 1.163 (1.47), 1.228 (1.82), 1.245 (1.61), 1.349 (0.49), 1.946 (0.87), 1.961 (5.88), 1.970 (6.41), 1.978 (16.00), 1.985 (6.27), 1.994 (5.80), 2.009 (0.59), 2.331 (0.47), 2.518 (2.47), 2.522 (1.57), 2.673 (0.46), 3.278 (5.64), 3.295 (14.93), 3.311 (5.35), 4.214 (1.21), 6.670 (12.35), 6.690 (4.17), 6.695 (2.87), 6.925 (0.67), 7.292 (0.65), 7.299 (0.66), 7.305 (0.78), 7.312 (1.14), 7.318 (0.66), 7.325 (0.79), 7.332 (0.97), 7.349 (0.60), 7.351 (0.65), 7.369 (0.64), 7.440 (1.48), 7.443 (1.68), 7.447 (1.86), 7.448 (1.98), 7.453 (3.04), 7.455 (2.92), 7.464 (0.78), 7.466 (0.74), 7.477 (11.64), 7.479 (12.57), 7.498 (5.68), 7.500 (4.73), 7.521 (5.53), 7.588 (0.79), 7.592 (0.87), 7.608 (0.85), 7.613 (1.02), 7.670 (1.08), 7.672 (1.30), 7.689 (0.57), 7.691 (0.54), 7.710 (0.43), 7.714 (0.75), 7.717 (0.62), 7.731 (0.41), 7.779 (0.56), 7.800 (0.59), 7.826 (1.94), 7.829 (1.96), 8.051 (1.07), 8.072 (1.35), 8.077 (1.06), 8.260 (1.52), 8.278 (1.66); LC-MS (method 1): $R_t$=1.08 min; MS (ESIpos): m/z=232 [M+H]$^+$.

Intermediate INT-18

Methyl 6-(dimethylamino)-1-benzothiophene-2-carboxylate

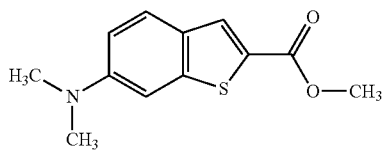

According to GP6, commercially available methyl 6-bromo-1-benzothiophene-2-carboxylate (CAS: 360576-01-8, 250 mg, 922 µmol), commercially available N—methylmethanamine (CAS: 124-40-3, 550 µL, 2.0 M, 1.1 mmol), caesium carbonate (751 mg, 2.31 mmol), commercially available catalyst palladium-Xphos G2 (CAS: 1310584-14-5, 72.5 mg, 92.2 µmol) were stirred in dioxane (2.4 mL) for 5 h. After reaction completion and workup the obtained residue (300 mg) was stirred according to GP4 with lithium hydroxide (137 mg, 5.74 mmol) in THF/water (9 mL/4.5 mL) were stirred at RT for 18 h. After reaction completion and work up a precipitate was collected giving the desired intermediate as a brown solid (251 mg, 71%, 70% purity) which was used without further purification. LC-MS (method 1): $R_t$=0.95 min; MS (ESIpos): m/z=222 $[M+H]^+$.

Intermediate INT-19

6-(Dimethylamino)-1-benzothiophene-2-carboxylic acid

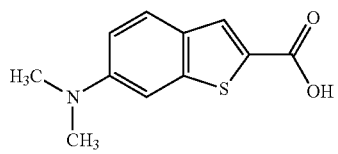

The aforementioned INT-18 was stirred according to GP4 with lithium hydroxide (137 mg, 5.74 mmol, 5.0 eq.) in THF/water (59 mL/28 mL) overnight. After workup the desired carboxylic acid was obtained as a brown solid (251 mg, 70% purity) which was used without further purification. LC-MS (method 1): $R_t$=0.95 min; MS (ESIpos): m/z=222 $[M+H]^+$.

Intermediate INT-20

5-N-([Biphenyl]-2-ylsulfonyl)-7-bromo-6-(dimethylamino)-1-benzofuran-2-carboxamide

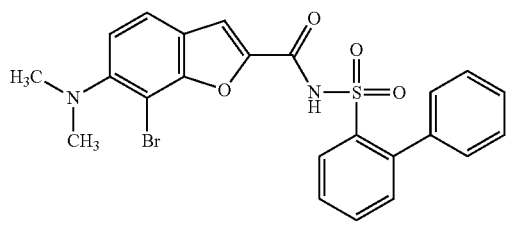

Example 14 (500 mg, 1.19 mmol) was added to a reaction flask along with DMF (5 mL), the flask cooled to 0° C., and N-bromosuccinimide (318 mg, 1.78 mmol) was added to the stirred mixture. The mixture was allowed to warm to RT and stirred for 5 h. The mixture was then diluted with EtOAc, and washed with an aqueous solution of $NaHCO_3$ and $Na_2S_2O_3$ (1:2 ratio), the organic phase was separated, and the aqueous mixture extracted twice with DCM. The organic phases were combined and passed through a water repellent filter and the solvent removed under reduced pressure. The crude mixture was then dissolved in a mixture of DCM:MeOH (9:1) and passed through a 10 g silica column, with the column being washed with the DCM:MeOH mixture until 40 mL of filtrate. No further purification was performed and the crude material (299 mg) was used without any in the subsequent purification steps. LC-MS (method 1): $R_t$=1.36 min; MS (ESIpos): m/z=499.1 $[M+H]^+$.

Intermediate INT-21

N-([1,1'-Biphenyl]-2-sulfonyl)-6-bromo-4-fluoro-1-benzofuran-2-carboxamide

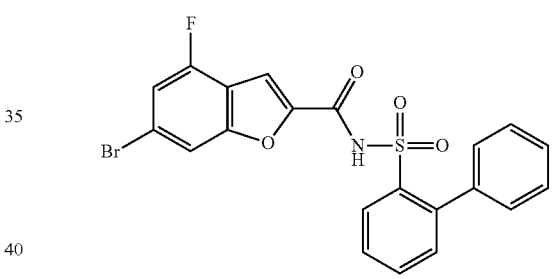

According to GP5A, INT-14 (440 mg, 1.70 mmol), [1,1'-biphenyl]-2-sulfonamide (CAS: 40182-06-7, 436 mg, 1.87 mmol), PyBOP (1.06 g, 2.04 mmol) and DIPEA (1.2 mL, 6.8 mmol) were stirred at RT in DCM (110 mL) for 3 d. After reaction completion, work-up and purification using HPLC (acid), the desired compound was obtained as a light ochre solid (420 mg, 50%). $^1$H-NMR (400 MHz, DMSO-$d_6$) δ [ppm]: 2.083 (16.00), 2.518 (1.60), 2.523 (0.97), 7.250 (1.41), 7.255 (2.00), 7.260 (0.74), 7.272 (4.64), 7.275 (3.87), 7.282 (2.35), 7.284 (2.83), 7.289 (0.74), 7.302 (4.32), 7.306 (1.58), 7.311 (1.96), 7.315 (2.12), 7.321 (1.79), 7.330 (2.05), 7.333 (2.05), 7.338 (1.26), 7.342 (1.73), 7.346 (0.94), 7.352 (0.69), 7.359 (1.54), 7.376 (0.48), 7.542 (1.87), 7.546 (1.98), 7.566 (1.83), 7.569 (1.90), 7.643 (0.74), 7.646 (0.76), 7.662 (1.61), 7.666 (1.53), 7.682 (1.37), 7.685 (1.28), 7.702 (1.80), 7.714 (1.44), 7.717 (1.42), 7.733 (1.73), 7.736 (1.68), 7.751 (0.69), 7.755 (0.64), 7.934 (2.48), 7.936 (3.54), 7.939 (2.27), 8.175 (1.93), 8.178 (2.06), 8.195 (1.78), 8.198 (1.71); LC-MS (method 1): $R_t$=1.39 min; MS (ESIpos): m/z=475 $[M+H]^+$.

Intermediate INT-22

6-Bromo-N-(2-ethoxybenzene-1-sulfonyl)-4-fluoro-1-benzofuran-2-carboxamide

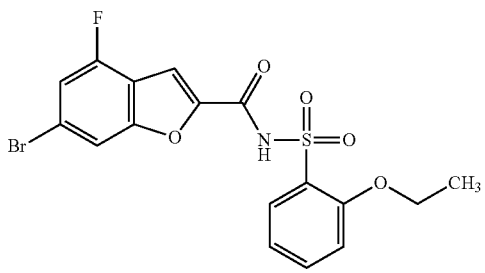 [SMILES: CCOc1ccccc1S(=O)(=O)NC(=O)c1cc2c(F)cc(Br)cc2o1]

According to GP5A, INT-14 (440 mg, 1.70 mmol), 2-ethoxybenzene-1-sulfonamide (CAS: 58734-61-5, 410 mg, 2.04 mmol), PyBOP (1.06 g, 2.04 mmol) and DIPEA (1.2 mL, 6.8 mmol) were stirred at RT in DCM (8.4 mL) for 20 h. After reaction completion, work-up and purification using HPLC (acid), the desired compound was obtained as a light ochre solid (380 mg, 48%). $^1$H-NMR (400 MHz, DMSO-$d_6$) δ [ppm]: 1.229 (6.66), 1.246 (16.00), 1.264 (6.86), 2.518 (1.76), 2.522 (1.09), 2.539 (0.95), 3.371 (0.73), 4.143 (1.74), 4.160 (5.55), 4.177 (5.69), 4.195 (1.65), 7.120 (1.48), 7.123 (1.55), 7.141 (2.70), 7.158 (1.59), 7.161 (1.65), 7.216 (2.40), 7.236 (2.70), 7.552 (2.76), 7.555 (2.69), 7.575 (2.69), 7.579 (2.53), 7.634 (1.30), 7.638 (1.40), 7.653 (1.51), 7.655 (1.76), 7.659 (1.51), 7.674 (1.13), 7.678 (1.07), 7.913 (2.87), 7.917 (2.91), 7.933 (2.88), 7.937 (2.60), 7.950 (3.38), 7.953 (4.63), 7.955 (3.07), 8.181 (2.64); LC-MS (method 6): $R_t$=1.24 min; MS (ESIpos): m/z=442 [M+H]$^+$.

Intermediate INT-23

6-Bromo-4-fluoro-N-(2-propoxybenzene-1-sulfonyl)-1-benzofuran-2-carboxamide

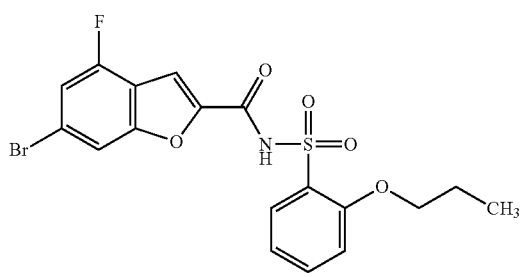 [SMILES: CCCOc1ccccc1S(=O)(=O)NC(=O)c1cc2c(F)cc(Br)cc2o1]

According to GP5A, INT-14 (370 mg, 1.43 mmol), commercially available 2-propoxybenzene-1-sulfonamide (CAS: 196107-68-3, 369 mg, 1.71 mmol), PyBOP (1.06 g, 2.04 mmol) and DIPEA (1 mL, 5.7 mmol) were stirred at RT in DCM (7 mL) for 20 h. After reaction completion, work-up and purification using HPLC (acid), the desired compound was obtained as a light ochre solid (205 mg, 30%). $^1$H-NMR (400 MHz, DMSO-$d_6$) δ [ppm]: 0.852 (6.28), 0.870 (15.47), 0.889 (6.90), 0.994 (0.42), 1.012 (0.96), 1.031 (0.44), 1.657 (0.42), 1.675 (1.57), 1.691 (3.32), 1.710 (3.50), 1.728 (2.75), 1.744 (0.96), 2.074 (16.00), 2.518 (1.72), 2.523 (1.11), 2.539 (0.45), 3.065 (0.42), 3.076 (0.66), 3.082 (1.26), 3.093 (1.24), 3.098 (0.63), 3.385 (0.72), 3.982 (0.46), 4.052 (2.88), 4.067 (6.22), 4.083 (2.88), 7.116 (1.31), 7.119 (1.40), 7.136 (2.52), 7.155 (1.45), 7.157 (1.50), 7.216 (2.21), 7.236 (2.44), 7.551 (2.41), 7.554 (2.54), 7.574 (2.37), 7.577 (2.55), 7.632 (1.15), 7.636 (1.20), 7.651 (1.36), 7.655 (1.63), 7.657 (1.35), 7.672 (1.03), 7.676 (0.99), 7.919 (2.73), 7.923 (2.80), 7.938 (2.75), 7.943 (4.70), 7.946 (4.64), 7.949 (2.98), 8.154 (2.38), LC-MS (method 5): $R_t$=1.32 min; MS (ESIpos): m/z=456 [M−H]$^+$.

Intermediate INT-24

6-Bromo-4-fluoro-N-(2-methylquinoline-8-sulfonyl)-1-benzofuran-2-carboxamide

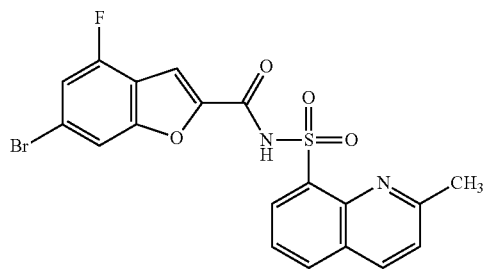 [SMILES: Cc1ccc2cccc(S(=O)(=O)NC(=O)c3cc4c(F)cc(Br)cc4o3)c2n1]

According to GP5A, INT-14 (370 mg, 1.43 mmol), commercially available 2-methylquinoline-8-sulfonamide (CAS: 157686-27-6, 381 mg, 1.71 mmol), PyBOP (892 mg, 1.71 mmol) and DIPEA (1 mL, 5.7 mmol) were stirred at RT in DCM (7 mL) for 20 h. After reaction completion, work-up and purification using HPLC (acid), the desired compound was obtained as an ochre solid (150 mg, 19%, 85% pure). $^1$H-NMR (400 MHz, DMSO-$d_6$) δ [ppm]: 2.327 (0.40), 2.518 (1.68), 2.523 (1.06), 2.669 (0.45), 2.698 (16.00), 7.529 (1.95), 7.533 (1.93), 7.540 (0.50), 7.545 (3.39), 7.553 (1.92), 7.556 (2.01), 7.566 (3.36), 7.751 (1.67), 7.770 (2.42), 7.790 (1.71), 7.894 (2.30), 7.896 (3.38), 7.900 (2.19), 8.227 (2.03), 8.307 (1.52), 8.311 (1.68), 8.328 (1.52), 8.331 (1.47), 8.426 (2.99), 8.448 (2.86), 8.478 (2.06), 8.482 (2.02), 8.497 (1.93), 8.501 (1.85); LC-MS (method 5): $R_t$=1.09 min; MS (ESIpos): m/z=465 [M+H]$^+$.

Intermediate INT-25

6-Bromo-4-fluoro-N-(2'-methyl[1,1'-biphenyl]-2-sulfonyl)-1-benzofuran-2-carboxamide

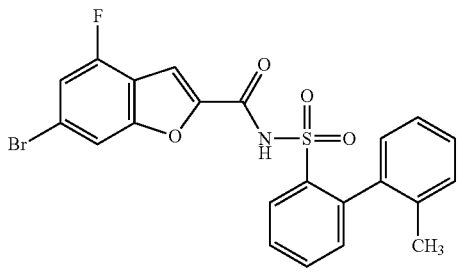 [SMILES: Cc1ccccc1-c1ccccc1S(=O)(=O)NC(=O)c1cc2c(F)cc(Br)cc2o1]

According to GP5A, INT-14 (90 mg, 347 μmol), commercially available 2'-methyl[1,1'-biphenyl]-2-sulfonamide (CAS: 217498-86-7, 103 mg, 417 μmol), PyBOP (217 mg, 417 μmol) and DIPEA (240 μL, 1.4 mmol) were stirred at RT in DCM (1.7 mL) for 20 h. After reaction completion, work-up and purification using HPLC (acid), the desired compound was obtained as an ochre solid (21 mg, 12%). $^1$H-NMR (400 MHz, DMSO-$d_6$) δ [ppm]: 1.893 (16.00), 2.518 (1.34), 2.523 (0.86), 2.539 (3.88), 6.993 (1.76), 6.996 (1.81), 7.012 (2.59), 7.015 (2.47), 7.091 (1.16), 7.110 (2.00), 7.129 (0.97), 7.176 (1.72), 7.195 (2.53), 7.234 (2.06), 7.238 (2.10), 7.253 (2.33), 7.257 (2.27), 7.264 (1.66), 7.267 (1.58), 7.282 (2.17), 7.286 (2.09), 7.301 (0.88), 7.304 (0.81), 7.550 (2.56), 7.554 (2.43), 7.573 (2.45), 7.577 (2.44), 7.646 (0.93), 7.650 (1.02), 7.665 (2.13), 7.669 (1.98), 7.685 (1.77), 7.688 (1.61), 7.714 (1.50), 7.717 (1.64), 7.733 (2.22), 7.736 (2.16), 7.751 (0.87), 7.755 (0.81), 7.847 (2.17), 7.955 (3.20), 7.957 (4.57), 7.960 (2.93), 8.204 (2.46), 8.208 (2.59), 8.224 (2.31), 8.227 (2.23); LC-MS (method 5): $R_t$=1.45 min; MS (ESIpos): m/z=490 [M+H]$^+$.

Intermediate INT-26

6-Bromo-4-methyl-1-benzofuran-2-carboxylic acid

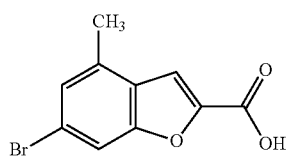

According to GP3, commercially available 4-bromo-2-hydroxy-6-methylbenzaldehyde (CAS: 1427438-58-1, 100 mg, 465 μmol), ethyl chloroacetate (50 μL, 470 μmol), potassium carbonate (630 mg, 4.56 mmol) were stirred in DMF (2.2 mL) for 2 h. After reaction completion and workup the desired residue was obtained as a dark brown solid (80 mg, 57%, 60% pure) which was used directly in the next step. $^1$H-NMR (400 MHz, DMSO-$d_6$) δ [ppm]: 10.16 (bs, 1H), 7.57, 7.46, 7.45 (3 mc, 1H each), 2.45 (s, 3H).

Intermediate INT-27

N-([1,1'-Biphenyl]-2-sulfonyl)-6-bromo-4-methyl-1-benzofuran-2-carboxamide

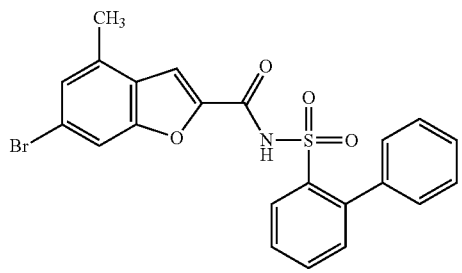 [SMILES: Cc1cc(Br)cc2oc(C(=O)NS(=O)(=O)c3ccccc3-c3ccccc3)cc12]

According to GP5A, the aforementioned INT-26 (320 mg, 1.25 mmol), commercially available [1,1'-biphenyl]-2-sulfonamide (CAS: 40182-06-7, 170 mg, 1.4 mmol), PyBOP (783 mg, 1.51 mmol) and DIPEA (870 μL, 5.0 mmol) were stirred at RT in DCM (83 mL) for 3 d. After reaction completion, work-up and purification using HPLC (acid), the desired compound was obtained as an ochre solid (260 mg, 42%). $^1$H-NMR (400 MHz, DMSO-$d_6$) δ [ppm]: 1.651 (0.67), 2.074 (0.83), 2.416 (0.51), 2.446 (16.00), 2.518 (1.32), 2.522 (0.78), 2.907 (0.53), 2.918 (0.54), 3.410 (0.67), 7.253 (1.99), 7.258 (2.82), 7.263 (1.00), 7.274 (6.63), 7.278 (5.14), 7.287 (2.93), 7.290 (4.00), 7.295 (1.04), 7.308 (6.40), 7.328 (3.72), 7.332 (2.84), 7.354 (1.28), 7.358 (2.26), 7.362 (1.17), 7.369 (0.89), 7.376 (2.18), 7.382 (0.59), 7.389 (0.52), 7.393 (0.76), 7.397 (0.42), 7.475 (4.98), 7.523 (4.41), 7.525 (4.45), 7.620 (2.38), 7.645 (1.01), 7.649 (1.11), 7.664 (2.19), 7.668 (2.11), 7.684 (1.81), 7.688 (1.68), 7.716 (1.63), 7.719 (1.69), 7.735 (2.32), 7.738 (2.36), 7.754 (0.97), 7.757 (0.86), 8.177 (2.64), 8.180 (2.83), 8.197 (2.42), 8.199 (2.36); LC-MS (method 1): $R_t$=1.41 min; MS (ESIpos): m/z=472 [M+H]$^+$.

Intermediate INT-28

N-([1,1'-Biphenyl]-2-sulfonyl)-6-bromo-1-benzofuran-2-carboxamide

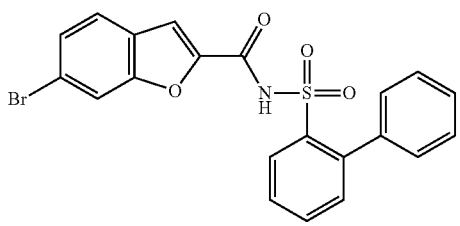 [SMILES: O=C(NS(=O)(=O)c1ccccc1-c1ccccc1)c1cc2ccc(Br)cc2o1]

According to GP5, commercially available 6-bromo-1-benzofuran-2-carboxylic acid (CAS: 439107-94-5, 4.50 g, 18.7 mmol), commercially available [1,1'-biphenyl]-2-sulfonamide (CAS: 4790-79-8, 4.79 g, 20.5 mmol), PyBOP (11.7 g, 22.4 mmol) and DIPEA (13 mL, 75 mmol) were stirred at RT in DCM (1.2 L) for 3 d. After reaction completion, work-up and purification using HPLC (acid), the desired product was obtained as a colourless solid (4.8 g, 51%); $^1$H-NMR (400 MHz, DMSO-$d_6$) δ [ppm]: 1.218 (0.42), 1.234 (0.51), 2.074 (1.54), 2.083 (1.47), 2.518 (1.70), 2.522 (1.20), 7.244 (6.27), 7.249 (8.49), 7.254 (2.89), 7.265 (14.43), 7.269 (13.56), 7.273 (2.48), 7.285 (6.27), 7.288 (9.14), 7.293 (2.47), 7.306 (16.00), 7.310 (6.61), 7.312 (7.57), 7.316 (7.37), 7.320 (4.75), 7.323 (7.56), 7.331 (7.98), 7.335 (7.55), 7.340 (4.53), 7.343 (7.47), 7.347 (3.63), 7.354 (2.45), 7.361 (6.77), 7.369 (1.40), 7.375 (1.26), 7.379 (1.92), 7.383 (1.03), 7.523 (9.16), 7.528 (8.67), 7.544 (9.62), 7.549 (10.46), 7.648 (2.99), 7.651 (3.07), 7.667 (6.39), 7.670 (6.14), 7.687 (6.20), 7.691 (7.24), 7.694 (13.16), 7.696 (13.08), 7.718 (5.19), 7.722 (5.75), 7.737 (7.52), 7.741 (7.25), 7.755 (2.97), 7.759 (2.97), 7.773 (12.98), 7.793 (10.87), 8.007 (10.99), 8.174 (7.22), 8.178 (7.69), 8.195 (6.71), 8.198 (6.62); LC-MS (method 1): $R_t$=1.32 min; MS (ESIpos): m/z=458 [M+H]$^+$.

Intermediate INT-29

Methyl 2-{[6-(dimethylamino)-1-benzofuran-2-carbonyl]sulfamoyl}benzoate

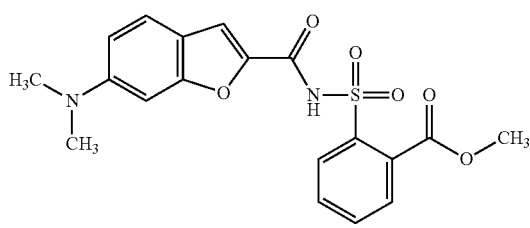

According to GP5A, INT-11 (874 mg, 4.26 mmol), commercially available methyl 2-sulfamoylbenzoate (CAS: 57683-71-3, 1.10 g, 5.11 mmol), PyBOP (2.66 g, 5.11 mmol) and DIPEA (3.0 mL, 17 mmol) were stirred at RT in DCM (21 mL) for 20 h. After reaction completion, work-up and purification using HPLC (acid), the desired product was obtained as a yellow solid (1.2 g, 56%, 80% pure). $^1$H-NMR (400 MHz, DMSO-$d_6$) δ [ppm]: 2.966 (0.46), 2.990 (16.00), 3.002 (0.42), 6.641 (1.46), 6.777 (0.88), 6.781 (0.96), 6.855 (0.75), 6.860 (0.68), 6.878 (0.79), 6.883 (0.70), 7.548 (0.41), 7.566 (0.46), 7.571 (1.51), 7.593 (1.34), 7.686 (0.58), 7.691 (0.51), 7.696 (0.47), 7.700 (0.48), 7.702 (0.56), 7.708 (0.92), 7.712 (0.44), 7.732 (0.44), 7.778 (0.90), 7.783 (1.49), 7.792 (1.81), 7.801 (1.23), 7.806 (0.78), 7.915 (1.50), 8.081 (0.70), 8.102 (0.60), 8.154 (0.78), 8.157 (0.96), 8.164 (0.56), 8.166 (0.49), 8.171 (0.59), 8.173 (0.50), 8.176 (1.01), 8.181 (0.73); LC-MS (method 1): $R_t$=1.00 min; MS (ESIpos): m/z=403 [M+H]$^+$.

Intermediate INT-30

6-(Diethylamino)-1-benzofuran-2-carboxylic acid

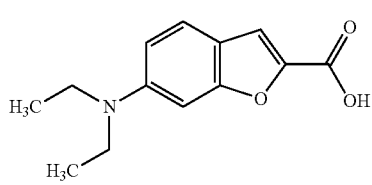 [SMILES: CCN(CC)c1ccc2cc(C(=O)O)oc2c1]

According to GP4, lithium hydroxide (121 mg, 5.05 mmol) was added to a solution of commercially available methyl 6-(diethylamino)-1-benzofuran-2-carboxylate (250 mg, 1.01 mmol) in THF/water (8.6 mL/4.3 mL). The corresponding reaction solution was stirred at RT for 18 h. After reaction completion and work up a precipitate was collected giving the desired intermediate as a yellow solid (220 mg, 90% purity following to UPLCMS) which was used directly in the next step. LC-MS (method 1): $R_t$=0.63 min; MS (ESIpos): m/z=233 [M+H]$^+$.

Intermediate INT-31

N-([1,1'-Biphenyl]-2-sulfonyl)-6-nitro-1-benzofuran-2-carboxamide

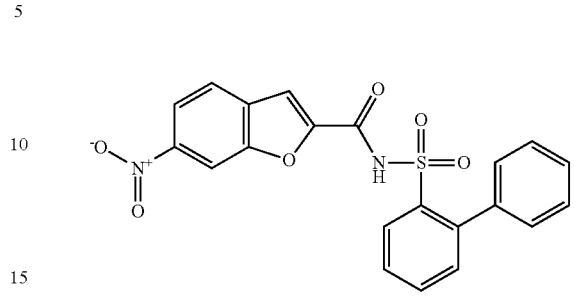

According to GP5A, 6-nitro-1-benzofuran-2-carboxylic acid (CAS: 64209-68-3, 400 mg, 1.93 mmol), commercially available [1,1'-biphenyl]-2-sulfonamide (CAS: 40182-06-7, 541 mg, 2.32 mmol), PyBOP (1.21 g, 2.32 mmol) and DIPEA (1.3 ml, 7.7 mmol) were stirred at RT in DCM (9.5 mL) for 20 h. After reaction completion, work-up and purification using HPLC (acid), the desired product was obtained as a light yellow solid (346 mg, 40%). $^1$H-NMR (400 MHz, DMSO-$d_6$) δ [ppm]: 2.074 (1.05), 2.083 (3.38), 2.518 (2.84), 2.522 (1.77), 3.504 (0.55), 7.261 (1.86), 7.266 (3.01), 7.272 (1.50), 7.282 (11.50), 7.287 (16.00), 7.303 (9.56), 7.308 (2.61), 7.314 (4.44), 7.317 (5.60), 7.321 (3.60), 7.322 (3.57), 7.332 (6.34), 7.336 (7.11), 7.342 (2.11), 7.345 (1.62), 7.354 (2.81), 7.362 (0.75), 7.366 (0.64), 7.369 (0.79), 7.374 (0.51), 7.648 (1.50), 7.651 (1.65), 7.667 (3.56), 7.670 (3.45), 7.686 (2.84), 7.689 (2.61), 7.716 (2.61), 7.720 (2.72), 7.735 (3.66), 7.738 (3.70), 7.753 (1.66), 7.756 (1.56), 7.773 (5.13), 8.064 (5.91), 8.086 (7.72), 8.187 (4.37), 8.190 (4.75), 8.209 (9.67), 8.214 (6.61), 8.231 (4.58), 8.236 (4.92), 8.602 (5.26), 8.607 (5.15); LC-MS (method 1): $R_t$=1.19 min; MS (ESIpos): m/z=423 [M+H]$^+$.

Intermediate INT-32

5-Chloro-4-(dimethylamino)-2-hydroxybenzaldehyde

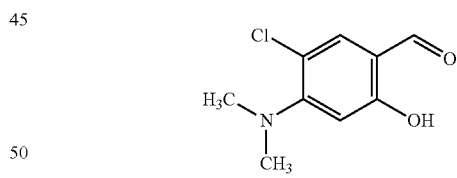

To a stirred solution of 5-chloro-4-fluoro-2-hydroxy-benzaldehyde (2.50 g, 14.3 mmol, 1.00 eq.) in anhydrous DMF (14.3 mL, 1.00 M) was added potassium carbonate (4.95 g, 35.8 mmol, 2.50 eq.) and dimethylamine hydrochloride (1.28 g, 15.8 mmol, 1.10 eq.). The resulting orange suspension was heated at 120° C. for 4 h and then cooled to room temperature. The mixture was diluted with ethyl acetate (50.0 mL) and filtered through a Celite plug, washing with ethyl acetate (2×25.0 mL). The filtrate was dry loaded onto Celite and then purified by flash column chromatography (80 g HP silica, 0-50% ethyl acetate/hexanes gradient) to give the title compound as a light yellow solid (1.14 g). $^1$H NMR (400 MHz, Chloroform-d) δ 11.22 (s, 1H), 9.61 (d, 1H), 7.42 (s, 1H), 6.43 (s, 1H), 2.98 (s, 6H); LC-MS (method 7): $R_t$=3.04 min; MS (ESIpos): m/z=200 [M+H]$^+$.

Intermediate INT-33

5-Chloro-6-(dimethylamino)benzofuran-2-carboxylic acid

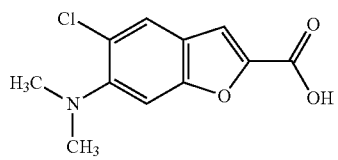 [SMILES: CN(C)c1cc2oc(C(=O)O)cc2cc1Cl]

To a room temperature stirred solution of 5-chloro-4-(dimethylamino)-2-hydroxy-benzaldehyde (1.14 g, 5.71 mmol, 1.00 eq.) in anhydrous N,N-dimethylformamide (38.1 mL, 0.15 M) was sequentially added potassium carbonate (1.18 g, 8.57 mmol, 1.50 eq.) and ethyl bromoacetate (0.70 mL, 6.28 mmol, 1.10 eq.). The resulting yellow suspension was heated at 160° C. for 2 h, after which sodium hydroxide (2.00 M in water, 7.14 mL, 14.3 mmol, 2.50 eq.) was added. After cooling to room temperature, the mixture was concentrated under reduced pressure and then diluted with water (20.0 mL). The mixture was acidified to pH 2.0 with hydrochloric acid (1.00 M in water, ~25.0 mL) and extracted with ethyl acetate (3×50.0 mL). The combined organic extracts were dried (magnesium sulfate), filtered and concentrated under reduced pressure. The reside was purified by reverse phase flash column chromatography (275 g HP $C_{18}$, 10-100% acetonitrile/water gradient buffered with 0.1% formic acid) to give the title compound as a tan solid (1.10 g). $^1$H NMR (400 MHz, DMSO-$d_6$) δ 13.50 (s, 1H), 7.81 (s, 1H), 7.53 (d, 1H), 7.46 (d, 1H), 2.78 (s, 6H), LC-MS (method 7): $R_t$=2.53 min; MS (ESIpos): m/z=240 [M+H]$^+$.

Intermediate INT-34

4-(Dimethylamino)-3-fluoro-2-hydroxybenzaldehyde

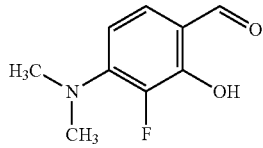

To a stirred solution of 3,4-difluoro-2-hydroxy-benzaldehyde (3.16 g, 20.0 mmol, 1.00 eq.) in anhydrous DMF (20.0 mL, 1.00 M) was added potassium carbonate (6.91 g, 50.0 mmol, 2.50 eq.) and dimethylamine hydrochloride (1.79 g, 22.0 mmol, 1.10 eq.). The resulting orange suspension was heated at 120° C. for 1 hour and then cooled to room temperature. The mixture was diluted with ethyl acetate (50.0 mL) and filtered through a Celite plug, washing with ethyl acetate (2×25.0 mL). The filtrate was dry loaded onto Celite and then purified by flash column chromatography (120 g silica, 0-50% ethyl acetate/hexanes gradient) to give the title compound as a white solid (3.21 g). $^1$H NMR (400 MHz, Chloroform-d) δ 11.37 (s, 1H), 9.59 (d, 1H), 7.12 (dd, 1H), 6.34 (dd, 1H), 3.10 (d, 6H); LC-MS (method 7): $R_t$=2.62 min; MS (ESIpos): m/z=184 [M+H]$^+$.

Intermediate INT-35

6-(Dimethylamino)-7-fluorobenzofuran-2-carboxylic acid

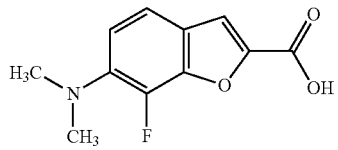

To a room temperature stirred solution of 4-(dimethylamino)-3-fluoro-2-hydroxy-benzaldehyde (3.18 g, 17.4 mmol, 1.00 eq.) in anhydrous DMF (116 mL, 0.15 M) was sequentially added potassium carbonate (3.60 g, 26.0 mmol, 1.50 eq.) and ethyl bromoacetate (2.12 mL, 19.1 mmol, 1.10 eq.). The resulting yellow suspension was heated at 160° C. for 20 h, after which sodium hydroxide (2.00 M in water, 21.7 mL, 43.4 mmol, 2.50 eq.) was added. After cooling to room temperature, the mixture was concentrated under reduced pressure and then diluted with water (20.0 mL). The mixture was acidified to pH 2.0 with hydrochloric acid (1.00 M in water, ~70.0 mL) and extracted with ethyl acetate (3×50.0 mL). The combined organic extracts were dried (magnesium sulfate), filtered and concentrated under reduced pressure. The reside was purified by reverse phase flash column chromatography (275 G HP $C_{18}$, 10-100% acetonitrile/water gradient buffered with 0.1% formic acid) to give the title compound as a tan solid (2.87 g). $^1$H NMR (400 MHz, DMSO-$d_6$) δ 13.47 (s, 1H), 7.62 (d, 1H), 7.42 (dd, 1H), 7.01 (dd, 1H), 2.89 (d, 6H); LC-MS (method 7): $R_t$=2.18 min; MS (ESIpos): m/z=224 [M+H]$^+$.

Intermediate INT-36

3-(Dimethylamino)-5-(trifluoromethyl)phenol

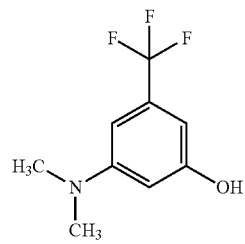

To a stirred suspension of 3-bromo-5-(trifluoromethyl)phenol (3.43 mL, 25.0 mmol, 1.00 eq.) and dimethylamine hydrochloride (2.44 g, 30.0 mmol, 1.20 eq.) under an argon atmosphere was added toluene (50.0 mL, 0.50 M) and lithium bis(trimethylsilyl)amide (1.00 M in tetrahydrofuran, 87.5 mL, 87.5 mmol, 3.50 eq.). To this mixture was then added triisobutylphosphatrane (887 μL, 2.50 mmol, 10.0 mol %) and palladium(II) acetate (280 mg, 1.25 mmol, 5.00 mol %), after which the dark brown solution was heated at 80° C. for 18 h. Following concentration, the residue was diluted with saturated aqueous ammonium chloride (60 mL) and extracted with dichloromethane (3×60 mL). The combined organic extracts were dried (magnesium sulfate), filtered through a Celite plug and concentrated under reduced pressure. The residue was purified by flash column chromatography (80 g HP silica, 0-50% ethyl acetate/hexanes gradient) to give the title compound as a light purple oil (3.60 g). $^1$H NMR (400 MHz, Chloroform-d) δ 6.51 (t, 1H), 6.43-6.39 (m, 1H), 6.30 (t, 1H), 2.97 (s, 6H); LC-MS (Method 8): $R_t$=4.23 min; MS (ESIpos): m/z=206 [M+H]$^+$.

Intermediate INT-37

4-(Dimethylamino)-2-hydroxy-6-(trifluoromethyl)benzaldehyde

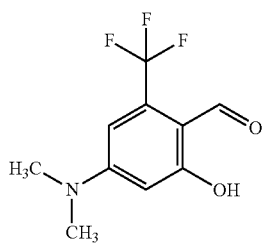

To anhydrous N,N-dimethylformamide (386 µL, 5.00 mmol, 10.0 eq.) at 0° C. under an argon atmosphere was added phosphoryl chloride (139 µL, 1.50 mmol, 3.00 eq.) was added dropwise. After stirring for 1 h at RT, a solution of 3-(dimethylamino)-5-(trifluoromethyl)phenol (102 mg, 0.50 mmol, 1.00 eq.) in anhydrous N,N-dimethylformamide (1.00 mL, 0.50 M) was rapidly added. Following complete addition, the resulting yellow solution was warmed to 60° C. and stirred for a further 2 h. The reaction mixture was poured onto ice (20 mL) and extracted with ethyl acetate (3×20 mL). The combined organic extracts were dried (magnesium sulfate), filtered and dry loaded onto Celite. The residue was purified by flash column chromatography (4 g HP silica, 0-40% ethyl acetate/hexanes gradient) to give the title compound as an off white solid (553 mg). $^1$H NMR (400 MHz, DMSO-d$_6$) δ 12.7 (s, 1H), 9.94-9.70 (m, 1H), 6.70 (d, 1H), 6.26 (d, 1H), 3.10 (s, 6H); LC-MS (Method 8): $R_t$=4.90 min; MS (ESIpos): m/z=234 [M+H]$^+$.

Intermediate INT-38

6-(Dimethylamino)-4-(trifluoromethyl)benzofuran-2-carboxylic acid

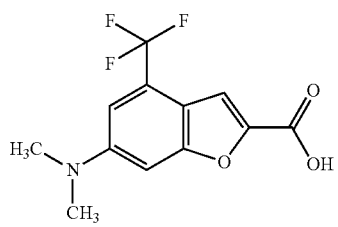 [SMILES: CN(C)c1cc(C(F)(F)F)c2cc(C(=O)O)oc2c1]

To a room temperature stirred suspension of 4-(dimethylamino)-2-hydroxy-6-(trifluoromethyl)benzaldehyde (547 mg, 2.34 mmol, 1.00 eq.) and potassium carbonate (485 mg, 3.51 mmol, 1.50 eq.) in anhydrous N,N-dimethylformamide (15.6 mL, 0.15 M) was added ethyl 2-bromoacetate (284 µL, 2.57 mmol, 1.10 eq.). The resulting yellow suspension was heated at 160° C. for 12 h, after which sodium hydroxide (2.00 M in water, 1.17 mL, 2.34 mmol, 1.00 eq.) was added and the resulting suspension was cooled to room temperature (~30 min). The reaction mixture was acidified to pH 2.0 with hydrochloric acid (1.00 M in water, ~6.00 mL) and then dry loaded onto Celite. The crude material was purified by reverse phase flash column chromatography (275 g HP C$_{18}$, 10-100% acetonitrile/water gradient buffered with 0.1% formic acid) to give the title compound as a yellow solid (523 mg). $^1$H NMR (400 MHz, DMSO-d$_6$) δ 13.49 (s, 1H), 7.53-7.51 (m, 1H), 7.25-7.23 (m, 1H), 7.21-7.18 (m, 1H), 3.14 (s, 6H); LC-MS (Method 8): $R_t$=4.40 min; MS (ESIpos): m/z=274 [M+H]$^+$.

Intermediate INT-39

3-(Dimethylamino)-4-fluorophenol

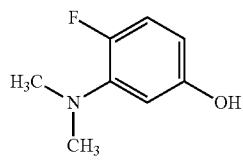

To a stirred suspension of 3-bromo-4-fluorophenol (12.5 g, 65.4 mmol, 1.00 eq.) and dimethylamine hydrochloride (6.39 g, 78.4 mmol, 1.20 eq.) under an argon atmosphere was added toluene (130 mL, 0.50 M) and lithium bis(trimethylsilyl)amide (1.00 M in tetrahydrofuran, 228 mL, 12.3 mmol, 3.50 eq.). To this mixture was then added triisobutylphosphatrane (2.23 g, 6.54 mmol, 10.0 mol %) and palladium(II) acetate (734 mg, 3.27 mmol, 5.00 mol %), after which the dark brown solution was heated at 80° C. for 18 h. Following concentration, the residue was diluted with saturated aqueous ammonium chloride (100 mL) and extracted with dichloromethane (3×100 mL). The combined organic extracts were dried (magnesium sulfate), filtered through a Celite plug and concentrated under reduced pressure. The residue was purified by flash column chromatography (330 g Silica, 0-60% ethyl acetate/hexanes gradient) to give the title compound as an off white solid (3.48 g). $^1$H NMR (400 MHz, Chloroform-d) δ 6.85 (dd, 1H), 6.39 (dd, 1H), 6.27 (dt, 1H), 4.83 (s, 1H), 2.82 (s, 6H); LC-MS (Method 8): $R_t$=1.88 min; MS (ESIpos): m/z=156 [M+H]$^+$.

Intermediate INT-40

4-(Dimethylamino)-5-fluoro-2-hydroxybenzaldehyde

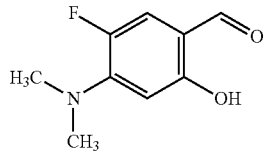

To anhydrous DMF (13.3 mL, 173 mmol, 10.0 eq.) at 0° C. under an argon atmosphere was added phosphoryl chloride (4.9 mL, 52.1 mmol, 3.00 eq.) was added dropwise. After stirring for 1 h at 0° C., a solution of 3-(dimethylamino)-4-fluorophenol (2.70 g, 17.4 mmol, 1.00 eq.) in anhydrous DMF (17.4 mL, 1.0 M) was rapidly added. Following complete addition, the resulting yellow solution was warmed to 60° C. and stirred for a further 2 h. The reaction mixture was poured onto ice (100 mL) and extracted with ethyl acetate (4×75 mL). The combined organic extracts were dried (magnesium sulfate), filtered and dry loaded onto Celite. The residue was purified by flash column chromatography (80 g HP silica, 0-40% ethyl acetate/hexanes gradient) to give the title compound as a light yellow solid (1.78 g). $^1$H NMR (400 MHz, Chloroform-d) δ 11.32 (s, 1H), 9.51 (s, 1H), 7.03 (d, 1H), 6.17 (d, 1H), 3.07 (d, 6H); LC-MS (Method 8): $R_t$=3.87 min; MS (ESIpos): m/z=184 [M+H]$^+$.

Intermediate INT-41

6-(Dimethylamino)-5-fluorobenzofuran-2-carboxylic acid

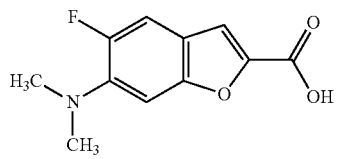

To a room temperature stirred suspension of 4-(dimethylamino)-5-fluoro-2-hydroxybenzaldehyde (1.76 g, 9.60 mmol, 1.00 eq.) and potassium carbonate (1.97 g, 14.3 mmol, 1.50 eq) in anhydrous N,N-dimethylformamide (64.0 mL, 0.15 M) was added ethyl 2-bromoacetate (1.15 mL, 10.5 mmol, 1.10 eq.). The resulting yellow suspension was heated at 160° C. for 13 h, after which sodium hydroxide (2.00 M in water, 1.17 mL, 2.34 mmol, 1.00 eq.) was added and the resulting suspension was cooled to room temperature (~1 hour). The reaction mixture was acidified to pH 2.0 with hydrochloric acid (1.00 M in water, ~27.0 mL) and then dry loaded onto Celite. The crude material was purified by reverse phase flash column chromatography (275 g HP $C_{18}$, 10-100% acetonitrile/water gradient buffered with 0.1% formic acid) to give the title compound as a tan solid (1.71 g). $^1$H NMR (400 MHz, DMSO-$d_6$) δ 13.30 (s, 1H), 7.52 (s, 1H), 7.47 (d, 1H), 7.21 (d, 1H), 2.84 (s, 6H); LC-MS (Method 8): $R_t$=2.96 min; MS (ESIpos): m/z=224 [M+H]$^+$ Intermediate INT-42

6-[(2-Methoxyethyl)(methyl)amino]-1-benzofuran-2-carboxylic acid

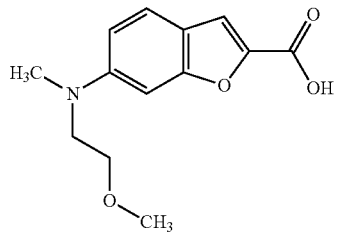 [SMILES: COCCN(C)c1ccc2cc(C(=O)O)oc2c1]

According to GP6, commercially available Methyl 6-bromo-1-benzofuran-2-carboxylate (CAS: 425675-94-1, 20.0 mg, 78.4 μmol), commercially available 2-methoxy-N-methylethanamine (CAS: 38256-93-8, 10 μL, 0.04 mmol), caesium carbonate (63.9 mg, 196 μmol), commercially available catalyst palladium-Xphos G2 (CAS: 1310584-14-5, 6.17 mg, 7.84 μmol) were heated in DMF (2 mL) for 4 h at 110° C. After reaction completion and workup the obtained residue (450 mg) was concentrated under vacuum. The residue, according to GP4, was dissolved in THF/water (4 mL/4 mL) and then lithium hydroxide (205 mg, 8.55 mmol) was added. The resulted mixture was stirred at RT for 18 h. After reaction completion and work up a precipitate was collected giving the desired intermediate as a yellow solid (28.8 mg, 6%) which was used directly in the next step. $^1$H-NMR (400 MHz, DMSO-$d_6$) δ [ppm]: 1.752 (1.66), 2.518 (0.71), 2.523 (0.49), 2.983 (8.42), 3.248 (16.00), 3.490 (0.52), 3.492 (0.56), 3.506 (2.07), 3.518 (1.29), 3.568 (1.04), 3.580 (1.39), 3.596 (0.48), 6.832 (2.99), 6.852 (0.96), 6.858 (0.64), 7.456 (1.92), 7.487 (1.07), 7.490 (0.79), 7.508 (0.67), 7.510 (1.05); LC-MS (Method 1): $R_t$=0.88 min; MS (ESIpos): m/z=250 [M+H]+.

Intermediate INT-43

6-(Ethylamino)-1-benzofuran-2-carboxylic acid

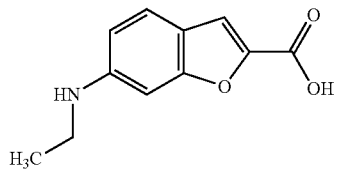

According to GP3: to a 0° C. stirred suspension of commercially available 4-(ethylamino)-2-hydroxybenzaldehyde (CAS: 1379171-03-5, 1.00 g, 6.05 mmol) and potassium carbonate (8.20 g, 59.3 mmol) in anhydrous DMF (28 mL) was added ethyl chroroacetate (650 μL, 6.1 mmol). Following complete addition, the mixture was heated at 160° C. for 16 h to give a mixture of the desired product and ethyl ester. After cooling to room temperature the mixture was concentrated under reduced pressure (one work-up following to the classical method was tried without success, product was still remaining in the water phase). The obtained crude product (1.5 g, brown oil). The residue, according to GP4, was dissolved in THF/water (55 mL/27 mL) and then lithium hydroxide (770 mg, 32.2 mmol) was added. The resulted mixture was stirred at RT for 18 h. After reaction completion and work up (with ethyl acetate), the desired product was still remaining in the water phase. The water phase was concentrated and the residue was diluted with water and a DCM/2-propanol (7:3) solution and extracted three times. The organic layers were combined and concentrated to give the title compound as a dark brown solid (800 mg)$^1$H-NMR (400 MHz, DMSO-$d_6$) δ [ppm]: 1.026 (7.65), 1.041 (8.06), 1.061 (0.95), 1.079 (0.57), 1.121 (0.51), 1.138 (0.82), 1.156 (0.70), 1.175 (5.96), 1.192 (12.67), 1.210 (5.97), 1.223 (1.12), 1.241 (0.56), 1.352 (0.42), 2.518 (2.53), 2.524 (4.11), 2.537 (1.44), 2.728 (12.55), 2.853 (0.46), 2.888 (16.00), 2.947 (0.67), 3.070 (1.30), 3.088 (3.79), 3.105 (3.72), 3.124 (1.30), 3.467 (0.60), 3.485 (0.64), 3.502 (0.53), 3.601 (0.62), 3.738 (0.58), 3.753 (0.87), 3.769 (1.01), 3.784 (0.80), 3.799 (0.47), 3.904 (10.44), 6.696 (0.96), 6.713 (1.16), 6.736 (1.17), 7.412 (1.80), 7.433 (1.78), 7.450 (4.50), 7.475 (0.41), 7.950 (1.99), 8.136 (0.46); LC-MS (Method 1): $R_t$=0.68 min; MS (ESIpos): m/z=206 [M+H]$^+$.

Intermediate INT-44 tert-butyl [2-(2-{2-[2-(2-sulfamoylphenoxy)ethoxy]ethoxy}ethoxy)ethyl]carbamate

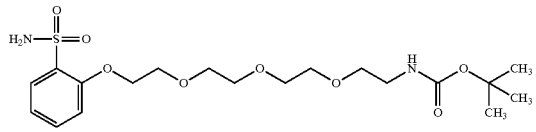

To a solution of commercially available tert-butyl (2-{2-[2-(2-hydroxyethoxy)ethoxy]ethoxy}ethyl)carbamate (337 mg, 1.15 mmol) and triethylamine (320 μL, 2.3 mmol) were stirred in DCM (4 mL) was methanesulfonylchloride (130 μL, 1.7 mmol) added dropwise. The mixture was stirred at RT for 1 h. The reaction mixture was dissolved with water and extracted with DCM. The organic phase was washed with a sat. solution of NaHCO$_3$ Lsg. And followed by a saturated solution of NaCl and finally dried (sodium sulfate). The organic phase was then concentrated under vacuum. The residue was diluted in DMF (2.5 mL). Commercially available 2-hydroxybenzene-1-sulfonamide (142 mg, 821 μmol, dissolved in 2.5 mL DMF), cesium carbonate (535 mg, 1.64 mmol) were successively added. The corresponding mixture was heated up to 70° C. and stirred for 4 h. After reaction completion and cooling to RT, water was added to the mixture. The phase was separated, and the water phase was extracted twice with DCM. The organic phase was concentrated, and the residue was purified using HPLC (water/acetonitrile) giving the title compound as a colorless solid (127 mg, 31% yield). LC-MS (Method 1): R$_t$=1.02 min; MS (ESIpos): m/z=448 [M+H]+.

Intermediate INT-45 tert-butyl [2-(2-{2-[2-(2-{[6-(dimethylamino)-1-benzofuran-2-carbonyl]sulfamoyl}phenoxy)ethoxy]ethoxy}ethoxy)ethyl]carbamate

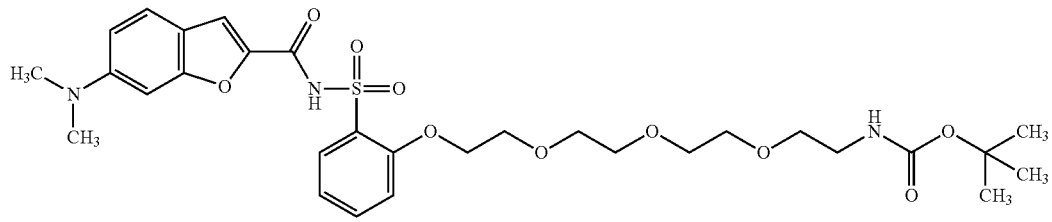 [SMILES: CN(C)c1ccc2cc(C(=O)NS(=O)(=O)c3ccccc3OCCOCCOCCOCCNC(=O)OC(C)(C)C)oc2c1]

According to GP5B, aforementioned 6-(dimethylamino)-1-benzofuran-2-carboxylic acid (INT-11, 52.4 mg, 255 μmol), aforementioned tert-butyl [2-(2-{2-[2-(2-sulfamoylphenoxy)ethoxy]ethoxy}ethoxy)ethyl]carbamate (INT-44, 126 mg, 281 μmol), CDI (53.8 mg, 332 μmol) and DBU (53 μL, 350 μmol) were stirred at RT in THF (1.3 mL) over night. After reaction completion, work-up and purification using HPLC (acid), the desired product was obtained as yellow film (111 mg, 43%). LC-MS (Method 1): Rt=1.28 min; MS (ESIpos): m/z=635 [M+H]+.

Intermediate INT-46

N-[2-(2-{2-[2-(2-aminoethoxy)ethoxy]ethoxy}ethoxy)benzene-1-sulfonyl]-6-(dimethylamino)-1-benzofuran-2-carboxamide-hydrogen chloride (1/1)

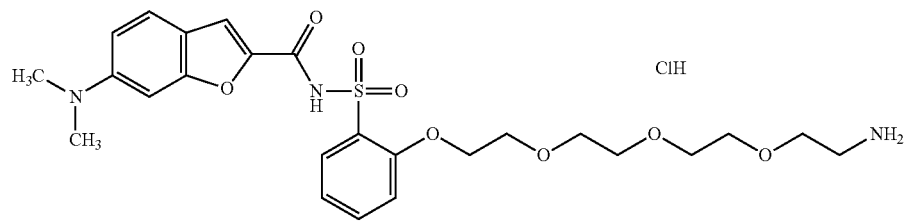 [SMILES: CN(C)c1ccc2cc(C(=O)NS(=O)(=O)c3ccccc3OCCOCCOCCOCCN)oc2c1 ; Cl]

Aforementioned tert-butyl [2-(2-{2-[2-(2-{[6-(dimethylamino)-1-benzofuran-2-carbonyl]sulfamoyl}phenoxy)ethoxy]ethoxy}ethoxy)ethyl]carbamate (INT-45, 42.0 mg, 66.1 μmol) was suspended in HCl/dioxane (680 μL, 4.0 M, 2.7 mmol) solution and the suspension was stirred for 30 min at RT. After reaction completion, the reaction mixture was concentrated under vacuum giving the desired product as yellow crystals (50 mg, 85%). LC-MS (Method 1): $R_t$=0.85 min; MS (ESIpos): m/z=535 [M+H]$^+$.

Intermediate INT-47

Methyl 6-(dimethylamino)-1-methyl-1H-indole-2-carboxylate

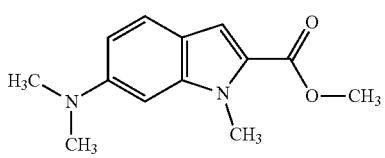

According to GP6, commercially available methyl 6-bromo-1-methyl-1H-indole-2-carboxylate (CAS: 680569-18-0, 100 mg, 373 μmol), commercially available N—methylmethanamine (CAS: 124-40-3, 220 μL, 2.0 M, 450 μmol), caesium carbonate (304 mg, 932 μmol), commercially available catalyst palladium-Xphos G2 (CAS: 1310584-14-5, 29.3 mg, 37.3 μmol) were stirred in dioxane (2.4 mL) for 5 h. After reaction completion and workup and purification, the desired product was obtained as a brown solid (30 mg, 33% yield). LC-MS (Method 1): $R_t$=0.86 min; MS (ESIpos): m/z=233 [M+H]$^+$.

Intermediate INT-48

6-(Dimethylamino)-1-methyl-1H-indole-2-carboxylic acid

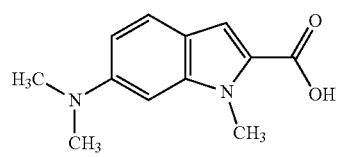

according to GP4, methyl 6-(dimethylamino)-1-methyl-1H-indole-2-carboxylate (intermediate INT-45, 30.0 mg, 129 μmol) was dissolved in THF/water (9.7 mL/4.9 mL) and then lithium hydroxide (15.5 mg, 646 μmol) was added. The resulted mixture was stirred at RT for 20 h. After reaction completion and work up, the desired product was obtained as a brown solid (25 mg) which was directly submitted to the next step without further purification step. LC-MS (Method 1): $R_t$=0.58 min; MS (ESIpos): m/z=219 [M+H]$^+$.

Intermediate INT-49

Ethyl 6-(dimethylamino)-5-methyl-1-benzofuran-2-carboxylate

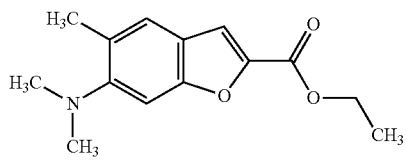 [SMILES: CCOC(=O)c1cc2cc(C)c(N(C)C)cc2o1]

According to GP3: to a 0° C. stirred suspension of commercially available 4-(dimethylamino)-2-hydroxy-5-methylbenzaldehyde (CAS: 58186-70-2, 3.00 g, 16.7 mmol) and potassium carbonate (22.7 g, 164 mmol) in anhydrous DMF (78 mL) was added ethyl chroroacetate (1.8 ml, 17 mmol). Following complete addition, the mixture was heated at 160° C. for 2 h. After reaction completion and work up, the desired crude product (3.5 g. brown oil) was obtained as a mixture of the desired product (acid) and the corresponding ethyl ester which was directly submitted to the next step without further purification step.

Intermediate INT-50

6-(Dimethylamino)-5-methyl-1-benzofuran-2-carboxylic acid

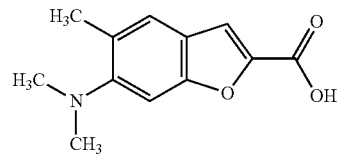

According to GP4, was dissolved in THF/water (150 mL/70 mL) and then lithium hydroxide (1.69 g, 70.8 mmol) was added. The resulted mixture was stirred at RT for 18 h. After reaction completion and work up, the desired residue (containing DMSO, 1.50 g) was used without further purification step. $^1$H-NMR (400 MHz, DMSO-d$_6$) δ [ppm]: 2.500 (0.41), 2.540 (16.00); LC-MS (Method 1): $R_t$=0.56 min; MS (ESIpos): m/z=220 [M+H]$^+$.

Intermediate INT-51

4-(Dimethylamino)-2-hydroxybenzaldehyde

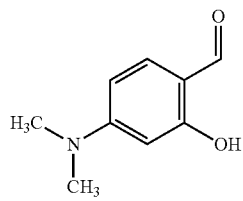

The Vilsmeier Haack adduct was prepared by addition of POCl$_3$ (53.0 g, 346 mmol) dropwise to dry DMF (300 mL) at 0° C., and the mixture was then stirred for 30 min at the same temperature. To the commercially available adduct, a solution of 3-(N,N-dimethylamino)phenol (23.8 g, 173 mmol) in dry DMF (50 mL) was added dropwise at 0° C. The reaction mixture was slowly warmed to room temperature, stirred for 4 h, and then heated at 85-90° C. for 30 min. The reaction mixture was allowed to cool to room temperature and stirred overnight. It was then poured into crushed ice and neutralized with saturated aqueous solution of $Na_2CO_3$ (120 mL). The precipitate was filtered off, washed with water and dried to obtain the desired title intermediate (17.7 g, 62% yield).

Intermediate INT-52

5-(Dimethylamino)-2-formylphenyl acetate

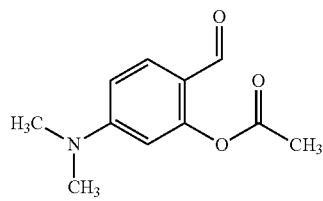

To a solution of aforementioned INT-51 (11.2 g, 68 mmol) and TEA (8.2 g, 81 mmol) in DCM, cooled to 0° C., was added acetyl chloride (5.9 g, 74 mmol) and the mixture was stirred overnight at RT. The organic phase was washed with water three times, dried over anhydrous $Na_2SO_4$ and evaporated under reduced pressure to obtain the title intermediate (13.9 g, 99% yield).

Intermediate INT-53

4-Bromo-5-(dimethylamino)-2-formylphenyl acetate

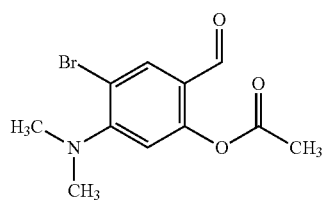 [SMILES: CC(=O)Oc1cc(N(C)C)c(Br)cc1C=O]

A stirred solution of aforementioned (INT-52 13.9 g, 67 mmol) in glacial acetic acid was treated with a solution of bromine (11.3 g, 70 mmol) in glacial acetic acid. After 1 h the solution was evaporated, poured into ice water, neutralized with ammonia to pH=7 and extracted with ethyl acetate. The organic phase was washed with water again and evaporated. The product was purified by column chromatography (ethyl acetate:hexane) pressure to obtain 14 g of compound 4 (73% yield).

Intermediate INT-54

5-Bromo-4-(dimethylamino)-2-hydroxybenzaldehyde

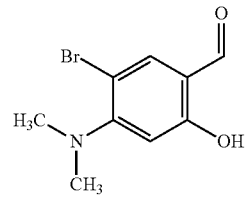

To a solution of aforementioned INT-53 (14 g, 489 mmol) in methanol was added excess of concentrated HCl and the reaction mixture was stirred for 4 h at 40° C. The mixture was partially evaporated, extracted with dichloromethane, washed with water three times and the combined organic layers were dried over anhydrous $Na_2SO_4$ and evaporated under reduced pressure to obtain the title intermediate (11.3 g, 95% yield).

Intermediate INT-55

5-Bromo-4-(dimethylamino)-2-hydroxybenzaldehyde

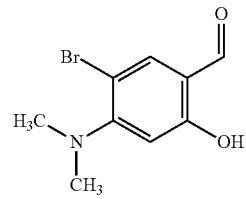

To a solution of aforementioned INT-54 (19.4 g, 79 mmol) in acetonitrile was added $K_2CO_3$ (21.96 g, 158 mmol). To obtained suspension was added dropwise a solution of methyl bromoacetate (12.76 g, 83 mmol) in acetonitrile and the reaction mixture was stirred overnight at RT. Upon completion, the mixture was filtrated, the filtrate was partially concentrated in vacuo, the residue was extracted with ethyl acetate, twice washed with water and the combined organic layers were dried over anhydrous $Na_2SO_4$ and evaporated under reduced pressure to obtain the title intermediate (17.4 g, 69% yield).

Intermediate INT-56

Methyl [4-bromo-5-(dimethylamino)-2-formylphenoxy]acetate

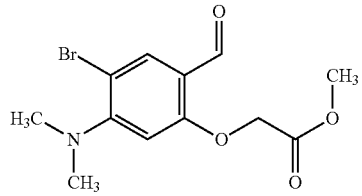

To a solution of aforementioned INT-55 (17.35 g, 54 mmol) in DMF was added K$_2$CO$_3$ (7.58 g, 54 mmol) and the reaction mixture was stirred for 6 h at 90° C. The reaction mixture was diluted with ethyl acetate, four times washed with water, dried over anhydrous Na$_2$SO$_4$ and evaporated under reduced pressure. Purification of the residue via column chromatography on silica gel (ethyl acetate/hexan) to obtain the title intermediate (7.3 g, 45% yield).

Intermediate INT-57

5-Bromo-6-(dimethylamino)-1-benzofuran-2-carboxylic acid

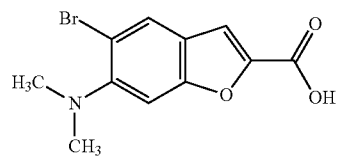 [SMILES: CN(C)c1cc2oc(C(=O)O)cc2cc1Br]

To a solution of aforementioned INT-56 (7.3 g, 24 mmol) in THF:water (3:1) was added LiOH (1.08 g, 25 mmol) and the mixture was stirred overnight at r.t. The reaction mixture was evaporated, dissolved in water, acidified with 20% aq. solution of lemon acid to pH=3. The precipitated solid was collected, washed with water and dried in vacuum to afford the title intermediate (6.7 g, 96% yield). $^1$H-NMR (400 MHz, DMSO-d$_6$) δ [ppm]: 2.520 (1.00), 2.525 (0.67), 2.771 (16.00), 7.508 (1.80), 7.528 (1.62), 8.002 (3.14); [M+H]+.

Intermediate INT-58

5-Bromo-6-(dimethylamino)-3-fluoro-1-benzofuran-2-carboxylic acid

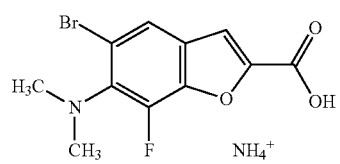 [SMILES: CN(C)c1c(Br)cc2cc(C(=O)O)oc2c1F ; [NH4+]]

Aforementioned 5-bromo-6-(dimethylamino)-1-benzofuran-2-carboxylic acid (INT-57, 335 mg, 1.18 mmol) was sealed in a vessel and flushed with argon, acetonitrile (5 mL) was added, followed by commercially available Selectfluor (CAS: 140681-55-6, 1.25 g, 3.54 mmol) and the mixture was stirred at RT for 2 h. The solvent was removed under reduced pressure, the residue was suspended in water, and extracted with DCM (three times), the water phase was made basic with NaHCO$_3$, and extracted again with DCM (three times), the combined organic phases combined and passed through a water repellent filter and concentrated under reduced pressure. The mixture was purified by reverse phase HPLC yielding the title compound (2 mg, 78% purity, 1% yield). $^1$H-NMR (600 MHz, DMSO_3 mm) δ [ppm]: 0.000 (0.55), 2.502 (5.22), 2.505 (11.78), 2.508 (16.00), 2.511 (11.02), 2.514 (5.35), 2.523 (0.31), 2.526 (0.30), 2.529 (0.24), 2.548 (0.30), 2.848 (0.16), 2.851 (0.47), 2.869 (9.35), 2.873 (9.66), 3.286 (0.24), 3.320 (0.19), 3.360 (0.17), 7.574 (0.84), 7.578 (0.79), 7.870 (1.79), 7.872 (1.70); LC-MS (method 9): R$_t$=1.14 min; MS (ESIpos): m/z=301.8 [M+H]$^+$ Intermediate INT-59

5-Cyano-6-(dimethylamino)-1-benzofuran-2-carboxylic acid

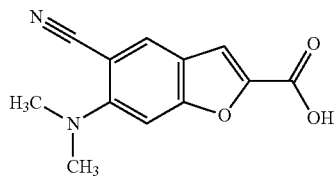 [SMILES: CN(C)c1cc2oc(C(=O)O)cc2cc1C#N]

Aforementioned 5-Bromo-6-(dimethylamino)-1-benzofuran-2-carboxylic acid (INT-57, 100 mg, 352 μmol), bis[cinnamyl palladium(II) chloride] (18.2 mg, 35.2 μmol), 1,1'-ferrocenediyl-bis(diphenylphosphine) (29.3 mg, 52.8 μmol) and zinc cyanide (62.0 mg, 528 μmol) were added to a 5 mL reaction vessel and the vessel sealed and flushed with argon. Degassed N,N-dimethylacetamide (1 mL) and N,N-diisopropylethylamine (120 μL, 0.07 mmol), were added and the mixture heated overnight at 80° C. The mixture was diluted with MTBE, the layers separated and solid was filtered and purified by reverse phase HPLC yielding the title compound (1 mg, 1% yield). $^1$H-NMR (400 MHz, DMSO-d$_6$) δ [ppm]: 2.518 (2.27), 2.522 (1.43), 2.970 (16.00), 7.350 (1.47), 7.513 (0.58), 8.126 (1.99); LC-MS (Method 1): R$_t$=0.50 min; MS (ESIpos): m/z=231.2 [M+H]$^+$ Intermediate INT-60

6-(Dimethylamino)-4-fluoro-1-benzofuran-2-carboxylic acid

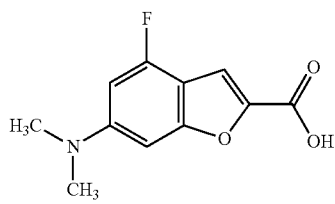 [SMILES: CN(C)c1cc(F)c2cc(C(=O)O)oc2c1]

According to GP6, aforementioned 6-bromo-4-fluoro-1-benzofuran-2 carboxylic acid (INT-14, 3.00 g, 11.6 mmol), commercially available N-methylmethanamine (CAS: 124-40-3, 6.9 ml, 2.0 M, 14 mmol), caesium carbonate (9.43 g, 29.0 mmol), commercially available catalyst palladium-Xphos G2 (CAS: 1310584-14-5, 911 mg, 1.16 mmol) were stirred in DMF (42 mL) and heated to 110° C. for 4.5 h. After reaction completion, workup and purification using HPLC, the tile compound was obtained as a solid. $^1$H-NMR (400 MHz, DMSO-d$_6$) δ [ppm]: 2.523 (0.58), 2.991 (16.00), 5.764 (0.45), 6.658 (0.58), 6.662 (0.72), 6.691 (0.49), 6.696 (0.82), 6.708 (1.01), 6.710 (1.09), 6.712 (0.87), 6.715 (0.74), 7.529 (1.96), 7.531 (2.21); LC-MS (method 4): R$_t$=0.89 min, MS (ESIpos): m/z=224 [M+H]$^+$.

EXAMPLES

Example 1

6-[Ethyl(methyl)amino]-N-(2-phenylphenyl)sulfonyl-benzofuran-2-carboxamide

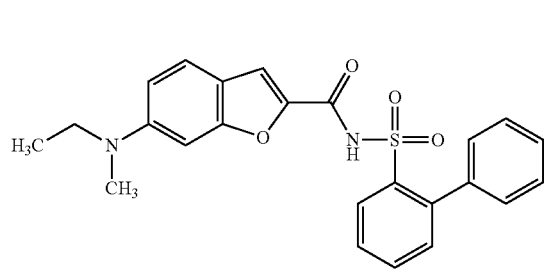 [SMILES: CCN(C)c1ccc2cc(C(=O)NS(=O)(=O)c3ccccc3-c3ccccc3)oc2c1]

To a RT stirred solution of INT-8 (35.0 mg, 0.16 mmol, 1.00 eq.), [1,1'-biphenyl]-2-sulfonamide (37.2 mg, 0.16 mmol, 1.00 eq.) and PyBOP (99.6 mg, 0.19 mmol, 1.20 eq.) in anhydrous dichloromethane (798 μL) was added DIPEA (111 μL, 0.64 mmol, 4.00 eq.). The resulting solution was stirred at RT for 23 h and then concentrated under reduced pressure. The residue was purified by reverse phase column chromatography (30 g HP $C_{18}$, 30-100% acetonitrile/water with 0.1% formic acid gradient) to give the title compound as a yellow solid (44.8 mg). $^1$H NMR (400 MHz, DMSO-$d_6$) δ [ppm]: 11.95 (s, 1H), 8.15 (d, 1H), 7.69 (s, 1H), 7.64 (s, 1H), 7.51 (d, 1H), 7.32 (dd, 7H), 6.84 (d, 1H), 6.74 (s, 1H), 3.47 (q, 2H), 2.94 (s, 3H), 1.06 (t, 3H); LC-MS (method 4): $R_t$=1.59 min, MS (ESIpos): m/z=435 [M+H]$^+$.

Example 2

N-(Benzenesulfonyl)-6-[ethyl(methyl)amino]benzofuran-2-carboxamide

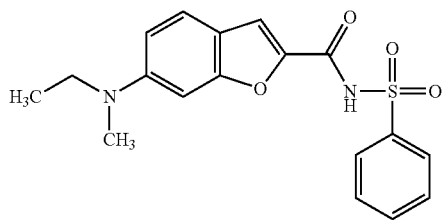 [SMILES: CCN(C)c1ccc2cc(C(=O)NS(=O)(=O)c3ccccc3)oc2c1]

To a RT stirred solution INT-8 (35.0 mg, 0.16 mmol, 1.00 eq.), benzenesulfonamide (25.0 mg, 0.16 mmol, 1.00 eq.) and PyBOP (99.6 mg, 0.19 mmol, 1.20 eq.) in anhydrous dichloromethane (798 μL, 0.20 M) was added DIPEA (111 μL, 0.64 mmol, 4.00 eq.). The resulting solution was stirred at RT for 23 h and then concentrated under reduced pressure. The residue was purified by reverse phase column chromatography (30 g HP $C_{18}$, 30-100% acetonitrile/water with 0.1% formic acid gradient) to give the title compound as a yellow solid (42.0 mg). $^1$H NMR (400 MHz, DMSO-$d_6$) δ [ppm]: 12.50 (s, 1H), 8.03-7.97 (m, 2H), 7.77 (s, 1H), 7.75-7.69 (m, 1H), 7.68-7.61 (m, 2H), 7.53 (d, 1H), 6.85 (dd, 1H), 6.78-6.73 (m, 1H), 3.46 (q, 2H), 2.93 (s, 3H), 1.06 (t, 3H); LC-MS (Method 2.0 min): $R_t$=1.38 min, MS (ESIpos): m/z=359 [M+H]$^+$.

Example 3

N-(2,4-Dichlorophenyl)sulfonyl-6-[ethyl(methyl)amino]benzofuran-2-carboxamide

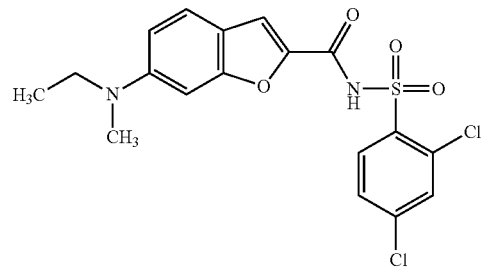 [SMILES: CCN(C)c1ccc2cc(C(=O)NS(=O)(=O)c3ccc(Cl)cc3Cl)oc2c1]

To a RT stirred solution of INT-8 (35.0 mg, 0.16 mmol, 1.00 eq.), 2,4-dichlorobenzene-1-sulfonamide (36.0 mg, 0.16 mmol, 1.00 eq.) and PyBOP (99.6 mg, 0.19 mmol, 1.20 eq.) in anhydrous dichloromethane (798 μL, 0.20 M) was added DIPEA (111 μL, 0.64 mmol, 4.00 eq.). The resulting solution was stirred at RT for 23 h and then concentrated under reduced pressure. The residue was purified by reverse phase column chromatography (30 g HP $C_{18}$, 30-100% acetonitrile/water with 0.1% formic acid gradient) to give the title compound as a yellow solid (54.3 mg). $^1$H NMR (400 MHz, DMSO-$d_6$) δ [ppm]: 8.15 (d, 1H), 7.87 (s, 2H), 7.71 (dd, 1H), 7.55 (d, 1H), 6.86 (d, 1H), 6.77 (s, 1H), 3.47 (q, 2H), 2.94 (s, 3H), 1.06 (t, 3H); LC-MS (method 4): $R_t$=1.50 min, MS (ESIpos): m/z=428 [M+H]$^+$.

Example 4

N-(2-Chlorophenyl)sulfonyl-6-[ethyl(methyl)amino]benzofuran-2-carboxamide

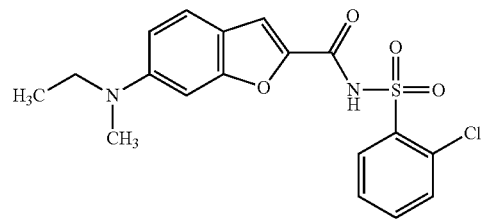 [SMILES: CCN(C)c1ccc2cc(C(=O)NS(=O)(=O)c3ccccc3Cl)oc2c1]

To a RT stirred solution of INT-8 (35.0 mg, 0.16 mmol, 1.00 eq.), 2-chlorobenzene-1-sulfonamide (30.5 mg, 0.16 mmol, 1.00 eq.) and PyBOP (99.6 mg, 0.19 mmol, 1.20 eq.) in anhydrous dichloromethane (798 μL, 0.20 M) was added DIPEA (111 μL, 0.64 mmol, 4.00 eq.). The resulting solution was stirred at room temperature for 23 h and then concentrated under reduced pressure. The residue was purified by reverse phase column chromatography (30 g HP $C_{18}$, 30-100% acetonitrile/water with 0.1% formic acid gradient) to give the title compound as a yellow solid (44.4 mg). $^1$H NMR (400 MHz, DMSO-$d_6$) δ [ppm]: 12.92 (s, 1H), 8.17 (dd1H), 7.91 (s, 1H), 7.75-7.59 (m, 3H), 7.55 (d, 1H), 6.86 (dd, 1H), 6.75 (s, 1H), 3.47 (q, 2H), 2.94 (s, 3H), 1.06 (t, 3H); LC-MS (method 4): $R_t$=1.38 min, MS (ESIneg): m/z=391 [M−H]$^-$.

Example 5

N-(2-Ethoxyphenyl)sulfonyl-6-[ethyl(methyl)amino]benzofuran-2-carboxamide

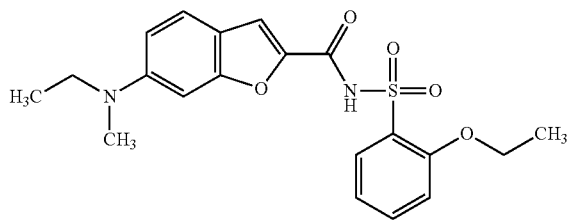 [SMILES: CCOc1ccccc1S(=O)(=O)NC(=O)c1cc2ccc(N(C)CC)cc2o1]

To a room temperature stirred solution INT-8 (35.0 mg, 0.16 mmol, 1.00 eq.), 2-ethoxybenzene-1-sulfonamide (32.1 mg, 0.16 mmol, 1.00 eq.) and PyBOP (99.6 mg, 0.19 mmol, 1.20 eq.) in anhydrous dichloromethane (798 µL, 0.20 M) was added N,N-diisopropylethylamine (111 µL, 0.64 mmol, 4.00 eq.). The resulting solution was stirred at room temperature for 23 h and then concentrated under reduced pressure. The residue was purified by reverse phase column chromatography (30 g HP $C_{18}$, 30-100% acetonitrile/water with 0.1% formic acid gradient) to give the title compound as a yellow solid (45.8 mg). $^1$H NMR (400 MHz, DMSO-$d_6$) δ [ppm]: 12.26 (s, 1H), 7.94 (s, 1H), 7.90 (dd, 1H), 7.63 (t, 1H), 7.59-7.52 (m, 1H), 7.21 (d, 1H), 7.13 (t, 1H), 6.85 (dd, 1H), 6.77-6.74 (m, 1H), 4.16 (q, 2H), 3.46 (q, 2H), 2.93 (s, 3H), 1.25 (t, 3H), 1.06 (t, 3H); LC-MS (method 4): $R_t$=1.47 min, MS (ESIpos): m/z=403 [M+H]$^+$.

Example 6

N-(2-Ethoxyphenyl)sulfonyl-6-(N-methylanilino)benzofuran-2-carboxamide

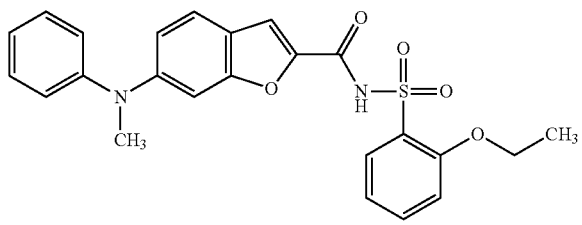 [SMILES: CCOc1ccccc1S(=O)(=O)NC(=O)c1cc2ccc(N(C)c3ccccc3)cc2o1]

To a room temperature stirred solution of INT-12 (30.0 mg, 0.11 mmol, 1.00 eq.), 2-ethoxybenzene1-sulfonamide (26.1 mg, 0.11 mmol, 1.00 eq.) and PyBOP (70.0 mg, 0.14 mmol, 1.20 eq.) in anhydrous dichloromethane (561 µL, 0.20 M) was added N,N-diisopropylethylamine (78.1 µL, 0.45 mmol, 4.00 eq.). The resulting solution was stirred at room temperature for 17 h and then concentrated under reduced pressure. The residue was purified by reverse phase flash column chromatography (30 g HP $C_{18}$, 30-100% acetonitrile/water with 0.1% formic acid gradient) to give the title compound as a yellow solid (37.3 mg). 1H NMR (400 MHz, DMSO-$d_6$) δ [ppm]: 12.40 (s, 1H), 7.97 (s, 1H), 7.91 (dd, 1H), 7.68-7.61 (m, 1H), 7.57 (d, 1H), 7.42-7.34 (m, 2H), 7.24-7.10 (m, 5H), 7.04 (d, 1H), 6.85 (dd, 1H), 4.16 (q, 2H), 3.32 (s, 3H), 1.25 (t, 3H); LC-MS (method 4): $R_t$=1.59 min, MS (ESIpos): m/z=451 [M+H]$^+$.

Example 7

N-(Benzenesulfonyl)-6-(ethylanilino)benzofuran-9-carboxamide

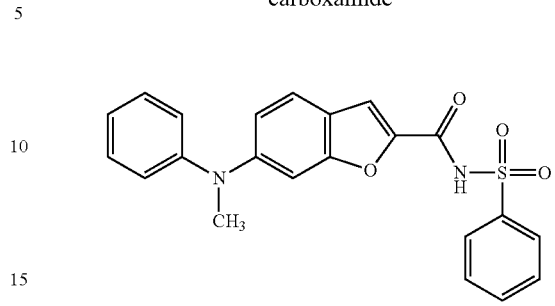

To a room temperature stirred solution of INT-12 (30.0 mg, 0.11 mmol, 1.00 eq.), benzenesulfonamide (17.6 mg, 0.11 mmol, 1.00 eq.) and PyBOP (70.0 mg, 0.14 mmol, 1.20 eq.) in anhydrous dichloromethane (561 µL, 0.20 M) was added N,N-diisopropylethylamine (78.1 µL, 0.45 mmol, 4.00 eq.). The resulting solution was stirred at room temperature for 17 h and then concentrated under reduced pressure. The residue was purified by reverse phase column chromatography (30 g HP $C_{18}$, 30-100% acetonitrile/water with 0.1% formic acid gradient) to give the title compound as a yellow solid (36.3 mg). $^1$H NMR (400 MHz, DMSO-$d_6$) δ [ppm]: 12.61 (s, 1H), 8.00 (dd, 2H), 7.79 (s, 1H), 7.72 (t, 1H), 7.64 (dd, 2H), 7.55 (d, 1H), 7.41-7.34 (m, 2H), 7.21-7.16 (m, 2H), 7.13 (t, 1H), 7.03 (d, 1H), 6.85 (dd, 1H), 3.35 (s, 3H); LC-MS (method 4): $R_t$=1.58 min, MS (ESIpos): m/z=407 [M+H]$^+$.

Example 8

N-(2-Chlorophenyl)sulfonyl-6-(N-methylanilino)benzofuran-2-carboxamide

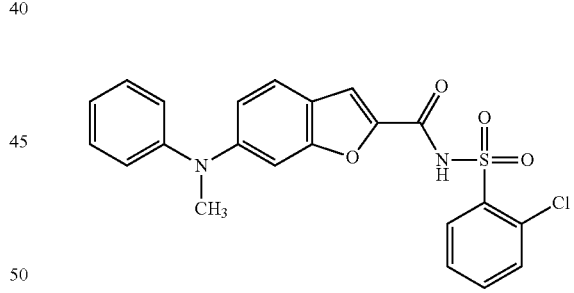

To a room temperature stirred solution of INT-12 (30.0 mg, 0.11 mmol, 1.00 eq.), 2-chlorobenzene1-sulfonamide (21.5 mg, 0.11 mmol, 1.00 eq.) and PyBOP (70.0 mg, 0.14 mmol, 1.20 eq.) in anhydrous dichloromethane (561 µL, 0.20 M) was added DIPEA (78.1 µL, 0.45 mmol, 4.00 eq.). The resulting solution was stirred at RT for 17 h and then concentrated under reduced pressure. The residue was purified by reverse phase column chromatography (30 g HP $C_{18}$, 30-100% acetonitrile/water with 0.1% formic acid gradient) to give the title compound as a yellow solid (44.2 mg). $^1$H NMR (400 MHz, DMSO-$d_6$) δ [ppm]: 8.17 (dd, 1H), 7.89 (s, 1H), 7.73-7.64 (m, 2H), 7.64-7.58 (m, 1H), 7.57 (d, 1H), 7.41-7.35 (m, 2H), 7.21-7.16 (m, 2H), 7.13 (t, 1H), 7.04 (d, 1H), 6.85 (dd, 1H), 3.33 (s, 3H); LC-MS (method 4): $R_t$=1.64 min, MS (ESIpos): m/z=441 [M+H]$^+$.

Example 9

N-(2,4-Dichlorophenyl)sulfonyl-6-(N-methylanilino)benzofuran-2-carboxamide

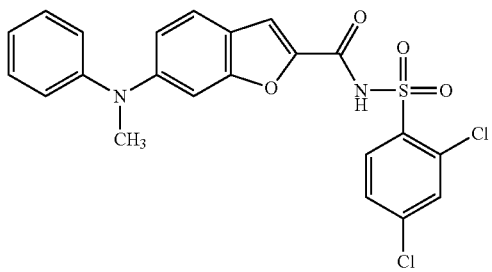 [SMILES: CN(c1ccccc1)c1ccc2cc(C(=O)NS(=O)(=O)c3ccc(Cl)cc3Cl)oc2c1]

To a RT stirred solution of INT-12 (30.0 mg, 0.11 mmol, 1.00 eq.), 2,4-dichlorobenzene-1-sulfonamide (25.3 mg, 0.11 mmol, 1.00 eq.) and PyBOP (70.0 mg, 0.14 mmol, 1.20 eq.) in anhydrous dichloromethane (561 µL, 0.20 M) was added N,N-diisopropylethylamine (78.1 µL, 0.45 mmol, 4.00 eq.). The resulting solution was stirred at room temperature for 17 h and then concentrated under reduced pressure. The residue was purified by reverse phase column chromatography (30 g HP $C_{18}$, 30-100% acetonitrile/water with 0.1% formic acid gradient) to give the title compound as a yellow solid (47.6 mg). $^1$H NMR (400 MHz, DMSO-$d_6$) δ [ppm]: 8.14 (d, 1H), 7.88-7.79 (m, 2H), 7.70 (dd, 1H), 7.56 (d, 1H), 7.40-7.34 (m, 2H), 7.20-7.15 (m, 2H), 7.12 (t, 1H), 7.04 (d, 1H), 6.86 (dd, 1H), 3.33 (s, 3H); LC-MS (method 4): $R_t$=1.84 min, MS (ESIpos): m/z=476 [M+H]$^+$.

Example 10

6-(N-Methylanilino)-N-(2-phenylphenyl)sulfonyl-benzofuran-2-carboxamide

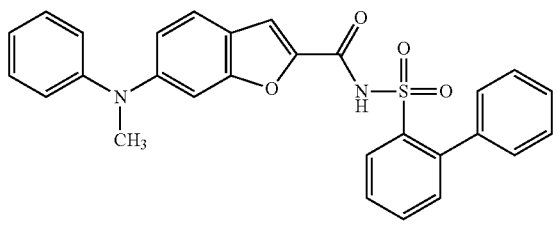 [SMILES: CN(c1ccccc1)c1ccc2cc(C(=O)NS(=O)(=O)c3ccccc3-c3ccccc3)oc2c1]

To a room temperature stirred solution of INT-12 (30.0 mg, 0.11 mmol, 1.00 eq.), [1,1'-biphenyl]-2-sulfonamide (26.1 mg, 0.11 mmol, 1.00 eq.) and PyBOP (70.0 mg, 0.14 mmol, 1.20 eq.) in anhydrous dichloromethane (561 µL, 0.20 M) was added N,N-diisopropylethylamine (78.1 µL, 0.45 mmol, 4.00 eq.). The resulting solution was stirred at room temperature for 3 h and then concentrated under reduced pressure. The residue was purified by reverse phase column chromatography (30 g HP $C_{18}$, 30-100% acetonitrile/water with 0.1% formic acid gradient) to give the title compound as a yellow solid (6.3 mg). $^1$H NMR (400 MHz, DMSO-$d_6$) δ [ppm]: 12.13 (s, 1H), 8.16 (d, J=7.8 Hz, 1H), 7.73-7.66 (m, 1H), 7.66-7.61 (m, 1H), 7.53 (d, J=8.7 Hz, 1H), 7.42-7.25 (m, 9H), 7.17 (d, 2H), 7.15-7.08 (m, 1H), 7.04 (s, 1H), 6.85 (dd, 1H), 3.33 (s, 3H); LC-MS (method 4): $R_t$=1.70 min, MS (ESIpos): m/z=483 [M+H]$^+$.

Example 11

6-(Methylamino)-N-(2-phenylphenyl)sulfonyl-benzofuran-2-carboxamide

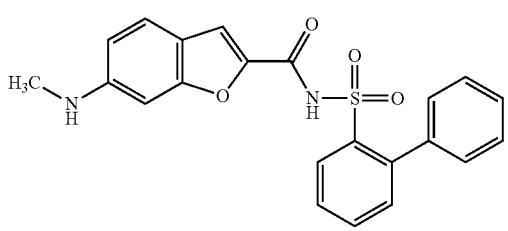 [SMILES: CNc1ccc2cc(C(=O)NS(=O)(=O)c3ccccc3-c3ccccc3)oc2c1]

To a RT stirred solution of INT-13 (23.0 mg, 0.12 mmol, 1.00 eq.), [1,1'-biphenyl]-2-sulfonamide (28.0 mg, 0.12 mmol, 1.00 eq.) and PyBOP (75.0 mg, 0.14 mmol, 1.20 eq.) in anhydrous DCM (601 µL, 0.20 M) was added N,N-diisopropylethylamine (83.6 µL, 0.48 mmol, 4.00 eq.). The resulting solution was stirred at room temperature for 16 h and then concentrated under reduced pressure. The residue was purified by reverse phase column chromatography (30 g HP $C_{18}$, 30-100% acetonitrile/water with 0.1% formic acid gradient) to give the title compound as a yellow solid (13.1 mg). $^1$H NMR (400 MHz, DMSO-$d_6$) δ [ppm]: 11.89 (s, 1H), 8.15 (d, 1H), 7.71 (t, 1H), 7.64 (t, 1H), 7.54 (s, 1H), 7.41 (d, 1H), 7.38-7.22 (m, 6H), 6.67 (dd, 1H), 6.53 (s, 1H), 6.34 (s, 1H), 2.72 (s, 3H); LC-MS (method 4): $R_t$=1.45 min, MS (ESIneg): m/z=405 [M−H]$^-$.

The following example compounds 12 and 13 were prepared according to GP6 using respectively INT-21 and INT-22.

TABLE 3 examples 12 and 13

| Examples | Structure, IUPAC-Name and analytics |
|---|---|
| 12 | 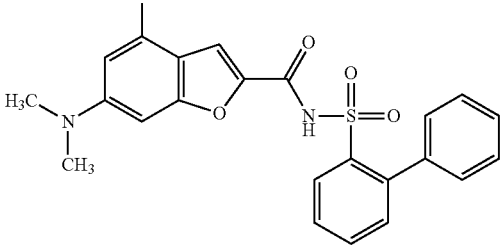<br>N-([1,1'-Biphenyl]-2-sulfonyl)-6-(dimethylamino)-4-fluoro-1-benzofuran-2-carboxamide<br>$^1$H-NMR (400 MHz, DMSO-$d_6$) δ [ppm]: 2.518 (0.86), 2.523 (0.61), 2.991 (16.00), 6.632 (1.10), 6.635 (1.23), 6.669 (0.74), 6.675 (0.60), 6.704 (0.69), 6.708 (0.63), 7.244 (0.83), 7.248 (1.21), 7.253 (0.41), 7.265 (2.01), 7.268 (1.67), 7.292 (0.78), 7.295 (1.17), 7.300 (0.43), 7.308 (1.33), 7.312 (2.56), 7.317 (0.94), 7.327 (1.31), 7.331 (1.68), 7.351 (0.51), 7.355 (0.87), 7.359 (0.47), 7.374 (0.88), 7.607 (0.99), 7.659 (0.76), 7.663 (0.72), 7.679 (0.63), 7.683 (0.58), 7.710 (0.55), 7.714 (0.62), 7.729 (0.81), 7.733 (0.80), 8.154 (0.91), 8.158 (0.97), 8.175 (0.86), 8.178 (0.81); LC-MS (method 1): $R_t$ = 1.33 min; MS (ESIpos): m/z = 439 [M + H]$^+$. |

TABLE 3-continued examples 12 and 13

| Examples | Structure, IUPAC-Name and analytics |
|---|---|
| 13 | 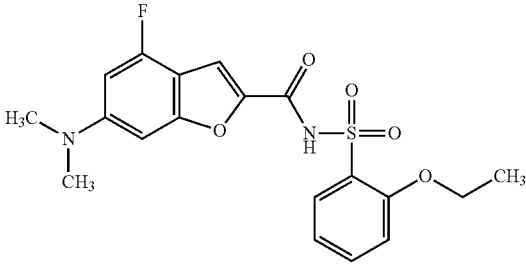 [SMILES: CCOc1ccccc1S(=O)(=O)NC(=O)c1cc2c(F)cc(N(C)C)cc2o1]

6-(Dimethylamino)-N-(2-ethoxybenzene-1-sulfonyl)-4-fluoro-1-benzofuran-2-carboxamide $^1$H-NMR (400 MHz, DMSO-$d_6$) δ [ppm]: 1.225 (2.22), 1.232 (1.19), 1.243 (4.31), 1.260 (2.08), 2.518 (2.58), 2.523 (1.66), 2.980 (16.00), 4.144 (0.68), 4.162 (0.67), 6.645 (1.54), 6.667 (0.45), 6.700 (0.43), 7.883 (0.49), 7.902 (0.47); LC-MS (method 1): $R_t$ = 1.18 min; MS (ESIpos): m/z = 407 [M + H]$^+$. |

The following example compounds 14-34 were prepared according to GP5A using INT-11 reacting with the respectively commercially available sulphonamides: biphenyl-2-sulfonamide (CAS: 40182-06-7), biphenyl-4-sulfonamide (CAS: 4371-23-7), 3'-chlorobiphenyl-2-sulfonamide (CAS: 1350725-94-8), 2'-methyl[1,1'-biphenyl]-2-sulfonamide (CAS: 217498-86-7), 2-bromobenzenesulfonamide (CAS: 92748-09-9), 2-ethoxybenzenesulfonamide (CAS: 58734-61-5), naphthalene-1-sulfonamide (CAS: 89456-57-5), 2-methylquinoline-8-sulfonamide (CAS: 157686-27-6), 2-chlorobenzenesulfonamide (CAS: 6961-82-6), 2-propoxybenzenesulfonamide (CAS: 196107-68-3), 5-methyl-[1,1'-Biphenyl]-2-sulfonamide (CAS: 936841-54-2) INT-4, 4-methylbenzenesulfonamide (CAS: 70-55-3), 2,4-dichlorobenzenesulfonamide (CAS: 20532-15-4), tetrahydro-2H-pyran-4-sulfonamide (CAS: 1058131-55-7), 4-cyanopyridine-2-sulfonamide (CAS: 1251259-15-0), 2,3-dihydro-1-benzofuran-7-sulfonamide (CAS: 89819-27-2), 2-(trifluoromethoxy)benzenesulfonamide (CAS: 37526-59-3), 2-methylbenzenesulfonamide (CAS: 88-19-7), 2-cyanobenzenesulfonamide (CAS: 73542-86-6), 2-fluorobenzenesulfonamide (CAS: 30058-40-3). Example 35 was also prepared according to GP5A using INT-27 reacting with commercially available biphenyl-2-sulfonamide.

TABLE 4 examples 14-35

| Example | Structure, IUPAC-Name and analytics |
|---|---|
| 14 | 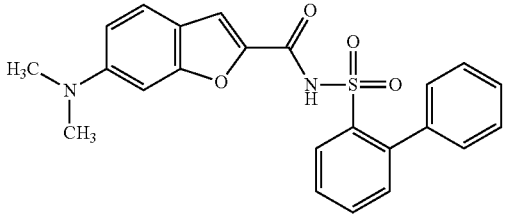 [SMILES: CN(C)c1ccc2cc(C(=O)NS(=O)(=O)c3ccccc3-c3ccccc3)oc2c1]

N-([1,1'-Biphenyl]-2-sulfonyl)-6-(dimethylamino)-1-benzofuran-2-carboxamide $^1$H-NMR (400 MHz, DMSO-$d_6$) δ [ppm]: 2.581 (0.52), 3.053 (16.00), 6.825 (1.10), 6.829 (1.18), 6.907 (0.82), 6.912 (0.72), 6.929 (0.83), 6.935 (0.77), 7.305 (0.87), 7.309 (1.24), 7.314 (0.42), 7.326 (2.09), 7.329 (1.72), 7.355 (0.73), 7.358 (1.07), 7.366 (1.02), 7.370 (1.13), 7.376 (2.09), 7.380 (0.96), 7.385 (1.10), 7.388 (1.09), 7.394 (1.06), 7.413 (0.52), 7.417 (0.87), 7.420 (0.48), 7.434 (0.90), 7.593 (1.55), 7.615 (1.44), 7.648 (1.54), 7.718 (0.82), 7.721 (0.77), 7.738 (0.65), 7.741 (0.59), 7.767 (0.61), 7.770 (0.64), 7.785 (0.87), 7.789 (0.86), 8.212 (0.94), 8.216 (1.00), 8.232 (0.87), 8.235 (0.85); LC-MS (method 1): $R_t$ = 1.26 min; MS (ESIpos): m/z = 421 [M + H]$^+$. |
| 15 | 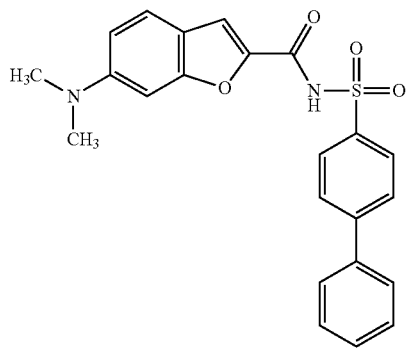 [SMILES: CN(C)c1ccc2cc(C(=O)NS(=O)(=O)c3ccc(-c4ccccc4)cc3)oc2c1]

N-([1,1'-biphenyl]-4-sulfonyl)-6-(dimethylamino)-1-benzofuran-2-carboxamide $^1$H-NMR (400 MHz, DMSO-$d_6$) δ [ppm]: 2.522 (0.85), 2.986 (16.00), 6.775 (1.25), 6.847 (0.79), 6.852 (0.76), 6.869 (0.85), 6.875 (0.89), 7.450 (0.99), 7.464 (0.45), 7.467 (0.87), 7.471 (0.57), 7.500 (1.28), 7.516 (0.89), 7.519 (1.97), 7.537 (0.86), 7.549 (1.64), 7.571 (150), 7.738 (1.95), 7.750 (0.47), 7.755 (1.70), 7.759 (1.30), 7.817 (1.97), 7.923 (1.88), 7.927 (0.89), 7.939 (0.76), 7.944 (2.74), 8.056 (2.79), 8.061 (1.07), 8.073 (0.66), 8.078 (2.07); LC-MS (method 5): $R_t$ = 1.33 min; MS (ESIpos): m/z = 421 [M + H]$^+$. |
| 16 | 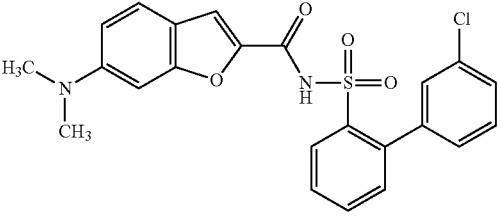 [SMILES: CN(C)c1ccc2cc(C(=O)NS(=O)(=O)c3ccccc3-c3cccc(Cl)c3)oc2c1]

N-(3'-Chloro[1,1'-biphenyl]-2-sulfonyl)-6-(dimethylamino)-1-benzofuran-2-carboxamide $^1$H-NMR (400 MHz, DMSO-$d_6$) δ [ppm]: 2.539 (0.71), 2.955 (0.43), 2.986 (16.00), 3.004 (0.68), 6.762 (0.96), 6.767 (1.05), 6.838 (0.81), 6.843 (0.68), 6.860 (0.81), 6.865 (0.75), 7.198 (0.47), 7.202 (0.77), 7.204 (0.74), 7.217 (0.56), 7.221 (0.88), 7.223 (0.65), 7.252 (0.94), 7.318 (0.63), 7.321 (0.62), 7.339 (1.28), 7.359 (1.36), 7.378 (0.80), 7.436 (0.63), 7.438 (0.68), 7.442 (0.63), 7.444 (0.58), 7.456 (0.42), 7.459 (0.43), 7.461 (0.44), 7.524 (1.43), 7.546 (1.31), 7.599 (0.41), 7.675 (0.59), 7.679 (0.62), 7.694 (0.49), 7.699 (0.46), 7.706 (0.44), 7.710 (0.46), 7.725 (0.53), 7.729 (0.52), 8.153 (0.85), 8.157 (0.94), 8.173 (0.73), 8.176 (0.76); LC-MS (method 5): $R_t$ = 1.35 min; MS (ESIpos): m/z = 455 [M + H]$^+$. |

TABLE 4-continued examples 14-35

| Example | Structure, IUPAC-Name and analytics |
|---|---|
| 17 | 6-(Dimethylamino)-N-(2'-methyl[1,1'-biphenyl]-2-sulfonyl)-1-benzofuran-2-carboxamide<br>¹H-NMR (400 MHz, DMSO-d₆) δ [ppm]: 1.894 (5.68), 2.989 (16.00), 6.773 (1.03), 6.778 (1.12), 6.848 (0.84), 6.853 (0.72), 6.870 (0.84), 6.875 (0.77), 6.980 (0.66), 6.982 (0.68), 6.998 (0.91), 7.001 (0.87), 7.094 (0.42), 7.113 (0.75), 7.175 (0.65), 7.194 (0.92), 7.219 (0.80), 7.222 (0.80), 7.237 (0.90), 7.241 (0.85), 7.264 (0.57), 7.267 (0.56), 7.282 (0.79), 7.286 (0.77), 7.547 (1.57), 7.569 (1.47), 7.657 (0.83), 7.660 (0.76), 7.676 (0.76), 7.680 (0.84), 7.686 (1.67), 7.700 (0.68), 7.704 (0.72), 7.719 (0.90), 7.723 (0.90), 8.185 (0.92), 8.189 (0.98), 8.205 (0.82), 8.208 (0.81); LC-MS (method 5): $R_t$ = 1.35 min; MS (ESIpos): m/z = 435 [M + H]⁺. |
| 18 | N-(2-Bromobenzene-1-sulfonyl)-6-(dimethylamino)-1-benzofuran-2-carboxamide<br>¹H-NMR (400 MHz, DMSO-d₆) δ [ppm]: 1.154 (1.01), 1.172 (2.14), 1.190 (1.05), 1.987 (3.38), 2.518 (1.74), 2.522 (1.14), 2.976 (0.46), 2.988 (16.00), 4.017 (0.74), 4.035 (0.75), 6.773 (0.91), 6.855 (0.72), 6.861 (0.61), 6.878 (0.74), 6.883 (0.69), 7.562 (1.38), 7.584 (1.41), 7.601 (0.63), 7.606 (0.61), 7.620 (0.52), 7.625 (0.47), 7.646 (0.52), 7.649 (0.57), 7.666 (0.70), 7.669 (0.75), 7.839 (0.84), 7.842 (0.85), 7.858 (0.72), 7.861 (0.66), 7.957 (0.69), 8.189 (0.86), 8.194 (0.83), 8.209 (0.85), 8.214 (0.77); LC-MS (method 4): $R_t$ = 1.03 min; MS (ESIpos): m/z = 425 [M + H]⁺. |
| 19 | 6-(Dimethylamino)-N-(2-ethoxybenzene-1-sulfonyl)-1-benzofuran-2-carboxamide<br>¹H-NMR (400 MHz, DMSO-d₆) δ [ppm]: 1.24 (t, 3 H), 2.98 (s, 6 H), 4.15 (q, 2 H), 6.77 (m_c, 1 H), 6.86 (dd, 1 H), 7.13, 7.21 (2 m_c, 1 H each), 7.57 (d, 1 H), 7.63 (m_c, 1 H), 7.90 (dd, 1 H), 7.96 (bs, 1 H), 12.32 (bs, 1 H); LC-MS (method 5): $R_t$ = 1.12 min; MS (ESIpos): m/z = 389 [M + H]⁺. |
| 20 | 6-(Dimethylamino)-N-(naphthalene-1-sulfonyl)-1-benzofuran-2-carboxamide<br>¹H-NMR (400 MHz, DMSO-d₆) δ [ppm]: 2.518 (1.39), 2.523 (1.05), 2.966 (16.00), 6.726 (0.86), 6.730 (0.91), 6.826 (0.74), 6.832 (0.65), 6.848 (0.72), 6.854 (0.71), 7.528 (1.36), 7.551 (1.26), 7.653 (0.52), 7.655 (0.71), 7.673 (0.50), 7.675 (0.46), 7.717 (0.43), 7.720 (0.53), 7.722 (0.76), 7.738 (0.71), 7.741 (1.36), 7.761 (0.76), 7.815 (0.58), 8.107 (0.65), 8.127 (0.60), 8.305 (0.62), 8.325 (0.57), 8.375 (0.74), 8.378 (0.72), 8.394 (0.72), 8.396 (0.64), 8.706 (0.69), 8.727 (0.65); LC-MS (method 1): $R_t$ = 1.19 min; MS (ESIpos): m/z = 395 [M + H]⁺. |
| 21 | 6-(Dimethylamino)-N-(2-methylquinoline-8-sulfonyl)-1-benzofuran-2-carboxamide<br>¹H-NMR (400 MHz, DMSO-d₆) δ [ppm]: 2.518 (0.42), 2.539 (1.37), 2.678 (7.58), 2.957 (16.00), 6.640 (0.41), 6.719 (1.00), 6.723 (1.06), 6.825 (0.80), 6.830 (0.74), 6.848 (0.78), 6.853 (0.74), 7.497 (1.52), 7.517 (1.51), 7.550 (1.53), 7.572 (1.34), 7.725 (0.76), 7.744 (1.15), 7.764 (0.79), 8.041 (1.14), 8.273 (0.77), 8.276 (0.81), 8.294 (0.75), 8.297 (0.70), 8.371 (1.43), 8.392 (1.32), 8.444 (0.98), 8.448 (0.96), 8.463 (0.91), 8.466 (0.85); LC-MS (§method 1): $R_1$ = 1.07 min; MS (ESIpos): m/z = 409 [M + H]⁺. |
| 22 | N-(2-Chlorobenzene-1-sulfonyl)-6-(dimethylamino)-1-benzofuran-2-carboxamide<br>¹H-NMR (400 MHz, DMSO-d₆) δ [ppm]: 2.518 (1.61), 2.523 (1.15), 2.986 (16.00), 6.772 (0.93), 6.850 (0.70), 6.856 (0.60), 6.872 (0.72), 6.878 (0.65), 7.556 (1.17), 7.578 (1.08), 7.614 (0.49), 7.667 (0.74), 7.682 (0.43), 8.152 (0.66), 8.156 (0.64), 8.172 (0.60), 8.176 (0.61); LC-MS (method 1): $R_t$ = 1.09 min; MS (ESIpos): m/z = 379 [M + H]⁺. |
| 23 | |

TABLE 4-continued examples 14-35

| Example | Structure, IUPAC-Name and analytics |
|---|---|
| | 6-(Dimethylamino)-N-(2-propoxybenzene-1-sulfonyl)-1-benzofuran-2-carboxamide<br>¹H-NMR (400 MHz, DMSO-d₆) δ [ppm]: 0.855 (2.20), 0.874 (4.59), 0.892 (2.31), 1.674 (0.76), 1.692 (1.42), 1.710 (1.37), 1.727 (0.73), 2.892 (16.00), 4.037 (1.11), 4.053 (2.14), 4.068 (1.09), 6.768 (1.54), 6.842 (0.81), 6.863 (0.84), 7.103 (0.51), 7.123 (0.98), 7.142 (0.59), 7.198 (0.84), 7.219 (0.92), 7.553 (1.29), 7.576 (1.22), 7.614 (0.44), 7.633 (0.70), 7.897 (0.95), 7.916 (1.03), 7.932 (0.87), 12.298 (0.84); LC-MS (method 1): R$_t$ = 1.24 min; MS (ESIpos): m/z = 403 [M + H]⁺. |
| 24 | 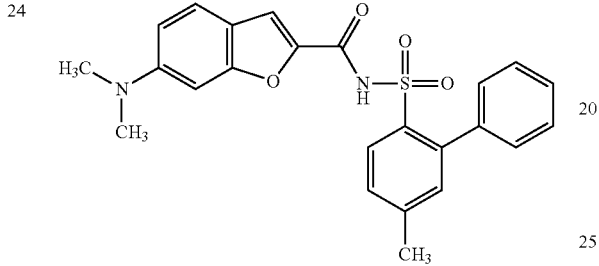<br>6-(Dimethylamino)-N-(5-methyl[1,1'-biphenyl]-2-sulfonyl)-1-benzofuran-2-carboxamide<br>¹H-NMR (400 MHz, DMSO-d₆) δ [ppm]: 2.402 (5.47), 2.518 (0.81), 2.522 (0.48), 2.990 (16.00), 6.762 (1.00), 6.766 (1.09), 6.842 (0.79), 6.848 (0.70), 6.865 (0.80), 6.870 (0.75), 7.126 (1.17), 7.129 (1.16), 7.228 (0.88), 7.231 (1.19), 7.248 (1.88), 7.252 (1.55), 7.285 (0.65), 7.288 (0.94), 7.306 (1.86), 7.310 (0.80), 7.324 (0.97), 7.343 (0.49), 7.347 (0.82), 7.351 (0.45), 7.365 (0.87), 7.439 (0.59), 7.442 (0.57), 7.460 (0.64), 7.462 (0.60), 7.527 (1.52), 7.549 (1.41), 7.575 (1.29), 8.028 (1.59), 8.049 (1.38); LC-MS (method 1): R$_t$ = 1.38 min; MS (ESIpos): m/z = 435 [M + H]⁺. |
| 25 | 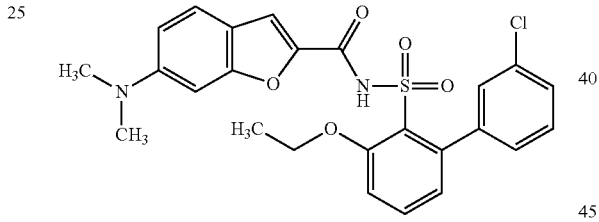<br>N-(3'-Chloro-3-ethoxy[1,1'-biphenyl]-2-sulfonyl)-6-(dimethylamino)-1-benzofuran-2-carboxamide<br>¹H-NMR (400 MHz, DMSO-d₆) δ [ppm]: 1.214 (2.32), 1.231 (4.80), 1.249 (2.32), 2.336 (0.69), 2.518 (8.11), 2.523 (5.66), 2.678 (0.69), 2.988 (16.00), 4.184 (1.12), 4.201 (1.07), 6.766 (2.14), 6.771 (2.32), 6.838 (0.86), 6.853 (1.29), 6.870 (0.82), 7.264 (0.69), 7.285 (0.86), 7.292 (0.86), 7.307 (1.20), 7.317 (0.90), 7.385 (1.80), 7.423 (1.42), 7.556 (0.84), 7.579 (1.16), 7.599 (0.73), 7.934 (1.20), 12.156 (1.67); LC-MS (method 1): R$_t$ = 1.41 min; MS (ESIpos): m/z = 499 [M + H]⁺. |
| 26 | 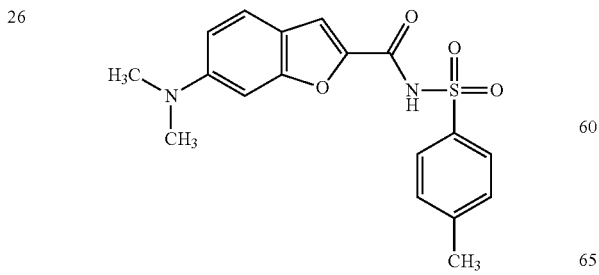 |
| 27 | 6-(Dimethylamino)-N-(4-methylbenzene-1-sulfonyl)-1-benzofuran-2-carboxamide<br>¹H-NMR (400 MHz, DMSO-d₆) δ [ppm]: 2.380 (5.26), 2.518 (1.27), 2.523 (0.81), 2.539 (0.66), 2.975 (16.00), 6.765 (0.97), 6.770 (1.08), 6.822 (0.75), 6.827 (0.60), 6.844 (0.75), 6.849 (0.65), 7.384 (1.08), 7.405 (1.17), 7.512 (1.21), 7.535 (1.11), 7.836 (1.72), 7.856 (1.52), LC-MS (method 1): R$_t$ = 1.16 min; MS (ESIpos): m/z = 359 [M + H]⁺.<br>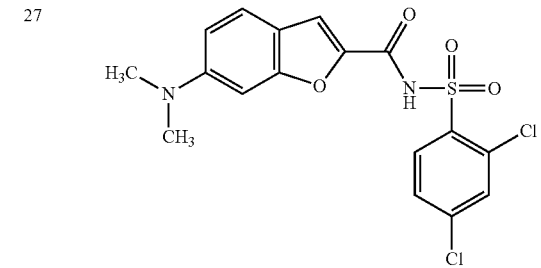<br>N-(2,4-Dichlorobenzene-1-sulfonyl)-6-(dimethylamino)-1-benzofuran-2-carboxamide<br>¹H-NMR (400 MHz, DMSO-d₆) δ [ppm]: 1.292 (0.54), 1.310 (1.20), 1.327 (0.54), 2.331 (0.99), 2.336 (0.45), 2.518 (5.11), 2.523 (3.20), 2.539 (0.42), 2.673 (1.01), 2.678 (0.45), 2.988 (16.00), 4.294 (0.49), 4.311 (0.49), 6.778 (0.85), 6.851 (0.66), 6.856 (0.59), 6.874 (0.90), 7.552 (1.15), 7.575 (1.46), 7.694 (0.45), 7.698 (0.45), 7.716 (0.49), 7.720 (0.49), 7.874 (0.71), 8.134 (1.18), 8.156 (1.04), LC-MS (method 1): R$_t$ = 1.13 min; MS (ESIpos): m/z = 419 [M + H]⁺. |
| 28 | 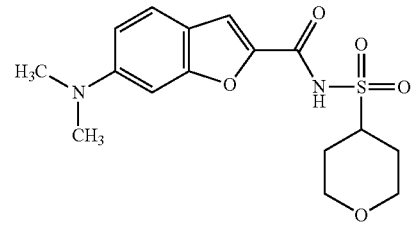 [SMILES: CN(C)c1ccc2cc(C(=O)NS(=O)(=O)C3CCOCC3)oc2c1]<br>6-(Dimethylamino)-N-(oxane-4-sulfonyl)-1-benzofuran-2-carboxamide<br>¹H-NMR (500 MHz, DMSO-d₆) δ [ppm]: −0.007 (0.58), 0.006 (0.56), 1.728 (0.42), 1.744 (0.47), 1.754 (0.43), 1.915 (0.55), 1.936 (0.42), 2.518 (1.12), 2.522 (1.09), 2.525 (0.84), 3.006 (16.00), 3.171 (0.56), 3.366 (0.91), 3.370 (0.89), 3.390 (0.48), 3.942 (0.51), 3.949 (0.51), 3.965 (0.47), 3.972 (0.46), 5.747 (0.51), 6.816 (0.84), 6.820 (0.97), 6.858 (0.72), 6.862 (0.57), 6.875 (0.72), 6.880 (0.63), 7.559 (1.20), 7.577 (1.08), 8.309 (0.83); LC-MS (method 1): R$_t$ = 0.93 min; MS (ESIpos): m/z = 353 [M + H]⁺. |
| 29 | 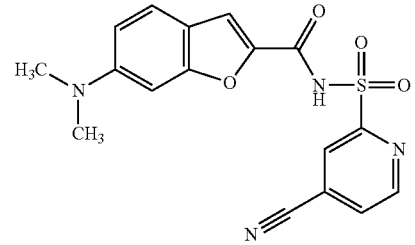 [SMILES: CN(C)c1ccc2cc(C(=O)NS(=O)(=O)c3cc(C#N)ccn3)oc2c1]<br>N-(4-Cyanopyridine-2-sulfonyl)-6-(dimethylamino)-1-benzofuran-2-carboxamide<br>¹H-NMR (400 MHz, DMSO-d₆) δ [ppm]: 2.332 (0.91), 2.336 (0.43), 2.518 (5.10), 2.522 (3.33), 2.673 (0.94), 2.678 (0.43), 2.938 (16.00), 6.743 (0.48), 6.749 (0.97), 6.760 (0.91), 6.766 (1.74), 7.031 (2.11), |

TABLE 4-continued examples 14-35

| Example | Structure, IUPAC-Name and analytics |
|---|---|
| | 7.034 (2.08), 7.412 (1.40), 7.435 (1.34), 7.896 (1.05), 7.900 (1.20), 7.908 (1.22), 7.912 (1.25), 8.206 (1.20), 8.208 (1.40), 8.212 (1.17), 8.780 (1.14), 8.782 (1.31), 8.792 (1.22), 8.794 (1.14); LC-MS (method 1): $R_t$ = 0.71 min; MS (ESIpos): m/z = 371 [M + H]$^+$. |
| 30 | N-(2,3-Dihydro-1-benzofuran-7-sulfonyl)-6-(dimethylamino)-1-benzofuran-2-carboxamide<br>$^1$H-NMR (400 MHz, DMSO-d$_6$) δ [ppm]: 2.332 (0.47), 2.518 (2.51), 2.523 (1.62), 2.673 (0.47), 2.984 (16.00), 3.207 (0.53), 3.229 (1.11), 3.250 (0.58), 4.633 (0.65), 4.655 (1.24), 4.677 (0.60), 6.774 (0.98), 6.779 (1.07), 6.844 (0.68), 6.850 (0.58), 6.866 (0.69), 6.872 (0.62), 7.002 (0.66), 7.516 (0.41), 7.556 (1.03), 7.578 (0.94), 7.594 (0.70), 7.613 (0.65); LC-MS (Method 5): $R_t$ = 1.07 min; MS (ESIpos): m/z = 387 [M + H]$^+$. |
| 31 | 6-(Dimethylamino)-N-[2-(trifluoromethoxy)benzene-1-sulfonyl]-1-benzofuran-2-carboxamide<br>$^1$H-NMR (400 MHz, DMSO-d$_6$) δ [ppm]: 2.074 (0.69), 2.522 (0.42), 2.987 (16.00), 6.772 (1.21), 6.855 (0.78), 6.860 (0.71), 6.877 (0.81), 6.882 (0.76), 7.566 (1.52), 7.589 (1.89), 7.607 (0.66), 7.621 (0.52), 7.623 (0.51), 7.641 (1.02), 7.660 (0.61), 7.826 (0.49), 7.830 (0.53), 7.847 (0.71), 7.849 (0.73), 7.904 (1.37), 8.135 (0.93), 8.140 (0.95), 8.155 (0.88), 8.159 (0.84); LC-MS (method 1): $R_t$ = 1.19 min; MS (ESIpos): m/z = 430 [M + H]$^+$. |
| 32 | 6-(Dimethylamino)-N-(2-methylbenzene-1-sulfonyl)-1-benzofuran-2-carboxamide<br>$^1$H-NMR (400 MHz, DMSO-d$_6$) δ [ppm]: 2.394 (0.44), 2.518 (6.33), 2.523 (3.97), 2.617 (5.36), 2.957 (0.58), 2.984 (16.00), 6.770 (1.19), 6.845 (0.68), 6.850 (0.56), 6.867 (0.71), 6.872 (0.61), 7.388 (0.44), 7.407 (0.54), 7.445 (0.58), 7.547 (1.07), 7.558 (0.46), 7.570 (1.12), 8.014 (0.63), 8.033 (0.58); LC-MS (method 6): $R_t$ = 1.11 min; MS (ESIpos): m/z = 359 [M + H]$^+$. |
| 33 | N-(2-Cyanobenzene-1-sulfonyl)-6-(dimethylamino)-1-benzofuran-2-carboxamide<br>$^1$H-NMR (400 MHz, DMSO-d$_6$) δ [ppm]: 1.178 (0.44), 1.216 (1.37), 1.232 (1.44), 2.327 (1.59), 2.332 (1.12), 2.337 (0.50), 2.518 (7.37), 2.523 (4.72), 2.669 (1.62), 2.674 (1.12), 2.679 (0.53), 2.964 (3.03), 3.003 (0.44), 3.035 (16.00), 6.901 (1.47), 6.910 (0.84), 6.932 (0.69), 6.937 (0.53), 7.636 (0.81), 7.658 (0.75), 7.920 (0.78); LC-MS (method 5): $R_t$ = 1.03 min; MS (ESIpos): m/z = 370 [M + H]$^+$. |
| 34 | 6-(Dimethylamino)-N-(2-fluorobenzene-1-sulfonyl)-1-benzofuran-2-carboxamide<br>$^1$H-NMR (400 MHz, DMSO-d$_6$) δ [ppm]: 2.518 (0.62), 2.990 (16.00), 6.772 (1.01), 6.775 (1.08), 6.855 (0.78), 6.860 (0.68), 6.877 (0.80), 6.882 (0.73), 7.439 (0.44), 7.445 (0.51), 7.447 (0.49), 7.461 (0.66), 7.466 (1.61), 7.485 (1.18), 7.563 (1.49), 7.585 (1.37), 7.892 (1.25), 8.000 (0.66), 8.003 (0.62); LC-MS (method 5): $R_t$ = 0.98 min; MS (ESIpos): m/z = 363 [M + H]$^+$. |
| 35 | N-([1,1'-biphenyl]-2-sulfonyl)-6-(dimethylamino)-4-methyl-1-benzofuran-2-carboxamide<br>$^1$H-NMR (400 MHz, DMSO-d$_6$) δ [ppm]: 2.345 (5.59), 2.518 (1.25), 2.522 (0.76), 3.079 (16.00), 6.300 (1.56), 6.730 (1.45), 7.234 (0.73), 7.238 (1.03), 7.255 (1.78), 7.258 (1.53), 7.283 (0.63), 7.286 (0.92), 7.303 (2.42), 7.318 (1.23), 7.321 (1.61), 7.336 (0.46), 7.341 (0.74), 7.344 (0.43), 7.359 (0.75), 7.660 (0.62), 7.663 (0.61), 7.680 (0.48), 7.683 (0.45), 7.709 (0.42), 7.712 (0.46), 7.727 (0.60), 7.731 (0.62), 7.976 (0.42), 8.159 (0.85), 8.162 (0.92), 8.179 (0.78), 8.182 (0.77); LC-MS (method 1): $R_t$ = 1.92 min; MS (ESIpos): m/z = 435 [M + H]$^+$. |

Example 36

2-{[6-(Dimethylamino)-1-benzofuran-2-carbonyl]sulfamoyl}benzoic acid

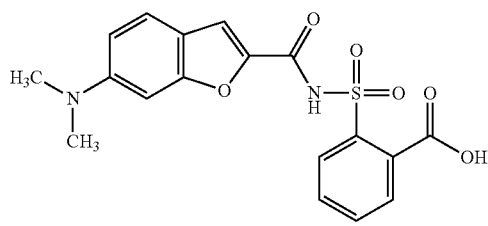 [SMILES: CN(C)c1ccc2cc(C(=O)NS(=O)(=O)c3ccccc3C(=O)O)oc2c1]

According to GP4, INT-29 (1.20 g, 2.98 mmol) was dissolved in THF (25 mL) at RT. Then an aq. solution of lithium hydroxide (1.20 g, 2.98 mmol, 13 mL water) was slowly added to the solution. The reaction mixture was stirred at RT for 18 h and the solvents were removed under vacuum. The aqueous residue was acidified with half concentrated HCl and ethyl acetate was added. The resulted precipitate was collected by filtration, washed with water and dried in the vacuum oven at 40° C. giving the desired product (1.05, 73%) which was used directly without further purification. For analytics a small fraction was purified by HPLC HT (acid) giving a light yellow solid with the following analytics: $^1$H-NMR (500 MHz, DMSO-$d_6$) δ [ppm]: 2.515 (1.18), 2.518 (1.44), 2.522 (0.95), 2.529 (0.88), 2.540 (0.47), 2.997 (16.00), 6.831 (0.44), 7.579 (1.13), 7.596 (1.04), 7.683 (0.72), 7.685 (0.68), 7.697 (1.11), 7.701 (1.13), 7.721 (0.44), 7.733 (1.07), 7.736 (0.86), 7.748 (0.95), 7.752 (0.78), 7.755 (0.94), 7.758 (1.08), 7.769 (0.99), 7.772 (0.79), 7.918 (2.09), 7.920 (2.07), 8.126 (0.96), 8.129 (1.09), 8.142 (0.75), 8.144 (0.81); LC-MS (method 1): $R_t$=0.89 min; MS (ESIpos): m/z=389 [M+H]$^+$.

Example 37

N-([1,1'-Biphenyl]-2-sulfonyl)-6-[methyl(propyl)amino]-1-benzofuran-2-carboxamide

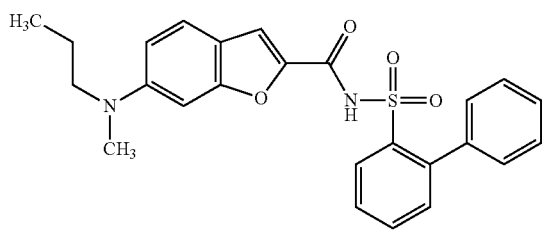 [SMILES: CCCN(C)c1ccc2cc(C(=O)NS(=O)(=O)c3ccccc3-c3ccccc3)oc2c1]

According to GP6, INT-28 (100 mg, 219 µmol), commercially available N-methylpropan-1-amine (CAS: 627-35-0, 19.2 mg, 263 µmol), caesium carbonate (179 mg, 548 µmol), commercially available catalyst palladium-Xphos G2 (17.2 mg, 21.9 µmol) were stirred in dioxane (2 mL). After reaction completion, workup and purification using HPLC HT (acid) the desired product 130 was obtained as a yellow solid (8 mg, 7%, purity: 85%). $^1$H-NMR (400 MHz, DMSO-$d_6$) δ [ppm]: 0.860 (3.68), 0.879 (9.54), 0.898 (4.23), 1.513 (0.93), 1.532 (1.57), 1.551 (1.57), 1.569 (0.90), 2.518 (2.20), 2.523 (1.45), 2.539 (1.69), 2.964 (16.00), 3.345 (3.49), 3.363 (3.28), 3.382 (1.93), 6.723 (1.98), 6.727 (2.10), 6.820 (1.47), 6.826 (1.28), 6.843 (1.52), 6.848 (1.42), 7.242 (1.82), 7.245 (2.48), 7.250 (0.82), 7.263 (4.04), 7.266 (3.43), 7.271 (0.77), 7.280 (1.00), 7.291 (1.87), 7.295 (2.25), 7.299 (2.86), 7.302 (2.63), 7.305 (2.45), 7.316 (4.62), 7.321 (3.79), 7.324 (2.36), 7.331 (1.28), 7.335 (2.27), 7.351 (1.15), 7.355 (1.83), 7.359 (1.03), 7.366 (0.67), 7.373 (1.92), 7.380 (0.41), 7.391 (0.57), 7.502 (3.43), 7.524 (3.19), 7.564 (2.21), 7.634 (0.79), 7.637 (0.84), 7.653 (1.64), 7.656 (1.53), 7.672 (1.36), 7.676 (1.24), 7.702 (1.22), 7.705 (1.29), 7.720 (1.69), 7.724 (1.68), 7.739 (0.86), 7.742 (0.84), 8.145 (1.97), 8.148 (2.15), 8.165 (1.82), 8.168 (1.87); LC-MS (method 1): $R_t$=1.36 min; MS (ESIpos): m/z=456 [M+H]$^+$.

Example 38

N-([1,1'-Biphenyl]-2-sulfonyl)-6-(diethylamino)-1-benzofuran-2-carboxamide

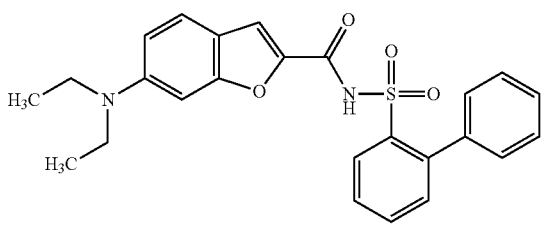 [SMILES: CCN(CC)c1ccc2cc(C(=O)NS(=O)(=O)c3ccccc3-c3ccccc3)oc2c1]

According to GP5, INT-30 (110 mg, 472 µmol), commercially available [1,1'-biphenyl]-2-sulfonamide (CAS: 40182-06-7, 132 mg, 566 µmol), PyBOP (294 mg, 566 µmol) and DIPEA (330 µL, 1.9 mmol) were stirred at RT in DCM (1.8 mL) for 4 d. After reaction completion, work-up and purification using HPLC (acid), the desired product was obtained as a yellow solid (17 mg, 8%). $^1$H-NMR (400 MHz, DMSO-$d_6$) δ [ppm]: 1.095 (6.48), 1.112 (16.00), 1.130 (6.66), 2.518 (1.70), 2.523 (1.15), 2.540 (0.48), 3.382 (1.74), 3.400 (4.45), 3.417 (4.32), 3.435 (1.43), 6.711 (1.55), 6.783 (0.96), 6.788 (0.90), 6.805 (0.99), 6.810 (0.94), 7.241 (1.98), 7.245 (2.68), 7.250 (0.91), 7.262 (4.21), 7.265 (3.60), 7.297 (1.72), 7.301 (3.53), 7.305 (2.52), 7.318 (5.25), 7.322 (3.37), 7.336 (2.31), 7.354 (1.16), 7.357 (1.91), 7.361 (1.08), 7.369 (0.67), 7.375 (1.99), 7.383 (0.44), 7.393 (0.56), 7.495 (2.22), 7.518 (2.07), 7.555 (2.67), 7.634 (0.73), 7.637 (0.76), 7.653 (1.68), 7.656 (1.59), 7.672 (1.34), 7.675 (1.23), 7.701 (1.24), 7.705 (1.32), 7.720 (1.73), 7.724 (1.76), 7.739 (0.72), 7.742 (0.63), 8.144 (2.19), 8.147 (2.31), 8.164 (1.98), 8.168 (1.94); LC-MS (method 1): $R_t$=1.22 min; MS (ESIpos): m/z=449 [M+H]$^+$.

Example 39

N-([1,1'-Biphenyl]-2-sulfonyl)-6-[(2-methoxyethyl)(methyl)amino]-1-benzofuran-2-carboxamide

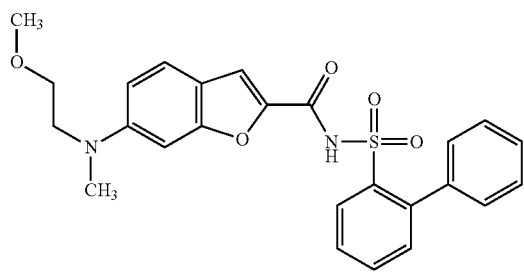 [SMILES: COCCN(C)c1ccc2cc(C(=O)NS(=O)(=O)c3ccccc3-c3ccccc3)oc2c1]

According to GP6, INT-28 (100 mg, 219 μmol), commercially available 2-methoxy-N—methylethan-1-amine (CAS: 38256-93-8, 23.4 mg, 263 μmol), caesium carbonate (179 mg, 548 μmol), commercially available catalyst palladium-Xphos G2 (17.2 mg, 21.9 μmol) were stirred in dioxane (2 mL). After reaction completion, workup and two purifications using HPLC (acid) the desired product was obtained as a yellow solid (7 mg, 7%). $^1$H-NMR (400 MHz, DMSO-$d_6$) δ [ppm]: 2.518 (2.52), 2.522 (1.58), 2.986 (8.72), 3.244 (16.00), 3.487 (0.68), 3.502 (2.31), 3.514 (1.46), 3.572 (1.12), 3.585 (1.49), 3.599 (0.57), 6.762 (1.25), 6.766 (1.32), 6.842 (0.75), 6.848 (0.66), 6.865 (0.76), 6.870 (0.71), 7.248 (1.09), 7.266 (1.95), 7.296 (1.55), 7.314 (2.45), 7.318 (1.71), 7.332 (1.15), 7.353 (0.83), 7.370 (0.83), 7.504 (1.51), 7.526 (1.42), 7.557 (0.42), 7.650 (0.65), 7.670 (0.47), 7.700 (0.45), 7.718 (0.59), 8.144 (1.06), 8.147 (1.11), 8.164 (0.95), 8.166 (0.92); LC-MS: $R_t$=1.26 min; MS (ESIpos): m/z=464 $[M+H]^+$.

Example 40

N-([1,1'-Biphenyl]-2-sulfonyl)-6-[(cyclopropylmethyl)(methyl)amino]-1-benzofuran-2-carboxamide

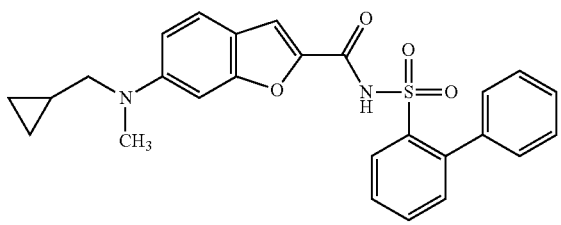 [SMILES: CN(CC1CC1)c1ccc2cc(C(=O)NS(=O)(=O)c3ccccc3-c3ccccc3)oc2c1]

According to GP6, INT-28 (100 mg, 219 μmol), commercially available 1-cyclopropyl-N—methylmethanamine (CAS: 18977-45-2, 22.4 mg, 263 μmol), caesium carbonate (179 mg, 548 μmol), commercially available catalyst palladium-Xphos G2 (17.2 mg, 21.9 μmol) were stirred in dioxane (2 mL). After reaction completion, workup and purification using HPLC HT (acid) the desired product was obtained as a yellow solid (12 mg, 11%). $^1$H-NMR (400 MHz, DMSO-$d_6$) δ [ppm]: 0.239 (0.75), 0.250 (2.72), 0.254 (2.54), 0.262 (2.99), 0.266 (2.66), 0.276 (1.08), 0.420 (1.04), 0.430 (2.42), 0.434 (2.54), 0.440 (1.34), 0.445 (1.19), 0.450 (2.64), 0.455 (2.40), 0.465 (0.86), 0.989 (0.54), 0.992 (0.53), 0.995 (0.54), 1.009 (0.87), 1.021 (0.51), 1.025 (0.51), 1.028 (0.45), 2.518 (2.58), 2.523 (1.62), 2.539 (13.54), 2.999 (16.00), 3.316 (4.00), 3.333 (5.98), 6.785 (2.20), 6.891 (1.43), 6.896 (1.28), 6.913 (1.46), 6.919 (1.36), 7.246 (1.64), 7.250 (2.15), 7.267 (3.76), 7.295 (1.92), 7.298 (3.35), 7.303 (2.26), 7.316 (4.97), 7.334 (2.09), 7.350 (1.04), 7.354 (1.62), 7.358 (0.91), 7.365 (0.60), 7.372 (1.62), 7.390 (0.44), 7.512 (3.00), 7.534 (2.79), 7.563 (0.91), 7.634 (0.56), 7.650 (1.26), 7.669 (0.95), 7.701 (0.91), 7.717 (1.21), 7.736 (0.52), 8.145 (1.95), 8.149 (2.09), 8.165 (1.80), 8.168 (1.75); traces of DMSO detected; LC-MS): $R_t$=1.38 min; MS (ESIpos): m/z=461 $[M+H]^+$.

Example 41

N-([1,1'-Biphenyl]-2-sulfonyl)-6-(dibutylamino)-1-benzofuran-2-carboxamide

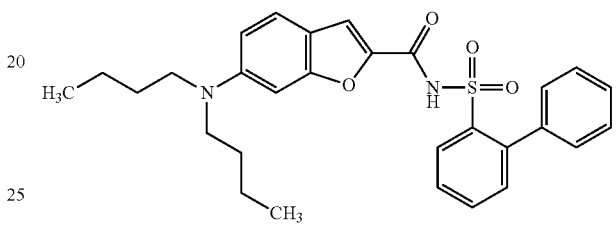

According to GP5, INT-15 (400 mg, 1.38 mmol), commercially available [1,1'-biphenyl]-2-sulfonamide (CAS: 40182-06-7, (387 mg, 1.66 mmol), PyBOP (863 mg, 1.66 mmol) and DIPEA (960 μL, 5.5 mmol) were stirred at RT in DCM (1.8 mL) for 3 d. After reaction completion, work-up and two purification steps using HPLC (acid), the desired product was obtained as a yellow solid (42 mg, 26%). $^1$H-NMR (400 MHz, DMSO-$d_6$) δ [ppm]: 0.898 (6.50), 0.916 (16.00), 0.935 (7.62), 1.284 (0.47), 1.302 (1.56), 1.320 (2.66), 1.339 (2.77), 1.358 (1.79), 1.376 (0.52), 1.479 (0.75), 1.500 (1.67), 1.516 (2.17), 1.536 (1.34), 1.554 (0.52), 2.518 (1.54), 2.523 (0.96), 3.313 (2.09), 3.334 (3.26), 3.350 (4.83), 6.664 (1.55), 6.757 (0.89), 6.762 (0.81), 6.779 (0.91), 6.785 (0.85), 7.240 (1.57), 7.243 (2.13), 7.248 (0.70), 7.260 (3.36), 7.264 (2.78), 7.296 (1.39), 7.300 (2.94), 7.303 (1.84), 7.317 (4.35), 7.322 (2.81), 7.336 (1.78), 7.351 (0.89), 7.355 (1.51), 7.358 (0.83), 7.366 (0.54), 7.373 (1.53), 7.391 (0.43), 7.484 (2.10), 7.506 (1.98), 7.543 (1.85), 7.632 (0.58), 7.635 (0.59), 7.651 (1.29), 7.654 (1.23), 7.671 (1.01), 7.674 (0.94), 7.700 (0.96), 7.704 (1.00), 7.719 (1.34), 7.723 (1.36), 7.738 (0.55), 7.741 (0.48), 8.142 (1.67), 8.146 (1.78), 8.162 (1.46), 8.165 (1.47); LC-MS (method 1): $R_t$=1.67 min; MS (ESIpos): m/z=505 $[M+H]^+$.

Example 42

6-Amino-N-([1,1'-biphenyl]-2-sulfonyl)-1-benzofuran-2-carboxamide

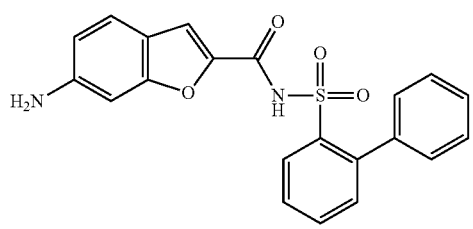 [SMILES: Nc1ccc2cc(C(=O)NS(=O)(=O)c3ccccc3-c3ccccc3)oc2c1]

The aforementioned nitro-compound INT-31 (340 mg, 805 μmol, 1.0 eq.) was dissolved in EtOH (50 mL) and tin(II)chloride was slowly added. The reaction mixture was refluxed for 3 h. After reaction completion water was added. The mixture was basified with sodium carbonate solution (w=10%) to pH 9 and afterwards extracted 3 times with EtOAc. The organic phase was washed with brine. After filtration over a coated filter, the solvent was removed under vacuum. The crude was purified using HPLC HT (acid) giving the desired aniline in two fractions with different purity as a light yellow solid (7 mg, 14%, 95% purity) and an additional fraction (12 mg, 23%, 90% purity). Analytic of the first fraction (95% purity). $^1$H-NMR (400 MHz, DMSO-$d_6$) δ [ppm]: 1.062 (0.58), 1.232 (0.64), 2.074 (0.53), 2.518 (4.25), 2.522 (2.77), 2.539 (0.90), 6.616 (7.55), 6.628 (6.81), 6.633 (4.10), 6.649 (5.99), 6.654 (4.71), 6.946 (0.68), 7.074 (0.75), 7.202 (0.70), 7.242 (4.52), 7.246 (6.17), 7.263 (10.65), 7.266 (9.09), 7.294 (9.19), 7.312 (16.00), 7.315 (8.49), 7.327 (3.14), 7.330 (5.57), 7.345 (2.86), 7.349 (4.69), 7.353 (2.65), 7.360 (1.86), 7.368 (10.58), 7.385 (1.86), 7.390 (7.81), 7.401 (0.47), 7.509 (3.52), 7.622 (1.58), 7.625 (1.66), 7.641 (3.71), 7.644 (3.67), 7.660 (2.90), 7.663 (2.71), 7.690 (2.56), 7.694 (2.77), 7.709 (3.67), 7.712 (3.71), 7.728 (1.49), 7.731 (1.43), 8.135 (5.35), 8.138 (5.72), 8.156 (4.91), 8.159 (4.76); LC-MS (method 6): $R_t$=1.15 min; MS (ESIpos): m/z=393 [M+H]$^+$.

Example 43

6-Acetamido-N-([1,1'-biphenyl]-2-sulfonyl)-1-benzofuran-2-carboxamide

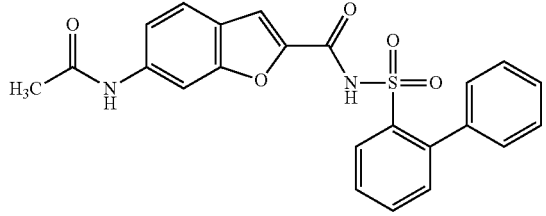 [SMILES: CC(=O)Nc1ccc2cc(C(=O)NS(=O)(=O)c3ccccc3-c3ccccc3)oc2c1]

According to GP5, the aforementioned aniline 42 (40.0 mg, 102 μmol), the commercially available acetic acid (CAS: 64-19-7, 4.9 μL, 85 μmol), PyBOP (53.0 mg, 102 μmol) and DIPEA (59 μL, 340 μmol) were stirred at RT in DCM (420 μL) for 18 h. After reaction completion, work-up and purification using HPLC (acid), the desired product was obtained as an ochre solid (13 mg, 32%). $^1$H-NMR (400 MHz, METHANOL-$d_4$) δ [ppm]: 1.136 (0.51), 2.175 (16.00), 6.535 (0.40), 7.197 (0.99), 7.200 (0.47), 7.216 (2.66), 7.229 (0.85), 7.233 (2.66), 7.257 (2.93), 7.261 (3.77), 7.267 (0.81), 7.278 (1.79), 7.281 (1.22), 7.295 (2.00), 7.298 (2.03), 7.300 (2.75), 7.305 (1.01), 7.309 (1.23), 7.313 (1.09), 7.317 (3.44), 7.321 (3.13), 7.327 (1.71), 7.333 (0.54), 7.341 (0.41), 7.345 (0.63), 7.392 (3.05), 7.394 (3.14), 7.606 (0.68), 7.609 (0.79), 7.617 (2.39), 7.625 (1.39), 7.628 (1.46), 7.638 (2.04), 7.645 (1.20), 7.648 (1.09), 7.678 (1.16), 7.681 (1.29), 7.697 (1.63), 7.700 (1.57), 7.715 (0.60), 7.719 (0.61), 8.129 (1.93), 8.264 (1.47), 8.267 (1.57), 8.284 (1.43), 8.286 (1.39); LC-MS (method 1): $R_t$=1.01 min; MS (ESIpos): m/z=435 [M+H]$^+$.

Example 44

N-([1,1'-Biphenyl]-2-sulfonyl)-6-[2-methylpyrrolidin-1-yl]-1-benzofuran-2-carboxamide (rac)

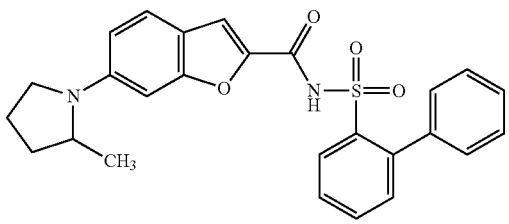 [SMILES: CC1CCCN1c1ccc2cc(C(=O)NS(=O)(=O)c3ccccc3-c3ccccc3)oc2c1]

According to GP5, INT-16 (CAS: 10242-08-7, 68.6 mg, 357 μmol), commercially available [1,1'-biphenyl]-2-sulfonamide (CAS: 40182-06-7, 205 mg, 881 μmol), PyBOP (458 mg, 881 μmol) and DIPEA (510 μL, 2.9 mmol) were stirred at RT in DCM (2.7 mL) for 3 h. After reaction completion, work-up and two purifications using HPLC (acid), the desired product was obtained as a yellow solid (10.9 mg, 3%). $^1$H-NMR (400 MHz, METHANOL-$d_4$) δ [ppm]: 1.201 (1.59), 1.216 (1.57), 2.658 (16.00), 6.603 (0.43), 7.201 (0.65), 7.206 (0.41), 7.220 (0.83), 7.240 (0.40), 7.313 (0.56), 7.317 (0.72), 7.334 (0.52), 7.377 (0.54), 7.399 (0.52); LC-MS (method 1): $R_t$=1.47 min; MS (ESIneg): m/z=459 [M−H]$^-$ Example 45

N-([1,1'-Biphenyl]-2-sulfonyl)-6-(pyrrolidin-1-yl)-1-benzofuran-2-carboxamide

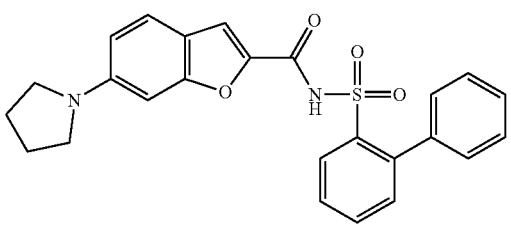 [SMILES: O=C(NS(=O)(=O)c1ccccc1-c1ccccc1)c1cc2ccc(N3CCCC3)cc2o1]

According to GP5, INT-17 (40.0 mg, 173 μmol), [1,1'-biphenyl]-2-sulfonamide (CAS: 40182-06-7, 48.4 mg, 208 μmol), PyBOP (108 mg, 208 μmol) and DIPEA (120 μL, 690 μmol) were stirred at RT in DCM (1.2 mL) for 18 h. After reaction completion, work-up and purification using HPLC (acid), the desired product was obtained as an ochre solid (10 mg, 13%). $^1$H-NMR (400 MHz, DMSO-$d_6$) δ [ppm]: 1.960 (1.26), 1.977 (3.68), 1.993 (1.33), 2.518 (4.40), 2.523 (2.86), 2.540 (0.49), 2.674 (0.74), 3.281 (1.35), 3.297 (3.51), 3.314 (1.72), 3.335 (16.00), 6.585 (1.49), 6.668 (0.77), 6.673 (0.70), 6.690 (0.79), 6.695 (0.74), 7.250 (0.98), 7.268 (1.93), 7.292 (1.32), 7.298 (1.04), 7.309 (2.46), 7.314 (1.30), 7.328 (1.18), 7.349 (0.81), 7.367 (0.82), 7.509 (1.47), 7.532 (1.40), 7.649 (0.63), 7.668 (0.47), 7.698 (0.44), 7.717 (0.58), 8.142 (1.11), 8.145 (1.16), 8.162 (1.00), 8.166 (0.96); LC-MS (method 1): $R_t$=1.43 min; MS (ESIneg): m/z=445 [M−H]$^-$.

Example 46

N-([1,1'-Biphenyl]-2-sulfonyl)-6-[cyclopentyl(methyl)amino]-1-benzofuran-2-carboxamide

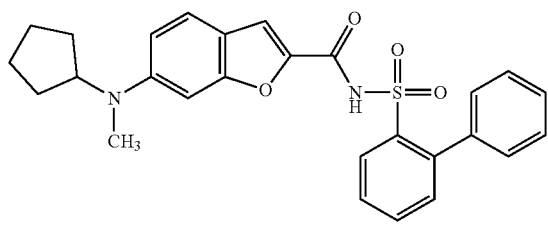 [SMILES: CN(c1ccc2cc(C(=O)NS(=O)(=O)c3ccccc3-c3ccccc3)oc2c1)C1CCCC1]

According to GP6, INT-28 (100 mg, 219 µmol), commercially available N-methylcyclopentanamine (CAS: 2439-56-7, 26.1 mg, 263 µmol), caesium carbonate (179 mg, 548 µmol), commercially available catalyst palladium-Xphos G2 (CAS: 1310584-14-5, 17.2 mg, 21.9 µmol) were stirred in dioxane (2 mL) for 5 h at 85°. After reaction completion, workup and two purification steps using HPLC HT (acid) the desired product was obtained as a yellow solid (3 mg, 3%). $^1$H-NMR (400 MHz, METHANOL-d$_4$) δ [ppm]: 1.292 (0.56), 1.674 (2.57), 1.699 (1.31), 1.713 (0.76), 1.790 (1.59), 1.936 (1.11), 1.945 (1.20), 2.035 (3.12), 2.900 (16.00), 4.303 (0.59), 4.323 (0.84), 4.343 (0.60), 6.886 (1.64), 6.974 (1.41), 6.980 (1.27), 6.996 (1.48), 7.002 (1.37), 7.201 (0.87), 7.204 (1.43), 7.207 (0.64), 7.222 (3.48), 7.224 (2.60), 7.235 (1.17), 7.240 (3.71), 7.266 (6.47), 7.271 (5.75), 7.278 (2.37), 7.283 (2.52), 7.288 (2.89), 7.291 (2.78), 7.296 (2.91), 7.300 (2.39), 7.307 (0.96), 7.312 (1.95), 7.319 (0.54), 7.326 (0.56), 7.331 (0.75), 7.454 (3.01), 7.476 (2.75), 7.582 (0.77), 7.585 (0.85), 7.601 (1.82), 7.604 (1.74), 7.620 (1.54), 7.624 (1.41), 7.647 (1.30), 7.651 (1.40), 7.666 (1.82), 7.669 (1.82), 7.685 (0.75), 7.688 (0.66), 8.256 (2.10), 8.260 (2.23), 8.276 (1.93), 8.279 (1.91); LC-MS (method 5): R$_t$=1.24 min; MS (ESIpos): m/z=474 [M+H]$^+$.

Example 47

N-([1,1'-Biphenyl]-2-sulfonyl)-6-(piperidin-1-yl)-1-benzofuran-2-carboxamide

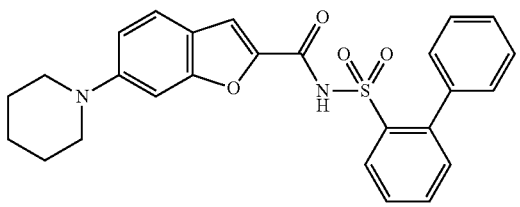 [SMILES: O=C(NS(=O)(=O)c1ccccc1-c1ccccc1)c1cc2ccc(N3CCCCC3)cc2o1]

According to GP6, INT-28 (100 mg, 219 µmol), commercially available piperidine (CAS: 110-89-4, 22.4 mg, 263 µmol, 1.2 eq.), caesium carbonate (179 mg, 548 µmol, 2.5 eq.), commercially available catalyst palladium-Xphos G2 (CAS: 1310584-14-5, 17.2 mg, 21.9 µmol) were stirred in dioxane (500 µL) for 5 h at 85° C. After reaction completion, workup and two purification steps using HPLC HT (acid) the desired product was obtained as a light yellow solid (11 mg, 12%). $^1$H-NMR (400 MHz, DMSO-d$_6$) δ [ppm]: 1.138 (5.17), 1.231 (0.42), 1.561 (4.11), 1.572 (5.42), 1.588 (7.84), 1.605 (9.35), 1.615 (9.46), 2.075 (5.36), 2.084 (0.81), 2.116 (2.16), 2.479 (2.18), 2.518 (3.57), 2.523 (2.39), 2.540 (6.33), 3.250 (11.38), 3.264 (14.45), 3.276 (10.29), 7.014 (7.00), 7.053 (5.15), 7.058 (4.20), 7.076 (5.33), 7.081 (4.64), 7.244 (6.72), 7.247 (9.39), 7.252 (2.97), 7.264 (15.70), 7.268 (12.89), 7.284 (1.00), 7.294 (5.66), 7.297 (8.93), 7.302 (8.86), 7.306 (7.40), 7.314 (16.00), 7.320 (9.85), 7.324 (7.70), 7.329 (4.55), 7.333 (7.74), 7.350 (4.08), 7.354 (7.03), 7.358 (3.71), 7.365 (2.29), 7.372 (7.05), 7.379 (1.48), 7.386 (1.37), 7.390 (1.93), 7.393 (1.04), 7.537 (11.20), 7.558 (10.64), 7.572 (8.74), 7.634 (2.69), 7.638 (2.92), 7.653 (5.98), 7.656 (5.54), 7.673 (4.75), 7.677 (4.20), 7.703 (4.29), 7.706 (4.57), 7.721 (6.21), 7.725 (6.14), 7.740 (2.50), 7.743 (2.23), 8.151 (7.40), 8.154 (7.89), 8.171 (6.63), 8.174 (6.49), 12.058 (0.49); LC-MS (method 1): R$_t$=1.31 min; MS (ESIpos): m/z=461 [M+H]$^+$.

Example 48

N-([1,1'-Biphenyl]-2-sulfonyl)-6-(dimethylamino)-1-benzothiophene-2-carboxamide

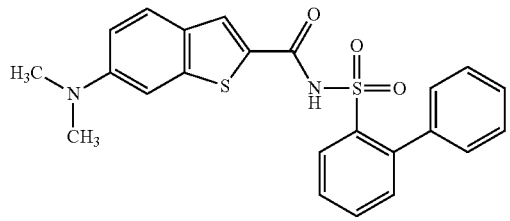

According to GP5, INT-19 (100 mg, 452 µmol), [1,1'-biphenyl]-2-sulfonamide (CAS: 40182-06-7, 116 mg, 497 µmol), PyBOP (282 mg, 542 µmol) and DIPEA (310 µL, 1.8 mmol) were stirred at RT in DCM (30 mL) for 3 d. After reaction completion, work-up and purification using HPLC (acid), the desired product was obtained as a strong yellow solid (25 mg, 12%). $^1$H-NMR (400 MHz, DMSO-d$_6$) δ [ppm]: 2.518 (0.50), 3.003 (16.00), 6.953 (0.73), 6.959 (0.75), 6.976 (0.75), 6.982 (0.79), 7.151 (1.11), 7.157 (1.06), 7.237 (0.81), 7.241 (1.16), 7.259 (1.90), 7.262 (1.64), 7.284 (0.80), 7.287 (1.20), 7.301 (1.29), 7.305 (2.56), 7.309 (0.92), 7.319 (1.24), 7.323 (1.65), 7.348 (0.49), 7.351 (0.87), 7.355 (0.43), 7.370 (0.89), 7.654 (0.80), 7.657 (0.74), 7.672 (1.69), 7.678 (0.69), 7.694 (1.37), 7.702 (0.67), 7.706 (0.70), 7.721 (0.86), 7.724 (0.90), 7.895 (1.83), 8.144 (0.92), 8.147 (1.00), 8.163 (0.83), 8.166 (0.83); LC-MS (method 5): R$_t$=1.37 min; MS (ESIpos): m/z=437 [M+H]$^+$.

Example 49

N-(3'-Chloro[1,1'-biphenyl]-2-sulfonyl)-6-(dimethylamino)-1-benzothiophene-2-carboxamide

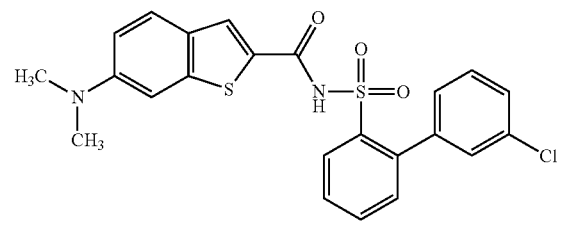 [SMILES: CN(C)c1ccc2cc(C(=O)NS(=O)(=O)c3ccccc3-c3cccc(Cl)c3)sc2c1]

According to GP5, INT-19 (151 mg, 682 μmol), commercially available 3'-chloro[1,1'-biphenyl]-2-sulfonamide (CAS: 1350725-94-8, 201 mg, 751 μmol, 1.1 eq.), PyBOP (426 mg, 819 μmol, 1.2 eq.) and DIPEA (480 μL, 2.7 mmol, 4.0 eq.) were stirred at RT in DCM (45 mL) for 3 d. After reaction completion, work-up and purification using HPLC (acid), the desired product was obtained as a strong yellow solid (20 mg, 6%). $^1$H-NMR (400 MHz, DMSO-$d_6$) δ [ppm]: 2.518 (1.43), 2.523 (1.00), 3.004 (16.00), 6.954 (0.66), 6.960 (0.71), 6.976 (0.68), 6.982 (0.74), 7.150 (1.07), 7.155 (1.00), 7.193 (0.43), 7.197 (0.68), 7.199 (0.57), 7.216 (1.15), 7.218 (1.35), 7.224 (1.00), 7.324 (0.68), 7.328 (0.68), 7.341 (0.97), 7.346 (0.78), 7.359 (1.26), 7.379 (0.75), 7.443 (0.61), 7.445 (0.71), 7.448 (0.66), 7.450 (0.61), 7.463 (0.43), 7.466 (0.45), 7.468 (0.47), 7.673 (1.45), 7.682 (0.68), 7.686 (0.64), 7.696 (1.36), 7.701 (0.59), 7.705 (0.51), 7.715 (0.47), 7.719 (0.50), 7.734 (0.59), 7.737 (0.57), 7.958 (0.84), 8.148 (0.89), 8.152 (0.98), 8.168 (0.76), 8.171 (0.79); LC-MS (method 6): $R_t$=1.42 min; MS (ESIpos): m/z=471 [M+H]$^+$.

Example 50

N-([Biphenyl]-2-ylsulfonyl)-7-bromo-6-(dimethylamino)-1-benzofuran-2-carboxamide

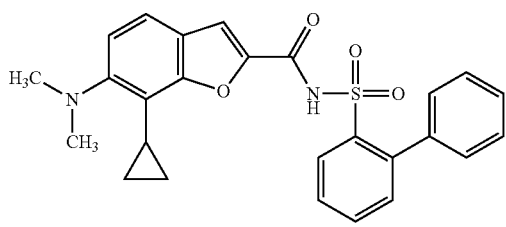 [SMILES: CN(C)c1ccc2cc(C(=O)NS(=O)(=O)c3ccccc3-c3ccccc3)oc2c1C1CC1]

Intermediate INT-20 (30.0 mg, 60 μmol) and commercially available Di-p-iodobis(tri-t-butylphosphino)dipalladium(I) (CAS: 166445-62-1, 5.2 mg, 6 μmol,) were placed in a reaction vessel (5 mL), the vessel was crimp sealed and flushed with argon. Degassed toluene (0.5 mL) was added, followed by cyclopropyl zinc bromide (0.5 M solution in THF, 360 μL, 180 μmol) and the mixture was stirred at RT for 1 h. The mixture was filtered through a 10 g silica column and the column was washed with a DCM:MeOH mixture (90:10), and the filtrated concentrated under reduced pressure. Purification by reverse phase HPLC yielding the title compound (3.5 mg, 12%). $^1$H-NMR (400 MHz, DMSO-$d_6$) δ [ppm]: 0.78-0.88 (m, 4H), 2.65 (s, 6H), 6.87 (d, 1H), 7.04-7.18 (m, 7H), 7.21 (d, 1H), 7.40-7.46 (m, 1H), 7.46-7.53 (m, 1H), 8.06 (dd, 1H), 8.44 (bs, 1H); LC-MS (method 1): $R_t$=1.28 min; MS (ESIpos): m/z=491.4 [M+H]$^+$.

Example 51

6-(Dimethylamino)-N-[4'-(hydroxymethyl)[1,1'-biphenyl]-2-sulfonyl]-1-benzofuran-2-carboxamide

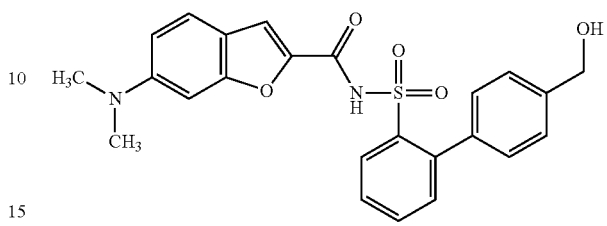

According to GP5, INT-11 (100 mg, 487 μmol), commercially available 4'-(hydroxymethyl)[1,1'-biphenyl]-2-sulfonamide (CAS: 158144-55-9, 154 mg, 585 μmol), PyBOP (304 mg, 585 μmol) and DIPEA (340 μL, 1.9 mmol) were stirred at RT in DCM (2.4 mL) over night. After reaction completion, work-up and purification using HPLC (acid), the desired product was obtained as a colourless solid (78 mg, 34%). $^1$H-NMR (400 MHz, DMSO-$d_6$) δ [ppm]: 2.331 (0.57), 2.518 (2.86), 2.523 (1.90), 2.674 (0.56), 2.994 (16.00), 4.524 (2.98), 6.763 (1.05), 6.768 (1.12), 6.849 (0.72), 6.854 (0.64), 6.871 (0.75), 6.876 (0.68), 7.205 (0.75), 7.226 (2.43), 7.243 (2.69), 7.264 (0.79), 7.287 (0.64), 7.303 (0.68), 7.533 (1.34), 7.555 (1.29), 7.638 (0.55), 7.710 (0.51), 8.137 (0.90), 8.141 (0.93), 8.157 (0.85), 8.160 (0.81); LC-MS (method 1): $R_t$=1.07 min; MS (ESIpos): m/z=450 [M+H]$^+$. A side product was also isolated as a colourless solid (14.3 mg) identified as the corresponding ester: (2'-sulfamoyl[1,1'-biphenyl]-4-yl)methyl 6-(dimethylamino)-1-benzofuran-2-carboxylate. $^1$H-NMR (400 MHz, DMSO-$d_6$) δ [ppm]: 2.331 (0.82), 2.518 (4.29), 2.523 (2.91), 2.673 (0.80), 2.993 (16.00), 5.399 (2.76), 6.861 (0.64), 6.867 (0.85), 6.883 (0.52), 6.888 (1.05), 6.897 (1.11), 7.289 (2.41), 7.310 (0.72), 7.314 (0.66), 7.329 (0.93), 7.332 (0.80), 7.416 (1.34), 7.421 (0.50), 7.432 (0.70), 7.437 (2.58), 7.478 (2.23), 7.499 (1.09), 7.537 (1.22), 7.559 (1.15), 7.582 (0.74), 7.586 (0.70), 7.600 (0.74), 7.605 (0.66), 7.609 (0.68), 7.614 (0.72), 7.628 (0.82), 7.632 (0.76), 7.685 (2.37), 7.688 (2.06), 8.024 (0.74), 8.028 (0.85), 8.044 (0.60), 8.047 (0.68); LC-MS (method 1): $R_t$=1.31 min; MS (ESIpos): m/z=450 [M+H]$^+$.

Example 52

6-(Dimethylamino)-N-(2-propylbenzene-1-sulfonyl)-1-benzofuran-2-carboxamide

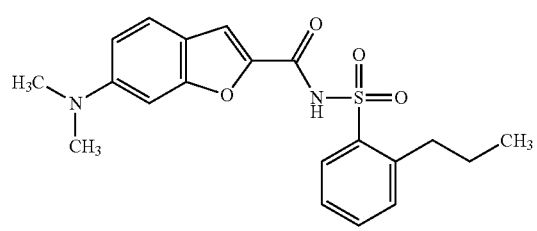 [SMILES: CCCc1ccccc1S(=O)(=O)NC(=O)c1cc2ccc(N(C)C)cc2o1]

According to GP5A, INT-11 (38.6 mg, 188 μmol), commercially available 2-propylbenzene-1-sulfonamide (CAS: 146533-54-2, 116 mg, 497 μmol), PyBOP (118 mg, 226 μmol) and DIPEA (130 μL, 750 μmol) were stirred at RT in DCM (930 µL) over night. After reaction completion, work-up and purification using HPLC (acid), the desired product was obtained as a yellow solid (53.6 mg, 70%). ¹H-NMR (400 MHz, DMSO-$d_6$) δ [ppm]: 0.903 (1.54), 0.921 (3.72), 0.939 (1.77), 1.528 (0.44), 1.547 (0.68), 1.567 (0.66), 1.586 (0.42), 2.518 (1.81), 2.522 (1.22), 2.969 (0.89), 2.984 (16.00), 3.008 (0.81), 6.761 (0.92), 6.765 (1.01), 6.847 (0.71), 6.853 (0.64), 6.870 (0.73), 6.875 (0.67), 7.435 (0.87), 7.438 (0.87), 7.453 (0.87), 7.556 (1.32), 7.578 (1.23), 7.615 (0.57), 7.864 (0.51), 8.020 (0.81), 8.022 (0.79), 8.040 (0.75), 8.044 (0.67); LC-MS (method 1): $R_t$=1.28 min; MS (ESIpos): m/z=386 [M+H]⁺.

Example 53

N-(4-Cyano-2-methoxybenzene-1-sulfonyl)-6-(dimethylamino)-1-benzofuran-2-carboxamide

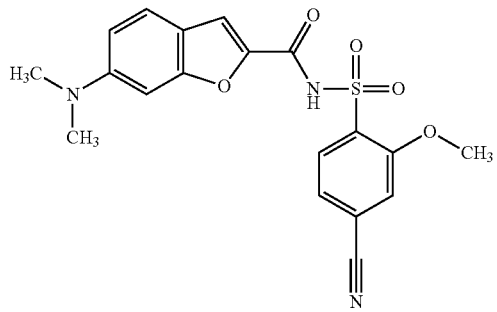

According to GP5B, INT-11 (100 mg, 487 µmol), commercially available 4-cyano-2-methoxybenzene-1-sulfonamide (CAS: 1261582-52-8, 114 mg, 536 µmol), CDI (93.2 mg, 575 µmol) and DBU (100 µL, 670 µmol) were stirred at RT in THF (2 mL) over night. After reaction completion, work-up and purification using HPLC (acid), the desired product was obtained as yellow crystals (111 mg, 57%). ¹H-NMR (400 MHz, DMSO-$d_6$) δ [ppm]: 1.137 (0.41), 1.229 (0.47), 2.083 (0.69), 2.518 (1.03), 2.522 (0.64), 2.985 (16.00), 3.928 (7.58), 6.769 (1.07), 6.774 (1.16), 6.849 (0.79), 6.855 (0.71), 6.872 (0.80), 6.877 (0.75), 7.556 (1.44), 7.578 (1.33), 7.616 (0.87), 7.619 (0.87), 7.636 (0.93), 7.639 (0.96), 7.778 (1.40), 7.780 (1.36), 7.908 (0.61), 8.046 (1.76), 8.066 (1.58); LC-MS (method 1): $R_t$=1.06 min; MS (ESIpos): m/z=400 [M+H]⁺.

Example 54

6-(Dimethylamino)-N-[2-(trifluoromethyl)benzene-1-sulfonyl]-1-benzofuran-2-carboxamide

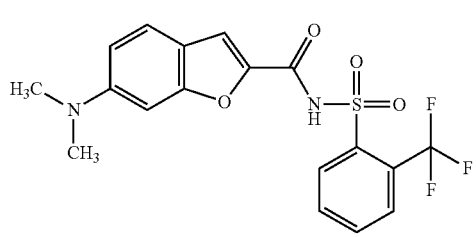 [SMILES: CN(C)c1ccc2cc(C(=O)NS(=O)(=O)c3ccccc3C(F)(F)F)oc2c1]

According to GP5A, INT-11 (100 mg, 487 µmol), commercially available 2-(trifluoromethyl)benzene-1-sulfonamide (CAS: 1869-24-5, 116 mg, 497 µmol), pyBOP (132 mg, 585 µmol) and DIPEA (340 µL, 1.9 mmol) were stirred at RT in DCM (2.4 mL) over night. After reaction completion, work-up and purification using HPLC (acid), the desired product was obtained as a yellow solid containing traces of ACN (66.3 mg, 30%). ¹H-NMR (400 MHz, DMSO-$d_6$) δ [ppm]: 2.074 (1.75), 2.518 (2.27), 2.523 (1.51), 2.540 (1.43), 2.987 (16.00), 6.776 (0.82), 6.851 (0.65), 6.856 (0.56), 6.873 (0.67), 6.879 (0.61), 7.557 (1.16), 7.579 (1.07), 7.957 (0.46), 7.991 (0.54), 8.354 (0.61), 8.373 (0.56); LC-MS (Method 5): $R_t$=1.11 min; MS (ESIpos): m/z=413 [M+H]⁺.

Example 55

N-[1-(2,4-Dichlorophenyl)ethanesulfonyl]-6-(dimethylamino)-1-benzofuran-2-carboxamide (rac)

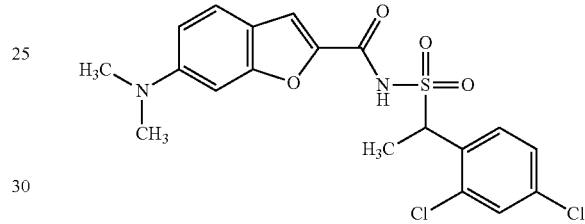

According to GP5B, INT-11 (100 mg, 487 µmol), commercially available 1-(2,4-dichlorophenyl)ethanesulfonamide (CAS: 1249874-04-1, 136 mg, 536 µmol), CDI (93.2 mg, 575 µmol) and DBU (100 µL, 670 µmol) were stirred at RT in THF (2 mL) for 1 h. After reaction completion and purification using HPLC (acid), the desired product was obtained as yellow crystals (137 mg, 61%). ¹H-NMR (400 MHz, DMSO-$d_6$) δ [ppm]: 1.698 (3.01), 1.717 (3.01), 2.073 (0.75), 2.083 (6.94), 2.518 (0.74), 2.522 (0.50), 3.003 (16.00), 5.474 (0.95), 5.492 (0.94), 6.825 (1.23), 6.861 (0.87), 6.867 (0.68), 6.883 (0.86), 6.889 (0.75), 7.528 (0.76), 7.533 (0.78), 7.549 (1.03), 7.554 (2.37), 7.576 (1.40), 7.686 (1.83), 7.692 (1.75), 7.711 (1.82), 7.733 (1.44), 7.787 (1.10); LC-MS (Method 1): $R_t$=1.35 min; MS (ESIneg): m/z=439 [M−H]⁻.

Example 56

N-[1-(2,6-Dichlorophenyl)ethanesulfonyl]-6-(dimethylamino)-1-benzofuran-2-carboxamide (rac)

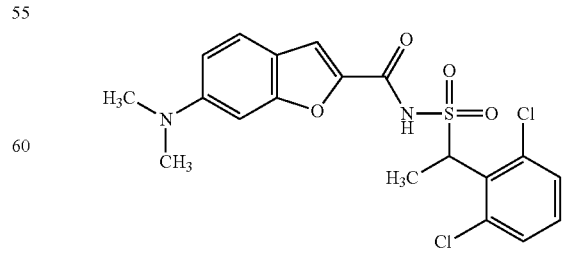

According to GP5B, INT-11 (100 mg, 487 µmol), commercially available 1-(2,6-dichlorophenyl)ethane-1-sulfonamide (CAS: 1249874-04-1, 136 mg, 536 µmol), CDI (93.2 mg, 575 µmol) and DBU (100 µL, 670 µmol) were stirred at RT in THF (2 mL) for 1 h. After reaction completion and purification using HPLC (acid), the desired product was obtained as yellow crystals (110 mg, 50%). $^1$H-NMR (400 MHz, DMSO-$d_6$) δ [ppm]: 1.938 (4.13), 1.956 (4.10), 2.084 (4.20), 2.518 (0.87), 2.523 (0.58), 3.008 (16.00), 5.885 (1.18), 5.903 (1.14), 6.834 (1.17), 6.866 (0.89), 6.872 (0.65), 6.889 (0.89), 6.894 (0.73), 7.392 (0.81), 7.412 (1.84), 7.432 (1.42), 7.516 (0.98), 7.520 (1.34), 7.537 (0.86), 7.540 (0.95), 7.543 (1.54), 7.546 (1.10), 7.563 (2.52), 7.585 (1.41), 7.838 (1.46); LC-MS (method 1): $R_t$=1.31 min; MS (ESIneg): m/z=439 [M–H]$^-$.

Example 57

N-(5-Bromo-2-ethoxybenzene-1-sulfonyl)-6-(dimethylamino)-1-benzofuran-2-carboxamide

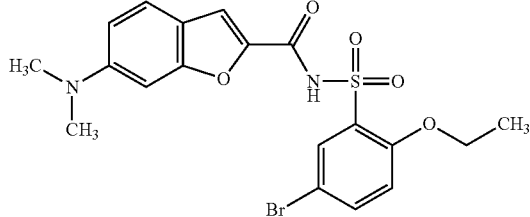 [SMILES: CCOc1ccc(Br)cc1S(=O)(=O)NC(=O)c1cc2ccc(N(C)C)cc2o1]

According to GP5B, INT-11 (100 mg, 487 µmol), commercially available 5-bromo-2-ethoxybenzene-1-sulfonamide (CAS: 327081-38-9, 150 mg, 536 µmol), CDI (93.2 mg, 575 µmol) and DBU (100 µL, 670 µmol) were stirred at RT in THF (2 mL) for 1 h. After reaction completion and purification using HPLC (acid), the desired product was obtained as light-yellow crystals (95 mg, 42%). $^1$H-NMR (400 MHz, DMSO-$d_6$) δ [ppm]: 1.206 (2.11), 1.224 (4.83), 1.241 (2.18), 2.084 (0.81), 2.518 (0.60), 2.523 (0.43), 2.986 (16.00), 4.139 (0.55), 4.156 (1.76), 4.174 (1.78), 4.191 (0.54), 6.767 (1.07), 6.772 (1.16), 6.848 (0.80), 6.854 (0.71), 6.870 (0.80), 6.876 (0.76), 7.203 (1.16), 7.226 (1.24), 7.562 (1.45), 7.584 (1.34), 7.810 (0.68), 7.816 (0.75), 7.832 (0.63), 7.838 (0.70), 7.940 (2.12), 7.946 (2.18), 7.952 (0.79); LC-MS (method 1): $R_t$=1.30 min; MS (ESIpos): m/z=467 [M+H]$^+$.

Example 58

6-(Dimethylamino)-N-(4-ethoxypyridine-3-sulfonyl)-1-benzofuran-2-carboxamide

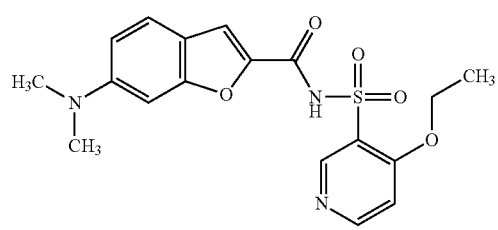 [SMILES: CCOc1ccncc1S(=O)(=O)NC(=O)c1cc2ccc(N(C)C)cc2o1]

According to GP5A, INT-11 (100 mg, 487 µmol), commercially 4-ethoxypyridine-3-sulfonamide (CAS: 1229666-

21-0, 118 mg, 585 µmol), PyBOP (304 mg, 585 µmol) and DIPEA (340 µL, 1.9 mmol) were stirred at RT in DCM (2.4 mL) for 20 h. After reaction completion, work-up and purification using HPLC (acid), the desired product was obtained as an ochre solid (55 mg, 28%). $^1$H-NMR (400 MHz, DMSO-$d_6$) δ [ppm]: 1.237 (2.18), 1.254 (5.03), 1.272 (2.22), 2.084 (0.42), 2.518 (2.64), 2.523 (1.84), 2.985 (16.00), 4.261 (0.51), 4.278 (1.61), 4.296 (1.64), 4.314 (0.50), 6.777 (1.03), 6.848 (0.69), 6.853 (0.62), 6.870 (0.73), 6.875 (0.66), 7.306 (0.58), 7.321 (0.58), 7.559 (1.21), 7.582 (1.14), 8.672 (0.52), 8.687 (0.50), 8.867 (0.91); LC-MS (method 9): $R_t$=0.77 min; MS (ESIneg): m/z=388 [M–H]$^-$.

Example 59

6-(Dimethylamino)-N-(2-hydroxybenzene-1-sulfonyl)-1-benzofuran-2-carboxamide

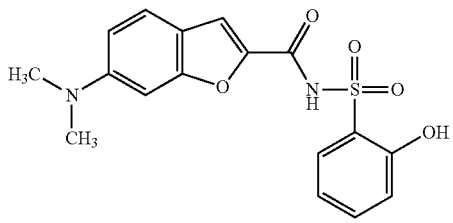 [SMILES: CN(C)c1ccc2cc(C(=O)NS(=O)(=O)c3ccccc3O)oc2c1]

According to GP5B, INT-11 (1.00 g, 4.87 mmol), commercially available 2-hydroxybenzene-1-sulfonamide (CAS: 3724-14-9, 928 mg, 5.36 mmol), CDI (1.03 g, 6.33 mmol) and DBU (1.0 mL, 6.7 mmol) were stirred at RT in THF (25 mL) for 1 h. After reaction completion and purification using HPLC (acid), the desired product was obtained as yellow-greenish crystals (1.20 g, 65%). $^1$H-NMR (400 MHz, DMSO-$d_6$) δ [ppm]: 2.981 (16.00), 3.368 (0.58), 5.759 (0.83), 6.777 (1.42), 6.840 (0.85), 6.846 (0.77), 6.862 (0.88), 6.868 (0.82), 6.941 (1.13), 6.961 (1.66), 6.978 (1.12), 6.997 (0.65), 7.459 (0.49), 7.463 (0.52), 7.481 (0.81), 7.498 (0.45), 7.502 (0.44), 7.550 (1.53), 7.572 (1.42), 7.790 (0.91), 7.794 (0.93), 7.810 (0.89), 7.814 (0.85), 7.917 (1.19); LC-MS (method 1): $R_t$=1.01 min; MS (ESIpos): m/z=361 [M+H]$^+$.

Example 60

Ethyl-4-{[6-(dimethylamino)-1-benzofuran-2-carbonyl]sulfamoyl}piperidine-1-carboxylate

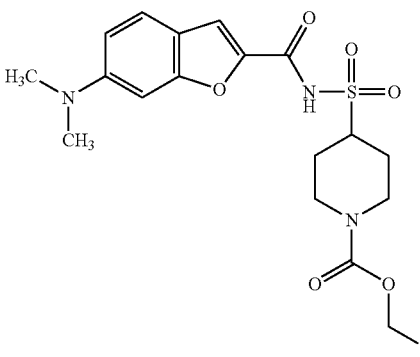

According to GP5B, INT-11 (100 mg, 487 μmol), commercially available ethyl 4-sulfamoylpiperidine-1-carboxylate (CAS: 1249785-27-0, 127 mg, 536 μmol), CDI (93.2 mg, 575 μmol) and DBU (100 μL, 670 μmol) were stirred at RT in THF (2 mL) for 1 h. After reaction completion and purification using HPLC (acid), the desired product was obtained as yellow crystals (93 mg, 42%). $^1$H-NMR (400 MHz, DMSO-d$_6$) δ [ppm]: 1.137 (0.56), 1.156 (2.69), 1.174 (5.79), 1.192 (2.74), 1.543 (0.51), 1.553 (0.54), 1.574 (0.57), 1.585 (0.52), 2.007 (0.52), 2.021 (0.68), 2.048 (0.61), 2.074 (0.79), 2.084 (14.22), 2.518 (1.18), 2.523 (0.78), 2.984 (0.92), 3.001 (16.00), 3.804 (0.42), 4.010 (0.71), 4.028 (2.15), 4.046 (2.38), 4.063 (1.00), 4.081 (0.44), 6.824 (1.27), 6.859 (0.89), 6.865 (0.68), 6.881 (0.87), 6.887 (0.74), 7.562 (1.50), 7.585 (1.38), 7.821 (1.03); LC-MS (method 1): R$_t$=1.09 min; MS (ESIneg): m/z=422 [M−H]$^-$.

Example 61

6-(Dimethylamino)-N-(ethanesulfonyl)-1-benzofuran-2-carboxamide

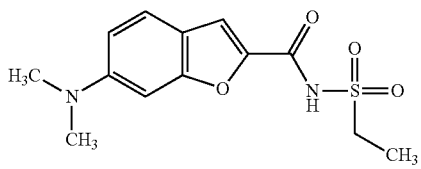 [SMILES: CCS(=O)(=O)NC(=O)c1cc2ccc(N(C)C)cc2o1]

According to GP5A, INT-11 (250 mg, 1.22 mmol), commercially ethanesulfonamide (CAS: 1520-70-3, 118 mg, 585 μmol), pyBOP (761 mg, 1.46 mmol) and DIPEA (850 μL, 4.9 mmol) were stirred at RT in DCM (7.5 mL) overnight. After reaction completion, work-up and purification using HPLC (acid), the desired product was obtained as a yellow solid (77 mg, 90%). $^1$H-NMR (400 MHz, DMSO-d$_6$) δ [ppm]: 1.236 (1.55), 1.254 (3.72), 1.272 (1.59), 1.728 (0.54), 2.518 (2.06), 2.523 (1.31), 3.001 (16.00), 3.015 (0.50), 3.474 (0.84), 3.492 (0.83), 6.825 (0.78), 6.830 (0.95), 6.858 (0.75), 6.863 (0.55), 6.880 (0.74), 6.886 (0.62), 7.560 (1.18), 7.582 (1.11), 7.820 (0.55); LC-MS (method 5): R$_t$=0.93 min; MS (ESIpos): m/z=297 [M+H]$^+$.

Example 62

N-([1,1'-Biphenyl]-2-sulfonyl)-6-(2-oxopyrrolidin-1-yl)-1-benzofuran-2-carboxamide

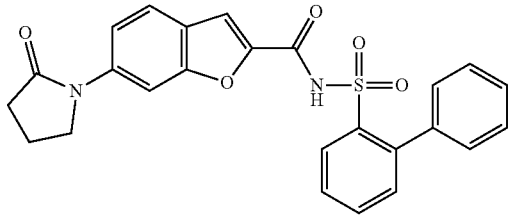 [SMILES: O=C(NS(=O)(=O)c1ccccc1-c1ccccc1)c1cc2ccc(N3CCCC3=O)cc2o1]

The aforementioned INT-28 (50.0 mg, 110 μmol) was suspended in toluene (1 mL) and commercially available pyrrolidin-2-one (CAS: 616-45-5, 18.7 mg, 219 μmol), commercially available N,N-dimethylethylendiamine (38.6 mg, 438 μmol), potassium carbonate (33.3 mg, 241 μmol) and copper iodide (4.17 mg, 21.9 μmol) were added. The reaction mixture was heated to 110° C. for 18 h. After reaction completion, work up and purification, the desired product (1.3 mg, 2%) was obtained as a brown solid. $^1$H-NMR (400 MHz, METHANOL-d$_4$) δ [ppm]: 0.100 (1.15), 0.903 (1.25), 1.290 (4.22), 2.036 (16.00), 2.207 (2.20), 2.226 (3.35), 2.245 (2.30), 2.263 (0.96), 2.636 (4.12), 2.657 (6.32), 2.660 (5.27), 2.677 (3.07), 3.133 (1.25), 3.482 (1.15), 3.999 (3.54), 4.017 (5.65), 4.034 (3.35), 7.196 (1.44), 7.214 (3.74), 7.233 (3.35), 7.269 (4.31), 7.286 (2.49), 7.305 (3.16), 7.324 (4.02), 7.409 (2.30), 7.605 (1.92), 7.609 (2.40), 7.626 (3.64), 7.631 (4.50), 7.649 (1.34), 7.680 (1.34), 7.700 (5.27), 7.722 (2.68), 7.964 (2.78), 8.273 (1.82), 8.291 (1.72); LC-MS (method 5): R$_t$=1.29 min; MS (ESIpos): m/z=460 [M+H]$^+$.

Example 63

6-(Dimethylamino)-N-(methanesulfonyl)-1-benzofuran-2-carboxamide

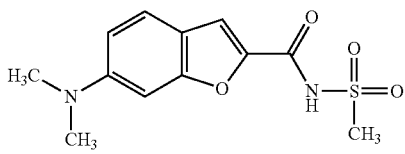 [SMILES: CN(C)c1ccc2cc(C(=O)NS(C)(=O)=O)oc2c1]

According to GP5A, INT-11 (100 mg, 487 μmol), commercially methanesulfonamide (CAS: 3144-09-0, 55.6 mg, 585 μmol), pyBOP (304 mg, 585 μmol) and DIPEA (340 μL, 1.9 mmol) were stirred at RT in DCM (3 mL) overnight. After reaction completion, work-up and purification using HPLC (acid), the desired product was obtained as a yellow solid (41 mg, 90%).

Example 64

N-([Biphenyl]-2-ylsulfonyl)-7-cyano-6-(dimethylamino)-1-benzofuran-2-carboxamide

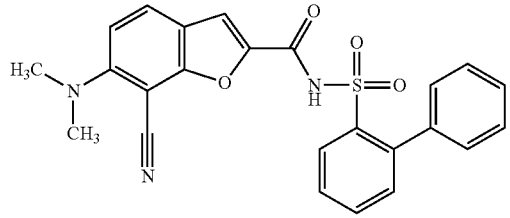 [SMILES: CN(C)c1ccc2cc(C(=O)NS(=O)(=O)c3ccccc3-c3ccccc3)oc2c1C#N]

Intermediate INT-20 (30.0 mg, 60 μmol), commercially available [Pd(cinnamyl)Cl]$_2$ (CAS: 12131-44-1, 1.6 mg, 3 μmol), commercially available 1,1'-bis(diphenylphosphino)ferrocene (CAS: 12150-46-8, 1.6 mg, 2.9 μmol), commercially available zinc cyanide (CAS: 557-21-1, 11.6 mg, 90 μmol) were placed in a 5 mL crimp sealable reaction vessel, sealed and flushed with argon. N,N-diisopropylethylamine (21 μL, 120 μmol) and degassed N,N-dimethylacetamide (0.5 mL) were added, and the mixture stirred for 14 h at 80° C. Saturated aqueous sodium bicarbonate solution was added, and the mixture extracted DCM (3 times). The combined organic layers were filtered using a water-repellent filter and concentrated in vacuum. The residue was purified by reverse phase HPLC, yielding the title compound (1 mg, 4% yield). $^1$H-NMR (400 MHz, ACETONITRILE-$d_3$) δ ppm 3.01 (s, 6H), 6.70-6.78 (m, 1H), 7.01-7.17 (m, 7H), 7.38-7.51 (m, 3H), 7.97-8.07 (m, 1H), 8.82 (br. S, 1H); LC-MS (Method 1): $R_t$=1.25 min; MS (ESIpos): m/z=432.4 [M+H]$^+$.

The following example compounds 65-109 were prepared (similarly to table 4) according to GP5A using INT-11 reacting with the commercially available sulphonamides.

TABLE 5 examples 65-109

| Example | Structure, IUPAC-Name and analytics |
|---|---|
| 65 | 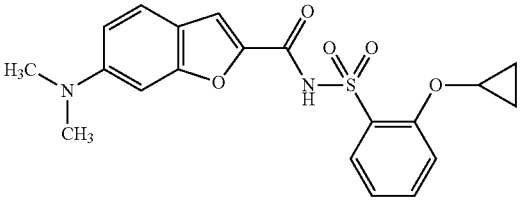 [SMILES: CN(C)c1ccc2cc(C(=O)NS(=O)(=O)c3ccccc3OC3CC3)oc2c1]<br>N-[2-(Cyclopropyloxy)benzene-1-sulfonyl]-6-(dimethylamino)-1-benzofuran-2-carboxamide<br>$^1$H-NMR (400 MHz, DMSO-$d_6$) δ [ppm]: 0.520 (0.80), 0.526 (1.27), 0.531 (0.80), 0.704 (0.97), 7.719 (0.78), 0.723 (0.86), 2.518 (1.82), 2.522 (1.25), 2.956 (0.49), 2.986 (16.00), 4.066 (0.40), 4.073 (0.55), 6.768 (0.97), 6.773 (1.04), 6.849 (0.76), 6.855 (0.65), 6.872 (0.76), 6.877 (0.70), 7.176 (0.77), 7.195 (0.44), 7.457 (0.69), 7.476 (0.85), 7.566 (1.30), 7.588 (1.20), 7.686 (0.50), 7.878 (0.83), 7.882 (0.80), 7.897 (0.82), 7.902 (0.73), 7.937 (0.64), 12.300 (0.50); LC-MS (Method 9): $R_6$ = 1.14 min; MS (ESIpos): m/z = 401 [M + H]$^+$. |
| 66 | 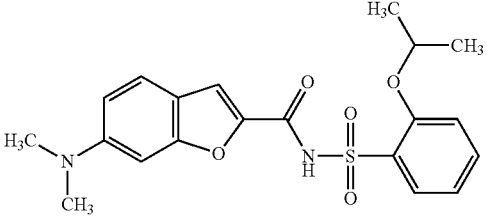 [SMILES: CC(C)Oc1ccccc1S(=O)(=O)NC(=O)c1cc2ccc(N(C)C)cc2o1]<br>6-(Dimethylamino)-N-{2-[(propan-2-yl)oxy]benzene-1-sulfonyl}-1-benzofuran-2-carboxamide<br>$^1$H-NMR (400 MHz, DMSO-$d_6$) δ [ppm]: 1.168 (8.46), 1.183 (8.71), 2.979 (16.00), 4.779 (0.50), 4.794 (0.68), 4.809 (0.50), 6.768 (1.07), 6.773 (1.15), 6.842 (0.85), 6.848 (0.71), 6.864 (0.86), 6.870 (0.78), 7.079 (0.51), 7.080 (0.54), 7.099 (1.04), 7.177 (0.56), 7.216 (0.92), 7.237 (1.00), 7.562 (1.54), 7.585 (1.44), 7.595 (0.50), 7.599 (0.51), 7.613 (0.56), 7.617 (0.69), 7.620 (0.53), 7.634 (0.41), 7.887 (0.97), 7.892 (0.94), 7.907 (0.96), 7.911 (0.86), 7.978 (1.85), 12.223 (0.83); LC-MS (method 9): $R_t$ = 1.18 min; MS (ESIpos): m/z = 403 [M + H]$^+$. |
| 67 | 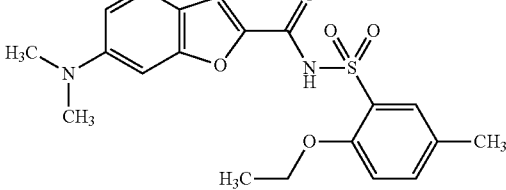<br>6-(Dimethylamino)-N-(2-ethoxy-5-methylbenzene-1-sulfonyl)-1-benzofuran-2-carboxamide<br>$^1$H-NMR (400 MHz, DMSO-$d_6$) δ [ppm]: 1.198 (2.21), 1.215 (5.13), 1.233 (2.24), 2.328 (5.60), 2.983 (16.00), 3.340 (0.77), 4.080 (0.58), 4.097 (1.87), 4.114 (1.82), 4.132 (0.55), 6.770 (1.01), 6.775 (1.07), 6.845 (0.80), 6.851 (0.69), 6.868 (0.83), 6.873 (0.73), 7.092 (1.04), 7.113 (1.14), 7.422 (0.52), 7.427 (0.54), 7.444 (0.47), 7.449 (0.46), 7.559 (1.50), 7.581 (1.38), 7.701 (1.12), 7.706 (1.02), 7.956 (0.75), 12.281 (0.55); LC-MS (Method 9): $R_t$ = 0.65 min; MS (ESIpos): m/z = 403 [M + H]$^+$. |

TABLE 5-continued examples 65-109

| Example | Structure, IUPAC-Name and analytics |
|---|---|
| 68 | 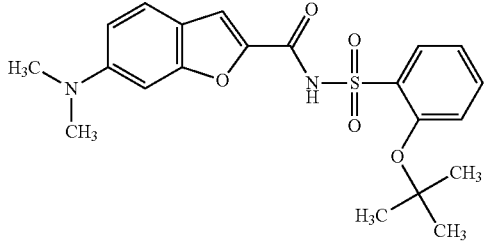 [SMILES: CN(C)c1ccc2cc(C(=O)NS(=O)(=O)c3ccccc3OC(C)(C)C)oc2c1] N-(2-tert-butoxybenzene-1-sulfonyl)-6-(dimethylamino)-1-benzofuran-2-carboxamide<br>$^1$H-NMR (400 MHz, DMSO-$d_6$) δ [ppm]: 1.394 (0.49), 1.424 (16.00), 2.984 (9.93), 6.769 (0.62), 6.774 (0.66), 6.848 (0.51), 6.854 (0.43), 6.870 (0.52), 6.876 (0.47), 7.139 (0.59), 7.328 (0.53), 7.330 (0.54), 7.349 (0.64), 7.351 (0.61), 7.566 (0.97), 7.572 (0.41), 7.576 (0.46), 7.588 (0.89), 7.901 (0.60), 7.906 (0.61), 7.921 (1.60), 7.25 (0.65); LC-MS (Method 9): $R_t$ = 1.25 min; MS (ESIneg): m/z = 415 [M − H]$^-$. |
| 69 | 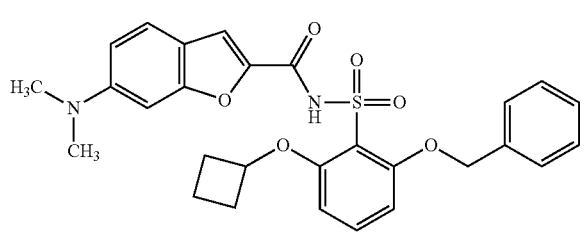 [SMILES: CN(C)c1ccc2cc(C(=O)NS(=O)(=O)c3c(OCc4ccccc4)cccc3OC3CCC3)oc2c1] N-[2-(Benzyloxy)-6-(cycolbutyloxy)benzene-1-sulfonyl]-6-(dimethylamino)-1-benzofuran-2-carboxamide<br>$^1$H-NMR (400 MHz, DMSO-$d_6$) δ [ppm]: 1.429 (0.44), 1.438 (0.52), 1.453 (0.56), 1.934 (0.47), 1.952 (0.44), 1.958 (0.66), 1.965 (0.49), 1.983 (0.50), 2.206 (0.54), 2.213 (0.48), 2.223 (0.48), 2.230 (0.46), 2.520 (1.83), 2.524 (1.22), 2.542 (1.07), 2.676 (0.40), 2.997 (16.00), 4.724 (0.58), 5.253 (2.64), 6.546 (0.82), 6.567 (0.85), 6.802 (1.10), 6.807 (1.29), 6.818 (0.80), 6.839 (0.83), 6.853 (0.73), 6.858 (0.60), 6.875 (0.73), 6.880 (0.64), 7.279 (0.88), 7.293 (0.52), 7.296 (0.91), 7.300 (0.51), 7.313 (1.43), 7.316 (0.69), 7.327 (0.87), 7.331 (1.89), 7.349 (0.75), 7.353 (0.52), 7.405 (0.47), 7.425 (0.85), 7.446 (0.45), 7.512 (1.41), 7.529 (1.20), 7.568 (1.12), 7.590 (1.02), 7.918 (1.29), 12.113 (1.48); LC-MS (Method 4): $R_t$ = 1.37 min; MS (ESIpos): m/z = 521 [M + H]$^+$. |
| 70 | 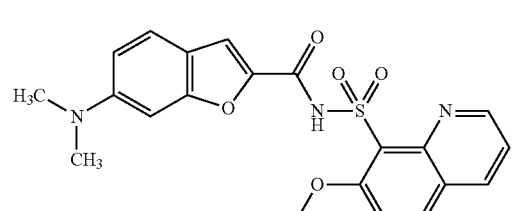 6-(Dimethylamino)-N-(7-methoxyquinoline-8-sulfonyl)-1-benzofuran-2-carboxamide<br>$^1$H-NMR (400 MHz, DMSO-$d_6$) δ [ppm]: −0.009 (0.59), 0.008 (0.72), 2.338 (0.42), 2.520 (5.08), 2.524 (3.35), 2.680 (0.42), 2.968 (16.00), 2.986 (0.55), 4.030 (2.17), 6.772 (1.31), 6.818 (0.53), 6.840 (0.57), 7.515 (0.68), 7.536 (0.66); LC-MS (method 4): $R_t$ = 1.30 min; MS (ESIpos): m/z = 426 [M + H]+. |

TABLE 5-continued examples 65-109

| Example | Structure, IUPAC-Name and analytics |
|---|---|
| 71 | 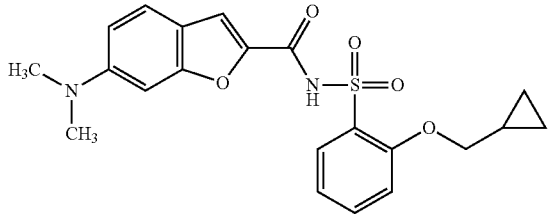 [SMILES: CN(C)c1ccc2cc(C(=O)NS(=O)(=O)c3ccccc3OCC3CC3)oc2c1]<br>N-[2-(Cyclopropylmethoxy)benzene-1-sulfonyl]-6-(dimethylamino)-1-benzofuran-2-carboxamide<br>$^1$H-NMR (400 MHz, DMSO-d$_6$) δ [ppm]: 0.158 (1.27), 1.62 (1.06), 0.170 (1.16), 0.174 (1.19), 0.184 (0.41), 0.311 (0.43), 0.321 (1.02), 0.326 (1.05), 0.331 (0.55), 0.341 (1.07), 0.346 (1.01), 1.199 (0.41), 2.980 (16.00), 3.963 (2.19), 3.980 (2.15), 6.766 (1.04), 6.771 (1.13), 6.841 (0.83), 6.847 (0.71), 6.863 (0.83), 6.869 (0.77), 7.101 (0.50), 7.103 (0.52), 7.122 (1.00), 7.140 (0.55), 7.142 (0.56), 7.207 (0.89), 7.228 (0.98), 7.554 (1.54), 7.576 (1.43), 7.600 (0.48), 7.605 (0.51), 7.619 (0.54), 7.623 (0.66), 7.626 (0.55), 7.897 (0.98), 7.902 (0.96), 7.917 (0.95), 7.921 (0.87), 7.960 (1.77), 12.301 (0.56); LC-MS (Method 9): R$_t$ = 1.20 min; MS (ESIpos): m/z = 415 [M + H]$^+$ |
| 72 | 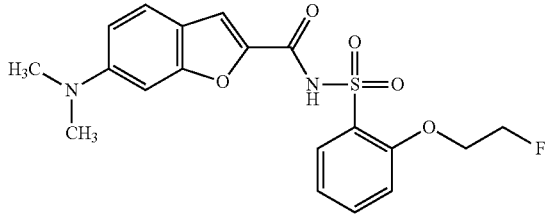 [SMILES: CN(C)c1ccc2cc(C(=O)NS(=O)(=O)c3ccccc3OCCF)oc2c1]<br>6-(Dimethylamino)-N-[2-(2-fluoroethoxy)benzene-1-sulfonyl]-1-benzofuran-2-carboxamide<br>$^1$H-NMR (400 MHz, DMSO-d$_6$) δ [ppm]: 2.518 (0.40), 2.978 (16.00), 4.333 (0.48), 4.343 (0.56), 4.352 (0.58), 4.409 (0.50), 4.418 (0.55), 4.428 (0.55), 4.677 (0.62), 4.683 (0.43), 4.686 (0.55), 4.696 (0.51), 4.796 (0.60), 4.802 (0.42), 4.805 (0.55), 4.815 (0.53), 6.762 (0.90), 6.767 (0.99), 6.838 (0.79), 6.843 (0.67), 6.860 (0.83), 6.866 (0.73), 7.155 (0.46), 7.157 (0.52), 7.175 (0.88), 7.193 (0.55), 7.195 (0.52), 7.247 (0.79), 7.266 (0.90), 7.545 (1.46), 7.567 (1.35), 7.639 (0.47), 7.643 (0.50), 7.657 (0.52), 7.660 (0.58), 7.661 (0.59), 7.664 (0.52), 7.918 (1.01), 7.922 (1.05), 7.931 (1.37), 7.938 (1.13), 7.942 (0.93), 12.371 (0.43); LC-MS (Method 9); R$_t$ = 1.06 min; MS (ESIpos): m/z = 407 [M + H]$^+$. |
| 73 | 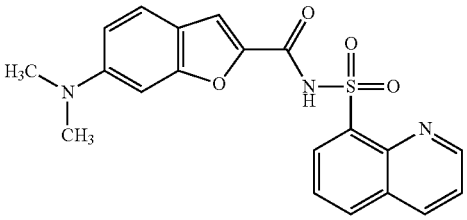<br>6-(Dimethylamino)-N-(quinoline-8-sulfonyl)-1-benzofuran-2-carboxamide<br>$^1$H-NMR (400 MHz, DMSO-d$_6$) δ [ppm]: 2.077 (2.96), 2.521 (1.11), 2.526 (0.81), 2.962 (16.00), 6.718 (0.91), 6.723 (0.98), 6.828 (0.74), 6.833 (0.68), 6.851 (0.76), 6.856 (0.70), 7.546 (1.36), 7.569 (1.25), 7.659 (0.77), 7.669 (0.77), 7.680 (0.76), 7.690 (0.78), 7.828 (0.71), 7.848 (0.97), 7.867 (0.74), 7.992 (0.65), 8.367 (0.63), 8.370 (0.68), 8.388 (0.61), 8.391 (0.60), 8.525 (0.88), 8.529 (0.87), 8.544 (1.21), 8.546 (1.25), 8.562 (0.72), 8.567 (0.69), 9.040 (0.91), 9.045 (0.94), 9.051 (0.90), 9.055 (0.82); LC-MS (method 4): R$_t$ = 0.93 min; MS (ESIpos): m/z = 393 [M + H]$^+$. |

TABLE 5-continued examples 65-109

| Example | Structure, IUPAC-Name and analytics |
|---|---|
| 74 | 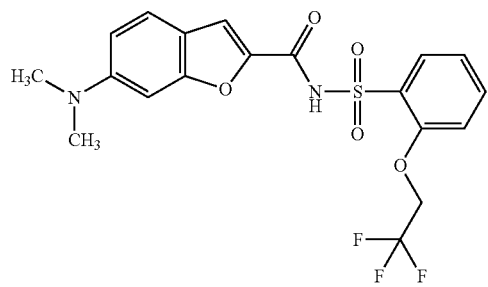 [SMILES: CN(C)c1ccc2cc(C(=O)NS(=O)(=O)c3ccccc3OCC(F)(F)F)oc2c1]

6-(Dimethylamino)-N-[2-(2,2,2-trifluoroethoxy)benzene-1-sulfonyl]-1-benzofuran-2-carboxamide
$^1$H-NMR (400 MHz, DMSO-d$_6$) δ [ppm]: 2.979 (16.00), 4.897 (0.56), 4.920 (1.63), 4.941 (1.53), 4.963 (0.48), 6.762 (1.07), 6.766 (1.16), 6.840 (0.84), 6.846 (0.71), 6.862 (0.86), 6.868 (0.78), 7.244 (0.51), 7.246 (0.53), 7.263 (1.05), 7.282 (0.60), 7.284 (0.58), 7.343 (0.90), 7.363 (1.01), 7.555 (1.57), 7.577 (1.44), 7.690 (0.50), 7.694 (0.53), 7.709 (0.58), 7.711 (0.68), 7.715 (0.57), 7.730 (0.41), 7.913 (1.88), 7.964 (1.00), 7.968 (0.97), 7.983 (0.97), 7.988 (0.88); LC-MS (Method 9:): R$_t$ = 1.15 min; MS (ESIpos): m/z = 443 [M + H]$^+$. |
| 75 | 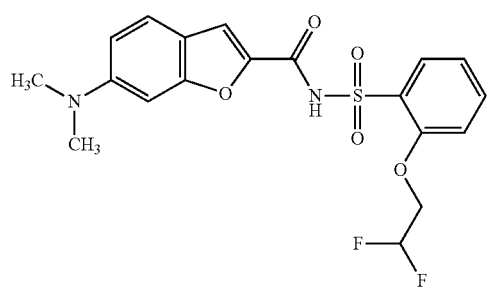 [SMILES: CN(C)c1ccc2cc(C(=O)NS(=O)(=O)c3ccccc3OCC(F)F)oc2c1]

N-[2-(2,2-Difluoroethoxy)benzene-1-sulfonyl]-6-(dimethylamino)-1-benzofuran-2-carboxamide
$^1$H-NMR (400 MHz, DMSO-d$_6$) δ [ppm]: 2.980 (16.00), 4.434 (0.52), 4.44 (0.54), 4.470 (1.07), 4.479 (1.07), 4.505 (0.52), 4.514 (0.47), 6.380 (0.71), 6.763 (1.03), 6.768 (1.17), 6.842 (0.82), 6.848 (0.75), 6.865 (0.83), 6.870 (0.81), 7.204 (0.50), 7.206 (0.52), 7.224 (0.99), 7.242 (0.56), 7.244 (0.55), 7.306 (0.91), 7.327 (1.03), 7.556 (1.55), 7.578 (1.43), 7.662 (0.48), 7.666 (0.50), 7.681 (0.57), 7.685 (0.66), 7.687 (0.58), 7.702 (0.41), 7.706 (0.43), 7.908 (1.90), 7.936 (1.02), 7.941 (1.04), 7.956 (0.91), 7.961 (0.86); LC-MS (Method 9): R$_t$ = 1.10 min; MS (ESIpos): m/z = 425 [M + H]$^+$. |
| 76 | 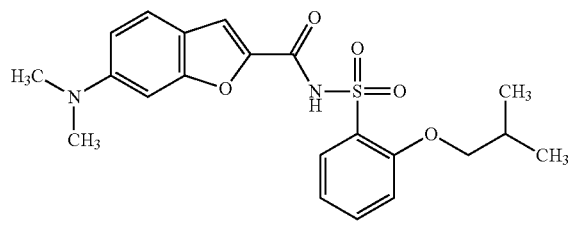 [SMILES: CC(C)COc1ccccc1S(=O)(=O)NC(=O)c1cc2ccc(N(C)C)cc2o1]

6-(Dimethylamino)-N-[2-(2-methylpropoxy)benzene-1-sulfonyl]-1-benzofuran-2-carboxamide
$^1$H-NMR (400 MHz, DMSO-d6) δ [ppm]: 0.906 (7.56), 0.922 (8.11), 2.071 (0.49), 2.979 (16.00), 3.855 (1.91), 3.872 (1.89), 6.756 (0.93), 6.761 (1.02), 6.838 (0.82), 6.843 (0.70), 6.860 (0.84), 6.865 (0.77), 7.103 (0.47), 7.105 (0.53), 7.123 (0.93), 7.141 (0.55), 7.143 (0.53), 7.190 (0.78), 7.209 (0.88), 7.550 (1.51), 7.572 (1.39), 7.610 (0.49), 7.614 (0.51), 7.628 (0.54), 7.630 (0.59), 7.632 (0.61), 7.635 (0.53), 7.905 (1.05), 7.909 (1.30), 7.913 (1.66), 7.925 (0.97), 7.929 (0.87), 12.282 (0.42); LC-MS (Method 9): R$_t$ = 1.28 min; MS (ESIpos): m/z = 417 [M + H]$^+$. |

TABLE 5-continued examples 65-109

| Example | Structure, IUPAC-Name and analytics |
|---|---|
| 77 | 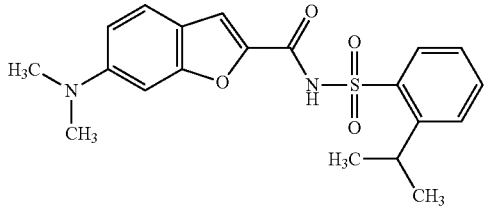 [SMILES: CC(C)c1ccccc1S(=O)(=O)NC(=O)c1cc2ccc(N(C)C)cc2o1]<br>6-(Dimethylamino)-N-[2-(propan-2-yl)benzene-1-sulfonyl]-1-benzofuran-2-carboxamide<br>$^1$H-NMR (400 MHz, DMSO-$d_6$) δ [ppm]: 1.148 (5.81), 1.165 (5.84), 2.074 (0.79), 2.979 (16.00), 3.945 (0.51), 6.763 (0.92), 6.767 (1.01), 6.846 (0.83), 6.852 (0.72), 6.868 (0.84), 6.873 (0.79), 7.410 (0.41), 7.414 (0.45), 7.428 (0.54), 7.431 (0.58), 7.434 (0.58), 7.448 (0.51), 7.452 (0.53), 7.554 (1.54), 7.576 (1.42), 7.599 (0.41), 7.603 (0.49), 7.619 (1.04), 7.623 (0.91), 7.642 (0.61), 7.645 (0.63), 7.660 (0.60), 7.662 (0.65), 7.886 (1.75), 7.887 (1.75), 8.012 (0.89), 8.015 (0.89), 8.031 (0.87), 8.034 (0.80); LC-MS (Method 9): $R_t$ = 1.22 min; MS (ESIpos): m/z = 387 [M + H]$^+$ |
| 78 | 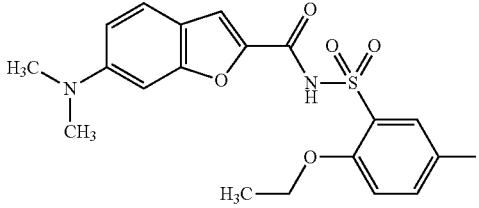<br>6-(Dimethylamino)-N-(2-ethoxy-5-iodobenzene-1-sulfonyl)-1-benzofuran-2-carboxamide<br>$^1$H-NMR (400 MHz, DMSO-$d_6$) δ [ppm]: 1.198 (2.13), 1.215 (5.04), 1.233 (2.18), 2.982 (16.00), 4.121 (0.58), 4.138 (1.91), 4.156 (1.91), 4.173 (0.56), 6.764 (1.07), 6.768 (1.15), 6.845 (0.86), 6.851 (0.73), 6.867 (0.87), 6.873 (0.80), 7.057 (1.38), 7.079 (1.46), 7.560 (1.59), 7.582 (1.46), 7.928 (0.97), 7.933 (1.03), 7.949 (0.95), 7.955 (1.16), 7.961 (1.92), 8.075 (2.41), 8.081 (2.23); LC-MS (Method 9): $R_t$ = 1.26 min; MS (ESIpos): m/z = 515 [M + H]$^+$. |
| 79 | 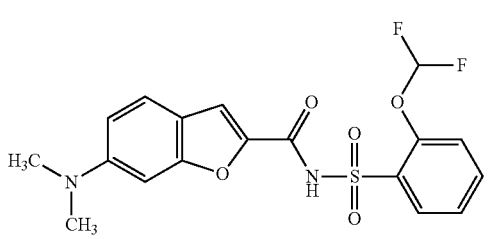 [SMILES: CN(C)c1ccc2cc(C(=O)NS(=O)(=O)c3ccccc3OC(F)F)oc2c1]<br>N-[2-(Difluoromethoxy)benzene-1-sulfonyl]-6-(dimethylamino)-1-benzofuran-2-carboxamide<br>$^1$H-NMR (400 MHz, DMSO-$d_6$) δ [ppm]: 2.984 (16.00), 6.767 (1.01), 6.772 (1.08), 6.849 (0.81), 6.855 (0.71), 6.872 (0.81), 6.877 (0.76), 7.182 (0.76), 7.363 (1.59), 7.403 (0.76), 7.422 (0.82), 7.457 (0.50), 7.460 (0.52), 7.477 (0.96), 7.496 (0.59), 7.498 (0.57), 7.544 (0.78), 7.562 (1.58), 7.585 (1.44), 7.755 (0.48), 7.759 (0.52), 7.776 (0.63), 7.778 (0.63), 7.923 (1.66), 8.056 (0.94), 8.060 (0.95), 8.076 (0.90), 8.080 (0.89), 8.135 (0.48); LC-MS (Method 9): $R_t$ = 1.08 min; MS (ESIpos): m/z = 411 [M + H]$^+$. |
| 80 | 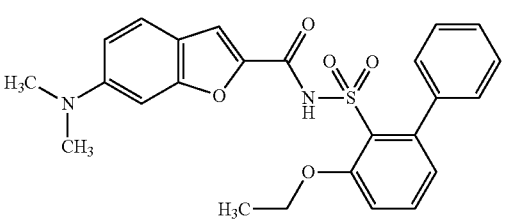 [SMILES: CCOc1cccc(-c2ccccc2)c1S(=O)(=O)NC(=O)c1cc2ccc(N(C)C)cc2o1] |

TABLE 5-continued examples 65-109

| Example | Structure, IUPAC-Name and analytics |
|---|---|
| | 6-(Dimethylamino)-N-(3-ethoxy[1,1'-biphenyl]-2-sulfonyl)-1-benzofuran-2-carboxamide<br>$^1$H-NMR (400 MHz, DMSO-$d_6$) δ [ppm]: 1.206 (2.19), 1.224 (4.96), 1.241 (2.27), 2.518 (1.85), 2.523 (1.22), 2.988 (16.00), 4.149 (0.44), 4.166 (1.37), 4.184 (1.35), 4.201 (0.43), 6.762 (1.09), 6.767 (1.20), 6.821 (0.78), 6.840 (0.84), 6.846 (0.81), 6.852 (0.67), 6.868 (0.74), 6.873 (0.68), 7.221 (0.67), 7.242 (0.74), 7.309 (0.45), 7.321 (0.64), 7.329 (0.73), 7.348 (5.26), 7.359 (2.26), 7.552 (1.67), 7.573 (1.83), 7.593 (0.43), 7.915 (1.23), 12.022 (1.33); LC-MS (Method 9): $R_t$ = 1.30 min; MS (ESIpos): m/z = 465 [M + H]$^+$. |
| 81 | 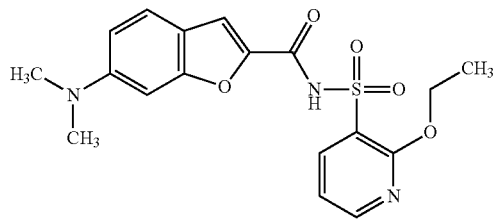<br>6-(Dimethylamino)-N-(2-ethoxypyridine-3-sulfonyl)-1-benzofuran-2-carboxamide<br>$^1$H-NMR (400 MHz, DMSO-$d_6$) δ [ppm]: 1.180 (2.49), 1.197 (5.97), 1.215 (2.61), 2.518 (0.68), 2.523 (0.47), 2.985 (16.00), 4.413 (0.69), 4.431 (2.33), 4.449 (2.20), 4.466 (0.67), 6.769 (0.89), 6.774 (0.97), 6.850 (0.75), 6.855 (0.66), 6.872 (0.77), 6.877 (0.69), 7.219 (0.86), 7.231 (0.87), 7.238 (0.89), 7.251 (0.83), 7.565 (1.40), 7.587 (1.29), 7.964 (0.67), 8.296 (0.88), 8.300 (0.97), 8.315 (0.88), 8.320 (0.84), 8.437 (0.83), 8.441 (0.79), 8.449 (0.81), 8.454 (0.72); LC-MS (method 4): $R_t$ = 1.09 min; MS (ESIpos): m/z = 390 [M + H]$^+$ |
| 82 | 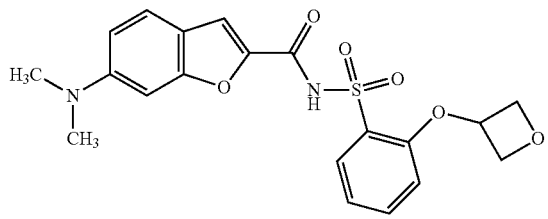 [SMILES: CN(C)c1ccc2cc(C(=O)NS(=O)(=O)c3ccccc3OC3COC3)oc2c1]<br>6-(Dimethylamino)-N-{2-[(oxetan-3-yl)oxy]benzene-1-sulfonyl}-1-benzofuran-2-carboxamide<br>$^1$H-NMR (400 MHz, DMSO-$d_6$) δ [ppm]: 2.074 (3.02), 2.518 (0.50), 2.982 (16.00), 4.561 (0.95), 4.574 (1.07), 4.580 (1.15), 4.593 (1.10), 4.800 (1.04), 4.817 (1.63), 4.834 (0.94), 5.410 (0.44), 5.423 (0.71), 5.438 (0.41), 6.770 (1.06), 6.774 (1.14), 6.843 (1.72), 6.849 (0.78), 6.865 (1.39), 6.871 (0.79), 7.174 (0.50), 7.176 (0.52), 7.194 (1.01), 7.212 (0.58), 7.214 (0.55), 7.554 (1.53), 7.576 (1.41), 7.594 (0.45), 7.598 (0.48), 7.613 (0.58), 7.615 (0.64), 7.617 (0.65), 7.634 (0.41), 7.938 (0.94), 7.942 (0.99), 7.958 (1.11), 7.964 (1.69), 12.481 (0.43); LC-MS (Method 9): $R_t$ = 0.99 min; MS (ESIpos): m/z = 417 [M + H]$^+$ |
| 83 | 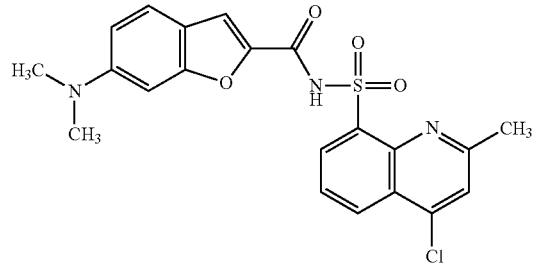<br>N-(4-Chloro-2-methylquinoline-8-sulfonyl)-6-(dimethylamino)-1-benzofuran-2-carboxamide<br>$^1$H-NMR (400 MHz, DMSO-$d_6$) δ [ppm]: 2.330 (0.43), 2.521 (1.54), 2.526 (1.03), 2.542 (0.44), 2.675 (7.96), 2.966 (16.00), 6.723 (0.96), 6.728 (1.04), 6.833 (0.76), 6.839 (0.70), 6.856 (0.80), 6.862 (0.73), |

TABLE 5-continued examples 65-109

| Example | Structure, IUPAC-Name and analytics |
|---|---|
| | 7.557 (1.42), 7.579 (1.32), 7.798 (3.37), 7.876 (0.71), 7.897 (0.93), 7.916 (0.77), 8.039 (0.60), 8.490 (0.77), 8.493 (0.87), 8.511 (0.74), 8.514 (0.75), 8.560 (0.95), 8.563 (0.91), 8.578 (0.89), 8.582 (0.79); LC-MS (method 4): $R_t$ = 1.28 min; MS (ESIpos): m/z = 444 [M + H]$^+$. |
| 84 | 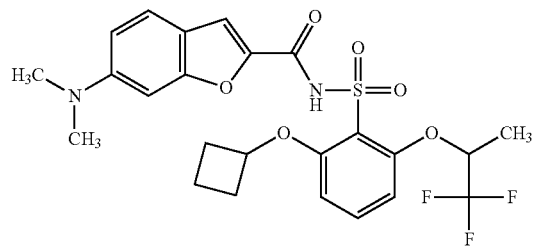 [SMILES: CC(Oc1cccc(OC2CCC2)c1S(=O)(=O)NC(=O)c1cc2ccc(N(C)C)cc2o1)C(F)(F)F] N-[2-(Cyclobutyloxy)-6-{[(2S)-1,1,1-trifluoropropan-2-yl]oxy}benzene-1-sulfonyl]-6-(dimethylamino)-1-benzofuran-2-carboxamide (rac) $^1$H-NMR (400 MHz, DMSO-d$_6$) δ [ppm]: 1.389 (0.46), 1.413 (3.28), 1.428 (2.97), 1.444 (0.54), 2.216 (0.41), 2.334 (0.55), 2.520 (2.61), 2.525 (1.68), 2.676 (0.56), 2.993 (16.00), 4.739 (0.56), 5.361 (0.41), 5.378 (0.53), 6.641 (0.89), 6.662 (0.92), 6.794 (1.11), 6.798 (1.25), 6.850 (0.77), 6.856 (0.65), 6.873 (0.78), 6.878 (0.68), 6.959 (0.68), 6.981 (0.74), 7.468 (0.49), 7.489 (0.87), 7.510 (0.42), 7.572 (1.21), 7.594 (1.10), 7.942 (1.43), 12.122 (1.43); LC-MS (Method 9): $R_t$ = 1.34 min; MS (ESIpos): m/z = 527 [M + H]$^+$. |
| 85 | 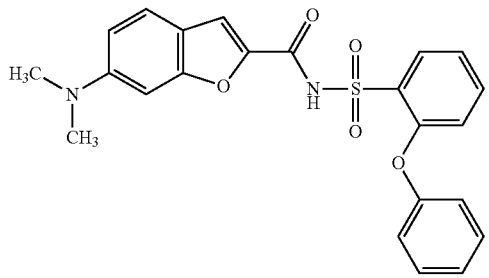 [SMILES: CN(C)c1ccc2cc(C(=O)NS(=O)(=O)c3ccccc3Oc3ccccc3)oc2c1] 6-(Dimethylamino)-N-(2-phenoxybenzene-1-sulfonyl)-1-benzofuran-2-carboxamide $^1$H-NMR (400 MHz, DMSO-d$_6$) δ [ppm]: 2.518 (0.43), 2.986 (16.00), 3.005 (1.11), 3.348 (0.69), 6.767 (1.00), 6.772 (1.09), 6.835 (0.86), 6.841 (0.75), 6.857 (0.83), 6.863 (0.75), 6.888 (0.95), 6.890 (0.98), 6.909 (1.00), 6.911 (1.01), 6.934 (1.37), 6.936 (1.57), 6.939 (0.86), 6.950 (0.50), 6.956 (1.80), 6.958 (1.44), 7.093 (0.48), 7.112 (1.03), 7.127 (0.42), 7.131 (0.63), 7.304 (1.41), 7.308 (0.50), 7.323 (1.95), 7.325 (2.03), 7.339 (0.53), 7.344 (1.88), 7.362 (0.53), 7.363 (0.51), 7.514 (1.48), 7.536 (1.36), 7.621 (0.44), 7.624 (0.44), 7.641 (0.60), 7.645 (0.55), 7.813 (0.84), 8.038 (0.92), 8.042 (0.89), 8.057 (0.92), 8.062 (0.81); LC-MS (Method 9): $R_t$ = 1.25 min; MS (ESIpos): m/z = 437 [M + H]$^+$. |
| 86 | 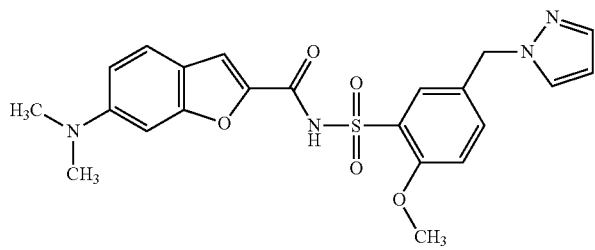 [SMILES: COc1ccc(Cn2cccn2)cc1S(=O)(=O)NC(=O)c1cc2ccc(N(C)C)cc2o1] 6-(Dimethylamino)-N-{2-methoxy-5-[(1H-pyrazol-1-yl)methyl]benzene-1-sulfonyl}-1-benzofuran-2-carboxamide $^1$H-NMR (400 MHz, DMSO-d$_6$) δ [ppm]: 1.214 (0.46), 1.232 (0.47), 2.518 (0.42), 2.540 (0.42), 2.964 (1.22), 2.982 (16.00), 3.344 (1.34), 5.378 (4.05), 6.273 (1.18), 6.279 (1.95), 6.284 (1.23), 6.764 (1.08), 6.769 (1.16), 6.845 (0.87), 6.850 (0.73), 6.866 (0.88), 6.872 (0.80), |

TABLE 5-continued examples 65-109

| Example | Structure, IUPAC-Name and analytics |
| --- | --- |

7.193 (1.27), 7.215 (1.46), 7.473 (1.37), 7.477 (1.40), 7.512 (0.76),
7.518 (0.76), 7.533 (0.66), 7.539 (0.68), 7.553 (1.64), 7.575 (1.50),
7.842 (1.55), 7.848 (1.54), 7.853 (1.50), 7.858 (1.45), 7.932 (1.64);
LC-MS (Method 9): $R_t$ = 1.03 min; MS (ESIpos): m/z = 455 [M + H]$^+$.

87

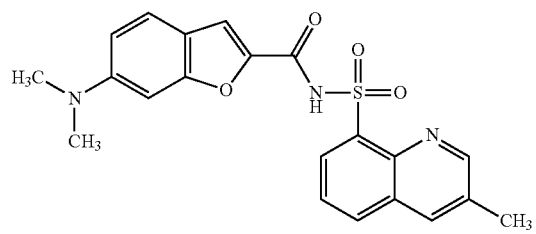

6-(Dimethylamino)-N-(3-methylquinoline-8-sulfonyl)-1-
benzofuran-2-carboxamide $^1$H-NMR (400 MHz, METHANOL-d$_4$) δ [ppm]: 2.522 (4.68), 2.660
(1.63), 3.017 (0.75), 3.032 (16.00), 6.814 (0.97), 6.844 (0.75), 6.849
(0.57), 6.865 (0.75), 6.871 (0.66), 7.451 (1.23), 7.473 (1.16), 7.494
(1.23), 7.716 (0.57), 7.735 (0.85), 7.754 (0.63), 8.164 (0.57), 8.185
(0.57), 8.197 (0.85), 8.515 (0.72), 8.518 (0.75), 8.533 (0.72), 8.536
(0.69), 8.892 (1.07), 8.898 (1.04); LC-MS (Method 1): $R_t$ = 1.14 min;
MS (ESIpos): m/z = 410 [M + H]$^+$

88

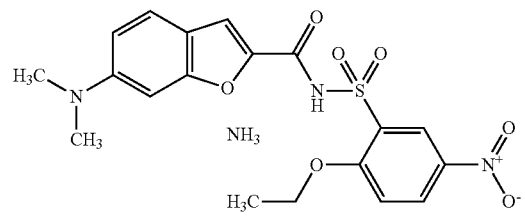

6-(Dimethylamino)-N-(2-ethoxy-5-nitrobenzene-1-sulfonyl)-1-
benzofuran-2-carboxamide $^1$H-NMR (400 MHz, DMSO-d$_6$) δ [ppm]: 1.238 (1.78), 1.256 (3.77),
1.273 (1.79), 2.521 (0.63), 2.526 (0.47), 2.968 (16.00), 4.272 (0.70),
4.288 (0.68), 6.769 (1.13), 6.775 (1.30), 6.810 (0.55), 6.815 (0.46),
6.832 (0.56), 6.837 (0.48), 6.963 (0.79), 7.090 (0.87), 7.218 (0.80),
7.506 (0.59), 7.528 (0.55), 8.640 (2.17), 8.647 (2.00); LC-MS (Method
9): $R_t$ = 0.63 min; MS (ESIpos): m/z = 434 [M + H]$^+$. Traces of
ammonium salt detected.

89

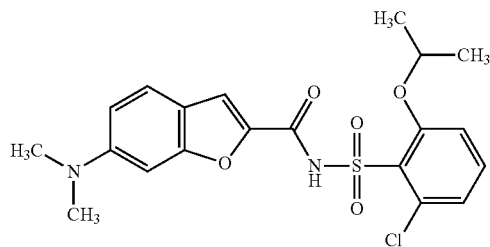 [SMILES: CC(C)Oc1cccc(Cl)c1S(=O)(=O)NC(=O)c1cc2ccc(N(C)C)cc2o1]

N-{2-chloro-6-[(propan-2-yl)oxy]benzene-1-sulfonyl}-6-
(dimethylamino)-1-benzofuran-2-carboxamide $^1$H-NMR (400 MHz, DMSO-d$_6$) δ [ppm]: 1.138 (8.74), 1.154 (8.62),
2.075 (2.12), 2.991 (16.00), 4.773 (0.45), 4.789 (0.62), 4.804 (0.46),
6.785 (0.93), 6.789 (1.03), 6.854 (0.85), 6.860 (0.71), 6.876 (0.86),
6.882 (0.78), 7.165 (1.00), 7.167 (1.12), 7.185 (1.10), 7.187 (1.17),
7.212 (0.80), 7.232 (0.95), 7.501 (1.09), 7.521 (1.26), 7.542 (0.76),
7.574 (1.53), 7.596 (1.41), 7.955 (1.70); LC-MS (Method 9): $R_t$ = 1.22
min; MS (ESIpos): m/z = 437 [M + H]$^+$ TABLE 5-continued examples 65-109

| Example | Structure, IUPAC-Name and analytics |
|---|---|
| 90 | 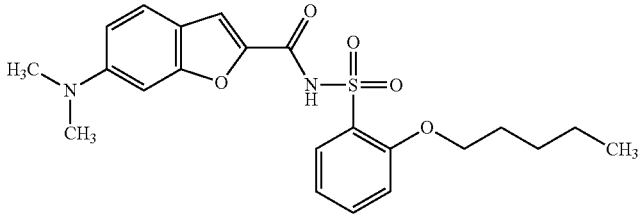 [SMILES: CCCCCOc1ccccc1S(=O)(=O)NC(=O)c1cc2ccc(N(C)C)cc2o1]

6-(Dimethylamino)-N-[2-(pentyloxy)benzene-1-sulfonyl]-1-benzofuran-2-carboxamide $^1$H-NMR (400 MHz, DMSO-d$_6$) δ [ppm]: 0.658 (1.72), 0.675 (4.37), 0.694 (2.27), 1.147 (0.64), 1.166 (0.78), 1.182 (0.52), 1.225 (0.53), 1.235 (0.41), 1.242 (0.61), 1.265 (0.45), 1.641 (0.67), 1.662 (0.70), 1.679 (0.60), 2.075 (2.10), 2.518 (0.72), 2.523 (0.47), 2.980 (16.00), 4.069 (0.89), 4.085 (1.91), 4.102 (0.87), 6.760 (0.96), 6.765 (1.06), 6.842 (0.79), 6.847 (0.67), 6.864 (0.82), 6.870 (0.75), 7.103 (0.47), 7.105 (0.49), 7.124 (0.93), 7.142 (0.51), 7.144 (0.53), 7.204 (0.80), 7.225 (0.89), 7.530 (1.48), 7.553 (1.37), 7.611 (0.44), 7.616 (0.46), 7.630 (0.49), 7.634 (0.60), 7.637 (0.51), 7.895 (0.94), 7.899 (0.95), 7.915 (0.94), 7.919 (0.87), 7.946 (1.26), 12.281 (0.59); LC-MS (Method 9): R$_t$ = 1.33 min; MS (ESIpos): m/z = 431 [M + H]$^+$ |
| 91 | 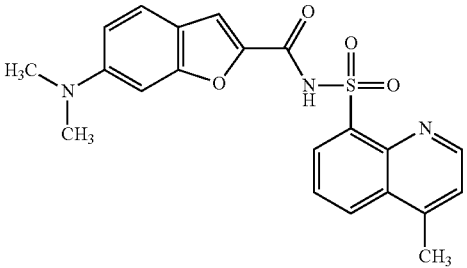 [SMILES: Cc1ccnc2c(S(=O)(=O)NC(=O)c3cc4ccc(N(C)C)cc4o3)cccc12]

6-(Dimethylamino)-N-(4-methylquinoline-8-sulfonyl)-1-benzofuran-2-carboxamide $^1$H-NMR (400 MHz, DMSO-d$_6$) δ [ppm]: 2.326 (0.46), 2.518 (1.53), 2.522 (1.04), 2.668 (0.46), 2.734 (5.07), 2.958 (16.00), 3.350 (0.66), 6.715 (1.01), 6.720 (1.05), 6.822 (0.80), 6.827 (0.73), 6.844 (0.84), 6.849 (0.75), 7.506 (0.86), 7.509 (0.85), 7.517 (0.84), 7.519 (0.87), 7.538 (1.55), 7.561 (1.42), 7.833 (0.80), 7.852 (0.99), 7.854 (0.97), 7.873 (0.89), 7.976 (1.61), 8.482 (0.83), 8.486 (1.02), 8.503 (0.84), 8.507 (0.89), 8.519 (1.12), 8.522 (0.94), 8.537 (1.04), 8.540 (0.80), 8.881 (1.70), 8.892 (1.59); LC-MS (Method 1): R$_t$ = 1.01 min; MS (ESIneg): m/z = 408 [M − H ]$^−$ |
| 92 | 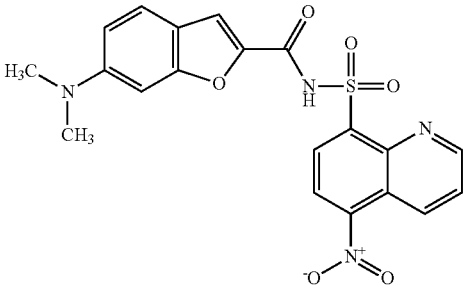

6-(Dimethylamino)-N-(5-nitroquinoline-8-sulfonyl)-1-benzofuran-2-carboxamide $^1$H-NMR (400 MHz, DMSO-d$_6$) δ [ppm]: 2.521 (1.50), 2.525 (0.96), 2.966 (16.00), 6.717 (0.98), 6.721 (1.04), 6.834 (0.78), 6.840 (0.69), 6.856 (0.80), 6.862 (0.75), 7.552 (1.44), 7.574 (1.32), 7.876 (0.88), 7.887 (0.85), 7.899 (0.88), 7.909 (0.87), 7.971 (0.55), 8.579 (1.55), 8.599 (2.09), 8.689 (1.86), 8.710 (1.31), 8.832 (1.03), 8.836 (1.05), 8.854 (1.00), 8.859 (0.90), 9.173 (0.95), 9.177 (1.01), 9.183 (0.99), 9.187 (0.86); LC-MS (Method 9): R$_t$ = 1.13 min; MS (ESIpos): m/z = 441 [M + H]$^+$ |

TABLE 5-continued examples 65-109

| Example | Structure, IUPAC-Name and analytics |
|---|---|
| 93 | 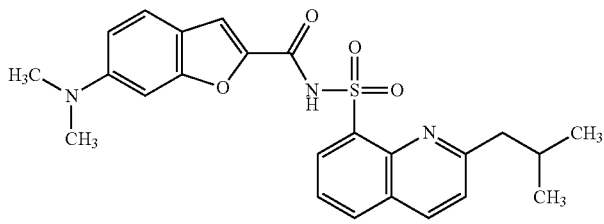 [SMILES: CC(C)Cc1ccc2cccc(S(=O)(=O)NC(=O)c3cc4ccc(N(C)C)cc4o3)c2n1]

6-(Dimethylamino)-N-[2-(2-methylpropyl)quinoline-8-sulfonyl]-1-benzofuran-2-carboxamide
¹H-NMR (400 MHz, DMSO-d₆) δ [ppm]: 0.623 (7.07), 0.639 (7.20), 2.111 (0.44), 2.518 (1.21), 2.523 (0.80), 2.796 (1.83), 2.815 (1.71), 2.963 (16.00), 6.702 (1.18), 6.707 (1.22), 6.826 (0.73), 6.832 (0.66), 6.848 (0.76), 6.854 (0.70), 7.495 (1.12), 7.516 (1.18), 7.527 (1.34), 7.549 (1.21), 7.736 (0.55), 7.755 (1.00), 7.774 (0.60), 7.987 (0.72), 8.295 (0.64), 8.315 (0.59), 8.396 (1.14), 8.418 (1.07), 8.462 (0.79), 8.465 (0.79), 8.481 (0.77), 8.483 (0.71); LC-MS (Method 9): $R_t$ = 1.30 min; MS (ESIpos): m/z = 452 [M + H]⁺ |
| 94 | 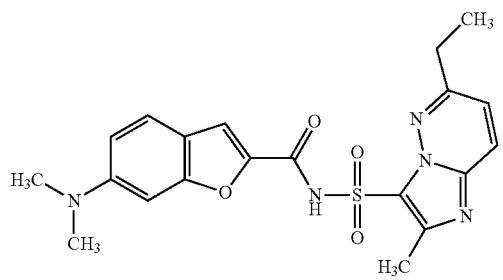 [SMILES: CCc1ccc2nc(C)c(S(=O)(=O)NC(=O)c3cc4ccc(N(C)C)cc4o3)n2n1]

6-(Dimethylamino)-N-(6-ethyl-2-methylimidazo[1,2-b]pyridazine-3-sulfonyl)-1-benzofuran-2-carboxamide
¹H-NMR (400 MHz, DMSO-d₆) δ [ppm]: 1.154 (2.71), 1.173 (6.52), 1.192 (2.83), 2.074 (0.55), 2.518 (0.94), 2.522 (0.65), 2.627 (6.17), 2.766 (0.45), 2.785 (1.32), 2.803 (1.23), 2.937 (0.72), 2.948 (16.00), 6.742 (1.20), 6.778 (0.51), 6.783 (0.44), 6.800 (0.52), 6.805 (0.46), 7.096 (0.41), 7.466 (0.54), 7.488 (0.51); LC-MS (Method 9): $R_t$ = 0.64 min; MS (ESIneg): m/z = 426 [M − H]⁻. Traces of ammonium salt detected. |
| 95 | 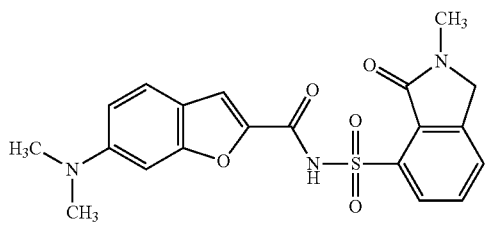 [SMILES: CN1Cc2cccc(S(=O)(=O)NC(=O)c3cc4ccc(N(C)C)cc4o3)c2C1=O]

6-(Dimethylamino)-N-(2-methyl-3-oxo-2,3-dihydro-1H-isoindole-4-sulfonyl)-1-benzofuran-2-carboxamide
¹H-NMR (400 MHz, DMOS-d₆) δ [ppm]: 2.962 (0.49), 2.988 (16.00), 3.051 (7.02), 3.340 (0.61), 4.542 (2.57), 6.796 (1.02), 6.800 (1.13), 6.852 (0.83), 6.858 (0.68), 6.874 (0.84), 6.880 (0.74), 7.561 (1.52), 7.583 (1.40), 7.820 (0.72), 7.839 (1.68), 7.859 (1.14), 7.891 (1.72), 7.927 (1.06), 7.945 (0.71), 8.081 (1.17), 8.099 (0.97), 8.101 (0.95); LC-MS (Method 9): $R_t$ = 1.04 min; MS (ESIpos): m/z = 414 [M + H]⁺ |

TABLE 5-continued examples 65-109

| Example | Structure, IUPAC-Name and analytics |
|---|---|
| 96 | 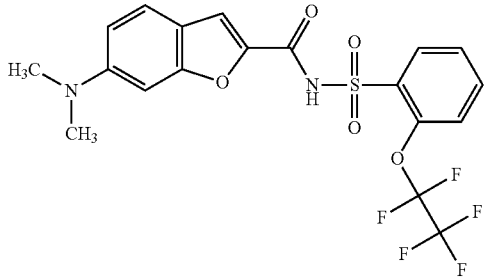 [SMILES: CN(C)c1ccc2cc(C(=O)NS(=O)(=O)c3ccccc3OC(F)(F)C(F)(F)F)oc2c1] 6-(Dimethylamino)-N-[2-(pentafluoroethoxy)benzene-1-sulfonyl]-1-benzofuran-2-carboxamide<br>$^1$H-NMR (400 MHz, DMSO-d$_6$) δ [ppm]: 2.991 (16.00), 6.777 (0.87), 6.859 (0.72), 6.863 (0.62), 6.880 (0.75), 6.886 (0.68), 7.572 (1.50), 7.594 (1.39), 7.618 (0.41), 7.620 (0.50), 7.639 (1.59), 7.658 (1.29), 7.822 (0.49), 7.826 (0.52), 7.846 (1.61), 8.125 (0.94), 8.129 (0.82), 8.145 (0.92), 8.150 (0.64); LC-MS (Method 9): R$_t$ = 1.26 min; MS (ESIpos): m/z = 479 [M + H]$^+$. |
| 97 | 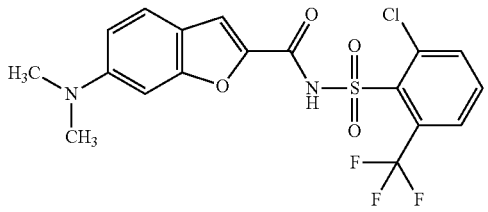 [SMILES: CN(C)c1ccc2cc(C(=O)NS(=O)(=O)c3c(Cl)cccc3C(F)(F)F)oc2c1] N-[2-Chloro-6-(trifluoromethyl)benzene-1-sulfonyl]-6-(dimethylamino)-1-benzofuran-2-carboxamide<br>$^1$H-NMR (400 MHz, DMSO-d$_6$) δ [ppm]: 2.074 (0.93), 2.995 (16.00), 6.768 (0.79), 6.868 (0.65), 6.873 (0.60), 6.891 (0.68), 6.896 (0.63), 7.570 (1.51), 7.592 (1.39), 7.844 (0.82), 7.864 (0.52), 7.910 (0.90), 7.971 (0.83), 7.974 (0.95), 7.991 (0.67), 7.995 (0.64), 8.052 (0.76), 8.055 (0.76), 8.072 (0.65), 8.075 (0.60); LC-MS (Method 9): R$_t$ = 1.07 min; MS (ESIpos): m/z = 447 [M + H]$^+$ |
| 98 | 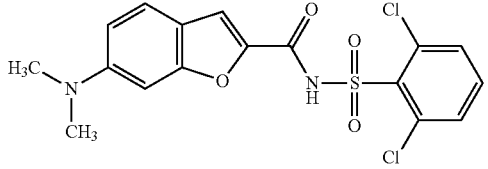 [SMILES: CN(C)c1ccc2cc(C(=O)NS(=O)(=O)c3c(Cl)cccc3Cl)oc2c1] N-(2,6-Dichlorobenzene-1-sulfonyl)-(dimethylamino)-1-benzofuran-2-carboxamide<br>$^1$H-NMR (400 MHz, DMSO-d$_6$) δ [ppm]: 2.074 (10.64), 2.522 (0.61), 2.994 (16.00), 6.772 (1.10), 6.863 (0.75), 6.869 (0.68), 6.886 (0.77), 6.891 (0.73), 7.569 (1.51), 7.591 (1.47), 7.603 (0.72), 7.609 (0.87), 7.626 (1.34), 7.667 (3.43), 7.685 (1.40), 7.689 (1.19), 7.920 (1.35); LC-MS (Method 9): R$_t$ = 1.05 min; MS (ESIpos): m/z = 413 [M + H]$^+$ |
| 99 | 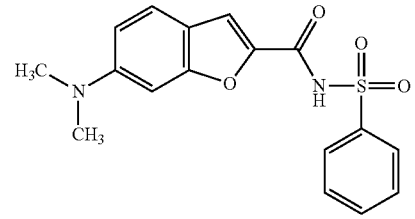 [SMILES: CN(C)c1ccc2cc(C(=O)NS(=O)(=O)c3ccccc3)oc2c1] N-(benzenesulfonyl)-6-(dimethylamino)-1-benzofuran-2-carboxamide<br>$^1$H-NMR (400 MHz, DMSO-d$_6$) δ [ppm]: 2.327 (0.48), 2.518 (1.49), 2.523 (1.07), 2.669 (0.48), 2.986 (16.00), 6.768 (0.94), 6.772 (1.01), 6.844 (0.80), 6.849 (0.68), 6.866 (0.81), 6.872 (0.73), 7.543 (1.45), |

TABLE 5-continued examples 65-109

| Example | Structure, IUPAC-Name and analytics |
|---|---|
| | 7.565 (1.34), 7.625 (0.66), 7.643 (1.68), 7.646 (0.89), 7.659 (0.56), 7.663 (1.17), 7.704 (0.68), 7.707 (0.41), 7.723 (0.83), 7.791 (1.16), 7.985 (1.30), 7.988 (1.88), 7.993 (0.41), 8.002 (0.74), 8.006 (1.36); LC-MS (Method 1): $R_t$ = 1.10 min; MS (ESIpos): m/z = 345 [M + H]$^+$ |

100

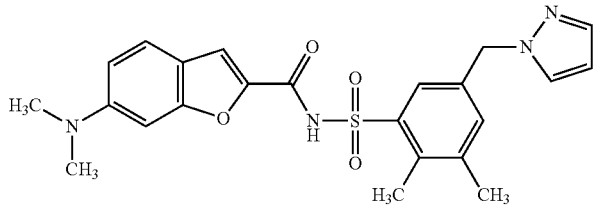 [SMILES: Cc1cc(Cn2cccn2)cc(S(=O)(=O)NC(=O)c2cc3ccc(N(C)C)cc3o2)c1C]

6-(Dimethylamino)-N-(2,3-dimethyl-5-[(1H-pyrazol-1-ylmethyl]benzene-1-sulfonyl]-1-benzofuran-2-carboxamide
$^1$H-NMR (400 MHz, DMSO-d$_6$) δ [ppm]: 2.253 (5.15), 2.482 (5.29), 2.986 (16.00), 5.382 (3.46), 6.269 (1.28), 6.274 (1.91), 6.280 (1.29), 6.764 (0.98), 6.769 (1.07), 6.850 (0.85), 6.855 (0.72), 6.872 (0.86), 6.877 (0.80), 7.340 (1.07), 7.342 (1.08), 7.465 (1.38), 7.467 (1.34), 7.469 (1.44), 7.471 (1.36), 7.556 (1.60), 7.578 (1.48), 7.822 (1.17), 7.826 (1.13), 7.841 (1.45), 7.843 (1.45), 7.847 (1.50), 7.849 (1.40), 7.863 (1.64); LC-MS (Method 9): $R_t$ = 1.11 min; MS (ESIpos): m/z = 453 [M + H]$^+$

101

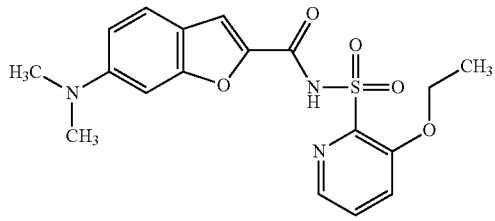 [SMILES: CCOc1cccnc1S(=O)(=O)NC(=O)c1cc2ccc(N(C)C)cc2o1]

6-(Dimethylamino)-N-(3-ethoxypyridine-2-sulfonyl)-1-benzofuran-2-carboxamide
$^1$H-NMR (400 MHz, DMSO-d$_6$) δ [ppm]: 1.249 (2.13), 1.266 (5.05), 1.284 (2.18), 1.728 (0.75), 2.518 (0.92), 2.523 (0.65), 2.971 (0.63), 2.997 (16.00), 3.005 (0.97), 3.015 (0.66), 4.190 (0.55), 4.208 (1.80), 4.225 (1.84), 4.243 (0.53), 6.802 (0.92), 6.807 (1.04), 6.863 (0.85), 6.869 (0.70), 6.886 (0.84), 6.891 (0.77), 7.580 (1.48), 7.603 (1.37), 7.652 (0.70), 7.663 (0.72), 7.674 (0.96), 7.684 (0.96), 7.770 (0.85), 7.773 (0.91), 7.792 (0.64), 7.795 (0.59), 7.934 (1.08), 8.189 (1.09), 8.193 (1.15), 8.201 (1.12), 8.204 (0.93); LC-MS (method 4): $R_t$ = 0.86 min; MS (ESIpos): m/z = 390 [M + H]+

102

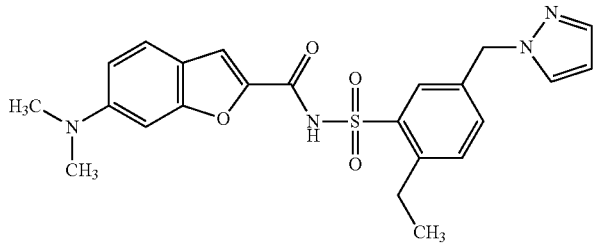

6-(Dimethylamino)-N-{2-ethyl-5-[(1H-pyrazol-1-yl)methyl]benzene-1-sulfonyl}-1-benzofuran-2-carboxamide
$^1$H-NMR (400 MHz, DMSO-d$_6$) δ [ppm]: 1.117 (1.78), 1.135 (4.39), 1.154 (1.84), 2.966 (0.75), 2.985 (16.00), 3.003 (1.54), 3.022 (1.43), 3.041 (0.43), 5.434 (4.06), 6.275 (1.30), 6.281 (1.89), 6.285 (1.20), 6.762 (0.96), 6.766 (1.04), 6.850 (0.80), 6.855 (0.71), 6.872 (0.82), 6.877 (0.75), 7.428 (3.84), 7.431 (3.67), 7.472 (1.35), 7.474 (1.35), 7.476 (1.42), 7.478 (1.35), 7.556 (1.59), 7.578 (1.46), 7.864 (1.58), 7.870 (3.16), 7.929 (1.67); LC-MS (Method 9): $R_t$ = 1.12 min; MS (ESIpos): m/z = 453 [M + H]$^+$ TABLE 5-continued examples 65-109

| Example | Structure, IUPAC-Name and analytics |
|---|---|
| 103 | 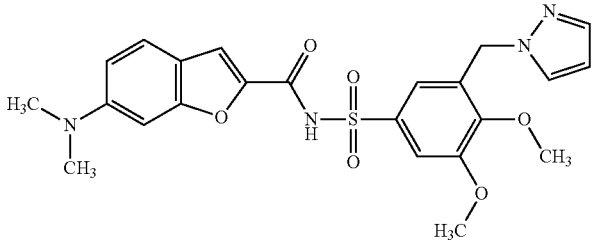 [SMILES: COc1cc(S(=O)(=O)NC(=O)c2cc3ccc(N(C)C)cc3o2)cc(Cn2cccn2)c1OC]

N-{3,4-Dimethoxy-5-[(1H-pyrazol-1-yl)methyl]benzene-1-sulfonyl}-6-(dimethylamino)-1-benzofuran-2-carboxamide $^1$H-NMR (400 MHz, DMSO-$d_6$) δ [ppm]: 2.990 (16.00), 3.895 (8.39), 5.393 (3.99), 6.272 (1.37), 6.277 (1.84), 6.282 (1.44), 6.777 (0.94), 6.782 (1.03), 6.847 (0.81), 6.853 (0.70), 6.870 (0.84), 6.875 (0.74), 7.187 (1.51), 7.193 (1.54), 7.457 (1.42), 7.459 (1.47), 7.462 (1.40), 7.464 (1.41), 7.546 (1.57), 7.568 (1.45), 7.587 (1.52), 7.592 (1.44), 7.775 (1.82), 7.777 (1.80), 7.813 (1.37), 7.818 (1.40); LC-MS (Method 9): $R_t$ = 1.09 min; MS (ESIpos): m/z = 485 [M + H]$^+$ |
| 104 | 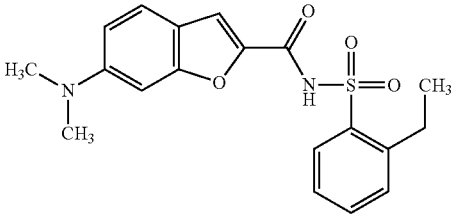 [SMILES: CCc1ccccc1S(=O)(=O)NC(=O)c1cc2ccc(N(C)C)cc2o1]

6-(Dimethylamino)-N-(2-ethylbenzene-1-sulfonyl)-1-benzofuran-2-carboxamide $^1$H-NMR (400 MHz, DMSO-$d_6$) δ [ppm]: 1.151 (1.97), 1.169 (4.52), 1.188 (2.04), 2.078 (1.79), 2.957 (0.64), 2.973 (16.00), 3.025 (0.55), 3.043 (1.64), 3.062 (1.60), 3.081 (0.51), 6.760 (1.18), 6.764 (1.28), 6.838 (0.88), 6.844 (0.78), 6.860 (0.87), 6.866 (0.82), 7.425 (0.41), 7.428 (0.52), 7.444 (1.69), 7.463 (1.64), 7.549 (1.61), 7.572 (1.50), 7.606 (0.59), 7.610 (0.61), 7.625 (0.86), 7.628 (0.88), 7.644 (0.41), 7.886 (2.22), 8.031 (1.00), 8.034 (0.99), 8.052 (0.98), 8.055 (0.81); LC-MS (Method 9): $R_t$ = 1.21 min; MS (ESIneg): m/z = 371 [M − H]$^-$ |
| 105 | 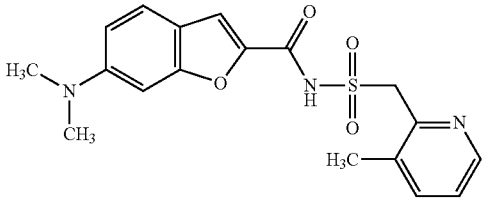 [SMILES: Cc1cccnc1CS(=O)(=O)NC(=O)c1cc2ccc(N(C)C)cc2o1]

6-(Dimethylamino)-N-[(3-methylpyridin-2-yl)methanesulfonyl]-1-benzofuran-2-carboxamide $^1$H-NMR (400 MHz, DMSO-$d_6$) δ [ppm]: 2.456 (5.84), 3.009 (16.00), 5.000 (3.46), 6.851 (1.26), 6.863 (1.03), 6.869 (0.55), 6.886 (0.91), 6.891 (0.69), 7.274 (0.70), 7.286 (0.74), 7.293 (0.76), 7.305 (0.76), 7.557 (1.44), 7.579 (1.34), 7.676 (0.66), 7.678 (0.68), 7.695 (0.62), 7.698 (0.59), 7.785 (2.09), 7.787 (2.21), 8.296 (0.67), 8.299 (0.69), 8.308 (0.69), 8.311 (0.63); LC-MS (Method 9): $R_t$ = 0.68 min; MS (ESIpos): m/z = 374 [M + H]$^+$ |
| 106 | 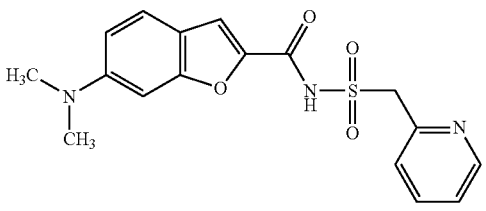 [SMILES: CN(C)c1ccc2cc(C(=O)NS(=O)(=O)Cc3ccccn3)oc2c1] |

TABLE 5-continued examples 65-109

| Example | Structure, IUPAC-Name and analytics |
|---|---|
| | 6-(Dimethylamino)-N-[(pyridin-2-yl)methanesulfonyl]-1-benzofuran-2-carboxamide<br>$^1$H-NMR (400 MHz, DMSO-$d_6$) δ [ppm]: 2.975 (16.00), 4.752 (1.25), 6.804 (0.52), 6.810 (0.79), 6.829 (2.69), 7.286 (0.40), 7.295 (0.41), 7.298 (0.45), 7.302 (0.45), 7.305 (0.43), 7.314 (0.42), 7.317 (0.42), 7.452 (0.82), 7.471 (0.93), 7.481 (0.88), 7.500 (0.57), 7.504 (0.74), 7.747 (0.40), 7.761 (0.65), 7.766 (0.64), 8.463 (0.53), 8.466 (0.59), 8.468 (0.62), 8.470 (0.54), 8.475 (0.53), 8.478 (0.61), 8.480 (0.55), 8.482 (0.50); LC-MS (Method 9): $R_t$ = 0.60 min; MS (ESIpos): m/z = 360 [M + H]$^+$. Traces of ammonium salt detected. |

The following example compounds 107-113 were prepared (similarly to table 4) according to GP5A using INT-11 reacting with the commercially available sulphonamides.

TABLE 6 examples 107-113

| Example | Structure, IUPAC-Name and analytics |
|---|---|
| 107 | 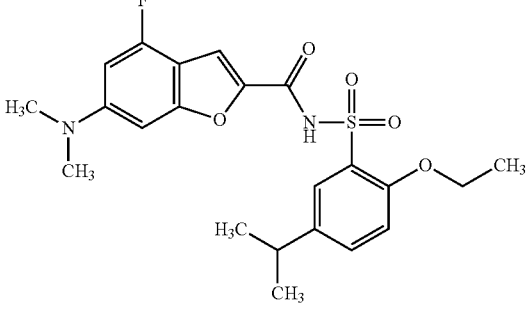<br>6-(Dimethylamino)-N-[2-ethoxy-5-(propan-2-yl)benzene-1-sulfonyl]-4-fluoro-1-benzofuran-2-carboxamide<br>$^1$H-NMR (400 MHz, DMSO-$d_6$) δ [ppm]: 1.207 (8.54), 1.213 (2.81), 1.225 (9.05), 1.230 (5.38), 1.248 (2.23), 2.521 (0.82), 2.525 (0.51), 2.943 (0.46), 2.960 (0.65), 2.966 (0.50), 2.986 (16.00), 4.103 (0.53), 4.120 (1.73), 4.155 (0.51), 4.318 (1.75), 6.634 (1.13), 6.636 (1.24), 6.677 (0.74), 6.682 (0.59), 6.711 (0.67), 6.716 (0.62), 7.134 (1.02), 7.156 (1.12), 7.514 (0.57), 7.519 (0.60), 7.535 (0.51), 7.541 (0.53), 7.728 (1.50), 7.734 (1.40), 8.047 (0.68), 12.371 (0.43); LC-MS Method 9): $R_t$ = 1.40 min; MS (ESIpos): m/z 449 [M + H]$^+$. |
| 108 | 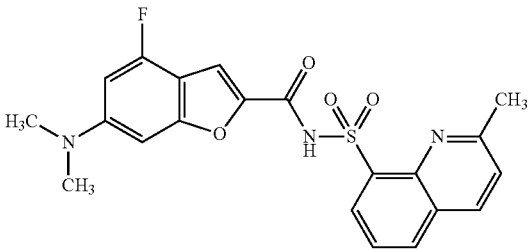<br>6-(Dimethylamino)-4-fluoro-N-(2-methylquinoline-8-sulfonyl)-1-benzofuran-2-carboxamide<br>$^1$H-NMR (400 MHz, DMSO-$d_6$) δ [ppm]: -0.008 (1.20), 0.008 (0.97), 2.521 (3.20), 2.525 (2.15), 2.542 (0.62), 2.676 (0.90), 2.687 (5.68), 2.963 (16.00), 6.594 (1.05), 6.596 (1.13), 6.660 (0.49), 6.664 (0.46), 6.693 (0.48), 6.698 (0.44), 7.514 (0.87), 7.534 (0.89), 7.748 (0.56), 8.385 (0.75), 8.406 (0.71), 8.447 (0.51), 8.465 (0.49); LC-MS (Method 9): $R_t$ = 1.11 min; MS (ESIpos): m/z = 428 [M + H]$^+$. |
| 109 | 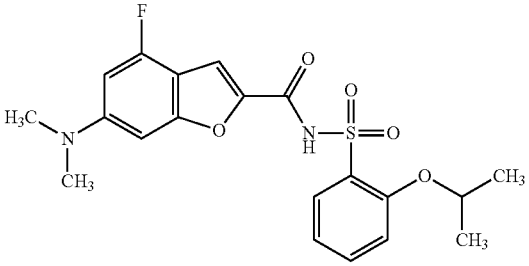 [SMILES: CC(C)Oc1ccccc1S(=O)(=O)NC(=O)c1cc2c(F)cc(N(C)C)cc2o1]<br>6-(Dimethylamino)-4-fluoro-N-{2-[(propan-2-yl)oxy]benzene-1-sulfonyl}-1-benzofuran-2-carboxamide<br>$^1$H-NMR (400 MHz, DMSO-$d_6$) δ [ppm]: 1.179 (8.57), 1.194 (8.46), 2.520 (1.36), 2.525 (0.80), 2.973 (0.59), 2.985 (16.00), 4.794 (0.41), 4.809 (0.55), 4.824 (0.40), 6.645 (1.18), 6.647 (1.29), 6.677 (0.73), 6.681 (0.58), 6.711 (0.68), 6.716 (0.60), 7.085 (0.46), 7.104 (0.88), 7.122 (0.48), 7.229 (0.73), 7.250 (0.79), 7.625 (0.57), 7.889 (0.90), 7.893 (0.88), 7.909 (0.86), 7.913 (0.79), 8.067 (0.71), 12.318 (0.57); LC-MS (Method 9): $R_t$ = 1.24 min; MS (ESIpos): m/z = 421 [M + H]$^+$. |
| 110 | 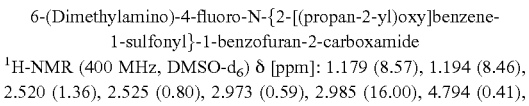<br>N-[2-(Cyclopropyloxy)benzene-1-sulfonyl]-6-(dimethylamino)-4-fluoro-1-benzofuran-2-carboxamide<br>$^1$H-NMR (400 MHz, DMSO-$d_6$) δ [ppm]: 0.531 (0.80), 0.536 (1.28), 0.541 (0.81), 0.727 (1.03), 0.731 (0.83), 0.742 (0.81), 0.747 (0.92), 2.521 (0.57), 2.989 (16.00), 4.076 (0.43), 4.083 (0.61), 4.090 (0.41), 6.644 (1.09), 6.647 (1.21), 6.683 (0.73), 6.688 (0.58), 6.717 (0.67), 6.722 (0.62), 7.163 (0.44), 7.165 (0.47), 7.184 (0.85), 7.201 (0.50), 7.204 (0.48), 7.468 (0.78), 7.487 (0.92), 7.489 (0.89), 7.675 (0.41), 7.679 (0.44), 7.693 (0.50), 7.697 (0.58), 7.700 (0.48), 7.885 (0.92), 7.890 (0.92), 7.905 (0.88), 7.909 (0.82), 8.026 (0.82); LC-MS (Method 1): $R_t$ = 1.23 min; MS (ESIpos): m/z = 419 [M + H]$^+$. |

TABLE 6-continued examples 107-113

| Example | Structure, IUPAC-Name and analytics |
|---|---|
| 111 | 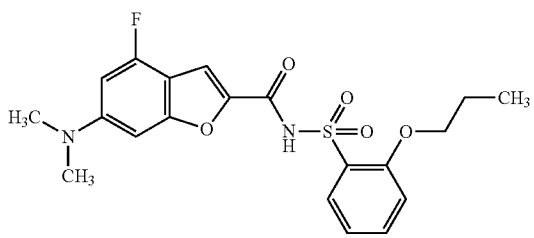 [SMILES: CCCOc1ccccc1S(=O)(=O)NC(=O)c1cc2c(F)cc(N(C)C)cc2o1]

6-(Dimethylamino)-4-fluoro-N-(2-propoxybenzene-1-sulfonyl)-1-benzofuran-2-carboxamide
$^1$H-NMR (400 MHz, DMSO-$d_6$) δ [ppm]: 0.862 (2.22), 0.881 (5.09), 0.899 (2.33), 1.684 (0.55), 1.701 (1.14), 1.719 (1.10), 1.735 (0.51), 2.521 (0.92), 2.526 (0.57), 2.985 (16.00), 4.050 (0.96), 4.066 (2.04), 4.082 (0.94), 6.640 (1.06), 6.642 (1.19), 6.674 (0.69), 6.678 (0.57), 6.707 (0.67), 6.712 (0.60), 7.109 (0.42), 7.111 (0.44), 7.129 (0.85), 7.147 (0.47), 7.149 (0.47), 7.209 (0.73), 7.229 (0.80), 7.643 (0.53), 7.900 (0.90), 7.905 (0.92), 7.920 (0.86), 7.924 (0.82), 8.023 (0.60); LC-MS (method 4): $R_t$ = 1.25 min; MS (ESIpos): m/z = 421 [M + H]+. |
| 112 | 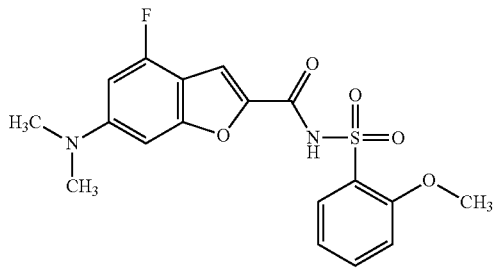

6-(Dimethylamino)-4-fluoro-N-(2-methoxybenzene-1-sulfonyl)-1-benzofuran-2-carboxamide
$^1$H-NMR (400 MHz, DMSO-$d_6$) δ [ppm]: 2.077 (1.29), 2.520 (0.91), 2.525 (0.58), 2.985 (16.00), 3.873 (8.08), 6.647 (1.10), 6.648 (1.23), 6.675 (0.75), 6.680 (0.58), 6.709 (0.69), 6.714 (0.62), 7.136 (0.45), 7.138 (0.50), 7.156 (0.89), 7.174 (0.52), 7.176 (0.51), 7.225 (0.83), 7.245 (0.92), 7.655 (0.42), 7.660 (0.44), 7.674 (0.50), 7.678 (0.60), 7.681 (0.50), 7.899 (0.93), 7.903 (0.95), 7.918 (0.89), 7.922 (0.84), 8.033 (0.83); LC-MS (method 9): $R_t$ = 1.12 min; MS (ESIpos): m/z = 393 [M + H]+ |
| 113 | 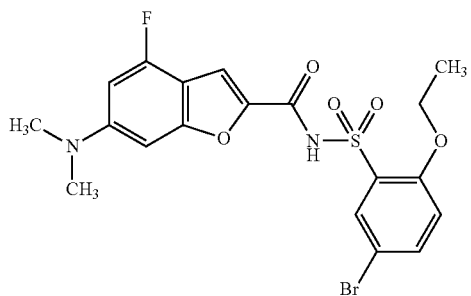 [SMILES: CCOc1ccc(Br)cc1S(=O)(=O)NC(=O)c1cc2c(F)cc(N(C)C)cc2o1]

N-(5-Bromo-2-ethoxybenzene-1-sulfonyl)-6-(dimethylamino)-4-fluoro-1-benzofuran-2-carboxamide
$^1$H-NMR (400 MHz, DMSO-$d_6$) δ [ppm]: 1.182 (1.57), 1.200 (2.92), 1.221 (2.43), 1.240 (9.02), 1.254 (7.09), 1.256 (7.76), 1.265 (1.75), 1.270 (5.47), 1.282 (0.50), 2.086 (7.93), 2.150 (0.56), 2.324 (0.94), 2.329 (1.31), 2.334 (0.93), 2.338 (0.41), 2.520 (4.17), 2.525 (3.04), 2.542 (1.50), 2.667 (0.96), 2.671 (1.33), 2.676 (0.92), 2.917 (0.56), 2.967 (16.00), 3.129 (0.75), 3.139 (0.77), 3.147 (0.73), 3.158 (0.69), 3.598 (0.41), 3.608 (0.44), 3.614 (0.55), 3.625 (0.55), 3.631 (0.41), 4.082 (0.51), 6.641 (2.80), 7.896 (0.90); LC-MS (method 4): $R_t$ = 1.25 min; MS (ESIpos): m/z = 487 [M − H]+. |

The following example compounds 116-154 were prepared (similarly to table 8) according to GP5B using INT-11 reacting with the commercially available sulphonamides.

TABLE 7 examples 114-152

| Example | Structure, IUPAC-Name and analytics |
|---|---|
| 114 | 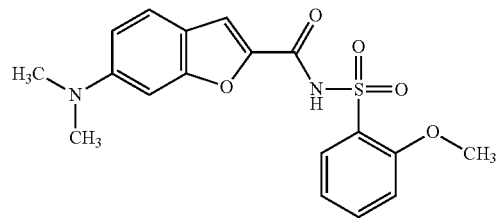

6-(Dimethylamino)-N-(2-methoxybenzene-1-sulfonyl)-1-benzofuran-2-carboxamide
$^1$H-NMR (400 MHz, DMSO-$d_6$) δ [ppm]: 2.084 (3.24), 2.522 (0.65), 2.981 (16.00), 3.859 (8.17), 6.771 (1.12), 6.775 (1.21), 6.843 (0.80), 6.849 (0.69), 6.865 (0.81), 6.871 (0.74), 7.129 (0.48), 7.147 (0.96), 7.166 (0.52), 7.212 (0.88), 7.232 (0.97), 7.552 (1.43), 7.574 (1.32), 7.645 (0.41), 7.663 (0.63), 7.891 (0.94), 7.896 (0.94), 7.911 (0.98), 7.915 (0.99), 7.927 (0.68); LC-MS (Method 1): $R_t$ = 1.10 min; MS (ESIpos): m/z = 375 [M + H]+ |

TABLE 7-continued examples 114-152

| Example | Structure, IUPAC-Name and analytics |
|---|---|
| 115 | 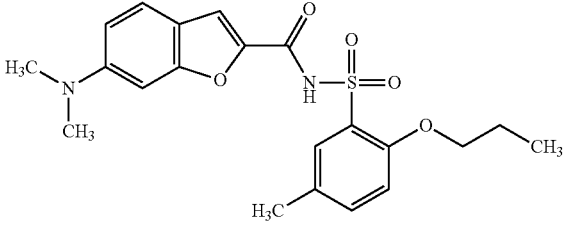 [SMILES: CCCOc1ccc(C)cc1S(=O)(=O)NC(=O)c1cc2ccc(N(C)C)cc2o1]

6-(Dimethylamino)-N-(5-methyl-2-propoxybenzene-1-sulfonyl)-1-benzofuran-2-carboxamide $^1$H-NMR (400 MHz, DMSO-d$_6$) δ [ppm]: 1.140 (8.86), 1.155 (9.08), 2.074 (0.65), 2.318 (6.20), 2.979 (16.00), 4.719 (0.50), 4.734 (0.68), 4.749 (0.51), 6.766 (1.22), 6.770 (1.32), 6.839 (0.84), 6.844 (0.74), 6.861 (0.88), 6.867 (0.79), 7.106 (1.02), 7.127 (1.18), 7.402 (0.64), 7.407 (0.65), 7.423 (0.58), 7.428 (0.57), 7.559 (1.57), 7.581 (1.45), 7.693 (1.33), 7.697 (1.25), 7.969 (1.10), 12.178 (0.86); LC-MS (Method 1): R$_t$ = 1.31 min; MS (ESIneg): m/z = 415 [M − H]$^-$ |
| 116 | 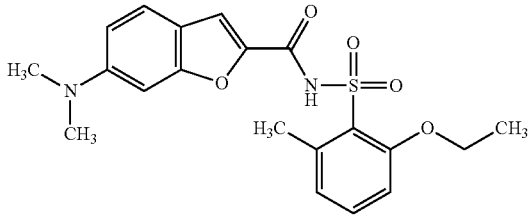 [SMILES: CCOc1cccc(C)c1S(=O)(=O)NC(=O)c1cc2ccc(N(C)C)cc2o1]

6-(Dimethylamino)-N-(2-ethoxy-6-methylbenzene-1-sulfonyl)-1-benzofuran-2-carboxamide $^1$H-NMR (400 MHz, DMSO-d$_6$) δ [ppm]: 1.199 (2.29), 1.217 (5.04), 1.234 (2.38), 2.523 (0.50), 2.637 (6.40), 2.982 (16.00), 4.099 (0.58), 4.116 (1.79), 4.134 (1.81), 4.151 (0.56), 6.759 (1.12), 6.763 (1.18), 6.844 (0.80), 6.849 (0.69), 6.866 (0.83), 6.872 (0.74), 6.928 (0.82), 6.947 (0.88), 7.038 (0.77), 7.059 (0.85), 7.423 (0.64), 7.443 (0.95), 7.463 (0.52), 7.556 (1.42), 7.578 (1.31), 7.928 (0.81), 12.170 (0.95); LC-MS (Method 1): R$_t$ = 1.27 min; (ESIneg): m/z = 401 [M − H]$^-$ |
| 117 | 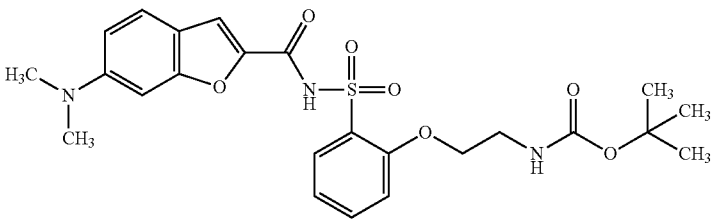 [SMILES: CN(C)c1ccc2cc(C(=O)NS(=O)(=O)c3ccccc3OCCNC(=O)OC(C)(C)C)oc2c1]

tert-butyl [2-(2-{[6-(dimethylamino)-1-benzofuran-2-carbonyl]sulfamoyl}phenoxy)ethyl]carbamate $^1$H-NMR (400 MHz, DMSO-d$_6$) δ [ppm]: 1.328 (0.40), 1.383 (16.00), 2.075 (0.58), 2.084 (11.71), 2.518 (3.56), 2.523 (2.32), 2.984 (13.52), 3.268 (0.93), 3.282 (0.96), 3.294 (0.53), 3.999 (0.74), 4.012 (1.38), 4.026 (0.75), 6.773 (1.35), 6.854 (0.54), 6.876 (0.56), 7.027 (0.41), 7.155 (0.59), 7.191 (0.49), 7.211 (0.52), 7.566 (0.59), 7.588 (0.56), 7.649 (0.41), 7.897 (1.15), 7.912 (0.70), 12.008 (0.65); LC-MS (Method 1): R$_t$ = 1.31 min; MS (ESIneg): m/z = 502 [M − H]$^-$ |

TABLE 7-continued examples 114-152

| Example | Structure, IUPAC-Name and analytics |
|---|---|
| 118 | 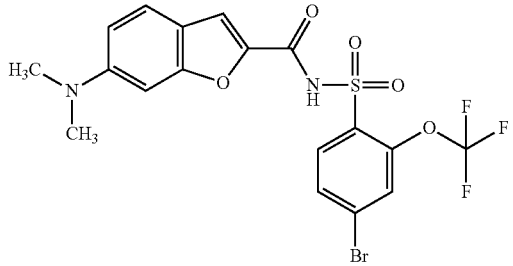 [SMILES: CN(C)c1ccc2cc(C(=O)NS(=O)(=O)c3ccc(Br)cc3OC(F)(F)F)oc2c1]

N-[4-Bromo-2-(trifluoromethoxy)benzene-1-sulfonyl]-6-(dimethylamino)-1-benzofuran-2-carboxamide
$^1$H-NMR (400 MHz, DMSO-d$_6$) δ [ppm]: 2.518 (1.66), 2.523 (1.14), 2.990 (16.00), 6.782 (0.78), 6.855 (0.61), 6.860 (0.55), 6.877 (0.63), 6.882 (0.59), 7.558 (1.32), 7.580 (1.21), 7.811 (1.04), 7.872 (0.62), 7.876 (0.55), 7.893 (0.75), 7.898 (0.70), 8.042 (1.71), 8.064 (1.35); LC-MS (Method 1): R$_t$ = 1.30 min; MS (ESIpos): m/z = 507 [M + H]$^+$ |
| 119 | 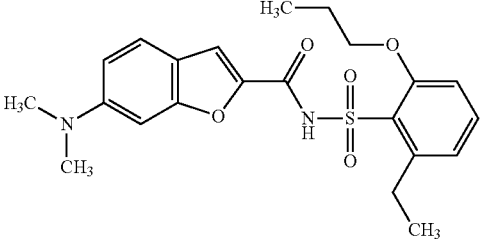 [SMILES: CCCOc1cccc(CC)c1S(=O)(=O)NC(=O)c1cc2ccc(N(C)C)cc2o1]

6-(Dimethylamino)-N-(2-ethyl-6-propoxybenzene-1-sulfonyl)-1-benzofuran-2-carboxamide
$^1$H-NMR (400 MHz, DMSO-d$_6$) δ [ppm]: 0.832 (2.18), 0.851 (5.00), 0.869 (2.37), 1.221 (1.65), 1.239 (3.87), 1.258 (1.65), 1.671 (0.65), 1.689 (1.28), 1.706 (1.24), 1.724 (0.60), 2.077 (0.53), 2.521 (0.46), 2.987 (16.00), 3.097 (0.43), 3.115 (1.39), 3.134 (1.36), 3.153 (0.43), 3.992 (0.95), 4.009 (1.91), 4.025 (0.92), 6.753 (1.07), 6.757 (1.16), 6.845 (0.76), 6.851 (0.67), 6.868 (0.78), 6.873 (0.72), 6.952 (0.79), 6.970 (0.83), 7.032 (0.69), 7.052 (0.76), 7.458 (0.52), 7.478 (0.83), 7.498 (0.43), 7.558 (1.33), 7.580 (1.23), 7.913 (0.65), 12.031 (1.06); LC-MS (Method 1): R$_t$ = 1.42 min; MS (ESIpos): m/z = 431 [M + H]$^+$ |
| 120 | 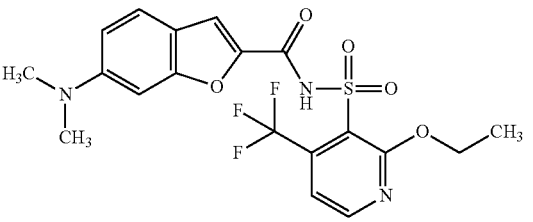 [SMILES: CCOc1nccc(C(F)(F)F)c1S(=O)(=O)NC(=O)c1cc2ccc(N(C)C)cc2o1]

6-(Dimethylamino)-N-[2-ethoxy-4-(trifluoromethyl)pyridine-3-sulfonyl]-1-benzofuran-2-carboxamide
$^1$H-NMR (400 MHz, DMSO-d$_6$) δ [ppm]: 1.110 (2.41), 1.127 (5.17), 1.145 (2.48), 2.521 (0.54), 2.997 (16.00), 4.439 (0.61), 4.456 (1.94), 4.474 (1.97), 4.492 (0.59), 6.771 (1.01), 6.775 (1.08), 6.866 (0.78), 6.872 (0.68), 6.889 (0.80), 6.894 (0.74), 7.583 (1.46), 7.604 (1.83), 7.615 (1.29), 7.960 (0.68), 8.677 (0.91), 8.690 (0.87); LC-MS (Method 1): R$_t$ = 1.27 min; MS (ESIpos): m/z = 458 [M + H]$^+$ |

TABLE 7-continued examples 114-152

| Example | Structure, IUPAC-Name and analytics |
|---|---|
| 121 | 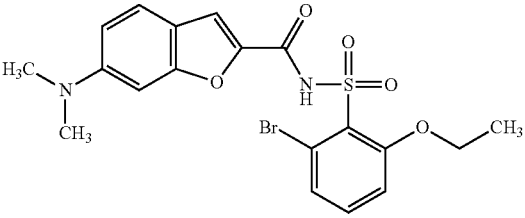 [SMILES: CCOc1cccc(Br)c1S(=O)(=O)NC(=O)c1cc2ccc(N(C)C)cc2o1]<br>N-(2-Bromo-6-ethoxybenzene-1-sulfonyl)-6-(dimethylamino)-1-benzofuran-2-carboxamide<br>$^1$H-NMR (400 MHz, DMSO-$d_6$) δ [ppm]: 1.137 (2.25), 1.154 (5.08), 1.172 (2.33), 2.518 (1.38), 2.523 (0.96), 2.942 (0.47), 2.982 (0.71), 2.992 (16.00), 4.105 (0.51), 4.123 (1.64), 4.140 (1.63), 4.157 (0.49), 6.782 (0.99), 6.787 (1.09), 6.856 (0.79), 6.861 (0.67), 6.878 (0.81), 6.884 (0.73), 7.228 (0.53), 7.232 (0.56), 7.247 (0.61), 7.252 (0.65), 7.404 (0.43), 7.419 (1.38), 7.425 (1.81), 7.445 (0.84), 7.570 (1.41), 7.592 (1.27), 7.935 (0.55); LC-MS (Method 1): $R_t$ = 1.24 min; MS (ESIpos): m/z = 467 [M + H]$^+$ |
| 122 | 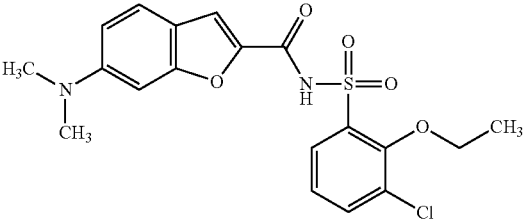 [SMILES: CCOc1c(Cl)cccc1S(=O)(=O)NC(=O)c1cc2ccc(N(C)C)cc2o1]<br>N-(3-Chloro-2-ethoxybenzene-1-sulfonyl)-6-(dimethylamino)-1-benzofuran-2-carboxamide<br>$^1$H-NMR (400 MHz, DMSO-$d_6$) δ [ppm]: 1.405 (1.60), 1.423 (3.80), 1.440 (1.65), 2.518 (0.66), 2.523 (0.46), 2.990 (16.00), 4.136 (0.45), 4.154 (1.56), 4.171 (1.55), 4.188 (0.43), 6.771 (0.94), 6.775 (1.02), 6.857 (0.75), 6.861 (0.65), 6.879 (0.78), 6.884 (0.71), 7.359 (0.66), 7.379 (1.40), 7.399 (0.77), 7.570 (1.35), 7.592 (1.25), 7.836 (0.61), 7.840 (0.68), 7.856 (0.58), 7.860 (0.60), 7.896 (0.49), 7.912 (1.20), 7.915 (1.09), 7.932 (0.98), 7.936 (0.91); LC-MS (Method 1): $R_t$ = 1.31 min; MS (ESIpos): m/z = 423 [M + H]$^+$ |
| 123 | 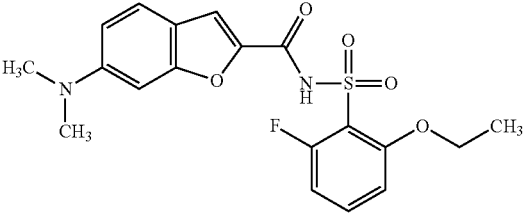 [SMILES: CCOc1cccc(F)c1S(=O)(=O)NC(=O)c1cc2ccc(N(C)C)cc2o1]<br>6-(Dimethylamino)-N-(2-ethoxy-6-fluorobenzene-1-sulfonyl)-1-benzofuran-2-carboxamide<br>$^1$H-NMR (400 MHz, DMSO-$d_6$) δ [ppm]: 1.182 (2.12), 1.200 (5.03), 1.217 (2.18), 2.518 (0.41), 2.989 (16.00), 4.119 (0.54), 4.317 (1.79), 4.154 (1.75), 4.172 (0.54), 6.781 (0.97), 6.785 (1.06), 6.853 (0.81), 6.858 (0.69), 6.875 (0.81), 6.881 (0.75), 6.961 (0.47), 6.966 (0.44), 6.987 (0.42), 7.025 (0.75), 7.047 (0.80), 7.567 (1.43), 7.589 (1.39), 7.605 (0.54), 7.621 (0.53), 7.941 (0.81); LC-MS (Method 1): $R_t$ = 1.17 min; MS (ESIpos): m/z = 407 [M + H]$^+$ |

TABLE 7-continued examples 114-152

| Example | Structure, IUPAC-Name and analytics |
|---|---|
| 124 | 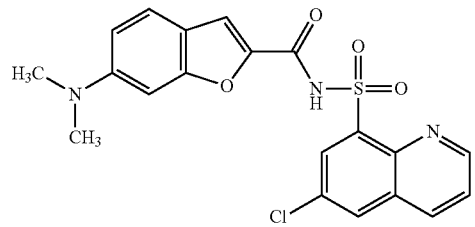 [SMILES: CN(C)c1ccc2cc(C(=O)NS(=O)(=O)c3cc(Cl)cc4cccnc34)oc2c1]

N-(6-Chloroquinolone-8-sulfonyl)-6-(dimethylamino)-1-benzofuran-2-carboxamide
$^1$H-NMR (400 MHz, DMSO-d$_6$) δ [ppm]: 2.518 (0.63), 2.523 (0.44), 2.959 (16.00), 3.411 (1.26), 6.708 (0.97), 6.713 (1.04), 6.824 (0.77), 6.829 (0.68), 6.846 (0.81), 6.852 (0.76), 7.543 (1.47), 7.565 (1.36), 7.700 (0.80), 7.711 (0.78), 7.721 (0.80), 7.732 (0.79), 7.969 (0.76), 8.403 (1.81), 8.409 (1.86), 8.502 (0.77), 8.506 (0.81), 8.523 (0.78), 8.527 (0.75), 8.560 (1.33), 8.567 (1.24), 9.048 (0.94), 9.052 (0.99), 9.058 (1.01), 9.063 (0.92); LC-MS (Method 1): R$_t$ = 1.21 min; MS (ESIpos): m/z = 430 [M + H]$^+$ |
| 125 | 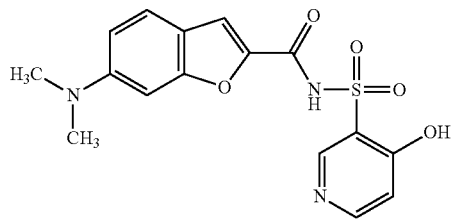 [SMILES: CN(C)c1ccc2cc(C(=O)NS(=O)(=O)c3cnccc3O)oc2c1]

N-(4-Chloropyridine-3-sulfonyl)-6-(dimethylamino)-1-benzofuran-2-carboxamide
$^1$H-NMR (400 MHz, DMSO-d$_6$) δ [ppm]: 2.077 (3.71), 2.521 (0.45), 2.543 (1.18), 2.989 (16.00), 6.284 (1.12), 6.302 (1.13), 6.773 (0.97), 6.778 (1.07), 6.844 (0.83), 6.849 (0.70), 6.865 (0.82), 6.871 (0.74), 7.562 (1.52), 7.584 (1.40), 7.781 (0.60), 7.784 (0.61), 7.800 (0.57), 7.803 (0.58), 7.918 (1.62), 8.425 (1.50), 8.429 (1.47); |
| 126 | 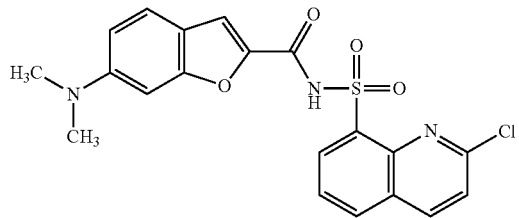 [SMILES: CN(C)c1ccc2cc(C(=O)NS(=O)(=O)c3cccc4ccc(Cl)nc34)oc2c1]

N-(2-Chloroquinoline-8-sulfonyl)-6-(dimethylamino)-1-benzofuran-2-carboxamide
$^1$H-NMR (400 MHz, DMSO-d$_6$) δ [ppm]: 2.966 (16.00), 6.728 (1.22), 6.732 (1.30), 6.834 (0.79), 6.839 (0.73), 6.856 (0.83), 6.862 (0.76), 7.559 (1.42), 7.581 (1.31), 7.715 (1.54), 7.736 (1.59), 7.865 (0.70), 7.885 (1.20), 7.904 (0.76), 8.056 (0.55), 8.407 (0.78), 8.425 (0.71), 8.558 (0.91), 8.561 (0.91), 8.577 (0.89), 8.580 (0.84), 8.592 (1.53), 8.614 (1.41); LC-MS (Method 1): R$_t$ = 1.23 min; MS (ESIpos): m/z = 430 [M + H]$^+$ |
| 127 | 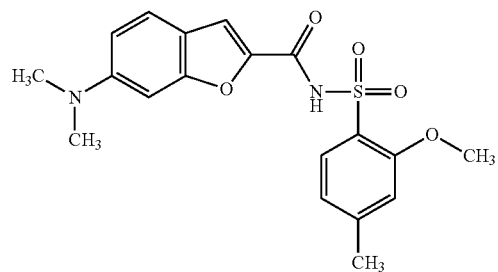 |

TABLE 7-continued examples 114-152

| Example | Structure, IUPAC-Name and analytics |
|---|---|
| | 6-(Dimethylamino)-N-(2-methoxy-4-methylbenzene-1-sulfonyl)-1-benzofuran-2-carboxamide<br>$^1$H-NMR (400 MHz, DMSO-d$_6$) δ [ppm]: 2.371 (5.76), 2.518 (0.80), 2.522 (0.54), 2.979 (16.00), 3.836 (7.46), 6.772 (1.03), 6.776 (1.15), 6.840 (0.78), 6.846 (0.66), 6.862 (0.78), 6.868 (0.71), 6.940 (0.66), 6.959 (0.69), 7.045 (1.25), 7.547 (1.37), 7.569 (1.27), 7.758 (1.52), 7.778 (1.40), 7.913 (0.45), 12.344 (0.52); LC-MS (Method 1): R$_t$ = 1.17 min; MS (ESIpos): m/z = 389 [M + H]$^+$. |
| 128 | 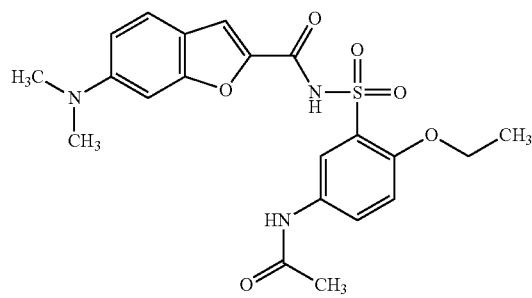 [SMILES: CCOc1ccc(NC(C)=O)cc1S(=O)(=O)NC(=O)c1cc2ccc(N(C)C)cc2o1]<br>N-(5-Acetamido-2-ethoxybenzene-1-sulfonyl)-6-(dimethylamino)-1-benzofuran-2-carboxamide<br>$^1$H-NMR (400 MHz, DMSO-d$_6$) δ [ppm]: 1.195 (2.16), 1.212 (5.06), 1.229 (2.20), 2.043 (8.39), 2.073 (0.61), 2.518 (0.61), 2.523 (0.43), 2.980 (16.00), 3.334 (1.51), 3.363 (0.41), 3.385 (0.48), 4.069 (0.48), 4.086 (1.55), 4.104 (1.54), 4.121 (0.47), 6.771 (1.11), 6.775 (1.22), 6.842 (0.79), 6.848 (0.69), 6.865 (0.79), 6.870 (0.74), 7.143 (0.75), 7.166 (0.80), 7.556 (1.32), 7.578 (1.21), 7.836 (0.78), 7.842 (0.79), 7.858 (0.69), 7.865 (0.74), 8.131 (0.83), 8.137 (0.80), 10.117 (1.26); LC-MS (Method 1): R$_t$ = 1.04 min; MS (ESIpos): m/z = 446 [M + H]$^+$ |
| 129 | 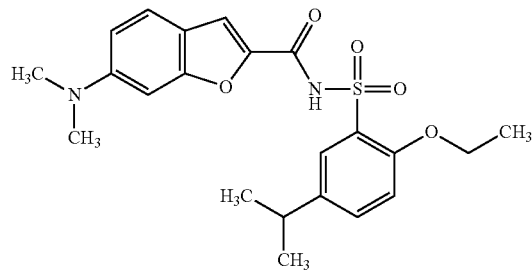 [SMILES: CCOc1ccc(C(C)C)cc1S(=O)(=O)NC(=O)c1cc2ccc(N(C)C)cc2o1]<br>6-(Dimethylamino)-N-[2-ethoxy-5-(propan-2-yl)benzene-1-sulfonyl]-1-benzofuran-2-carboxamide<br>$^1$H-NMR (400 MHz, DMSO-d$_6$) δ [ppm]: 1.204 (9.02), 1.218 (6.26), 1.221 (9.49), 1.235 (2.33), 2.073 (0.52), 2.518 (0.77), 2.523 (0.50), 2.937 (0.49), 2.954 (0.66), 2.981 (16.00), 4.087 (0.54), 4.104 (1.75), 4.122 (1.73), 4.139 (0.53), 6.759 (1.10), 6.763 (1.19), 6.843 (0.77), 6.848 (0.70), 6.865 (0.79), 6.870 (0.74), 7.121 (0.99), 7.142 (1.10), 7.500 (0.56), 7.506 (0.59), 7.521 (0.52), 7.527 (0.53), 7.556 (1.42), 7.578 (1.30), 7.723 (1.53), 7.728 (1.44), 7.945 (0.58), 12.281 (0.46); LC-MS (Method 1): R$_t$ = 1.37 min; MS (ESIpos): m/z = 431 [M + H]$^+$ |
| 130 | 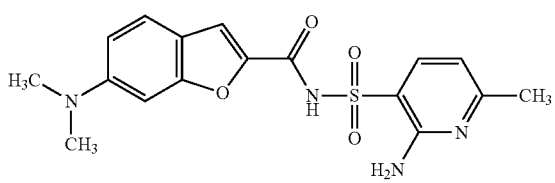<br>N-(2-Amino-6-methylpyridine-3-sulfonyl)-6-(dimethylamino)-1-benzofuran-2-carboxamide<br>$^1$H-NMR (400 MHz, DMSO-d$_6$) δ [ppm]: 2.201 (5.76), 2.521 (0.65), 2.526 (0.42), 2.991 (16.00), 3.348 (0.55), 6.774 (0.97), 6.778 (1.09), 6.845 (0.85), 6.851 (0.68), 6.867 (0.78), 6.872 (0.72), 7.535 (1.25), |

| Example | Structure, IUPAC-Name and analytics |
|---|---|
| | 7.557 (1.14), 7.908 (0.67), 8.065 (0.87), 8.070 (0.84); LC-MS (Method 1): $R_t$ = 0.70 min; MS (ESIpos): m/z = 375 [M + H]⁺. |
| 131 | 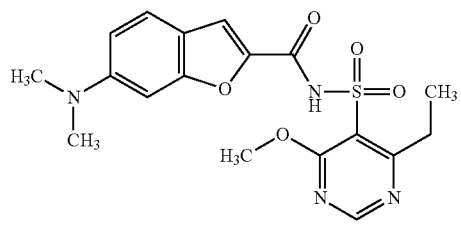 [SMILES: CCc1ncnc(OC)c1S(=O)(=O)NC(=O)c1cc2ccc(N(C)C)cc2o1]<br>6-(Dimethylamino)-N-(4-ethyl-6-methoxypyrimidine-5-sulfonyl)-1-benzofuran-2-carboxamide<br>¹H-NMR (400 MHz, DMSO-d₆) δ [ppm]: 1.259 (2.17), 1.277 (5.22), 1.296 (2.19), 2.521 (0.76), 2.526 (0.48), 2.981 (0.44), 2.994 (16.00), 3.227 (0.64), 3.246 (2.01), 3.265 (1.94), 3.283 (0.68), 3.988 (9.26), 6.764 (0.97), 6.768 (1.05), 6.859 (0.79), 6.865 (0.70), 6.881 (0.78), 6.887 (0.74), 7.567 (1.45), 7.589 (1.33), 7.919 (0.76), 8.870 (2.88); LC-MS (Method 1): $R_t$ = 1.09 min; MS (ESIneg): m/z = 403 [M − H]⁻ |
| 132 | 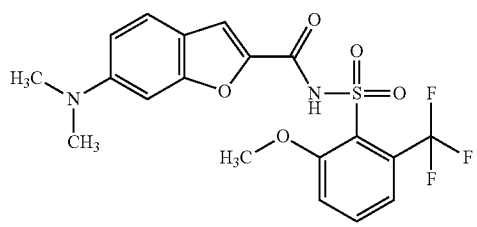 [SMILES: COc1cccc(C(F)(F)F)c1S(=O)(=O)NC(=O)c1cc2ccc(N(C)C)cc2o1]<br>6-(Dimethylamino)-N-[2-methoxy-6-(trifluoromethyl)benzene-1-sulfonyl]-1-benzofuran-2-carboxamide<br>¹H-NMR (400 MHz, DMSO-d₆) δ [ppm]: 2.991 (16.00), 3.878 (7.74), 6.768 (0.96), 6.773 (1.05), 6.859 (0.79), 6.864 (0.69), 6.881 (0.80), 6.886 (0.76), 7.570 (1.66), 7.574 (0.92), 7.592 (2.20), 7.607 (0.92), 7.795 (0.49), 7.815 (0.71), 7.962 (0.85); LC-MS (Method 1): $R_t$ = 1.20 min; MS (ESIneg): m/z = 441 [M − H]⁻ |
| 133 | 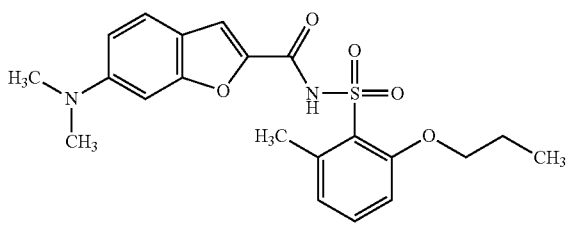 [SMILES: CCCOc1cccc(C)c1S(=O)(=O)NC(=O)c1cc2ccc(N(C)C)cc2o1]<br>6-(Dimethylamino)-N-(2-methyl-6-propoxybenzene-1-sulfonyl)-1-benzofuran-2-carboxamide<br>¹H-NMR (400 MHz, DMSO-d₆) δ [ppm]: 0.846 (2.18), 0.865 (5.09), 0.883 (2.37), 1.679 (0.60), 1.695 (1.21), 1.714 (1.18), 1.731 (0.57), 2.077 (1.29), 2.521 (0.67), 2.525 (0.42), 2.646 (5.92), 2.985 (16.00), 4.001 (0.97), 4.017 (2.02), 4.033 (0.96), 6.752 (0.97), 6.757 (1.07), 6.844 (0.76), 6.849 (0.68), 6.865 (0.78), 6.871 (0.73), 6.926 (0.72), 6.945 (0.77), 7.043 (0.65), 7.064 (0.72), 7.424 (0.55), 7.444 (0.81), 7.464 (0.45), 7.555 (1.36), 7.577 (1.26), 7.905 (0.64), 12.111 (0.88); LC-MS (Method 1): $R_t$ = 1.36 min; MS (ESIneg): m/z = 415 [M − H]⁻ |
| 134 | 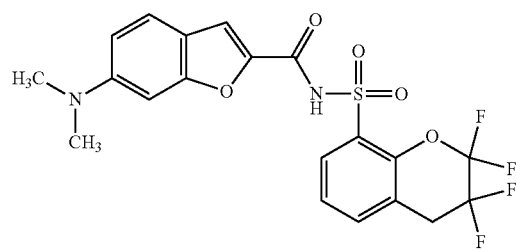 [SMILES: CN(C)c1ccc2cc(C(=O)NS(=O)(=O)c3cccc4c3OC(F)(F)C(F)(F)C4)oc2c1] |

TABLE 7-continued examples 114-152

| Example | Structure, IUPAC-Name and analytics |
|---|---|
| | 6-(Dimethylamino)-N-(2,2,3,3-tetrafluoro-2,3-dihydro-1,4-benzodioxine-5-sulfonyl)-1-benzofuran-2-carboxamide<br>$^1$H-NMR (400 MHz, DMSO-$d_6$) δ [ppm]: 2.523 (0.49), 2.996 (16.00), 6.795 (0.79), 6.869 (0.64), 6.874 (0.56), 6.891 (0.66), 6.897 (0.60), 7.576 (1.48), 7.581 (0.79), 7.599 (1.59), 7.602 (1.59), 7.622 (0.86), 7.840 (0.76), 7.843 (0.82), 7.860 (0.69), 7.864 (0.69), 7.886 (0.79), 7.952 (0.97), 7.956 (0.91), 7.971 (0.85), 7.975 (0.78); LC-MS (Method 1): $R_t$ = 1.23 min; MS (ESIneg): m/z = 473 [M − H]$^-$ |
| 135 | 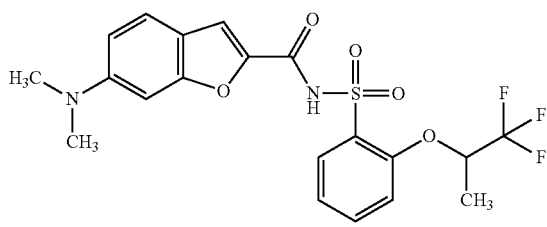 [SMILES: CC(Oc1ccccc1S(=O)(=O)NC(=O)c1cc2ccc(N(C)C)cc2o1)C(F)(F)F]<br>6-(Dimethylamino)-N-(2-[-1,1,1-trifluoropropan-2-yl)oxy]benzene-1-sulfonyl)-1-benzofuran-2-carboxamide (rac)<br>$^1$H-NMR (400 MHz, DMSO-$d_6$) δ [ppm]: 1.360 (2.95), 1.375 (2.95), 2.522 (0.49), 2.980 (16.00), 5.523 (0.51), 6.766 (1.37), 6.840 (0.80), 6.845 (0.71), 6.862 (0.83), 6.868 (0.77), 7.216 (0.54), 7.234 (1.06), 7.254 (0.60), 7.429 (0.67), 7.451 (0.78), 7.555 (1.39), 7.577 (1.29), 7.686 (0.64), 7.917 (0.58), 7.952 (0.93), 7.955 (0.95), 7.971 (0.89), 7.975 (0.84); LC-MS (Method 1): $R_t$ = 1.26 min; MS (ESIpos): m/z = 457 [M + H]$^+$ |
| 136 | N-(5-Bromo-2-chloropyridine-3-sulfonyl)-6-(dimethylamino)-1-benzofuran-2-carboxamide<br>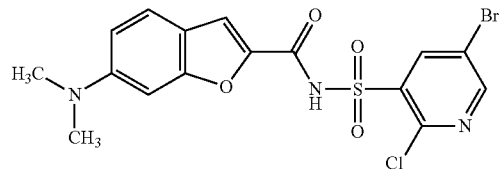<br>$^1$H-NMR (400 MHz, DMSO-$d_6$) δ [ppm]: 2.087 (0.64), 2.522 (0.53), 3.014 (16.00), 5.762 (5.31), 6.866 (0.45), 6.909 (0.48), 6.931 (0.49), 7.582 (1.43), 7.604 (1.32), 7.800 (0.95), 8.626 (2.16), 8.632 (2.18), 8.862 (1.86), 8.868 (1.74); LC-MS (Method 1): $R_t$ = 0.94 min; MS (ESIneg): m/z = 456 [M − H]$^-$ |
| 137 | 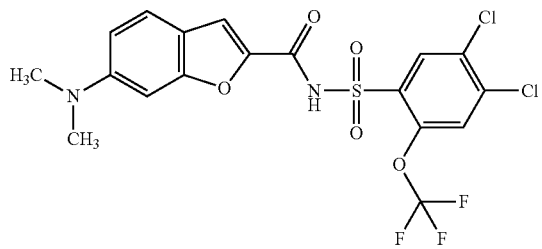 [SMILES: CN(C)c1ccc2cc(C(=O)NS(=O)(=O)c3cc(Cl)c(Cl)cc3OC(F)(F)F)oc2c1]<br>N-[4,5-Dichloro-2-(trifluoromethoxy)benzene-1-sulfonyl]-6-(dimethylamino)-1-benzofuran-2-carboxamide<br>$^1$H-NMR (400 MHz, DMSO-$d_6$) δ [ppm]: 2.518 (1.16), 2.523 (0.85), 2.999 (16.00), 6.829 (0.51), 6.879 (0.52), 6.901 (0.53), 7.562 (1.39), 7.584 (1.27), 7.733 (0.61), 7.768 (1.04), 7.940 (1.18), 8.243 (3.51); LC-MS (Method 1): $R_t$ = 1.33 min; MS (ESIpos): m/z = 497 [M + H]$^+$ |

TABLE 7-continued examples 114-152

| Example | Structure, IUPAC-Name and analytics |
|---|---|
| 138 | 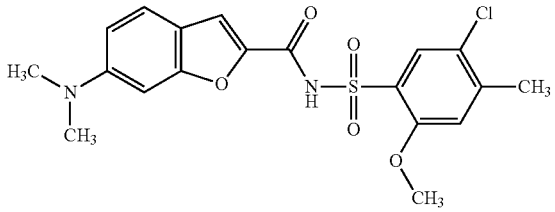<br>N-(5-Chloro-2-methoxy-4-methylbenzene-1-sulfonyl)-6-(dimethylamino)-1-benzofuran-2-carboxamide<br>$^1$H-NMR (400 MHz, DMSO-d$_6$) δ [ppm]: 2.394 (5.90), 2.518 (1.00), 2.523 (0.69), 2.983 (16.00), 3.853 (6.37), 6.767 (1.03), 6.772 (1.09), 6.842 (0.74), 6.848 (0.63), 6.865 (0.74), 6.870 (0.67), 7.284 (1.09), 7.548 (1.17), 7.570 (1.07), 7.799 (2.80); LC-MS (Method 1): R$_t$ = 1.28 min; MS (ESIpos): m/z = 423 [M + H]$^+$ |
| 139 | 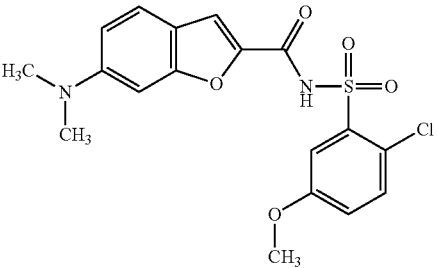 [SMILES: COc1ccc(Cl)c(S(=O)(=O)NC(=O)c2cc3ccc(N(C)C)cc3o2)c1]<br>N-(2-Chloro-5-methoxybenzene-1-sulfonyl)-6-(dimethylamino)-1-benzofuran-2-carboxamide<br>$^1$H-NMR (400 MHz, DMSO-d$_6$) δ [ppm]: 2.518 (0.50), 2.989 (16.00), 6.766 (1.02), 6.770 (1.07), 6.855 (0.80), 6.861 (0.68), 6.877 (0.82), 6.883 (0.73), 7.276 (0.69), 7.284 (0.70), 7.298 (0.79), 7.306 (0.79), 7.564 (2.33), 7.586 (2.13), 7.610 (1.90), 7.617 (1.75), 7.930 (0.99); LC-MS (Method 1): R$_t$ = 1.16 min; MS (ESIpos): m/z = 409 [M + H]$^+$ |
| 140 | 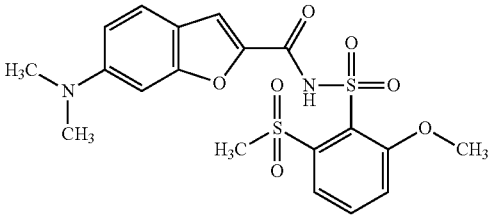<br>6-(Dimethylamino)-N-[2-(methanesulfonyl)-6-methoxybenzene-1-sulfonyl]-1-benzofuran-2-carboxamide<br>$^1$H-NMR (400 MHz, DMSO-d$_6$) δ [ppm]: 2.074 (7.23), 2.523 (0.71), 2.986 (16.00), 3.592 (9.10), 3.912 (7.05), 6.737 (1.17), 6.741 (1.24), 6.857 (0.77), 6.862 (0.72), 6.879 (0.80), 6.884 (0.75), 7.568 (1.41), 7.590 (1.30), 7.645 (0.56), 7.653 (0.47), 7.662 (0.65), 7.669 (0.66), 7.869 (1.01), 7.879 (1.59), 7.886 (2.46), 7.968 (0.51); LC-MS (Method 1): R$_t$ = 1.03 min; MS (ESIpos): m/z = 453 [M + H]$^+$ |
| 141 | 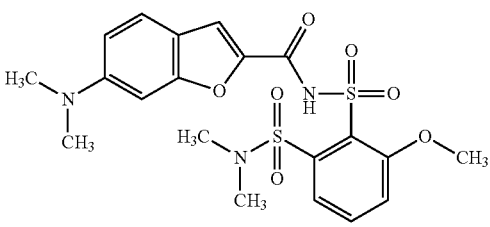<br>6-(Dimethylamino)-N-[2-(dimethylsulfamoyl)-6-methoxybenzene-1-sulfonyl]-1-benzofuran-2-carboxamide<br>$^1$H-NMR (400 MHz, DMSO-d$_6$) δ [ppm]: 2.073 (5.99), 2.522 (0.66), 2.923 (16.00), 2.986 (15.01), 3.823 (6.42), 6.782 (1.17), 6.785 (1.25), |

TABLE 7-continued examples 114-152

| Example | Structure, IUPAC-Name and analytics |
|---|---|
| | 6.852 (0.76), 6.858 (0.64), 6.874 (0.77), 6.880 (0.69), 7.424 (0.98), 7.426 (1.02), 7.444 (1.10), 7.495 (0.78), 7.516 (0.91), 7.561 (1.28), 7.583 (1.18), 7.733 (0.54), 7.754 (0.85), 7.948 (0.43), 12.284 (0.50); LC-MS (Method 1): $R_t$ = 1.04 min; MS (ESIpos): m/z = 482 [M + H]$^+$ |
| 142 | 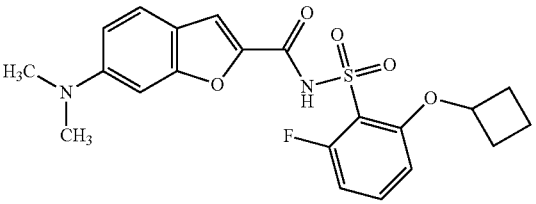 [SMILES: CN(C)c1ccc2cc(C(=O)NS(=O)(=O)c3c(F)cccc3OC3CCC3)oc2c1]<br>N-[2-(Cyclobutyloxy)-6-fluorobenzene-1-sulfonyl]-6-(dimethylamino)-1-benzofuran-2-carboxamide<br>$^1$H-NMR (400 MHz, DMSO-d$_6$) δ [ppm]: 1.462 (0.51), 1.950 (0.46), 1.968 (0.42), 1.974 (0.64), 1.980 (0.46), 1.999 (0.48), 2.077 (3.04), 2.256 (0.51), 2.262 (0.49), 2.268 (0.43), 2.275 (0.49), 2.281 (0.46), 2.521 (0.59), 2.542 (0.40), 2.994 (16.00), 4.819 (0.59), 6.789 (1.02), 6.794 (1.12), 6.823 (0.71), 6.845 (0.76), 6.856 (0.83), 6.861 (0.69), 6.878 (0.80), 6.884 (0.72), 6.964 (0.45), 6.970 (0.42), 7.581 (1.52), 7.591 (0.51), 7.603 (1.34), 7.974 (0.52); LC-MS (Method 1): $R_t$ = 1.25 min; MS (ESIpos): m/z = 433 [M + H]$^+$ |
| 143 | 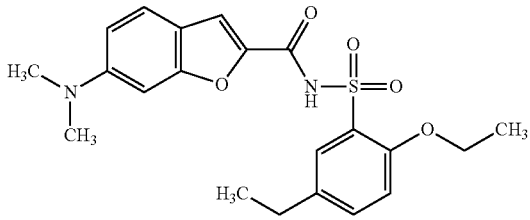 [SMILES: CCOc1ccc(CC)cc1S(=O)(=O)NC(=O)c1cc2ccc(N(C)C)cc2o1]<br>6-(Dimethylamino)-N-(2-ethoxy-5-ethylbenzene-1-sulfonyl)-1-benzofuran-2-carboxamide<br>$^1$H-NMR (400 MHz, DMSO-d$_6$) δ [ppm]: 1.169 (2.37), 1.189 (5.52), 1.199 (2.39), 1.208 (2.65), 1.216 (4.96), 1.234 (2.27), 2.075 (1.25), 2.518 (0.64), 2.523 (0.41), 2.611 (0.52), 2.630 (1.57), 2.649 (1.52), 2.668 (0.56), 2.981 (16.00), 4.085 (0.59), 4.103 (1.88), 4.120 (1.89), 4.138 (0.57), 6.763 (1.12), 6.767 (1.23), 6.843 (0.83), 6.848 (0.73), 6.865 (0.85), 6.870 (0.79), 7.114 (1.09), 7.135 (1.22), 7.459 (0.62), 7.464 (0.64), 7.480 (0.55), 7.485 (0.57), 7.556 (1.51), 7.578 (1.39), 7.710 (1.44), 7.715 (1.39), 7.949 (0.78), 12.280 (0.59); LC-MS (Method 1): $R_t$ = 1.32 min; MS (ESIneg): m/z = 415 [M − H]$^-$ |
| 144 | 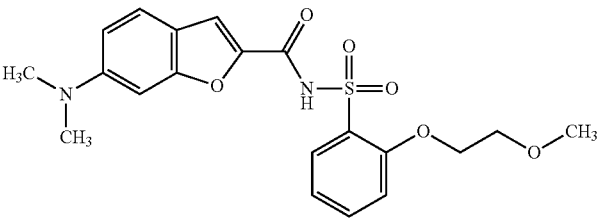<br>6-(Dimethylamino)-N-(2-ethoxy-5-ethylbenzene-1-sulfonyl)-1-benzofuran-2-carboxamide<br>$^1$H-NMR (400 MHz, DMSO-d$_6$) δ [ppm]: 2.518 (0.94), 2.522 (0.61), 2.980 (16.00), 3.096 (10.02), 3.619 (1.24), 3.631 (1.48), 3.634 (1.21), 3.642 (1.30), 4.219 (1.08), 4.231 (1.32), 4.242 (0.97), 6.770 (1.14), 6.775 (1.22), 6.839 (0.80), 6.844 (0.67), 6.861 (0.82), 6.867 (0.72), 7.122 (0.46), 7.141 (0.91), 7.159 (0.49), 7.239 (0.76), 7.260 (0.82), 7.550 (1.33), 7.573 (1.22), 7.633 (0.57), 7.890 (0.96), 7.894 (0.96), 7.910 (1.13), 7.915 (1.12), 12.207 (0.45); LC-MS (Method 1): $R_t$ = 1.14 min; MS (ESIneg): m/z = 417 [M − H]$^-$ |

TABLE 7-continued examples 114-152

| Example | Structure, IUPAC-Name and analytics |
|---|---|
| 145 | 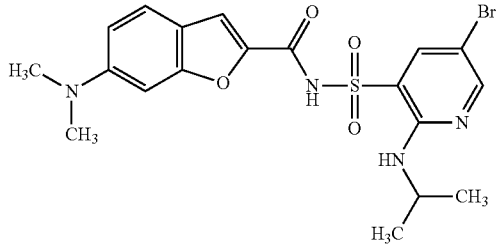 [SMILES: CC(C)Nc1ncc(Br)cc1S(=O)(=O)NC(=O)c1cc2ccc(N(C)C)cc2o1]<br>N-{5-Bromo-2-[(propan-2-yl)amino]pyridine-3-sulfonyl}-6-(dimethylamino)-1-benzofuran-2-carboxamide<br>$^1$H-NMR (400 MHz, DMSO-$d_6$) δ [ppm]: 1.148 (7.89), 1.165 (7.78), 2.521 (2.12), 2.525 (1.46), 2.542 (1.91), 2.996 (16.00), 6.791 (0.80), 6.857 (0.60), 6.862 (0.53), 6.879 (0.62), 6.884 (0.57), 7.552 (1.24), 7.574 (1.15), 8.046 (1.20), 8.052 (1.26), 8.376 (0.79), 8.382 (0.78); LC-MS (Method 1): $R_t$ = 1.37 min; MS (ESIpos): m/z = 481 [M + H]$^+$ |
| 146 | 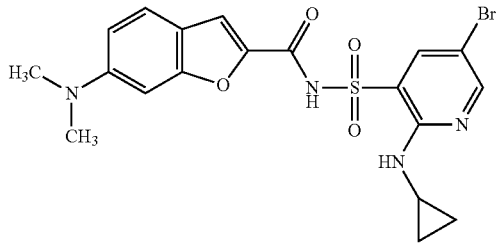 [SMILES: CN(C)c1ccc2cc(C(=O)NS(=O)(=O)c3cc(Br)cnc3NC3CC3)oc2c1]<br>N-[5-Bromo-2-(cyclopropylamino)pyridine-3-sulfonyl]-6-(dimethylamino)-1-benzofuran-2-carboxamide<br>$^1$H-NMR (400 MHz, DMSO-$d_6$) δ [ppm]: 0.474 (1.12), 0.479 (1.14), 0.483 (1.23), 0.489 (1.17), 0.500 (0.41), 0.736 (0.41), 0.747 (1.10), 7.52 (1.37), 0.765 (1.40), 0.769 (1.05), 2.521 (1.04), 2.526 (0.61), 2.818 (0.50), 3.006 (16.00), 5.762 (0.74), 6.794 (1.20), 6.873 (0.67), 6.878 (0.60), 6.895 (0.69), 6.901 (0.64), 7.565 (1.48), 7.587 (1.36), 7.692 (1.06), 8.075 (1.87), 8.081 (1.96), 8.476 (1.48), 8.482 (1.41); LC-MS (Method 1): $R_t$ = 1.22 min; MS (ESIpos): m/z = 479 [M + H]$^+$ |
| 147 | 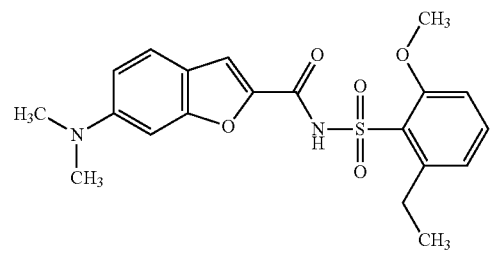 [SMILES: CCc1cccc(OC)c1S(=O)(=O)NC(=O)c1cc2ccc(N(C)C)cc2o1]<br>6-(Dimethylamino)-N-(2-ethyl-6-methoxybenzene-1-sulfonyl)-1-benzofuran-2-carboxamide<br>$^1$H-NMR (400 MHz, DMSO-$d_6$) δ [ppm]: 1.220 (1.72), 1.239 (4.08), 1.257 (1.77), 2.981 (16.00), 3.091 (0.47), 3.109 (1.48), 3.127 (1.44), 3.146 (0.45), 3.804 (8.57), 6.759 (1.17), 6.763 (1.24), 6.844 (0.84), 6.850 (0.75), 6.867 (0.85), 6.872 (0.79), 6.971 (0.95), 6.988 (0.98), 6.990 (0.97), 7.035 (0.89), 7.054 (1.00), 7.483 (0.79), 7.503 (1.20), 7.523 (0.67), 7.553 (1.54), 7.575 (1.41), 7.947 (1.29), 12.250 (1.05); LC-MS (Method 1): $R_t$ = 1.26 min; MS (ESIneg): m/z = 401 [M − H]$^-$ |
| 148 | 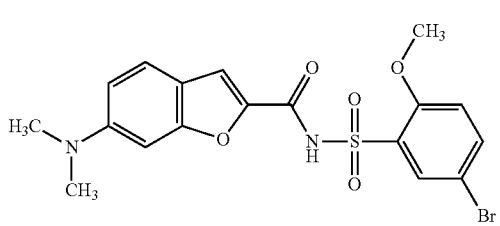 [SMILES: COc1ccc(Br)cc1S(=O)(=O)NC(=O)c1cc2ccc(N(C)C)cc2o1] |

TABLE 7-continued examples 114-152

| Example | Structure, IUPAC-Name and analytics |
|---|---|
| | N-(5-Bromo-2-methoxybenzene-1-sulfonyl)-6-(dimethylamino)-1-benzofuran-2-carboxamide<br>¹H-NMR (400 MHz, DMSO-d₆) δ [ppm]: 2.072 (0.43), 2.984 (16.00), 3.867 (8.31), 6.770 (1.29), 6.848 (0.81), 6.853 (0.74), 6.870 (0.85), 6.875 (0.79), 7.216 (1.39), 7.238 (1.49), 7.556 (1.54), 7.578 (1.42), 7.845 (0.85), 7.851 (0.95), 7.867 (0.77), 7.874 (0.89), 7.929 (1.57), 7.943 (2.06), 7.950 (1.77); LC-MS (Method 1): R$_t$ = 1.23 min; MS (ESIpos): m/z = 453 [M + H]⁺ |
| 149 | 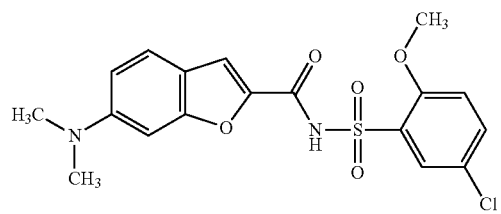 [SMILES: COc1ccc(Cl)cc1S(=O)(=O)NC(=O)c1cc2ccc(N(C)C)cc2o1]<br>N-(5-chloro-2-methoxybenzene-1-sulfonyl)-6-(dimethylamino)-1-benzofuran-2-carboxamide<br>¹H-NMR (400 MHz, DMSO-d₆) δ [ppm]: 2.518 (0.49), 2.986 (16.00), 3.874 (8.26), 6.769 (0.93), 6.773 (1.02), 6.849 (0.80), 6.855 (0.69), 6.871 (0.80), 6.877 (0.75), 7.273 (1.24), 7.296 (1.41), 7.558 (1.47), 7.580 (1.35), 7.735 (0.79), 7.741 (0.86), 7.757 (0.70), 7.64 (0.81), 7.837 (2.11), 7.843 (1.80), 7.931 (1.00); LC-MS (Method 1): R$_t$ = 1.21 min; MS (ESIpos): m/z = 409 [M + H]⁺ |
| 150 | 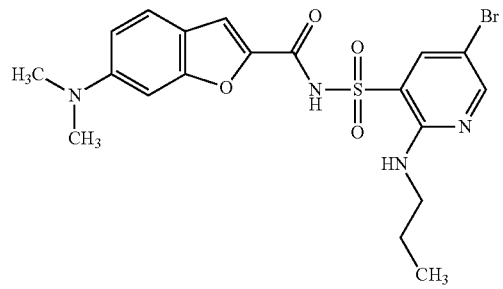 [SMILES: CCCNc1ncc(Br)cc1S(=O)(=O)NC(=O)c1cc2ccc(N(C)C)cc2o1]<br>N-[5-bromo-2-(propylamino)pyridine-3-sulfonyl]-6-(dimethylamino)-1-benzofuran-2-carboxamide<br>¹H-NMR (400 MHz, DMSO-d₆) δ [ppm]: 0.823 (2.19), 0.842 (5.30), 0.861 (2.47), 1.514 (0.72), 1.531 (1.27), 1.549 (1.25), 1.567 (0.66), 2.087 (3.16), 2.521 (1.24), 2.526 (0.79), 3.000 (16.00), 3.360 (0.84), 3.377 (1.37), 3.395 (0.93), 3.475 (0.45), 6.787 (1.04), 6.861 (0.67), 6.867 (0.59), 6.883 (0.69), 6.889 (0.63), 7.552 (1.36), 7.574 (1.25), 7.671 (0.55), 8.050 (1.44), 8.056 (1.50), 8.378 (1.01), 8.384 (0.98); LC-MS (Method 1): R$_t$ = 1.38 min; MS (ESIpos): m/z = 481 [M + H]⁺ |
| 151 | 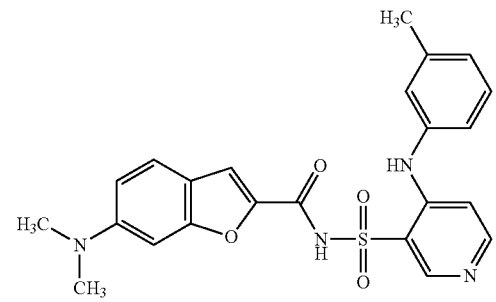 [SMILES: Cc1cccc(Nc2ccncc2S(=O)(=O)NC(=O)c2cc3ccc(N(C)C)cc3o2)c1]<br>6-(Dimethylamino)-N-[4-(3-methylanilino)pyridine-3-sulfonyl]-1-benzofuran-2-carboxamide<br>¹H-NMR (400 MHz, DMSO-d₆) δ [ppm]: 2.328 (6.12), 2.521 (0.94), 2.525 (0.59), 2.951 (16.00), 6.766 (1.33), 6.777 (1.03), 6.783 (0.55), 6.799 (0.89), 6.804 (0.70), 7.125 (1.52), 7.143 (1.54), 7.163 (1.81), 7.182 (0.97), 7.196 (0.82), 7.220 (1.59), 7.389 (0.72), 7.408 (1.12), 7.427 (0.49), 7.444 (1.43), 7.465 (1.31), 8.197 (0.91), 8.199 (0.90), |

TABLE 7-continued examples 114-152

| Example | Structure, IUPAC-Name and analytics |
|---|---|
| 152 | 8.215 (0.86), 8.217 (0.86), 8.740 (1.98), 8.742 (1.97); LC-MS (Method 1): $R_t$ = 0.97 min; MS (ESIpos): m/z = 451 [M + H]$^+$ 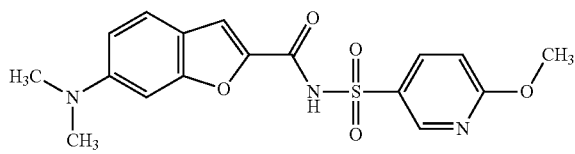<br><br>6-(Dimethylamino)-N-(6-methoxypyridine-3-sulfonyl)-1-benzofuran-2-carboxamide<br>$^1$H-NMR (400 MHz, DMSO-d$_6$) δ [ppm]: 2.992 (16.00), 3.362 (0.41), 3.956 (10.12), 6.775 (1.00), 6.779 (1.08), 6.849 (0.80), 6.854 (0.69), 6.871 (0.83), 6.876 (0.73), 7.041 (1.33), 7.063 (1.37), 7.547 (1.53), 7.569 (1.42), 7.785 (1.82), 8.194 (1.14), 8.201 (1.11), 8.216 (1.06), 8.223 (1.07), 8.766 (1.32), 8.771 (1.33); LC-MS (Method 1): $R_t$ = 1.06 min; MS (ESIpos): m/z = 376 [M + H]$^+$ |

The following reaction were conducted in metal racks equipped with 48 glass vials according to GP5B, with example 55: to a solution of aforementioned 6-(dimethylamino)-1-benzofuran-2-carboxylic acid (INT-11, 30.8 mg, 150 μmol) in 2 mL DMF, 1,1'-Carbonyldiimidazol (29.2 mg, 180 mol) in 0.5 mL DMF were added. The reaction mixture was placed on the shaker for 1 h at RT. 2,3,4-trifluorobenzene-1-sulfonamide (63.3 mg, 300 mol) in 0.5 mL DMF and 1,8-Diazabicyclo(5.4.0)undec-7-en (45.7 mg, 300 μmol) were added. The reaction mixture was placed on the shaker for 12 h at RT. The crude mixture was filtered through a pad of Celite and purified by preparative HPLC to give the title compound 3.75 mg (6% yield)

TABLE 8 examples 153-165

| Example | Structure, IUPAC-Name and analytics |
|---|---|
| 153 | 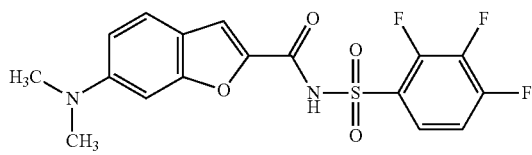<br>6-(Dimethylamino)-N-(2,3,4-trifluorobenzene-1-sulfonyl)-1-benzofuran-2-carboxamide<br>LC-MS (Method 10): $R_t$ = 1.15 min; MS (ESIpos): m/z = 399 [M + H]$^+$ |
| 154 | 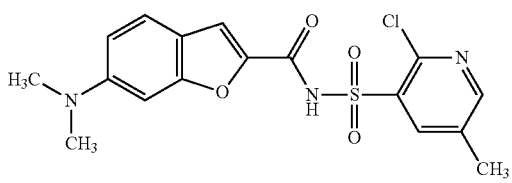<br>N-(2-Chloro-5-methylpyridine-3-sulfonyl)-6-(dimethylamino)-1-benzofuran-2-carboxamide<br>LC-MS (method 10): $R_t$ = 1.00 min; MS (ESIpos): m/z = 394 [M + H]$^+$ |

TABLE 8-continued examples 153-165

| Example | Structure, IUPAC-Name and analytics |
|---|---|
| 155 | 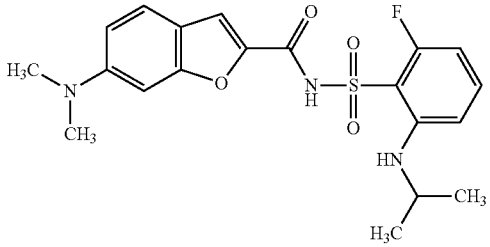
6-(Dimethylamino)-N-{2-fluoro-6-[(propan-2-yl)amino]benzene-1-sulfonyl}-1-benzofuran-2-carboxamide
LC-MS (method 10): $R_t$ = 1.34 min; MS (ESIpos): m/z = 420 [M + H]$^+$ |
| 156 | 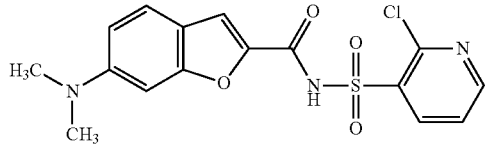
N-(2-chloropyridine-3-sulfonyl)-6-(dimethylamino)-1-benzofuran-2-carboxamide
LC-MS (method 10): $R_t$ = 0.88 min; MS (ESIpos): m/z = 380 [M + H]$^+$ |
| 157 | 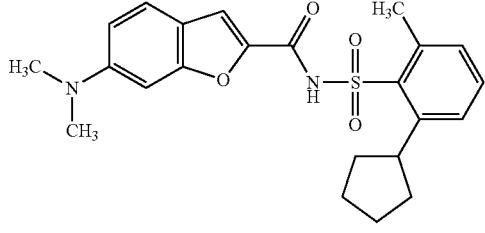
N-(2-Cyclopentyl-6-methylbenzene-1-sulfonyl)-6-(dimethylamino)-1-benzofuran-2-carboxamide
LC-MS (Method 10): $R_t$ = 1.44 min; MS (ESIpos): m/z = 427 [M + H]$^+$ |
| 158 | 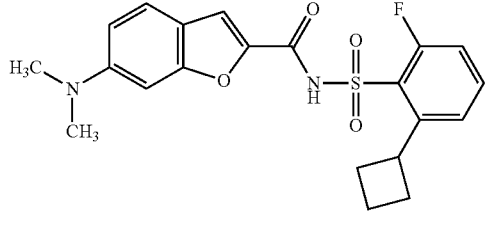
N-(2-Cyclobutyl-6-fluorobenzene-1-sulfonyl)-6-(dimethylamino)-1-benzofuran-2-carboxamide
LC-MS (method 10): $R_t$ = 1.33 min; MS (ESIpos): m/z = 417 [M + H]$^+$ |

TABLE 8-continued examples 153-165

| Example | Structure, IUPAC-Name and analytics |
|---|---|
| 159 | 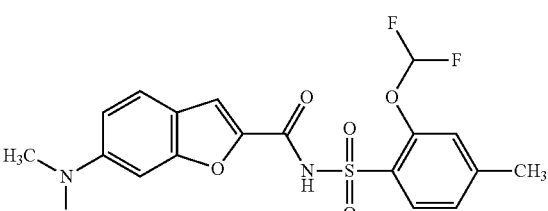
N-[2-(difluoromethoxy)-4-methylbenzene-1-sulfonyl]-6-(dimethylamino)-1-benzofuran-2-carboxamide
LC-MS (method 10): $R_t$ = 1.21 min; MS (ESIpos): m/z = 425 [M + H]$^+$ |
| 160 | 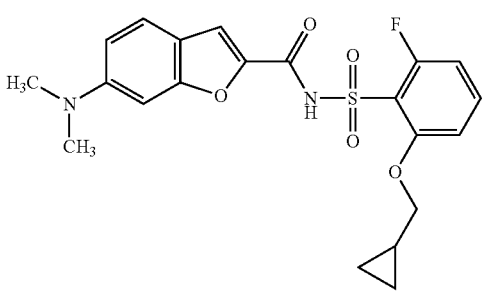
N-[2-(Cyclopropylmethoxy)-6-fluorobenzene-1-sulfonyl]-6-(dimethylamino)-1-benzofuran-2-carboxamide
LC-MS (method 10): $R_t$ = 1.23 min; MS (ESIpos): m/z = 433 [M + H]$^+$ |
| 161 | 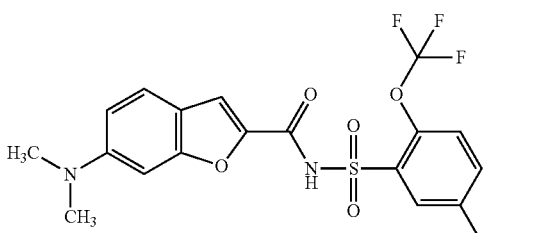
6-(Dimethylamino)-N-[5-(hydroxymethyl)-2-(trifluoromethoxy)benzene-1-sulfonyl]-1-benzofuran-2-carboxamide
LC-MS (method 10): $R_t$ = 1.23 min; MS (ESIpos): m/z = 459 [M + H]$^+$ |
| 162 | 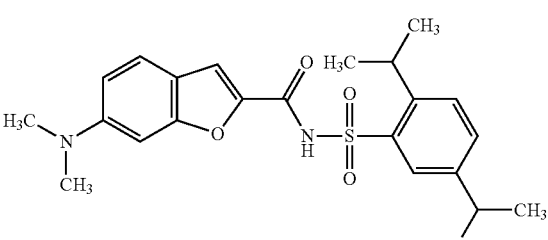
6-(Dimethylamino)-N-[2,5-di(propan-2-yl)benzene-1-sulfonyl]-1-benzofuran-2-carboxamide
LC-MS (method 10): $R_t$ = 1.45 min; MS (ESIpos): m/z = 429 [M + H]$^+$ |

TABLE 8-continued examples 153-165

| Example | Structure, IUPAC-Name and analytics |
|---|---|
| 163 | 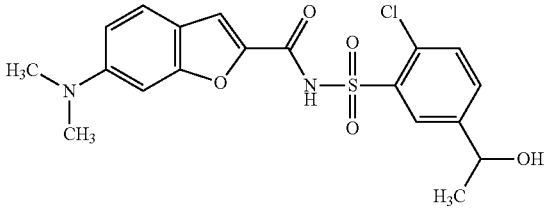
N-[2-Chloro-5-(1-hydroxyethyl)benzene-1-sulfonyl]-6-(dimethylamino)-1-benzofuran-2-carboxamide
LC-MS (method 10): $R_t$ = 1.21 min; MS (ESIpos): m/z = 423 [M + H]$^+$ |
| 164 | 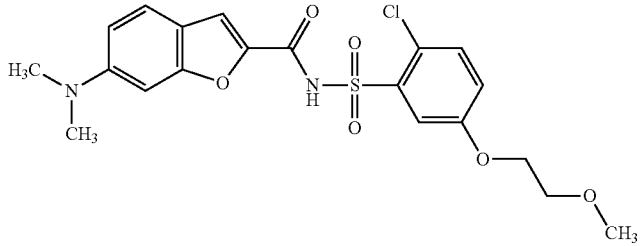
N-[2-Chloro-5-(2-methoxyethoxy)benzene-1-sulfonyl]-6-(dimethylamino)-1-benzofuran-2-carboxamide
LC-MS (method 10): $R_t$ = 1.17 min; MS (ESIpos): m/z = 453 [M + H]$^+$ |
| 165 | 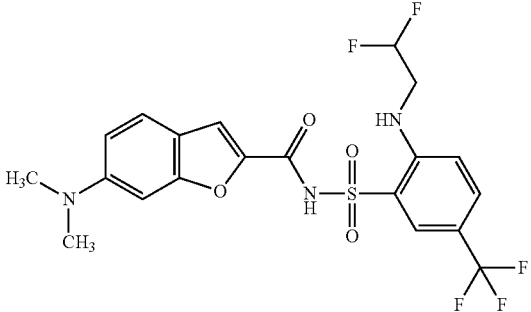
N-{2-[(2,2-difluoroethyl)amino]-5-(trifluoromethyl)benzene-1-sulfonyl}-6-(dimethylamino)-1-benzofuran-2-carboxamide
LC-MS (method 10): $R_t$ = 1.34 min; MS (ESIpos): m/z = 492 [M + H]$^+$ |

Example 166

N-(5-Aminoquinoline-8-sulfonyl)-6-(dimethylamino)-1-benzofuran-2-carboxamide

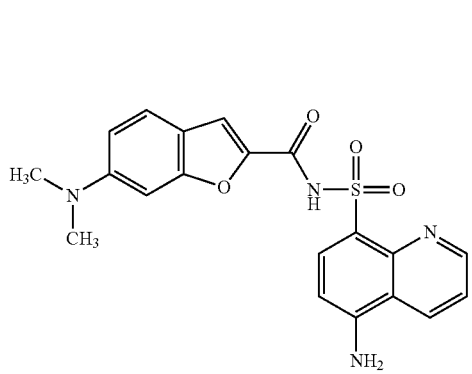 [SMILES: CN(C)c1ccc2cc(C(=O)NS(=O)(=O)c3ccc(N)c4cccnc34)oc2c1]

6-(Dimethylamino)-N-(5-nitroquinoline-8-sulfonyl)-1-benzofuran-2-carboxamide (92, 340 mg, 772 μmol) was dissolved in EtOH (34 mL) and Tin(II)chloride (697 mg, 3.09 mmol) was added. The reaction mixture was heated to reflux for 4 d. After reaction completion, Water was added to the reaction mixture. The mixture was basified with sodium carbonate solution (w=10%) to pH 9 and afterwards extracted 3 times with DCM. The combined organic layers were dried over a hydrophobic filter and evaporated and purified by acidic HPLC to give the title compound as a yellow solid (15 mg, 4% yield). $^1$H-NMR (400 MHz, DMSO-$d_6$) δ [ppm]: 2.099 (0.40), 2.323 (0.52), 2.327 (0.73), 2.332 (0.52), 2.518 (2.32), 2.523 (1.61), 2.539 (0.84), 2.665 (0.53), 2.669 (0.74), 2.673 (0.52), 2.933 (1.72), 2.955 (16.00), 6.724 (2.29), 6.731 (1.24), 6.744 (1.80), 6.810 (0.81), 6.815 (0.72), 6.833 (0.85), 6.838 (0.74), 7.151 (1.59), 7.443 (0.81), 7.454 (0.80), 7.464 (0.80), 7.475 (0.76), 7.516 (1.51), 7.539 (1.38), 7.925 (1.40), 8.158 (1.90), 8.179 (1.68), 8.634 (0.72), 8.638 (0.76), 8.656 (0.71), 8.659 (0.69), 8.892 (0.97), 8.896 (0.94), 8.903 (0.95), 8.907 (0.85); LC-MS (method 4): $R_t$=0.71 min; MS (ESIpos): m/z=411 [M+H]$^+$.

Example 167

N-[2-(2-Aminoethoxy)benzene-1-sulfonyl]-6-(dimethylamino)-1-benzofuran-2-carboxamide hydrogen chloride (1/1)

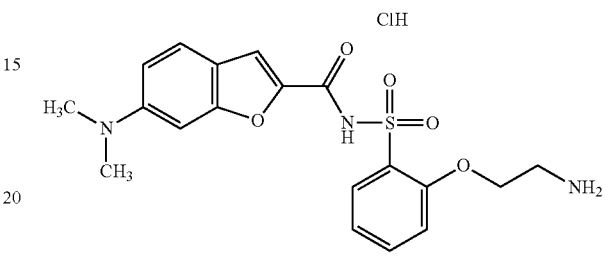

Aforementioned tert-butyl [2-(2-{[6-(dimethylamino)-1-benzofuran-2-carbonyl]sulfamoyl}phenoxy)ethyl] carbamate (119, 50.0 mg, 99.3 μmol) was suspended in HCl/dioxan (4 M, 1 mL) solution and the suspension was stirred for 1 h at RT. After reaction completion, the reaction mixture was solubilized in DMF (1 mL) and direction purified using HPLC to give the desired boc-deprotected product as yellow crystals (13.8 mg, 29% yield). $^1$H-NMR (400 MHz, DMSO-$d_6$) δ [ppm]: 1.137 (1.15), 2.084 (10.21), 2.115 (0.51), 2.326 (0.56), 2.331 (0.40), 2.518 (2.10), 2.522 (1.42), 2.668 (0.56), 2.673 (0.40), 2.947 (16.00), 3.156 (0.71), 3.168 (1.07), 3.179 (0.72), 4.193 (0.92), 4.206 (1.33), 4.217 (0.87), 5.759 (0.57), 6.756 (0.75), 6.761 (0.81), 6.778 (0.79), 6.784 (0.86), 6.865 (1.24), 7.027 (2.34), 7.084 (0.51), 7.086 (0.53), 7.105 (1.07), 7.124 (0.69), 7.130 (0.97), 7.150 (1.11), 7.401 (1.61), 7.422 (1.55), 7.427 (0.63), 7.431 (0.56), 7.447 (0.72), 7.450 (0.70), 7.466 (0.41), 7.772 (0.98), 7.776 (0.97), 7.792 (0.93), 7.795 (0.83), 8.137 (1.04), 8.266 (0.44); LC-MS (Method 1): $R_t$=0.72 min; MS (ESIpos): m/z=404 [M+H]$^+$.

Example 168

6-(Dimethylamino)-N-(2-{2-[2-(2-{2-[(7-nitro-2,1,3-benzoxadiazol-4-yl)amino]ethoxy}ethoxy)ethoxy]ethoxy}benzene-1-sulfonyl)-1-benzofuran-2-carboxamide

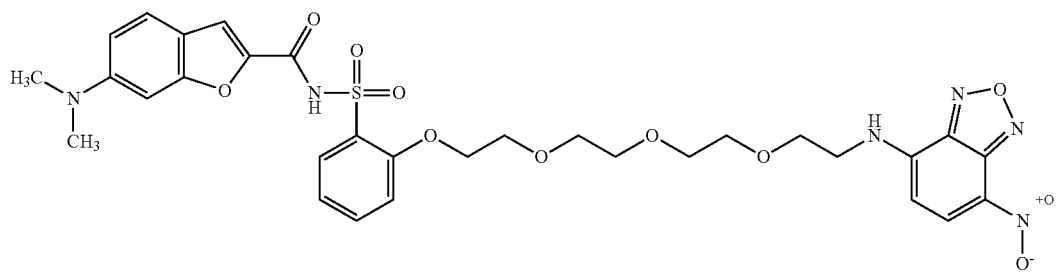

aforementioned N-[2-(2-{2-[2-(2-Aminoethoxy)ethoxy]ethoxy}ethoxy)benzene-1-sulfonyl]-6-(dimethylamino)-1-benzofuran-2-carboxamide hydrogen chloride (1/1) (INT-46, 5.00 mg, 8.74 µmol) was dissolved in a water/dioxane solution (1:1; 500 µL) and sodium carbonate (4 mg, 35 µmol) and 4-chloro-7-nitro-2,1,3-benzoxadiazole (3.49 mg, 17.5 µmol) were successively added. The reaction mixture was stirred at RT for 19 h. After reaction completion, the dark reaction mixture was filtrated and purified using HPLC to give the desired product as red crystals (3.00 mg, 44% yield). $^1$H-NMR (400 MHz, DMSO-d$_6$) δ [ppm]: 0.854 (0.42), 1.139 (3.29), 1.235 (2.30), 2.086 (16.00), 2.117 (1.40), 2.334 (1.33), 2.520 (7.51), 2.525 (4.60), 2.676 (1.32), 2.940 (4.73), 3.274 (0.56), 3.287 (0.58), 3.368 (0.55), 3.445 (0.41), 3.458 (0.62), 3.472 (0.50), 3.647 (0.43), 3.658 (0.53), 3.674 (0.45), 3.685 (0.47), 3.795 (3.21), 4.562 (0.52), 5.295 (0.82), 6.740 (0.44), 7.010 (0.69), 7.032 (0.72), 7.473 (0.57), 7.493 (0.43), 7.639 (0.75), 7.661 (0.67); LC-MS (Method 1): R$_t$=1.24 min; MS (ESIpos): m/z=699 [M+H]$^+$.

Example 169

6-(Dimethylamino)-N-(2-ethoxy-3-fluoro-phenyl)sulfonyl-benzofuran-2-carboxamide

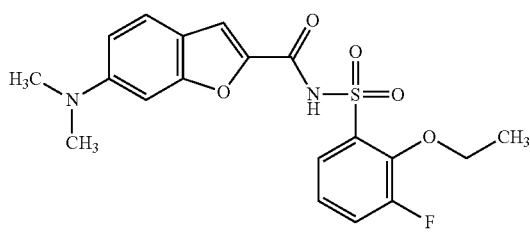 [SMILES: CCOc1c(F)cccc1S(=O)(=O)NC(=O)c1cc2ccc(N(C)C)cc2o1]

To a room temperature stirred solution of 6-(dimethylamino)benzofuran-2-carboxylic acid (20.5 mg, 0.10 mmol, 1.00 eq.) in anhydrous tetrahydrofuran (0.50 mL, 0.20 M) was added carbonyldiimidazole (19.5 mg, 0.12 mmol, 1.20 eq.). After stirring for 1 hour, 2-ethoxy-3-fluoro-benzenesulfonamide (24.1 mg, 0.11 mmol, 1.10 eq.) and 1,8-diazabicyclo[5.4.0]undec-7-ene (20.0 µL, 0.14 mmol, 1.40 eq.) were sequentially added. The resulting mixture was stirred at room temperature for 16 h and then concentrated down under reduced pressure. The residue was purified by reverse phase preparative column chromatography (Waters XBridge PREP C$_{18}$, 5 µM OBD, 30×150 mm, 50-58% acetonitrile/water gradient buffered with 0.1% formic acid) to give the title compound as a yellow solid (21.0 mg). $^1$H NMR (400 MHz, DMSO-d$_6$) δ 12.61 (s, 1H), 7.89-7.84 (m, 1H), 7.75 (d, 1H), 7.66-7.53 (m, 2H), 7.35-7.25 (m, 1H), 6.90-6.82 (m, 1H), 6.80-6.75 (m, 1H), 4.19 (q, 2H), 2.99 (s, 6H), 1.33 (t, 3H); LC-MS (method 7): R$_t$=2.74 min; MS (ESIpos): m/z=407 [M+H]$^+$ Example 170

6-(Dimethylamino)-N-(2-ethoxy-5-sec-butyl-phenyl)sulfonyl-benzofuran-2-carboxamide (rac)

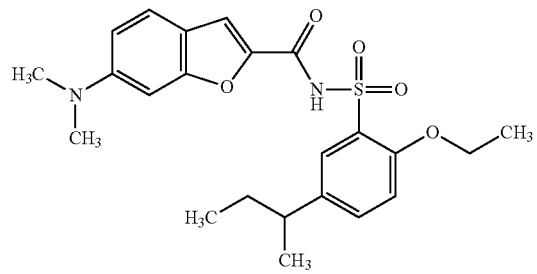 [SMILES: CCOc1ccc(C(C)CC)cc1S(=O)(=O)NC(=O)c1cc2ccc(N(C)C)cc2o1]

To a room temperature stirred solution of 6-(dimethylamino)benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 2-ethoxy-5-sec-butyl-benzenesulfonamide (113 mg, 0.44 mmol, 1.10 eq.) and 1,8-diazabicyclo[5.4.0]undec-7-ene (80.0 µL, 0.56 mmol, 1.40 eq.) were sequentially added. The resulting mixture was stirred at room temperature for 16 hours and then concentrated down under reduced pressure. The residue was purified by reverse phase preparative column chromatography (Waters XBridge PREP C$_{18}$, 5 µM OBD, 30×150 mm, 62-70% acetonitrile/water gradient buffered with 0.1% formic acid) to give the title compound as a yellow solid (124 mg). $^1$H NMR (400 MHz, DMSO-d$_6$) δ 12.23 (s, 1H), 7.94 (s, 1H), 7.71-7.66 (m, 1H), 7.56 (d, 1H), 7.50-7.42 (m, 1H), 7.13 (d, 1H), 6.90-6.82 (m, 1H), 6.79-6.73 (m, 1H), 4.12 (q, 2H), 2.98 (s, 6H), 2.67 (h, 1H), 1.62-1.48 (m, 2H), 1.28-1.17 (m, 6H), 0.79 (t, 3H); LC-MS (method 7): R$_t$=3.21 min; MS (ESIpos): m/z=445 [M+H]$^+$.

Example 171

6-(Dimethylamino)-N-(2-ethoxy-4-fluoro-phenyl)sulfonyl-benzofuran-2-carboxamide

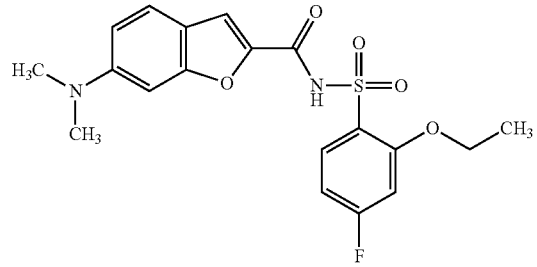 [SMILES: CCOc1cc(F)ccc1S(=O)(=O)NC(=O)c1cc2ccc(N(C)C)cc2o1]

To a room temperature stirred solution of 6-(dimethylamino)benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 2-ethoxy-4-fluoro-benzenesulfonamide (96.5 mg, 0.44 mmol, 1.10 eq.) and 1,8-diazabicyclo[5.4.0]undec-7-ene (80.0 µL, 0.56 mmol, 1.40 eq.) were sequentially added. The resulting mixture was stirred at room temperature for 16 hours and then concentrated down under reduced pressure. The residue was purified by reverse phase preparative column chromatography (Waters XBridge PREP $C_{18}$, 5 μM OBD, 30×150 mm, 49-57% acetonitrile/water gradient buffered with 0.1% formic acid) to give the title compound as a yellow solid (119 mg). $^1$H NMR (400 MHz, DMSO-$d_6$) δ 12.36 (s, 1H), 8.00-7.90 (m, 2H), 7.60-7.53 (m, 1H), 7.19-7.11 (m, 1H), 7.02-6.92 (m, 1H), 6.90-6.82 (m, 1H), 6.80-6.74 (m, 1H), 4.17 (q, 2H), 3.01-2.96 (m, 6H), 1.29-1.20 (m, 3H); LC-MS (method 7): $R_t$=2.70 min; MS (ESIpos): m/z=407 [M+H]$^+$.

Example 172

6-(Dimethylamino)-N-[2-ethoxy-5-(trifluoromethyl)phenyl]sulfonyl-benzofuran-2-carboxamide

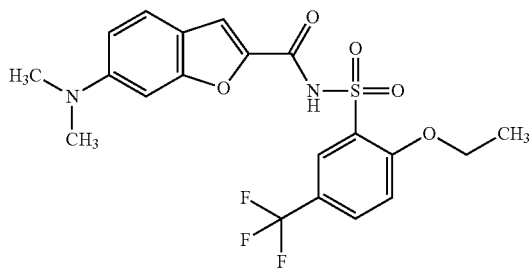 [SMILES: CCOc1ccc(C(F)(F)F)cc1S(=O)(=O)NC(=O)c1cc2ccc(N(C)C)cc2o1]

To a room temperature stirred solution of 6-(dimethylamino)benzofuran-2-carboxylic acid (10.3 mg, 0.05 mmol, 1.00 eq.) in anhydrous tetrahydrofuran (0.25 mL, 0.20 M) was added carbonyldiimidazole (9.73 mg, 0.06 mmol, 1.20 eq.). After stirring for 1 hour, 2-ethoxy-5-(trifluoromethyl)benzenesulfonamide (14.8 mg, 0.05 mmol, 1.10 eq.) and 1,8-diazabicyclo[5.4.0]undec-7-ene (10.0 μL, 0.07 mmol, 1.40 eq.) were sequentially added. The resulting mixture was stirred at room temperature for 16 hours and then concentrated down under reduced pressure. The residue was purified by reverse phase preparative column chromatography (Waters XBridge PREP $C_{18}$, 5 μM OBD, 19×250 mm, 55-63% acetonitrile/water gradient buffered with 0.1% formic acid) to give the title compound as a yellow solid (6.38 mg). $^1$H NMR (400 MHz, DMSO-$d_6$) δ 8.15-8.09 (m, 1H), 8.02-7.97 (m, 1H), 7.92-7.87 (m, 1H), 7.60-7.53 (m, 1H), 7.46-7.39 (m, 1H), 6.92-6.82 (m, 1H), 6.79-6.73 (m, 1H), 4.32-4.22 (m, 2H), 3.05-2.96 (m, 6H), 1.26 (t, 3H); LC-MS (method 7): $R_t$=2.94 min; MS (ESIpos): m/z=457 [M+H]$^+$ Example 173

6-(Dimethylamino)-N-(2-ethoxy-5-fluoro-phenyl)sulfonyl-benzofuran-2-carboxamide

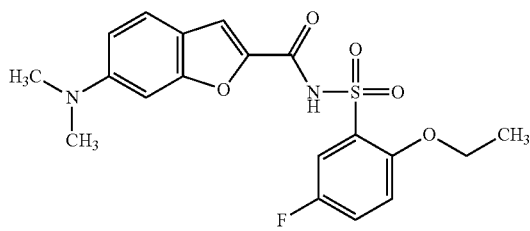 [SMILES: CCOc1ccc(F)cc1S(=O)(=O)NC(=O)c1cc2ccc(N(C)C)cc2o1]

To a room temperature stirred solution of 6-(dimethylamino)benzofuran-2-carboxylic acid (41.0 mg, 0.20 mmol, 1.00 eq.) in anhydrous tetrahydrofuran (1.00 mL, 0.20 M) was added carbonyldiimidazole (38.9 mg, 0.24 mmol, 1.20 eq.). After stirring for 1 hour, 2-ethoxy-5-fluoro-benzenesulfonamide (48.2 mg, 0.22 mmol, 1.10 eq.) and 1,8-diazabicyclo[5.4.0]undec-7-ene (40.0 μL, 0.28 mmol, 1.40 eq.) were sequentially added. The resulting mixture was stirred at room temperature for 19 hours and then concentrated down under reduced pressure. The residue was purified by reverse phase preparative column chromatography (Waters XBridge PREP $C_{18}$, 5 μM OBD, 30×150 mm, 48-56% acetonitrile/water gradient buffered with 0.1% formic acid) to give the title compound as a yellow solid (46.0 mg). $^1$H NMR (400 MHz, DMSO-$d_6$) δ 12.48 (s, 1H), 7.92 (s, 1H), 7.66 (dd, 1H), 7.60-7.47 (m, 2H), 7.30-7.21 (m, 1H), 6.90-6.82 (m, 1H), 6.80-6.74 (m, 1H), 4.14 (q, 2H), 2.99 (s, 6H), 1.23 (t, 3H); LC-MS (method 7): $R_t$=2.68 min; MS (ESIpos): m/z=407 [M+H]$^+$.

Example 174

6-(Dimethylamino)-N-(2-ethoxy-5-phenoxy-phenyl)sulfonyl-benzofuran-2-carboxamide

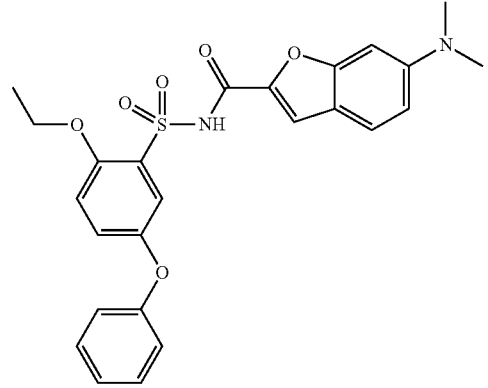 [SMILES: CCOc1ccc(Oc2ccccc2)cc1S(=O)(=O)NC(=O)c1cc2ccc(N(C)C)cc2o1]

To a room temperature stirred solution of 6-(dimethylamino)benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 2-ethoxy-5-phenoxy-benzenesulfonamide (129 mg, 0.44 mmol, 1.10 eq.) and 1,8-diazabicyclo[5.4.0]undec-7-ene (80.0 μL, 0.56 mmol, 1.40 eq.) were sequentially added. The resulting mixture was stirred at room temperature for 16 h and then concentrated under reduced pressure. The residue was purified by reverse phase preparative column chromatography (Waters XBridge PREP $C_{18}$, 5 μM OBD, 30×150 mm, 60-68% acetonitrile/water gradient buffered with 0.1% formic acid) to give the title compound as a yellow solid (122 mg). $^1$H NMR (400 MHz, DMSO-$d_6$) δ 12.43 (s, 1H), 7.96 (s, 1H), 7.58 (d, 1H), 7.50 (d, 1H), 7.47-7.34 (m, 3H), 7.30-7.23 (m, 1H), 7.17 (t, 1H), 7.08-7.01 (m, 2H), 6.91-6.83 (m, 1H), 6.82-6.76 (m, 1H), 4.16 (q, 2H), 3.00 (s, 6H), 1.26 (t, 3H); LC-MS (method 7): $R_t$=3.14 min; MS (ESIpos): m/z=481 [M+H]$^+$

Example 175

6-(Dimethylamino)-N-[2-ethoxy-5-(trifluoromethoxy)phenyl]sulfonyl-benzofuran-2-carboxamide

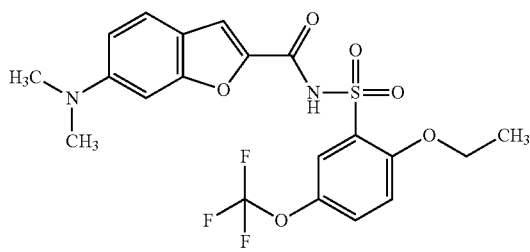 [SMILES: CCOc1ccc(OC(F)(F)F)cc1S(=O)(=O)NC(=O)c1cc2ccc(N(C)C)cc2o1]

To a room temperature stirred solution of 6-(dimethylamino)benzofuran-2-carboxylic acid (8.21 mg, 0.04 mmol, 1.00 eq.) in anhydrous tetrahydrofuran (0.200 mL, 0.20 M) was added carbonyldiimidazole (7.78 mg, 0.05 mmol, 1.20 eq.). After stirring for 1 hour, 2-ethoxy-5-(trifluoromethoxy)benzenesulfonamide (12.6 mg, 0.04 mmol, 1.10 eq.) and 1,8-diazabicyclo[5.4.0]undec-7-ene (10.0 μL, 0.06 mmol, 1.40 eq.) were sequentially added. The resulting mixture was stirred at room temperature overnight and then concentrated under reduced pressure. The residue was purified by reverse phase preparative column chromatography (Waters XBridge PREP $C_{18}$, 5 μM OBD, 30×150 mm, 62-70% acetonitrile/water gradient buffered with 0.1% formic acid) to give the title compound as a yellow solid (0.08 mg). $^1$H NMR (400 MHz, DMSO-$d_6$) δ 12.41 (s, 1H), 7.88 (s, 1H), 7.76 (d, 1H), 7.57 (d, 1H), 7.50-7.43 (m, 1H), 7.37 (d, 2H), 7.24-7.08 (m, 4H), 6.88 (dd, 1H), 6.79-6.74 (m, 1H), 5.29 (s, 2H), 3.00 (s, 6H), 2.99-2.87 (m, 1H), 1.20 (d, 6H); LC-MS (method 7): $R_t$=3.01 min; MS (ESIpos): m/z=473 [M+H]$^+$.

Example 176

N-(2-Benzyloxy-5-isopropyl-phenyl)sulfonyl-6-(dimethylamino)benzofuran-2-carboxamide

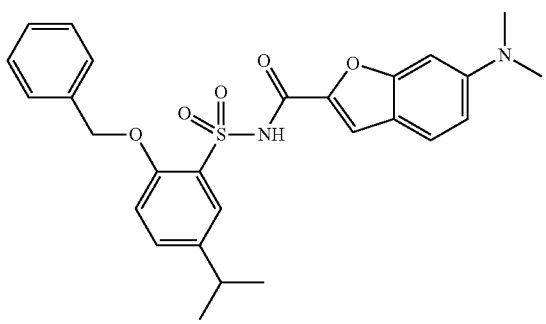 [SMILES: CC(C)c1ccc(OCc2ccccc2)c(S(=O)(=O)NC(=O)c2cc3ccc(N(C)C)cc3o2)c1]

To a room temperature stirred solution of 6-(dimethylamino)-4-fluoro-benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 2-benzyloxy-5-isopropyl-benzenesulfonamide (134 mg, 0.44 mmol, 1.10 eq.) and 1,8-diazabicyclo[5.4.0]undec-7-ene (80.0 μL, 0.56 mmol, 1.40 eq.) were sequentially added. The resulting mixture was stirred at room temperature over two hours and then concentrated under reduced pressure. The residue was purified by reverse phase preparative column chromatography (Waters XBridge PREP $C_{18}$, 5 μM OBD, 30×150 mm, 64-72% acetonitrile/water gradient buffered with 0.1% formic acid) to give the title compound as a yellow solid (93 mg). $^1$H NMR (400 MHz, DMSO-$d_6$) δ 12.41 (s, 1H), 7.88 (s, 1H), 7.76 (d, 1H), 7.57 (d, 1H), 7.50-7.43 (m, 1H), 7.37 (d, 2H), 7.24-7.08 (m, 4H), 6.88 (dd, 1H), 6.79-6.74 (m, 1H), 5.29 (s, 2H), 3.00 (s, 6H), 2.99-2.87 (m, 1H), 1.20 (d, 6H); LC-MS (method 7): $R_t$=3.30 min; MS (ESIpos): m/z=493 [M+H]$^+$.

Example 177

N-[2-(cyclopropylmethoxy)-5-isopropyl-phenyl]sulfonyl-6-(dimethylamino)benzofuran-2-carboxamide

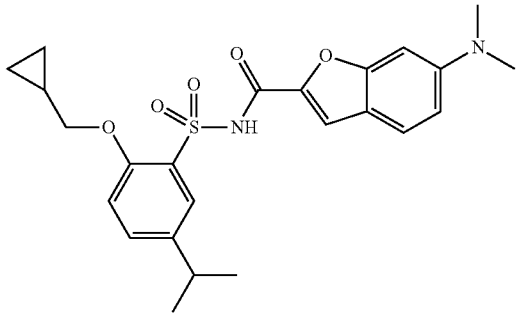 [SMILES: CC(C)c1ccc(OCC2CC2)c(S(=O)(=O)NC(=O)c2cc3ccc(N(C)C)cc3o2)c1]

To a room temperature stirred solution of 6-(dimethylamino)benzofuran-2-carboxylic acid (34.9 mg, 0.17 mmol, 1.00 eq.) in anhydrous tetrahydrofuran (0.85 mL, 0.20 M) was added carbonyldiimidazole (33.1 mg, 0.20 mmol, 1.20 eq.). After stirring for 1 hour, 2-(cyclopropylmethoxy)-5-isopropyl-benzenesulfonamide (50.4 mg, 0.19 mmol, 1.10 eq.) and 1,8-diazabicyclo[5.4.0]undec-7-ene (40.0 μL, 0.24 mmol, 1.40 eq.) were sequentially added. The resulting mixture was stirred at room temperature over five hours and then concentrated under reduced pressure. The residue was purified by reverse phase preparative column chromatography (Waters XBridge PREP $C_{18}$, 5 μM OBD, 30×150 mm, 62-70% acetonitrile/water gradient buffered with 0.1% formic acid) to give the title compound as a yellow solid (57 mg). $^1$H NMR (400 MHz, DMSO-$d_6$) δ 12.20 (s, 1H), 7.93 (s, 1H), 7.76-7.71 (m, 1H), 7.56 (d, 1H), 7.53-7.46 (m, 1H), 7.14 (d, 1H), 6.90-6.82 (m, 1H), 6.79-6.73 (m, 1H), 3.93 (d, 2H), 3.01-2.96 (m, 6H), 1.25-1.19 (m, 6H), 0.38-0.29 (m, 2H), 0.20-0.12 (m, 2H); LC-MS (method 7): $R_t$=3.22 min; MS (ESIpos): m/z=457 [M+H]$^+$.

Example 178

6-(Dimethylamino)-N-[5-isopropyl-2-(2,2,2-trifluoroethoxy)phenyl]sulfonyl-benzofuran-2-carboxamide

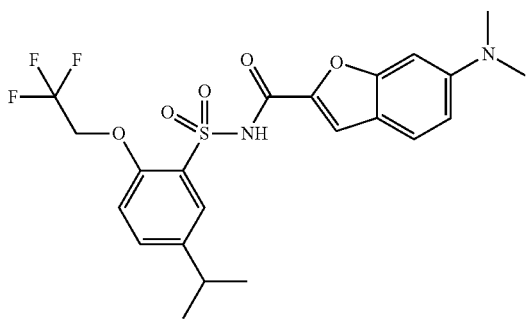 [SMILES: CC(C)c1ccc(OCC(F)(F)F)c(S(=O)(=O)NC(=O)c2cc3ccc(N(C)C)cc3o2)c1]

To a room temperature stirred solution of 6-(dimethylamino)benzofuran-2-carboxylic acid (14.8 mg, 0.07 mmol, 1.00 eq.) in anhydrous tetrahydrofuran (0.36 mL, 0.20 M) was added carbonyldiimidazole (14.0 mg, 0.09 mmol, 1.20 eq.). After stirring for 1 hour, 5-isopropyl-2-(2,2,2-trifluoroethoxy)benzenesulfonamide (23.6 mg, 0.08 mmol, 1.10 eq.) and 1,8-diazabicyclo[5.4.0]undec-7-ene (20.0 µL, 0.10 mmol, 1.40 eq.) were sequentially added. The resulting mixture was stirred at room temperature over four hours and then concentrated under reduced pressure. The residue was purified by reverse phase preparative column chromatography (Waters XBridge PREP $C_{18}$, 5 µM OBD, 30×150 mm, 59-67% acetonitrile/water gradient buffered with 0.1% formic acid) to give the title compound as a yellow solid (19.0 mg). $^1$H NMR (400 MHz, DMSO-$d_6$) δ 12.35 (s, 1H), 7.87 (s, 1H), 7.79 (d, 1H), 7.62-7.52 (m, 2H), 7.27 (d, 1H), 6.85 (dd, 1H), 6.78-6.73 (m, 1H), 4.87 (q, 2H), 3.01-2.96 (m, 7H), 1.23 (d, 6H); LC-MS (method 7): $R_t$=3.10 min; MS (ESIpos): m/z=485 [M+H]$^+$.

Example 179

N-[(2-(Benzyloxy)-5-(tert-butyl)phenyl)sulfonyl]-6-(dimethylamino)benzofuran-2-carboxamide

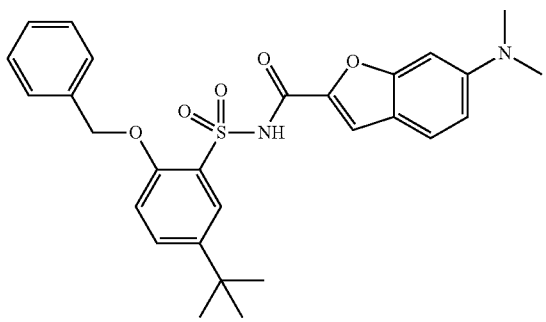 [SMILES: CN(C)c1ccc2cc(C(=O)NS(=O)(=O)c3cc(C(C)(C)C)ccc3OCc3ccccc3)oc2c1]

To a room temperature stirred solution of 6-(dimethylamino)benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 2-benzyloxy-5-tert-butyl-benzenesulfonamide (141 mg, 0.44 mmol, 1.10 eq.) and 1,8-diazabicyclo[5.4.0]undec-7-ene (80.0 µL, 0.56 mmol, 1.40 eq.) were sequentially added. The resulting mixture was stirred at room temperature for 15 hours and then concentrated under reduced pressure. The residue was purified by reverse phase preparative column chromatography (Waters XBridge PREP $C_{18}$, 5 µM OBD, 30×150 mm, 64-72% acetonitrile/water gradient buffered with 0.1% formic acid) to give the title compound as a yellow solid (130 mg). $^1$H NMR (400 MHz, DMSO-$d_6$) δ 12.48 (s, 1H), 7.92-7.86 (m, 2H), 7.65-7.54 (m, 2H), 7.41-7.33 (m, 2H), 7.24-7.07 (m, 4H), 6.87 (dd, 1H), 6.79-6.74 (m, 1H), 5.30 (s, 2H), 3.00 (s, 6H), 1.28 (s, 9H); LC-MS (method 7): $R_t$=3.29 min; MS (ESIneg): m/z=505 [M−H]$^-$.

Example 180

N-((5-(tert-butyl)-2-(cyclopropylmethoxy)phenyl)sulfonyl)-6-(dimethylamino)benzofuran-2-carboxamide

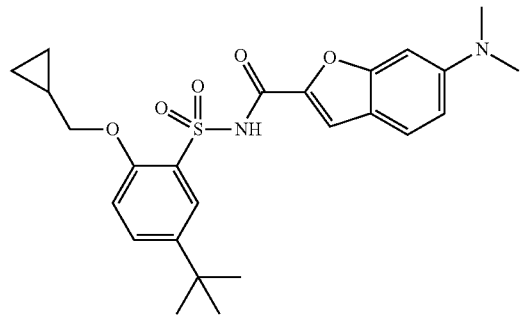 [SMILES: CN(C)c1ccc2cc(C(=O)NS(=O)(=O)c3cc(C(C)(C)C)ccc3OCC3CC3)oc2c1]

To a room temperature stirred solution of 6-(dimethylamino)benzofuran-2-carboxylic acid (92.3 mg, 0.45 mmol, 1.00 eq.) in anhydrous tetrahydrofuran (2.25 mL, 0.20 M) was added carbonyldiimidazole (87.6 mg, 0.54 mmol, 1.20 eq.). After stirring for 1 h, 5-tert-butyl-2-(cyclopropylmethoxy)benzenesulfonamide (140 mg, 0.49 mmol, 1.10 eq.) and 1,8-diazabicyclo[5.4.0]undec-7-ene (90.0 µL, 0.63 mmol, 1.40 eq.) were sequentially added. The resulting mixture was stirred at room temperature for 15 hours and then concentrated under reduced pressure. The residue was purified by reverse phase preparative column chromatography (Waters XBridge PREP $C_{18}$, 5 µM OBD, 30×150 mm, 62-70% acetonitrile/water gradient buffered with 0.1% formic acid) to give the title compound as a yellow solid (134 mg). 1H NMR (400 MHz, DMSO-$d_6$) δ 12.26 (s, 1H), 7.94 (s, 1H), 7.86 (d, J=2.6 Hz, 1H), 7.69-7.61 (m, 1H), 7.56 (d, J=8.8 Hz, 1H), 7.14 (d, 1H), 6.89-6.82 (m, 1H), 6.78-6.73 (m, 1H), 3.94 (d, 2H), 2.98 (s, 6H), 1.30 (s, 9H), 1.25-1.12 (m, 1H), 0.37-0.28 (m, 2H), 0.23-0.11 (m, 2H); LC-MS (method 7): $R_t$=3.21 min; MS (ESIpos): m/z=471 [M+H]$^+$.

Example 181

N-[(5-(tert-butyl)-2-(2,2,2-trifluoroethoxy)phenyl)sulfonyl]-6-(dimethylamino)benzofuran-2-carboxamide

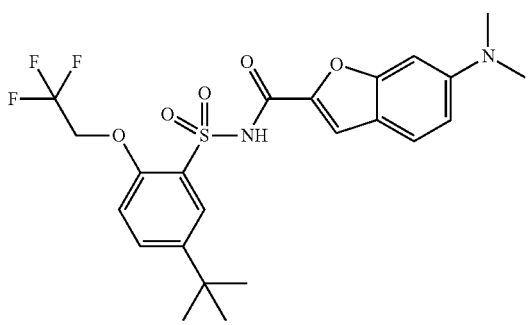 [SMILES: CN(C)c1ccc2cc(C(=O)NS(=O)(=O)c3cc(C(C)(C)C)ccc3OCC(F)(F)F)oc2c1]

To a room temperature stirred solution of 6-(dimethylamino)benzofuran-2-carboxylic acid (18.5 mg, 0.09 mmol, 1.00 eq.) in anhydrous tetrahydrofuran (0.45 mL, 0.20 M) was added carbonyldiimidazole (17.5 mg, 0.11 mmol, 1.20 eq.). After stirring for 1 h, 5-tert-butyl-2-(2,2,2-trifluoroethoxy)benzenesulfonamide (30.8 mg, 0.10 mmol, 1.10 eq.) and 1,8-diazabicyclo[5.4.0]undec-7-ene (20.0 µL, 0.13 mmol, 1.40 eq.) were sequentially added. The resulting mixture was stirred at room temperature for 15 hours and then concentrated under reduced pressure. The residue was purified by reverse phase preparative column chromatography (Waters XBridge PREP $C_{18}$, 5 µM OBD, 30×150 mm, 59-67% acetonitrile/water gradient buffered with 0.1% formic acid) to give the title compound as a yellow solid (18.2 mg). $^1$H NMR (400 MHz, DMSO-$d_6$) δ 12.41 (s, 1H), 7.94-7.87 (m, 2H), 7.77-7.69 (m, 1H), 7.60-7.52 (m, 1H), 7.31-7.24 (m, 1H), 6.89-6.81 (m, 1H), 6.78-6.72 (m, 1H), 4.94-4.83 (m, 2H), 2.98 (s, 6H), 1.31 (s, 9H); LC-MS (method 7): $R_t$=3.11 min; MS (ESIpos): m/z=499 [M+H]$^+$.

Example 182

N-[(5-(tert-butyl)-2-cyclobutoxyphenyl)sulfonyl]-6-(dimethylamino)benzofuran-2-carboxamide

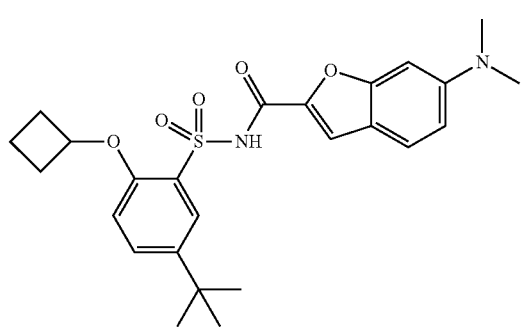 [SMILES: CN(C)c1ccc2cc(C(=O)NS(=O)(=O)c3cc(C(C)(C)C)ccc3OC3CCC3)oc2c1]

To a room temperature stirred solution of 6-(dimethylamino)benzofuran-2-carboxylic acid (92.3 mg, 0.45 mmol, 1.00 eq.) in anhydrous tetrahydrofuran (2.25 mL, 0.20 M) was added carbonyldiimidazole (87.6 mg, 0.54 mmol, 1.20 eq.). After stirring for 1 hour, 5-tert-butyl-2-(cyclobutoxy)benzenesulfonamide (140 mg, 0.49 mmol, 1.10 eq.) and 1,8-diazabicyclo[5.4.0]undec-7-ene (90.0 µL, 0.63 mmol, 1.40 eq.) were sequentially added. The resulting mixture was stirred at room temperature for 15 h and then concentrated under reduced pressure. The residue was purified by reverse phase preparative column chromatography (Waters XBridge PREP $C_{18}$, 5 µM OBD, 30×150 mm, 63-71% acetonitrile/water gradient buffered with 0.1% formic acid) to give the title compound as a yellow solid (116 mg). $^1$H NMR (400 MHz, DMSO-$d_6$) δ 12.29 (s, 1H), 7.99 (s, 1H), 7.84 (d, 1H), 7.66-7.54 (m, 2H), 6.94 (d, 1H), 6.86 (dd1H), 6.79-6.73 (m, 1H), 4.81 (p, 1H), 2.98 (s, 6H), 2.34-2.21 (m, 2H), 2.04-1.89 (m, 2H), 1.57-1.36 (m, 2H), 1.29 (s, 9H); LC-MS (method 7): $R_t$=3.24 min; MS (ESIpos): m/z=471 [M+H]$^+$.

Example 183

N-((5-(tert-butyl)-2-isopropoxyphenyl)sulfonyl)-6-(dimethylamino)benzofuran-2-carboxamide

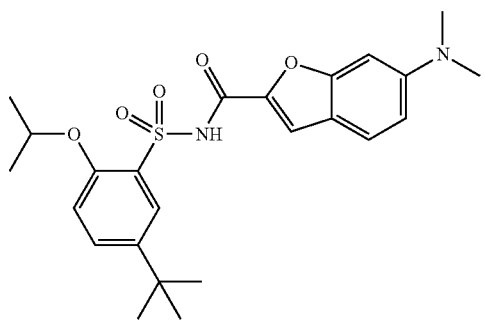 [SMILES: CC(C)Oc1ccc(C(C)(C)C)cc1S(=O)(=O)NC(=O)c1cc2ccc(N(C)C)cc2o1]

To a room temperature stirred solution of 6-(dimethylamino)benzofuran-2-carboxylic acid (92.3 mg, 0.45 mmol, 1.00 eq.) in anhydrous tetrahydrofuran (2.25 mL, 0.20 M) was added carbonyldiimidazole (87.6 mg, 0.54 mmol, 1.20 eq.). After stirring for 1 hour, 5-tert-butyl-2-isopropoxybenzenesulfonamide (134 mg, 0.49 mmol, 1.10 eq.) and 1,8-diazabicyclo[5.4.0]undec-7-ene (90.0 µL, 0.63 mmol, 1.40 eq.) were sequentially added. The resulting mixture was stirred at room temperature for 15 hours and then concentrated under reduced pressure. The residue was purified by reverse phase preparative column chromatography (Waters XBridge PREP $C_{18}$, 5 µM OBD, 30×150 mm, 61-69% acetonitrile/water gradient buffered with 0.1% formic acid) to give the title compound as a yellow solid (160 mg). $^1$H NMR (400 MHz, DMSO-$d_6$) δ 12.18 (s, 1H), 7.96 (s, 1H), 7.84 (d, 1H), 7.68-7.60 (m, 1H), 7.61-7.53 (m, 1H), 7.15 (d, 1H), 6.85 (dd, 1H), 6.78-6.73 (m, 1H), 4.80-4.69 (m, 1H), 2.98 (s, 6H), 1.30 (s, 9H), 1.16 (d, 6H); LC-MS (method 7): $R_t$=3.18 min; MS (ESIpos): m/z=459 [M+H]$^+$.

Example 184

N-((2-Cyclobutoxy-5-isopropylphenyl)sulfonyl)-6-(dimethylamino)benzofuran-2-carboxamide

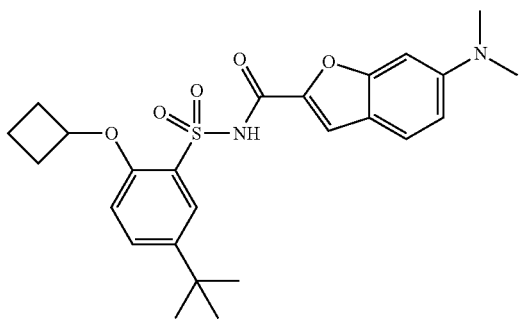 [SMILES: CN(C)c1ccc2cc(C(=O)NS(=O)(=O)c3cc(C(C)(C)C)ccc3OC3CCC3)oc2c1]

To a room temperature stirred solution of 6-(dimethylamino)benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 2-(cyclobutoxy)-5-isopropyl-benzenesulfonamide (119 mg, 0.44 mmol, 1.10 eq.) and 1,8-diazabicyclo[5.4.0]undec-7-ene (80.0 μL, 0.56 mmol, 1.40 eq.) were sequentially added. The resulting mixture was stirred at room temperature for one hour and then concentrated under reduced pressure. The residue was purified by reverse phase preparative column chromatography (Waters XBridge PREP C18, 5 μM OBD, 30×150 mm, 62-70% acetonitrile/water gradient buffered with 0.1% formic acid) to give the title compound as a yellow solid (102 mg). $^1$H NMR (400 MHz, DMSO-d$_6$) δ 12.28 (s, 1H), 7.99 (s, 1H), 7.71 (d, 1H), 7.61-7.54 (m, 1H), 7.51-7.43 (m, 1H), 6.93 (d, 1H), 6.89-6.81 (m, 1H), 6.79-6.73 (m, 1H), 4.80 (p, 1H), 3.00-2.95 (m, 6H), 2.98-2.86 (m, 1H), 2.31-2.22 (m, 2H), 2.03-1.88 (m, 2H), 1.56-1.35 (m, 2H), 1.20 (d, 6H); LC-MS (method 7): R$_t$=3.17 min; MS (ESIpos): m/z=457 [M+H]$^+$.

Example 185

N-((5-(tert-butyl)-2-methoxyphenyl)sulfonyl)-6-(dimethylamino)benzofuran-2-carboxamide

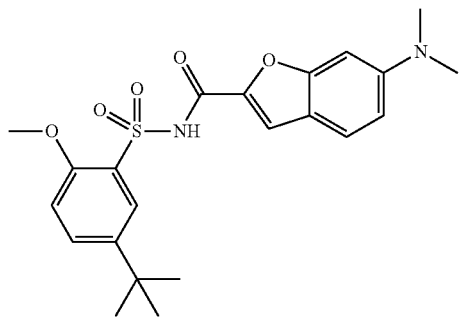

To a room temperature stirred solution of 6-(dimethylamino)benzofuran-2-carboxylic acid (92.3 mg, 0.45 mmol, 1.00 eq.) in anhydrous tetrahydrofuran (2.25 mL, 0.20 M) was added carbonyldiimidazole (87.6 mg, 0.54 mmol, 1.20 eq.). After stirring for 1 hour, 5-tert-butyl-2-methoxy-benzenesulfonamide (120 mg, 0.49 mmol, 1.10 eq.) and 1,8-diazabicyclo[5.4.0]undec-7-ene (90.0 μL, 0.63 mmol, 1.40 eq.) were sequentially added. The resulting mixture was stirred at room temperature for 19 hours and then concentrated under reduced pressure. The residue was purified by reverse phase preparative column chromatography (Waters XBridge PREP C$_{18}$, 5 μM OBD, 30×150 mm, 56-64% acetonitrile/water gradient buffered with 0.1% formic acid) to give the title compound as a yellow solid (123 mg). $^1$H NMR (400 MHz, DMSO-d$_6$) δ 12.41 (s, 1H), 7.94 (s, 1H), 7.87 (d, 1H), 7.70 (dd, 1H), 7.61-7.54 (m, 1H), 7.16 (d, 1H), 6.87 (dd, 1H), 6.80-6.74 (m, 1H), 3.84 (s, 3H), 2.99 (s, 6H), 1.31 (s, 9H); LC-MS (method 7): R$_t$=2.94 min; MS (ESIpos): m/z=431 [M+H]$^+$.

Example 186

N-((2-((2,2-difluorocyclopropyl)methoxy)-5-isopropylphenyl)sulfonyl)-6-(dimethylamino)benzofuran-2-carboxamide (rac)

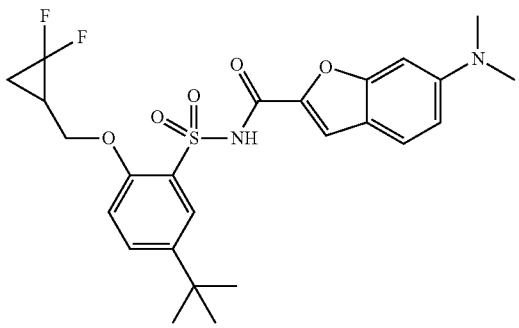 [SMILES: CN(C)c1ccc2cc(C(=O)NS(=O)(=O)c3cc(C(C)(C)C)ccc3OCC3CC3(F)F)oc2c1]

To a room temperature stirred solution of 6-(dimethylamino)benzofuran-2-carboxylic acid (12.3 mg, 0.06 mmol, 1.00 eq.) in anhydrous tetrahydrofuran (0.30 mL, 0.20 M) was added carbonyldiimidazole (11.7 mg, 0.07 mmol, 1.20 eq.). After stirring for 1 hour, 2-[(2,2-difluorocyclopropyl)methoxy]-5-isopropyl-benzenesulfonamide (20.2 mg, 0.07 mmol, 1.10 eq.) and 1,8-diazabicyclo[5.4.0]undec-7-ene (10.0 μL, 0.08 mmol, 1.40 eq.) were sequentially added. The resulting mixture was stirred at room temperature for 16 one hour and then concentrated under reduced pressure. The residue was purified by reverse phase preparative column chromatography (Waters XBridge PREP C1$_8$, 5 μM OBD, 30×150 mm, 60-68% acetonitrile/water gradient buffered with 0.1% formic acid) to give the title compound as a yellow solid (7.23 mg). $^1$H NMR (400 MHz, DMSO-d$_6$) δ 12.27 (s, 1H), 7.90 (s, 1H), 7.75 (d, 1H), 7.54 (t, 2H), 7.19 (d, 1H), 6.85 (dd, 1H), 6.75 (d, 1H), 4.23 (t, 1H), 4.13 (d, 1H), 2.98 (s, 7H), 2.22 (tq, 1H), 1.52 (dq, 1H), 1.35 (dd, 1H), 1.22 (d, 6H); LC-MS (method 7): R$_t$=3.15 min; MS (ESIpos): m/z=493 [M+H]$^+$.

Example 187

5-Chloro-6-(dimethylamino)-N-((2-methylquinolin-8-yl)sulfonyl)benzofuran-2-carboxamide

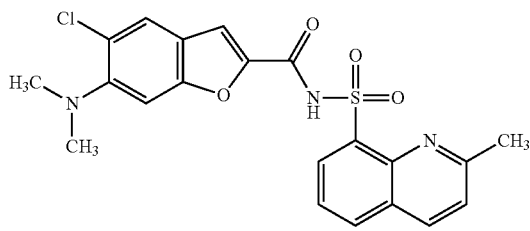

To a room temperature stirred solution of 5-chloro-6-(dimethylamino)benzofuran-2-carboxylic acid (71.9 mg, 0.30 mmol, 1.00 eq.) in anhydrous tetrahydrofuran (1.00 mL, 0.30 M) was added carbonyldiimidazole (58.4 mg, 0.36 mmol, 1.20 eq.). After stirring for 1 h, commercially available 2-methylquinoline-8-sulfonamide (CAS: 157686-27-6, 73.4 mg, 0.33 mmol, 1.10 eq.) and 1,8-diazabicyclo[5.4.0]undec-7-ene (62.8 µL, 0.42 mmol, 1.40 eq.) were sequentially added. The resulting mixture was stirred at room temperature for a further 16 hours and the concentrated under reduced pressure. The residue was purified by reverse phase preparative column chromatography (Waters XBridge PREP $C_{18}$, 5 µM OBD, 30×150 mm, 56-64% acetonitrile/water gradient buffered with 0.1% formic acid) to give the title compound as a yellow solid (116 mg). $^1$H NMR (400 MHz, DMSO-$d_6$) δ 12.74 (s, 1H), 8.47 (dd, 1H), 8.40 (d, 1H), 8.30 (dd, 1H), 8.07 (s, 1H), 7.91 (s, 1H), 7.76 (t, 1H), 7.52 (d, 1H), 7.34 (d, 1H), 2.75 (s, 6H), 2.68 (s, 3H); LC-MS (method 7): $R_t$=3.01 min; MS (ESIpos): m/z=444 [M+H]$^+$.

Example 188

5-Chloro-6-(dimethylamino)-N-((2-ethoxyphenyl)sulfonyl)benzofuran-2-carboxamide

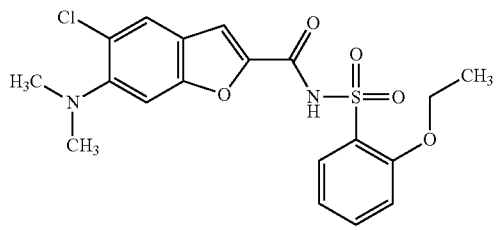 [SMILES: CCOc1ccccc1S(=O)(=O)NC(=O)c1cc2cc(Cl)c(N(C)C)cc2o1]

To a room temperature stirred solution of 5-chloro-6-(dimethylamino)benzofuran-2-carboxylic acid (71.9 mg, 0.30 mmol, 1.00 eq.) in anhydrous tetrahydrofuran (1.00 mL, 0.30 M) was added carbonyldiimidazole (58.4 mg, 0.36 mmol, 1.20 eq.). After stirring for 1 hour, 2-ethoxybenzenesulfonamide (66.4 mg, 0.33 mmol, 1.10 eq.) and 1,8-diazabicyclo[5.4.0]undec-7-ene (62.8 µL, 0.42 mmol, 1.40 eq.) were sequentially added. The resulting mixture was stirred at room temperature for a further 16 hours and the concentrated under reduced pressure. The residue was purified by reverse phase preparative column chromatography (Waters XBridge PREP C18, 5 µM OBD, 30×150 mm, 65-73% acetonitrile/water gradient buffered with 0.1% formic acid) to give the title compound as a white solid (116 mg). $^1$H NMR (400 MHz, DMSO-$d_6$) δ 12.64 (s, 1H), 8.00 (s, 1H), 7.94-7.89 (m, 2H), 7.65 (ddd, 1H), 7.39 (d, 1H), 7.22 (dd, 1H), 7.14 (td, 1H), 4.16 (q, 2H), 2.78 (s, 6H), 1.24 (t, 3H); LC-MS (method 7): $R_t$=3.34 min; MS (ESIpos): m/z=423 [M+H]$^+$.

Example 189

N-([1,1'-biphenyl]-2-ylsulfonyl)-5-chloro-6-(dimethylamino)benzofuran-2-carboxamide

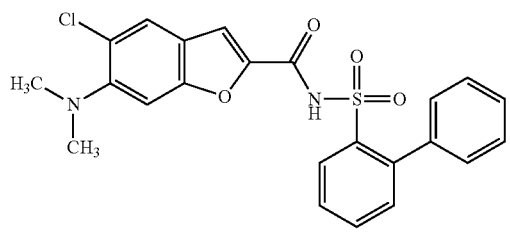 [SMILES: CN(C)c1cc2oc(C(=O)NS(=O)(=O)c3ccccc3-c3ccccc3)cc2cc1Cl]

To a room temperature stirred solution of 5-chloro-6-(dimethylamino)benzofuran-2-carboxylic acid (71.9 mg, 0.30 mmol, 1.00 eq.) in anhydrous tetrahydrofuran (1.00 mL, 0.30 M) was added carbonyldiimidazole (58.4 mg, 0.36 mmol, 1.20 eq.). After stirring for 1 h, commercially available 2-phenylbenzenesulfonamide (CAS: 40182-06-7, 77.0 mg, 0.33 mmol, 1.10 eq.) and 1,8-diazabicyclo[5.4.0]undec-7-ene (62.8 µL, 0.42 mmol, 1.40 eq.) were sequentially added. The resulting mixture was stirred at room temperature for a further 1 hour and the concentrated under reduced pressure. The residue was purified by reverse phase preparative column chromatography (Waters XBridge PREP $C_{18}$, 5 µM OBD, 30×150 mm, 73-81% acetonitrile/water gradient buffered with 0.1% formic acid) to give the title compound as a light yellow solid (117 mg). $^1$H NMR (400 MHz, DMSO-$d_6$) δ 12.27 (s, 1H), 8.17 (dd, 1H), 7.88 (s, 1H), 7.73 (td, 1H), 7.66 (td, 1H), 7.59 (s, 1H), 7.39-7.34 (m, 2H), 7.34-7.27 (m, 3H), 7.28-7.21 (m, 2H), 2.79 (s, 6H); LC-MS (method 7): $R_t$=3.67 min; MS (ESIpos): m/z=455 [M+H]$^+$.

Example 190

6-(Dimethylamino)-7-fluoro-N-((2-methylquinolin-8-yl)sulfonyl)benzofuran-2-carboxamide

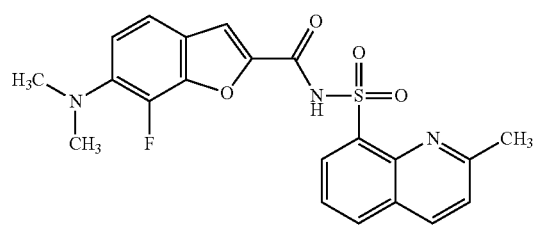

To a room temperature stirred solution of 6-(dimethylamino)-7-fluoro-benzofuran-2-carboxylic acid (67.0 mg, 0.30 mmol, 1.00 eq.) in anhydrous tetrahydrofuran (1.00 mL, 0.30 M) was added carbonyldiimidazole (58.4 mg, 0.36 mmol, 1.20 eq.). After stirring for 1 h, commercially available 2-methylquinoline-8-sulfonamide (CAS: 157686-27-6, 73.4 mg, 0.33 mmol, 1.10 eq.) and 1,8-diazabicyclo[5.4.0]

undec-7-ene (62.8 µL, 0.42 mmol, 1.40 eq.) were sequentially added. The resulting mixture was stirred at room temperature for a further 18 hours and the concentrated under reduced pressure. The residue was purified by reverse phase preparative column chromatography (Waters XBridge PREP $C_{18}$, 5 µM OBD, 30×150 mm, 50-58% acetonitrile/water gradient buffered with 0.1% formic acid) to give the title compound as a light yellow solid (101 mg). $^1$H NMR (400 MHz, DMSO-$d_6$) δ 8.47 (dd, 1H), 8.41 (d, 1H), 8.30 (dd, 1H), 8.11 (d, 1H), 7.76 (t, 1H), 7.53 (d, 1H), 7.47 (d, 1H), 6.99 (dd, 1H), 2.88 (d, 6H), 2.68 (s, 3H); LC-MS (method 7): $R_t$=2.74 min; MS (ESIpos): m/z=428 [M+H]$^+$.

Example 191

6-(Dimethylamino)-N-((2-ethoxyphenyl)sulfonyl)-7-fluorobenzofuran-2-carboxamide

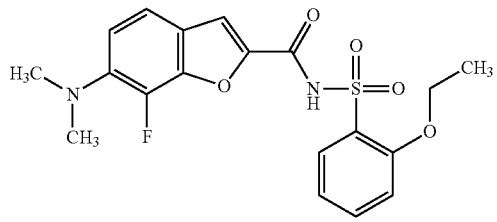 [SMILES: CCOc1ccccc1S(=O)(=O)NC(=O)c1cc2ccc(N(C)C)c(F)c2o1]

To a room temperature stirred solution of 6-(dimethylamino)-7-fluoro-benzofuran-2-carboxylic acid (67.0 mg, 0.30 mmol, 1.00 eq.) in anhydrous tetrahydrofuran (1.00 mL, 0.30 M) was added carbonyldiimidazole (58.4 mg, 0.36 mmol, 1.20 eq.). After stirring for 1 hour, 2-ethoxybenzenesulfonamide (66.4 mg, 0.33 mmol, 1.10 eq.) and 1,8-diazabicyclo[5.4.0]undec-7-ene (62.8 µL, 0.42 mmol, 1.40 eq.) were sequentially added. The resulting mixture was stirred at room temperature for a further 18 h and the concentrated under reduced pressure. The residue was purified by reverse phase preparative column chromatography (Waters XBridge PREP $C_{18}$, 5 µM OBD, 30×150 mm, 58-66% acetonitrile/water gradient buffered with 0.1% formic acid) to give the title compound as a white solid (108 mg). $^1$H NMR (400 MHz, DMSO-$d_6$) δ 12.63 (s, 1H), 8.04 (d, 1H), 7.92 (dd, 1H), 7.69-7.61 (m, 1H), 7.48 (d, 1H), 7.22 (dd, 1H), 7.14 (td, 1H), 7.01 (dd, 1H), 4.16 (q, 2H), 2.90 (d, 6H), 1.24 (t, 3H); LC-MS (method 7): $R_t$=3.09 min; MS (ESIpos): m/z=407 [M+H]$^+$.

Example 192

N-([1,1'-biphenyl]-2-ylsulfonyl)-6-(dimethylamino)-7-fluorobenzofuran-2-carboxamide

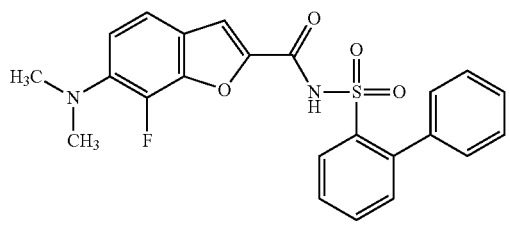 [SMILES: CN(C)c1ccc2cc(C(=O)NS(=O)(=O)c3ccccc3-c3ccccc3)oc2c1F]

To a room temperature stirred solution of 6-(dimethylamino)-7-fluoro-benzofuran-2-carboxylic acid (67.0 mg, 0.30 mmol, 1.00 eq.) in anhydrous tetrahydrofuran (1.00 mL, 0.30 M) was added carbonyldiimidazole (58.4 mg, 0.36 mmol, 1.20 eq.). After stirring for 1 h, commercially available 2-phenylbenzenesulfonamide (CAS: 40182-06-7, 77.0 mg, 0.33 mmol, 1.10 eq.) and 1,8-diazabicyclo[5.4.0]undec-7-ene (62.8 µL, 0.42 mmol, 1.40 eq.) were sequentially added. The resulting mixture was stirred at room temperature for a further 18 hours and the concentrated under reduced pressure. The residue was purified by reverse phase preparative column chromatography (Waters XBridge PREP $C_{18}$, 5 µM OBD, 30×150 mm, 68-76% acetonitrile/water gradient buffered with 0.1% formic acid) to give the title compound as a yellow solid (112 mg). $^1$H NMR (400 MHz, DMSO-$d_6$) δ 12.29 (s, 1H), 8.18 (dd, 1H), 7.73 (td, 1H), 7.71-7.61 (m, 2H), 7.45 (d, 1H), 7.41-7.22 (m, 6H), 7.01 (dd, 1H), 2.91 (d, 6H); LC-MS (method 7): $R_t$=3.43 min; MS (ESIpos): m/z=439 [M+H]$^+$.

Example 193

N-([1,1'-biphenyl]-2-ylsulfonyl)-6-(dimethylamino)-4-(trifluoromethyl)benzofuran-2-carboxamide

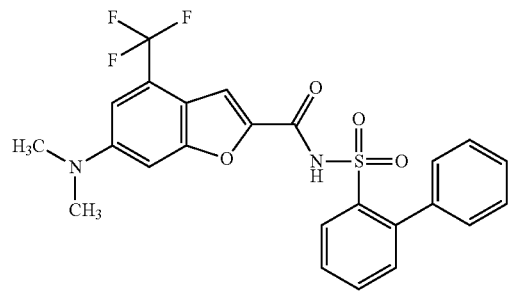 [SMILES: CN(C)c1cc(C(F)(F)F)c2cc(C(=O)NS(=O)(=O)c3ccccc3-c3ccccc3)oc2c1]

To a room temperature stirred suspension of 6-(dimethylamino)-4-(trifluoromethyl)-1-benzofuran-2-carboxylic acid (20.7 mg, 0.08 mmol, 1.00 eq.) in anhydrous tetrahydrofuran (252 µL, 0.30 M) was added carbonyldiimidazole (14.7 mg, 0.09 mmol, 1.20 eq.). After stirring at room temperature for 1 hour, 1,8-diazabicyclo[5.4.0]undec-7-ene (15.8 µL, 0.42 mmol, 1.40 eq.) and commercially available [1,1'-biphenyl]-2-sulfonamide (CAS: 40182-06-7, 19.4 mg, 0.08 mmol, 1.10 eq.) were sequentially added.

The resulting mixture was stirred at room temperature for a further 2 hours and then concentrated under reduced pressure. The mixture was purified by reverse phase preparative column chromatography (Waters XBridge PREP C18, 5 µM OBD, 19×250 mm, 56-64% acetonitrile/water gradient buffered with 0.1% formic acid) to give the title compound as a yellow solid (27.3 mg). $^1$H NMR (400 MHz, DMSO-$d_6$) δ 12.11 (s, 1H), 8.18 (dd, 1H), 7.76-7.62 (m, 3H), 7.39-7.22 (m, 6H), 7.09 (dd, 2H), 3.05 (s, 6H); LC-MS (Method 8): $R_t$=6.13 min; MS (ESIpos): m/z=489 [M+H]$^+$.

Example 194

6-(Dimethylamino)-N-(phenylsulfonyl)-4-(trifluoromethyl)benzofuran-2-carboxamide

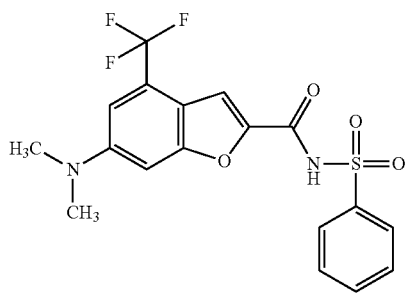 [SMILES: CN(C)c1cc(C(F)(F)F)c2cc(C(=O)NS(=O)(=O)c3ccccc3)oc2c1]

To a room temperature stirred suspension of 6-(dimethylamino)-4-(trifluoromethyl)-1-benzofuran-2-carboxylic acid (81.9 mg, 0.30 mmol, 1.00 eq.) in anhydrous tetrahydrofuran (2.00 mL, 0.15 M) was added carbonyldiimidazole (58.3 mg, 0.36 mmol, 1.20 eq.). After stirring at room temperature for 1 h, 1,8-diazabicyclo[5.4.0]undec-7-ene (62.7 µL, 0.42 mmol, 1.40 eq.) and benzenesulfonamide (51.8 mg, 0.33 mmol, 1.10 eq.) were sequentially added. The resulting mixture was stirred at room temperature for a further 2 hours and then concentrated under reduced pressure. The mixture was purified by reverse phase preparative column chromatography (Waters XBridge PREP $C_{18}$, 5 µM OBD, 30×150 mm, 47-55% acetonitrile/water gradient buffered with 0.1% formic acid) to give the title compound as a yellow solid (97.4 mg). $^1$H NMR (400 MHz, DMSO-$d_6$) δ 12.68 (s, 1H), 8.04-7.99 (m, 3H), 7.76-7.70 (m, 1H), 7.68-7.62 (m, 2H), 7.17-7.01 (m, 2H), 3.04 (s, 6H); LC-MS (Method 8): $R_t$=5.29 min; MS (ESIpos): m/z=413 [M+H]$^+$.

Example 195

6-(Dimethylamino)-N-((2-ethoxyphenyl)sulfonyl)-4-(trifluoromethyl)benzofuran-2-carboxamide

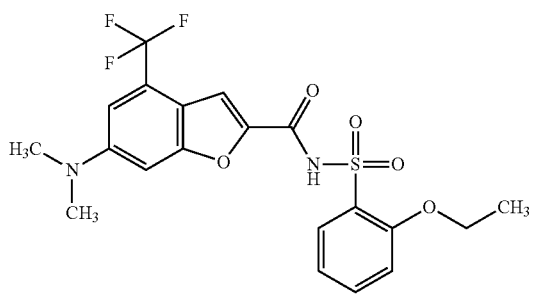 [SMILES: CCOc1ccccc1S(=O)(=O)NC(=O)c1cc2c(C(F)(F)F)cc(N(C)C)cc2o1]

To a room temperature stirred suspension of 6-(dimethylamino)-4-(trifluoromethyl)-1-benzofuran-2-carboxylic acid (109 mg, 0.40 mmol, 1.00 eq.) in anhydrous tetrahydrofuran (1.33 mL, 0.30 M) was added carbonyldiimidazole (77.8 mg, 0.56 mmol, 1.20 eq.). After stirring at room temperature for 1 hour, 1,8-diazabicyclo[5.4.0]undec-7-ene (83.6 µL, 0.48 mmol, 1.40 eq.) and 2-ethoxybenzene-1-sulfonamide (88.5 mg, 0.44 mmol, 1.10 eq.) were sequentially added. The resulting mixture was stirred at room temperature for a further 14 hours and then concentrated under reduced pressure. The mixture was purified by reverse phase preparative column chromatography (Waters XBridge PREP $C_{18}$, 5 µM OBD, 30×150 mm, 63.5-71.5% acetonitrile/water gradient buffered with 0.1% formic acid) to give the title compound as a light yellow solid (161 mg). $^1$H NMR (400 MHz, DMSO-$d_6$) δ 12.52 (s, 1H), 8.24 (s, 1H), 7.91 (dd, 1H), 7.64 (ddd, 1H), 7.24-7.18 (m, 1H), 7.17-7.05 (m, 3H), 4.15 (q, 2H), 3.04 (s, 6H), 1.26 (t, 3H); LC-MS (Method 8): $R_t$=5.71 min; MS (ESIpos): m/z=457 [M+H]$^+$.

Example 196

6-(Dimethylamino)-N-((2-methylquinolin-8-yl)sulfonyl)-4-(trifluoromethyl)benzofuran-2-carboxamide

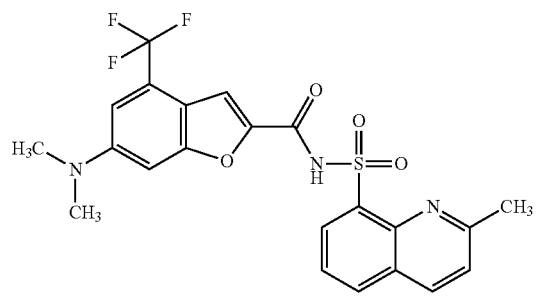

To a room temperature stirred suspension of 6-(dimethylamino)-4-(trifluoromethyl)-1-benzofuran-2-carboxylic acid (81.9 mg, 0.30 mmol, 1.00 eq.) in anhydrous tetrahydrofuran (2.00 mL, 0.15 M) was added carbonyldiimidazole (58.3 mg, 0.36 mmol, 1.20 eq.). After stirring at room temperature for 1 h, 1,8-diazabicyclo[5.4.0]undec-7-ene (62.7 µL, 0.42 mmol, 1.40 eq.) and commercially available 2-methylquinoline-8-sulfonamide (CAS: 157686-27-6, 73.3 mg, 0.33 mmol, 1.10 eq.) were sequentially added. The resulting mixture was stirred at room temperature for a further 2 hours and then concentrated under reduced pressure. The mixture was purified by reverse phase preparative column chromatography (Waters XBridge PREP $C_{18}$, 5 µM OBD, 30×150 mm, 46-54% acetonitrile/water gradient buffered with 0.1% formic acid) to give the title compound as a yellow solid (93.7 mg). $^1$H NMR (400 MHz, DMSO-$d_6$) δ 12.58 (s, 1H), 8.47 (dd, 1H), 8.38 (d, 1H), 8.33 (s, 1H), 8.29 (dd, 1H), 7.75 (t, 1H), 7.51 (d, 1H), 7.06 (dd, 2H), 3.01 (s, 6H), 2.67 (s, 3H); LC-MS (Method 8): $R_t$=5.17 min; MS (ESIpos): m/z=478 [M+H]$^+$.

Example 197

6-(Dimethylamino)-5-fluoro-N-((2-methylquinolin-8-yl)sulfonyl)benzofuran-2-carboxamide

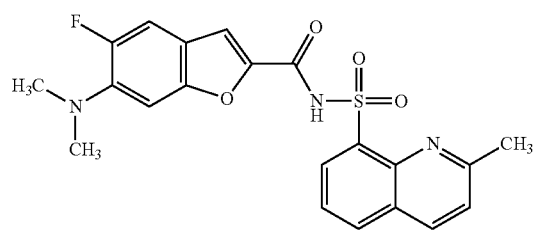

To a room temperature stirred suspension of 6-(dimethylamino)-5-fluoro-1-benzofuran-2-carboxylic acid (66.9 mg, 0.30 mmol, 1.00 eq.) in anhydrous tetrahydrofuran (2.00 mL, 0.15 M) was added carbonyldiimidazole (58.3 mg, 0.36 mmol, 1.20 eq.). After stirring at RT for 1 h, 1,8-diazabicyclo[5.4.0]undec-7-ene (62.7 µL, 0.42 mmol, 1.40 eq.) and commercially available 2-methylquinoline-8-sulfonamide (CAS: 157686-27-6, 73.3 mg, 0.33 mmol, 1.10 eq.) were sequentially added. The resulting mixture was stirred at room temperature for a further 12 hours and then concentrated under reduced pressure. The mixture was purified by reverse phase preparative column chromatography (Waters XBridge PREP $C_{18}$, 5 µM OBD, 30×150 mm, 46-54% acetonitrile/water gradient buffered with 0.1% formic acid) to give the title compound as a yellow solid (117 mg). 1H NMR (400 MHz, DMSO-$d_6$) δ 12.56 (s, 1H), 8.46 (dd, 1H), 8.39 (d, 1H), 8.29 (dd, 1H), 8.04 (s, 1H), 7.75 (t, 1H), 7.56 (d, 1H), 7.52 (d, 1H), 7.09 (d, 1H), 2.82 (s, 6H), 2.68 (s, 3H); LC-MS (Method 8): $R_t$=4.11 min; MS (ESIpos): m/z=428 [M+H]$^+$.

Example 198

6-(Dimethylamino)-N-((2-ethoxyphenyl)sulfonyl)-5-fluorobenzofuran-2-carboxamide

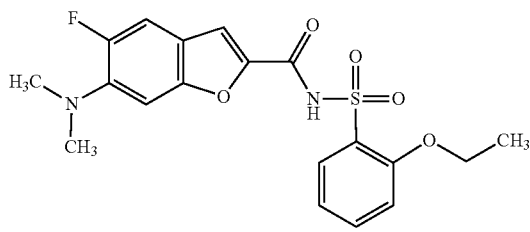 [SMILES: CCOc1ccccc1S(=O)(=O)NC(=O)c1cc2cc(F)c(N(C)C)cc2o1]

To a RT stirred suspension of 6-(dimethylamino)-5-fluoro-1-benzofuran-2-carboxylic acid (66.9 mg, 0.30 mmol, 1.00 eq.) in anhydrous tetrahydrofuran (2.00 mL, 0.15 M) was added carbonyldiimidazole (58.3 mg, 0.36 mmol, 1.20 eq.). After stirring at room temperature for 1 hour, 1,8-diazabicyclo[5.4.0]undec-7-ene (62.7 µL, 0.42 mmol, 1.40 eq.) and 2-ethoxybenzene-1-sulfonamide (66.4 mg, 0.33 mmol, 1.10 eq.) were sequentially added. The resulting mixture was stirred at room temperature for a further 12 h and then concentrated under reduced pressure. The mixture was purified by reverse phase preparative column chromatography (Waters XBridge PREP $C_{18}$, 5 µM OBD, 30×150 mm, 54-62% acetonitrile/water gradient buffered with 0.1% formic acid) to give the title compound as a light yellow solid (117 mg). 1H NMR (400 MHz, DMSO-$d_6$) δ 12.49 (s, 1H), 7.98 (s, 1H), 7.91 (dd, 1H), 7.67-7.60 (m, 1H), 7.57 (d, 1H), 7.21 (d, 1H), 7.17-7.10 (m, 2H), 4.16 (q, 2H), 2.85 (s, 6H), 1.24 (t, 3H); LC-MS (Method 8): $R_t$=4.77 min; MS (ESIpos): m/z=407 [M+H]$^+$.

Example 199

N-([1,1'-biphenyl]-2-ylsulfonyl)-6-(dimethylamino)-5-fluorobenzofuran-2-carboxamide

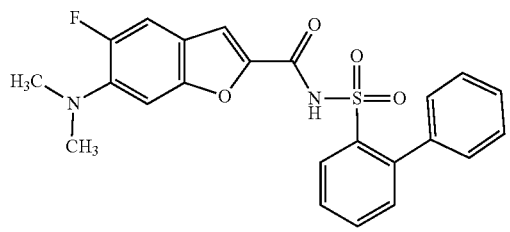 [SMILES: CN(C)c1cc2oc(C(=O)NS(=O)(=O)c3ccccc3-c3ccccc3)cc2cc1F]

To a room temperature stirred suspension of 6-(dimethylamino)-5-fluoro-1-benzofuran-2-carboxylic acid (66.9 mg, 0.30 mmol, 1.00 eq.) in anhydrous tetrahydrofuran (2.00 mL, 0.15 M) was added carbonyldiimidazole (58.3 mg, 0.36 mmol, 1.20 eq.). After stirring at room temperature for 1 hour, 1,8-diazabicyclo[5.4.0]undec-7-ene (62.7 µL, 0.42 mmol, 1.40 eq.) and commercially available [1,1'-biphenyl]-2-sulfonamide (CAS: 40182-06-7, 76.9 mg, 0.33 mmol, 1.10 eq.) were sequentially added. The resulting mixture was stirred at room temperature for a further 12 h and then concentrated under reduced pressure. The mixture was purified by reverse phase preparative column chromatography (Waters XBridge PREP $C_{18}$, 5 µM OBD, 30×150 mm, 62-70% acetonitrile/water gradient buffered with 0.1% formic acid) to give the title compound as a light yellow solid (127 mg). $^1$H NMR (400 MHz, DMSO-$d_6$) δ 12.14 (s, 1H), 8.17 (dd, 1H), 7.73 (td, 1H), 7.66 (td, 1H), 7.59 (s, 1H), 7.53 (d, 1H), 7.41-7.22 (m, 6H), 7.13 (d, 1H), 2.86 (s, 6H); LC-MS (Method 8): $R_t$=5.50 min; MS (ESIpos): m/z=439 [M+H]$^+$.

Example 200

6-(Dimethylamino)-N-(2-ethoxybenzene-1-sulfonyl)-5-methyl-1-benzofuran-2-carboxamide

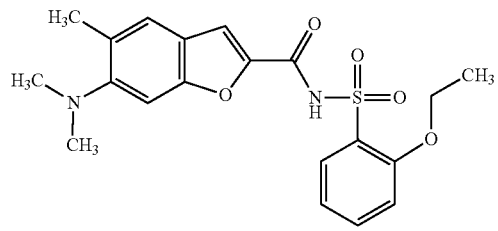 [SMILES: CCOc1ccccc1S(=O)(=O)NC(=O)c1cc2cc(C)c(N(C)C)cc2o1]

5-Bromo-6-(dimethylamino)-N-(2-ethoxybenzene-1-sulfonyl)-1-benzofuran-2-carboxamide (INT-50, 80.0 mg, 171 µmol), methylboronic acid (51.2 mg, 856 µmol; CAS-RN:[13061-96-6]), potassium carbonate (71 mg, 514 µmol, CAS 584-08-7), [1,1'-Bis(diphenylphosphino)ferrocene]dichloropalladium(II), complex with dichloromethane (14 mg, 17.1 µmol, CAS 95464-05-4) were added to a reaction vessel, the vessel was sealed and flushed with argon. 1,4-dioxane (600 µL) and water (400 µL) (both degassed by sparging with argon) were added and the mixture was stirred at 130° C. for 1 h. The mixture was filtered through a 10 g silica column, and the column flushed with a DCM:MeOH mixture (90:10), the filtrated collected and the solvent removed under reduced pressure. Reverse phase HPLC purification yielded the title compound (35.4 mg, 95% purity, 51% yield). $^1$H-NMR (400 MHz, DMSO-$d_6$) δ [ppm]: 1.213 (2.04), 1.230 (4.39), 1.247 (2.12), 2.337 (6.22), 2.685 (16.00), 4.118 (0.47), 4.135 (1.33), 4.153 (1.31), 4.170 (0.45), 7.125 (0.70), 7.144 (0.40), 7.191 (0.61), 7.213 (2.79), 7.550 (1.53), 7.629 (0.48), 7.895 (0.82), 7.911 (0.82); LC-MS (method 3): $R_t$=1.13 min; MS (ESIneg): m/z=401 [M−H]⁻.

Example 201

6-(Dimethylamino)-N-(2-ethoxybenzene-1-sulfonyl)-5-(trifluoromethyl)-1-benzofuran-2-carboxamide

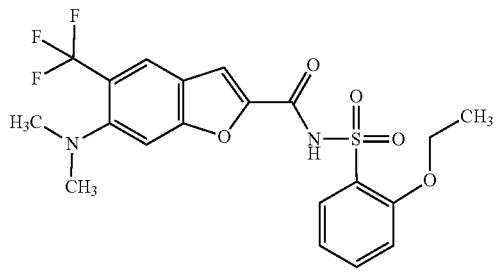 [SMILES: CCOc1ccccc1S(=O)(=O)NC(=O)c1cc2cc(C(F)(F)F)c(N(C)C)cc2o1]

In vial number 1, copper Bromide (9.56 mg, 42.8 μmol; CAS-RN:[7789-45-9]) and lithium bromide (7.43 mg, 85.6 μmol; CAS-RN:[7550-35-8]) were sealed in a vial and were flushed with argon. Acetone (0.5 ml), sparged with argon, was added and the mixture was stirred at RT for 15 min. In vial number 2, 5-bromo-6-(dimethylamino)-N-(2-ethoxybenzene-1-sulfonyl)-1-benzofuran-2-carboxamide (100 mg, 214 μmol, Example 223), potassium phosphate tribasic (182 mg, 856 μmol; CAS-RN:[7778-53-2]), Ir[dFMeppy]2-(4,4'-dCF3bpy)PF$_6$ (2.22 mg, 2.14 μmol), and dimesityl(trifluoromethyl)sulfonium trifluoromethanesulfonate, (80 μL, 320 μmol, CAS-RN:[1895006-01-5]) were added, the vial was sealed and was flushed with argon. The contents of vial number 1, were then added to vial number 2, vial number 1 was rinsed with a an additional volume of acetone (1.5 mL) and this was in turn added to vial number 2. To this commercially available mixture 1,1,1,3,3,3-hexamethyl-2-(trimethylsilyl)trisilan-2-ol (CAS: 7428-60-6, 80 μL, 320 μmol) was added and the mixture was stirred at RT overnight while being illuminated by blue LEDs type Kessil Lamps A160 WE Tuna Blue. The mixture was diluted in H$_2$O and was extracted three times with DCM, the organic layers were combined, passed through a water repellent filter and concentrated under reduced pressure. Purification by reverse phased HPLC yielded the title compound 2.90 mg (89% purity, 3% yield), $^1$H-NMR (400 MHz, DMSO-$d_6$) δ [ppm]: 0.698 (0.55), 0.715 (0.54), 0.880 (0.99), 0.897 (1.09), 1.113 (0.75), 1.130 (0.91), 1.137 (1.39), 1.148 (1.10), 1.165 (1.25), 1.180 (0.47), 1.213 (2.25), 1.231 (6.58), 1.249 (4.04), 1.269 (0.63), 1.289 (0.46), 1.306 (0.45), 2.115 (0.44), 2.322 (0.41), 2.326 (0.57), 2.331 (0.41), 2.522 (1.45), 2.665 (0.52), 2.669 (0.72), 2.673 (0.74), 2.687 (16.00), 3.008 (1.11), 3.038 (2.66), 4.124 (0.83), 4.141 (0.88), 6.926 (0.99), 7.078 (0.51), 7.088 (0.57), 7.095 (0.61), 7.114 (1.01), 7.193 (0.48), 7.205 (0.52), 7.837 (2.14), 7.887 (0.66), 7.905 (0.61), 8.208 (0.58); LC-MS (method 3): $R_t$=1.32 min; MS (ESIpos): m/z=457 [M+H]⁺.

Example 202

N-([1,1'-biphenyl]-2-sulfonyl)-6-(dimethylamino)-7-(trifluoromethyl)-1-benzofuran-2-carboxamide

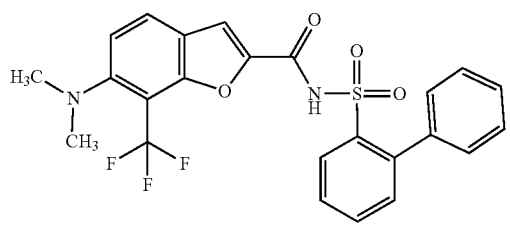 [SMILES: CN(C)c1ccc2cc(C(=O)NS(=O)(=O)c3ccccc3-c3ccccc3)oc2c1C(F)(F)F]

Aforementioned N-([1,1'-biphenyl]-2-sulfonyl)-6-(dimethylamino)-1-benzofuran-2-carboxamide (200 mg, 476 μmol, Example 14), sodium trifluoromethanesulfinate (594 mg, 3.81 mmol; CAS-RN:[2926-29-6]), copper (II) trifluoromethanesulfonate (34.4 mg, 95.1 μmol; CAS-RN:[34946-82-2]) were added to a flask, the flask was sealed and flushed with argon. Acetonitrile (2.0 mL, 38 mmol; CAS-RN:[75-05-8]) was added, and tert-butylhydroperoxide (70% in water, (650 μL, 70% purity, 4.8 mmol; CAS-RN:[75-91-2]) was added dropwise and the mixture was stirred at RT for 2 h. The mixture was diluted with DCM, and washed with a mixture of saturated aqueous sodium bicarbonate solution and saturated sodium thiosulfate (2:1), the organic phase separated and passed over a water repellent filter, concentrated under reduced pressure and the solvent removed under reduced pressure. The mixture was purified by reverse phase HPLC yielding the title compound (8 mg, 90% purity, 3% yield). $^1$H-NMR (400 MHz, DMSO-$d_6$) δ [ppm]: 1.232 (0.57), 1.907 (0.62), 2.518 (4.06), 2.523 (2.49), 2.540 (1.92), 2.700 (4.10), 2.815 (16.00), 7.257 (1.18), 7.261 (1.42), 7.278 (2.90), 7.302 (1.94), 7.319 (3.21), 7.323 (2.52), 7.338 (2.83), 7.349 (1.52), 7.361 (2.00), 7.384 (0.56), 7.643 (0.53), 7.659 (1.15), 7.681 (1.52), 7.712 (0.87), 7.728 (1.02), 7.747 (0.50), 7.829 (0.54), 7.943 (1.46), 7.965 (1.35), 8.170 (1.33), 8.174 (1.29), 8.191 (1.35), 8.194 (1.46); LC-MS (Method 1): $R_t$=1.44 min; MS (ESIneg): m/z=487 [M−H]-.

Example 203

N-([1,1'-biphenyl]-2-sulfonyl)-7-bromo-6-(dimethylamino)-1-benzofuran-2-carboxamide

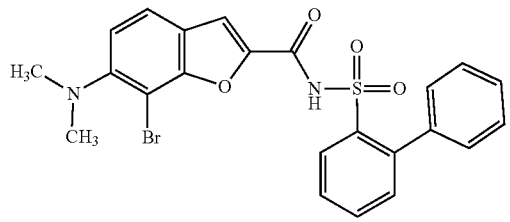 [SMILES: CN(C)c1ccc2cc(C(=O)NS(=O)(=O)c3ccccc3-c3ccccc3)oc2c1Br]

Aforementioned N-([1,1'-biphenyl]-2-sulfonyl)-6-(dimethylamino)-1-benzofuran-2-carboxamide (Example 14, 360 mg, 856 μmol), was added to a flask, followed by NBS (305 mg, 1.71 mmol). DCE (2 mL) was added, followed by trifluoroacetic acid (330 μL, 4.2 mmol) and the mixture was stirred at RT for 2 h. The mixture was diluted with EtOAc, the organic layer was washed with water, followed by brine, passed through a water repellant filter and the solvent removed under reduced pressure. A portion of the crude product (50 mg, 12% of the total mass) was purified by reverse phase HPLC, yielding the title compound 12.6 mg (99% purity, 25% yield). $^1$H-NMR (400 MHz, DMSO-d$_6$) δ [ppm]: 2.074 (0.79), 2.518 (1.84), 2.522 (1.16), 2.804 (16.00), 6.944 (1.31), 7.072 (1.47), 7.167 (1.01), 7.188 (1.10), 7.200 (1.43), 7.272 (0.62), 7.307 (2.64), 7.657 (0.71), 7.678 (0.57), 8.143 (0.64), 8.163 (0.58); LC-MS (Method 2): R$_t$=0.80 min; MS (ESIpos): m/z=501 [M+H]$^+$ Example 204

5-Cyano-6-(dimethylamino)-N-(2-ethoxybenzene-1-sulfonyl)-1-benzofuran-2-carboxamide

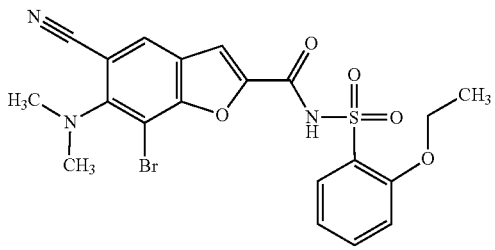 [SMILES: CCOc1ccccc1S(=O)(=O)NC(=O)c1cc2cc(C#N)c(N(C)C)c(Br)c2o1]

5-Bromo-6-(dimethylamino)-N-(2-ethoxybenzene-1-sulfonyl)-1-benzofuran-2-carboxamide (INT-59, 80.0 mg, 171 µmol), commercially available bis[cinnamyl palladium (II) chloride] (CAS: 12131-44-1, 4.43 mg, 8.56 µmol), commercially available 1,1'-ferrocenediyl-bis(diphenylphosphine) (CAS: 12150-46-84, 74 mg, 8.56 µmol) and zinc cyanide (30.2 mg, 257 µmol) were added to a 5 mL reaction vessel and the vessel sealed and flushed with argon. Degassed N,N-dimethylacetamide (500 µL, 5.4 mmol) and N,N-diisopropylethylamine (60 µL, 340 µmol), were added and the mixture heated overnight at 80° C. The mixture was diluted in MTBE and was washed once with saturated sodium bicarbonate solution followed by brine. The pH of the aqueous layers was then adjusted to 5 using concentrated hydrochloric acid, and extracted with DCM, the organic layer was passed through a water repellent filter, the solvent was removed under reduced pressure and the mixture purified by reverse phase HPLC, yielding the title compound 28.9 mg (98% purity, 40% yield). $^1$H-NMR (500 MHz, DMSO-d$_6$) δ [ppm]: 1.229 (1.80), 1.243 (4.11), 1.257 (1.94), 2.544 (0.40), 2.980 (16.00), 3.347 (0.66), 4.145 (0.46), 4.159 (1.52), 4.173 (1.51), 4.187 (0.45), 7.139 (0.73), 7.154 (0.40), 7.214 (0.65), 7.231 (0.70), 7.273 (1.61), 7.652 (0.45), 7.906 (0.74), 7.910 (0.75), 7.922 (0.70), 7.925 (0.68), 8.045 (0.51), 8.270 (2.17); LC-MS (method 9): R$_t$=1.09 min; MS (ESIpos): m/z=414 [M+H]$^+$.

Example 205

6-[(2-Methoxyethyl)(methyl)amino]-N-(2-methylquinoline-8-sulfonyl)-1-benzofuran-2-carboxamide

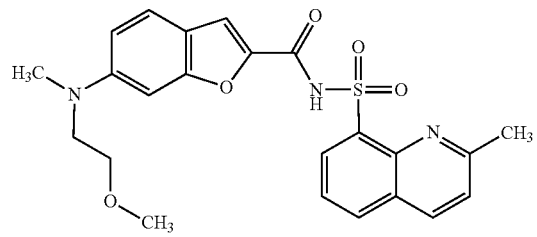

According to GP5A, 6-[(2-methoxyethyl)(methyl)amino]-1-benzofuran-2-carboxylic acid (INT-42, 200 mg, 50% purity, 401 µmol), commercially available 2-methylquinoline-8-sulfonamide (CAS: 157686-27-6, 436 mg, 1.87 mmol), PyBOP (107 mg, 481 µmol) and DIPEA (280 µL, 1.6 mmol) were stirred at RT in DCM (3 mL) overnight. The conversion was not complete so that additional DIPEA and sulfonamide were added. After further 15 h stirring and complete conversion. After work-up and purification using HPLC (acid), the desired product was obtained as a orange-yellowish solid (35 mg, 17%). $^1$H-NMR (400 MHz, DMSO-d$_6$) δ [ppm]: 2.074 (8.60), 2.326 (0.48), 2.518 (1.67), 2.522 (1.09), 2.664 (0.72), 2.669 (1.12), 2.678 (15.30), 2.955 (16.00), 3.338 (0.83), 3.393 (0.72), 3.457 (1.42), 3.473 (4.33), 3.485 (2.66), 3.544 (2.09), 3.557 (2.70), 3.571 (1.05), 6.639 (0.53), 6.723 (2.13), 6.727 (2.22), 6.827 (1.37), 6.832 (1.22), 6.849 (1.37), 6.855 (1.29), 7.498 (2.73), 7.519 (2.94), 7.526 (2.72), 7.549 (2.51), 7.723 (1.05), 7.742 (1.85), 7.762 (1.13), 8.027 (0.79), 8.274 (1.11), 8.294 (1.02), 8.373 (2.41), 8.394 (2.29), 8.438 (1.60), 8.441 (1.56), 8.456 (1.50), 8.460 (1.40); LC-MS (method 9): R$_t$=1.06 min; MS (ESIpos): m/z=454 [M+H]$^+$.

Example 206

N-([1,1'-Biphenyl]-2-sulfonyl)-5-bromo-6-(dimethylamino)-7-fluoro-1-benzofuran-2-carboxamide

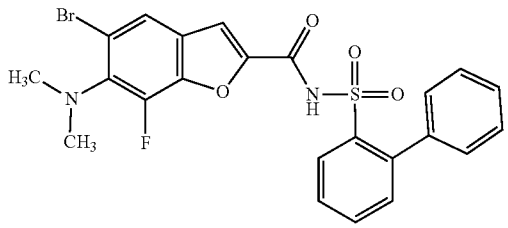 [SMILES: CN(C)c1c(Br)cc2cc(C(=O)NS(=O)(=O)c3ccccc3-c3ccccc3)oc2c1F]

According to GP5A, aforementioned 5-bromo-6-(dimethylamino)-7-fluoro-1-benzofuran-2-carboxylic acid (INT-58, 90 mg, 298 µmol), commercially available 1,1'-biphenyl]-2-sulfonamide (CAS: 40182-06-7, 83.4 mg, 357 µmol), PyBOP (186 mg, 357 µmol) and DIPEA (210 µL, 1.2 mmol) were stirred at RT in DCM (2 mL) overnight. After reaction completion, work-up and purification using HPLC (acid), the desired product was obtained as a beige brown solid (10 mg, 6%). $^1$H-NMR (500 MHz, DMSO-d$_6$) δ [ppm]: 1.678 (0.45), 2.499 (4.17), 2.502 (3.45), 2.506 (2.98), 2.523 (1.32), 2.612 (0.40), 2.878 (15.52), 2.882 (16.00), 2.953 (0.61), 2.961 (0.66), 2.975 (0.50), 3.169 (1.38), 7.270 (1.24), 7.273 (1.30), 7.283 (4.49), 7.292 (11.27), 7.301 (0.92), 7.308 (1.31), 7.316 (0.95), 7.318 (0.81), 7.326 (0.93), 7.536 (0.97), 7.541 (1.00), 7.589 (0.54), 7.592 (0.58), 7.605 (1.12), 7.607 (1.15), 7.620 (0.94), 7.623 (0.85), 7.656 (0.80), 7.659 (0.82), 7.671 (1.22), 7.674 (1.27), 7.686 (0.53), 7.689 (0.50), 7.869 (2.55), 7.872 (2.57), 8.158 (1.38), 8.161 (1.42), 8.175 (1.28), 8.177 (1.32); LC-MS (method 9): $R_t$=148.00 min; MS (ESIpos): m/z=518 [M+H]$^+$.

Example 207

5-Bromo-N-[2-(cyclopropyloxy)benzene-1-sulfonyl]-6-(dimethylamino)-1-benzofuran-2-carboxamide

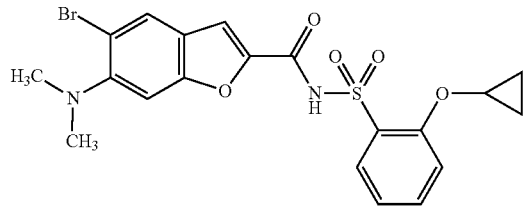 [SMILES: CN(C)c1cc2oc(C(=O)NS(=O)(=O)c3ccccc3OC3CC3)cc2cc1Br]

According to GP5A, aforementioned 5-bromo-6-(dimethylamino)-1-benzofuran-2-carboxylic acid (200 mg, 704 µmol), commercially available 2-(cyclopropyloxy)benzene-1-sulfonamide (CAS: 1243451-33-3, 83.4 mg, 357 µmol), PyBOP (440 mg, 845 µmol) and DIPEA (490 µL, 2.8 mmol) were stirred at RT in DCM (3 mL) overnight. After reaction completion, work-up and purification using HPLC (acid), the desired product was obtained as an off white solid (199 mg, 56%). $^1$H-NMR (400 MHz, DMSO-d$_6$) δ [ppm]: 0.524 (0.82), 0.530 (1.32), 0.535 (0.83), 0.717 (1.04), 0.722 (0.84), 0.733 (0.81), 0.737 (0.94), 2.521 (0.46), 2.771 (16.00), 4.070 (0.45), 4.077 (0.63), 4.085 (0.43), 7.170 (0.45), 7.172 (0.48), 7.190 (0.91), 7.208 (0.51), 7.210 (0.50), 7.436 (2.06), 7.470 (0.82), 7.490 (0.98), 7.681 (0.42), 7.685 (0.46), 7.700 (0.51), 7.703 (0.61), 7.893 (0.89), 7.898 (0.92), 7.914 (0.89), 7.917 (0.81), 7.982 (1.05), 8.116 (3.39); LC-MS (Method 4): $R_t$=1.24 min; MS (ESIpos): m/z=481 [M+H]$^+$.

Example 208

5-Bromo-6-(dimethylamino)-N-{2-[(propan-2-yl)oxy]benzene-1-sulfonyl}-1-benzofuran-2-carboxamide

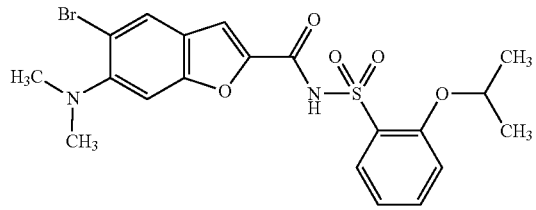 [SMILES: CC(C)Oc1ccccc1S(=O)(=O)NC(=O)c1cc2cc(Br)c(N(C)C)cc2o1]

According to GP5A, aforementioned 5-bromo-6-(dimethylamino)-1-benzofuran-2-carboxylic acid (INT-57, 200 mg, 704 µmol), commercially available 2-[(propan-2-yl)oxy]benzene-1-sulfonamide (CAS: 1517704-54-9, 182 mg, 845 µmol), PyBOP (440 mg, 845 µmol) and DIPEA (490 µL, 2.8 mmol) were stirred at RT in DCM (3 mL) overnight. After reaction completion, work-up and purification using HPLC (acid), the desired product was obtained as an off white solid (210 mg, 56%). $^1$H-NMR (400 MHz, DMSO-d$_6$) δ [ppm]: 1.172 (8.38), 1.187 (8.64), 1.280 (1.19), 1.295 (1.16), 2.521 (0.46), 2.767 (16.00), 4.791 (0.46), 4.807 (0.62), 4.822 (0.45), 7.091 (0.47), 7.093 (0.49), 7.111 (0.96), 7.129 (0.52), 7.131 (0.52), 7.233 (0.82), 7.254 (0.96), 7.435 (2.06), 7.615 (0.41), 7.629 (0.48), 7.632 (0.61), 7.899 (0.92), 7.903 (0.94), 7.919 (0.88), 7.922 (0.81), 8.024 (1.02), 8.115 (3.36); LC-MS (Method 1): $R_t$=1.32 min; MS (ESIpos): m/z=482 [M+H]$^+$.

Example 209

5-Cyano-6-(dimethylamino)-N-(2-methylquinoline-8-sulfonyl)-1-benzofuran-2-carboxamide

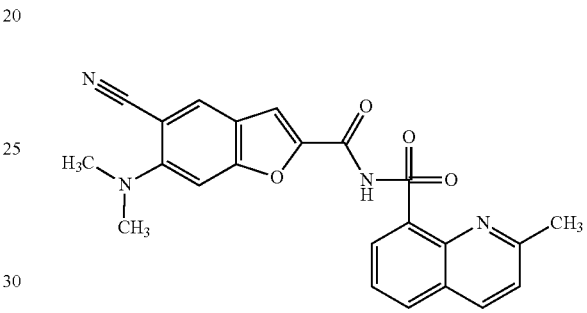

According to GP5A, aforementioned 5-cyano-6-(dimethylamino)-1-benzofuran-2-carboxylic acid (INT-59, 115 mg, 500 µmol), commercially available 2-methylquinoline-8-sulfonamide (CAS: 157686-27-6, 133 mg, 599 µmol), PyBOP (312 mg, 599 µmol) and DIPEA (530 µL, 2.80 mmol) were stirred at RT in DCM (33 mL) overnight. After reaction completion, work-up and purification using HPLC (acid), the desired product was obtained as a off white solid (10 mg, 4%); $^1$H-NMR (400 MHz, DMSO-d$_6$) δ [ppm]: 1.232 (0.42), 2.077 (1.06), 2.325 (0.51), 2.329 (0.70), 2.334 (0.54), 2.339 (0.54), 2.521 (2.73), 2.525 (1.69), 2.542 (0.71), 2.667 (0.61), 2.672 (0.98), 2.680 (4.97), 2.687 (1.47), 2.953 (16.00), 7.227 (1.62), 7.520 (0.69), 7.542 (0.73), 7.752 (0.49), 8.258 (0.86), 8.396 (0.60), 8.417 (0.58), 8.454 (0.45), 8.472 (0.44); LC-MS (Method 1): $R_t$=96.00 min; MS (ESIpos): m/z=434 [M+H]$^+$ Example 210

N-([1,1'-Biphenyl]-2-sulfonyl)-6-(dimethylamino)-1-methyl-1H-indole-2-carboxamide

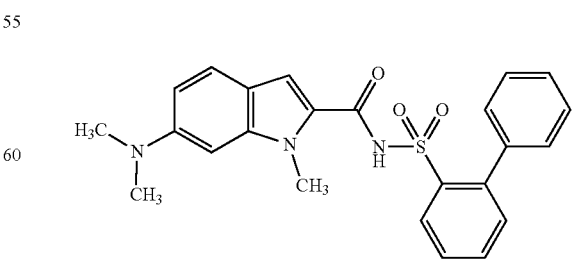

According to GP5A, aforementioned 6-(dimethylamino)-1-methyl-1H-indole-2-carboxylic acid (INT-48, 32.1 mg, 137 μmol), commercially available [1,1'-biphenyl]-2-sulfonamide (CAS: 40182-06-7, 133 mg, 599 μmol), PyBOP (71.5 mg, 137 μmol) and DIPEA (80 μL, 460 μmol) were stirred at RT in DCM (560 μl) overnight. After reaction completion, work-up and purification using HPLC (acid), the desired product was obtained as a yellow solid (8 mg, 15%); $^1$H-NMR (400 MHz, DMSO-d$_6$) δ [ppm]: 2.520 (0.88), 2.524 (0.62), 2.542 (0.43), 2.975 (16.00), 3.763 (9.37), 6.525 (0.69), 6.769 (0.58), 6.774 (0.57), 6.791 (0.62), 6.796 (0.60), 7.092 (2.07), 7.284 (0.80), 7.288 (0.98), 7.300 (0.95), 7.307 (2.42), 7.325 (1.66), 7.328 (1.60), 7.334 (0.41), 7.346 (2.03), 7.350 (0.69), 7.365 (1.11), 7.368 (0.79), 7.373 (0.99), 7.377 (0.56), 7.390 (0.77), 7.425 (1.34), 7.448 (1.24), 7.651 (0.85), 7.655 (0.78), 7.671 (0.74), 7.674 (0.68), 7.694 (0.69), 7.698 (0.76), 7.712 (0.94), 7.716 (0.95), 8.159 (0.95), 8.163 (1.05), 8.180 (0.88), 8.183 (0.87); LC-MS (method 9): R$_t$=1.17 min; MS (ESIpos): m/z=434 [M+H]$^+$.

Example 211

N-([1,1'-biphenyl]-2-sulfonyl)-6-(ethylamino)-1-benzofuran-2-carboxamide

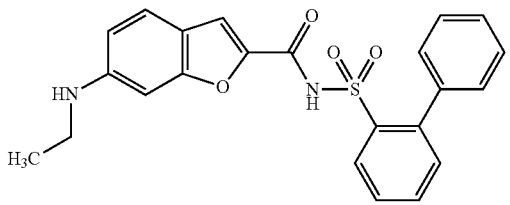 [SMILES: CCNc1ccc2cc(C(=O)NS(=O)(=O)c3ccccc3-c3ccccc3)oc2c1]

According to GP5A, aforementioned 6-(ethylamino)-1-benzofuran-2-carboxylic acid (INT-43, 100 mg, 487 μmol), commercially available, 1'-biphenyl]-2-sulfonamide (CAS: 40182-06-7, 136 mg, 585 μmol), PyBOP (304 mg, 585 μmol) and DIPEA (340 μL, 1.9 mmol) were stirred at RT in DCM (3.4 mL) overnight. After reaction completion, work-up and purification using HPLC (acid), the desired product was obtained as an ochre solid (6 mg, 3%); $^1$H-NMR (400 MHz, METHANOL-d$_4$) δ [ppm]: 1.258 (7.48), 1.277 (16.00), 1.294 (7.84), 2.033 (1.85), 2.656 (10.35), 3.138 (2.07), 3.157 (6.62), 3.174 (6.61), 3.192 (1.95), 6.598 (3.08), 6.668 (3.26), 6.673 (2.81), 6.689 (3.32), 6.694 (3.00), 7.197 (1.21), 7.200 (2.08), 7.204 (1.07), 7.209 (5.06), 7.211 (5.16), 7.216 (3.47), 7.219 (4.31), 7.221 (3.27), 7.232 (1.36), 7.237 (4.46), 7.261 (2.25), 7.264 (2.33), 7.271 (3.64), 7.275 (6.80), 7.280 (3.66), 7.284 (3.76), 7.289 (2.48), 7.292 (3.99), 7.296 (2.38), 7.300 (1.38), 7.305 (2.54), 7.311 (0.60), 7.319 (0.72), 7.326 (4.92), 7.348 (4.23), 7.560 (1.02), 7.564 (1.06), 7.579 (2.35), 7.582 (2.20), 7.598 (2.08), 7.602 (1.79), 7.622 (1.84), 7.625 (2.06), 7.640 (2.51), 7.644 (2.54), 7.659 (1.03), 7.663 (0.89), 8.249 (2.53), 8.252 (2.84), 8.269 (2.23), 8.272 (2.41); LC-MS (method 9): R$_t$=0.71 min; MS (ESIpos): m/z=421 [M+H]$^+$ Example 212

N-(2-Ethoxybenzene-1-sulfonyl)-6-(ethylamino)-1-benzofuran-2-carboxamide

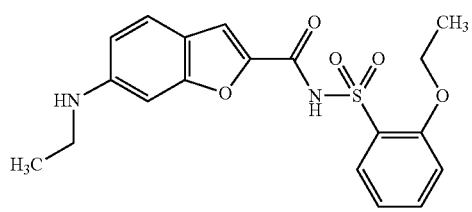 [SMILES: CCNc1ccc2cc(C(=O)NS(=O)(=O)c3ccccc3OCC)oc2c1]

According to GP5A, aforementioned 6-(ethylamino)-1-benzofuran-2-carboxylic acid (INT-43, 100 mg, 585 μmol), commercially available, 2-ethoxybenzene-1-sulfonamide (CAS: 58734-61-5, 118 mg, 585 μmol), PyBOP (304 mg, 585 μmol) and DIPEA (340 μL, 1.9 mmol) were stirred at RT in DCM (3.4 mL) overnight. After reaction completion, work-up and purification using HPLC (acid), the desired product was obtained as an ochre solid (4 mg, 2%); $^1$H-NMR (400 MHz, METHANOL-d$_4$) δ [ppm]: 1.247 (7.59), 1.265 (15.57), 1.283 (7.77), 1.340 (7.83), 1.357 (16.00), 1.375 (8.08), 2.656 (8.76), 3.130 (2.15), 3.148 (6.84), 3.166 (6.85), 3.184 (2.02), 4.125 (2.06), 4.143 (6.72), 4.161 (6.54), 4.178 (2.00), 6.667 (9.71), 6.686 (3.65), 6.691 (2.24), 7.053 (1.39), 7.056 (1.49), 7.074 (2.74), 7.094 (4.16), 7.114 (2.87), 7.343 (3.90), 7.347 (1.60), 7.363 (1.29), 7.366 (3.63), 7.438 (4.96), 7.529 (1.19), 7.534 (1.22), 7.547 (1.42), 7.551 (1.69), 7.554 (1.38), 7.568 (1.03), 7.573 (1.00), 7.994 (2.86), 7.998 (2.89), 8.014 (2.76), 8.018 (2.69); LC-MS (method 9): R$_t$=0.61 min; MS (ESIpos): m/z=389 [M+H]$^+$.

Example 213

N-(5-Bromo-2-ethoxybenzene-1-sulfonyl)-6-[(2-methoxyethyl)(methyl)amino]-1-benzofuran-2-carboxamide

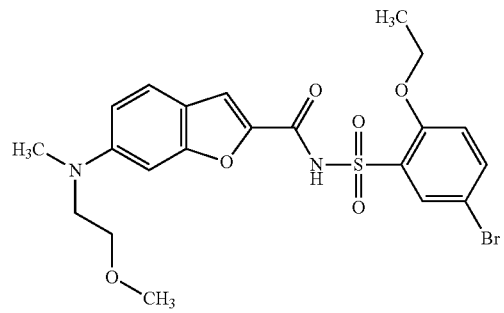 [SMILES: CCOc1ccc(Br)cc1S(=O)(=O)NC(=O)c1cc2ccc(N(C)CCOC)cc2o1]

According to GP5A, aforementioned 6-[(2-methoxyethyl)(methyl)amino]-1-benzofuran-2-carboxylic acid (INT-42, 175 mg, 50% purity, 351 μmol), commercially available, -5-bromo-2-ethoxybenzene-1-sulfonamide (CAS: 327081-38-9, 118 mg, 421 μmol), PyBOP (219 mg, 421 μmol) and DIPEA (240 μL, 1.4 mmol) were stirred at RT in DCM (3 mL) overnight. After reaction completion, work-up and purification using HPLC (acid), the desired product was obtained as an ochre solid (30 mg, 16%). $^1$H-NMR (400 MHz, DMSO-d$_6$) delta [ppm]: 1.206 (2.56), 1.224 (5.49), 1.241 (2.58), 2.074 (0.52), 2.326 (0.82), 2.331 (0.58), 2.518 (2.84), 2.522 (1.89), 2.668 (0.82), 2.673 (0.60), 2.980 (8.81), 3.236 (16.00), 3.478 (0.70), 3.494 (2.41), 3.507 (1.49), 3.568 (1.14), 3.582 (1.53), 4.152 (1.42), 4.169 (1.41), 6.768 (1.25), 6.773 (1.34), 6.848 (0.68), 6.853 (0.63), 6.870 (0.72), 6.876 (0.65), 7.200 (0.68), 7.222 (0.71), 7.536 (1.20), 7.558 (1.10), 7.935 (2.34), 7.941 (2.14); LC-MS (method 9): $R_t$=1.24 min; MS (ESIpos): m/z=512 $[M+H]^+$.

Example 214

6-[(2-Methoxyethyl)(methyl)amino]-N-(5-methyl[1,1'-biphenyl]-2-sulfonyl)-1-benzofuran-2-carboxamide

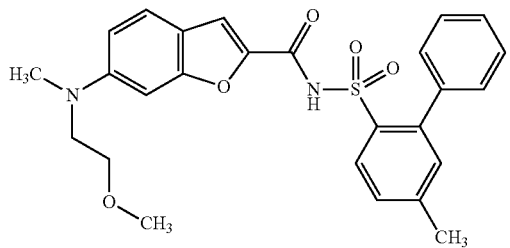 [SMILES: COCCN(C)c1ccc2cc(C(=O)NS(=O)(=O)c3ccc(C)cc3-c3ccccc3)oc2c1]

According to GP5A, aforementioned 6-[(2-methoxyethyl)(methyl)amino]-1-benzofuran-2-carboxylic acid (INT-42, 175 mg, 50% purity, 351 μmol), commercially available-5-methyl[1,1'-biphenyl]-2-sulfonamide (CAS: 936841-54-2, 104 mg, 421 μmol), PyBOP (219 mg, 421 μmol) and DIPEA (240 μL, 1.4 mmol) were stirred at RT in DCM (3 mL) overnight. After reaction completion, work-up and purification using HPLC (acid), the desired product was obtained as light green solid (30 mg, 17%); $^1$H-NMR (400 MHz, DMSO-$d_6$) δ [ppm]: 2.401 (5.14), 2.518 (2.87), 2.523 (2.02), 2.986 (7.45), 3.245 (16.00), 3.488 (0.53), 3.502 (1.96), 3.514 (1.21), 3.572 (0.89), 3.585 (1.20), 3.599 (0.45), 6.762 (1.01), 6.766 (1.11), 6.841 (0.55), 6.846 (0.49), 6.863 (0.57), 6.868 (0.53), 7.122 (0.89), 7.235 (0.77), 7.252 (1.35), 7.289 (0.81), 7.306 (1.67), 7.324 (0.89), 7.346 (0.59), 7.364 (0.60), 7.435 (0.41), 7.454 (0.44), 7.501 (1.11), 7.523 (1.05), 8.024 (1.36), 8.045 (1.24); LC-MS (method 9): $R_t$=1.32 min; MS (ESIpos): m/z=479 $[M+H]^+$.

Example 215

N-(2-Ethoxybenzene-1-sulfonyl)-6-[(2-methoxyethyl)(methyl)amino]-1-benzofuran-2-carboxamide

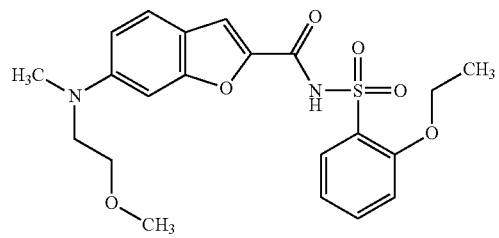 [SMILES: CCOc1ccccc1S(=O)(=O)NC(=O)c1cc2ccc(N(C)CCOC)cc2o1]

According to GP5A, aforementioned 6-[(2-methoxyethyl)(methyl)amino]-1-benzofuran-2-carboxylic acid (INT-42, 200 mg, 50% purity, 401 μmol), commercially available ethoxybenzene-1-sulfonamide (CAS: 58734-61-5, 96.9 mg, 481 μmol), PyBOP (251 mg, 481 μmol) and DIPEA (280 μL, 1.6 mmol) were stirred at RT in DCM (2 mL) overnight. After reaction completion, work-up and purification using HPLC (acid), the desired product was obtained as beige solid (49 mg, 27%); $^1$H-NMR (400 MHz, DMSO-$d_6$) δ [ppm]: 1.223 (2.36), 1.241 (5.45), 1.258 (2.42), 2.326 (0.40), 2.518 (1.40), 2.522 (0.93), 2.977 (7.59), 3.235 (16.00), 3.478 (0.56), 3.492 (1.99), 3.505 (1.19), 3.564 (0.95), 3.578 (1.26), 3.592 (0.47), 4.126 (0.52), 4.144 (1.60), 4.161 (1.61), 4.179 (0.48), 6.770 (1.00), 6.774 (1.08), 6.844 (0.67), 6.849 (0.56), 6.867 (0.68), 6.872 (0.61), 7.108 (0.41), 7.126 (0.81), 7.144 (0.44), 7.196 (0.70), 7.217 (0.75), 7.535 (1.28), 7.557 (1.17), 7.633 (0.50), 7.887 (0.89), 7.891 (0.86), 7.906 (0.87), 7.911 (0.80), 7.949 (0.54), 12.300 (0.68). LC-MS (method 9): $R_t$=1.14 min; MS (ESIpos): m/z=433 $[M+H]^+$.

Example 216

5-Bromo-6-(dimethylamino)-N-(2-methylquinoline-8-sulfonyl)-1-benzofuran-2-carboxamide

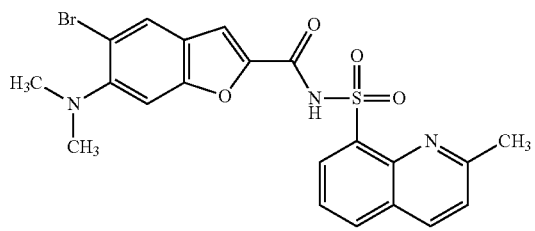

According to GP5A, aforementioned 5-bromo-6-(dimethylamino)-1-benzofuran-2-carboxylic acid (INT-48, 250 mg, 880 μmol), commercially available 2-methylquinoline-8-sulfonamide (CAS: 157686-27-6, 235 mg, 1.06 mmol), PyBOP (549 mg, 1.06 mmol) and DIPEA (610 μL, 3.5 mmol) were stirred at RT in DCM (4.3 mL) overnight. After reaction completion, work-up and purification using HPLC (acid), the desired product was obtained as yellow solid (190 mg, 42%). $^1$H-NMR (400 MHz, DMSO-$d_6$) δ [ppm]: 2.524 (0.42), 2.685 (7.88), 2.741 (16.00), 7.385 (2.15), 7.520 (1.54), 7.541 (1.62), 7.743 (0.81), 7.763 (1.26), 7.783 (0.85), 8.080 (1.85), 8.100 (3.69), 8.297 (0.86), 8.300 (0.90), 8.317 (0.84), 8.321 (0.77), 8.398 (1.53), 8.420 (1.42), 8.466 (1.02), 8.470 (1.00), 8.485 (0.99), 8.488 (0.87); LC-MS (method 9): $R_t$=1.11 min; MS (ESIneg): m/z=486 $[M-H]^-$.

Example 217

N-([1,1'-biphenyl]-2-sulfonyl)-5-bromo-6-(dimethylamino)-1-benzofuran-2-carboxamide

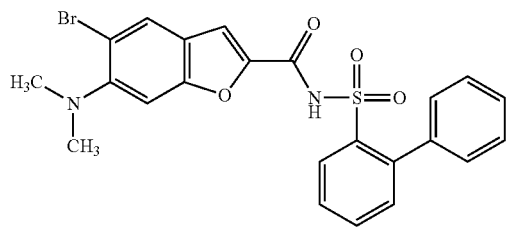 [SMILES: CN(C)c1cc2oc(C(=O)NS(=O)(=O)c3ccccc3-c3ccccc3)cc2cc1Br]

According to GP5A, aforementioned 5-bromo-6-(dimethylamino)-1-benzofuran-2-carboxylic acid (INT-48, 250 mg, 880 µmol), commercially available 2-phenylbenzene-1-sulfonamide (CAS: 40182-06-7, 549 mg, 1.06 mmol), PyBOP (549 mg, 1.06 mmol) and DIPEA (610 µL, 3.5 mmol) were stirred at RT in DCM (4.3 mL) overnight. After reaction completion, work-up and purification using HPLC (acid), the desired product was obtained as ochre solid (300 mg, 65%). $^1$H-NMR (400 MHz, DMSO-$d_6$) δ [ppm]: 2.521 (0.41), 2.775 (16.00), 7.240 (0.87), 7.244 (1.20), 7.261 (1.94), 7.297 (0.62), 7.301 (0.90), 7.313 (1.17), 7.318 (2.15), 7.323 (0.83), 7.332 (1.14), 7.335 (1.50), 7.354 (0.49), 7.358 (0.81), 7.361 (0.44), 7.375 (0.87), 7.425 (2.14), 7.601 (1.41), 7.667 (0.77), 7.671 (0.73), 7.687 (0.61), 7.691 (0.55), 7.718 (0.56), 7.722 (0.60), 7.737 (0.82), 7.740 (0.79), 8.071 (3.46), 8.166 (0.92), 8.169 (0.93), 8.186 (0.84), 8.189 (0.80); LC-MS (method 9): $R_t$=1.35 min; MS (ESIpos): m/z=499 [M+H]$^+$ Example 218

5-Bromo-6-(dimethylamino)-N-(2-ethoxybenzene-1-sulfonyl)-1-benzofuran-2-carboxamide

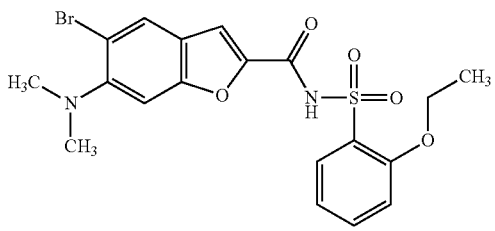 [SMILES: CCOc1ccccc1S(=O)(=O)NC(=O)c1cc2cc(Br)c(N(C)C)cc2o1]

According to GP5A, 5-bromo-6-(dimethylamino)-1-benzofuran-2-carboxylic acid (INT-48, 5-bromo-6-(dimethylamino)-1-benzofuran-2-carboxylic acid), commercially available 2-ethoxybenzene-1-sulfonamide (CAS: 58734-61-5, 425 mg, 2.11 mmol), PyBOP (1.10 g, 2.11 mmol) and DIPEA (1.2 mL, 7.0 mmol) were stirred at RT in DCM (8.7 mL) overnight. After reaction completion, work-up and purification using HPLC (acid), the desired product was obtained as ochre solid (460 mg, 53%). $^1$H-NMR (400 MHz, DMSO-$d_6$) δ [ppm]: 1.223 (2.15), 1.240 (4.72), 1.258 (2.20), 2.079 (0.94), 2.766 (16.00), 4.137 (0.60), 4.154 (1.96), 4.171 (1.94), 4.189 (0.59), 7.123 (0.52), 7.142 (1.05), 7.160 (0.58), 7.212 (0.95), 7.232 (1.04), 7.436 (2.23), 7.631 (0.45), 7.635 (0.48), 7.653 (0.69), 7.906 (0.94), 7.910 (0.93), 7.926 (0.92), 7.930 (0.84), 8.010 (1.75), 8.109 (3.53); LC-MS (method 9): $R_t$=1.24 min; MS (ESIpos): m/z=467 [M+H]$^+$.

Example 219

N-(2-butoxybenzene-1-sulfonyl)-6-[(2-methoxyethyl)(methyl)amino]-1-benzofuran-2-carboxamide

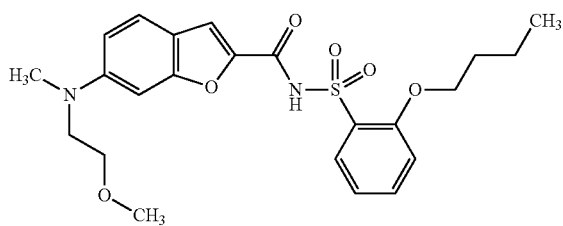 [SMILES: CCCCOc1ccccc1S(=O)(=O)NC(=O)c1cc2ccc(N(C)CCOC)cc2o1]

According to GP5A, 6-[(2-methoxyethyl)(methyl)amino]-1-benzofuran-2-carboxylic acid (INT-42, 175 mg, 50% purity, 351 µmol), 2-butoxybenzene-1-sulfonamide (96.6 mg, 421 µmol), PyBOP (219 mg, 421 µmol) and DIPEA (240 µL, 1.4 mmol) were stirred at RT in DCM (3 mL) overnight. After reaction completion, work-up and purification using HPLC (acid), the desired product was obtained in two fractions; the first one as beige solid (13 mg, 8% yield, 95% purity) and the second one (10 mg, 5% yield, 75% purity). Analytics of the first fraction: $^1$H-NMR (400 MHz, DMSO-$d_6$) δ [ppm]: −0.008 (0.79), 0.008 (0.93), 0.720 (2.51), 0.739 (5.82), 0.757 (2.81), 1.272 (0.67), 1.290 (1.06), 1.296 (0.47), 1.310 (1.03), 1.328 (0.65), 1.622 (0.85), 1.637 (0.70), 1.642 (0.87), 1.660 (0.75), 2.334 (0.46), 2.520 (2.62), 2.524 (1.70), 2.676 (0.46), 2.980 (8.68), 3.237 (16.00), 3.480 (0.61), 3.495 (2.18), 3.508 (1.38), 3.565 (1.06), 3.579 (1.41), 3.593 (0.54), 4.073 (0.94), 4.089 (1.90), 4.105 (0.91), 6.766 (1.15), 6.770 (1.25), 6.845 (0.71), 6.851 (0.64), 6.867 (0.72), 6.872 (0.67), 7.104 (0.45), 7.123 (0.89), 7.142 (0.49), 7.206 (0.73), 7.227 (0.80), 7.527 (1.39), 7.549 (1.28), 7.633 (0.57), 7.893 (0.96), 7.897 (1.01), 7.913 (1.45), 7.917 (1.59), 12.262 (0.73); LC-MS (method 9): $R_t$=1.26 min; MS (ESIpos): m/z=461 [M+H]$^+$.

Example 220

6-(Ethylamino)-N-(2-methylquinoline-8-sulfonyl)-1-benzofuran-2-carboxamide

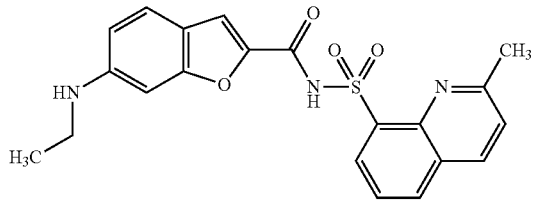 [SMILES: CCNc1ccc2cc(C(=O)NS(=O)(=O)c3cccc4ccc(C)nc34)oc2c1]

According to GP5A, 6-(ethylamino)-1-benzofuran-2-carboxylic acid (INT-43, 100 mg, 487 µmol), commercially available 2-methylquinoline-8-sulfonamide (CAS: 157686-27-6, 130 mg, 585 µmol), PyBOP (304 mg, 585 µmol) and DIPEA (340 µL, 1.9 mmol) were stirred at RT in DCM (3.4 mL) for 20 h. After reaction completion, work-up and purification using HPLC (acid), the desired product was obtained in two fractions; the first one as ochre solid (3 mg, 1% yield): $^1$H-NMR (400 MHz, METHANOL-$d_4$) δ [ppm]: 1.230 (4.54), 1.247 (9.55), 1.266 (4.57), 2.035 (1.05), 2.657 (11.70), 2.717 (16.00), 3.101 (1.28), 3.119 (4.02), 3.137 (4.06), 3.155 (1.30), 3.868 (0.52), 6.617 (1.26), 6.622 (2.15), 6.635 (1.55), 6.641 (5.95), 7.296 (2.70), 7.300 (0.63), 7.314 (0.71), 7.319 (2.70), 7.335 (3.17), 7.377 (2.52), 7.398 (2.56), 7.592 (1.19), 7.611 (1.96), 7.630 (1.36), 8.040 (1.20), 8.043 (1.21), 8.060 (1.11), 8.063 (1.07), 8.181 (2.22), 8.202 (2.14), 8.491 (1.86), 8.495 (1.86), 8.509 (1.79), 8.513 (1.72); LC-MS (method 9): $R_t$=0.62 min; MS (ESIpos): m/z=410 [M+H]$^+$.

Example 84 was purified using chiral chromatography:

Example 221 (Enantiomer 1)

Orange coloured solid, optical rotation: −5.62°; $^1$H-NMR (400 MHz, DMSO-$d_6$) δ [ppm]: −0.149 (0.44), −0.008 (4.37), 0.008 (3.85), 0.146 (0.44), 0.783 (0.61), 0.857 (0.70), 0.862 (0.70), 0.875 (0.96), 0.883 (0.52), 0.893 (0.44), 0.994

(0.44), 1.110 (0.61), 1.137 (4.28), 1.156 (8.31), 1.174 (4.98), 1.235 (1.84), 1.282 (0.79), 1.355 (1.05), 1.408 (3.76), 1.870 (0.61), 1.895 (0.79), 1.909 (0.61), 1.962 (0.52), 2.010 (0.61), 2.076 (1.31), 2.086 (2.36), 2.117 (0.44), 2.204 (0.87), 2.320 (1.57), 2.324 (3.50), 2.329 (4.90), 2.334 (3.50), 2.338 (1.49), 2.520 (16.00), 2.525 (10.58), 2.662 (1.57), 2.667 (3.50), 2.671 (4.98), 2.676 (3.58), 2.680 (1.57), 2.985 (6.91), 3.374 (0.52), 4.736 (0.44), 5.383 (0.52), 6.638 (0.61), 6.794 (3.15), 6.849 (0.61), 6.977 (0.61), 7.486 (0.52), 7.571 (0.52), 7.941 (0.70), 12.119 (1.22).

Example 222 (Enantiomer 2)

off-white solid, optical rotation: +2.89°; $^1$H-NMR (400 MHz, DMSO-$d_6$) δ [ppm]: −0.008 (2.05), 0.008 (2.00), 0.763 (0.79), 0.855 (0.63), 0.875 (0.74), 0.994 (0.53), 1.011 (0.47), 1.091 (0.53), 1.137 (7.53), 1.155 (16.00), 1.174 (9.21), 1.225 (1.26), 1.235 (1.89), 1.336 (0.84), 1.395 (4.42), 1.876 (0.74), 1.897 (0.89), 1.920 (0.79), 1.962 (0.53), 2.004 (0.79), 2.025 (0.63), 2.086 (0.42), 2.118 (0.47), 2.185 (1.11), 2.334 (2.16), 2.338 (1.00), 2.520 (10.00), 2.525 (6.68), 2.676 (2.16), 2.680 (0.95), 2.920 (2.16), 2.939 (2.74), 2.970 (8.42), 5.401 (0.63), 6.620 (0.53), 6.790 (4.00), 7.477 (0.42), 12.120 (0.42).

The following example compounds 223-227 were prepared using 19, 66, 21, 14 and 110, according to the same method, as the example 223 as follows: aforementioned example 110 was dissolved in DCM and shacked with a sodium hydroxide solution (1 M) and the water phase was extracted three times with DCM. The combined organic layers were filtered through an hydrophilic filter and concentrated under vacuum. The resulted residue was stirred with a solution of hexane/DCM (8:2), the resulted solid was collected by filtration and dried to give the title compound as the corresponding sodium salt.

TABLE 6 examples 223-227

| Examples | Structure, IUPAC-Name and analytics |
|---|---|
| 223 | 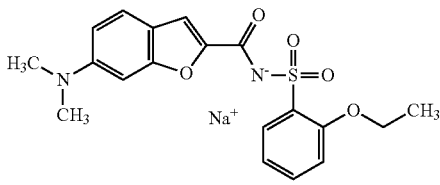 Sodium [6-(dimethylamino)-1-benzofuran-2-carbonyl](2-ethoxybenzene-1-sulfonyl)azanide<br>$^1$H-NMR (400 MHz, DMSO-$d_6$) δ [ppm]: 1.182 (2.24), 1.199 (4.88), 1.217 (2.29), 2.931 (16.00), 3.993 (0.65), 4.010 (2.09), 4.028 (2.09), 4.045 (0.62), 6.740 (0.68), 6.746 (0.87), 6.762 (0.63), 6.767 (1.04), 6.781 (1.36), 6.917 (0.50), 6.919 (0.55), 6.937 (1.03), 6.954 (0.57), 6.956 (0.58), 6.990 (0.94), 7.010 (1.06), 7.037 (2.39), 7.039 (2.41), 7.336 (0.50), 7.340 (0.53), 7.354 (0.62), 7.356 (0.68), 7.358 (0.68), 7.360 (0.61), 7.374 (0.43), 7.379 (0.41), 7.412 (1.49), 7.433 (1.37), 7.787 (0.98), 7.792 (0.98), 7.806 (0.93), 7.811 (0.87); LC-MS (Method 1): $R_t$ = 1.19 min; MS (ESIpos): m/z = 389 [M + H]$^+$ |

TABLE 6-continued examples 223-227

| Examples | Structure, IUPAC-Name and analytics |
|---|---|
| 224 | 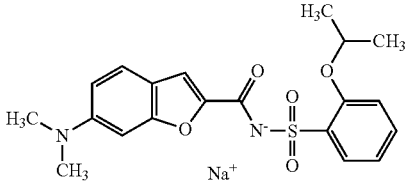 Sodium [6-(dimethylamino)-1-benzofuran-2-carbonyl]{2-[(propan-2-yl)oxy]benzene-1-sulfonyl}azanide<br>$^1$H-NMR (400 MHz, DMSO-$d_6$) δ [ppm]: 1.136 (8.81), 1.151 (8.70), 2.520 (0.45), 2.932 (16.00), 4.564 (0.52), 4.579 (0.69), 4.594 (0.52), 6.733 (0.65), 6.739 (0.83), 6.756 (0.61), 6.761 (0.97), 6.776 (1.22), 6.879 (0.47), 6.882 (0.49), 6.900 (0.91), 6.916 (0.53), 6.919 (0.54), 6.968 (0.90), 6.980 (2.30), 6.982 (2.32), 6.988 (1.04), 7.296 (0.48), 7.301 (0.49), 7.315 (0.56), 7.317 (0.61), 7.319 (0.62), 7.322 (0.55), 7.406 (1.38), 7.428 (1.27), 7.767 (0.88), 7.771 (0.90), 7.786 (0.89), 7.790 (0.82); LC-MS (Method 1): $R_t$ = 1.25 min; MS (ESIpos): m/z = 403 [M + H]$^+$ |
| 225 | 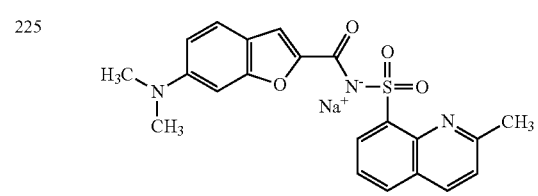 Sodium [6-(dimethylamino)-1-benzofuran-2-carbonyl](2-methylquinoline-8-sulfonyl)azanide<br>$^1$H-NMR (400 MHz, DMSO-$d_6$) δ [ppm]: 2.620 (7.73), 2.904 (16.00), 6.720 (0.44), 6.725 (1.45), 6.729 (1.42), 6.731 (1.37), 6.734 (1.18), 6.743 (1.21), 6.749 (0.57), 7.161 (2.42), 7.378 (1.70), 7.385 (1.80), 7.400 (1.60), 7.405 (1.74), 7.564 (0.81), 7.583 (1.27), 7.602 (0.88), 8.009 (0.88), 8.012 (0.94), 8.029 (0.87), 8.033 (0.81), 8.256 (1.54), 8.277 (1.49), 8.338 (1.04), 8.342 (1.05), 8.357 (1.00), 8.361 (0.92); LC-MS (Method 1): $R_t$ = 1.10 min; MS (ESIpos): m/z = 410 [M + H]$^+$ |

TABLE 6-continued examples 223-227

| Examples | Structure, IUPAC-Name and analytics |
|---|---|
| 226 | 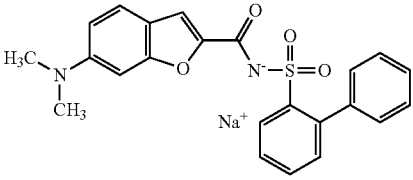<br>Sodium ([1,1'-biphenyl]-2-sulfonyl)[6-(dimethylamino)-1-benzofuran-2-carbonyl]azanide<br>$^1$H-NMR (400 MHz, DMSO-d$_6$) δ [ppm]: 2.518 (1.14), 2.523 (0.82), 2.935 (16.00), 6.734 (0.65), 6.740 (0.82), 6.756 (0.57), 6.762 (1.04), 6.772 (1.17), 6.812 (2.43), 6.814 (1.96), 7.097 (0.69), 7.101 (0.61), 7.103 (0.54), 7.115 (0.87), 7.119 (0.78), 7.209 (0.64), 7.212 (2.07), 7.218 (1.29), 7.221 (2.21), 7.223 (1.29), 7.229 (2.06), 7.233 (0.61), 7.389 (0.89), 7.394 (1.84), 7.404 (1.00), 7.407 (1.12), 7.411 (1.16), 7.412 (1.08), 7.416 (1.42), 7.423 (1.11), 7.426 (1.82), 7.430 (0.86), 7.433 (1.12), 7.437 (0.86), 7.440 (1.08), 7.442 (1.06), 7.445 (0.75), 7.450 (0.87), 8.058 (0.80), 8.062 (0.92), 8.074 (0.56), 8.077 (0.62), 8.081 (0.71); LC-MS (method 4): R$_t$ = 1.24 min; MS (ESIpos): m/z = 428 [M + H]$^+$. |
| 227 | 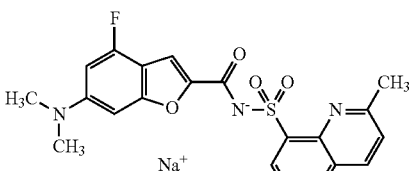<br>Sodium [6-(dimethylamino)-4-fluoro-1-benzofuran-2-carbonyl](2-methylquinoline-8-sulfonyl)azanide<br>$^1$H-NMR (400 MHz, DMSO-d$_6$) δ [ppm]: 2.518 (0.70), 2.523 (0.48), 2.615 (7.29), 2.928 (16.00), 3.313 (1.32), 3.332 (0.91), 6.535 (0.69), 6.540 (0.78), 6.569 (0.65), 6.573 (0.83), 6.600 (1.33), 7.109 (2.26), 7.111 (2.18), 7.386 (1.57), 7.407 (1.64), 7.542 (0.80), 7.561 (1.25), 7.580 (0.87), 7.986 (0.87), 7.989 (0.92), 8.006 (0.84), 8.010 (0.80), 8.241 (1.53), 8.262 (1.44), 8.293 (0.99), 8.297 (1.00), 8.312 (0.96), 8.316 (0.89). LC-MS (method 4): R$_t$ = 1.07 min; MS (ESIpos): m/z = 421 [M + H]$^+$. |

Example 228

6-(Dimethylamino)-N-((2-ethoxy-4,5-difluorophenyl)sulfonyl)benzofuran-2-carboxamide

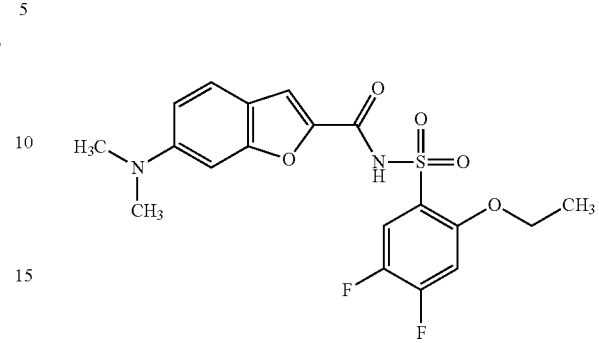

To a room temperature stirred solution of 6-(dimethylamino)benzofuran-2-carboxylic acid (34.9 mg, 0.17 mmol, 1.00 eq.) in anhydrous tetrahydrofuran (0.85 mL, 0.20 M) was added carbonyldiimidazole (33.1 mg, 0.20 mmol, 1.20 eq.). After stirring for 1 h, 2-ethoxy-4,5-difluoro-benzenesulfonamide (44.4 mg, 0.19 mmol, 1.10 eq.) and 1,8-diazabicyclo[5.4.0]undec-7-ene (40.0 µL, 0.24 mmol, 1.40 eq.) were sequentially added. The resulting mixture was stirred at room temperature for 15 h and then concentrated under reduced pressure. The residue was purified by reverse phase preparative column chromatography (Waters XBridge PREP C$_{18}$, 5 µM OBD, 30×150 mm, 49-57% acetonitrile/water gradient buffered with 0.1% formic acid) to give the title compound as a yellow solid (44.0 mg). 1H NMR (400 MHz, DMSO-d$_6$) δ 12.54 (s, 1H), 7.96-7.86 (m, 2H), 7.60-7.53 (m, 1H), 7.45 (dd, 1H), 6.90-6.82 (m, 1H), 6.79-6.74 (m, 1H), 4.16 (q, 2H), 2.98 (s, 6H), 1.22 (t, 3H); LC-MS (Method 7): R$_t$=2.70 min; MS (ESIpos): m/z=425 [M+H]$^+$

Example 229

N-((5-cyclopropyl-2-ethoxyphenyl)sulfonyl)-6-(dimethylamino)benzofuran-2-carboxamide

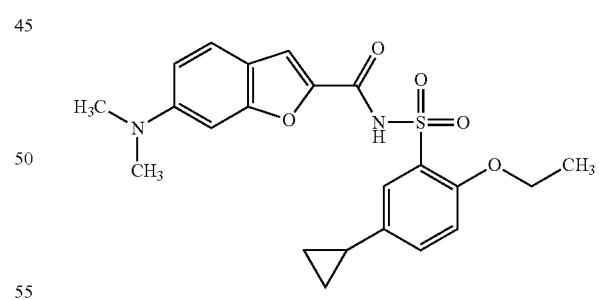

To a room temperature stirred solution of 6-(dimethylamino)benzofuran-2-carboxylic acid (8.21 mg, 0.04 mmol, 1.00 eq.) in anhydrous tetrahydrofuran (200 µL, 0.20 M) was added carbonyldiimidazole (7.78 mg, 0.5 mmol, 1.20 eq.). After stirring for 1 h, 5-cyclopropyl-2-ethoxy-benzenesulfonamide (10.6 mg, 0.04 mmol, 1.10 eq.) and 1,8-diazabicyclo[5.4.0]undec-7-ene (10.0 µL, 0.06 mmol, 1.40 eq.) were sequentially added. The resulting mixture was stirred at room temperature for 16 hours and then concentrated under reduced pressure. The residue was purified by reverse phase preparative column chromatography (Waters XBridge PREP $C_{18}$, 5 μM OBD, 19×250 mm, 53-61% acetonitrile/water gradient buffered with 0.1% formic acid) to give the title compound as a yellow solid (4.50 mg). 1H NMR (400 MHz, DMSO-d6) δ 12.28 (s, 1H), 7.97-7.92 (m, 1H), 7.64-7.52 (m, 2H), 7.30-7.25 (m, 1H), 7.11-7.04 (m, 1H), 6.89-6.81 (m, 1H), 6.79-6.74 (m, 1H), 4.14-4.04 (m, 2H), 2.98 (s, 6H), 2.04-1.95 (m, 1H), 1.25-1.17 (m, 3H), 1.01-0.91 (m, 2H), 0.68-0.59 (m, 2H); LC-MS (Method 7): $R_t$=2.87 min; MS (ESIpos): m/z=429 [M+H]$^+$ Example 230

6-(Dimethylamino)-N-((2-methoxy-5-(2-oxopropyl) phenyl)sulfonyl)benzofuran-2-carboxamide

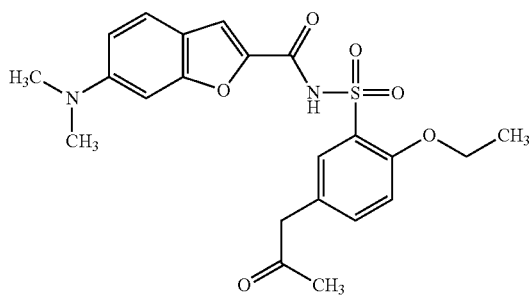 [SMILES: CCOc1ccc(CC(C)=O)cc1S(=O)(=O)NC(=O)c1cc2ccc(N(C)C)cc2o1]

To a room temperature stirred solution of 6-(dimethylamino)benzofuran-2-carboxylic acid (82.1 mg, 0.40 mmol, 1.00 eq.) in anhydrous tetrahydrofuran (2.00 mL, 0.20 M) was added carbonyldiimidazole (77.8 mg, 0.48 mmol, 1.20 eq.). After stirring for 1 hour, 5-acetonyl-2-methoxy-benzenesulfonamide (107 mg, 0.44 mmol, 1.10 eq.) and 1,8-diazabicyclo[5.4.0]undec-7-ene (80.0 μL, 0.56 mmol, 1.40 eq.) were sequentially added. The resulting mixture was stirred at room temperature for one hour and then concentrated under reduced pressure. The residue was purified by reverse phase preparative column chromatography (Waters XBridge PREP $C_{18}$, 5 μM OBD, 30×150 mm, 38-46% acetonitrile/water gradient buffered with 0.1% formic acid) to give the title compound as a yellow solid (95 mg). $^1$H NMR (400 MHz, DMSO-d$_6$) δ 12.41 (s, 1H), 7.94 (s, 1H), 7.78-7.70 (m, 1H), 7.56 (d, 1H), 7.48-7.41 (m, 1H), 7.21-7.14 (m, 1H), 6.90-6.82 (m, 1H), 6.80-6.74 (m, 1H), 3.89-3.82 (m, 5H), 2.98 (s, 5H), 2.16 (s, 3H); LC-MS (Method 7): $R_t$=2.30 min; MS (ESIpos): m/z=431 [M+H]$^+$ Example 231

N-((5-(tert-butyl)-2-cyclopropoxyphenyl)sulfonyl)-6-(dimethylamino)benzofuran-2-carboxamide

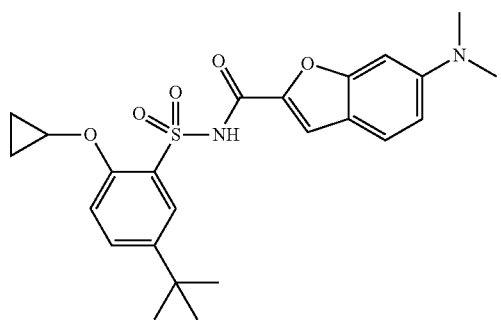 [SMILES: CN(C)c1ccc2cc(C(=O)NS(=O)(=O)c3cc(C(C)(C)C)ccc3OC3CC3)oc2c1]

To a room temperature stirred solution of 6-(dimethylamino)benzofuran-2-carboxylic acid (20.5 mg, 0.10 mmol, 1.00 eq.) in anhydrous THF (0.50 mL, 0.20 M) was added carbonyldiimidazole (19.5 mg, 0.12 mmol, 1.20 eq.). After stirring for 1 h, 5-tert-butyl-2-(cyclopropoxy)benzenesulfonamide (29.6 mg, 0.11 mmol, 1.10 eq.) and 1,8-diazabicyclo [5.4.0]undec-7-ene (20 μL, 0.14 mmol, 1.40 eq.) were sequentially added. The resulting mixture was stirred at room temperature for 15 h and then concentrated under reduced pressure. The residue was purified by reverse phase preparative column chromatography (Waters XBridge PREP $C_{18}$, 5 μM OBD, 30×150 mm, 67-75% acetonitrile/water gradient buffered with 0.1% formic acid) to give the title compound as a yellow solid (18 mg). 1H NMR (400 MHz, DMSO-d$_6$) δ 12.22 (s, 1H), 7.93-7.88 (m, 1H), 7.84 (d, 1H), 7.74-7.67 (m, 1H), 7.57 (d, 1H), 7.38 (d, 1H), 6.90-6.82 (m, 1H), 6.78-6.73 (m, 1H), 4.02 (s, 1H), 2.99 (s, 6H), 1.31 (s, 9H), 0.73-0.66 (m, 1H), 0.56-0.49 (m, 2H); LC-MS (method 7): $R_t$=3.40 min; MS (ESIpos): m/z=457 [M+H]$^+$ Experimental Section—Biological Assays Examples were tested in selected biological assays one or more times. When tested more than once, data are reported as either average values or as median values, wherein
  the average value, also referred to as the arithmetic mean value, represents the sum of the values obtained divided by the number of times tested, and
  the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

An empty field in any of the following tables means that the respective compound has not been tested in that Assay.

The in vitro activity of the compounds of the present invention can be demonstrated in the following assays:

Kat6a Activity Assay

Kat6a inhibitory activities of the compounds described in the present invention were quantified using a Fluorescence Resonance Energy Transfer (TR-FRET) assay which measures acetylation of a synthetic, biotinylated Histone-H4-derived peptide by the enzyme.

Recombinant human His-tagged Kat6a protein (amino acids 194-810), was purified in-house from Baculovirus-infected insect cells (Sf9). Histone H4 peptide (amino acids 1-24, SGRGKGGKGLGKGGAKRHRK-VLRD-K(Btn)-amide), which was used as substrate, was synthesized by Biosyntan GmbH, Berlin, Germany. Acetyl Coenzyme A was purchased from Sigma-Aldrich (#A-2056).

Kat6a was incubated for 60 mins at 22° C. in the presence of different concentrations of test substances (0 μM, and within the range 0.01-20 μM) in assay buffer [25 mM Tris/HCl pH 8, 1 mM EGTA, 2.5 mM Glutathion, 0.02% Chicken Albumin, 0.05% Pluronic F127, 25 mM NaCl, 220 nM H4 peptide and 600 nM Acetyl Coenzym A].

The reaction was stopped by addition of Detection Solution (25 mM HEPES pH 7.5, 0.1% BSA, 22 nM SAXL665 (Cisbio #610SAXLE), 100 μM Anacardic Acid (Enzo #ALX-270-381), 1 nM Anti-Histone H4 (ACETYL K8)

Antibody (ABCAM #AB15823) and 0.5 nM Anti-Rabbit IgG Eu (Perkin Elmer #AD0083).

Kat6b Activity Assay

Kat6b inhibitory activities of the compounds described in the present invention were quantified using a Fluorescence Resonance Energy Transfer (TR-FRET) assay which measures acetylation of a synthetic, biotinylated Histone-H4-derived peptide by the enzyme.

Recombinant human GST-tagged Kat6b protein (431-end, N-terminal GST-tag), purified from Baculovirus-infected insect cells (Sf9), was purchased from SignalChem (#K315-381 BG). Histone H4 peptide (amino acids 1-24, SGRGKGGKGLGKGGAKRHRK-VLRD-K(Btn)-amide), which was used as substrate, was synthesized by Biosyntan GmbH, Berlin, Germany. Acetyl Coenzym A was purchased from Sigma-Aldrich (#A-2056).

Kat6b was incubated for 30 mins at 22° C. in the presence of different concentrations of test substances (0 µM, and within the range 0.01-20 µM) in assay buffer [25 mM Tris/HCl pH 8, 1 mM EGTA, 2.5 mM Glutathion, 0.02% Chicken Albumin, 0.05% Pluronic F127, 25 mM NaCl, 500 nM H4 peptide and 600 nM Acetyl Coenzym A].

The reaction was stopped by addition of Detection Solution (25 mM HEPES pH 7.5, 0.1% BSA, 22 nM SAXL665 (Cisbio #610SAXLE), 100 µM Anacardic Acid (Enzo #ALX-270-381), 1 nM Anti-Histone H4 (ACETYL K8) Antibody (ABCAM #AB15823), 0.5 nM Anti-Rabbit IgG Eu (Perkin Elmer #AD0083).

The fluorescence emission at 620 nm and 665 nm after excitation at 330-350 nm was measured in a TR-FRET measuring instrument, for instance a Rubystar or a Pherastar (both from BMG Lab Technologies, Offenburg, Germany) or a Viewlux (Perkin-Elmer). The ratio of the emission at 665 nm and at 622 nm was used as indicator of the amount of acetylated peptide.

The resulting data (ratio) were normalized, taking 0% inhibition as the mean value of control measurements where all reagents were included. In this case 50 nl DMSO were used instead of compounds. A 100% inhibition corresponded to the mean value of control measurements where all reagents except enzyme were included. IC50 values were determined by regression analysis based on a 4 parameter equation (minimum, maximum, ICM, Hill; Y=Max+(Min−Max)/(1+(X/ICso) Hill) using the Screener Software (Genedata).

Table 5 depicts the IC50 values of selected examples in biochemical KAT6A and KAT6B3 assays.

TABLE 5

IC$_{50}$ values of selected examples in biochemical KAT6A and KAT6B assays.

| Example | KAT6A-DPF/ HAT domain IC$_{50}$ [mol/l] (arithmetic mean) | KAT6B activity assay IC$_{50}$ [mol/l] (arithmetic mean) |
| --- | --- | --- |
| 01 | 5.99 E−7 | 8.36 E−7 |
| 02 | 4.80 E−6 | 5.70 E−6 |
| 03 | 1.39 E−6 | 8.10 E−7 |
| 04 | 2.70 E−6 | 1.41 E−6 |
| 05 | 1.10 E−6 | 4.95 E−7 |
| 06 | 1.83 E−6 | 4.28 E−6 |
| 07 | 9.60 E−6 | >2.00 E−5 |
| 08 | 5.03 E−6 | 4.40 E−6 |
| 09 | 2.55 E−6 | 5.72 E−6 |
| 10 | 9.00 E−7 | 1.49 E−6 |
| 11 | 1.23 E−7 | 2.05 E−7 |
| 12 | 1.33 E−8 | 1.82 E−8 |
| 13 | 1.25 E−8 | 1.16 E−8 |
| 14 | 6.76 E−8 | 8.33 E−8 |
| 15 | 1.12 E−7 | 2.35 E−7 |
| 16 | 6.63 E−8 | 5.05 E−8 |
| 17 | 7.24 E−8 | 6.45 E−8 |
| 18 | 1.29 E−7 | |
| 19 | 8.46 E−8 | 6.69 E−8 |
| 20 | 1.04 E−7 | 8.84 E−8 |
| 21 | 2.34 E−8 | 2.67 E−8 |
| 22 | 2.19 E−7 | 2.00 E−7 |
| 23 | 7.93 E−8 | 9.92 E−8 |
| 24 | 3.10 E−8 | 4.90 E−8 |
| 25 | 3.11 E−8 | 5.06 E−8 |
| 26 | 4.06 E−7 | 7.78 E−7 |
| 27 | 1.34 E−7 | |
| 28 | 5.44 E−6 | 2.68 E−6 |
| 29 | 6.24 E−6 | 5.92 E−6 |
| 30 | 1.37 E−7 | 4.97 E−7 |
| 31 | 5.30 E−8 | 5.91 E−8 |
| 32 | 2.24 E−7 | 4.23 E−7 |
| 33 | 2.72 E−6 | >2.00 E−5 |
| 34 | 4.17 E−7 | 5.04 E−7 |
| 35 | 4.52 E−7 | 6.54 E−7 |
| 36 | 2.27 E−7 | 1.69 E−7 |
| 37 | 7.51 E−7 | 1.06 E−6 |
| 38 | 9.75 E−7 | 1.89 E−6 |
| 39 | 1.35 E−6 | 5.34 E−7 |
| 40 | 1.15 E−6 | 1.42 E−6 |
| 41 | 2.31 E−6 | 2.56 E−6 |
| 42 | 1.07 E−6 | 3.59 E−6 |
| 43 | 5.14 E−6 | 1.03 E−5 |
| 44 | 3.17 E−6 | 5.18 E−6 |
| 45 | 3.60 E−6 | 1.48 E−6 |
| 46 | 3.65 E−6 | 1.12 E−7 |
| 47 | 7.80 E−6 | 1.59 E−5 |
| 48 | 3.10 E−7 | 4.50 E−7 |
| 49 | 3.10 E−7 | 5.28 E−7 |
| 50 | 4.23 E−6 | |
| 51 | 5.73 E−8 | 1.03 E−7 |
| 52 | 1.87E−7 | |
| 53 | 4.40 E−7 | |
| 54 | 4.30 E−7 | |
| 55 | 8.64 E−8 | |
| 56 | 6.76 E−8 | |
| 57 | 3.82 E−8 | |
| 58 | 5.34 E−7 | |
| 59 | 8.61 E−8 | |
| 60 | 3.20 E−6 | |
| 61 | 1.61 E−5 | 9.85 E−6 |
| 62 | 1.35 E−5 | >2.00 E−5 |
| 63 | 1.65 E−5 | >2.00 E−5 |
| 64 | 1.43E−5 | |
| 65 | 2.83E−08 | 3.45E−08 |
| 66 | 4.94E−08 | 5.91E−08 |
| 67 | 4.29E−08 | 1.18E−07 |
| 68 | 6.96E−08 | 8.45E−08 |
| 69 | 4.50E−09 | |
| 70 | 1.22E−07 | 1.09E−07 |
| 71 | 7.24E−08 | 1.31E−07 |
| 72 | 9.67E−08 | 1.90E−07 |
| 73 | 1.17E−07 | 7.85E−08 |
| 74 | 1.28E−07 | 2.28E−07 |
| 75 | 1.63E−07 | 2.46E−07 |
| 76 | 8.87E−08 | 1.90E−07 |
| 77 | 2.72E−07 | 5.46E−07 |
| 78 | 3.27E−08 | 8.70E−08 |
| 79 | 1.88E−07 | 2.00E−07 |
| 80 | 7.38E−08 | 6.88E−08 |
| 81 | 3.20E−07 | 3.77E−07 |
| 82 | 2.37E−07 | 2.65E−07 |
| 83 | 4.88E−08 | 5.54E−08 |
| 84 | 4.06E−08 | |

TABLE 5-continued

IC$_{50}$ values of selected examples in biochemical KAT6A and KAT6B assays.

| Example | KAT6A-DPF/ HAT domain IC$_{50}$ [mol/l] (arithmetic mean) | KAT6B activity assay IC$_{50}$ [mol/l] (arithmetic mean) |
|---|---|---|
| 85 | 1.15E−07 | 1.86E−07 |
| 86 | 6.49E−08 | 8.00E−08 |
| 87 | 9.73E−08 | 1.04E−07 |
| 88 | 1.05E−07 | 2.05E−07 |
| 89 | 1.31E−07 | 1.72E−07 |
| 90 | 1.94E−07 | 3.57E−07 |
| 91 | 7.42E−08 | 9.22E−08 |
| 92 | 1.51E−07 | |
| 93 | 1.00E−07 | 1.73E−07 |
| 94 | 2.87E−07 | |
| 95 | 1.50E−07 | |
| 96 | 2.60E−07 | |
| 97 | 4.65E−07 | |
| 98 | 4.65E−07 | |
| 99 | 6.45E−07 | |
| 100 | 1.77E−07 | |
| 101 | 5.02E−07 | 6.10E−07 |
| 102 | 4.89E−07 | |
| 103 | 1.21E−06 | |
| 104 | 1.10E−06 | |
| 105 | 1.96E−06 | |
| 106 | 3.20E−06 | |
| 107 | 2.29E−09 | |
| 108 | 4.60E−09 | |
| 109 | 7.09E−09 | |
| 110 | 7.48E−09 | 3.82E−09 |
| 111 | 8.93E−09 | 1.90E−08 |
| 112 | 1.77E−08 | 1.81E−08 |
| 113 | 7.25E−09 | 7.24E−09 |
| 114 | 1.14E−07 | 1.50E−07 |
| 115 | 6.46E−08 | 8.72E−08 |
| 116 | 4.53E−07 | 5.08E−07 |
| 117 | 2.94E−07 | 3.42E−07 |
| 118 | 5.24E−08 | |
| 119 | 1.85E−07 | 3.74E−07 |
| 120 | 1.85E−06 | |
| 121 | 1.79E−07 | 2.27E−07 |
| 122 | 2.52E−07 | |
| 123 | 2.75E−07 | 2.57E−07 |
| 124 | 9.28E−08 | 5.22E−08 |
| 125 | 2.58E−06 | |
| 126 | 2.05E−08 | 2.38E−08 |
| 127 | 7.12E−08 | 5.62E−08 |
| 128 | 3.51E−07 | |
| 129 | 1.35E−08 | 1.68E−08 |
| 130 | 2.18E−06 | |
| 131 | 4.70E−07 | |
| 132 | 1.34E−07 | 7.27E−08 |
| 133 | 3.25E−07 | |
| 134 | 3.07E−08 | 2.59E−08 |
| 135 | 5.79E−08 | 1.86E−07 |
| 136 | 7.96E−07 | |
| 137 | 8.15E−08 | 1.07E−07 |
| 138 | 5.67E−08 | 7.95E−08 |
| 139 | 3.29E−08 | 3.69E−07 |
| 140 | 5.67E−06 | |
| 141 | 3.17E−07 | |
| 142 | 1.39E−07 | 2.29E−07 |
| 143 | 2.93E−08 | 4.31E−08 |
| 144 | 2.26E−07 | 2.94E−07 |
| 145 | 4.38E−07 | |
| 146 | 2.66E−07 | |
| 147 | 9.86E−08 | 6.92E−08 |
| 148 | 1.04E−07 | 6.80E−08 |
| 149 | 1.23E−07 | 3.79E−07 |
| 150 | 4.29E−07 | |
| 151 | 2.34E−07 | |
| 152 | 1.40E−06 | |
| 153 | 9.06E−07 | |
| 154 | 3.08E−06 | |
| 155 | 9.32E−07 | |
| 156 | 3.53E−06 | |
| 157 | 3.18E−06 | |
| 158 | 6.84E−07 | |
| 159 | 2.33E−07 | |
| 160 | 3.24E−06 | |
| 161 | 6.77E−06 | |
| 162 | 3.66E−07 | |
| 163 | 4.35E−06 | |
| 164 | 4.45E−06 | |
| 165 | 1.29E−06 | |
| 166 | 5.64E−08 | |
| 167 | 2.06E−06 | |
| 168 | 1.28E−07 | |
| 169 | 3.35E−07 | |
| 170 | 4.40E−09 | 8.84E−09 |
| 171 | 9.49E−08 | |
| 172 | 5.40E−08 | |
| 173 | 9.73E−08 | |
| 174 | 1.18E−08 | |
| 175 | | |
| 176 | 1.28E−08 | |
| 177 | 7.91E−09 | 2.40E−08 |
| 178 | 1.10E−08 | |
| 179 | 8.95E−09 | 1.94E−08 |
| 180 | 4.36E−09 | 2.13E−08 |
| 181 | 1.18E−08 | 4.35E−08 |
| 182 | 2.67E−09 | 1.19E−08 |
| 183 | 1.54E−08 | |
| 184 | 1.59E−08 | 4.78E−08 |
| 185 | 2.63E−09 | 1.39E−08 |
| 186 | 8.47E−09 | 2.61E−08 |
| 187 | 6.64E−06 | |
| 188 | 1.03E−05 | |
| 189 | 2.44E−06 | |
| 190 | 1.40E−06 | |
| 191 | 4.70E−06 | |
| 192 | 2.98E−06 | |
| 193 | 7.14E−09 | 1.28E−08 |
| 194 | 4.49E−08 | |
| 195 | 5.73E−09 | 1.47E−08 |
| 196 | 1.47E−09 | 1.78E−09 |
| 197 | 8.94E−07 | |
| 198 | 4.06E−06 | |
| 199 | 2.65E−06 | |
| 200 | 6.74E−06 | |
| 201 | 1.37E−07 | |
| 202 | 1.97E−06 | 3.01E−06 |
| 203 | 8.38E−06 | |
| 204 | 2.59E−06 | |
| 205 | 4.85E−07 | |
| 206 | 4.70E−06 | |
| 207 | 6.81E−06 | |
| 208 | 7.76E−06 | |
| 209 | 9.03E−07 | |
| 210 | 6.66E−06 | |
| 211 | 3.50E−07 | |
| 212 | 1.13E−06 | |
| 213 | 1.06E−06 | |
| 214 | 7.32E−07 | |
| 215 | 2.66E−06 | |
| 216 | 2.05E−06 | |
| 217 | 5.54E−06 | |
| 218 | 4.73E−06 | |
| 219 | 1.28E−06 | |
| 220 | 1.88E−07 | |
| 221 | 4.44E−08 | |
| 222 | 3.06E−08 | |
| 223 | 1.06E−07 | 9.91E−08 |
| 224 | 5.83E−08 | 7.64E−08 |
| 225 | 2.27E−08 | 2.58E−08 |
| 226 | 1.14E−07 | 1.02E−07 |
| 227 | 4.00E−09 | |

Repression of ESR1 Transcription Upon Treatment of Cells with Compounds

KAT6A controls transcription of the ESR1 gene in breast cancer cells. Compound treatment that interferes with this mechanism was quantified using MVLN cells. These cells constitutively express the ER and are stably transfected with the luciferase (LUC) reporter gene and the corresponding hormone responsive element derived from the 5'-flanking region of the Xenopus Vitellogenin A2 gene (Pons et al., 1990, Demirpense et al., 1993, Joyeux et al., 1993). The repressive effect on ERα transcription activity of a test chemical is directly related to the luciferase measured in the lysate of treated MVLN cells.

For measurements the MVLN cells were plated (20,000 cells per well in a 96-well format) in 100 µl culture medium (RPMI 1640 Medium without phenol red (Life Technologies; 11835-063), Pen Strep (Gibco, 15140-122), 10% FCS (Sigma; F2442)) for 24 h in humidified incubator at 37° C. and 5% $CO_2$. Then medium was replaced by 100 µl assay medium (RPMI 1640 Medium without phenol red (Life Technologies; 11835-063), Pen Strep (Gibco, 15140-122), 2.5% FCS (Sigma; F2442)) and cells were treated with compounds (stock solution, 10 mM in DMSO) using the HP D300 Digital Dispenser in a concentration range of 2×10E-5 M to 4.69×10E-9 M in a single-dot curve with 8 dilutions and a DMSO concentration of 0.2%. Each sample was prepared as duplicate and rim wells were excluded. For luciferase signal determination 100 µl of a 1:1 mixture of Steadylite plus (Perkin Elmer; 6016759) and assay medium was added after 24 h for 15 minutes and measured in Victor X3 (Perkin Elmer). To exclude any effects caused by cell loss during the treatment, cell density was determined using Alamar Blue (Invitrogen; DAL1100). Prior to the luciferase measurement 10 µl Alamar Blue were added to each well and the plates were incubated for 2 h in the incubator. Then fluorescence was measured with Victor X3 (Perkin Elmer) at 530 nm/590 nm.

For the evaluation of the results, the values were normalized to DMSO-only treated cells and the Bella DRC Master Sheet was used to calculate EC50s ($EC_{50}$ is the concentration for 50% of maximal reduction of luciferase signal achieved by Fulvestrant).

Table 6 shows the results of the inhibition of luciferase signal in MVLN cells upon treatment with the compounds of the invention.

Proliferation Assays for Compound Characterization

For compound characterization cell survival assays were routinely run in two cell lines. ZR-75-1 is a breast carcinoma cell line containing a focal KAT6A amplification and high KAT6A protein expression. Proliferation of this cell line is inhibited upon treatment with KAT6A inhibitors. As a negative control cell line MDA-MB-436 were used. These cells carry a heterogeneous deletion of the KAT6A gene, have a low KAT6A protein expression and are not growth inhibited upon treatment with KAT6A inhibitors.

For measurements cell lines were plated at the below indicated concentration per 100 mL in 96-well plates in a humidified incubator at 37° C. and 5% CO2.

ZR-75-1 (ATCC, CRL-1500; breast carcinoma); 3000 cells per well; culture medium: RPMI 1640 (Biochrom #FG 1215) medium containing 2.5% FBS (Biochrom #S0615).

MDA-MB-436 (CLS, 300278; breast adenocarcinoma); 3000 cells per well; culture medium: DMEM/Ham's F12 (Biochrom #FG 4815) medium containing 2.5% FBS (Biochrom #S0615).

24 hours later, cells were treated with compounds (stock solution, 10 mM in DMSO) using the HP D300 Digital Dispenser in a concentration range of 2.0×10E-5 M to 2.0×10E-9 M in a single-dot curve with 9 dilutions and a DMSO concentration of 0.2%. Each sample was prepared as triplicate and rim wells were excluded. Plates were incubated at 37° C. and 5% $CO_2$ for 144 h. Cell viability was measured by adding 10 µL of Alamar Blue Reagent (Invitrogen #DAL 1100) and plates were incubated for 2 h at 37° C. and 5% CO2. Fluorescence was measured at 590 nM wavelength with a Tecan Spark or Victor X3 MTP-Reader (PerkinElmer).

For the evaluation of the results, the values were normalized to DMSO-only treated cells and the Bella DRC Master Sheet was used to calculate EC50s ($EC_{50}$ is the concentration for 50% of maximal inhibition of cell proliferation).

Table 6 shows the results of the inhibition in proliferation assays performed in ZR-75-1 and MDA-MB-436 cells upon treatment with the compounds of the invention.

TABLE 6

$IC_{50}$ values of selected examples in proliferation assays performed in MVLN, ZR-75-1 and MDA-MB-436 cells.

| Example | MVLN reporter assay; IC50 [M] (arithmetic mean) | ZR75-1 proliferation assay; EC50 [M] (arithmetic mean) | MDA-MB-436 proliferation assay; EC50 [M] (arithmetic mean) |
|---|---|---|---|
| 01 | 1.84 E−6 | 8.93 E−7 | >2.00 E−5 |
| 02 | 3.50 E−6 | 1.08 E−5 | >2.00 E−5 |
| 03 | 4.28 E−6 | 2.00 E−5 | >2.00 E−5 |
| 04 | 2.57 E−6 | 3.25 E−6 | >2.00 E−5 |
| 05 | 5.20 E−7 | 8.76 E−7 | >2.00 E−5 |
| 06 | >2.00 E−5 | >2.00 E−5 | >2.00 E−5 |
| 07 | >2.00 E−5 | >2.00 E−5 | >2.00 E−5 |
| 08 | >2.00 E−5 | >2.00 E−5 | >2.00 E−5 |
| 09 | >2.00 E−5 | >2.00 E−5 | >2.00 E−5 |
| 10 | 1.36 E−5 | | |
| 11 | 1.93 E−6 | 2.84 E−7 | >2.00 E−5 |
| 12 | 6.17 E−8 | 5.72 E−8 | |
| 13 | 1.67 E−8 | 2.28 E−8 | >2.00 E−5 |
| 14 | 1.21 E−7 | 1.20 E−7 | 1.84 E−5 |
| 15 | 5.00 E−6 | 4.28 E−6 | |
| 16 | 1.26 E−7 | 1.55 E−7 | >2.00 E−5 |
| 17 | 1.48 E−7 | 3.87 E−8 | >2.00 E−5 |
| 18 | | | |
| 19 | 4.22 E−8 | 5.96 E−8 | >2.00 E−5 |
| 20 | 3.43 E−7 | 2.50 E−7 | >2.00 E−5 |
| 21 | 4.85 E−8 | 4.21 E−8 | 1.53 E−5 |
| 22 | 2.14 E−7 | 2.02 E−7 | >2.00 E−5 |
| 23 | 9.80 E−8 | 2.34 E−8 | >2.00 E−5 |
| 24 | 1.81 E−7 | 1.33 E−7 | >2.00 E−5 |
| 25 | 1.39 E−7 | 1.50 E−7 | 1.80 E−5 |
| 26 | 8.99 E−7 | 3.89 E−7 | >2.00 E−5 |
| 27 | 1.75 E−6 | 1.73 E−6 | >2.00 E−5 |
| 28 | >2.00 E−5 | 4.73 E−6 | >2.00 E−5 |
| 29 | >2.00 E−5 | 1.88 E−5 | >2.00 E−5 |
| 30 | >2.00 E−5 | | |
| 31 | | 8.14 E−8 | >2.00 E−5 |
| 32 | | 3.78 E−7 | >2.00 E−5 |
| 33 | | 6.26 E−6 | >2.00 E−5 |
| 34 | | 5.78 E−7 | >2.00 E−5 |
| 35 | 1.49 E−5 | 6.03 E−6 | >2.00 E−5 |
| 36 | 4.03 E−6 | 1.04 E−5 | >2.00 E−5 |
| 37 | 1.40 E−5 | >2.00 E−5 | >2.00 E−5 |
| 38 | 4.99 E−6 | 1.45 E−5 | >2.00 E−5 |
| 39 | 1.00 E−7 | 3.41 E−8 | >2.00 E−5 |
| 40 | >2.00 E−5 | >2.00 E−5 | >2.00 E−5 |
| 41 | 1.49 E−5 | 8.30 E−6 | 1.85 E−5 |
| 42 | >2.00 E−5 | >2.00 E−5 | >2.00 E−5 |
| 43 | >2.00 E−5 | >2.00 E−5 | >2.00 E−5 |
| 44 | >2.00 E−5 | >2.00 E−5 | >2.00 E−5 |
| 45 | 6.45 E−6 | 1.19 E−5 | >2.00 E−5 |
| 46 | >2.00 E−5 | >2.00 E−5 | >2.00 E−5 |
| 47 | >2.00 E−5 | >2.00 E−5 | >2.00 E−5 |
| 48 | 7.85 E−7 | | >2.00 E−5 |
| 49 | 2.47 E−6 | 5.17 E−6 | >2.00 E−5 |

TABLE 6-continued

IC$_{50}$ values of selected examples in proliferation assays performed in MVLN, ZR-75-1 and MDA-MB-436 cells.

| Example | MVLN reporter assay; IC50 [M] (arithmetic mean) | ZR75-1 proliferation assay; EC50 [M] (arithmetic mean) | MDA-MB-436 proliferation assay; EC50 [M] (arithmetic mean) |
|---|---|---|---|
| 50 | | | |
| 51 | | 1.01 E−7 | >2.00 E−5 |
| 52 | | 1.94 E−7 | >2.00 E−5 |
| 53 | | 2.64 E−7 | >2.00 E−5 |
| 54 | | | |
| 55 | | | |
| 56 | | | |
| 57 | | | |
| 58 | | | |
| 59 | | | |
| 60 | | | |
| 61 | >2.00 E−5 | 1.77 E−5 | >2.00 E−5 |
| 62 | 3.07 E−6 | 1.09 E−6 | 1.14 E−5 |
| 63 | >2.00 E−5 | >2.00 E−5 | >2.00 E−5 |
| 64 | | | |
| 65 | 2.04E−08 | 4.44E−08 | >2.00E−5 |
| 66 | 3.10E−08 | 5.47E−08 | >2.00E−5 |
| 67 | 4.02E−08 | 4.08E−08 | >2.00E−5 |
| 68 | 5.10E−08 | 8.44E−08 | >2.00E−5 |
| 69 | 5.21E−08 | 3.84E−07 | |
| 70 | 7.13E−08 | 1.63E−07 | >2.00E−5 |
| 71 | 7.19E−08 | 1.92E−07 | >2.00E−5 |
| 72 | 7.65E−08 | 1.31E−07 | >2.00E−5 |
| 73 | 9.94E−08 | 2.48E−07 | >2.00E−5 |
| 74 | 1.17E−07 | 1.65E−07 | >2.00E−5 |
| 75 | 1.30E−07 | 1.65E−07 | >2.00E−5 |
| 76 | 1.46E−07 | 1.95E−07 | >2.00E−5 |
| 77 | 1.52E−07 | 1.48E−06 | >2.00E−5 |
| 78 | 1.53E−07 | 2.79E−06 | >2.00E−5 |
| 79 | 1.64E−07 | 2.22E−07 | >2.00E−5 |
| 80 | 1.72E−07 | 3.29E−07 | >2.00E−5 |
| 81 | 1.88E−07 | 4.06E−07 | >2.00E−5 |
| 82 | 2.01E−07 | 2.00E−07 | >2.00E−5 |
| 83 | 2.09E−07 | 1.13E−06 | |
| 84 | 2.26E−07 | | |
| 85 | 2.32E−07 | 4.00E−07 | >2.00E−5 |
| 86 | 2.35E−07 | 1.57E−07 | >2.00E−5 |
| 87 | 2.49E−07 | 4.18E−07 | >2.00E−5 |
| 88 | 2.56E−07 | 3.20E−07 | 4.65E−06 |
| 89 | 2.79E−07 | 4.45E−07 | >2.00E−5 |
| 90 | 3.12E−07 | 8.08E−07 | >2.00E−5 |
| 91 | 3.65E−07 | 7.79E−07 | >2.00E−5 |
| 92 | 3.94E−07 | 3.43E−07 | |
| 93 | 4.57E−07 | 8.56E−07 | >2.00E−5 |
| 94 | 4.60E−07 | | >2.00E−5 |
| 95 | 4.88E−07 | 7.18E−07 | >2.00E−5 |
| 96 | 5.56E−07 | 1.00E−06 | >2.00E−5 |
| 97 | 5.71E−07 | 6.15E−07 | >2.00E−5 |
| 98 | 6.03E−07 | 8.17E−07 | >2.00E−5 |
| 99 | 6.72E−07 | 6.63E−07 | >2.00E−5 |
| 100 | 9.74E−07 | 1.12E−06 | >2.00E−5 |
| 101 | 1.44E−06 | 1.40E−06 | >2.00E−5 |
| 102 | 1.47E−06 | 1.95E−06 | >2.00E−5 |
| 103 | 2.95E−06 | 2.60E−06 | >2.00E−5 |
| 104 | 3.19E−06 | 3.00E−06 | >2.00E−5 |
| 105 | 1.16E−05 | 3.72E−06 | >2.00E−5 |
| 106 | >2.00E−5 | | >2.00E−5 |
| 107 | 8.63E−09 | 4.49E−08 | |
| 108 | 9.10E−09 | 8.07E−08 | >1.86E−5 |
| 109 | 9.67E−09 | 3.70E−08 | >2.00E−5 |
| 110 | 1.24E−08 | 7.12E−08 | >2.00E−5 |
| 111 | 1.54E−08 | 4.89E−08 | >2.00E−5 |
| 112 | 4.52E−08 | 4.78E−08 | >2.00E−5 |
| 113 | 7.03E−08 | 1.02E−07 | >2.00E−5 |
| 114 | 5.80E−08 | 1.07E−07 | >2.00E−5 |
| 115 | 6.42E−08 | 7.02E−08 | >2.00E−5 |
| 116 | 2.70E−07 | 3.24E−07 | >2.00E−5 |
| 117 | 2.76E−07 | 6.03E−07 | >2.00E−5 |
| 118 | 5.55E−07 | 9.57E−07 | >2.00E−5 |
| 119 | 2.18E−07 | 6.98E−07 | >2.00E−5 |
| 120 | 8.91E−07 | 4.57E−7 | >2.00E−5 |
| 121 | 2.75E−07 | 3.56E−07 | >2.00E−5 |
| 122 | 4.53E−07 | 9.44E−07 | >2.00E−5 |
| 123 | 1.79E−07 | 1.19E−07 | >2.00E−5 |
| 124 | 2.54E−07 | | >2.00E−5 |
| 125 | >2.00E−5 | 7.35E−6 | |
| 126 | 3.06E−08 | 6.98E−08 | >2.00E−5 |
| 127 | 6.25E−08 | | >2.00E−5 |
| 128 | 7.80E−06 | 1.49E−06 | >2.00E−5 |
| 129 | 2.86E−08 | 6.17E−07 | >2.00E−5 |
| 130 | 4.36E−06 | 2.93E−06 | 1.51E−05 |
| 131 | 3.25E−07 | 8.31E−07 | >2.00E−5 |
| 132 | 8.01E−08 | 1.05E−07 | >2.00E−5 |
| 133 | 3.23E−07 | 4.88E−07 | >2.00E−5 |
| 134 | 7.68E−08 | 1.26E−07 | >2.00E−5 |
| 135 | 6.86E−08 | 1.46E−07 | >2.00E−5 |
| 136 | 1.54E−05 | 5.54E−06 | >2.00E−5 |
| 137 | 5.50E−06 | 5.61E−06 | >2.00E−5 |
| 138 | 2.16E−06 | 5.01E−06 | >2.00E−5 |
| 139 | 1.37E−06 | 7.07E−07 | >2.00E−5 |
| 140 | 9.65E−06 | 7.83E−06 | >2.00E−5 |
| 141 | 1.76E−06 | 1.92E−06 | >2.00E−5 |
| 142 | 1.66E−07 | 4.37E−07 | >2.00E−5 |
| 143 | 4.08E−08 | 6.42E−08 | >2.00E−5 |
| 144 | 2.15E−07 | 1.62E−07 | >2.00E−5 |
| 145 | 6.80E−06 | 7.20E−06 | >2.00E−5 |
| 146 | 5.16E−06 | 3.73E−06 | >2.00E−5 |
| 147 | 8.68E−08 | 7.83E−08 | >2.00E−5 |
| 148 | 1.21E−07 | 1.28E−07 | >2.00E−5 |
| 149 | 1.38E−07 | 1.74E−07 | >2.00E−5 |
| 150 | 8.29E−06 | >2.00E−5 | 1.02E−05 |
| 151 | 9.85E−06 | 2.87E−06 | >2.00E−5 |
| 152 | 2.93E−06 | 2.16E−06 | >2.00E−5 |
| 153 | 2.72E−06 | 2.77E−06 | |
| 154 | 1.15E−05 | 7.00E−06 | |
| 155 | 1.93E−06 | 7.62E−06 | |
| 156 | 9.71E−07 | 4.97E−06 | |
| 157 | 6.45E−06 | 9.45E−06 | |
| 158 | 1.49E−06 | 7.93E−06 | |
| 159 | 5.19E−07 | 6.97E−07 | |
| 160 | 7.41E−07 | 5.70E−06 | |
| 161 | >2.00E−5 | >2.00E−5 | |
| 162 | 2.55E−06 | >2.00E−5 | |
| 163 | >2.00E−5 | 9.38E−07 | |
| 164 | >2.00E−5 | >2.00E−5 | |
| 165 | 5.77E−06 | 9.21E−06 | |
| 166 | 1.50E−07 | 1.50E−07 | 6.31E−06 |
| 167 | 9.10E−06 | 9.52E−06 | >2.00E−5 |
| 168 | 8.60E−06 | 1.24E−05 | >2.00E−5 |
| 169 | 3.40E−07 | | |
| 170 | 2.21E−08 | 3.02E−08 | >2.00E−5 |
| 171 | 1.02E−07 | | |
| 172 | 7.23E−08 | 8.08E−08 | >2.00E−5 |
| 173 | 6.74E−08 | 1.10E−07 | >2.00E−5 |
| 174 | 1.23E−07 | | |
| 175 | | | |
| 176 | 3.48E−08 | 9.71E−08 | 1.95E−05 |
| 177 | 2.91E−08 | 6.97E−08 | |
| 178 | 6.96E−08 | 8.65E−08 | >2.00E−5 |
| 179 | 1.59E−08 | 6.79E−08 | >2.00E−5 |
| 180 | 2.29E−08 | 3.77E−08 | >2.00E−5 |
| 181 | 3.01E−08 | 9.93E−08 | >2.00E−5 |
| 182 | 2.20E−08 | 6.10E−08 | >2.00E−5 |
| 183 | 4.55E−08 | 7.53E−08 | >2.00E−5 |
| 184 | 2.25E−08 | 6.98E−08 | >2.00E−5 |
| 185 | 1.51E−08 | 1.69E−08 | >2.00E−5 |
| 186 | 2.36E−08 | 5.59E−08 | >2.00E−5 |
| 187 | >2.00E−5 | >2.00E−5 | >2.00E−5 |
| 188 | >2.00E−5 | >2.00E−5 | >2.00E−5 |
| 189 | 6.48E−06 | >2.00E−5 | >2.00E−5 |
| 190 | 1.93E−06 | 3.30E−06 | 1.04E−05 |
| 191 | 1.12E−05 | 5.64E−06 | >2.00E−5 |
| 192 | 1.64E−05 | >2.00E−5 | >2.00E−5 |
| 193 | 1.69E−06 | 6.55E−06 | >2.00E−5 |

TABLE 6-continued

IC$_{50}$ values of selected examples in proliferation assays performed in MVLN, ZR-75-1 and MDA-MB-436 cells.

| Example | MVLN reporter assay; IC50 [M] (arithmetic mean) | ZR75-1 proliferation assay; EC50 [M] (arithmetic mean) | MDA-MB-436 proliferation assay; EC50 [M] (arithmetic mean) |
|---|---|---|---|
| 194 | 4.09E−06 | 1.12E−06 | >2.00E−5 |
| 195 | 7.16E−07 | 8.71E−07 | >2.00E−5 |
| 196 | 2.95E−07 | 2.12E−06 | >1.41E−5 |
| 197 | 1.27E−06 | 2.84E−06 | >2.00E−5 |
| 198 | 2.32E−06 | 7.20E−06 | >2.00E−5 |
| 199 | 9.40E−06 | >2.00E−5 | >2.00E−5 |
| 200 | >2.00E−5 | >2.00E−5 | >2.00E−5 |
| 201 | 4.23E−06 | 2.90E−06 | |
| 202 | >2.00E−5 | >2.00E−5 | >2.00E−5 |
| 203 | >2.00E−5 | >2.00E−5 | >2.00E−5 |
| 204 | 5.80E−06 | 6.40E−06 | >2.00E−5 |
| 205 | 2.34E−06 | 2.17E−06 | 7.61E−06 |
| 206 | 9.50E−06 | >2.00E−5 | >2.00E−5 |
| 207 | 1.18E−05 | >2.00E−5 | >2.00E−5 |
| 208 | 1.46E−05 | 1.83E−05 | >2.00E−5 |
| 209 | >2.00E−5 | 9.40E−06 | |
| 210 | 1.13E−05 | >2.00E−5 | |
| 211 | 4.84E−06 | 1.21E−06 | >2.00E−5 |
| 212 | 9.28E−06 | 4.19E−06 | >2.00E−5 |
| 213 | 9.88E−06 | 8.48E−06 | >2.00E−5 |
| 214 | 5.53E−06 | 6.14E−06 | >2.00E−5 |
| 215 | 1.18E−05 | 1.01E−05 | >2.00E−5 |
| 216 | >2.00E−5 | >2.00E−5 | >2.00E−5 |
| 217 | >2.00E−5 | 8.13E−06 | >2.00E−5 |
| 218 | 7.90E−06 | 8.31E−06 | >2.00E−5 |
| 219 | 4.06E−06 | 6.05E−06 | >2.00E−5 |
| 220 | 7.16E−07 | 8.91E−07 | >2.00E−5 |
| 221 | 5.82E−07 | | 8.25E−06 |
| 222 | 5.95E−07 | | >2.00E−5 |
| 223 | 8.02E−08 | 5.87E−08 | >2.00E−5 |
| 224 | 3.14E−08 | 5.24E−08 | >2.00E−5 |
| 225 | 3.62E−08 | 7.21E−08 | >2.00E−5 |
| 226 | 1.80E−07 | 2.46E−07 | >2.00E−5 |
| 227 | 1.40E−08 | 6.85E−08 | >1.49E−5 |

Assessment of the Anti-Proliferative Effect of Compounds in Different Cell Lines To determine further cancer indications that respond to treatment with KAT6A or KAT6B3 inhibitors various cell lines carrying a KAT6A and/or KAT6B3 focal amplification or high KAT6A and/or KAT6B3 protein expression were used for proliferation assays with selected compounds.

For measurements cell lines were plated at the below indicated concentration per 100 mL in 96-well plates in a humidified incubator at 37° C. and 5% CO$_2$.

CAMA-1 (ATCC, HTB-21; breast adenocarcinoma); 6000 cells per well; culture medium: RPMI 1640 (Biochrom #FG 1215) medium containing 2.5% FBS (Biochrom #S0615)

T47D (NCI 60-Panel, Lot No. 0507307; breast ductal carcinoma); 5000 cells per well; culture medium: RPMI 1640 (Biochrom #FG 1215) medium containing 5% FBS (Biochrom #S0615)

EFM-19 (DSMZ, ACC-231; breast carcinoma); 10000 cells per well; culture medium: RPMI 1640 (Biochrom #FG 1215) medium containing 2.5% FBS (Biochrom #S0615)

DMS 53 (ECACC, 10B027; small cell lung cancer); 5000 cells per well; culture medium Waymouth's MB 752/1 (Gibco; #31220-023) medium containing 2.5% FBS (Biochrom #S0615)

LCLC-97TM1 (DSMZ, ACC 388; large cell lung carcinoma); 6000 cells per well; culture medium: RPMI 1640 (Biochrom #FG 1215) medium containing 2.5% FBS (Biochrom #S0615)

DMS 114 (ATCC, CRL-2066; small cell lung cancer); 5000 cells per well; culture medium: RPMI 1640 (Biochrom #FG 1215) medium containing 2.5% FBS (Biochrom #S0615)

LNCAP (DSMZ, ACC256; prostate carcinoma); 4000 cells per well; culture medium: RPMI 1640 (Biochrom #FG 1215) medium containing 10% FBS (Biochrom #S0615) and 10 nM R1881 (Sigma Aldrich)

JMSU-1 (DSMZ, ACC 505; bladder carcinoma); 1000 cells per well; culture medium: RPMI 1640 (Biochrom #FG 1215) medium containing 2.5% FBS (Biochrom #S0615)

THP-1 (ATCC, TIB-202; acute monocytic leukemia); 2000 cells per well; culture medium: RPMI 1640 (Biochrom #FG 1215) medium containing 2.5% FBS (Biochrom #S0615)

COLO 684 (Sigma-Aldrich, 87061203-1VL; uterus adenocarcinoma); 5000 cells per well; culture medium: RPMI 1640 (Biochrom #FG 1215) medium containing 2.5% FBS (Biochrom #S0615)

24 hours later, cells were treated with compounds (stock solution, 10 mM in DMSO) using the HP D300 Digital Dispenser in a concentration range of 2.0×10E-5 M to 2.0×10E-9 M in a single-dot curve with 9 dilutions and a DMSO concentration of 0.2%. Each sample was prepared as triplicate and rim wells were excluded. Plates were incubated at 37° C. and 5% CO2 for 144 h. Cell viability was measured by adding 10 µL of Alamar Blue Reagent (Invitrogen #DAL 1100) and plates were incubated for 2 h at 37° C. and 5% CO2. Fluorescence was measured at 590 nM wavelength with a Tecan Spark or Victor X3 MTP-Reader (PerkinElmer).

For the evaluation of the results, the values were normalized to DMSO-only treated cells and the Bella DRC Master Sheet was used to calculate EC50s (EC$_{50}$ is the concentration for 50% of maximal inhibition of cell proliferation achieved in the respective cell line).

Table 7 shows the results of proliferation assays performed in various cell lines upon treatment with selected compounds of the invention.

TABLE 7

IC$_{50}$ values of selected examples in proliferation assays with various cell lines.
proliferation assays; EC$_{50}$ [M]

| cell line | Example 14 | Example 23 | Example 19 |
|---|---|---|---|
| LCLC97TM1 | 2.30E−07 | 1.57E−07 | 4.47E−07 |
| DMS53 | 4.90E−07 | 3.67E−07 | 1.30E−07 |
| DMS114 | 2.11E−07 | 2.05E−07 | 1.36E−07 |
| LNCAP | 4.16E−06 | >2.00E−5 | 1.63E−06 |
| JMSU1 | 6.05E−07 | | 7.06E−08 |
| THP1 | 2.38E−07 | | 9.58E−08 |
| CAMA1 | 4.53E−07 | 4.15E−07 | 2.68E−07 |
| T47D | 1.35E−07 | 1.97E−07 | 1.70E−07 |
| EFM19 | 2.23E−07 | 1.55E−07 | 1.05E−07 |
| COLO684 | 1.84E−07 | 9.29E−08 | 1.56E−07 |

The invention claimed is:
1. A compound of formula (I)

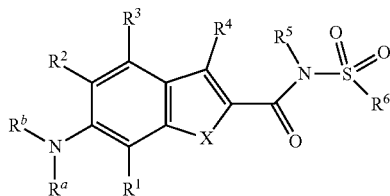

wherein
X is an oxygen atom;
$R^1$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^2$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group, a $C_1$-$C_6$-haloalkyl group, a heterocycloalkyl group, a phenyl group, a naphthyl group and a heteroaryl group,
wherein said heterocycloalkyl group is connected to the rest of the molecule via a carbon atom of said heterocycloalkyl group,
wherein said phenyl, naphthyl, heterocycloalkyl or heteroaryl group is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $R^7R^8N$— group, a heterocycloalkyl group, a phenyl group, a naphthyl group and a heteroaryl group,
wherein said heterocycloalkyl group is connected to the rest of the molecule via a carbon atom of said heterocycloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a $C_1$-$C_6$-thioalkyl group, a heterocycloalkyl group, a (heterocycloalkyl)-O— group, a $R^7R^8N$— group, a $(R^7R^8N)$—$(S(=O)_2)$— group, a ($C_1$-$C_2$-alkyl)-$(S(=O)_2)$— group, a $CH_3$—$C(=O)$—$CH_2$— group, a $(R^7R^8N)$—($C_1$-$C_6$-alkyl)-$(C=O)$—NH— group, a $(R^7R^8N)$—($C_1$-$C_6$-alkyl)- group, a $(R^7R^8N)$—($C_1$-$C_6$-alkyl)-O— group, a $R^9OOC$— group, a phenyl group, a naphthyl group, a (phenyl)-($C_1$-$C_2$-alkyl)-O— group, a (phenyl)-O— group, a heteroaryl group and a heteroaryl-($C_1$-$C_2$-alkyl)- group,
wherein said heterocycloalkyl group is connected to the rest of the molecule via a carbon atom of said heterocycloalkyl group,
wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a heterocycloalkyl group, a $R^7R^8N$— group, a $(R^7R^8N)$—$(S$=$O)_2$— group, a $(R^7R^8N)$—$(C_1$-$C_6$-alkyl)-$(C$=$O)$—NH— group, a $(R^7R^8N)$—$(C_1$-$C_6$-alkyl)- group, and a $R^9OOC$— group,
- wherein said heterocycloalkyl group is connected to the rest of the molecule via a carbon atom of said heterocycloalkyl group;

$R^7$ and $R^8$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_2$-alkyl)-(C(=O))— group, a $(C_1$-$C_6$-alkyl) C(=O)— group, a $(C_1$-$C_6$-haloalkyl) C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a (phenyl)-(S=O)$_2$— group, a $(C_1$-$C_6$-alkyl)-(S=O)$_2$— group, a $(C_1$-$C_6$-haloalkyl)-(S=O)$_2$— group, a $R^9OOC$— group, a phenyl group, a heterocycloalkyl group and a heteroaryl group, wherein said heterocycloalkyl group is connected to the rest of the molecule via a carbon atom of said heterocycloalkyl group,
- wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, and a $R^9OOC$— group,
  - wherein said heterocycloalkyl group is connected to the rest of the molecule via a carbon atom of said heterocycloalkyl group;

or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group and a $R^9OOC$— group,
- wherein said heterocycloalkyl group is connected to the rest of the molecule via a carbon atom of said heterocycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a HC(=O)— group, a $(C_1$-$C_2$-alkyl) C(=O)— group, a $(C_1$-$C_6$-haloalkyl) C(=O)— group, a $(C_3$-$C_8$-cycloalkyl)-$(C_1$-$C_6$-alkyl)- group, a $C_1$-$C_6$-hydroxyalkyl group, a $(C_1$-$C_6$-alkoxy)-$(C_1$-$C_6$-alkyl)- group, a heterocycloalkyl group, a heteroaryl group and a phenyl group,
- wherein said heterocycloalkyl group is connected to the rest of the molecule via a carbon atom of said heterocycloalkyl group,
- wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-alkylsulfanyl group, a $C_1$-$C_6$-haloalkyl group, a $C_1$-$C_6$-alkoxy group, a $C_1$-$C_6$-haloalkoxy group, a $C_2$-$C_6$-alkenyl group, a $C_2$-$C_6$-alkynyl group, a $C_3$-$C_8$-cycloalkyl group, a $C_4$-$C_8$-cycloalkenyl group, a $C_3$-$C_8$-cycloalkoxy group, a $C_1$-$C_6$-thioalkyl group, a heterocycloalkyl group, a $R^7R^8N$— group, a $(R^7R^8N)$—$(S$=$O)_2$— group, a $(R^7R^8N)$—$(C_1$-$C_6$-alkyl)-$(C$=$O)$—NH— group, a $(R^7R^8N)$—$(C_1$-$C_6$-alkyl)- group and a $R^9OOC$— group,
  - wherein said heterocycloalkyl group is connected to the rest of the molecule via a carbon atom of said heterocycloalkyl group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group,
- wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group, a $(H_2N)$—$(C$=$O)$— group and oxo;

or a tautomer, or a salt thereof, or a salt of a tautomer, or a mixture of same.

2. The compound of general formula (I) according to claim 1, wherein

X is an oxygen atom;

$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;

$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;

$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a phenyl group, a naphthyl group, a heteroaryl group, a (phenyl)-$(C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
   wherein said heterocycloalkyl group is connected to the rest of the molecule via a carbon atom of said heterocycloalkyl group,
   wherein said phenyl, naphthyl, heteroaryl or heterocycloalkyl group is each optionally substituted with one or more substituents independently selected from a halogen atom, a cyano group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a $R^9OOC$— group, a phenyl group, a (phenyl)-O— group, a (phenyl)-($C_1$-$C_2$-alkyl)-O— group, a heteroaryl-($C_1$-$C_2$-alkyl)- group and a heteroaryl group,
      wherein said heterocycloalkyl group is connected to the rest of the molecule via a carbon atom of said heterocycloalkyl group,
      wherein said phenyl, heteroaryl or heterocycloalkyl group is each optionally substituted with one or more substituents independently selected from a halogen atom, a cyano group, a $C_1$-$C_6$-alkyl group, a
$C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;
$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl) C(=O)— group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group,
or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;
$R^9$ is selected from a hydrogen atom, a $C_1$-$C_6$-alkyl group and a $C_3$-$C_8$-cycloalkyl group;
$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;
or $R^a$ and $R^b$ together with the nitrogen atom to which they are attached form a 4- to 7-membered nitrogen-containing heterocycloalkyl group,
or $R^1$ and one of $R^a$ and $R^b$, together with the carbon and the nitrogen atom to which they are respectively attached form a 5- to 7-membered nitrogen-containing heterocycloalkyl group,
or $R^2$ and one of $R^a$ and $R^b$, together with the carbon and the nitrogen atom to which they are respectively attached form a 5- to 7-membered nitrogen-containing heterocycloalkyl group,
wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;
or a tautomer, or a salt thereof, or a salt of a tautomer, or a mixture of same.

3. The compound of general formula (I) according to claim 1, wherein
X is an oxygen atom;
$R^1$ is selected from a hydrogen atom, a halogen atom, a $C_1$-$C_6$-alkyl group, a $C_3$-$C_8$-cycloalkyl group, a $C_1$-$C_6$-alkoxy group and a $C_1$-$C_6$-haloalkyl group;
$R^2$ is selected from a hydrogen atom, a halogen atom, a cyano group, a $C_1$-$C_6$-alkyl group, a $C_3$-$C_8$-cycloalkyl group, a $C_1$-$C_6$-alkoxy group and a $C_1$-$C_6$-haloalkyl group;
$R^3$ is selected from a hydrogen atom, a halogen atom, a cyano group, a nitro group, a $R^7R^8N$— group, a $C_1$-$C_6$-alkyl group, a $C_3$-$C_8$-cycloalkyl group, a $C_1$-$C_6$-alkoxy group and a $C_1$-$C_6$-haloalkyl group;
$R^4$ is selected from a hydrogen atom, a halogen atom, a $C_1$-$C_6$-alkyl group and a $C_3$-$C_8$-cycloalkyl group;
$R^5$ is selected from a hydrogen atom and a $C_1$-$C_6$-alkyl group;
$R^6$ is selected from a phenyl group, a naphthyl group, a heteroaryl group, a (phenyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group,
   wherein said heterocycloalkyl group is connected to the rest of the molecule via a carbon atom of said heterocycloalkyl group,
   wherein said phenyl, naphthyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a $R^9OOC$— group, a phenyl group, a (phenyl)-O— group and a heteroaryl group,
      wherein said heterocycloalkyl group is connected to the rest of the molecule via a carbon atom of said heterocycloalkyl group,
      wherein said phenyl, heteroaryl or heterocycloalkyl group is each optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group, and a $R^9OOC$— group;
$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl) C(=O)— group, a ($C_1$-$C_6$-haloalkyl) C(=O)— group, a ($C_3$-$C_8$-cycloalkyl)-($C_1$-

$C_6$-alkyl)- group, a $C_1$-$C_6$-hydroxyalkyl group and a ($C_1$-$C_6$-alkoxy)-($C_1$-$C_6$-alkyl)- group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group and a ($C_1$-$C_6$-alkoxy)-($C_1$-$C_6$-alkyl)- group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or a salt thereof, or a salt of a tautomer, or a mixture of same.

4. The compound of general formula (I) according to claim 1, wherein

X is an oxygen atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a heterocycloalkyl group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a (phenyl)-O— group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl) C(=O)— group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl) C(=O)— group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or a salt thereof, or a salt of a tautomer, or a mixture of same.

5. The compound of general formula (I) according to claim 1, wherein

X is an oxygen atom;

$R^1$ is selected from a hydrogen atom, a halogen atom, a $C_1$-$C_6$-alkoxy group, a $C_1$-$C_6$-alkyl group, and a $C_3$-$C_8$-cycloalkyl group;

$R^2$ is selected from a hydrogen atom, a halogen atom, a cyano group, a $C_1$-$C_6$-alkoxy group, a $C_1$-$C_6$-alkyl group, and a $C_3$-$C_8$-cycloalkyl group;

$R^3$ is selected from a hydrogen atom, a halogen atom, a cyano group, a $R^7R^8N$— group, a $C_1$-$C_6$-alkoxy group, a $C_1$-$C_6$-alkyl group, and a $C_3$-$C_8$-cycloalkyl group;

$R^4$ is selected from a hydrogen atom, a halogen atom, a $C_1$-$C_6$-alkyl group and a $C_3$-$C_8$-cycloalkyl group;

$R^5$ is selected from a hydrogen atom and a $C_1$-$C_6$-alkyl group;

$R^6$ is selected from a $C_1$-$C_6$-alkyl group, a phenyl group, a naphthyl group, a heteroaryl group, a (phenyl)-($C_1$-$C_6$-alkyl)- group, a (naphthyl)-($C_1$-$C_6$-alkyl)- group, a (heteroaryl)-($C_1$-$C_6$-alkyl)- group, a (heterocycloalkyl)-($C_1$-$C_6$-alkyl)- group and a heterocycloalkyl group, wherein said heterocycloalkyl group is connected to the rest of the molecule via a carbon atom of said heterocycloalkyl group, wherein said phenyl, naphthyl, heteroaryl or heterocycloalkyl group is each optionally substituted with one or more substituents independently selected from a halogen atom, a cyano group, a nitro group, a hydroxy group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group, a ($C_1$-$C_2$-alkyl)-O—($C_1$-$C_2$-alkyl)-O— group, a ($C_3$-$C_8$-cycloalkyl)-($C_1$-$C_2$-alkyl)-O— group, a ($C_3$-$C_8$-halocycloalkyl)-($C_1$-$C_2$-alkyl)-O— group, a (heterocycloalkyl)-O— group, a heterocycloalkyl group, a ($R^7R^8N$)—($C_1$-$C_6$-alkyl)-O— group, a $R^7R^8N$— group, a ($R^7R^8N$)—($C_1$-$C_6$-alkyl)-(C=O)—NH— group, a ($R^7R^8N$)—($C_1$-$C_6$-alkyl)- group, a $R^9OOC$— group, a phenyl group, a (phenyl)-O— group, a (phenyl)-($C_1$-$C_2$-alkyl)-O— group, a heteroaryl-($C_1$-$C_2$-alkyl)- group and a heteroaryl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $R^7R^8N$— group and a $R^9OOC$— group;

$R^7$ and $R^8$ are each independently selected from a $C_1$-$C_6$-alkyl group, a $C_3$-$C_8$-cycloalkyl group, a $C_1$-$C_6$-haloalkyl group, a ($C_1$-$C_6$-alkyl) C(=O)— group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a phenyl group, a heterocycloalkyl group and a heteroaryl group, wherein said heterocycloalkyl group is connected to the rest of the molecule via a carbon atom of said heterocycloalkyl group, or $R^7$ and $R^8$ together with the nitrogen atom to which they are attached form a 4- to 7-membered nitrogen-containing heterocycloalkyl group, wherein said heterocycloalkyl group optionally contains one, two or three further heteroatoms independently selected from nitrogen, oxygen and sulfur and/or is optionally substituted with one or more substituents independently selected from a halogen atom, a cyano group, a nitro group, a $C_1$-$C_6$-alkyl group, a $C_1$-$C_6$-hydroxyalkyl group, a $C_1$-$C_6$-haloalkyl group, a $C_1$-$C_6$-alkoxy group, a $C_1$-$C_6$-haloalkoxy group, and a $C_3$-$C_8$-cycloalkyl group;

$R^9$ is selected from a hydrogen atom, a $C_1$-$C_6$-alkyl group and a $C_3$-$C_8$-cycloalkyl group;

$R^a$ and $R^b$ are each independently selected from a hydrogen atom, a $C_1$-$C_6$-alkyl group, a $C_3$-$C_8$-cycloalkyl group, a $C_1$-$C_6$-haloalkyl group, a ($C_1$-$C_6$-alkyl) C(=O)— group, a ($C_1$-$C_6$-haloalkyl) C(=O)— group, a ($C_3$-$C_8$-cycloalkyl)-($C_1$-$C_6$-alkyl)- group, a $C_1$-$C_6$-hydroxyalkyl group, a ($C_1$-$C_6$-alkoxy)-($C_1$-$C_6$-alkyl)- group, a heterocycloalkyl group, a heteroaryl group and a phenyl group, wherein said heterocycloalkyl group is connected to the rest of the molecule via a carbon atom of said heterocycloalkyl group, wherein said phenyl, heteroaryl or heterocycloalkyl group is each optionally substituted with one or more substituents independently selected from a halogen atom, a $C_1$-$C_6$-alkyl group and a $R^7R^8N$— group;

or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or a salt thereof, or a salt of a tautomer, or a mixture of same.

6. The compound of general formula (I) according to claim 1, wherein

X is an oxygen atom;
$R^1$ is a hydrogen atom;
$R^2$ is a hydrogen atom;
$R^3$ is selected from a hydrogen atom and a halogen atom;
$R^4$ is a hydrogen atom;
$R^5$ is a hydrogen atom;
$R^6$ is selected from a phenyl group, a naphthyl group and a heteroaryl group, wherein said phenyl, naphthyl or heteroaryl group is each optionally substituted with one or more substituents independently selected from a halogen atom, a $C_1$-$C_6$-alkyl group, a $C_1$-$C_6$-alkoxy group and a phenyl group, wherein said phenyl group is optionally substituted with one or more substituents independently selected from a halogen atom, a $C_1$-$C_6$-alkyl group, a $C_1$-$C_6$-hydroxyalkyl group, a $C_1$-$C_6$-haloalkyl group, a $C_1$-$C_6$-alkoxy group and a $C_3$-$C_8$-cycloalkyl group;

$R^a$ and $R^b$ are each independently selected from a $C_1$-$C_6$-alkyl group, a $C_3$-$C_8$-cycloalkyl group, a $C_1$-$C_6$-haloalkyl group and a ($C_1$-$C_6$-alkoxy)-($C_1$-$C_6$-alkyl)- group, or $R^a$ and $R^b$ together with the nitrogen atom to which they are attached form a 4- to 7-membered nitrogen-containing heterocycloalkyl group, or $R^1$ and one of $R^a$ and $R^b$, together with the carbon and the nitrogen atom to which they are respectively attached form a 5- to 7-membered nitrogen-containing heterocycloalkyl group, or $R^2$ and one of $R^a$ and $R^b$, together with the carbon and the nitrogen atom to which they are respectively attached form a 5- to 7-membered nitrogen-containing heterocycloalkyl group, wherein said 4- to 7-membered or 5- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or a salt thereof, or a salt of a tautomer, or a mixture of same.

7. The compound of general formula (I) according to claim 1, wherein

X is an oxygen atom;
$R^1$ is a hydrogen atom;
$R^2$ is a hydrogen atom;
$R^3$ is selected from a hydrogen atom and a halogen atom;
$R^4$ is a hydrogen atom;
$R^5$ is a hydrogen atom;
$R^6$ is selected from a phenyl group, a naphthyl group and a heteroaryl group, wherein said phenyl, naphthyl or heteroaryl group is each optionally substituted with one or more substituents independently selected from a halogen atom, a $C_1$-$C_6$-alkyl group, a $C_1$-$C_6$-alkoxy group and a phenyl group, wherein said phenyl group is optionally substituted with one or more substituents independently selected from a halogen atom, a $C_1$-$C_6$-alkyl group, a $C_1$-$C_6$-hydroxyalkyl group, a $C_1$-$C_6$-haloalkyl group, a $C_1$-$C_6$-alkoxy group and a $C_3$-$C_8$-cycloalkyl group;

$R^a$ and $R^b$ are each independently selected from a $C_1$-$C_6$-alkyl group, a $C_3$-$C_8$-cycloalkyl group, a $C_1$-$C_6$-haloalkyl group and a ($C_1$-$C_6$-alkoxy)-($C_1$-$C_6$-alkyl)- group, or $R^a$ and $R^b$ together with the nitrogen atom to which they are attached form a 4- to 7-membered nitrogen-containing heterocycloalkyl group, wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or a salt thereof, or a salt of a tautomer, or a mixture of same.

8. The compound of general formula (I) according to claim 1, wherein

X is an oxygen atom;
$R^1$ is a hydrogen atom;
$R^2$ is a hydrogen atom;
$R^3$ is selected from a hydrogen atom and a halogen atom;
$R^4$ is a hydrogen atom;
$R^5$ is a hydrogen atom;
RE is selected from a phenyl group, a naphthyl group and a heteroaryl group, wherein said phenyl, naphthyl or heteroaryl group is each optionally substituted with one or more substituents independently selected from a halogen atom, a $C_1$-$C_6$-alkyl group, a $C_1$-$C_6$-alkoxy group, a $C_3$-$C_8$-cycloalkoxy group and a phenyl group, wherein said phenyl group is optionally substituted with one or more substituents independently selected from a halogen atom, a $C_1$-$C_6$-alkyl group, a $C_1$-$C_6$-hydroxyalkyl group, a $C_1$-$C_6$-haloalkyl group, a $C_1$-$C_6$-alkoxy group, a $C_3$-$C_8$-cycloalkyl group and a $C_3$-$C_8$-cycloalkoxy group;

$R^a$ and $R^b$ are each independently selected from a $C_1$-$C_6$-alkyl group, a $C_3$-$C_8$-cycloalkyl group, a $C_1$-$C_6$-haloalkyl group and a ($C_1$-$C_6$-alkoxy)-($C_1$-$C_6$-alkyl)- group, or $R^a$ and $R^b$ together with the nitrogen atom to which they are attached form a 4- to 7-membered nitrogen-containing heterocycloalkyl group, wherein said 4- to 7-membered nitrogen-containing heterocycloalkyl group optionally contains one, two or three further heteroatoms independently selected from nitrogen, oxygen and sulfur and/or is optionally substituted one, two or three times, each substituent independently selected from a halogen atom or a group selected from cyano, hydroxy, a $C_1$-$C_2$-alkyl group, a $C_1$-$C_2$-haloalkyl group, a $C_1$-$C_2$-alkoxy group, a $C_3$-$C_4$-cycloalkyl group and oxo;

or a tautomer, or an N-oxide, or a salt thereof, or a salt of a tautomer, or a salt of an N-oxide, or a mixture of same.

9. The compound of general formula (I) according to claim 1, wherein
$R^a$ and $R^b$ are each independently selected from, a $C_1$-$C_6$-alkyl group, a $C_3$-$C_8$-cycloalkyl group and a $C_1$-$C_6$-haloalkyl group, or an N-oxide, or a salt thereof, or a salt of a tautomer, or a mixture of same.

10. The compound of general formula (I) according to claim 1, wherein
$R^3$ is a fluorine atom, or a tautomer, or a salt thereof, or a salt of a tautomer, or a mixture of same.

11. The compound of general formula (I) according to claim 1, wherein
X is an oxygen atom;
$R^1$ is selected from a hydrogen atom and a halogen atom;
$R^2$ is a hydrogen atom;
$R^3$ is selected from a hydrogen atom and a halogen atom;
$R^4$ is a hydrogen atom;
$R^5$ is selected from a hydrogen atom and a $C_1$-$C_6$-alkyl group;
$R^6$ is selected from a phenyl group and a heteroaryl group, wherein said phenyl or heteroaryl group is each optionally substituted with one or more substituents independently selected from a halogen atom, a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkyl group, a $C_3$-$C_8$-cycloalkoxy group,
$R^a$ and $R^b$ are each independently selected from a hydrogen atom and a $C_1$-$C_6$-alkyl group,
or a tautomer, or a salt thereof, or a salt of a tautomer, or a mixture of same.

12. The compound of general formula (I) according to claim 11, wherein
X is an oxygen atom;
$R^1$ is a hydrogen atom;
$R^2$ is a hydrogen atom;
$R^3$ is a fluorine atom;
$R^4$ is a hydrogen atom;
$R^5$ is a hydrogen atom;
$R^6$ is selected from a phenyl group and a heteroaryl group, wherein said phenyl or heteroaryl group is each optionally substituted with one or more substituents independently selected from a $C_1$-$C_6$-alkyl group, a $C_1$-$C_6$-haloalkyl group, a $C_1$-$C_6$-alkoxy group, a $C_1$-$C_6$-haloalkoxy group, a $C_3$-$C_8$-cycloalkoxy group,
$R^a$ and $R^b$ are each independently selected from a hydrogen atom and a methyl group,
or a tautomer, or a salt thereof, or a salt of a tautomer, or a mixture of same.

13. The compound of general formula (I) according to claim 1 selected from the list consisting of
N-([1,1'-biphenyl]-2-sulfonyl)-6-[ethyl(methyl)amino]-1-benzofuran-2-carboxamide,
N-(benzenesulfonyl)-6-[ethyl(methyl)amino]-1-benzofuran-2-carboxamide,
N-(2,4-dichlorobenzene-1-sulfonyl)-6-[ethyl(methyl)amino]-1-benzofuran-2-carboxamide,
N-(2-chlorobenzene-1-sulfonyl)-6-[ethyl(methyl)amino]-1-benzofuran-2-carboxamide,
N-(2-ethoxybenzene-1-sulfonyl)-6-[ethyl(methyl)amino]-1-benzofuran-2-carboxamide,
N-(2-ethoxybenzene-1-sulfonyl)-6-[methyl(phenyl)amino]-1-benzofuran-2-carboxamide,
N-(benzenesulfonyl)-6-[methyl(phenyl)amino]-1-benzofuran-2-carboxamide,
N-(2-chlorobenzene-1-sulfonyl)-6-[methyl(phenyl)amino]-1-benzofuran-2-carboxamide,
N-(2,4-dichlorobenzene-1-sulfonyl)-6-[methyl(phenyl)amino]-1-benzofuran-2-carboxamide,
N-([1,1'-biphenyl]-2-sulfonyl)-6-[methyl(phenyl)amino]-1-benzofuran-2-carboxamide,
N-([1,1'-biphenyl]-2-sulfonyl)-6-(methylamino)-1-benzofuran-2-carboxamide,
6-(dimethylamino)-N-(2-ethoxybenzene-1-sulfonyl)-4-fluoro-1-benzofuran-2-carboxamide,
N-([1,1'-biphenyl]-2-sulfonyl)-6-(dimethylamino)-1-benzofuran-2-carboxamide,
N-([1,1'-biphenyl]-4-sulfonyl)-6-(dimethylamino)-1-benzofuran-2-carboxamide,
N-(3'-chloro[1,1'-biphenyl]-2-sulfonyl)-6-(dimethylamino)-1-benzofuran-2-carboxamide,
6-(dimethylamino)-N-(2'-methyl[1,1'-biphenyl]-2-sulfonyl)-1-benzofuran-2-carboxamide,
N-(2-bromobenzene-1-sulfonyl)-6-(dimethylamino)-1-benzofuran-2-carboxamide,
6-(dimethylamino)-N-(2-ethoxybenzene-1-sulfonyl)-1-benzofuran-2-carboxamide,
6-(dimethylamino)-N-(naphthalene-1-sulfonyl)-1-benzofuran-2-carboxamide,
6-(dimethylamino)-N-(2-methylquinoline-8-sulfonyl)-1-benzofuran-2-carboxamide,
N-(2-chlorobenzene-1-sulfonyl)-6-(dimethylamino)-1-benzofuran-2-carboxamide,
6-(dimethylamino)-N-(2-propoxybenzene-1-sulfonyl)-1-benzofuran-2-carboxamide,
6-(dimethylamino)-N-(5-methyl[1,1'-biphenyl]-2-sulfonyl)-1-benzofuran-2-carboxamide,
N-(3'-chloro-3-ethoxy[1,1'-biphenyl]-2-sulfonyl)-6-(dimethylamino)-1-benzofuran-2-carboxamide,
6-(dimethylamino)-N-(4-methylbenzene-1-sulfonyl)-1-benzofuran-2-carboxamide,
N-(2,4-dichlorobenzene-1-sulfonyl)-6-(dimethylamino)-1-benzofuran-2-carboxamide,
6-(dimethylamino)-N-(oxane-4-sulfonyl)-1-benzofuran-2-carboxamide,
N-(4-cyanopyridine-2-sulfonyl)-6-(dimethylamino)-1-benzofuran-2-carboxamide,
N-(2,3-dihydro-1-benzofuran-7-sulfonyl)-6-(dimethylamino)-1-benzofuran-2-carboxamide,
6-(dimethylamino)-N-[2-(trifluoromethoxy)benzene-1-sulfonyl]-1-benzofuran-2-carboxamide,
6-(dimethylamino)-N-(2-methylbenzene-1-sulfonyl)-1-benzofuran-2-carboxamide,
N-(2-cyanobenzene-1-sulfonyl)-6-(dimethylamino)-1-benzofuran-2-carboxamide,
6-(dimethylamino)-N-(2-fluorobenzene-1-sulfonyl)-1-benzofuran-2-carboxamide,
N-([1,1'-biphenyl]-2-sulfonyl)-6-(dimethylamino)-4-methyl-1-benzofuran-2-carboxamide,
2-{[6-(dimethylamino)-1-benzofuran-2-carbonyl]sulfamoyl}benzoic acid,
N-([1,1'-biphenyl]-2-sulfonyl)-6-[methyl(propyl)amino]-1-benzofuran-2-carboxamide,
N-([1,1'-biphenyl]-2-sulfonyl)-6-(diethylamino)-1-benzofuran-2-carboxamide,
N-([1,1'-biphenyl]-2-sulfonyl)-6-[(2-methoxyethyl)(methyl)amino]-1-benzofuran-2-carboxamide,
N-([1,1'-biphenyl]-2-sulfonyl)-6-[(cyclopropylmethyl)(methyl)amino]-1-benzofuran-2-carboxamide,
N-([1,1'-biphenyl]-2-sulfonyl)-6-(dibutylamino)-1-benzofuran-2-carboxamide,
6-amino-N-([1,1'-biphenyl]-2-sulfonyl)-1-benzofuran-2-carboxamide, 6-acetamido-N-([1,1'-biphenyl]-2-sulfonyl)-1-benzofuran-2-carboxamide,
N-([1,1'-biphenyl]-2-sulfonyl)-6-[(2S)-2-methylpyrrolidin-1-yl]-1-benzofuran-2-carboxamide,
N-([1,1'-biphenyl]-2-sulfonyl)-6-(pyrrolidin-1-yl)-1-benzofuran-2-carboxamide,
N-([1,1'-biphenyl]-2-sulfonyl)-6-[cyclopentyl(methyl)amino]-1-benzofuran-2-carboxamide,
N-([1,1'-biphenyl]-2-sulfonyl)-6-(piperidin-1-yl)-1-benzofuran-2-carboxamide,
N-([1,1'-biphenyl]-2-sulfonyl)-6-(dimethylamino)-1-benzothiophene-2-carboxamide,
N-(3'-chloro[1,1'-biphenyl]-2-sulfonyl)-6-(dimethylamino)-1-benzothiophene-2-carboxamide,
N-([1,1'-biphenyl]-2-sulfonyl)-7-cyclopropyl-6-(dimethylamino)-1-benzofuran-2-carboxamide,
6-(dimethylamino)-N-[4'-(hydroxymethyl) [1,1'-biphenyl]-2-sulfonyl]-1-benzofuran-2-carboxamide,
6-(dimethylamino)-N-(2-propylbenzene-1-sulfonyl)-1-benzofuran-2-carboxamide,
N-(4-cyano-2-methoxybenzene-1-sulfonyl)-6-(dimethylamino)-1-benzofuran-2-carboxamide,
6-(dimethylamino)-N-[2-(trifluoromethyl)benzene-1-sulfonyl]-1-benzofuran-2-carboxamide ammonia (1/1),
N-[1-(2,4-dichlorophenyl) ethanesulfonyl]-6-(dimethylamino)-1-benzofuran-2-carboxamide,
N-[1-(2,6-dichlorophenyl) ethanesulfonyl]-6-(dimethylamino)-1-benzofuran-2-carboxamide,
N-(5-bromo-2-ethoxybenzene-1-sulfonyl)-6-(dimethylamino)-1-benzofuran-2-carboxamide,
6-(dimethylamino)-N-(4-ethoxypyridine-3-sulfonyl)-1-benzofuran-2-carboxamide,
6-(dimethylamino)-N-(2-hydroxybenzene-1-sulfonyl)-1-benzofuran-2-carboxamide, ethyl 4-{[6-(dimethylamino)-1-benzofuran-2-carbonyl]sulfamoyl}piperidine-1-carboxylate,
6-(dimethylamino)-N-(ethanesulfonyl)-1-benzofuran-2-carboxamide,
N-([1,1'-biphenyl]-2-sulfonyl)-6-(2-oxopyrrolidin-1-yl)-1-benzofuran-2-carboxamide,
6-(dimethylamino)-N-(methanesulfonyl)-1-benzofuran-2-carboxamide,
N-([1,1'-biphenyl]-2-sulfonyl)-7-cyano-6-(dimethylamino)-1-benzofuran-2-carboxamide,
N-[2-(cyclopropyloxy)benzene-1-sulfonyl]-6-(dimethylamino)-1-benzofuran-2-carboxamide,
6-(dimethylamino)-N-{2-[(propan-2-yl)oxy]benzene-1-sulfonyl}-1-benzofuran-2-carboxamide,
6-(dimethylamino)-N-(2-ethoxy-5-methylbenzene-1-sulfonyl)-1-benzofuran-2-carboxamide,
N-(2-tert-butoxybenzene-1-sulfonyl)-6-(dimethylamino)-1-benzofuran-2-carboxamide,
N-[2-(benzyloxy)-6-(cyclobutyloxy)benzene-1-sulfonyl]-6-(dimethylamino)-1-benzofuran-2-carboxamide,
6-(dimethylamino)-N-(7-methoxyquinoline-8-sulfonyl)-1-benzofuran-2-carboxamide,
N-[2-(cyclopropylmethoxy)benzene-1-sulfonyl]-6-(dimethylamino)-1-benzofuran-2-carboxamide,
6-(dimethylamino)-N-[2-(2-fluoroethoxy)benzene-1-sulfonyl]-1-benzofuran-2-carboxamide,
6-(dimethylamino)-N-(quinoline-8-sulfonyl)-1-benzofuran-2-carboxamide,
6-(dimethylamino)-N-[2-(2,2,2-trifluoroethoxy)benzene-1-sulfonyl]-1-benzofuran-2-carboxamide,
N-[2-(2,2-difluoroethoxy)benzene-1-sulfonyl]-6-(dimethylamino)-1-benzofuran-2-carboxamide,
6-(dimethylamino)-N-[2-(2-methylpropoxy)benzene-1-sulfonyl]-1-benzofuran-2-carboxamide,
6-(dimethylamino)-N-[2-(propan-2-yl)benzene-1-sulfonyl]-1-benzofuran-2-carboxamide,
6-(dimethylamino)-N-(2-ethoxy-5-iodobenzene-1-sulfonyl)-1-benzofuran-2-carboxamide,
N-[2-(difluoromethoxy)benzene-1-sulfonyl]-6-(dimethylamino)-1-benzofuran-2-carboxamide,
6-(dimethylamino)-N-(3-ethoxy[1,1'-biphenyl]-2-sulfonyl)-1-benzofuran-2-carboxamide,
6-(dimethylamino)-N-(2-ethoxypyridine-3-sulfonyl)-1-benzofuran-2-carboxamide,
6-(dimethylamino)-N-{2-[(oxetan-3-yl)oxy]benzene-1-sulfonyl}-1-benzofuran-2-carboxamide,
N-(4-chloro-2-methylquinoline-8-sulfonyl)-6-(dimethylamino)-1-benzofuran-2-carboxamide,
N-[2-(cyclobutyloxy)-6-{[(2S)-1,1,1-trifluoropropan-2-yl]oxy}benzene-1-sulfonyl]-6-(dimethylamino)-1-benzofuran-2-carboxamide,
6-(dimethylamino)-N-(2-phenoxybenzene-1-sulfonyl)-1-benzofuran-2-carboxamide,
6-(dimethylamino)-N-{2-methoxy-5-[(1H-pyrazol-1-yl)methyl]benzene-1-sulfonyl}-1-benzofuran-2-carboxamide,
6-(dimethylamino)-N-(3-methylquinoline-8-sulfonyl)-1-benzofuran-2-carboxamide,
6-(dimethylamino)-N-(2-ethoxy-5-nitrobenzene-1-sulfonyl)-1-benzofuran-2-carboxamide ammonia (1/1),
N-{2-chloro-6-[(propan-2-yl)oxy]benzene-1-sulfonyl}-6-(dimethylamino)-1-benzofuran-2-carboxamide,
6-(dimethylamino)-N-[2-(pentyloxy)benzene-1-sulfonyl]-1-benzofuran-2-carboxamide,
6-(dimethylamino)-N-(4-methylquinoline-8-sulfonyl)-1-benzofuran-2-carboxamide,
6-(dimethylamino)-N-(5-nitroquinoline-8-sulfonyl)-1-benzofuran-2-carboxamide,
6-(dimethylamino)-N-[2-(2-methylpropyl) quinoline-8-sulfonyl]-1-benzofuran-2-carboxamide,
6-(dimethylamino)-N-(6-ethyl-2-methylimidazo[1,2-b]pyridazine-3-sulfonyl)-1-benzofuran-2-carboxamide ammonia (1/1),
6-(dimethylamino)-N-(2-methyl-3-oxo-2,3-dihydro-1H-isoindole-4-sulfonyl)-1-benzofuran-2-carboxamide,
6-(dimethylamino)-N-[2-(pentafluoroethoxy)benzene-1-sulfonyl]-1-benzofuran-2-carboxamide,
N-[2-chloro-6-(trifluoromethyl)benzene-1-sulfonyl]-6-(dimethylamino)-1-benzofuran-2-carboxamide,
N-(2,6-dichlorobenzene-1-sulfonyl)-6-(dimethylamino)-1-benzofuran-2-carboxamide,
N-(benzenesulfonyl)-6-(dimethylamino)-1-benzofuran-2-carboxamide,
6-(dimethylamino)-N-{2,3-dimethyl-5-[(1H-pyrazol-1-yl)methyl]benzene-1-sulfonyl}-1-benzofuran-2-carboxamide,
6-(dimethylamino)-N-(3-ethoxypyridine-2-sulfonyl)-1-benzofuran-2-carboxamide,
6-(dimethylamino)-N-{2-ethyl-5-[(1H-pyrazol-1-yl)methyl]benzene-1-sulfonyl}-1-benzofuran-2-carboxamide,
N-{3,4-dimethoxy-5-[(1H-pyrazol-1-yl)methyl]benzene-1-sulfonyl}-6-(dimethylamino)-1-benzofuran-2-carboxamide,
6-(dimethylamino)-N-(2-ethylbenzene-1-sulfonyl)-1-benzofuran-2-carboxamide,
6-(dimethylamino)-N-[(3-methylpyridin-2-yl) methanesulfonyl]-1-benzofuran-2-carboxamide, 6-(dimethylamino)-N-[(pyridin-2-yl) methanesulfonyl]-1-benzofuran-2-carboxamide ammonia (1/1),
6-(dimethylamino)-N-[2-ethoxy-5-(propan-2-yl)benzene-1-sulfonyl]-4-fluoro-1-benzofuran-2-carboxamide,
6-(dimethylamino)-4-fluoro-N-(2-methylquinoline-8-sulfonyl)-1-benzofuran-2-carboxamide,
6-(dimethylamino)-4-fluoro-N-{2-[(propan-2-yl)oxy]benzene-1-sulfonyl}-1-benzofuran-2-carboxamide,
N-[2-(cyclopropyloxy)benzene-1-sulfonyl]-6-(dimethylamino)-4-fluoro-1-benzofuran-2-carboxamide,
6-(dimethylamino)-4-fluoro-N-(2-propoxybenzene-1-sulfonyl)-1-benzofuran-2-carboxamide,
6-(dimethylamino)-4-fluoro-N-(2-methoxybenzene-1-sulfonyl)-1-benzofuran-2-carboxamide,
6-(dimethylamino)-N-(2-methoxybenzene-1-sulfonyl)-1-benzofuran-2-carboxamide,
6-(dimethylamino)-N-(5-methyl-2-propoxybenzene-1-sulfonyl)-1-benzofuran-2-carboxamide,
6-(dimethylamino)-N-(2-ethoxy-6-methylbenzene-1-sulfonyl)-1-benzofuran-2-carboxamide,
tert-butyl[2-(2-{[6-(dimethylamino)-1-benzofuran-2-carbonyl] sulfamoyl}phenoxy)ethyl]carbamate,
N-[4-bromo-2-(trifluoromethoxy)benzene-1-sulfonyl]-6-(dimethylamino)-1-benzofuran-2-carboxamide,
6-(dimethylamino)-N-(2-ethyl-6-propoxybenzene-1-sulfonyl)-1-benzofuran-2-carboxamide,
6-(dimethylamino)-N-[2-ethoxy-4-(trifluoromethyl)pyridine-3-sulfonyl]-1-benzofuran-2-carboxamide,
N-(2-bromo-6-ethoxybenzene-1-sulfonyl)-6-(dimethylamino)-1-benzofuran-2-carboxamide,
N-(3-chloro-2-ethoxybenzene-1-sulfonyl)-6-(dimethylamino)-1-benzofuran-2-carboxamide,
6-(dimethylamino)-N-(2-ethoxy-6-fluorobenzene-1-sulfonyl)-1-benzofuran-2-carboxamide,
N-(6-chloroquinoline-8-sulfonyl)-6-(dimethylamino)-1-benzofuran-2-carboxamide,
6-(dimethylamino)-N-(4-hydroxypyridine-3-sulfonyl)-1-benzofuran-2-carboxamide,
6-(dimethylamino)-N-(2-methoxy-4-methylbenzene-1-sulfonyl)-1-benzofuran-2-carboxamide,
N-(5-acetamido-2-ethoxybenzene-1-sulfonyl)-6-(dimethylamino)-1-benzofuran-2-carboxamide,
6-(dimethylamino)-N-[2-ethoxy-5-(propan-2-yl)benzene-1-sulfonyl]-1-benzofuran-2-carboxamide,
N-(2-amino-6-methylpyridine-3-sulfonyl)-6-(dimethylamino)-1-benzofuran-2-carboxamide,
6-(dimethylamino)-N-(4-ethyl-6-methoxypyrimidine-5-sulfonyl)-1-benzofuran-2-carboxamide,
6-(dimethylamino)-N-[2-methoxy-6-(trifluoromethyl)benzene-1-sulfonyl]-1-benzofuran-2-carboxamide,
6-(dimethylamino)-N-(2-methyl-6-propoxybenzene-1-sulfonyl)-1-benzofuran-2-carboxamide,
6-(dimethylamino)-N-(2,2,3,3-tetrafluoro-2,3-dihydro-1,4-benzodioxine-5-sulfonyl)-1-benzofuran-2-carboxamide,
6-(dimethylamino)-N-(2-{[(2R)-1,1,1-trifluoropropan-2-yl]oxy}benzene-1-sulfonyl)-1-benzofuran-2-carboxamide,
N-(5-bromo-2-chloropyridine-3-sulfonyl)-6-(dimethylamino)-1-benzofuran-2-carboxamide,
N-[4,5-dichloro-2-(trifluoromethoxy)benzene-1-sulfonyl]-6-(dimethylamino)-1-benzofuran-2-carboxamide,
N-(5-chloro-2-methoxy-4-methylbenzene-1-sulfonyl)-6-(dimethylamino)-1-benzofuran-2-carboxamide,
N-(2-chloro-5-methoxybenzene-1-sulfonyl)-6-(dimethylamino)-1-benzofuran-2-carboxamide,
6-(dimethylamino)-N-[2-(methanesulfonyl)-6-methoxybenzene-1-sulfonyl]-1-benzofuran-2-carboxamide,
6-(dimethylamino)-N-[2-(dimethylsulfamoyl)-6-methoxybenzene-1-sulfonyl]-1-benzofuran-2-carboxamide,
N-[2-(cyclobutyloxy)-6-fluorobenzene-1-sulfonyl]-6-(dimethylamino)-1-benzofuran-2-carboxamide,
6-(dimethylamino)-N-(2-ethoxy-5-ethylbenzene-1-sulfonyl)-1-benzofuran-2-carboxamide,
6-(dimethylamino)-N-[2-(2-methoxyethoxy)benzene-1-sulfonyl]-1-benzofuran-2-carboxamide,
N-{5-bromo-2-[(propan-2-yl)amino]pyridine-3-sulfonyl}-6-(dimethylamino)-1-benzofuran-2-carboxamide,
N-[5-bromo-2-(cyclopropylamino)pyridine-3-sulfonyl]-6-(dimethylamino)-1-benzofuran-2-carboxamide,
6-(dimethylamino)-N-(2-ethyl-6-methoxybenzene-1-sulfonyl)-1-benzofuran-2-carboxamide,
N-(5-bromo-2-methoxybenzene-1-sulfonyl)-6-(dimethylamino)-1-benzofuran-2-carboxamide,
N-(5-chloro-2-methoxybenzene-1-sulfonyl)-6-(dimethylamino)-1-benzofuran-2-carboxamide,
N-[5-bromo-2-(propylamino)pyridine-3-sulfonyl]-6-(dimethylamino)-1-benzofuran-2-carboxamide,
6-(dimethylamino)-N-[4-(3-methylanilino)pyridine-3-sulfonyl]-1-benzofuran-2-carboxamide,
6-(dimethylamino)-N-(6-methoxypyridine-3-sulfonyl)-1-benzofuran-2-carboxamide,
6-(dimethylamino)-N-(2,3,4-trifluorobenzene-1-sulfonyl)-1-benzofuran-2-carboxamide,
N-(2-chloro-5-methylpyridine-3-sulfonyl)-6-(dimethylamino)-1-benzofuran-2-carboxamide,
6-(dimethylamino)-N-{2-fluoro-6-[(propan-2-yl)amino]benzene-1-sulfonyl}-1-benzofuran-2-carboxamide,
N-(2-chloropyridine-3-sulfonyl)-6-(dimethylamino)-1-benzofuran-2-carboxamide,
N-(2-cyclopentyl-6-methylbenzene-1-sulfonyl)-6-(dimethylamino)-1-benzofuran-2-carboxamide,
N-(2-cyclobutyl-6-fluorobenzene-1-sulfonyl)-6-(dimethylamino)-1-benzofuran-2-carboxamide,
N-[2-(difluoromethoxy)-4-methylbenzene-1-sulfonyl]-6-(dimethylamino)-1-benzofuran-2-carboxamide,
N-[2-(cyclopropylmethoxy)-6-fluorobenzene-1-sulfonyl]-6-(dimethylamino)-1-benzofuran-2-carboxamide,
6-(dimethylamino)-N-[5-(hydroxymethyl)-2-(trifluoromethoxy)benzene-1-sulfonyl]-1-benzofuran-2-carboxamide,
6-(dimethylamino)-N-[2,5-di(propan-2-yl)benzene-1-sulfonyl]-1-benzofuran-2-carboxamide,
N-[2-chloro-5-(1-hydroxyethyl)benzene-1-sulfonyl]-6-(dimethylamino)-1-benzofuran-2-carboxamide,
N-[2-chloro-5-(2-methoxyethoxy)benzene-1-sulfonyl]-6-(dimethylamino)-1-benzofuran-2-carboxamide,
N-{2-[(2,2-difluoroethyl)amino]-5-(trifluoromethyl)benzene-1-sulfonyl}-6-(dimethylamino)-1-benzofuran-2-carboxamide,
N-(5-aminoquinoline-8-sulfonyl)-6-(dimethylamino)-1-benzofuran-2-carboxamide,
N-[2-(2-aminoethoxy)benzene-1-sulfonyl]-6-(dimethylamino)-1-benzofuran-2-carboxamide hydrogen chloride (1/1),
6-(dimethylamino)-N-(2-{2-[2-(2-{2-[(7-nitro-2,1,3-benzoxadiazol-4-yl)amino]ethoxy}ethoxy) ethoxy] ethoxy}benzene-1-sulfonyl)-1-benzofuran-2-carboxamide,
6-(dimethylamino)-N-(2-ethoxy-3-fluorobenzene-1-sulfonyl)-1-benzofuran-2-carboxamide, N-{5-[(2S)-butan-2-yl]-2-ethoxybenzene-1-sulfonyl}-6-(dimethylamino)-1-benzofuran-2-carboxamide,
6-(dimethylamino)-N-(2-ethoxy-4-fluorobenzene-1-sulfonyl)-1-benzofuran-2-carboxamide,
6-(dimethylamino)-N-[2-ethoxy-5-(trifluoromethyl)benzene-1-sulfonyl]-1-benzofuran-2-carboxamide,
6-(dimethylamino)-N-(2-ethoxy-5-fluorobenzene-1-sulfonyl)-1-benzofuran-2-carboxamide,
6-(dimethylamino)-N-(2-ethoxy-5-phenoxybenzene-1-sulfonyl)-1-benzofuran-2-carboxamide,
6-(Dimethylamino)-N-[2-ethoxy-5-(trifluoromethoxy)phenyl]sulfonyl-benzofuran-2-carboxamide,
N-[2-(benzyloxy)-5-(propan-2-yl)benzene-1-sulfonyl]-6-(dimethylamino)-1-benzofuran-2-carboxamide,
N-[2-(cyclopropylmethoxy)-5-(propan-2-yl)benzene-1-sulfonyl]-6-(dimethylamino)-1-benzofuran-2-carboxamide,
6-(dimethylamino)-N-[5-(propan-2-yl)-2-(2,2,2-trifluoroethoxy)benzene-1-sulfonyl]-1-benzofuran-2-carboxamide,
N-[2-(benzyloxy)-5-tert-butylbenzene-1-sulfonyl]-6-(dimethylamino)-1-benzofuran-2-carboxamide,
N-[5-tert-butyl-2-(cyclopropylmethoxy)benzene-1-sulfonyl]-6-(dimethylamino)-1-benzofuran-2-carboxamide,
N-[5-tert-butyl-2-(2,2,2-trifluoroethoxy)benzene-1-sulfonyl]-6-(dimethylamino)-1-benzofuran-2-carboxamide,
N-[5-tert-butyl-2-(cyclobutyloxy)benzene-1-sulfonyl]-6-(dimethylamino)-1-benzofuran-2-carboxamide,
N-{5-tert-butyl-2-[(propan-2-yl)oxy]benzene-1-sulfonyl}-6-(dimethylamino)-1-benzofuran-2-carboxamide,
N-[2-(cyclobutyloxy)-5-(propan-2-yl)benzene-1-sulfonyl]-6-(dimethylamino)-1-benzofuran-2-carboxamide,
N-(5-tert-butyl-2-methoxybenzene-1-sulfonyl)-6-(dimethylamino)-1-benzofuran-2-carboxamide,
N-[2-{[(1R)-2,2-difluorocyclopropyl]methoxy}-5-(propan-2-yl)benzene-1-sulfonyl]-6-(dimethylamino)-1-benzofuran-2-carboxamide,
5-chloro-6-(dimethylamino)-N-(2-ethoxybenzene-1-sulfonyl)-1-benzofuran-2-carboxamide,
N-([1,1'-biphenyl]-2-sulfonyl)-6-(dimethylamino)-4-(trifluoromethyl)-1-benzofuran-2-carboxamide,
N-(benzenesulfonyl)-6-(dimethylamino)-4-(trifluoromethyl)-1-benzofuran-2-carboxamide,
6-(dimethylamino)-N-(2-ethoxybenzene-1-sulfonyl)-4-(trifluoromethyl)-1-benzofuran-2-carboxamide,
6-(Dimethylamino)-N-((2-methylquinolin-8-yl) sulfonyl)-4-(trifluoromethyl)benzofuran-2-carboxamide,
6-(Dimethylamino)-5-fluoro-N-((2-methylquinolin-8-yl) sulfonyl)benzofuran-2-carboxamide,
6-(Dimethylamino)-N-((2-ethoxyphenyl) sulfonyl)-5-fluorobenzofuran-2-carboxamide,
N-([1,1'-biphenyl]-2-ylsulfonyl)-6-(dimethylamino)-5-fluorobenzofuran-2-carboxamide,
6-(dimethylamino)-N-(2-ethoxybenzene-1-sulfonyl)-5-(trifluoromethyl)-1-benzofuran-2-carboxamide,
N-([1,1'-biphenyl]-2-sulfonyl)-7-bromo-6-(dimethylamino)-1-benzofuran-2-carboxamide,
5-cyano-6-(dimethylamino)-N-(2-ethoxybenzene-1-sulfonyl)-1-benzofuran-2-carboxamide,
6-[(2-methoxyethyl)(methyl)amino]-N-(2-methylquinoline-8-sulfonyl)-1-benzofuran-2-carboxamide,
N-([1,1'-biphenyl]-2-sulfonyl)-5-bromo-6-(dimethylamino)-7-fluoro-1-benzofuran-2-carboxamide,
5-bromo-N-[2-(cyclopropyloxy)benzene-1-sulfonyl]-6-(dimethylamino)-1-benzofuran-2-carboxamide,
5-bromo-6-(dimethylamino)-N-{2-[(propan-2-yl)oxy]benzene-1-sulfonyl}-1-benzofuran-2-carboxamide,
N-([1,1'-biphenyl]-2-sulfonyl)-6-(dimethylamino)-1-methyl-1H-indole-2-carboxamide,
N-([1,1'-biphenyl]-2-sulfonyl)-6-(ethylamino)-1-benzofuran-2-carboxamide,
N-(2-ethoxybenzene-1-sulfonyl)-6-(ethylamino)-1-benzofuran-2-carboxamide,
N-(5-bromo-2-ethoxybenzene-1-sulfonyl)-6-[(2-methoxyethyl)(methyl)amino]-1-benzofuran-2-carboxamide,
6-[(2-methoxyethyl)(methyl)amino]-N-(5-methyl[1,1'-biphenyl]-2-sulfonyl)-1-benzofuran-2-carboxamide,
N-(2-ethoxybenzene-1-sulfonyl)-6-[(2-methoxyethyl)(methyl)amino]-1-benzofuran-2-carboxamide,
5-bromo-6-(dimethylamino)-N-(2-methylquinoline-8-sulfonyl)-1-benzofuran-2-carboxamide,
N-([1,1'-biphenyl]-2-sulfonyl)-5-bromo-6-(dimethylamino)-1-benzofuran-2-carboxamide,
5-bromo-6-(dimethylamino)-N-(2-ethoxybenzene-1-sulfonyl)-1-benzofuran-2-carboxamide,
6-(ethylamino)-N-(2-methylquinoline-8-sulfonyl)-1-benzofuran-2-carboxamide,
N-[2-(cyclobutyloxy)-6-{[(2R*)-1,1,1-trifluoropropan-2-yl]oxy}benzene-1-sulfonyl]-6-(dimethylamino)-1-benzofuran-2-carboxamide,
N-[2-(cyclobutyloxy)-6-{[(2R*)-1,1,1-trifluoropropan-2-yl]oxy}benzene-1-sulfonyl]-6-(dimethylamino)-1-benzofuran-2-carboxamide,
sodium [6-(dimethylamino)-1-benzofuran-2-carbonyl](2-ethoxybenzene-1-sulfonyl) azanide,
sodium [6-(dimethylamino)-1-benzofuran-2-carbonyl]{2-[(propan-2-yl)oxy]benzene-1-sulfonyl}azanide,
sodium [6-(dimethylamino)-1-benzofuran-2-carbonyl](2-methylquinoline-8-sulfonyl) azanide,
sodium [6-(dimethylamino)-4-fluoro-1-benzofuran-2-carbonyl](2-methylquinoline-8-sulfonyl) azanide,
6-(Dimethylamino)-N-((2-ethoxy-4,5-difluorophenyl) sulfonyl)benzofuran-2-carboxamide,
N-((5-cyclopropyl-2-ethoxyphenyl) sulfonyl)-6-(dimethylamino)benzofuran-2-carboxamide,
6-(Dimethylamino)-N-((2-methoxy-5-(2-oxopropyl)phenyl) sulfonyl)benzofuran-2-carboxamide, and
N-((5-(tert-butyl)-2-cyclopropoxyphenyl) sulfonyl)-6-(dimethylamino)benzofuran-2-carboxamide.

14. A pharmaceutical composition comprising a compound of general formula (I) according to claim 1; one or more pharmaceutically acceptable excipients, and optionally one or more further anti-cancer agents.

15. A compound of general formula (II)

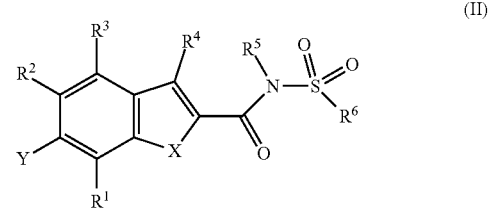

wherein X, $R^1$, $R^2$, $R^3$, $R^4$, $R^5$ and $R^6$ are as defined for the compound of general formula (I) according to claim 1 and Y is a halogen atom selected from chlorine and bromine or a tautomer, or a salt thereof, or a salt of a tautomer, or a mixture of same.

16. A method of preparing a compound of general formula (I) according to claim 1, said method comprising the reaction of an intermediate compound of formula (II) with an amine

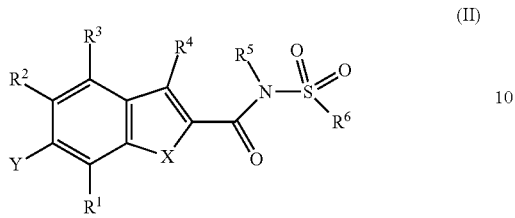

(II)

wherein X, $R^1$, $R^2$, $R^3$, $R^4$, $R^5$ and $R^6$ are as defined for the compound of general formula (I) according to claim 1 or a tautomer, or a salt thereof, or a salt of a tautomer, or a mixture of same and Y is a halogen atom selected from chlorine and bromine.

17. A method of treating comprising administering an effective amount of at least one compound of general formula (I) to a subject in need thereof according to claim 1 wherein the cancer is selected from lung cancer, breast cancer, bladder cancer, uterine cancer, endometrial cancer, prostate cancer and leukemia.

* * * * *